US012171801B2

(12) United States Patent
Martinez et al.

(10) Patent No.: US 12,171,801 B2
(45) **Date of Patent: *Dec. 24, 2024**

(54) COMPOSITIONS AND RELATED METHODS FOR CONTROLLING VECTOR-BORNE DISEASES

(71) Applicant: Flagship Pioneering Innovations V, Inc., Cambridge, MA (US)

(72) Inventors: Ignacio Martinez, Lexington, MA (US); Zachary Garo Armen, Boston, MA (US); Christine Cezar, Sammamish, WA (US); Barry Andrew Martin, Boston, MA (US); Maier Steve Avendano Amado, Cambridge, MA (US)

(73) Assignee: Flagship Pioneering Innovations V, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/120,476

(22) Filed: Dec. 14, 2020

(65) Prior Publication Data

US 2021/0275635 A1 Sep. 9, 2021

Related U.S. Application Data

(63) Continuation of application No. 16/826,728, filed on Mar. 23, 2020, now abandoned, which is a continuation of application No. 16/480,053, filed as application No. PCT/US2018/015065 on Jan. 24, 2018, now abandoned.

(60) Provisional application No. 62/583,912, filed on Nov. 9, 2017, provisional application No. 62/450,057, filed on Jan. 24, 2017.

(51) Int. Cl.
*A61K 38/17* (2006.01)

(52) U.S. Cl.
CPC ................................ *A61K 38/1729* (2013.01)

(58) Field of Classification Search
None
See application file for complete search history.

(56) References Cited

U.S. PATENT DOCUMENTS

| | | | |
|---|---|---|---|
| 4,011,391 | A | 3/1977 | Horii et al. |
| 4,089,947 | A | 5/1978 | Horii et al. |
| 8,101,732 | B2 | 1/2012 | Mahmud et al. |
| 8,334,366 | B1 | 12/2012 | Hughes et al. |
| 9,303,076 | B2 | 4/2016 | Brinkmann et al. |
| 10,051,860 | B2 | 8/2018 | Kiguchi et al. |
| 2009/0285937 | A1 | 11/2009 | Vadis et al. |
| 2011/0150780 | A1 | 6/2011 | Krieger et al. |
| 2011/0209228 | A1 | 8/2011 | Cocks et al. |
| 2011/0229937 | A1 | 9/2011 | Pompejus et al. |
| 2011/0263487 | A1 | 10/2011 | Meagher |
| 2012/0316220 | A1 | 12/2012 | Ward et al. |
| 2014/0349917 | A1* | 11/2014 | Eckert .................... A61Q 11/00 435/7.1 |
| 2017/0015716 | A1 | 1/2017 | Walensky et al. |
| 2019/0191741 | A1 | 6/2019 | Martinez et al. |
| 2019/0216093 | A1 | 7/2019 | Martinez et al. |
| 2019/0246647 | A1 | 8/2019 | Martinez et al. |
| 2019/0365853 | A1 | 12/2019 | Martinez et al. |
| 2019/0367943 | A1 | 12/2019 | Martinez et al. |
| 2019/0387748 | A1 | 12/2019 | Martinez et al. |
| 2020/0060286 | A1 | 2/2020 | Martinez et al. |
| 2020/0128856 | A1 | 4/2020 | Martinez et al. |
| 2020/0129565 | A1 | 4/2020 | Martinez et al. |
| 2020/0261536 | A1 | 8/2020 | Martinez et al. |
| 2021/0195917 | A1 | 7/2021 | Martinez et al. |
| 2021/0275635 | A1 | 9/2021 | Martinez et al. |
| 2021/0360934 | A1 | 11/2021 | Martinez et al. |

FOREIGN PATENT DOCUMENTS

| | | | |
|---|---|---|---|
| CN | 102405053 | A | 4/2012 |
| CN | 107637597 | A | 1/2018 |
| JP | 10-511955 | A | 11/1998 |
| JP | 2004-99465 | A | 4/2004 |
| JP | 2012-504623 | A | 2/2012 |
| RU | 2311767 | C2 | 12/2007 |
| RU | 2556800 | C2 | 7/2015 |
| WO | WO-88/00976 | A1 | 2/1988 |
| WO | WO-95/16776 | A1 | 6/1995 |

(Continued)

OTHER PUBLICATIONS

Orkin (downloaded on Feb. 5, 2022 from URL:< Mosquito Habitats (orkin.com)>) (Year: 2022).*
El Chamy Maluf et al. (Peptides 78 (2016) 11-16) (Year: 2016).*
Carter et al., "Killer bee molecules: antimicrobial peptides as effector molecules to target sporogonic stages of Plasmodium," PLoS Pathog. 9(11):e1003790 (2013) (13 pages).
Douglas, "Symbiotic microorganisms: untapped resources for insect pest control," Trends Biotechnol. 25(8):338-342 (2007).
Fieck et al., "Trypanosoma cruzi: synergistic cytotoxicity of multiple amphipathic anti-microbial peptides to T. cruzi and potential bacterial hosts," Exp Parasitol. 125(4):342-7 (2010).
Gendrin et al., "Differential Effects of Azithromycin, Doxycycline, and Cotrimoxazole in Ingested Blood on the Vectorial Capacity of Malaria Mosquitoes," Open Forum Infect Dis. 3(2):ofw074 (2016) (8 pages).

(Continued)

*Primary Examiner* — Sergio Coffa
(74) *Attorney, Agent, or Firm* — Clark & Elbing LLP

(57) ABSTRACT

Provided herein are methods and compositions useful for human health, e.g., for targeting one or more microorganisms resident in a host insect (e.g., arthropod, e.g., insect, e.g., pathogen vector), the modulation resulting in a decrease in the fitness of the host. The invention features a composition that includes a modulating agent (e.g., phage, peptide, small molecule, antibiotic, or combinations thereof) that can alter the host's microbiota in a manner that is detrimental to the host. By disrupting microbial levels, microbial activity, microbial metabolism, or microbial diversity, the modulating agent described herein may be used to decrease the fitness of a variety of insects that carry vector-home pathogens that cause disease in humans.

11 Claims, 68 Drawing Sheets

Specification includes a Sequence Listing.

(56) References Cited

FOREIGN PATENT DOCUMENTS

| | | | |
|---|---|---|---|
| WO | WO-96/20596 | A1 | 7/1996 |
| WO | WO 2005/034863 | * | 4/2005 |
| WO | WO-2005/034863 | A2 | 4/2005 |
| WO | WO-2010/039652 | A2 | 4/2010 |
| WO | WO-2010/080819 | A1 | 7/2010 |
| WO | WO-2011157713 | A2 | 12/2011 |
| WO | WO-2015/100432 | A2 | 7/2015 |
| WO | WO-2018/140507 | A1 | 8/2018 |
| WO | WO-2018/140518 | A1 | 8/2018 |
| WO | WO-2018140496 | A1 | 8/2018 |
| WO | WO-2018140519 | A1 | 8/2018 |
| WO | WO-2018156998 | A1 | 8/2018 |
| WO | WO-20180140479 | A1 | 8/2018 |

OTHER PUBLICATIONS

International Preliminary Report on Patentability for International Application No. PCT/US2018/015065, dated Aug. 8, 2019 (7 pages).
International Search Report and Written Opinion for International Application No. PCT/US2018/015065, mailed Apr. 23, 2018 (16 pages).
Rahbe et al., "Protein toxicity to aphids: an in vitro test on Acyrthosiphon pisum," Entomologia Experimentalis Et Applicata. 67(2):149-160 (1993).
Wang et al., "Fighting malaria with engineered symbiotic bacteria from vector mosquitoes," Proc Natl Acad Sci USA. 109(31):12734-9 (2012).
Zhou et al., "Oral Administration of TAT-PTD-Diapause Hormone Fusion Protein Interferes With Helicoverpa armigera (Lepidoptera: Noctuidae) Development," J Insect Sci. 15(1):123 (2015) (6 pages).
Cermenati et al., "The CPP Tat enhances eGFP cell internalization and transepithelial transport by the larval midgut of Bombyx mori (Lepidoptera, Bombycidae)," J Insect Physiol. 57(12):1689-97 (2011).
Gregory et al., "A quantitative model for the all-or-none permeabilization of phospholipid vesicles by the antimicrobial peptide cecropin A," Biophys J. 94(5):1667-80 (2008).
"Chemical Summary for Validamycin," Pesticide Action Network North America, <http://pesticideinfo.org/Summary_Chemical.jsp?Rec_Id=PRI6495>, retrieved on Apr. 5, 2019 (1 page).
"Compound Summary: Validamycin," PubChem, <https://pubchem.ncbi.nlm.nih.gov/compound/Validamycin>, created on Jun. 24, 2005, modified on Mar. 30, 2019, retrieved on Apr. 5, 2019 (17 pages).
"General Information for Validamycin," BPDB: Bio-Pesticides DataBase, <https://sitem.herts.ac.uk/aeru/bpdb/Reports/677.htm>, updated on May 3, 2018, retrieved on Apr. 5, 2019 (9 pages).
"Pentatomidae," NCSU, <https://genent.cals.ncsu.edu/insect-identification/order-hemiptera-suborder-heteroptera/family-pentatomidae/>, retrieved on Sep. 14, 2020 (2 pages).
"Validamycin," EXTOXNET: Extension Toxicology Network, <http://pmep.cce.cornell.edu/profiles/extoxnet/pyrethrins-ziram/validamycin-ext.html>, published in Sep. 1995, retrieved on Apr. 5, 2019 (4 pages).
Amos, "UBC students give bees a chance," University of British Columbia News, dated Sep. 18, 2015 (3 pages).
Asano et al., "Trehalase Inhibitors, Validoxylamine A and Related Compounds as Insecticides," J Antibiot (Tokyo). 43(6):722-26 (1990).
Bini et al., Trehalose mimetics as inhibitors of trehalose processing enzymes, *Carbohydrate Chemistry: Chemical and Biological Approaches: vol. 37.* A.P. Rauter and T.K. Lindhorst, 259-302 (2012).
Cole et al., "Insects in Vegetables," Texas Agricultural Extension Service of the Texas A&M University System, <http://bio-nica.info/Biblioteca/Cole2004InsectsVegetables.pdf>, last modified on Jul. 9, 1997, retrieved on Feb. 3, 2004 (37 pages).
Crotti et al., "Microbial symbionts: a resource for the management of insect-related problems," Microb Biotechnol. 5(3):307-17 (2012).
Douglas, "Symbiotic microorganisms: untapped resources for insect pest control," Trends Biotechnol. 25(8):338-42 (2007).
Extended European Search Report for European Application No. 18744684.4, dated Nov. 25, 2020 (10 pages).
Hmed et al., "Scorpion peptides: potential use for new drug development," J Toxicol. 2013:958797 (2013) (15 pages).
International Preliminary Report on Patentability for International Application No. PCT/US2018/015076, mailed Aug. 8, 2019 (7 pages).
International Preliminary Report on Patentability for International Application No. PCT/US2018/015077, mailed Aug. 8, 2019 (7 pages).
International Search Report and Written Opinion for International Application No. PCT/US2018/015076, mailed Apr. 23, 2018 (16 pages).
International Search Report and Written Opinion for International Application No. PCT/US2018/015077, mailed Apr. 23, 2018 (16 pages).
Ishikawa et al., "Foliar spray of validamycin A or validoxylamine A controls tomato fusarium wilt," Phytopathology. 95(10):1209-16 (2005).
Jiang et al., "Genome sequences of the primary endosymbiont 'Candidatus Portiera aleyrodidarum' in the whitefly Bemisia tabaci B and Q biotypes," J Bacteriol. 194(23):6678-9 (2012).
Jin et al., "Inhibitory effects of validamycin compounds on the termites trehalase," Pesticide Biochemistry and Physiology. 95(1):28-32 (2009).
Kameda et al., "Validoxylamines as Trehalase Inhibitors," J Antibiot (Tokyo). 40(4):563-5 (1987).
Kikuchi et al., "Symbiont-mediated insecticide resistance," Proc Natl Acad Sci U.S.A. 109(22):8618-22 (2012).
Knuesel et al., "Comparative studies of suidatrestin, a specific inhibitor of trehalases," Comp Biochem Physiol B Biochem Mol Biol. 120(4): 639-46 (1998).
Kono et al., "Inhibition of flight in *Periplaneta americana* (Linn.) by a trehalase inhibitor, validoxylamine A," Journal of Insect Physiology. 40(6):455-61 (1994).
Kono et al., "Lethal Activity of a Trehalase Inhibitor, Validoxylamine A, and its Influence on the Blood Sugar Level in *Bombyx mori* (Lepidoptera: Bombycidae)," Appl Entomol Zool. 28(3):379-86 (1993).
Krafsur, "Tsetse flies: genetics, evolution, and role as vectors," Infect Genet Evol. 9(1):124-41 (2009).
Le-Feuvre et al., "Effect of the antimicrobial peptide indolicidin on the green peach aphid *Myzus persicae* (Sulzer)," J Appl Entomol. 131(2):71-5 (2007).
Liu et al., "Disruption of Methionine Metabolism in *Drosophila melanogaster* Impacts Histone Methylation and Results in Loss of Viability," G3 (Bethesda). 6(1):121-32 (2016).
Luna-Ramirez et al., "Orally delivered scorpion antimicrobial peptides exhibit activity against pea aphid (*Acyrthosiphon pisum*) and its bacterial symbionts," Toxins (Basel). 9(9):261 (Aug. 2017) (16 pages).
Luna-Ramirez et al., "Whole Transcriptome of the Venom Gland from Urodacus yaschenkoi Scorpion," PloS One. 10(5): e0127883 (2015) (33 pages).
Mosquito Habitats, Orkin, 2022, available <www.orkin.com>, (10 pages).
Office Action for Russian Patent Application No. 2019126301, issued May 12, 2021 (21 pages).
Office Action for Ukrainian Patent Application No. a201909450, issued Jul. 16, 2021 (12 pages).
Partial Supplementary European Search Report for European Application No. 18745296.6, dated Aug. 25, 2020 (14 pages).
Partial Supplementary European Search Report for European Patent Application No. 18744684.4 dated Aug. 24, 2020 (13 pages).
Rahbe et al., "Protein toxicity to aphids: an in vitro test on *Acyrthosiphon pisum*," Entomol Exp Appl. 67:149-60 (1993).
Rai et al., "Role of nanotechnology in agriculture with special reference to management of insect pests," Appl Microbiol Biotechnol. 94(2):287-93 (2012).
Ross et al., "Toxic and antifeeding actions of melittin in the corn earworm, *Heliothis zea* (Boddie): comparisons to bee venom and the insecticides chlorpyriphos and cyromazine," Toxicon. 25(3):307-13 (1987).

(56) References Cited

OTHER PUBLICATIONS

Ryu et al., "Innate immune homeostasis by the homeobox gene caudal and commensal-gut mutualism in *Drosophila*," Science. 319(5864):777-82 (2008) (7 pages).
Santo Domingo et al., "Characterization of the Cricket Hindgut Microbiota with Fluorescently Labeled rRNA-Targeted Oligonucleotide Probes," Appl Environ Microbiol. 64(2):752-5 (1998).
Sharma et al., "Metabolism of 1-naphthyl-N-methyl carbamate (carbaryl) by bacterial isolates from honey bees and the effect of bacterial inoculations on carbaryl tolerance in bees," Journal of Applied Bacteriology. 81(3):235-41 (1996).
Tang et al., "Suppressing the activity of trehalase with validamycin disrupts the trehalose and chitin biosynthesis pathways in the rice brown planthopper, *Nilaparvata lugens*," Pesticide Biochemistry and Physiology. <http://dx.doi.org/10.1016/j.pestbp.2016.10.003>, accepted Oct. 10, 2016 (2016) (10 pages).
Tatun et al., "Developmental and Lethal Effects of Trehalase Inhibitor (Validamycin) on the *Tribolium castaneum* (Coleoptera: Tenebrionidae)," Annals of the Entomological Society of America. doi: 10.1093/aesa/sav.111, Advance Access published Nov. 9, 2015 (2015) (8 pages).
Tatun et al., "Trehalase Activity in Fungus-Growing Termite, *Odontotermes feae* (Isoptera: Termitideae) and Inhibitory Effect of Validamycin," J Econ Entomol. 107(3):1224-32 (2014).
Trinder et al., "Probiotic Lactobacillus rhamnosus reduces organophosphate pesticide absorption and toxicity to Drosophila melanogaster," Applied and Environmental Microbiology (2016) vol. 82, No. 20, pp. 6204-6213.
Trötschel et al., "Characterization of methionine export in Corynebacterium glutamicum," J Bacteriol. 187(11):3786-94 (2005).
Written Opinion for International Application No. PCT/US2018/015077, mailed Apr. 23, 2018 (11 pages).
Zhang et al., "Bacterial symbionts, Buchnera, and starvation on wing dimorphism in English grain aphid, Sitobion avenae (F.) (Homoptera: Aphididae), " Front Physiol. 6:155 (2015) (9 pages).
Zhang et al., "Inhibitory effect of valienamine on the enzymatic activity of honeybee (*Apis cerana* Fabr.) alpha-glucosidase," Pesticide Biochemistry and Physiology. 87(1):73-7 (2007).
Chen et al., Validamycin and Its Derivatives: Discovery, Chemical Synthesis and Biological Activity. Elsevier (Apr. 2017) (Table of Contents Only) (5 pages).
Decision to Grant for Russian Patent Application No. 2019126318, dated Jul. 21, 2023 (15 pages).
Gros et al., "A non-covalent peptide-based strategy for protein and peptide nucleic acid transduction," Biochim Biophys Acta. 1758(3):384-93 (Mar. 2006).
Office Action for Chinese Patent Application No. 2018800081043, dated Mar. 1, 2023 (11 pages).
Parn et al., Chapter 15: The Antimicrobial and Antiviral Applications of Cell-Penetrating Peptides. *Cell-Penetrating Peptides: Methods and Protocols*. Ülo Langel, 1324: 223-245 (2015).
Ackermann, Hans-W. "Bacteriophage taxonomy" Microbiology Australia (pp. 90-94) (2011).
Hughes et al., "Cell-penetrating recombinant peptides for potential use in agricultural pest control applications," Pharmaceuticals (Basel). 5(10):1054-63 (Sep. 2012).
Nobuchi, "The tropical forestry, Insect Enemies in the Tropical Forests (2)," Mode of Feeding Habits. 12:56-58 (1988).
Walrant et al., "Different membrane behaviour and cellular uptake of three basic arginine-rich peptides," Biochim Biophys Acta. 1808(1):382-93 (Jan. 2011).
Final Rejection for U.S. Appl. No. 16/480,142, dated Jan. 3, 2023 (14 pages).
Reply to Final Rejection for U.S. Appl. No. 16/480,142, dated Jul. 3, 2023 (7 pages).

* cited by examiner

Instar stage
5
4
3
2
1
Day 0
Day 1
Day 2
Day 4
Day 5
Day 6
Day 7
Day 8
Day 9
Day 11
Day 12
Day 13
Percent
100
50
0
AD only
AD + Rif
AD + Rif + EAA
no remaining aphids alive
no remaining aphids alive

[Scatter plot: Day 3 topical spray; y-axis "Copy number of Buchnera/aphid" from -20 to 100; two groups "Silwett L-77" and "Rifampicin (50 µg/ml)"; p=0.0093]

Day 0
Day 1
Day 3
Day 6
Day 7
Day 8
Percent
100
75
50
25
0
water inj/plant
1.6 mg/ml nisin
7 mg/ml nisin
no living aphids
Instar stage:
5R
5
4
3
2
1

COMPOSITIONS AND RELATED METHODS FOR CONTROLLING VECTOR-BORNE DISEASES

CROSS-REFERENCE TO RELATED APPLICATIONS

This application claims priority to U.S. Provisional Application No. 62/450,032, filed on Jan. 24, 2017, and U.S. Provisional Application No. 62/583,925, filed on Nov. 9, 2017, the contents of which are hereby incorporated herein by reference in their entireties.

SEQUENCE LISTING

The instant application contains a Sequence Listing which has been submitted electronically in ASCII format and is hereby incorporated by reference in its entirety. Said ASCII copy, created Oct. 13, 2023, is named 51215-006005_Sequence_Listing_10_13_23_ST25 and is 282,500 bytes in size.

BACKGROUND

Insects function as vectors for pathogens causing severe human disease such as dengue, trypanosomiases, and malaria. With 174 million diagnoses and 655,000 million deaths in 2011, malaria is considered as one of the most significant diseases worldwide. Thus, there is need in the art for methods and compositions to control insects that carry vector-borne diseases.

SUMMARY OF THE INVENTION

Disclosed herein are compositions and methods for modulating the fitness of insects for controlling the spread of vector-borne diseases in humans. The composition includes an agent that alters a level, activity, or metabolism of one or more microorganisms resident in a host, the alteration resulting in a modulation in the host's fitness.

In one aspect, provided herein is a method of decreasing fitness of a vector (e.g., insect vector) for a human pathogen, the method including delivering an antimicrobial peptide having at least 90% sequence identity (e.g., at least 90%, 92%, 94%, 96%, 98%, or 100% sequence identity) with one or more of the following: cecropin (SEQ ID NO: 82), melittin, copsin, drosomycin (SEQ ID NO: 93), dermcidin (SEQ ID NO: 81), andropin (SEQ ID NO: 83), moricin (SEQ ID NO: 84), ceratotoxin (SEQ ID NO: 85), abaecin (SEQ ID NO: 86), apidaecin (SEQ ID NO: 87), prophenin (SEQ ID NO: 88), indolicidin (SEQ ID NO: 89), protegrin (SEQ ID NO: 90), tachyplesin (SEQ ID NO: 91), or defensin (SEQ ID NO: 92) to the vector.

In some embodiments, the delivery includes delivering the antimicrobial peptide to at least one habitat where the vector grows, lives, reproduces, feeds, or infests.

In some embodiments, the antimicrobial peptide may be delivered in an insect comestible composition for ingestion by the vector.

In some embodiments, the antimicrobial peptide may be formulated as a liquid, a solid, an aerosol, a paste, a gel, or a gas composition.

In some embodiments, the insect may be at least one of a mosquito, midge, louse, sandfly, tick, triatomine bug, tsetse fly, or flea.

In another aspect, provided herein is a composition including an antimicrobial peptide having at least 90% sequence identity (e.g., at least 90%, 92%, 94%, 96%, 98%, or 100% sequence identity) with one or more of the following: cecropin (SEQ ID NO: 82), melittin, copsin, drosomycin (SEQ ID NO: 93), dermcidin (SEQ ID NO: 81), andropin (SEQ ID NO: 83), moricin (SEQ ID NO: 84), ceratotoxin (SEQ ID NO: 85), abaecin (SEQ ID NO: 86), apidaecin (SEQ ID NO: 87), prophenin (SEQ ID NO: 88), indolicidin (SEQ ID NO: 89), protegrin (SEQ ID NO: 90), tachyplesin (SEQ ID NO: 91), or defensin (SEQ ID NO: 92) formulated for targeting a microorganism in a vector (e.g., an insect vector) for a human pathogen.

In some embodiments of the second aspect, the antimicrobial peptide may be at a concentration of about 0.1 ng/g to about 100 mg/g (about 0.1 ng/g to about 1 ng/g, about 1 ng/g to about 10 ng/g, about 10 ng/g to about 100 ng/g, about 100 ng/g to about 1000 ng/g, about 1 mg/g to about 10 mg/g, about 10 mg/g to about 100 mg/g) or about 0.1 ng/mL to about 100 mg/mL (about 0.1 ng/mL to about 1 ng/mL, about 1 ng/mL to about 10 ng/mL, about 10 ng/mL to about 100 ng/mL, about 100 ng/mL to about 1000 ng/mL, about 1 mg/mL to about 10 mg/mL, about 10 mg/mL to about 100 mg/mL) in the composition.

In some embodiments of the second aspect, the antimicrobial peptide may further include a targeting domain.

In some embodiments of the second aspect, the antimicrobial peptide may further include a cell penetrating peptide.

In yet another aspect, the composition includes an agent that alters a level, activity, or metabolism of one or more microorganisms resident in an insect host, the alteration resulting in a decrease in the insect host's fitness.

In some embodiments of any of the above compositions, the one or more microorganisms may be a bacterium or fungus resident in the host. In some embodiments, the bacterium resident in the host is at least one selected from the group consisting of *Candidatus* spp, *Buchenera* spp, *Blattabacterium* spp, *Baumania* spp, *Wigglesworthia* spp, *Wolbachia* spp, *Rickettsia* spp, *Orientia* spp, *Sodalis* spp, *Burkholderia* spp, *Cupriavidus* spp, *Frankia* spp, *Snirhizobium* spp, *Streptococcus* spp, *Wolinella* spp, *Xylella* spp, *Erwinia* spp, *Agrobacterium* spp, *Bacillus* spp, *Paenibacillus* spp, *Streptomyces* spp, *Micrococcus* spp, *Corynebacterium* spp, *Acetobacter* spp, *Cyanobacteria* spp, *Salmonella* spp, *Rhodococcus* spp, *Pseudomonas* spp, *Lactobacillus* spp, *Enterococcus* spp, *Alcaligenes* spp, *Klebsiella* spp, *Paenibacillus* spp, *Arthrobacter* spp, *Corynebacterium* spp, *Brevibacterium* spp, *Thermus* spp, *Pseudomonas* spp, *Clostridium* spp, and *Escherichia* spp. In some embodiments, the fungus resident in the host is at least one selected from the group consisting of *Candida, Metschnikowia, Debaromyces, Starmerella, Pichia, Cryptococcus, Pseudozyma, Symbiotaphrina bucneri, Symbiotaphrina Scheffersomyces shehatae, Scheffersomyces stipites, Cryptococcus, Trichosporon, Amylostereum areolatum, Epichloe* spp, *Pichia pinus, Hansenula capsulate, Daldinia decipien, Ceratocytis* spp, *Ophiostoma* spp, and *Attamyces bromatificus*. In certain embodiments, the bacteria is a *Wolbachia* spp. (e.g., in a mosquito host). In certain embodiments, the bacteria is a *Rickettsia* spp. (e.g., in a tick host).

In any of the above compositions, the agent, which hereinafter may also be referred to as a modulating agent, may alter the growth, division, viability, metabolism, and/or longevity of the microorganism resident in the host. In any of the above embodiments, the modulating agent may decrease the viability of the one or more microorganisms resident in the host. In some embodiments, the modulating agent increases growth or viability of the one or more microorganisms resident in the host.

In any of the above embodiments, the modulating agent is a phage, a polypeptide, a small molecule, an antibiotic, a bacterium, or any combination thereof.

In some embodiments, the phage binds a cell surface protein on a bacterium resident in the host. In some embodiments, the phage is virulent to a bacterium resident in the host. In some embodiments, the phage is at least one selected from the group consisting of Myoviridae, Siphoviridae, Podoviridae, Lipothrixviridae, Rudiviridae, Ampullaviridae, Bicaudaviridae, Clavaviridae, Corticoviridae, Cystoviridae, Fuselloviridae, Gluboloviridae, Guttaviridae, Inoviridae, Leviviridae, Microviridae, Plasmaviridae, and Tectiviridae.

In some embodiments, the polypeptide is at least one of a bacteriocin, R-type bacteriocin, nodule C-rich peptide, antimicrobial peptide, lysin, or bacteriocyte regulatory peptide.

In some embodiments, the small molecule is a metabolite.

In some embodiments, the antibiotic is a broad-spectrum antibiotic.

In some embodiments, the modulating agent is a naturally occurring bacteria. In some embodiments, the bacteria is at least one selected from the group consisting of *Bartonella apis, Parasaccharibacter apium, Frischella perrara, Snodgrassella alvi, Gilliamela apicola, Bifidobacterium* spp, and *Lactobacillus* spp. In some embodiments, the bacterium is at least one selected from the group consisting of *Candidatus* spp, *Buchenera* spp, *Blattabacterium* spp, *Baumania* spp, *Wigglesworthia* spp, *Wolbachia* spp, *Rickettsia* spp, *Orientia* spp, *Sodalis* spp, *Burkholderia* spp, *Cupriavidus* spp, *Frankia* spp, *Snirhizobium* spp, *Streptococcus* spp, *Wolinella* spp, *Xylella* spp, *Erwinia* spp, *Agrobacterium* spp, *Bacillus* spp, *Paenibacillus* spp, *Streptomyces* spp, *Micrococcus* spp, *Corynebacterium* spp, *Acetobacter* spp, *Cyanobacteria* spp, *Salmonella* spp, *Rhodococcus* spp, *Pseudomonas* spp, *Lactobacillus* spp, *Enterococcus* spp, *Alcaligenes* spp, *Klebsiella* spp, *Paenibacillus* spp, *Arthrobacter* spp, *Corynebacterium* spp, *Brevibacterium* spp, *Thermus* spp, *Pseudomonas* spp, *Clostridium* spp, and *Escherichia* spp.

In any of the above compositions, host fitness may be measured by survival, reproduction, or metabolism of the host. In any of the above embodiments, the modulating agent may modulate the host's fitness by increasing pesticidal susceptibility of the host (e.g., susceptibility to a pesticide listed in Table 12). In some embodiments, the modulating agent modulates the host's fitness by increasing pesticidal susceptibility of the host. In some embodiments, the pesticidal susceptibility is bactericidal or fungicidal susceptibility. In some embodiments, the pesticidal susceptibility is insecticidal susceptibility.

In any of the above compositions, the composition may include a plurality of different modulating agents. In some embodiments, the composition includes a modulating agent and a pesticidal agent (e.g., a pesticide listed in Table 12). In some embodiments, the pesticidal agent is a bactericidal or fungicidal agent. In some embodiments, the pesticidal agent is an insecticidal agent.

In any of the above compositions, modulating agent may be linked to a second moiety. In some embodiments, the second moiety is a modulating agent.

In any of the above compositions, the modulating agent may be linked to a targeting domain. In some embodiments, the targeting domain targets the modulating agent to a target site in the host. In some embodiments, the targeting domain targets the modulating agent to the one or more microorganisms resident in the host.

In any of the above compositions, the modulating agent may include an inactivating pre- or pro-sequence, thereby forming a precursor modulating agent. In some embodiments, the precursor modulating agent is converted to an active form in the host.

In any of the above compositions, the modulating agent may include a linker. In some embodiments, the linker is a cleavable linker.

In any of the above compositions, the composition may further include a carrier. In some instances, the carrier may be an agriculturally acceptable carrier.

In any of the above compositions, the composition may further include a host bait, a sticky agent, or a combination thereof. In some embodiments, the host bait is a comestible agent and/or a chemoattractant.

In any of the above compositions, the composition may be at a dose effective to modulate host fitness. I In any of the above compositions, the composition may be formulated for delivery to a microorganism inhabiting the gut of the host. In any of the above compositions, the composition may be formulated for delivery to a microorganism inhabiting a bacteriocyte of the host and/or the gut of the host.

In some embodiments, the composition may be formulated for delivery to a plant. In some embodiments, the composition may be formulated for use in a host feeding station.

In any of the above compositions, the composition may be formulated as a liquid, a powder, granules, or nanoparticles. In some embodiments, the composition is formulated as one selected from the group consisting of a liposome, polymer, bacteria secreting peptide, and synthetic nanocapsule. In some embodiments, the synthetic nanocapsule delivers the composition to a target site in the host. In some embodiments, the target site is the gut of the host. In some embodiments, the target site is a bacteriocyte in the host.

In a further aspect, also provided herein are hosts that include any of the above compositions. In some embodiments, the host is an insect. In some embodiments, the insect is a mosquito, midge, louse, sandfly, tick, triatomine bug, tsetse fly, or flea. In certain embodiments, the insect is a mosquito. In certain embodiments, the insect is a tick. In certain embodiments, the insect is a mite. In certain embodiments, the insect is a louse.

Also provided herein is a system for modulating a host's fitness comprising a modulating agent that targets a microorganism that is required for a host's fitness, wherein the system is effective to modulate the host's fitness, and wherein the host is an insect. The modulating agent may include any of the compositions described herein. In some embodiments, the modulating agent is formulated as a powder. In some embodiments, the modulating agent is formulated as a solvent. In some embodiments, the modulating agent is formulated as a concentrate. In some embodiments, the modulating agent is formulated as a diluent. In some embodiments, the modulating agent is prepared for delivery by combining any of the previous compositions with a carrier.

In yet a further aspect, also provided herein are methods for modulating the fitness of an insect using any of the compositions described herein. In one instance, the method of modulating the fitness of an insect host includes delivering the composition of any one of the previous claims to the host, wherein the modulating agent targets the one or more microorganisms resident in the host, and thereby modulates the host's fitness. In another instance, the method of modulating microbial diversity in an insect host includes delivering the composition of any one of the previous claims to the host, wherein the modulating agent targets the one or more microorganisms resident in the host, and thereby modulates microbial diversity in the host.

In some embodiments of any of the above methods, the modulating agent may alter the levels of the one or more microorganisms resident in the host. In some embodiments of any of the above methods, the modulating agent may alter the function of the one or more microorganisms resident in the host. In some embodiments, the one or more microorganisms may be a bacterium and/or fungus. In some embodiments, the one or more microorganisms are required for host fitness. In some embodiments, the one or more microorganisms are required for host survival.

In some embodiments of any of the above methods, the delivering step may include providing the modulating agent at a dose and time sufficient to effect the one or more microorganisms, thereby modulating microbial diversity in the host. In some embodiments, the delivering step includes topical application of any of the previous compositions to a plant. In some embodiments, the delivering step includes providing the modulating agent through a genetically engineered plant. In some embodiments, the delivering step includes providing the modulating agent to the host as a comestible. In some embodiments, the delivering step includes providing a host carrying the modulating agent. In some embodiments the host carrying the modulating agent can transmit the modulating agent to one or more additional hosts.

In some embodiments of any of the above methods, the composition may be effective to increase the host's sensitivity to a pesticidal agent (e.g., a pesticide listed in Table 12). In some embodiments, the host is resistant to the pesticidal agent prior to delivery of the modulating agent. In some embodiments, the pesticidal agent is an allelochemical agent. In some embodiments, the allelochemical agent is caffeine, soyacystatin N, monoterpenes, diterpene acids, or phenolic compounds. In some embodiments, the composition is effective to selectively kill the host. In some embodiments, the composition is effective to decrease host fitness. In some embodiments, the composition is effective to decrease the production of essential amino acids and/or vitamins in the host.

In some embodiments of any of the above methods, the host is an insect. In some embodiments, the host is a vector for a human pathogen. In some embodiments, the vector is a mosquito, midge, louse, sandfly, tick, triatomine bug, tsetse fly, or flea. In certain embodiments, the vector is a mosquito. In certain embodiments, the vector is a tick. In certain embodiments, the vector is a mite. In certain embodiments, the vector is a louse.

In some embodiments, the human pathogen is a virus, a protozoan, a bacterium, a protist, or a nematoda. In some embodiments, the virus is one belonging to the group Togaviridae, Flaviviridae, Bunyaviridae, Rhabdoviridae, or Orbiviridae. In some embodiments, the bacterium is one belonging to the genus *Yersinia, Francisella, Rickettsia*, Orientia, or *Borrelia*. In some embodiments, the protozoan is one belonging to the genus *Plasmodium, Trypanosoma, Leishmania*, or *Babesia*. In some embodiments, the nematode is one belonging to the genus *Brugia*. In some embodiments, the composition is effective to prevent or decrease transmission of the pathogen to humans. In some embodiments, the composition is effective to prevent or decrease horizontal or vertical transmission of the pathogen between hosts. In some embodiments, the composition is effective to decrease host fitness, host development, or vectorial competence.

In another aspect, also provided herein are screening assays to identify modulating agent that modulate the fitness of a host. In one instance, the screening assay to identify a modulating agent that modulates the fitness of a host, includes the steps of (a) exposing a microorganism that can be resident in the host to one or more candidate modulating agents and (b) identifying a modulating agent that decreases the fitness of the host.

In some embodiments of the screening assay, the modulating agent is a microorganism resident in the host. In some embodiments, the microorganism is a bacterium. In some embodiments, the bacterium, when resident in the host, decreases host fitness. In some embodiments of the screening assay, the modulating agent affects an allelochemical-degrading microorganism. In some embodiments, the modulating agent is a phage, an antibiotic, or a test compound. In some embodiments, the antibiotic is timentin or azithromycin.

In some embodiments of the screening assay, the host may be an invertebrate. In some embodiments, the invertebrate is an insect. In some embodiments, the insect is a mosquito. In some embodiments, the insect is a tick. In certain embodiments, the insect is a mite. In certain embodiments, the insect is a louse.

In any of the above embodiments of the screening assay, host fitness may be modulated by modulating the host microbiota.

Definitions

As used herein, the term "bacteriocin" refers to a peptide or polypeptide that possesses anti-microbial properties. Naturally occurring bacteriocins are produced by certain prokaryotes and act against organisms related to the producer strain, but not against the producer strain itself. Bacteriocins contemplated herein include, but are not limited to, naturally occurring bacteriocins, such as bacteriocins produced by bacteria, and derivatives thereof, such as engineered bacteriocins, recombinantly expressed bacteriocins, and chemically synthesized bacteriocins. In some instances, the bacteriocin is a functionally active variant of the bacteriocins described herein. In some instances, the variant of the bacteriocin has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a bacteriocin described herein or a naturally occurring bacteriocin.

As used herein, the term "bacteriocyte" refers to a specialized cell found in certain insects where intracellular bacteria reside with symbiotic bacterial properties.

As used herein, the term "effective amount" refers to an amount of a modulating agent (e.g., a phage, lysin, bacteriocin, small molecule, or antibiotic) or composition including said agent sufficient to effect the recited result, e.g., to decrease or reduce the fitness of a host organism (e.g., insect, e.g., mosquito, tick, mite, louse); to reach a target level (e.g., a predetermined or threshold level) of a modulating agent concentration inside a target host; to reach a target level (e.g., a predetermined or threshold level) of a modulating agent concentration inside a target host gut; to reach a target level (e.g., a predetermined or threshold level) of a modulating agent concentration inside a target host bacteriocyte;

to modulate the level, or an activity, of one or more microorganism (e.g., endosymbiont) in the target host.

As used herein, the term "fitness" refers to the ability of a host organism to survive, and/or to produce surviving offspring. Fitness of an organism may be measured by one or more parameters, including, but not limited to, life span, reproductive rate, mobility, body weight, and metabolic rate. Fitness may additionally be measured based on measures of activity (e.g., biting animals or humans) or disease transmission (e.g., vector-vector transmission or vector-human transmission).

As used herein, the term "gut" refers to any portion of a host's gut, including, the foregut, midgut, or hindgut of the host.

As used herein, the term "host" refers to an organism (e.g., insect, e.g., mosquito, louse, mite, or tick) carrying resident microorganisms (e.g., endogenous microorganisms, endosymbiotic microorganisms (e.g., primary or secondary endosymbionts), commensal organisms, and/or pathogenic microorganisms).

As used herein "decreasing host fitness" or "decreasing host fitness" refers to any disruption to host physiology, or any activity carried out by said host, as a consequence of administration of a modulating agent, including, but not limited to, any one or more of the following desired effects: (1) decreasing a population of a host by about 10%, 20%, 30%, 40%, 50%, 60%, 70%, 80%, 90%, 95%, 99%, 100% or more; (2) decreasing the reproductive rate of a host (e.g., insect, e.g., mosquito, tick, mite, louse) by about 10%, 20%, 30%, 40%, 50%, 60%, 70%, 80%, 90%, 95%, 99%, 100% or more; (3) decreasing the mobility of a host (e.g., insect, e.g., mosquito, tick, mite, louse) by about 10%, 20%, 30%, 40%, 50%, 60%, 70%, 80%, 90%, 95%, 99%, 100% or more; (4) decreasing the body weight of a host (e.g., insect, e.g., mosquito, tick, mite, louse) by about 10%, 20%, 30%, 40%, 50%, 60%, 70%, 80%, 90%, 95%, 99%, 100% or more; (5) increasing the metabolic rate or activity of a host (e.g., insect, e.g., mosquito, tick, mite, louse) by about 10%, 20%, 30%, 40%, 50%, 60%, 70%, 80%, 90%, 95%, 99%, 100% or more; (6) decreasing vector-vector pathogen transmission (e.g., vertical or horizontal transmission of a pathogen from one insect to another) by a host (e.g., insect, e.g., mosquito, tick, mite, louse) by about 10%, 20%, 30%, 40%, 50%, 60%, 70%, 80%, 90%, 95%, 99%, 100% or more; (7) decreasing vector-human pathogen transmission (e.g., insect, e.g., mosquito, tick, mite, louse) by about 10%, 20%, 30%, 40%, 50%, 60%, 70%, 80%, 90%, 95%, 99%, 100% or more; (8) decreasing host (e.g., insect, e.g., mosquito, tick, mite, louse) lifespan by about 10%, 20%, 30%, 40%, 50%, 60%, 70%, 80%, 90%, 95%, 99%, 100% or more; (9) increasing host (e.g., insect, e.g., mosquito, tick, mite, louse) susceptibility to pesticides (e.g., insecticides) by about 10%, 20%, 30%, 40%, 50%, 60%, 70%, 80%, 90%, 95%, 99%, 100% or more; or (10) decreasing vector competence by a host (e.g., insect, e.g., mosquito, tick, mite, louse) by about 10%, 20%, 30%, 40%, 50%, 60%, 70%, 80%, 90%, 95%, 99%, 100% or more. A decrease in host fitness can be determined in comparison to a host organism to which the modulating agent has not been administered.

The term "insect" includes any organism belonging to the phylum Arthropoda and to the class Insecta or the class Arachnida, in any stage of development, i.e., immature and adult insects.

As used herein, "lysin" also known as endolysin, autolysin, murein hydrolase, peptidoglycan hydrolase, or cell wall hydrolase refers to a hydrolytic enzyme that can lyse a bacterium by cleaving peptidoglycan in the cell wall of the bacterium. Lysins contemplated herein include, but are not limited to, naturally occurring lysins, such as lysins produced by phages, lysins produced by bacteria, and derivatives thereof, such as engineered lysins, recombinantly expressed lysins, and chemically synthesized lysins. A functionally active variant of the bacteriocin may have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a synthetic, recombinant, or naturally derived bacteriocin, including any described herein.

As used herein, the term "microorganism" refers to bacteria or fungi. Microorganisms may refer to microorganisms resident in a host organism (e.g., endogenous microorganisms, endosymbiotic microorganisms (e.g., primary or secondary endosymbionts)) or microorganisms exogenous to the host, including those that may act as modulating agents. As used herein, the term "target microorganism" refers to a microorganism that is resident in the host and impacted by a modulating agent, either directly or indirectly.

As used herein, the term "agent" or "modulating agent" refers to an agent that is capable of altering the levels and/or functioning of microorganisms resident in a host organism (e.g., insect, e.g., mosquito, tick, mite, louse), and thereby modulate (e.g., decrease) the fitness of the host organism (e.g., insect, e.g., mosquito, tick, mite, louse).

As used herein, the term "pesticide" or "pesticidal agent" refers to a substance that can be used in the control of agricultural, environmental, or domestic/household pests, such as insects, fungi, bacteria, or viruses. The term "pesticide" is understood to encompass naturally occurring or synthetic insecticides (larvicides, and adulticides), insect growth regulators, acaricides (miticides), nematicides, ectoparasiticides, bactericides, fungicides, or herbicides (substance which can be used in agriculture to control or modify plant growth). Further examples of pesticides or pesticidal agents are listed in Table 12. In some instances, the pesticide is an allelochemical. As used herein, "allelochemical" or "allelochemical agent" is a substance produced by an organism that can effect a physiological function (e.g., the germination, growth, survival, or reproduction) of another organism (e.g., a host insect, e.g., mosquito).

As used herein, the term "peptide," "protein," or "polypeptide" encompasses any chain of naturally or non-naturally occurring amino acids (either D- or L-amino acids), regardless of length (e.g., at least 2, 3, 4, 5, 6, 7, 10, 12, 14, 16, 18, 20, 25, 30, 40, 50, 100, or more amino acids), the presence or absence of post-translational modifications (e.g., glycosylation or phosphorylation), or the presence of, e.g., one or more non-amino acyl groups (for example, sugar, lipid, etc.) covalently linked to the peptide, and includes, for example, natural proteins, synthetic, or recombinant polypeptides and peptides, hybrid molecules, peptoids, or peptidomimetics.

As used herein, "percent identity" between two sequences is determined by the BLAST 2.0 algorithm, which is described in Altschul et al., (1990) J. Mol. Biol. 215:403-410. Software for performing BLAST analyses is publicly available through the National Center for Biotechnology Information.

As used herein, the term "bacteriophage" or "phage" refers to a virus that infects and replicates in bacteria. Bacteriophages replicate within bacteria following the injection of their genome into the cytoplasm and do so using either a lytic cycle, which results in bacterial cell lysis, or a lysogenic (non-lytic) cycle, which leaves the bacterial cell intact. The phage may be a naturally occurring phage isolate, or an engineered phage, including vectors, or nucleic acids that encode either a partial phage genome (e.g., including at least all essential genes necessary to carry out the life cycle of the phage inside a host bacterium) or the full phage genome.

As used herein, the term "plant" refers to whole plants, plant organs, plant tissues, seeds, plant cells, seeds, and progeny of the same. Plant cells include, without limitation, cells from seeds, suspension cultures, embryos, meristematic regions, callus tissue, leaves, roots, shoots, gametophytes, sporophytes, pollen, and microspores. Plant parts include differentiated and undifferentiated tissues including, but not limited to the following: roots, stems, shoots, leaves, pollen, seeds, tumor tissue, and various forms of cells and culture (e.g., single cells, protoplasts, embryos, and callus tissue). The plant tissue may be in a plant or in a plant organ, tissue, or cell culture. In addition, a plant may be genetically engineered to produce a heterologous protein or RNA, for example, of any of the modulating agents in the methods or compositions described herein.

As used herein, the term "vector" refers to an insect that can carry or transmit a human pathogen from a reservoir to a human. Exemplary vectors include insects, such as those with piercing-sucking mouthparts, as found in Hem iptera and some Hymenoptera and Diptera such as mosquitoes, bees, wasps, midges, lice, tsetse fly, fleas and ants, as well as members of the Arachnidae such as ticks and mites.

Other features and advantages of the invention will be apparent from the following Detailed Description and the Claims.

BRIEF DESCRIPTION OF THE DRAWINGS

The figures are meant to be illustrative of one or more features, aspects, or embodiments of the invention and are not intended to be limiting.

FIG. 2A is a series of graphs showing the percentage of living aphids at each developmental stage (sample size=33 aphids/group). FIG. 2B shows representative images from each treatment taken at 12 days. Scale bars 2.5 mm. FIG. 2C shows area measurements from aphid bodies showing the drastic effect of rifampicin treatment. Adding back essential amino acids partially rescues development defects.

FIG. 6A is a series of graphs showing the developmental stage over time for each condition. Shown is the percentage of living aphids at each developmental stage (sample size=20 aphids/group). FIG. 6B is a graph showing area measurements from aphid bodies showing the drastic effect of rifampicin coated leaves on aphid size. Statistically significant differences were determined using a one-way-ANOVA followed by Tukey's Post-Test; *, $p<0.05$.

DNA to aphid DNA. Shown is the mean ratio of *Buchnera* DNA to aphid DNA±SD. Statistically significant differences were determined using a one-way-ANOVA followed by Tukey's Post-Test; *, $p<0.05$.

Figure 11:
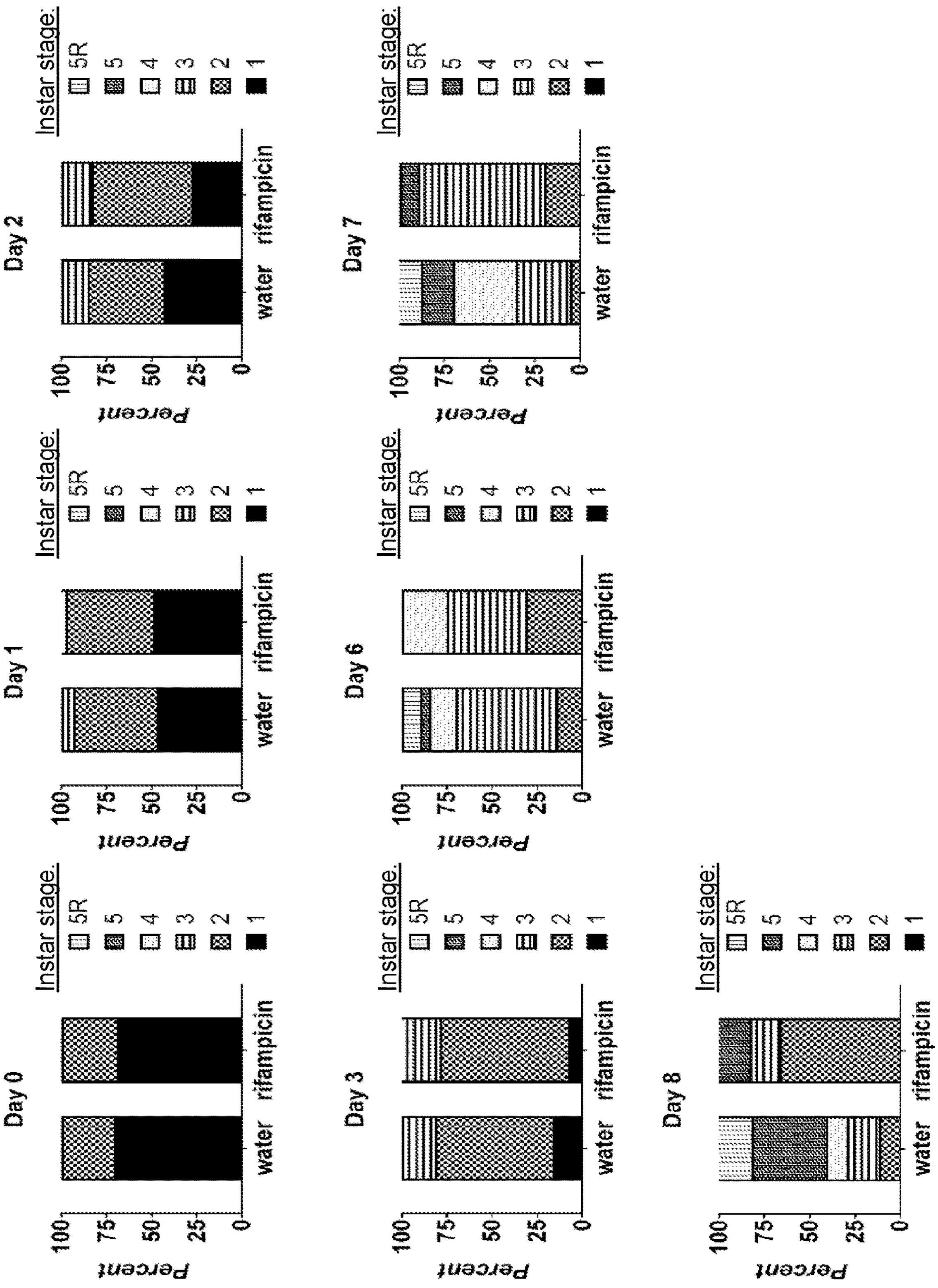

FIG. 11 shows a panel of graphs demonstrating that 1st and 2nd instar LSR-1 aphids were placed on leaves perfused with water plus food coloring or 50 μg/ml rifampicin in water plus food coloring. Developmental stage was measured over time for each condition. Shown is the percentage of living aphids at each developmental stage (sample size=74-81 aphids/group).

Figure 12:
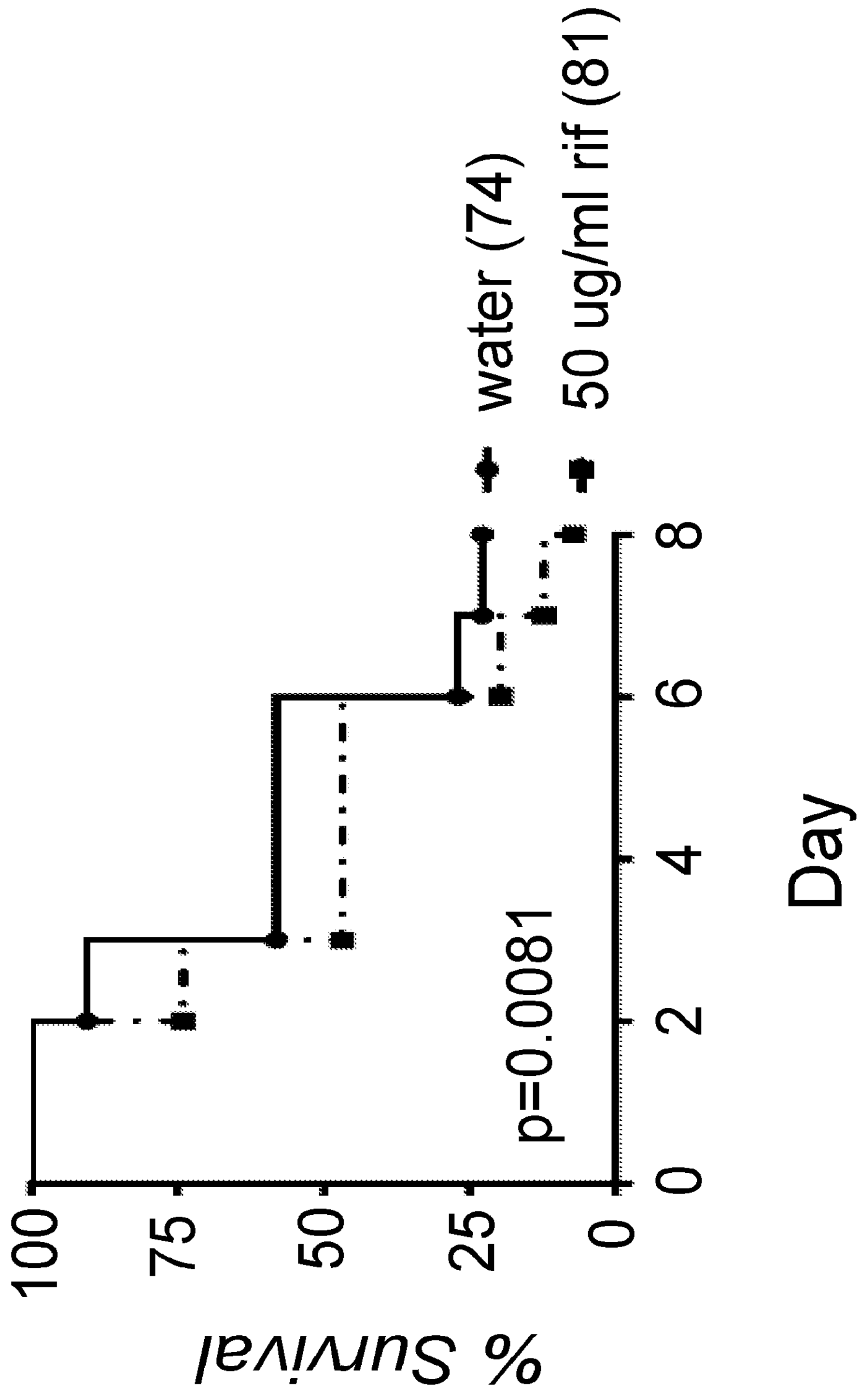

FIG. 12 shows a graph demonstrating survival of 1st and 2nd instar LSR-1 aphids placed on leaves perfused with water plus food coloring or 50 μg/ml rifampicin in water plus food coloring. Number in parentheses represents the number of aphids in each group. Statistical significance was determined by Log-Rank Test.

Figure 13:
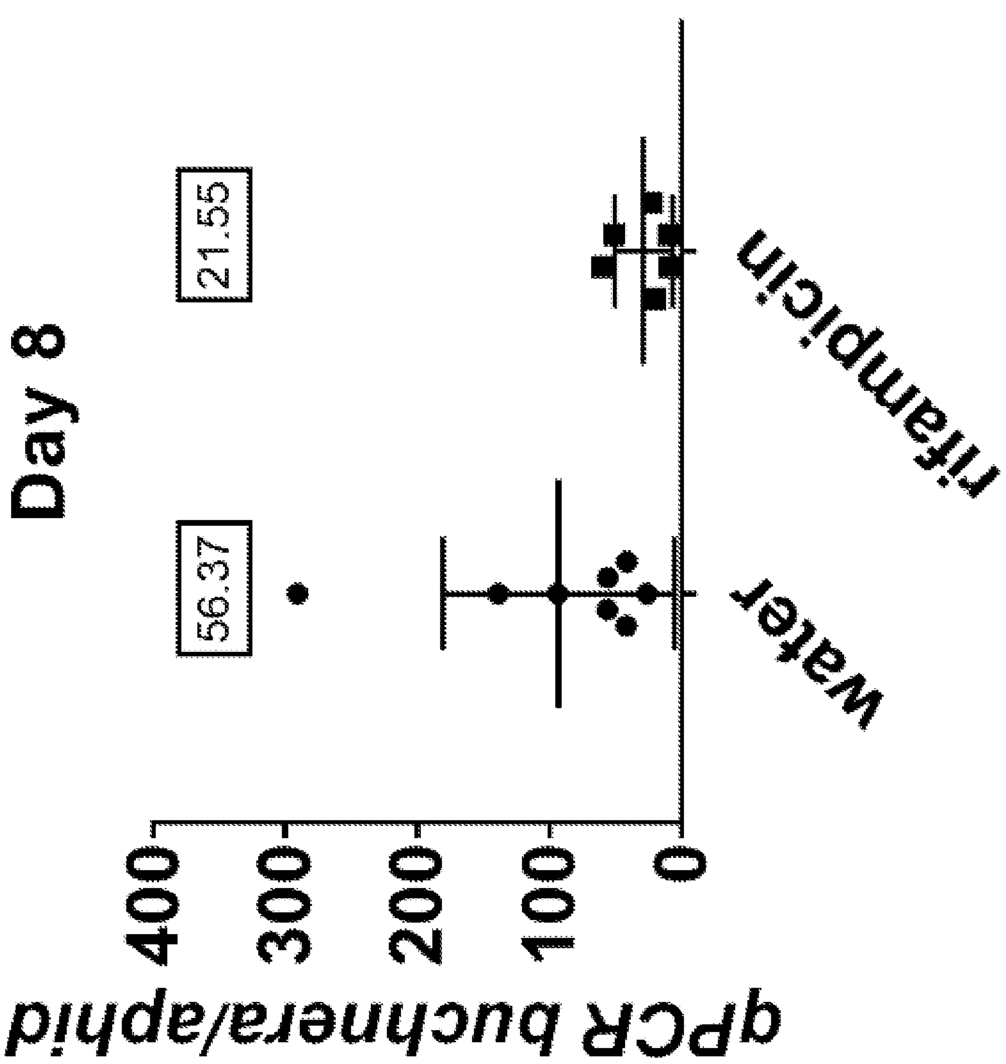

FIG. 13 shows a graph demonstrating symbiont titer determined 8 days post-treatment with leaves perfused with water and food coloring or rifampicin plus water and food coloring. DNA from aphids was extracted and qPCR was performed to determine the ratio of *Buchnera* DNA to aphid DNA. Shown is the mean ratio of *Buchnera* DNA to aphid DNA±SD. Number in box indicates the median of the experimental group.

Figure 14:
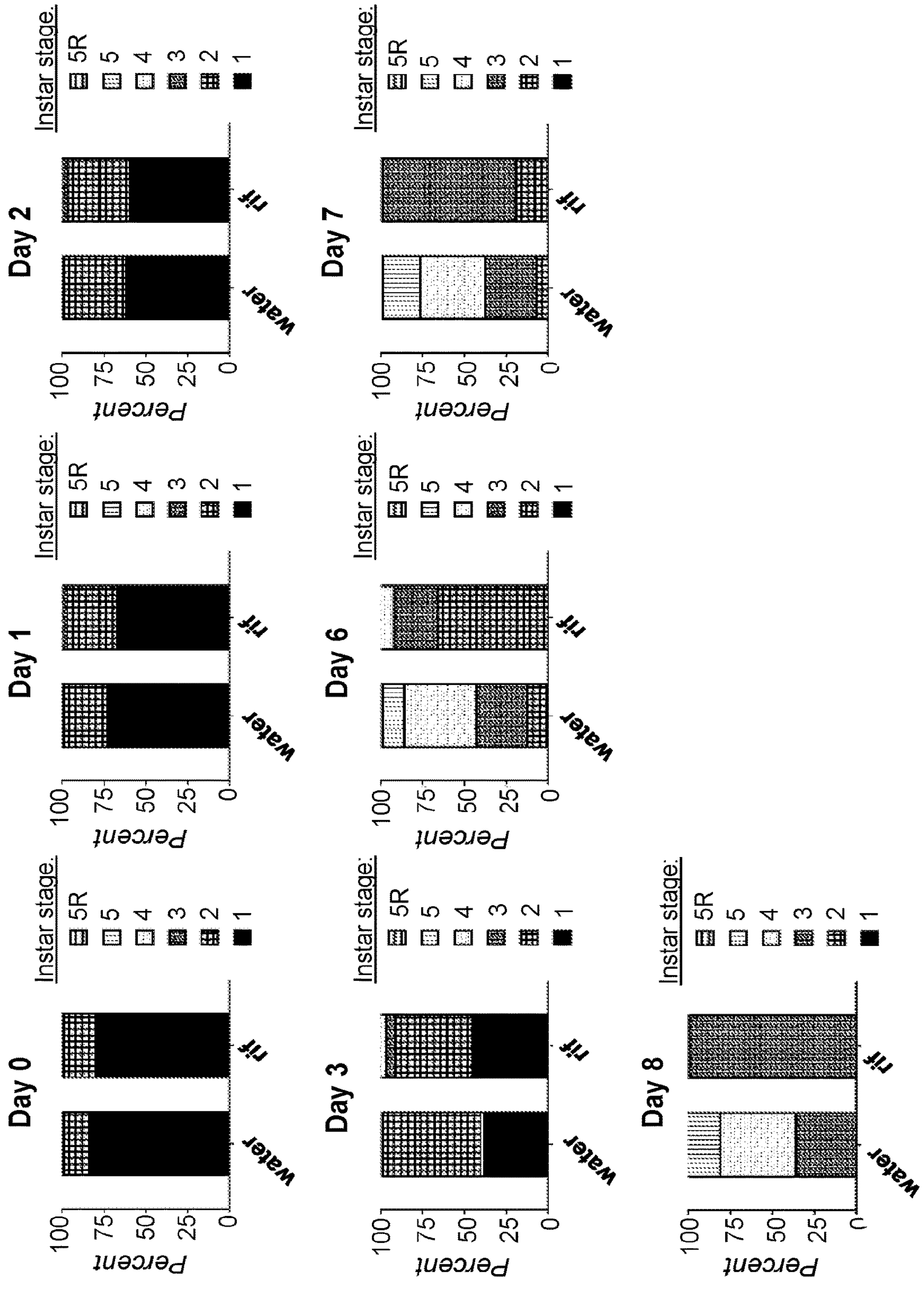

FIG. 14 shows a panel of graphs demonstrating 1st and 2nd instar LSR-1 aphids treated via leaf injection and through the plant with water plus food coloring or 100 μg/ml rifampicin in water plus food coloring. Developmental stage was measured over time for each condition. Shown is the percentage of living aphids at each developmental stage (sample size=49-50 aphids/group).

Figure 15:
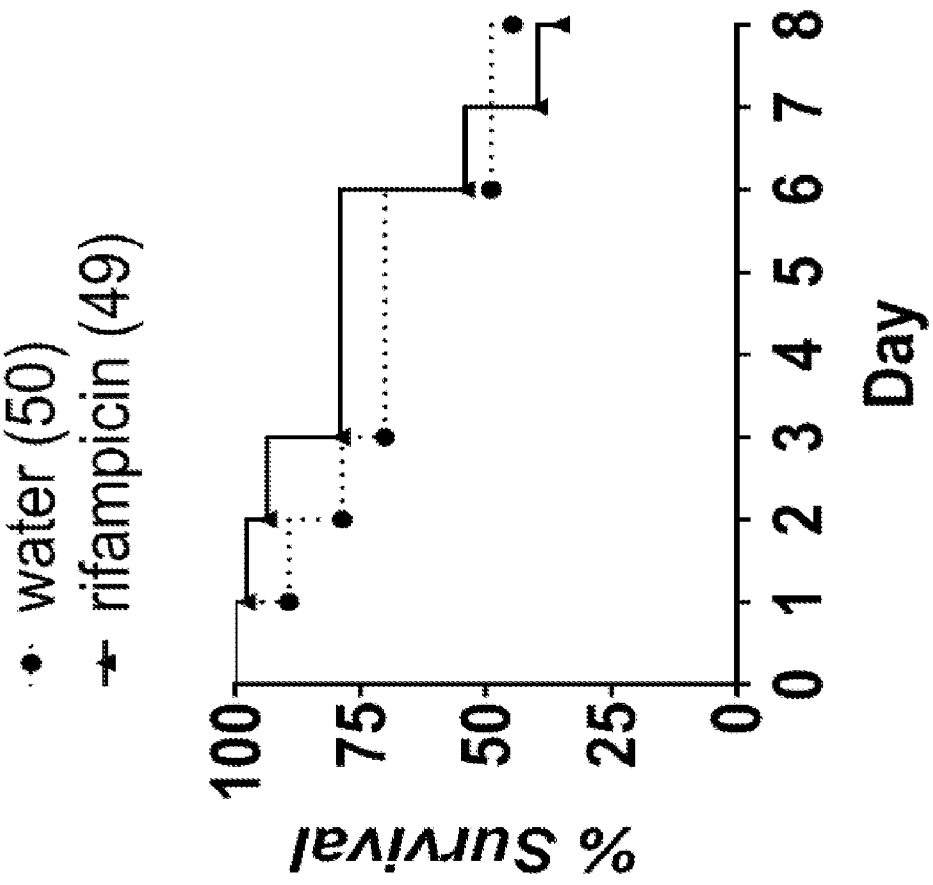

FIG. 15 is a graph demonstrating survival of 1st and 2nd instar LSR-1 aphids placed on leaves perfused and treated with water plus food coloring or 100 μg/ml rifampicin in water plus food coloring. Number in parentheses represents the number of aphids in each group. A Log-Rank Test was performed and determined that there were no statistically significant differences between groups.

Figure 16A:
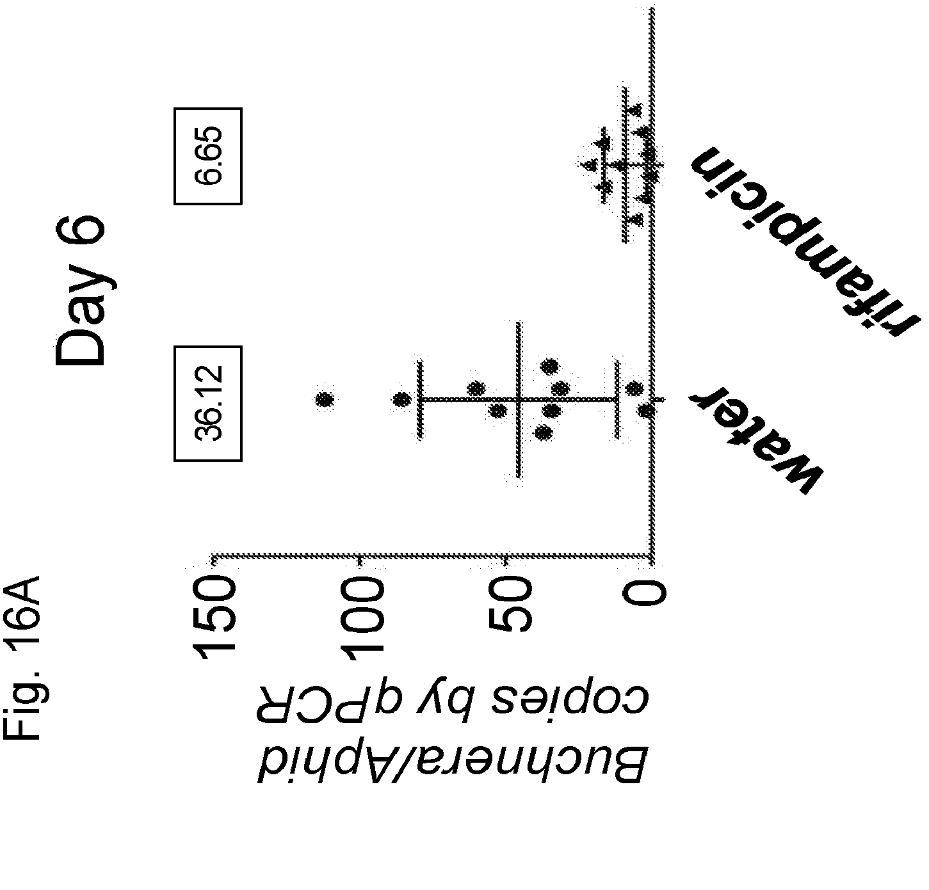
Figure 16B:
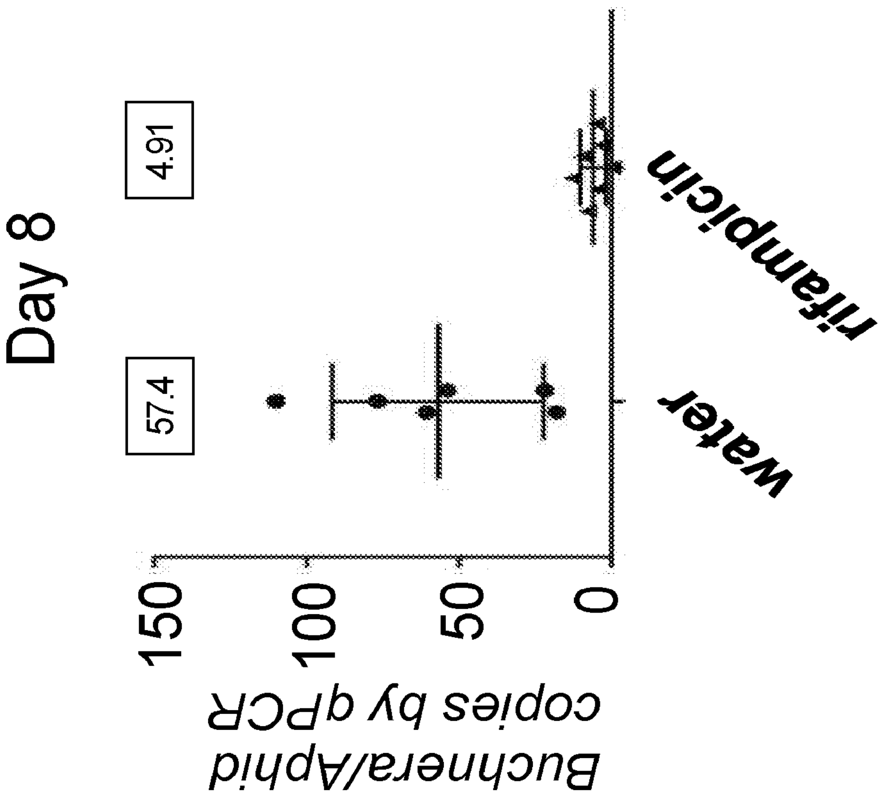

FIGS. 16A and 16B are graphs showing symbiont titer determined 6 (16A) and 8 (16B) days post-treatment in aphids feeding on leaves perfused and treated with water and food coloring or rifampicin plus water and food coloring. DNA was extracted from aphids and qPCR was performed to determine the ratio of *Buchnera* DNA to aphid DNA. Shown is the mean ratio of *Buchnera* DNA to aphid DNA±SD. Number in box indicates the median of the experimental group.

Figure 17:
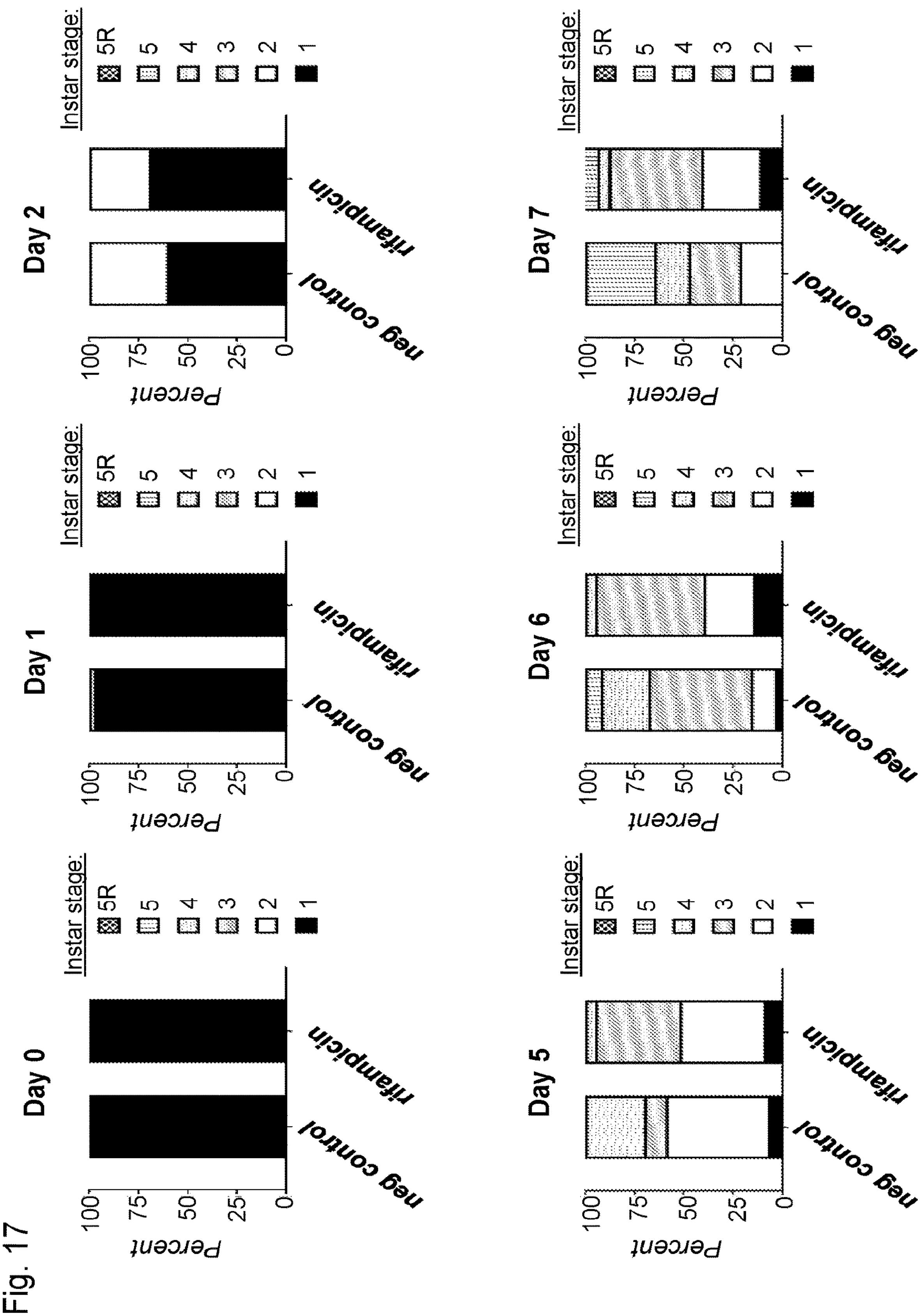

FIG. 17 is a panel of graphs showing that 1st and 2nd instar LSR-1 aphids were treated with control solutions (water and Silwet L-77) or a combination of treatments with 100 μg/ml rifampicin. Developmental stage was measured over time for each condition. Shown is the percentage of living aphids at each developmental stage (sample size=76-80 aphids/group).

Figure 18:
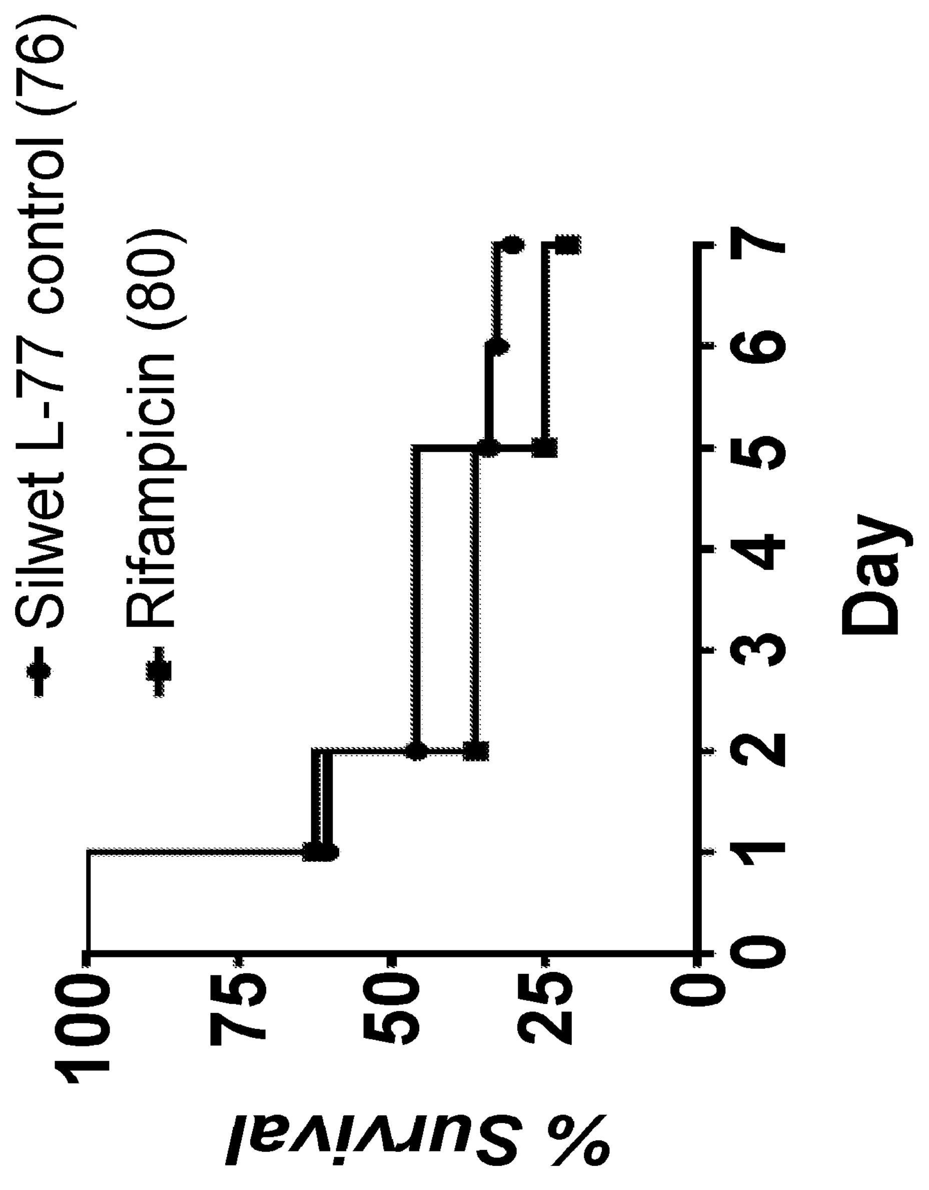

FIG. 18 is a graph showing 1st and 2nd instar LSR-1 aphids were treated with control solutions of a combination of treatments containing rifampicin. Number in parentheses represents the number of aphids in each group. A Log-Rank Test was performed and determined that there were no statistically significant differences between groups.

Figure 19:
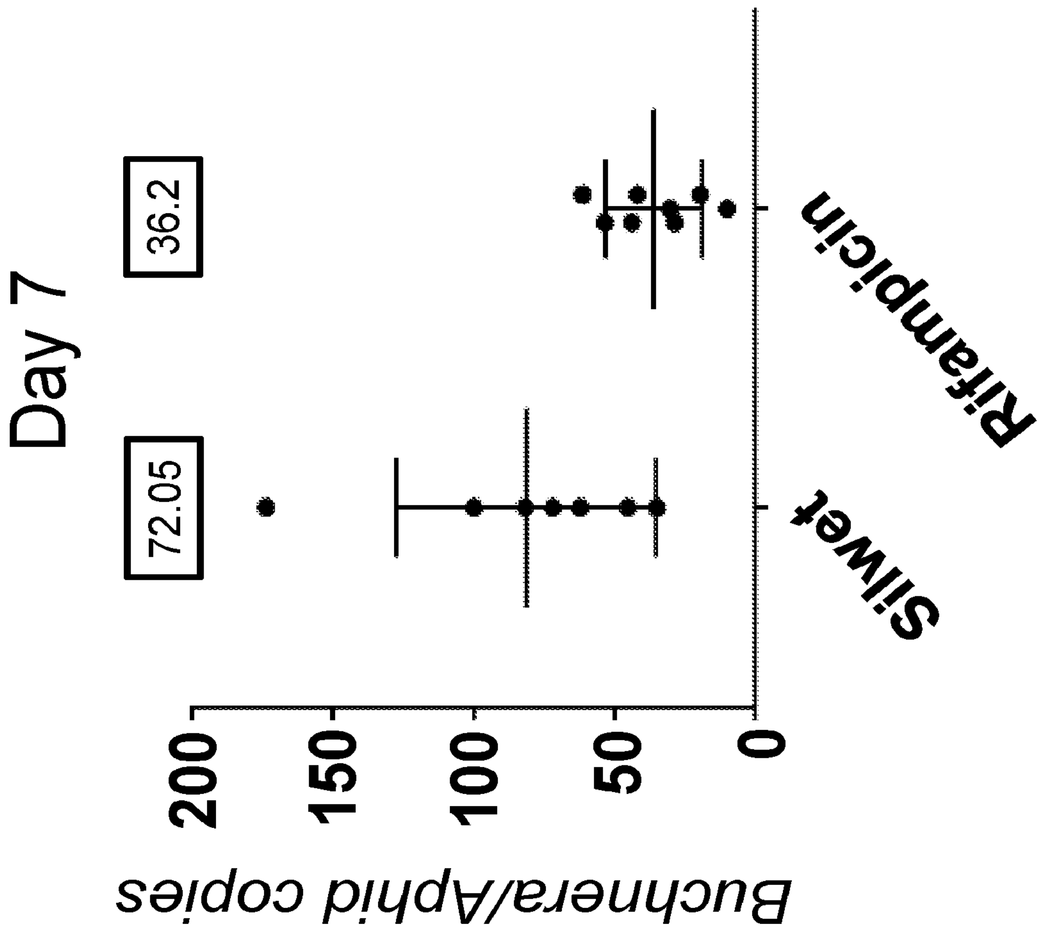

FIG. 19 is a graph showing symbiont titer determined at 7 days post-treatment with control or rifampicin solutions. DNA from aphids was extracted and qPCR was performed to determine the ratio of *Buchnera* DNA to aphid DNA. Shown is the mean ratio of *Buchnera* DNA to aphid DNA±SD. Number in box indicates the median of the experimental group. Statistically significant differences were determined by t-test.

Figure 20:
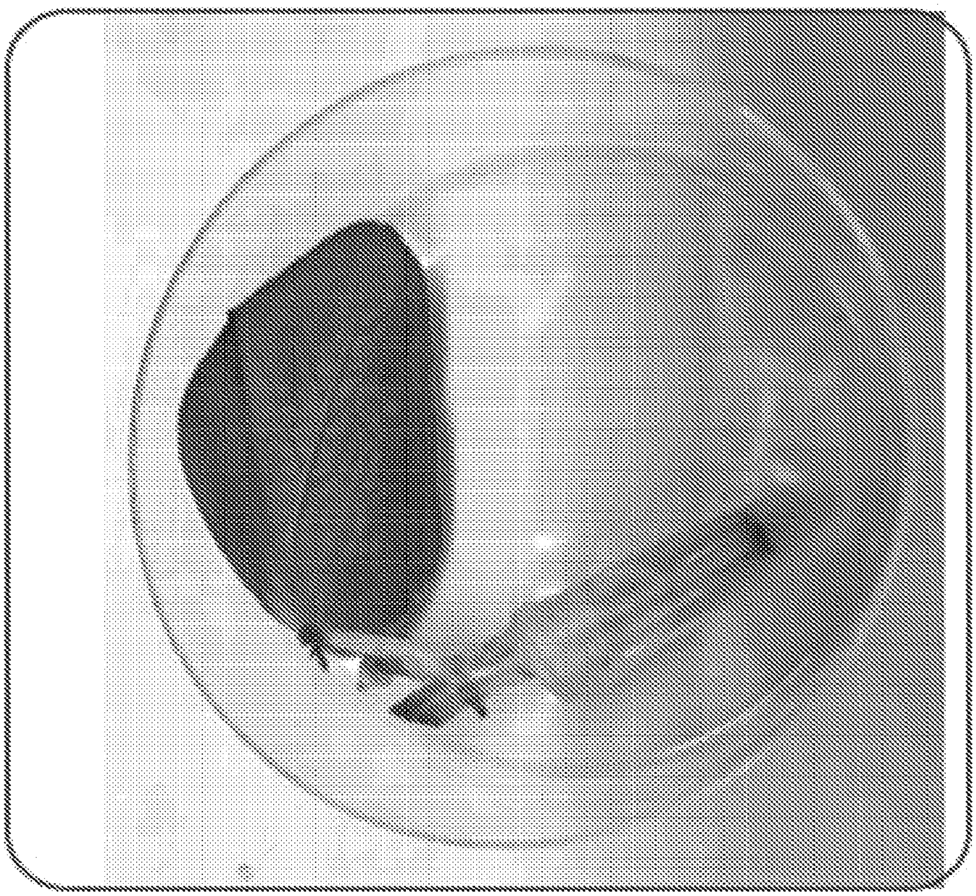

FIG. 20 is an image showing the chitosan delivery system. *A. pisum* aphids were treated with a therapeutic solution by delivery through leaf perfusion and through the plants as shown.

Figure 21:
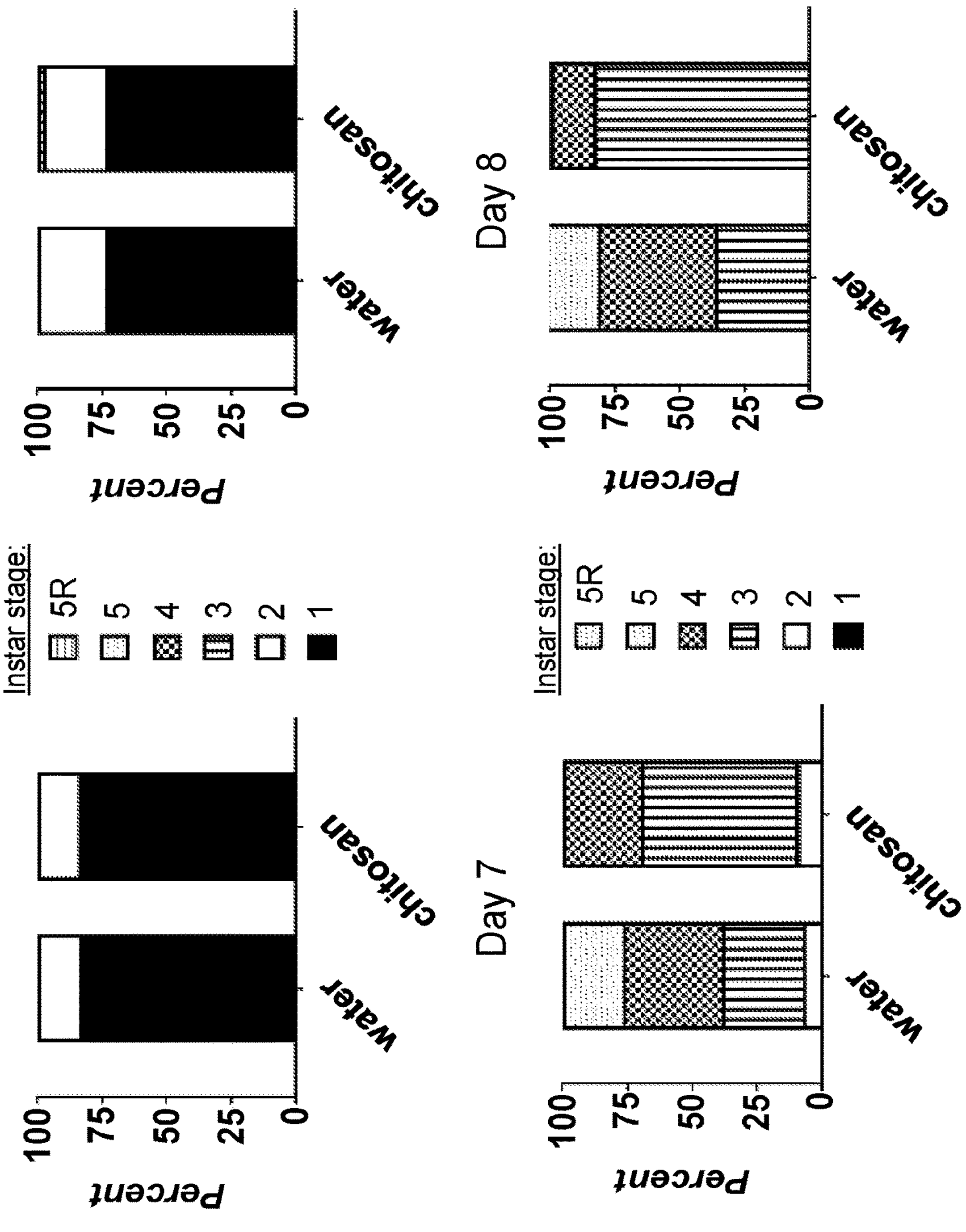

FIG. 21 is a panel of graphs showing that chitosan treatment resulted in delayed aphid development. First and second instar *A. pisum* aphids were treated by delivery through plants and leaf perfusion with the control solution (Water), and 300 ug/ml chitosan in water. Developmental stage was monitored throughout the experiment. Shown are the percent of aphids at each developmental stage (1st instar, 2nd instar, 3rd instar, 4th instar, 5th instar, or 5 R which represents a reproducing 5th instar) per treatment group.

Figure 22:
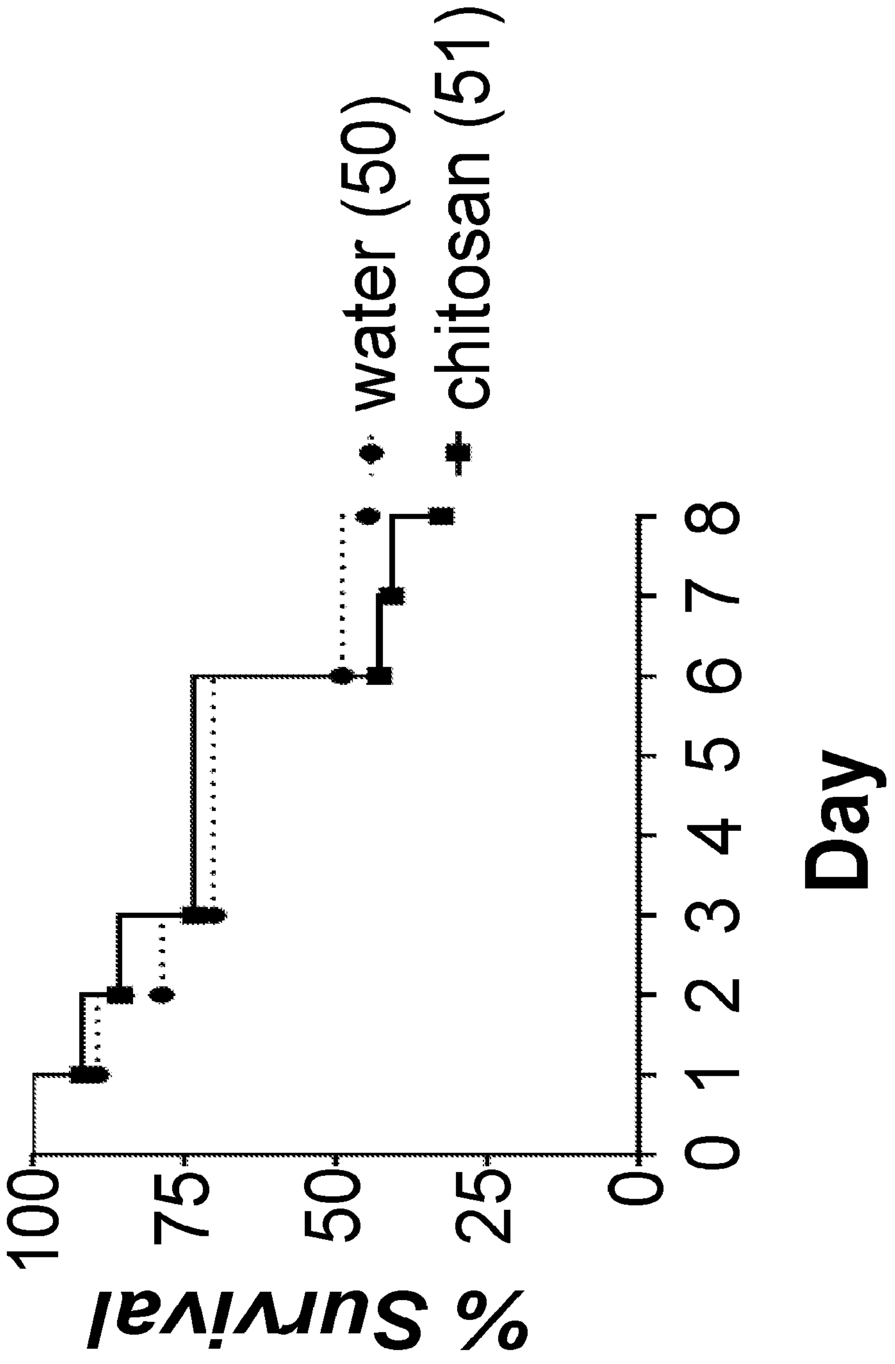

FIG. 22 is a graph showing there was a decrease in insect survival upon treatment with chitosan. First and second instar *A. pisum* aphids were treated by delivery through plants and leaf perfusion with just water or chitosan solution and survival was monitored daily over the course of the experiment. Number in parentheses represents the total number of aphids in the treatment group.

Figure 23:
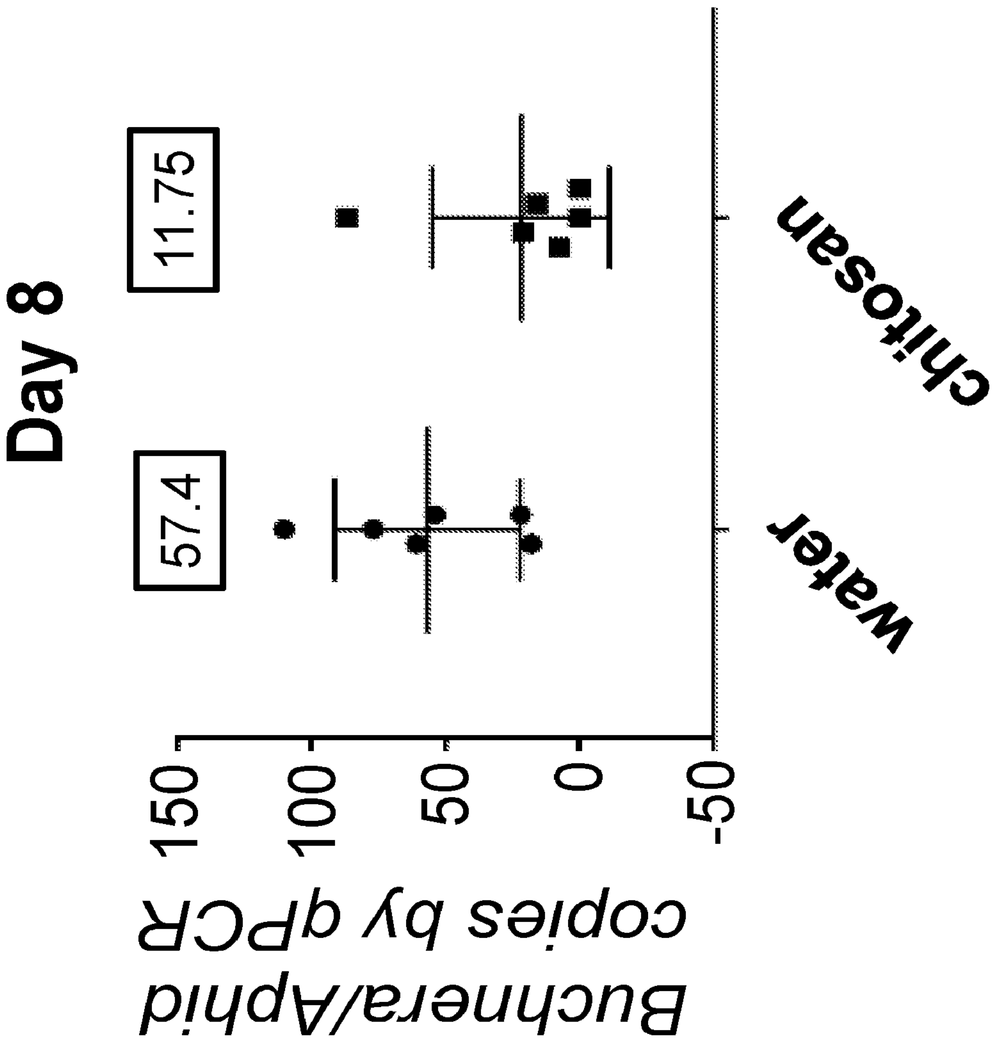

FIG. 23 is a graph showing treatment with chitosan reduced endosymbiotic *Buchnera*. First and second instar *A. pisum* aphids were treated by delivery through plants and leaf perfusion with water or 300 ug/ml chitosan in water. At 8 days post-treatment, DNA from aphids was extracted and qPCR was performed to determine the ratio of *Buchnera* DNA to aphid DNA. Shown is the mean ratio of *Buchnera* DNA to aphid DNA±SD of 6 aphids/group. The median value for each group is shown in box.

Figure 24:
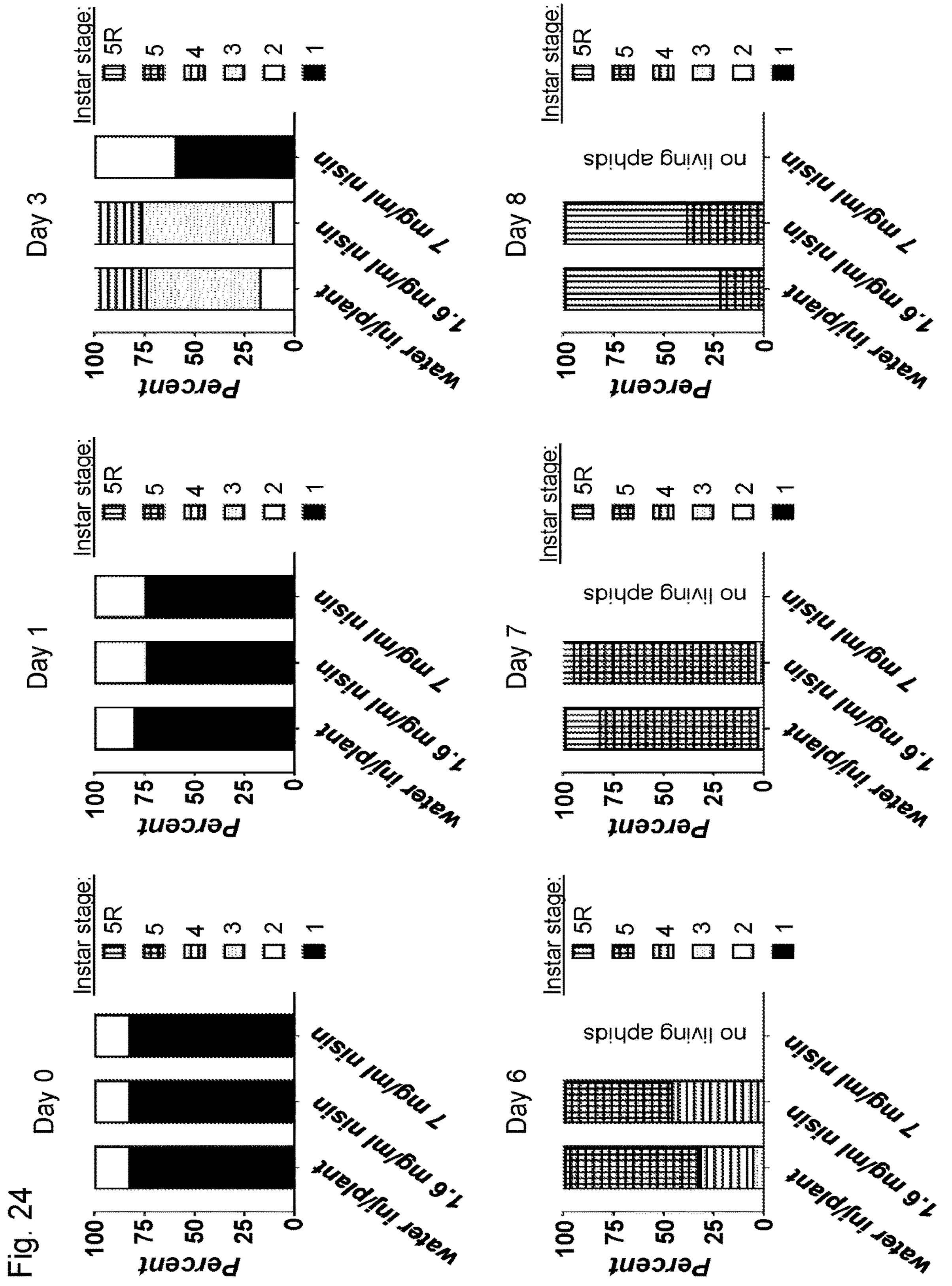

FIG. 24 is a panel of graphs showing treatment with nisin resulted in delayed aphid development. First and second instar LSR-2 *A. pisum* aphids were treated with water (control) or 1.6 or 7 mg/ml nisin via delivery by leaf injection and through the plant and development was measured over time. Shown are the percent of aphids at each life stage (1st, 2nd, 3rd, 4th, 5th, and 5 R (reproducing 5th) instar) at the indicated time point. N=56-59 aphids/group.

Figure 25:
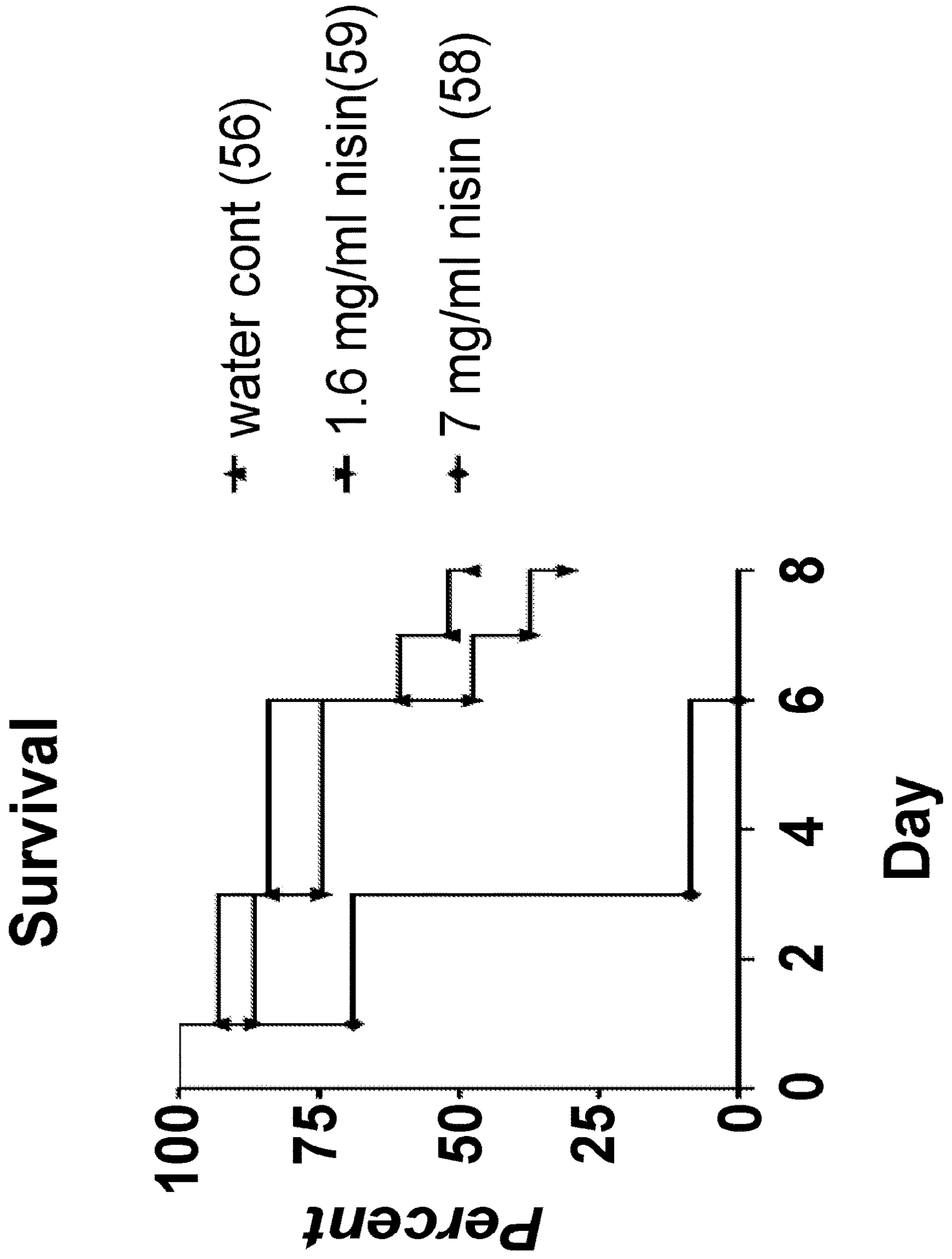

FIG. 25 is a graph showing there was a dose dependent decrease in insect survival upon treatment with nisin. First and second instar LSR-1 *A. pisum* aphids were treated with water (control) or 1.6 or 7 mg/ml nisin via delivery by leaf injection and through the plant and survival was monitored over time. Number in parentheses indicates the number of aphids/group. Statistically significant differences were determined by Log Rank (Mantel-Cox) test.

Figure 26:
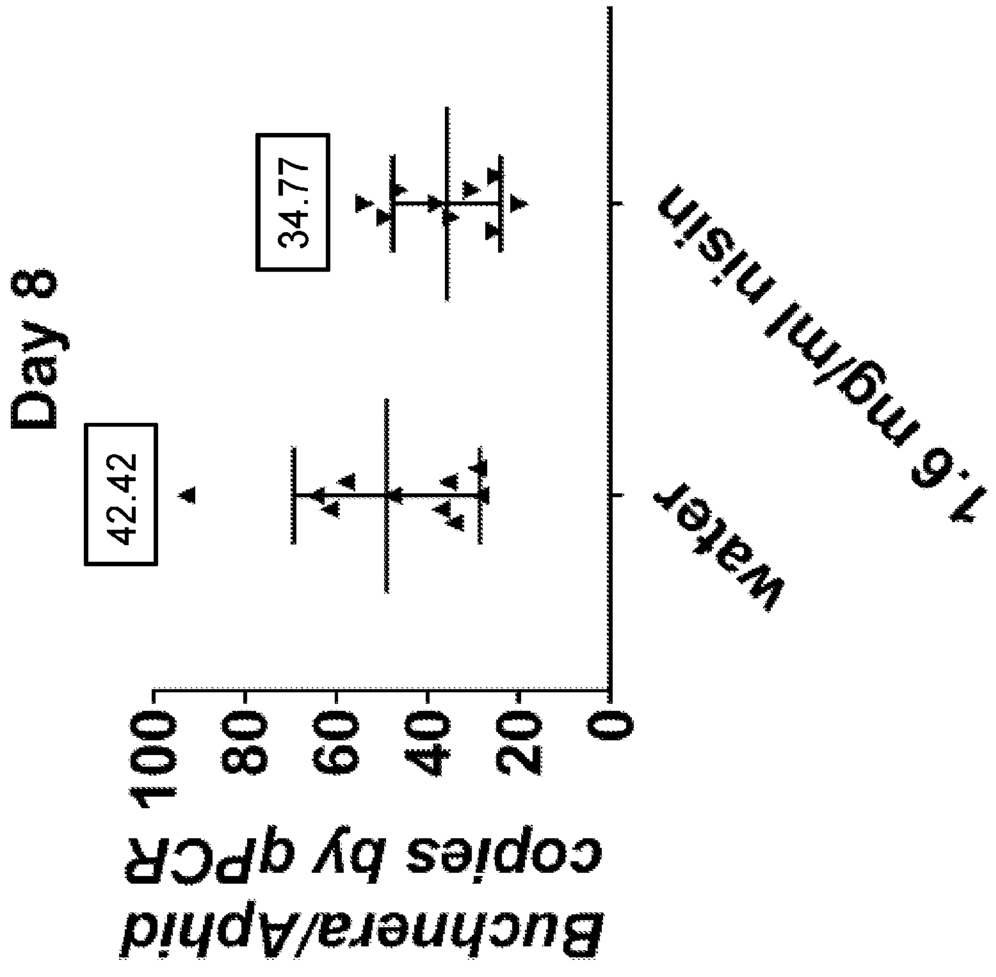

FIG. 26 is a graph showing treatment with nisin reduced endosymbiotic *Buchnera*. First and second instar LSR-1 *A. pisum* aphids were treated with water (control) or 1.6 mg/ml nisin via delivery by leaf injection and through the plant and DNA was extracted from select aphids at eight days post-treatment and used for qPCR to determine *Buchnera* copy numbers. Shown are the mean *Buchnera*/aphid ratios for each treatment+/−SEM. Number in the box above each experimental group indicates the median value for that group. Each data point represents a single aphid.

Figure 27:
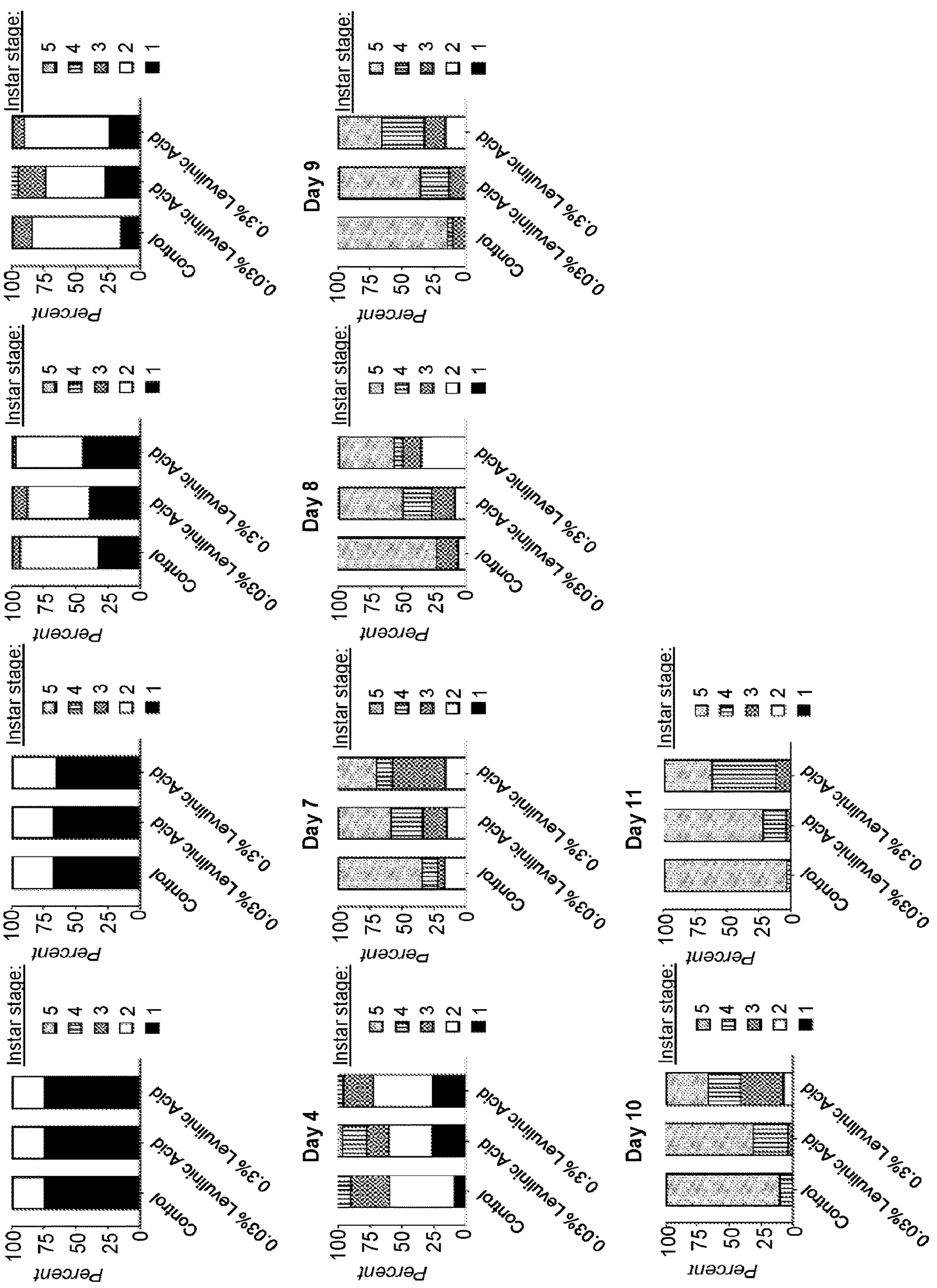

FIG. 27 is a panel of graphs showing treatment with levulinic acid resulted in delayed aphid development. First and second instar eNASCO *A. pisum* aphids were treated with water (control) or 0.03 or 0.3% levulinic acid via delivery by leaf injection and through the plant and development was measured over time. Shown are the percent of aphids at each life stage (1st, 2nd 3rd 4th and 5th instar) at the indicated time point. N=57-59 aphids/group.

Figure 28:
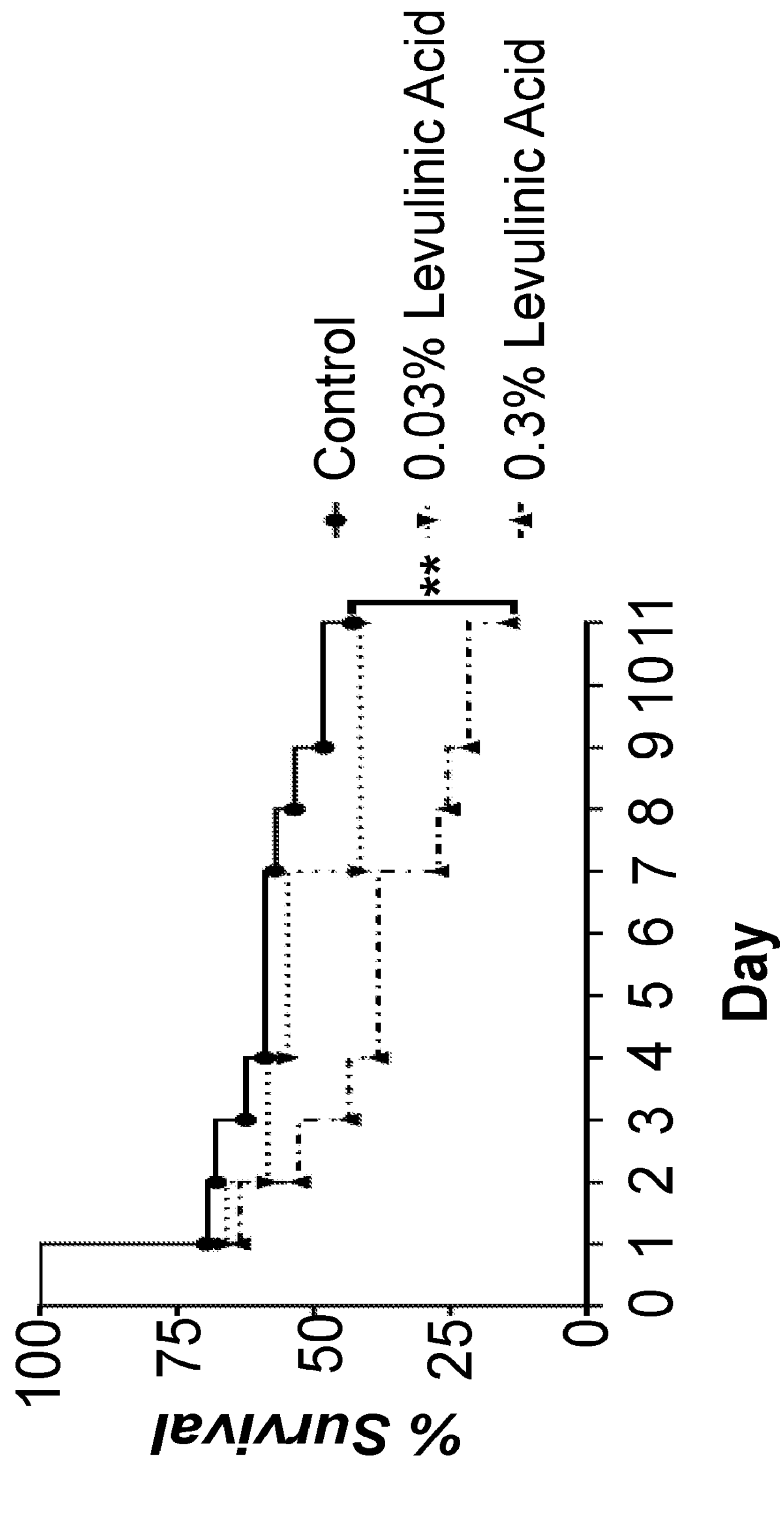

FIG. 28 is a graph showing there was a decrease in insect survival upon treatment with levulinic acid. First and second instar eNASCO *A. pisum* aphids were treated with water (control) or 0.03 or 0.3% levulinic acid via delivery by leaf injection and through the plant and survival was monitored over time. N=57-59 aphids/group. Statistically significant differences were determined by Log Rank (Mantel-Cox) test; **, $p<0.01$.

Figure 29:
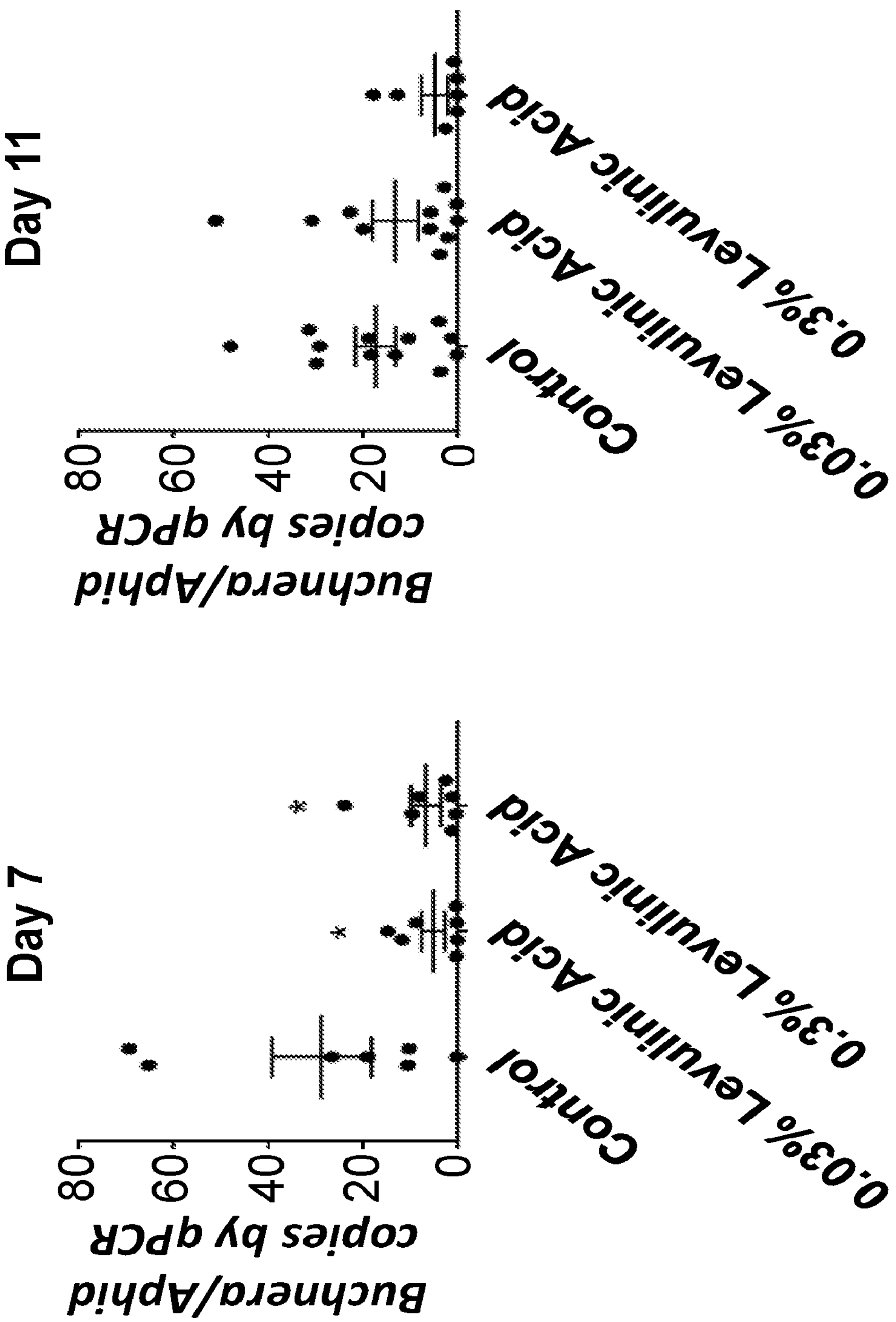

FIG. 29 is a panel of graphs showing treatment with levulinic acid reduced endosymbiotic *Buchnera*. First and second instar eNASCO *A. pisum* aphids were treated with water (control) or 0.03 or 0.3% levulinic acid via delivery by leaf injection and through the plant and DNA was extracted from select aphids at seven and eleven days post-treatment and used for qPCR to determine *Buchnera* copy numbers. Shown are the mean *Buchnera*/aphid ratios for each treatment+/−SEM. Statistically significant differences were determined by One-way ANOVA and Dunnett's Multiple Comparison Test; *, $p<0.05$. Each data point represents a single aphid.

Figure 30A:
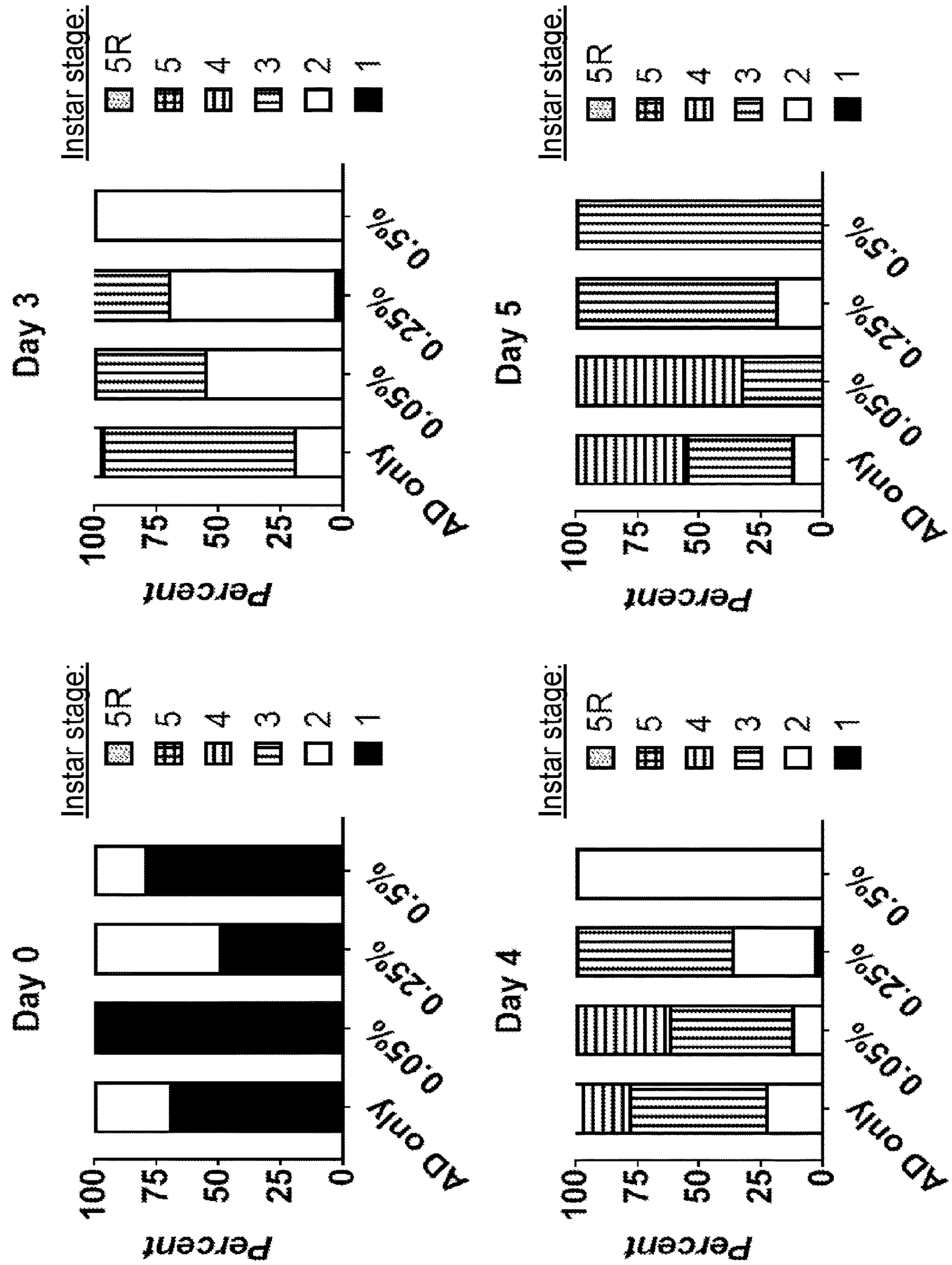
Figure 30B:
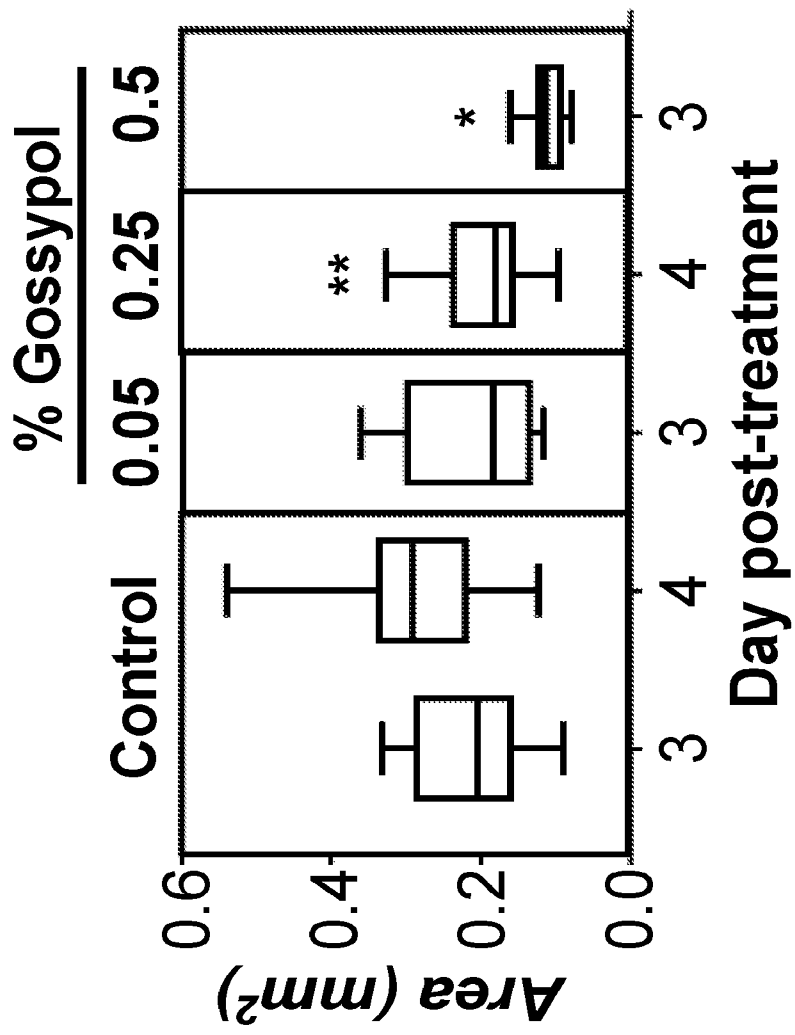

FIGS. 30A and 30B show graphs demonstrating that gossypol treatment resulted in delayed aphid development. First and second instar *A. pisum* aphids were treated by delivery through plants with artificial diet without essential amino acids (AD only), and artificial diet without essential amino acids with different concentrations of gossypol (0.05%, 0.25% and 0.5%). Developmental stage was monitored throughout the experiment. FIG. 30A is a series of graphs showing the mean number of aphids at each developmental stage (1st instar, 2nd instar, 3rd instar, 4th instar, 5th instar, or 5 R which represents a reproducing 5th instar) per treatment group. At the indicated time, aphids were imaged and their size was determined using Image J. FIG. 30B is a graph showing the mean aphid area±SD of artificial diet treated (Control) or gossypol treated aphids. Statistical significance was determined using a One-Way ANOVA followed by Tukey's post-test. *, $p<0.05$. **, $p<0.01$.

Figure 31:
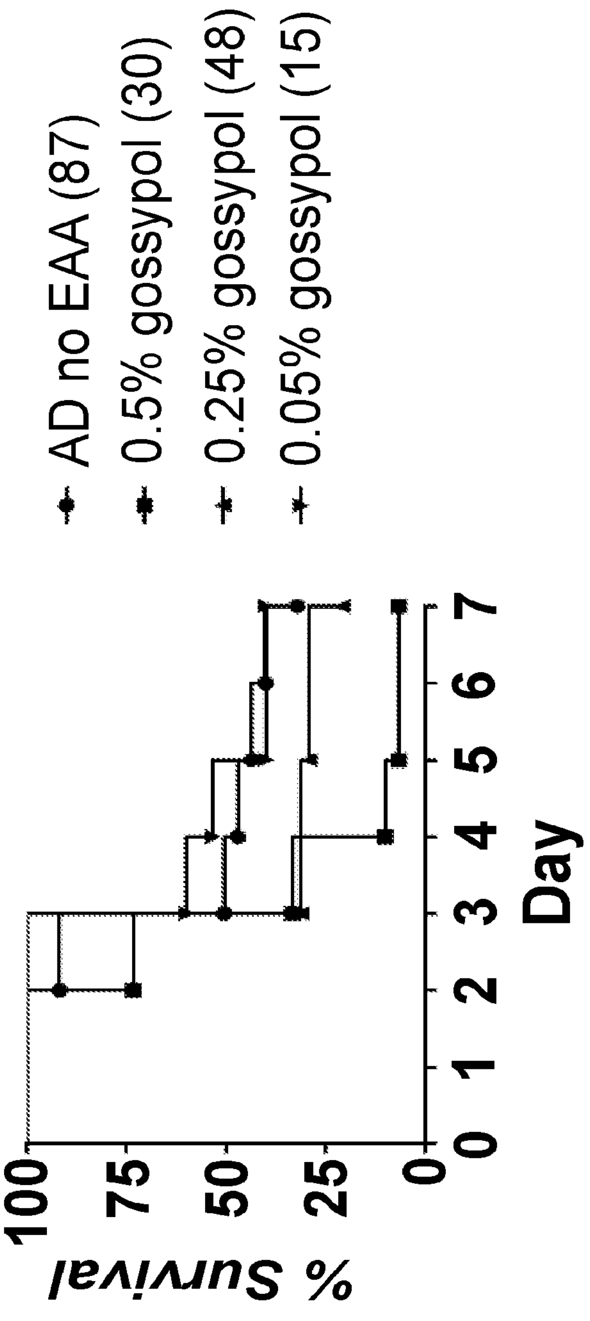

FIG. 31 is a graph showing a dose-dependent decrease in survival of aphids upon treatment with the allelochemical gossypol. First and second instar *A. pisum* aphids were treated by delivery through plants with artificial diet without essential amino acids (AD no EAA), artificial diet without essential amino acids with 0.5% gossypol acetic acid (0.5% gossypol), artificial diet without essential amino acids with 0.25% gossypol acetic acid (0.25% gossypol), and artificial diet without essential amino acids and 0.05% gossypol acetic acid (0.05% gossypol) and survival was monitored daily over the course of the experiment. Number in parentheses represents the essential amino acids number of aphids in each group. Statistically significant differences were determined by Log-Rank test and AD no EAA and 0.5% gossypol are significantly different, $p=0.0002$.

Figure 32A:
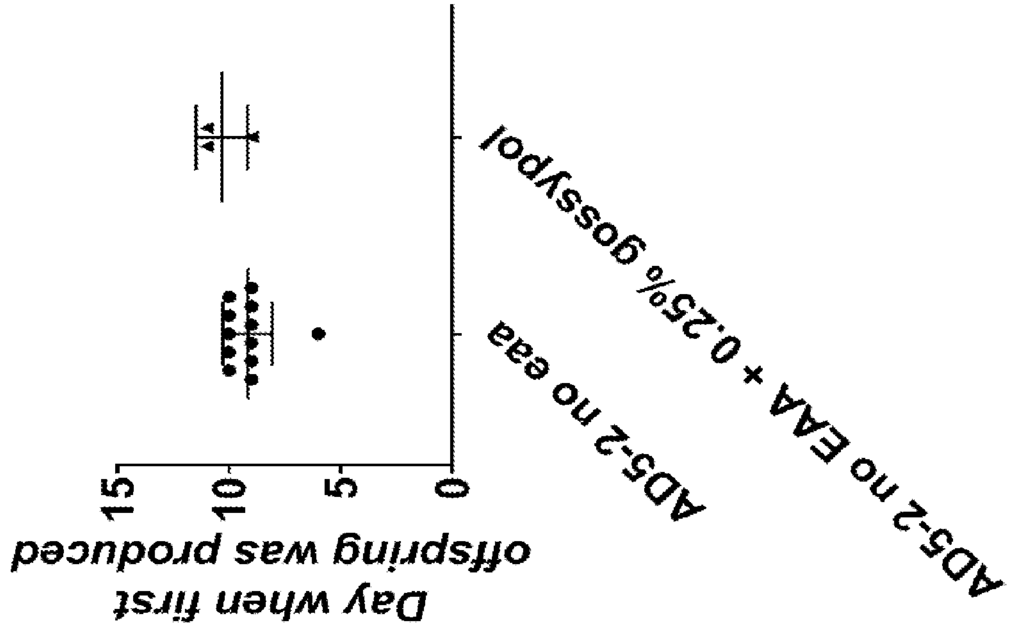
Figure 32B:
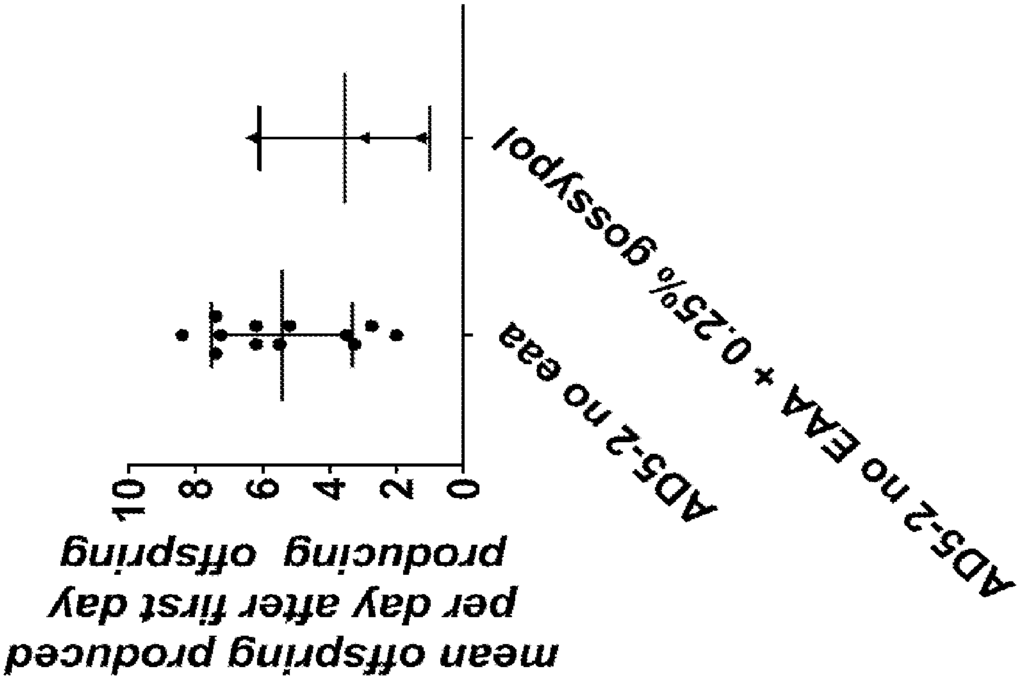

FIGS. 32A and 32B are two graphs showing that treatment with 0.25% gossypol resulted in decreased fecundity. First and second instar *A. pisum* aphids were treated by delivery through plants with artificial diet without essential amino acids (AD5-2 no EAA), or artificial diet without essential amino acids with 0.25% gossypol acetic acid (AD5-2 no EAA+0.25% gossypol), and fecundity was determined throughout the time course of the experiment. FIG. 32A shows the mean day±SD at which aphids began producing offspring was measured and gossypol treatment delayed production of offspring. FIG. 32B shows the mean number of offspring produced after the aphid began a reproducing adult±SD was measured and gossypol treatment results in decreased number of offspring produced. Each data point represents one aphid.

Figure 33:
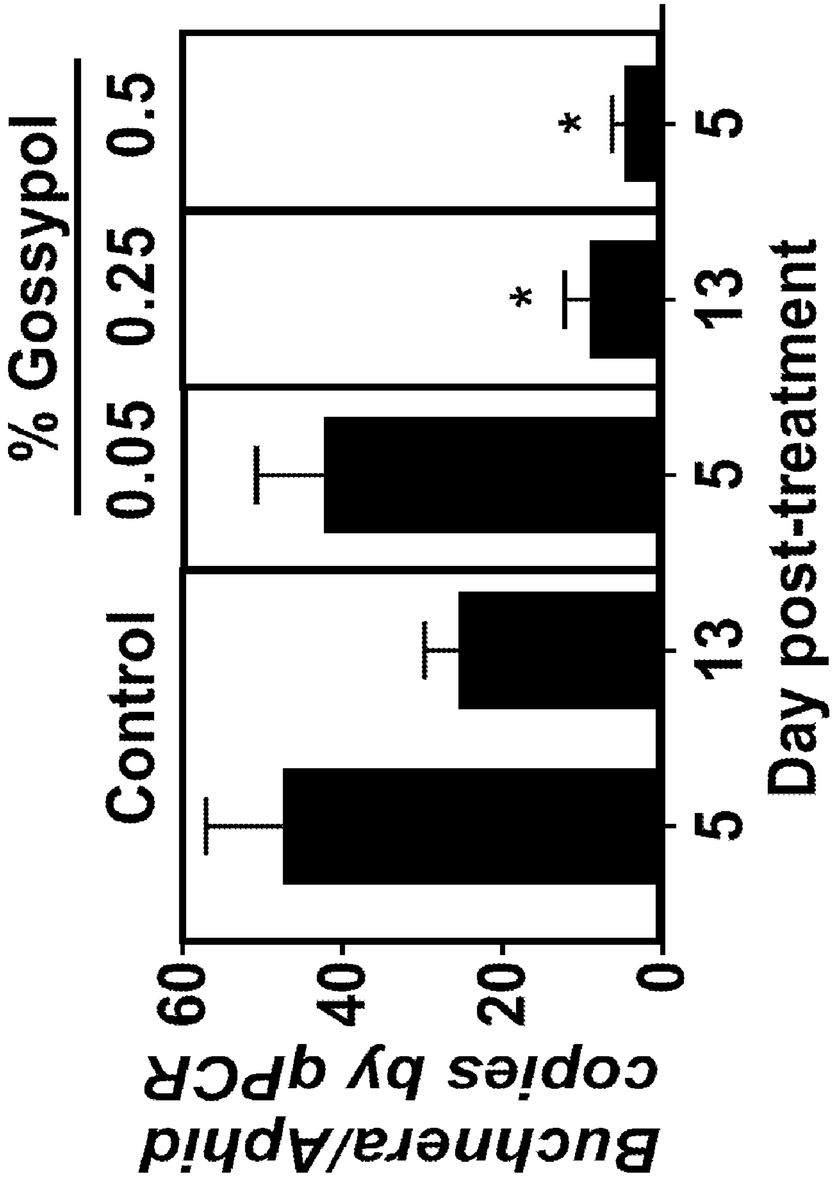

FIG. 33 is a graph showing that treatment with different concentrations of gossypol reduced endosymbiotic *Buchnera*. First and second instar *A. pisum* aphids were treated by delivery through plants with artificial diet without essential amino acids (Control)) or artificial diet without essential amino acids with 0.5%, 0.25%, or 0.05% gossypol. At 5 or 13 days post-treatment, DNA from aphids was extracted and qPCR was performed to determine the ratio of *Buchnera* DNA to aphid DNA. Shown is the mean ratio of *Buchnera* DNA to aphid DNA±SD of 2-6 aphids/group. Statistically significant differences were determined by Unpaired T-test; *, $p<0.05$.

Figure 34:
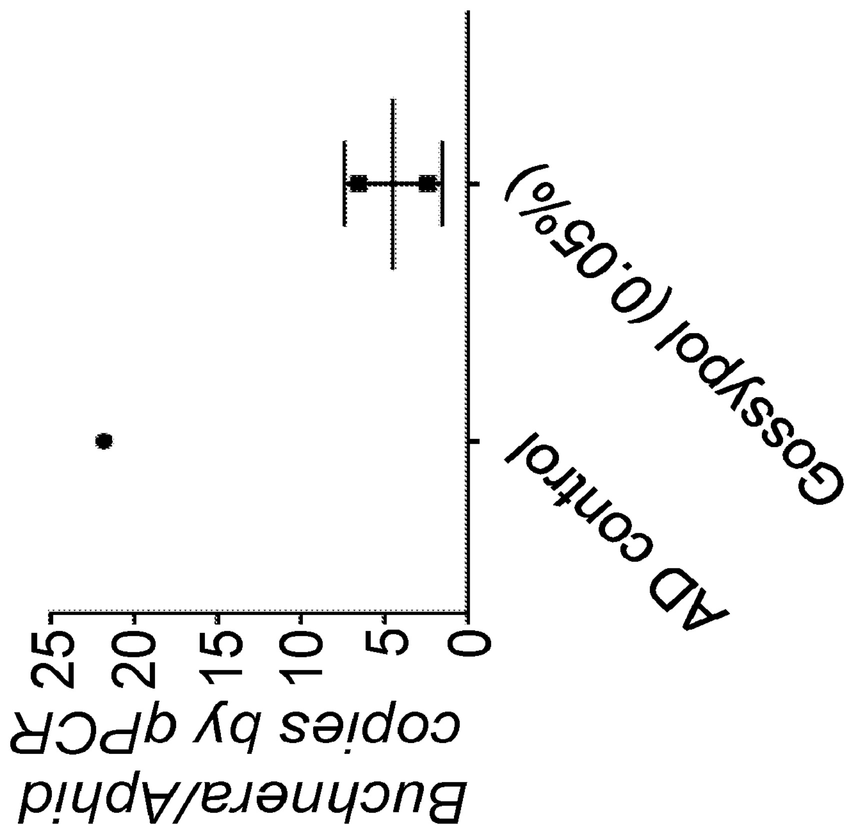

FIG. 34 is a graph showing that microinjection of gossypol resulted in decreased *Buchnera* levels in aphids. *A. pisum* LSR-1 aphids <3rd instar stage (nymphs) were injected with 20 nl of artificial diet without essential amino acids (AD) or artificial diet without essential amino acids with 0.05% gossypol (gossypol (0.05%)). Three days after injection, DNA was extracted from aphids and *Buchnera* levels were assessed by qPCR. Shown are the mean ratios of *Buchnera*/aphid DNA±SD. Each data point represents one aphid.

Figure 35:
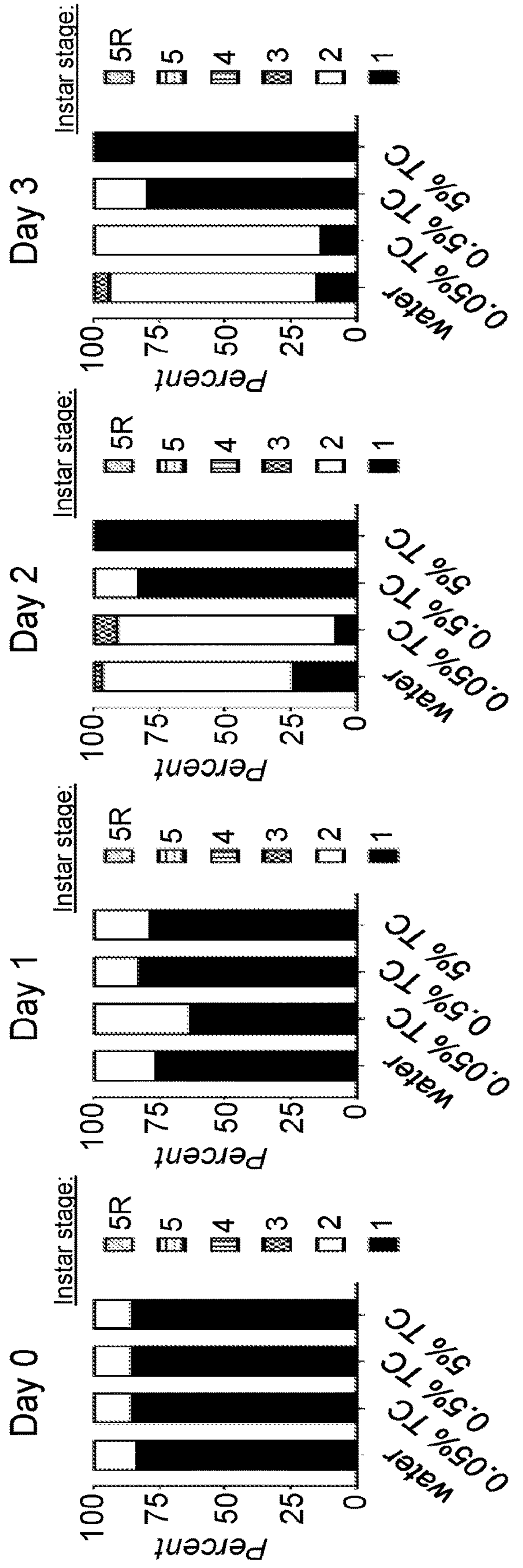

FIG. 35 is a panel of graphs showing Trans-cinnemaldehyde treatment resulted in delayed aphid development. First and second instar *A. pisum* aphids were treated by delivery through plants with water and water with different concentrations of trans-cinnemaldehyde (TC, 0.05%, 0.5%, and 5%). Developmental stage was monitored throughout the experiment. Shown are the mean number of aphids at each developmental stage (1st instar, 2nd instar, 3rd instar, 4th instar, 5th instar, or 5 R which represents a reproducing 5th instar) per treatment group. N=40-49 aphids/experimental group.

Figure 36:
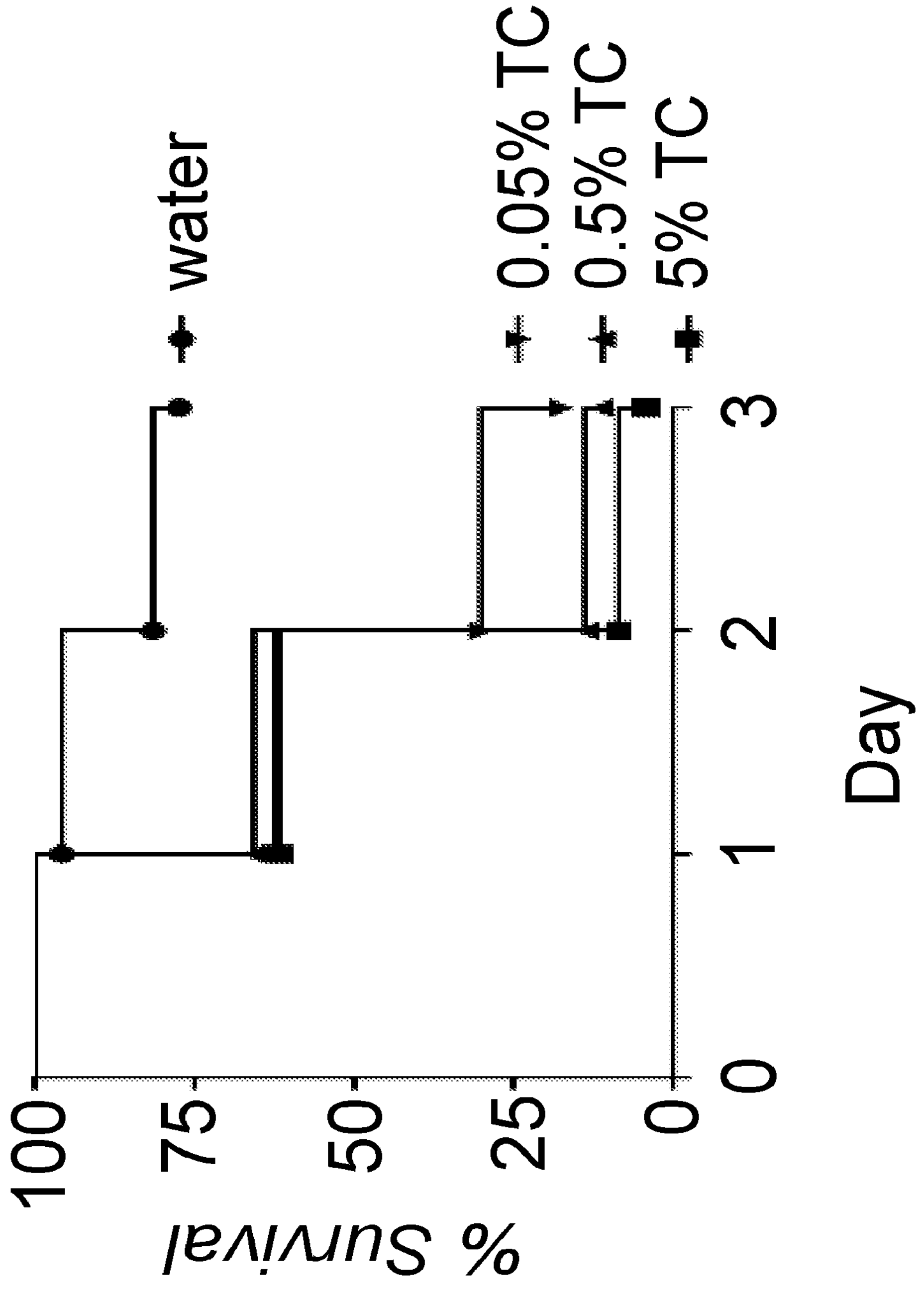

FIG. 36 is a graph showing there was a dose-dependent decrease in survival upon treatment the natural antimicrobial trans-cinnemaldehyde. First and second instar *A. pisum* aphids were treated by delivery through plants with water and water with different concentrations of trans-cinnemaldehyde (TC, 0.05%, 0.5%, and 5%). Survival was monitored throughout the course of the treatment. Statistically significant differences were determined by Log-Rank test. N=40-49 aphids/group.

Figure 37:
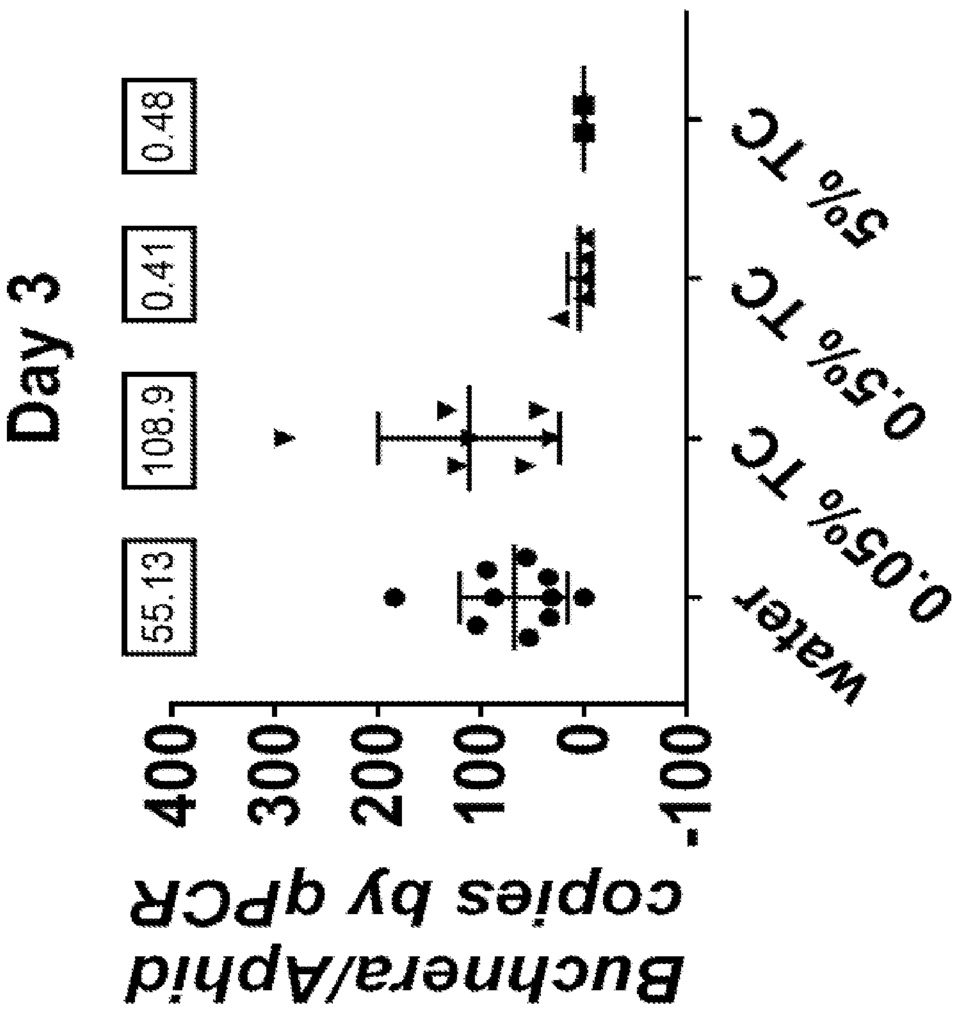

FIG. 37 is a graph showing treatment with different concentrations of trans-cinnemaldehyde reduced endosymbiotic *Buchnera*. First and second instar *A. pisum* aphids were treated by delivery through plants with water and water with different concentrations of trans-cinnemaldehyde (0.05%, 0.5%, and 5%). At 3 days post-treatment, DNA from aphids was extracted and qPCR was performed to determine the ratio of *Buchnera* DNA to aphid DNA. Shown is the mean ratio of *Buchnera* DNA to aphid DNA±SD of 2-11 aphids/group. The median of each treatment group is shown in the box above the data points. Statistically significant differences were determined by Unpaired T-test; *, $p<0.05$. There was a statistically significant difference between the water control and the 0.5% trans-cinnemaldehyde group.

Figure 38:
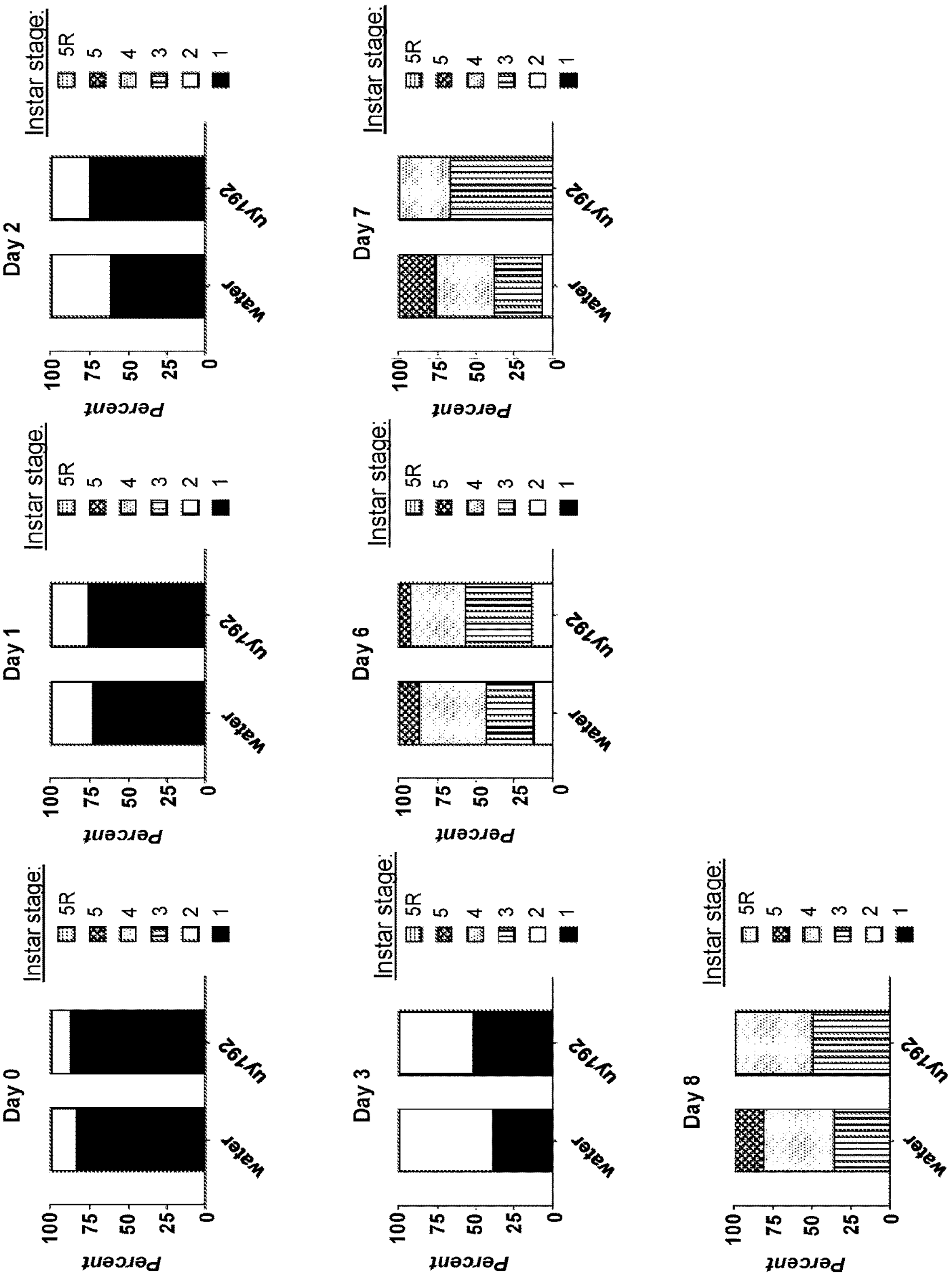

FIG. 38 is a panel of graphs showing treatment with scorpion peptide Uy192 resulted in delayed aphid development. First and second instar *A. pisum* aphids were treated by delivery through plants and leaf perfusion with the control solution (water), and 100 ug/ml Uy192 in water. a) developmental stage was monitored throughout the experiment. Shown are the percent of aphids at each developmental stage (1st instar, 2nd instar, 3rd instar, 4th instar, 5th instar, or 5 R which represents a reproducing 5th instar) per treatment group.

Figure 39:
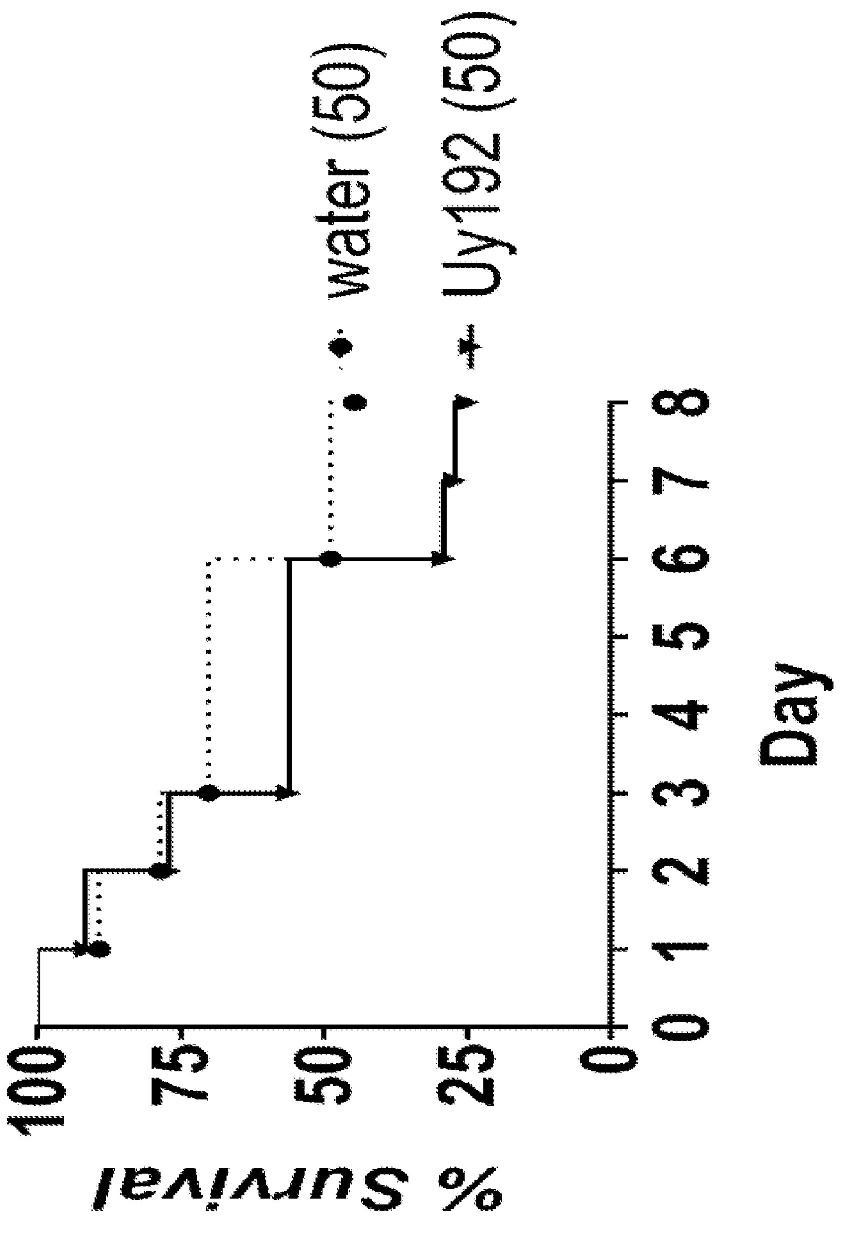

FIG. 39 is a graph showing there was a decrease in insect survival upon treatment with the scorpion AMP Uy192. First and second instar *A. pisum* aphids were treated by delivery through plants and leaf perfusion with just water or Uy192 solution and survival was monitored daily over the course of the experiment. Number in parentheses represents the total number of aphids in the treatment group.

Figure 40:
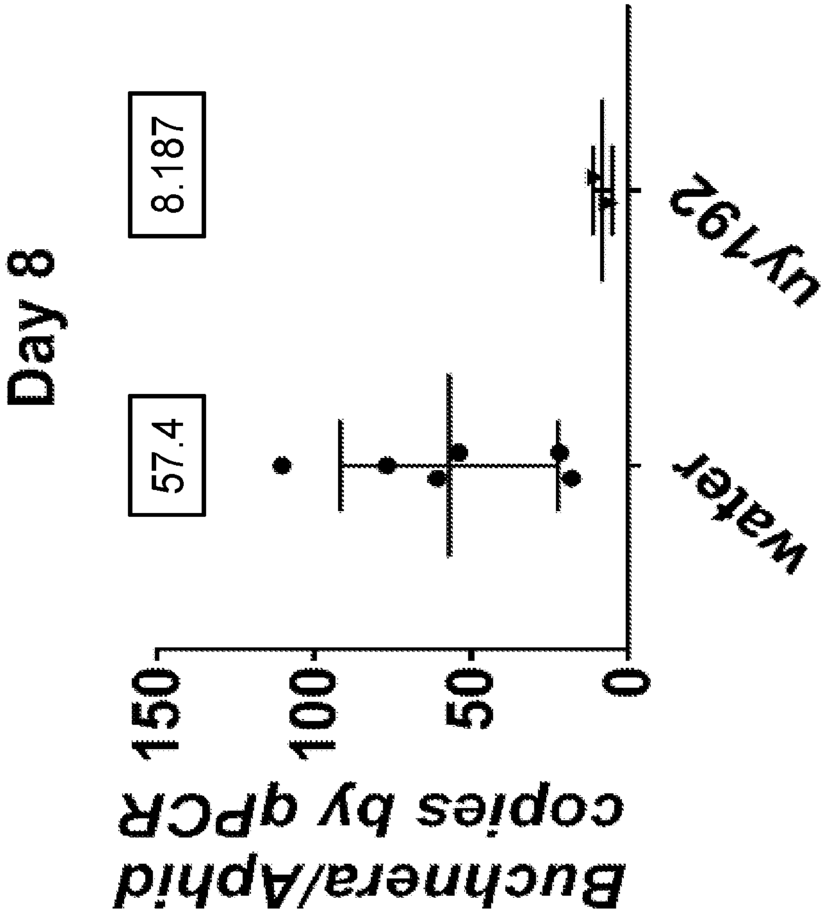

FIG. 40 is a graph showing treatment with Uy192 reduced endosymbiotic *Buchnera*. First and second instar *A. pisum* aphids were treated by delivery through plants and leaf perfusion with water or 100 ug/ml Uy192 in water, at 8 days post-treatment, DNA from aphids was extracted and qPCR was performed to determine the ratio of *Buchnera* DNA to aphid DNA. Shown is the mean ratio of *Buchnera* DNA to aphid DNA±SD of 2-6 aphids/group. The median value for each group is shown in box.

Figure 41:
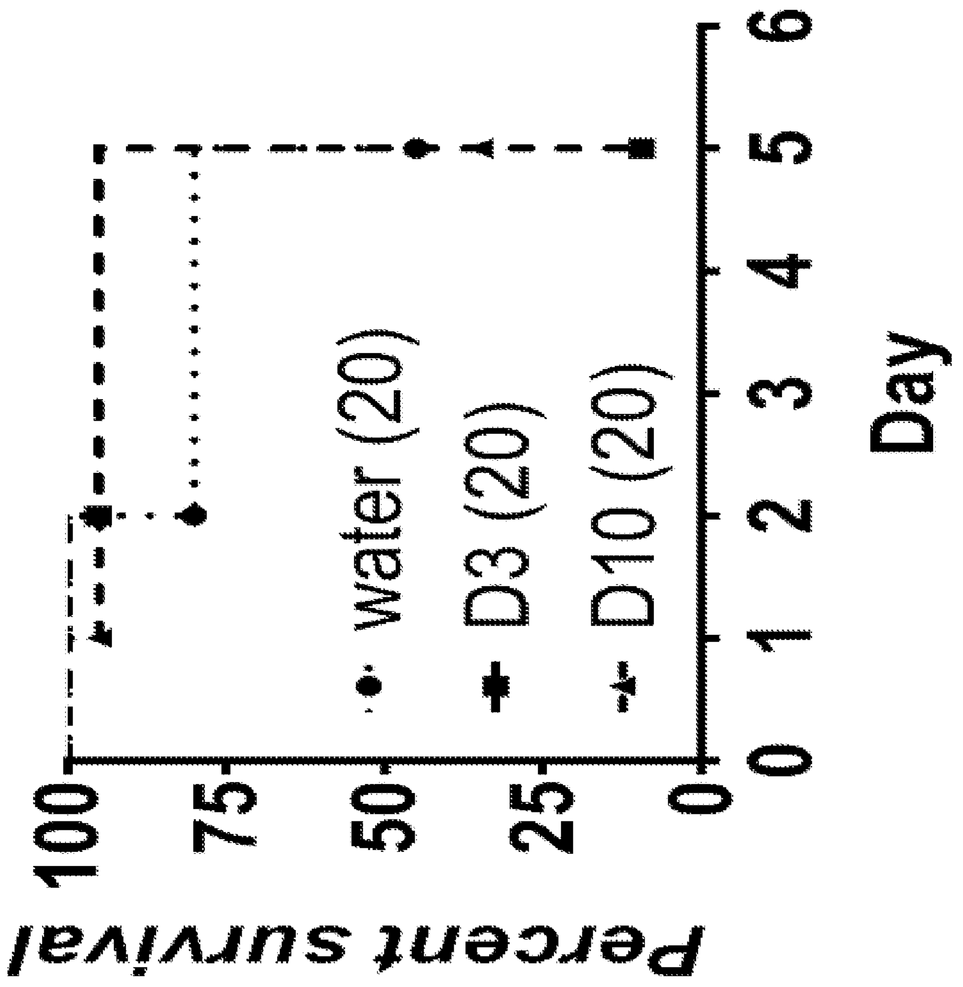

FIG. 41 is a graph showing a decrease in survival in aphids microinjected with scorpion peptides D10 and D3. LSR-1 *A. pisum* aphids were microinjected with water (control) or with 100 ng of either scorpion peptide D3 or D10. After injection, aphids were released to fava bean leaves and survival was monitored throughout the course of the experiment. The number in parentheses indicates the number of aphids in each experimental treatment group.

Figure 42:
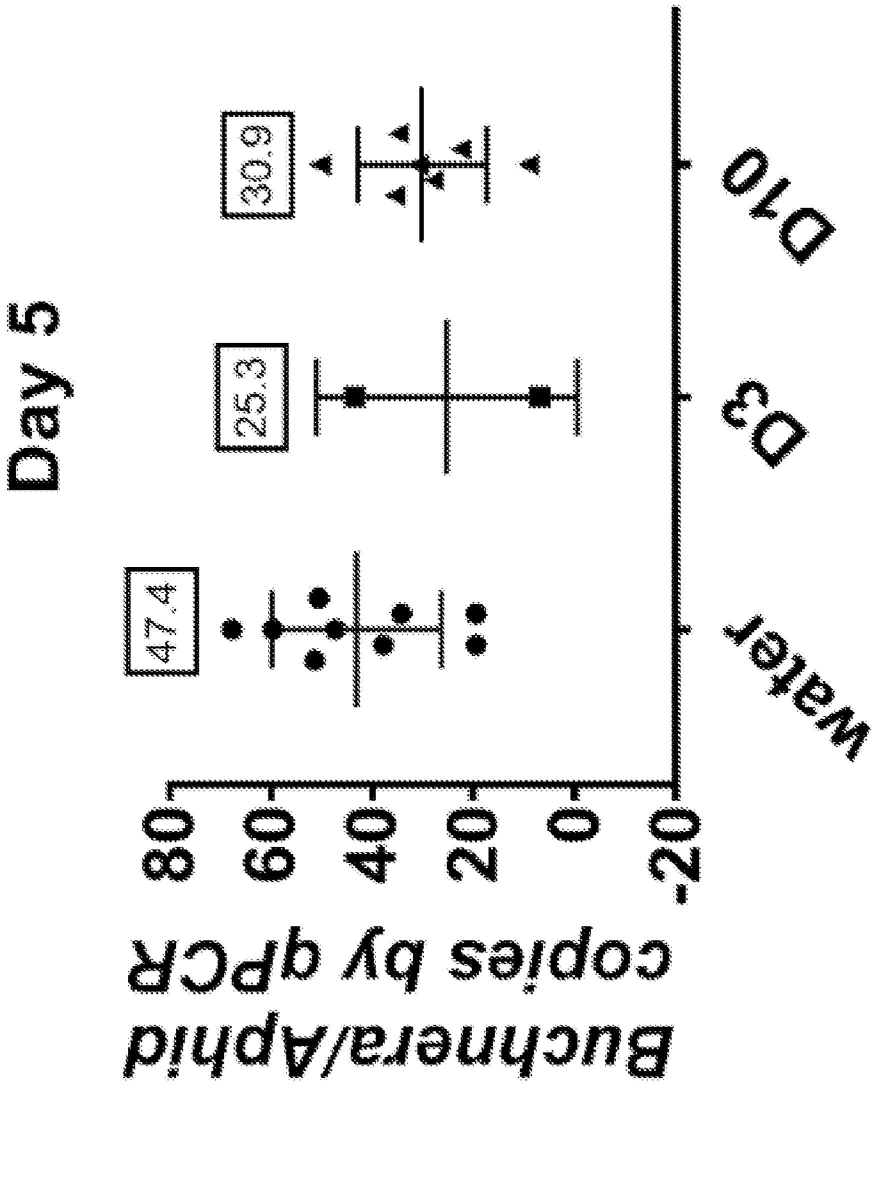

FIG. 42 is a graph showing a decrease in endosymbiont titers upon injection with scorpion peptides D3 and D10. LSR-1 *A. pisum* aphids were microinjected with water (control) or with 100 ng of either scorpion peptide D3 or D10. After injection, aphids were released to fava bean leaves and at 5 days post-treatment, DNA was extracted from the remaining living aphids and qPCR was performed to determine the ratio of *Buchnera*/aphid DNA. Shown are the mean±SD of each treatment group. N=2-9 aphids/group. The number above each treatment group in the box represents the median of the dataset.

Figure 43:
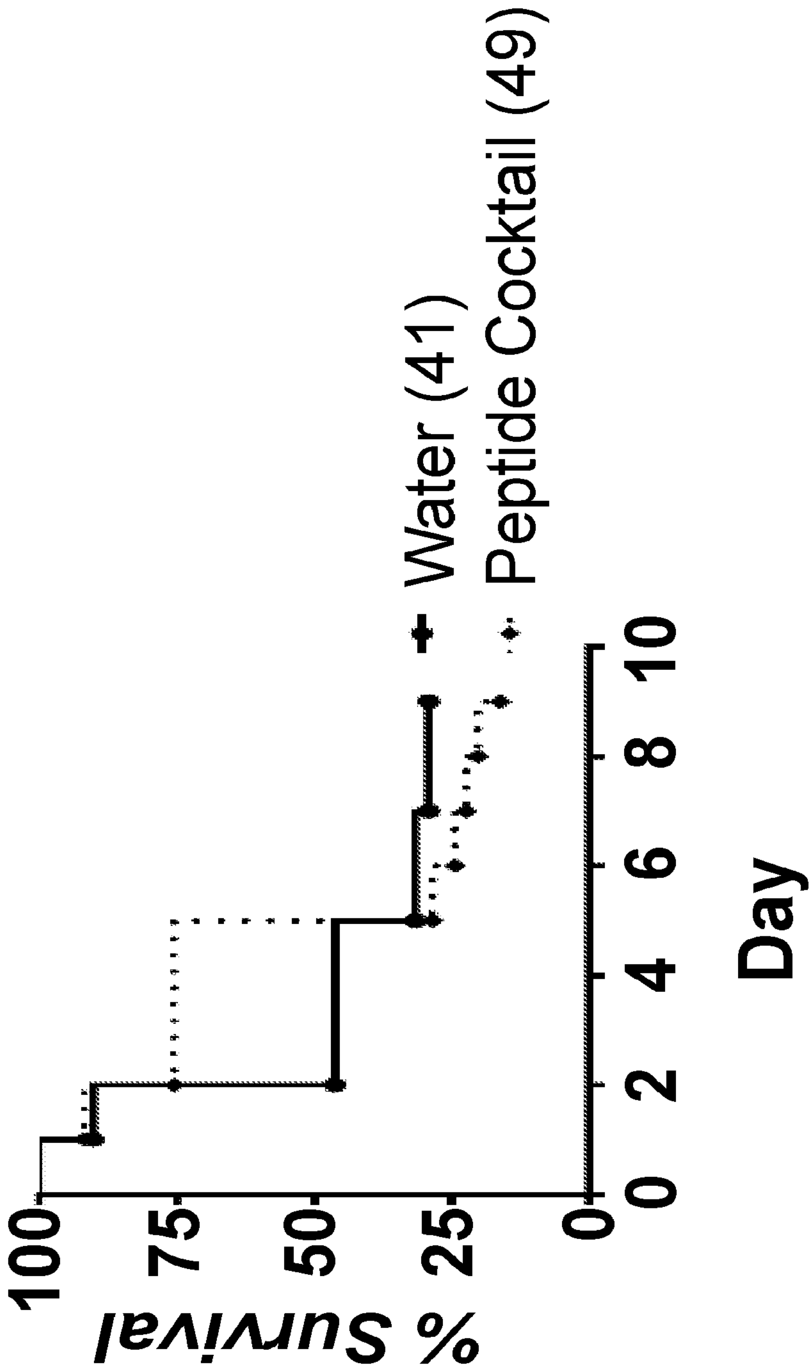

FIG. 43 is a graph showing a decrease in insect survival upon treatment with a cocktail of scorpion AMPs. First and second instar eNASCO aphids were treated by delivery through leaf perfusion and through plants with a cocktail of scorpion peptides (40 μg/ml of each of Uy17, D3, UyCt3, and D10) and survival was monitored over the course of the experiment. The number in parentheses represents the number of aphids in each treatment group.

Figure 44:
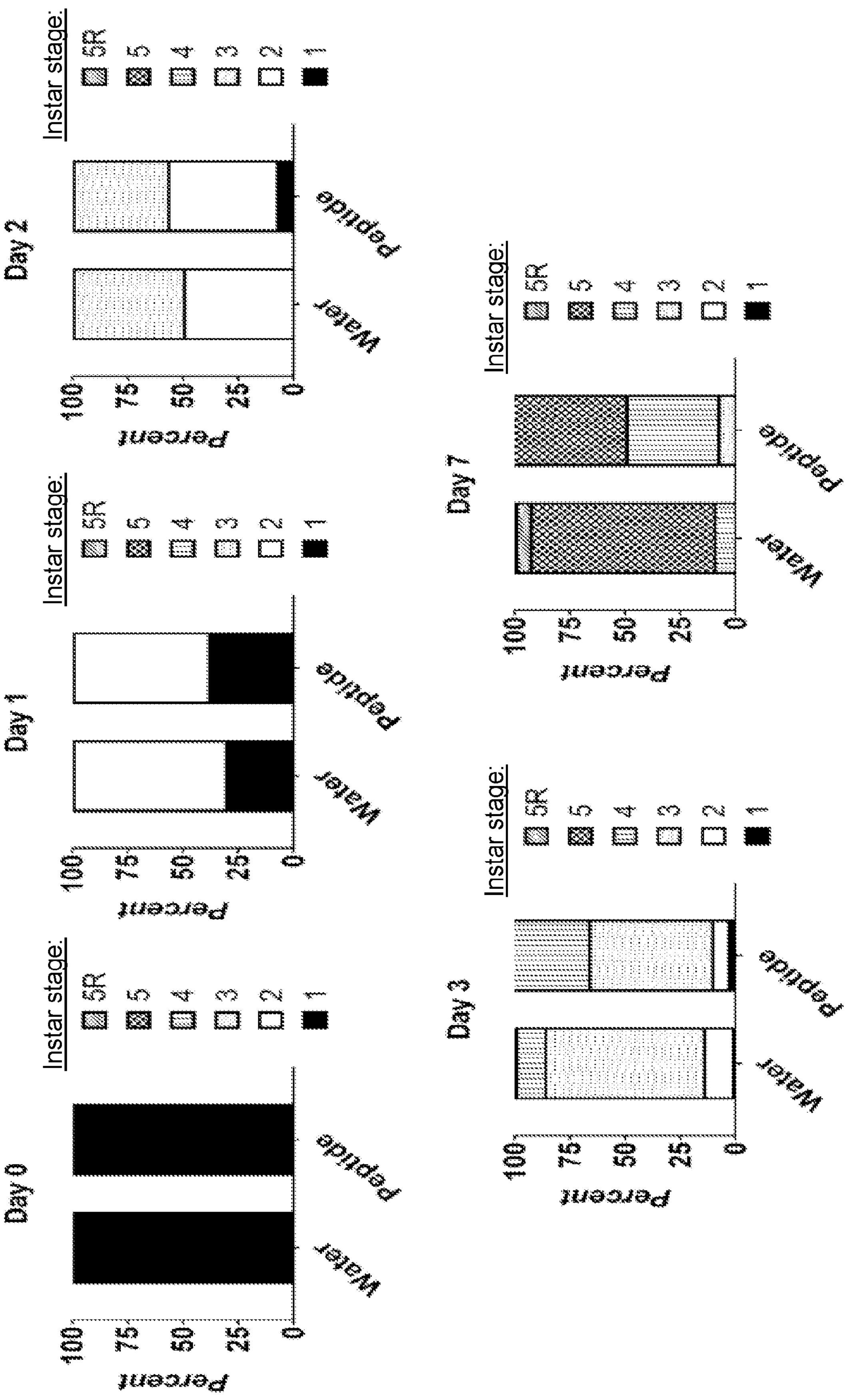

FIG. 44 is a panel of graphs showing treatment with scorpion peptide fused to a cell penetrating peptide resulted in delayed aphid development. First instar LSR-2 *A. pisum* aphids were treated with water (control) or 100 μg/ml Uy192+CPP+FAM via delivery by leaf injection and through the plant and development was measured over time. Shown are the percent of aphids at each life stage (1st, 2nd, 3rd, 4th, 5th, and 5 R (reproducing 5th) instar) at the indicated time point. N=90 aphids/group.

Figure 45:
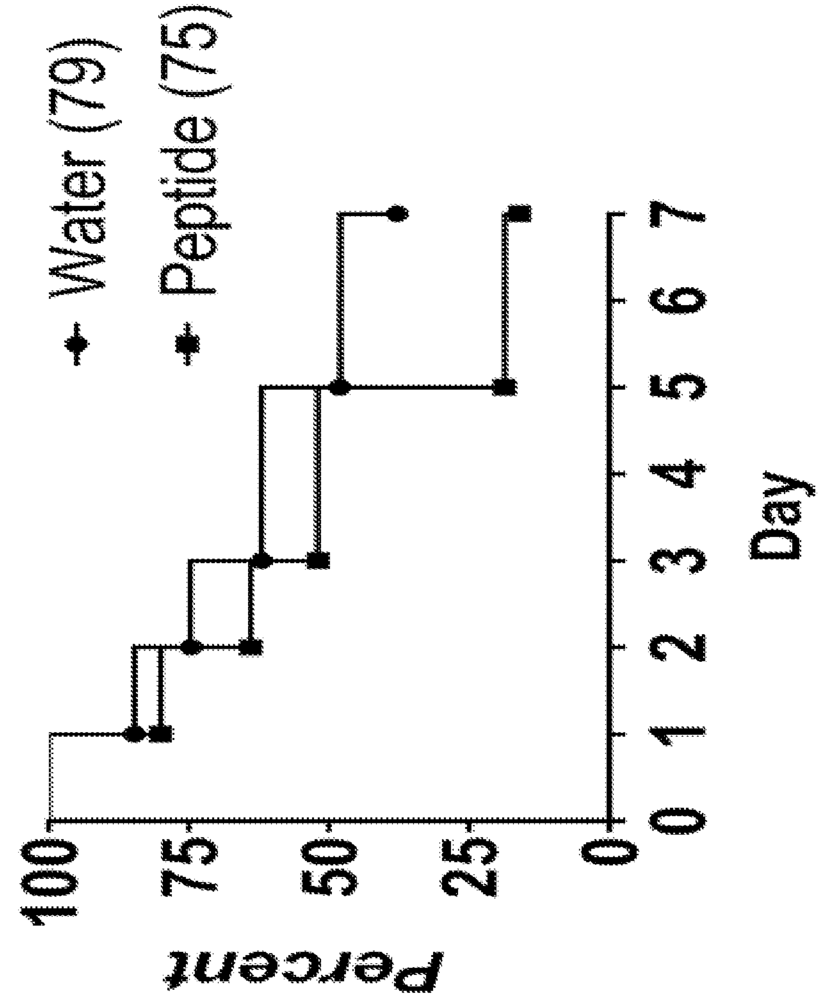

FIG. 45 is a graph showing treatment of aphids with a scorpion peptide fused to a cell penetrating peptide increased mortality. First instar LSR-1 *A. pisum* aphids were treated with water or 100 μg/ml UY192+CPP+FAM (peptide) in water delivered by leaf injection and through the plant. Survival was monitored over time. The number in parentheses indicates the number of aphids/group. Statistically significant differences were determined by Log Rank (Mantel-Cox) test and there is a significant difference between the two experimental groups (p=0.0036).

Figure 46:
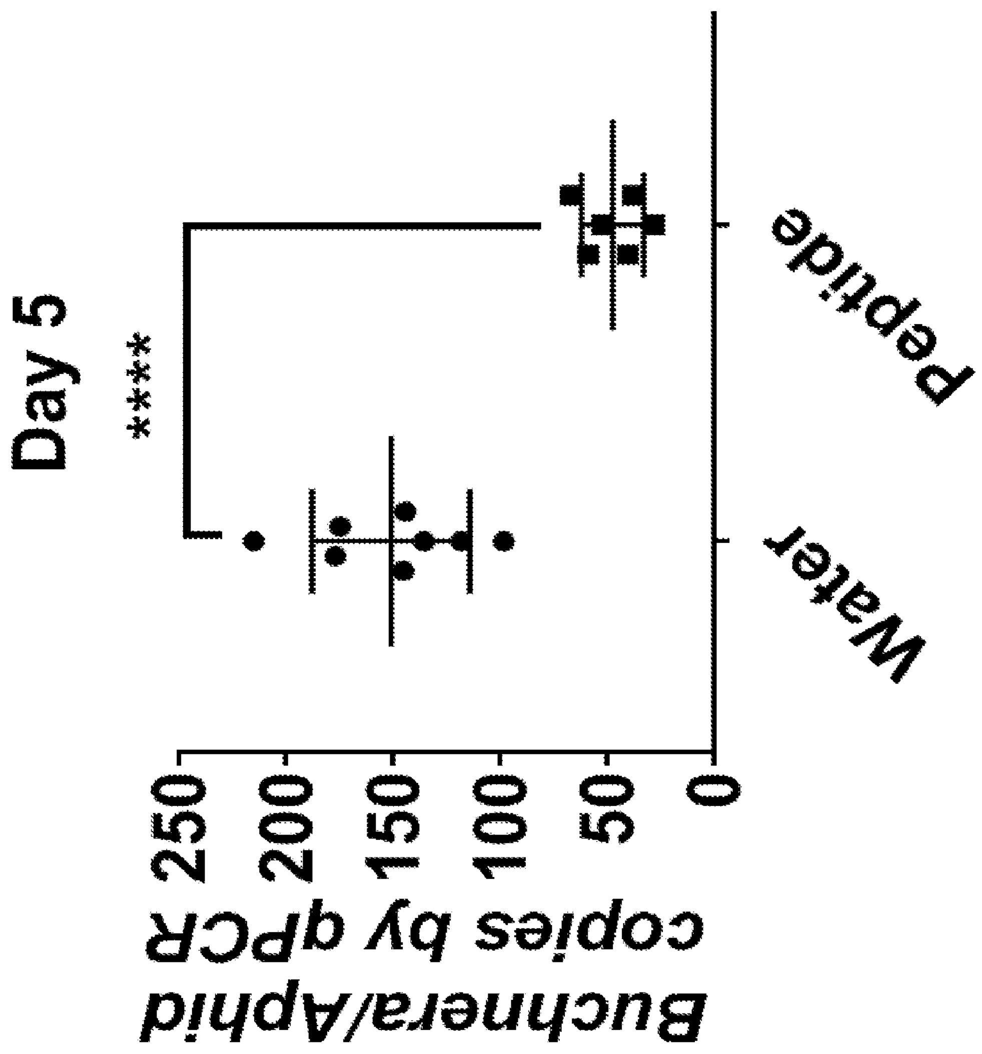

FIG. 46 is a graph showing treatment with Uy192+CPP+FAM reduced endosymbiotic *Buchnera*. First instar LSR-1 *A. pisum* aphids were treated with water or 100 μg/mlUy192+CPP+FAM (peptide) in water delivered by leaf injection and through the plant. DNA was extracted from select aphids at five days post-treatment and used for qPCR to determine *Buchnera* copy numbers. Shown are the mean *Buchnera*/aphid ratios for each treatment +/−SEM. Number in the box above each experimental group indicates the median value for that group. Each data point represents a single aphid. Statistically significant differences were determined by Student's T-test; ****, p<0.0001.

Figure 47:
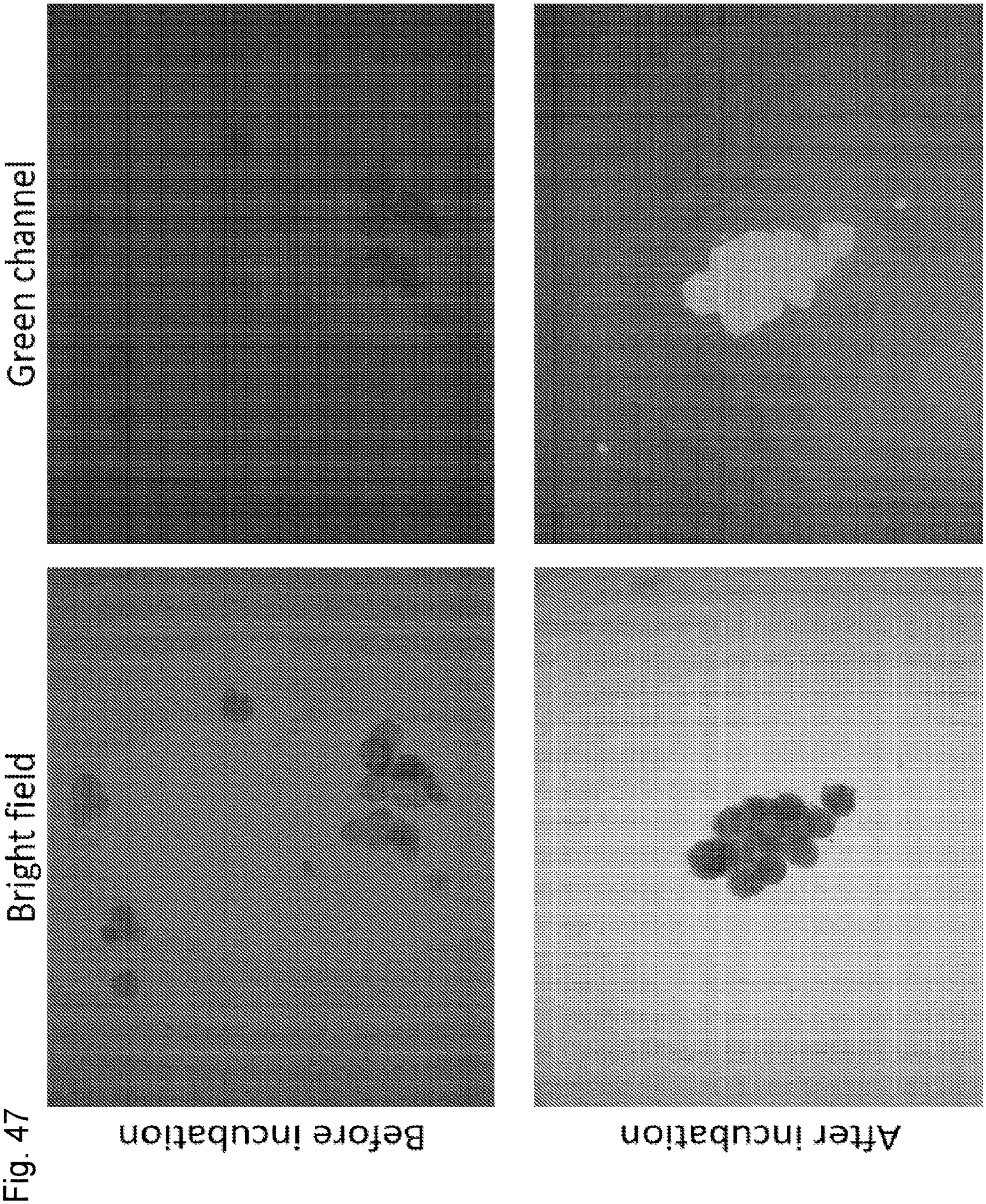

FIG. 47 is a panel of images showing Uy192+CPP+FAM penetrated bacteriocyte membranes. Bacteriocytes were dissected from the aphids and incubated with 250 ug/ml of the Uy192+CPP+FAM peptide for 30 min. Upon washing and imaging, the Uy192+CPP+FAM can be seen at high quantities inside the bacteriocytes.

Figure 48B:
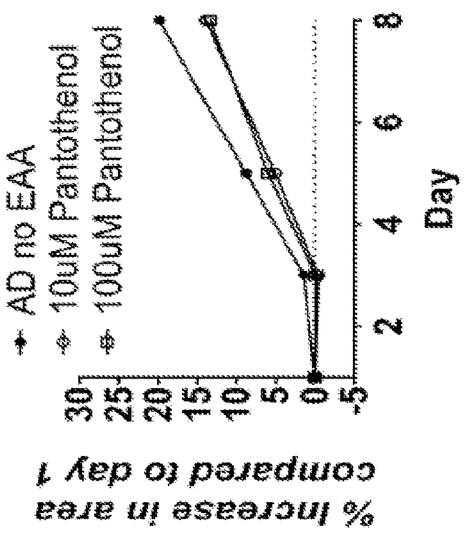
Figure 48A:
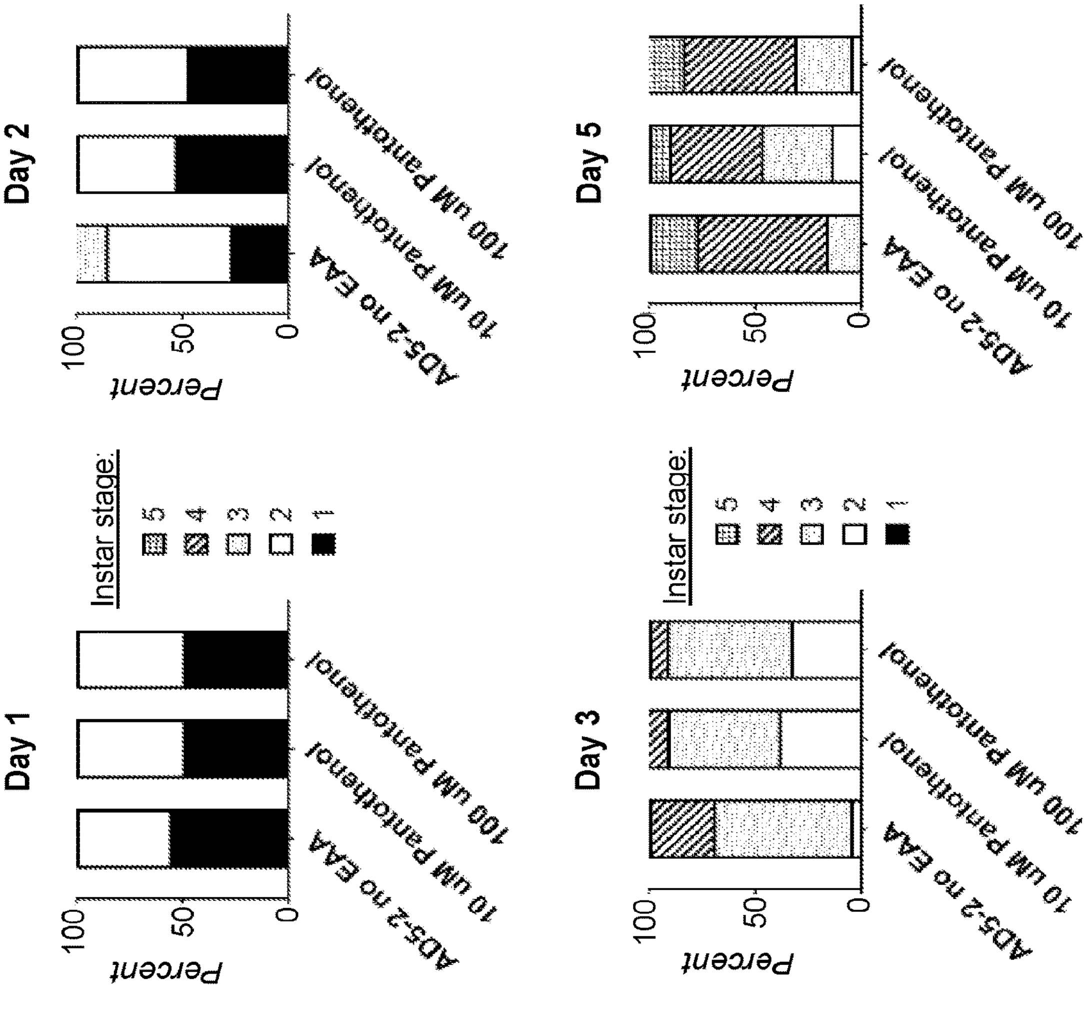

FIG. 48A and FIG. 48B are a panel of graphs showing pantothenol treatment delayed aphid development. First instar and second eNASCO aphids were treated by delivery through plants with three different conditions: artificial diet without essential amino acids (AD no EAA), artificial diet without essential amino acids with 10 uM pantothenol (10 uM pantothenol), and artificial diet without essential amino acids with 100 uM pantothenol (100 uM pantothenol), artificial diet without essential amino acids with 100 uM pantothenol, and artificial diet without essential amino acids with 10 uM pantothenol. FIG. 48A shows developmental stage monitored over time for each condition. FIG. 48B shows relative area measurements from aphid bodies showing the drastic effect of pantothenol treatment.

Figure 49:
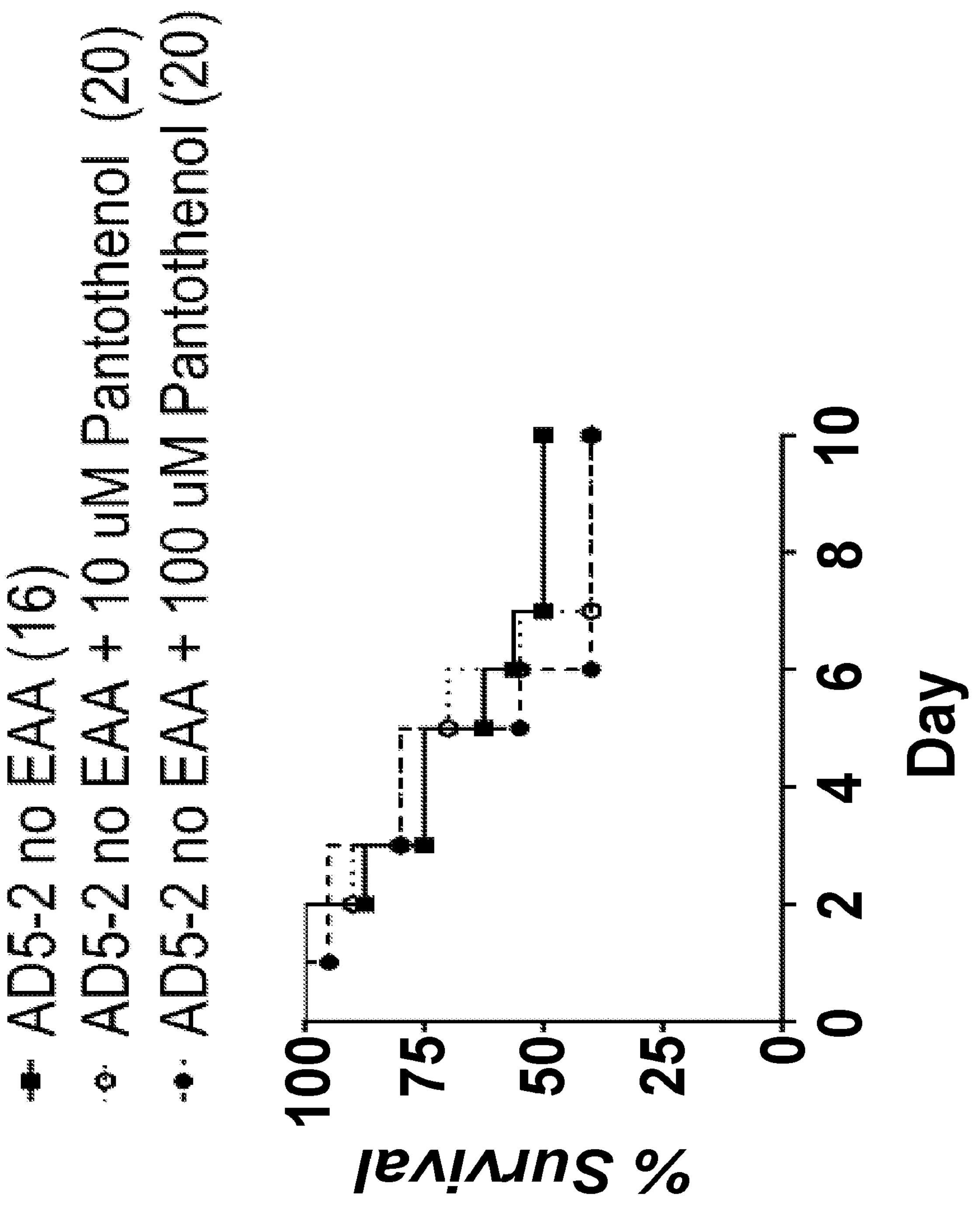

FIG. 49 is a graph showing that treatment with pantothenol increased aphid mortality. Survival was monitored daily for eNASCO aphids treated by delivery through plants with artificial diet without essential amino acids, or artificial diet without essential amino acids containing 10 or 100 uM pantothenol. Number in parentheses represents number of aphids in each group.

Figures 50A, 50B, 50C:
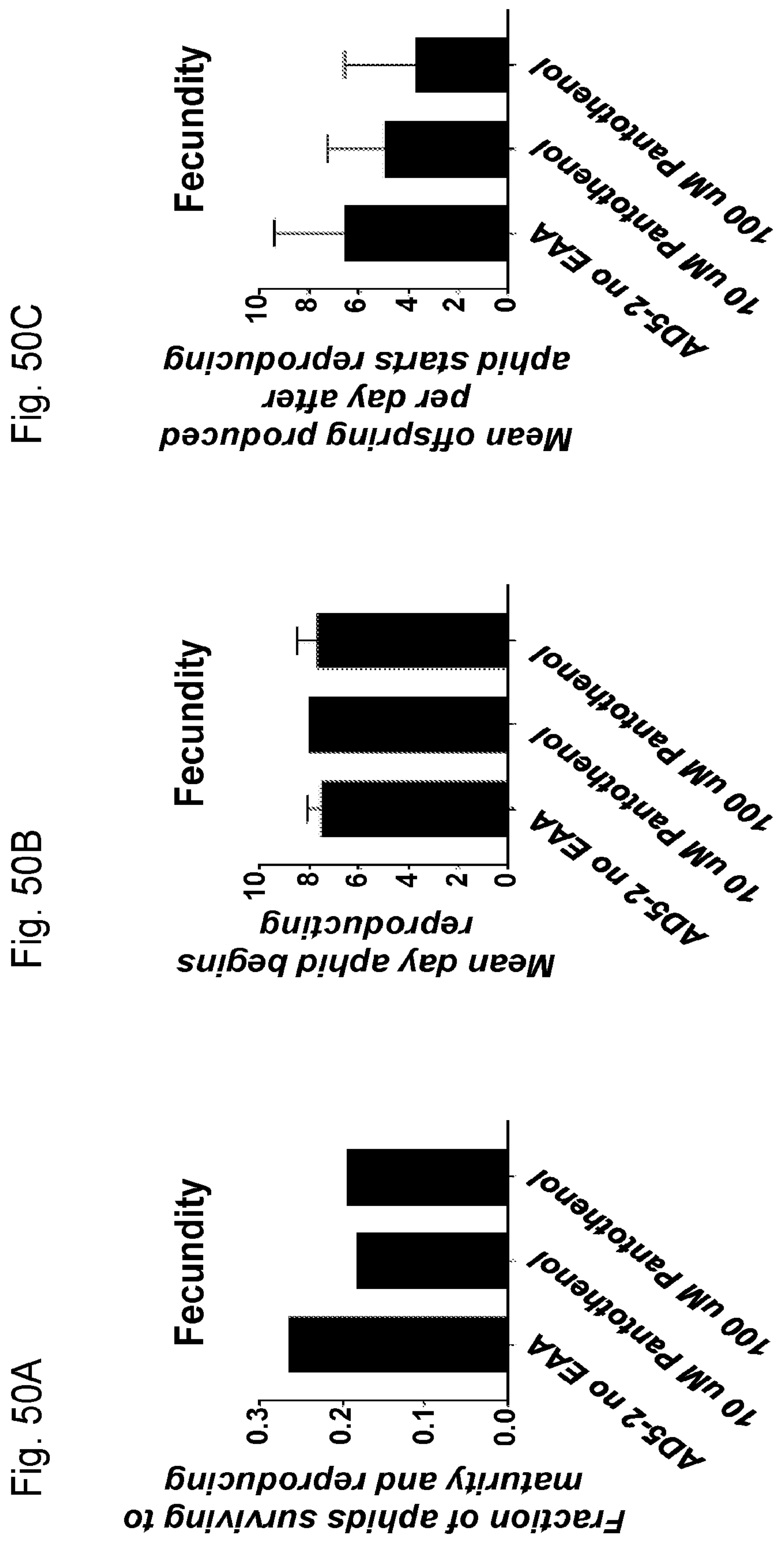

FIGS. 50A, 50B, and 50C are a panel of graphs showing Pantothenol treatment resulted in loss of reproduction. First and second instar eNASCO aphids were treated by delivery through plants with artificial diet without essential amino acids or with artificial diet without essential amino acids with 10 or 100 uM pantothenol. FIG. 50A shows the fraction of aphids surviving to maturity and reproducing. FIG. 50B shows the mean day aphids in each group began reproducing. Shown is the mean day an aphid began reproducing±SD. FIG. 50C shows the mean number of offspring produced per day after an aphid began reproducing. Shown are the mean number of offspring/day±SD.

Figure 51:
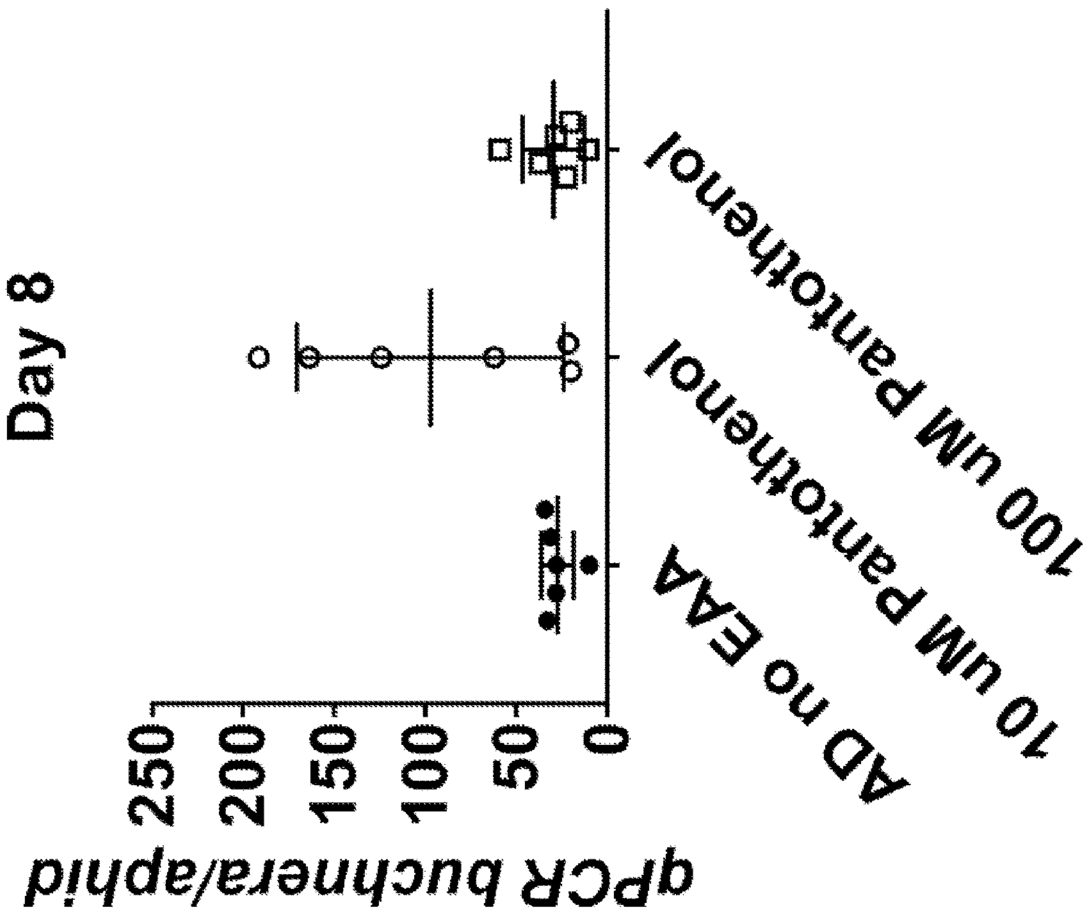

FIG. 51 is a graph showing Pantothenol treatment did not affect endosymbiotic *Buchnera*. Symbiont titer was determined for the different conditions at 8 days post-treatment. DNA from aphids was extracted and qPCR was performed to determine the ratio of *Buchnera* DNA to aphid DNA. Shown is the mean ratio of *Buchnera* DNA to aphid DNA±SD of 6 aphids per group.

Figure 52:
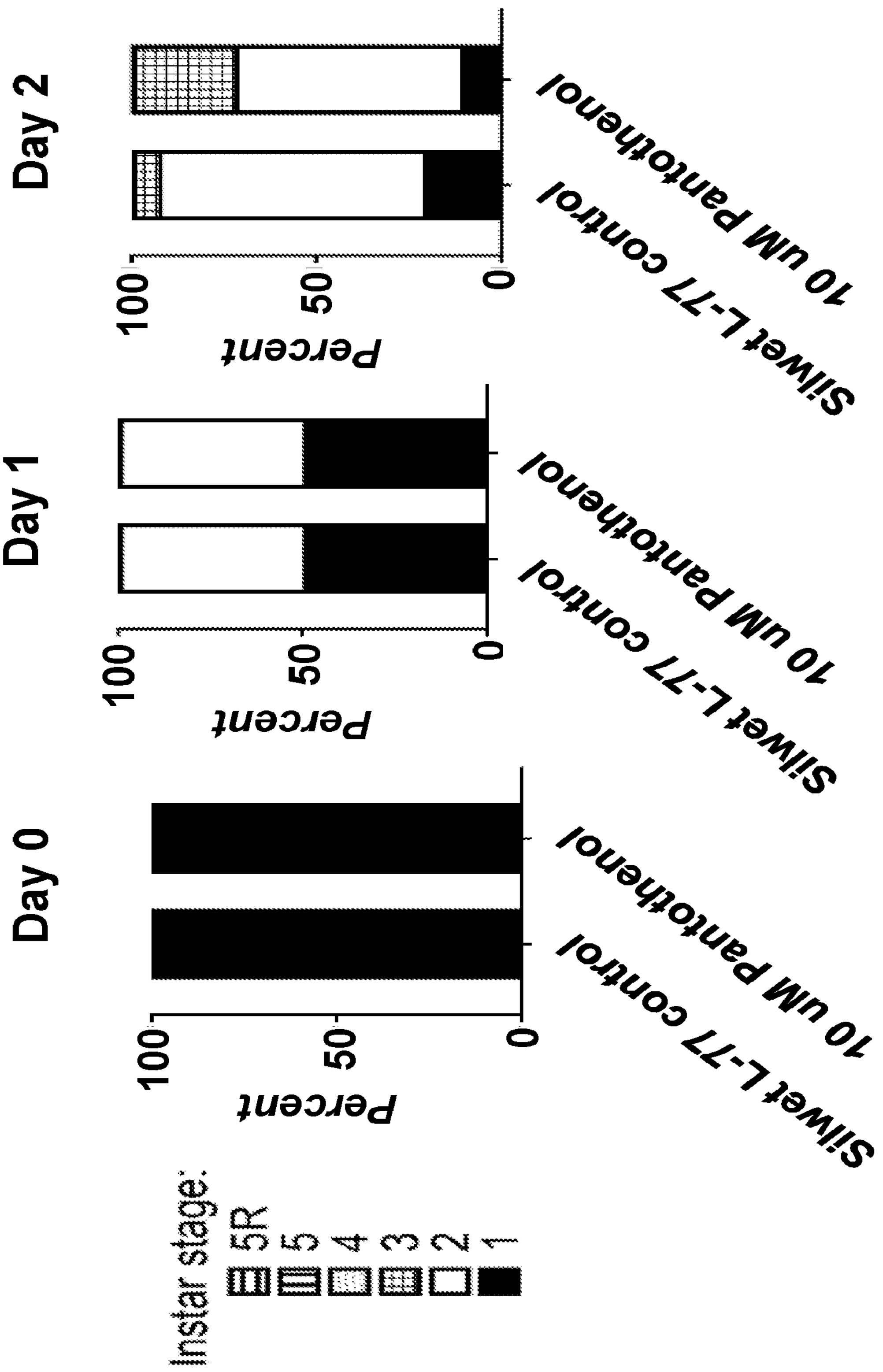

FIG. 52 is a panel of graphs showing Pantothenol treatment delivered through plants did not affect aphid development. First instar eNASCO aphids were treated by coating leaves with 100 μl of two different solutions:solvent control (0.025% Silwet L-77), and 10 uM pantothenol and the developmental stage was measured over time for each condition. Shown is the percentage of living aphids at each developmental stage (sample size=20 aphids/group).

Figure 53:
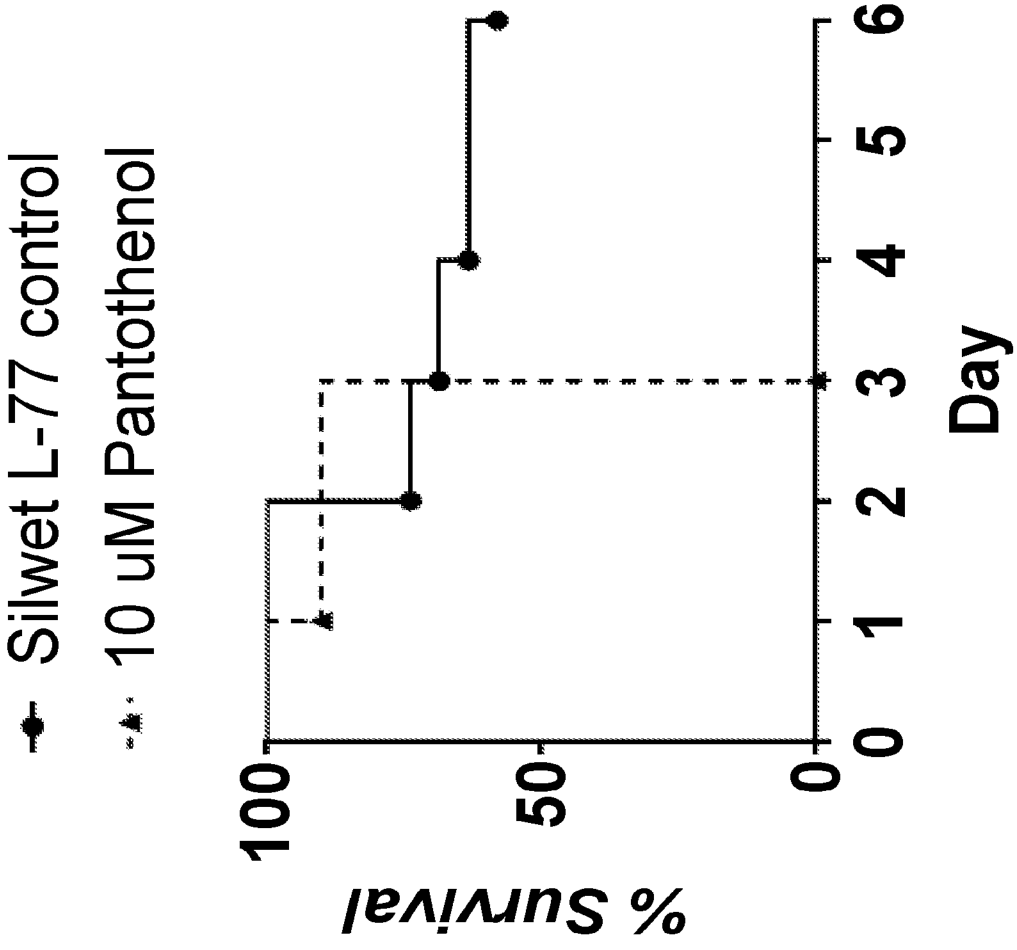

FIG. 53 is a graph showing Pantothenol treatment delivered through leaf coating resulted in aphid death. Survival was monitored daily for eNASCO aphids treated by coating leaves with 100 μl of two different solutions:solvent control (Silwet L-77), and 10 uM pantothenol. Treatment affects survival rate of aphids. Sample size=20 aphids/group. Log- Rank Mantel Cox test was used to determine whether there were statistically significant differences between groups and identified that the two group are significantly different ($p=0.0019$).

Figure 54A:
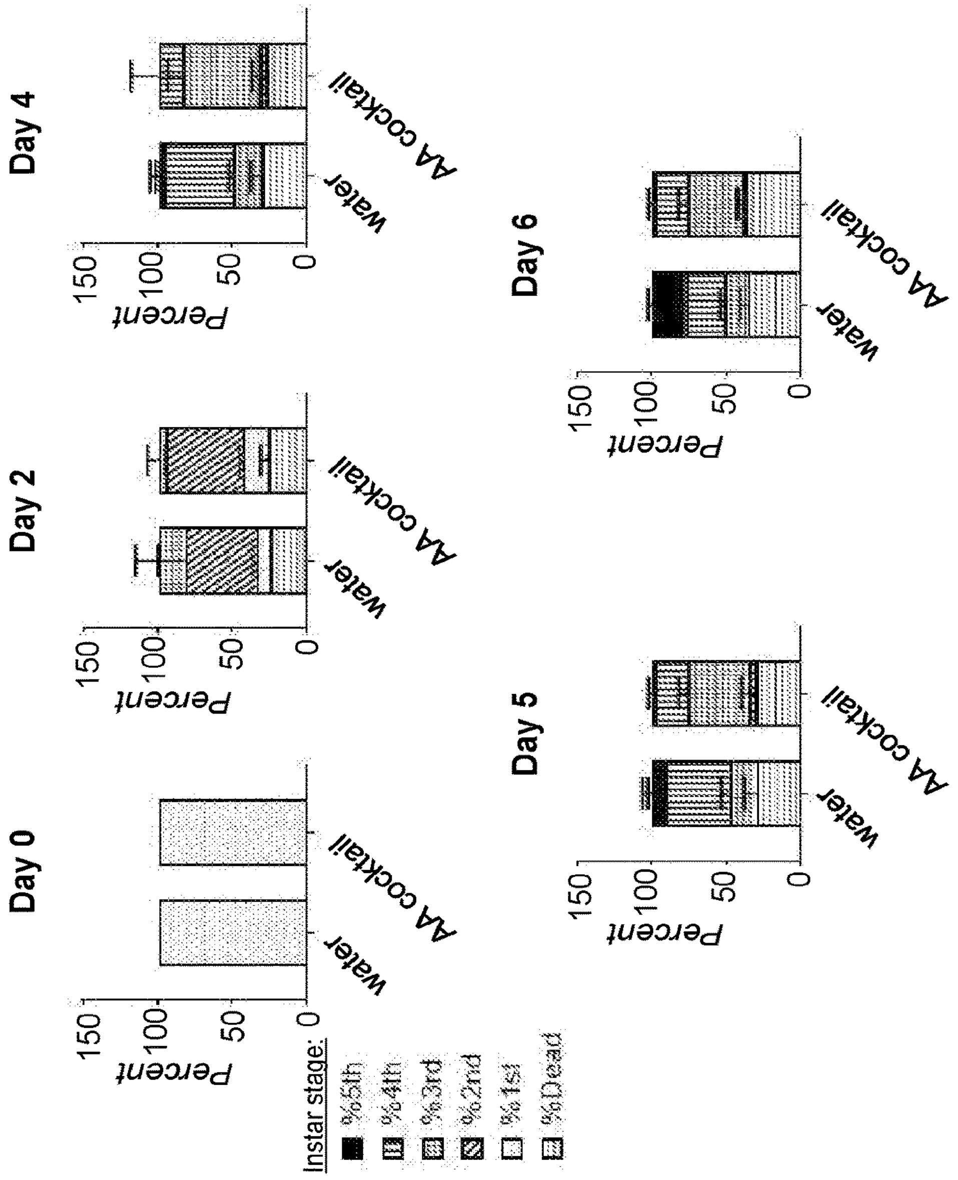
Figure 54B:
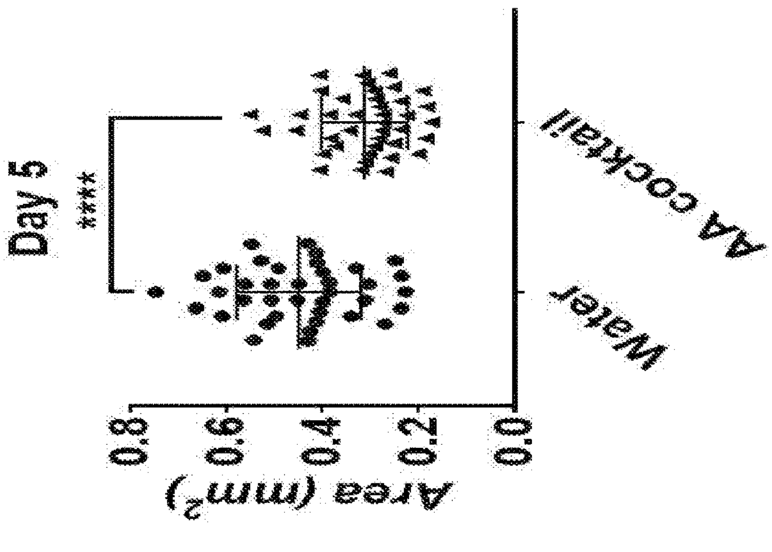

FIGS. 54A and 54B are a panel of graphs showing treatment with a cocktail of amino acid analogs delayed aphid development. First instar LSR-1 aphids were treated by delivery through leaf perfusion and through plants with water or a cocktail of amino acid analogs in water (AA cocktail). FIG. 54A shows the developmental stage measured over time for each condition. Shown are the percentage of living aphids at each developmental stage. FIG. 54B shows the area measurements from aphid bodies showing the drastic effect of treatment with an amino acid analog cocktail (AA cocktail). Statistically significant differences were determined using a Student's T-test; ****, $p<0.0001$.

Figure 55:
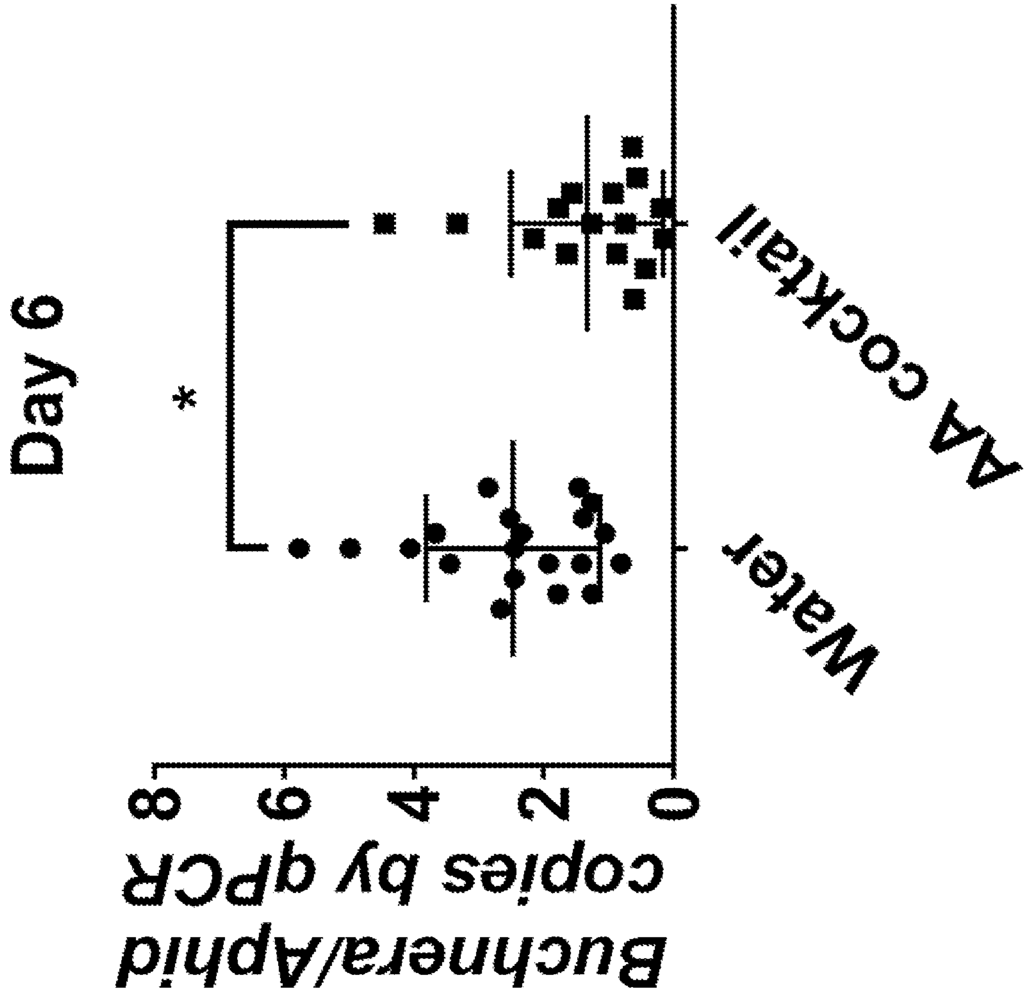

FIG. 55 is a graph showing treatment with a cocktail of amino acid analogs eliminated endosymbiotic *Buchnera*. Symbiont titer was determined for the different conditions at 6 days post-treatment. DNA from aphids was extracted and qPCR was performed to determine the ratio of *Buchnera* DNA to aphid DNA. Shown are the mean ratios of *Buchnera* DNA to aphid DNA±SD of 19-20 aphids per group. Each data point represents an individual aphid. Statistically significant differences were determined using a Student's T-test; *, $p<0.05$.

Figure 56B:
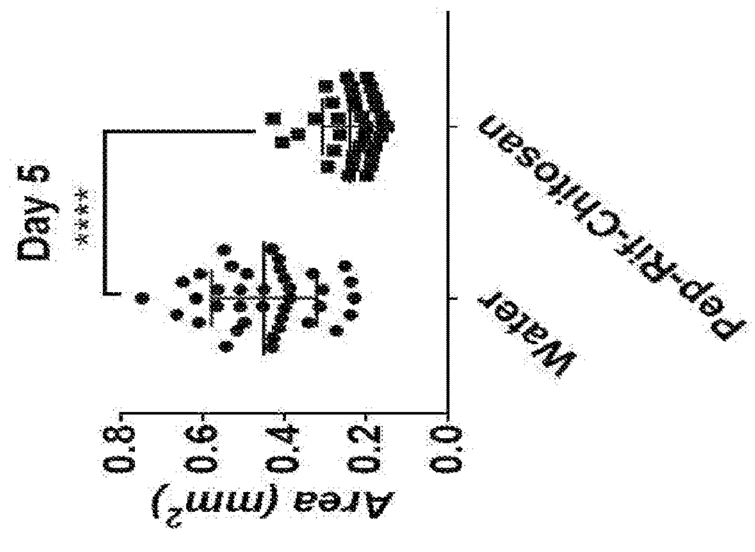
Figure 56A:
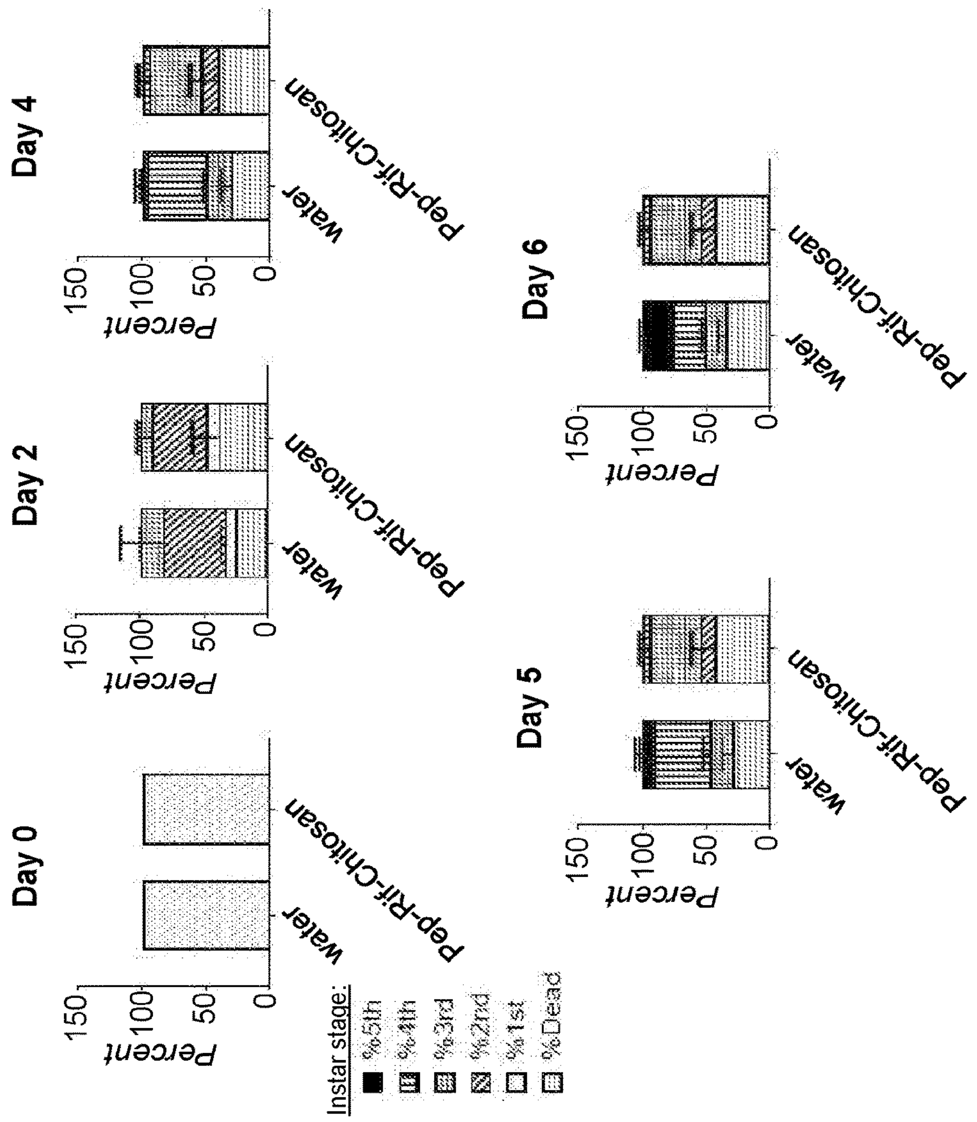

FIGS. 56A and 56B is a panel of graphs showing treatment with a combination of three agents delayed aphid development. First instar LSR-1 aphids were treated by delivery through leaf perfusion and through plants with water or a combination of three agents in water (Pep-Rif-Chitosan). FIG. 56A shows the developmental stage measured over time for each condition. Shown are the percentage of living aphids at each developmental stage. FIG. 56B shows the area measurements from aphid bodies showing the drastic effect of treatment with a combination of three treatments (Pep-Rif-Chitosan). Statistically significant differences were determined using a Student's T-test; ****, $p<0.0001$.

Figure 57:
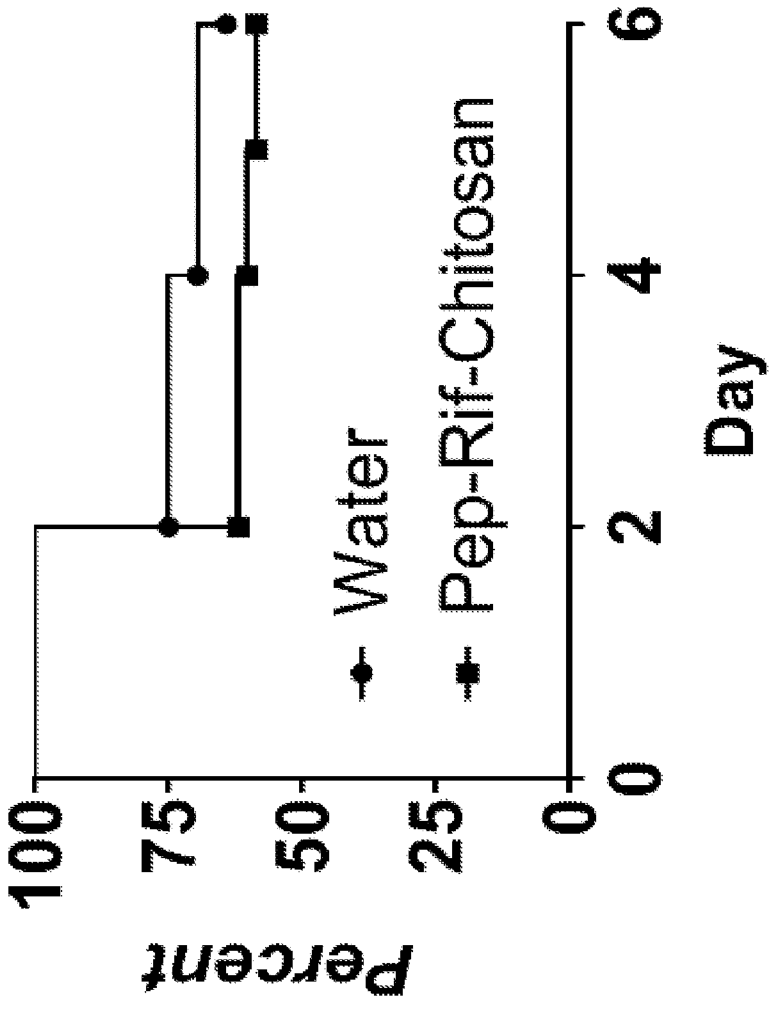

FIG. 57 is a graph showing treatment with a combination of a peptide, antibiotic, and natural antimicrobial agent increased aphid mortality. LSR-1 aphids were treated with water or a combination of three treatments (Pep-Rif-Chitosan) and survival was monitored daily after treatment.

Figure 58:
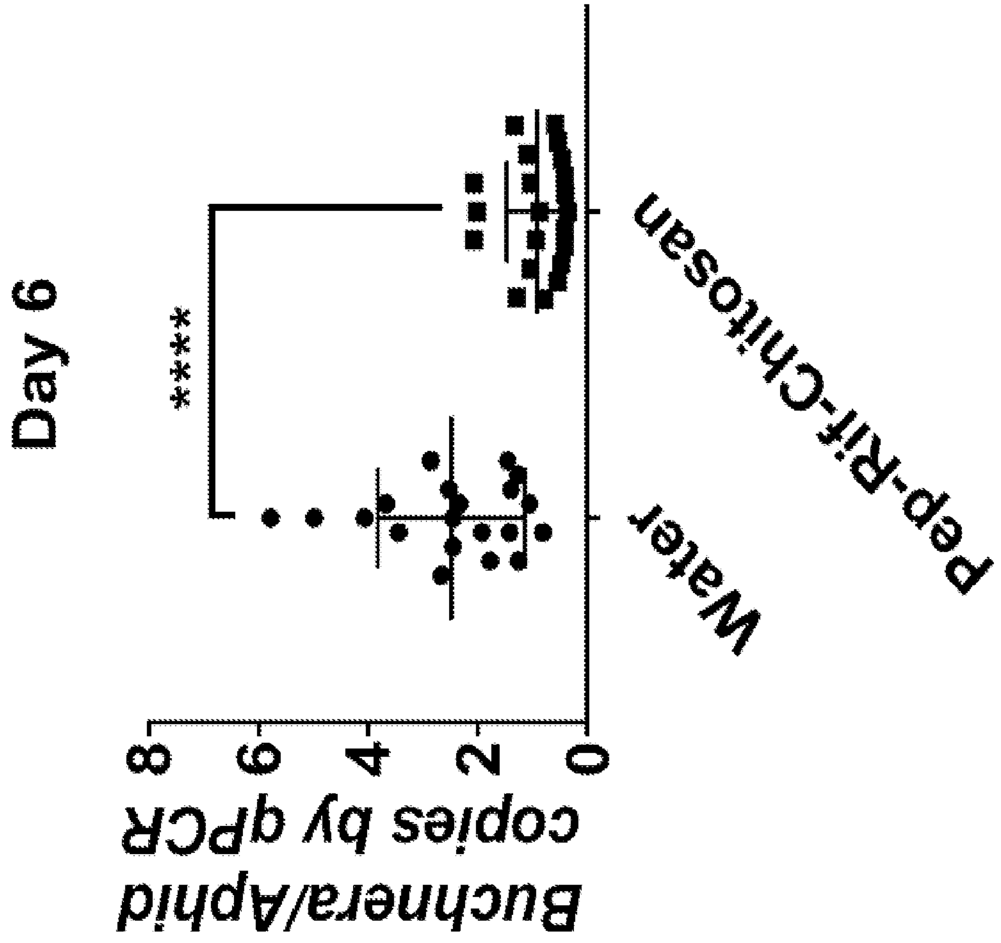

FIG. 58 is a graph showing treatment with a combination of a peptide, antibiotic, and natural antimicrobial agent eliminated endosymbiotic *Buchnera*. Symbiont titer was determined for the different conditions at 6 days post-treatment. DNA from aphids was extracted and qPCR was performed to determine the ratio of *Buchnera* DNA to aphid DNA. Shown are the mean ratios of *Buchnera* DNA to aphid DNA±SD of 20-21 aphids per group. Each data point represents an individual aphid.

Figure 59B:
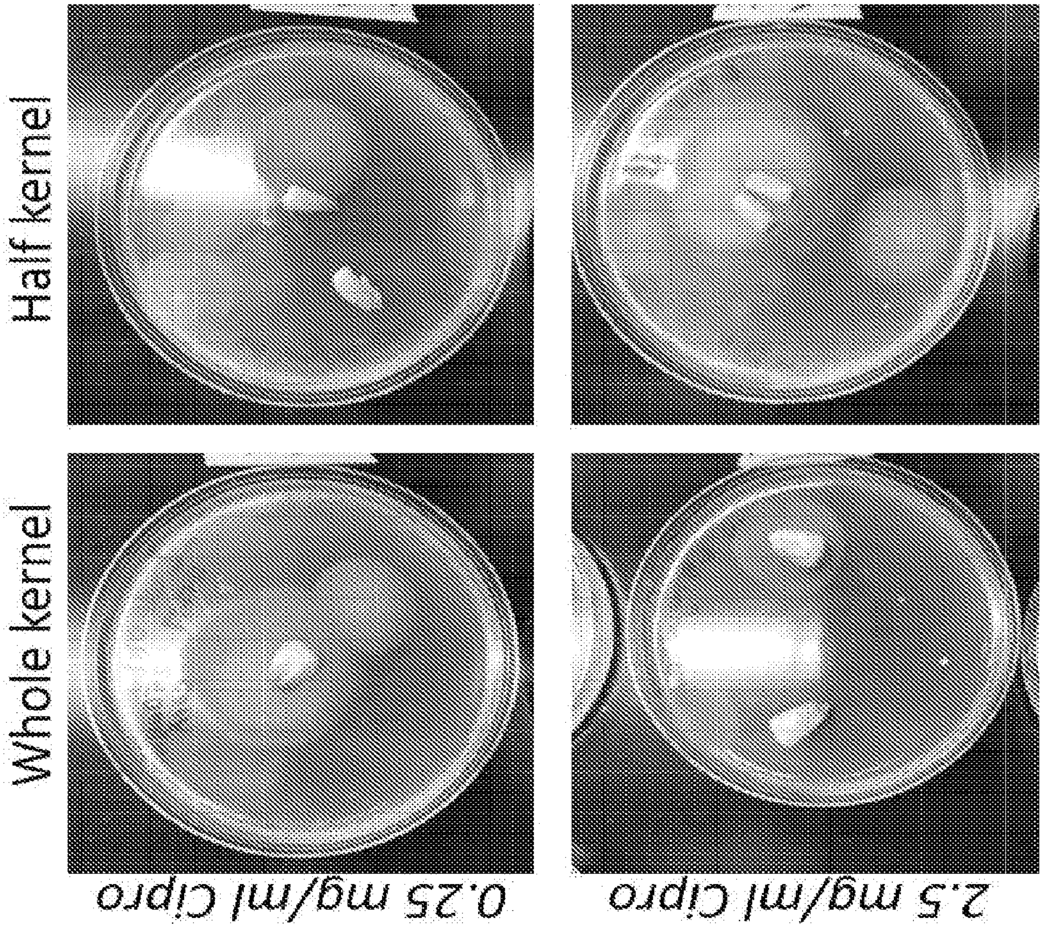
Figure 59A:
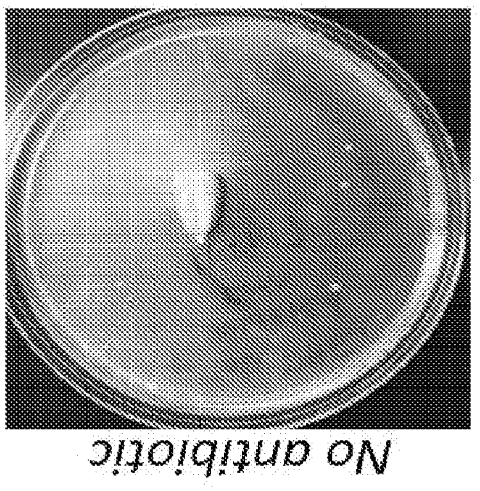

FIGS. 59A and 59B are a panel of images showing ciprofloxacin coated and penetrated corn kernels. Corn kernels were soaked in water (no antibiotic) or the indicated concentration of ciprofloxacin in water and whole kernels or kernel were tested to see whether they can inhibit the growth of *E. coli* DH5a. FIG. 59A shows bacterial growth in the presence of a corn kernel soaked in water without antibiotics and FIG. 59B shows the inhibition of bacterial growth when whole or half corn kernels that have been soaked in antibiotics are placed on a plate spread with *E. coli.*

Figure 60:
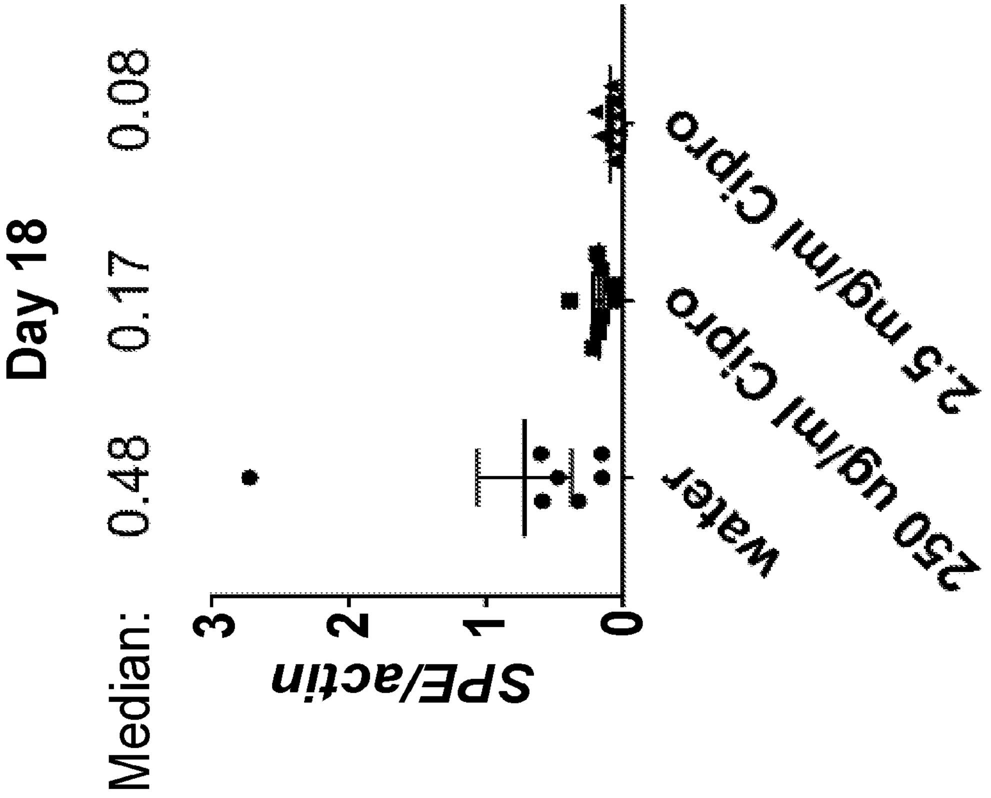

FIG. 60 is a graph showing that adult *S. zeamais* weevils were treated with ciprofloxacin (250 ug/ml or 2.5 mg/ml) or mock treated with water. After 18 days of treatment, genomic DNA was isolated from weevils and the amount of *Sitophilus* primary endosymbiont was determined by qPCR. Shown is the mean±SEM of each group. Each data point represents one weevil. The median of each group is listed above the dataset.

Figure 61B:
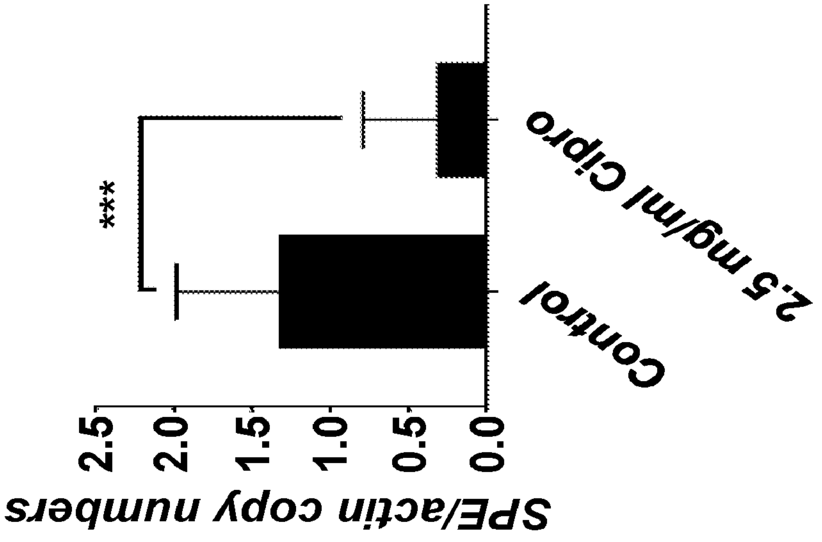
Figure 61A:
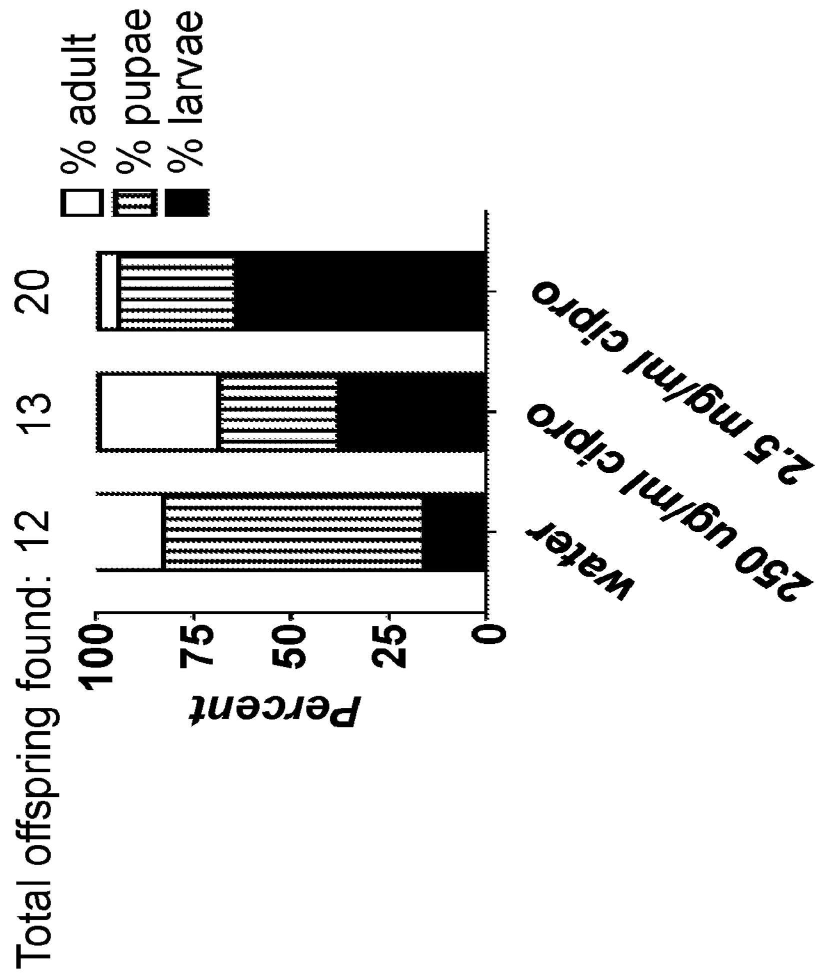

FIGS. 61A and 61B are graphs showing weevil development after treatment with ciprofloxacin. FIG. 61A shows individual corn kernels cut open 25 days after adults were removed from one replicate each of the initial corn kernels soaked/coated with water (control) or ciprofloxacin (250 ug/ml or 2.5 mg/ml) and examined for the presence of larvae, pupae, or almost fully developed (adult) weevils. Shown is the percent of each life stage found in kernels from each treatment group. The total number of offspring found in the kernels from each treatment group is indicated above each dataset. FIG. 61B shows genomic DNA isolated from offspring dissected from corn kernels from the control (water) and 2.5 mg/ml ciprofloxacin treatment groups and qPCR was done to measure the amount of *Sitophilus* primary endosymbiont present. Shown are the mean±SD for each group. Statistically significant differences were determined by unpaired t-test; ***, $p\leq 0.001$.

Figure 62B:
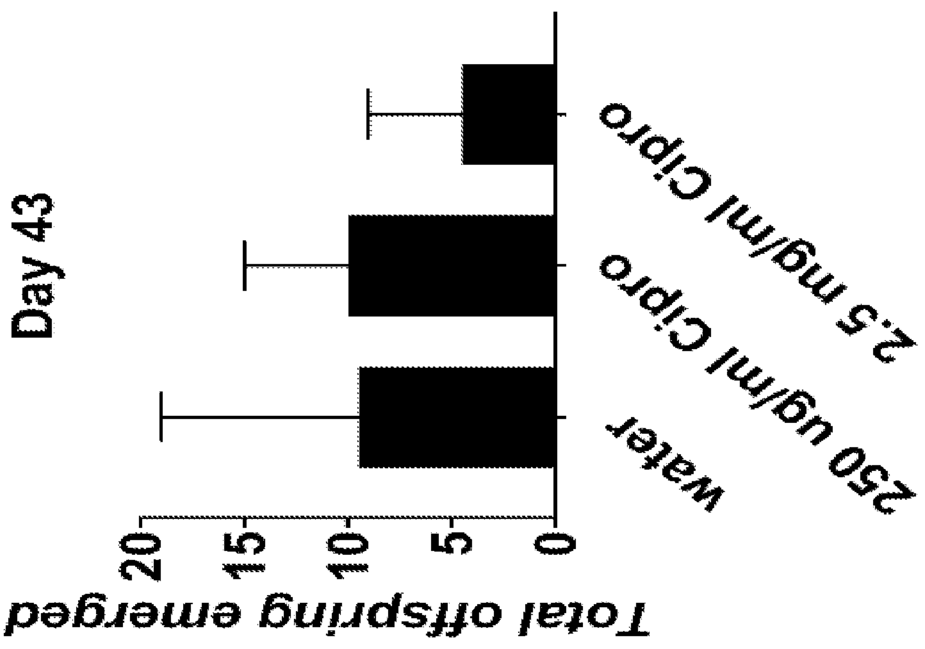
Figure 62A:
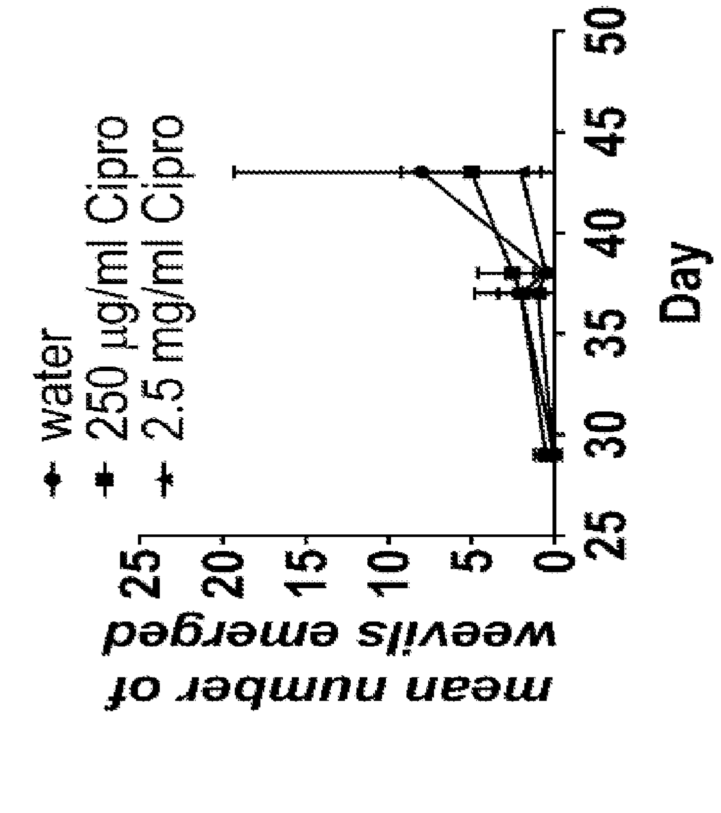

FIGS. 62A and 62B are graphs showing the two remaining replicates of corn kernels mock treated (water) or treated with 250 ug/ml or 2.5 mg/ml ciprofloxacin monitored for the emergence of offspring after mating pairs were removed (at 7 days post-treatment). FIG. 62A shows the mean number of newly emerged weevils over time±SD for each treatment group. FIG. 62B shows the mean number±SEM of emerged weevils for each treatment group at 43 days after mating pairs were removed.

Figure 63:
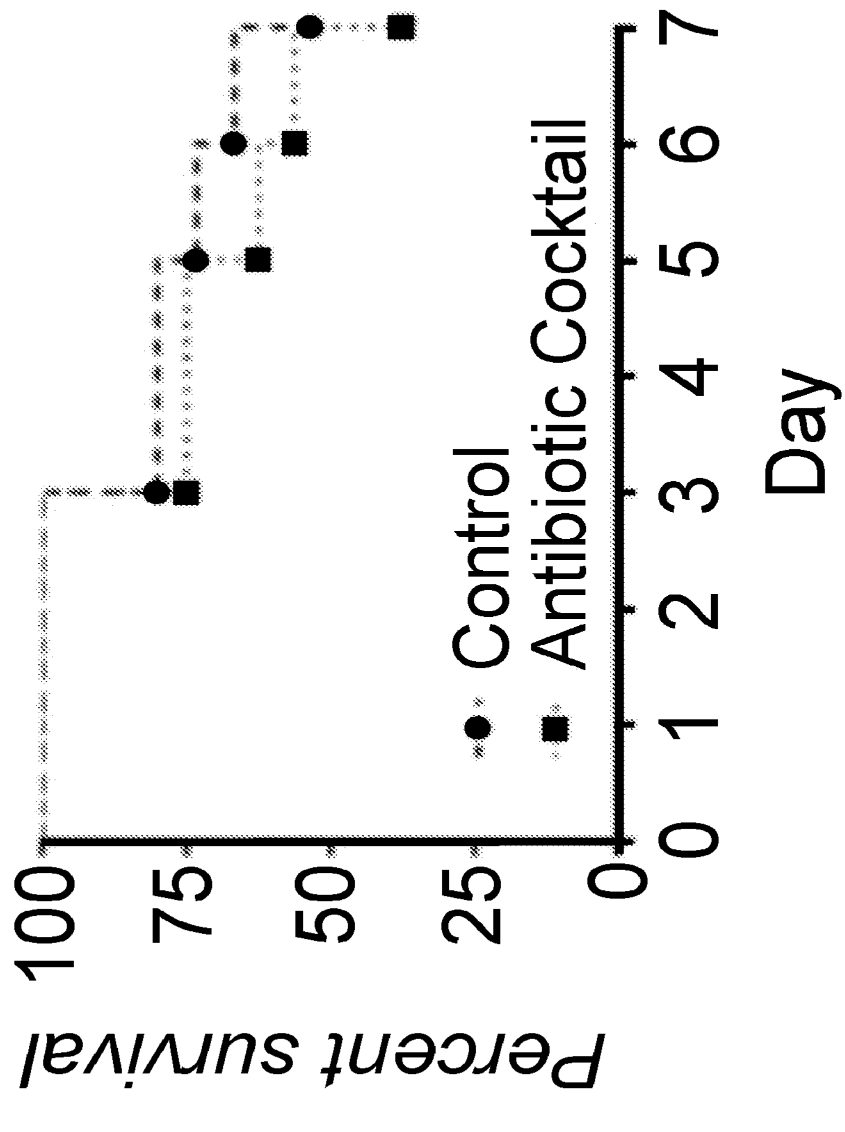

FIG. 63 is a graph showing rifampicin and doxycycline treatment resulted in mite mortality. Survival was monitored daily for untreated two-spotted spider mites and mites treated with 250 μg/ml rifampicin and 500 μg/ml doxycycline in 0.025% Silwet L-77.

Figure 64:
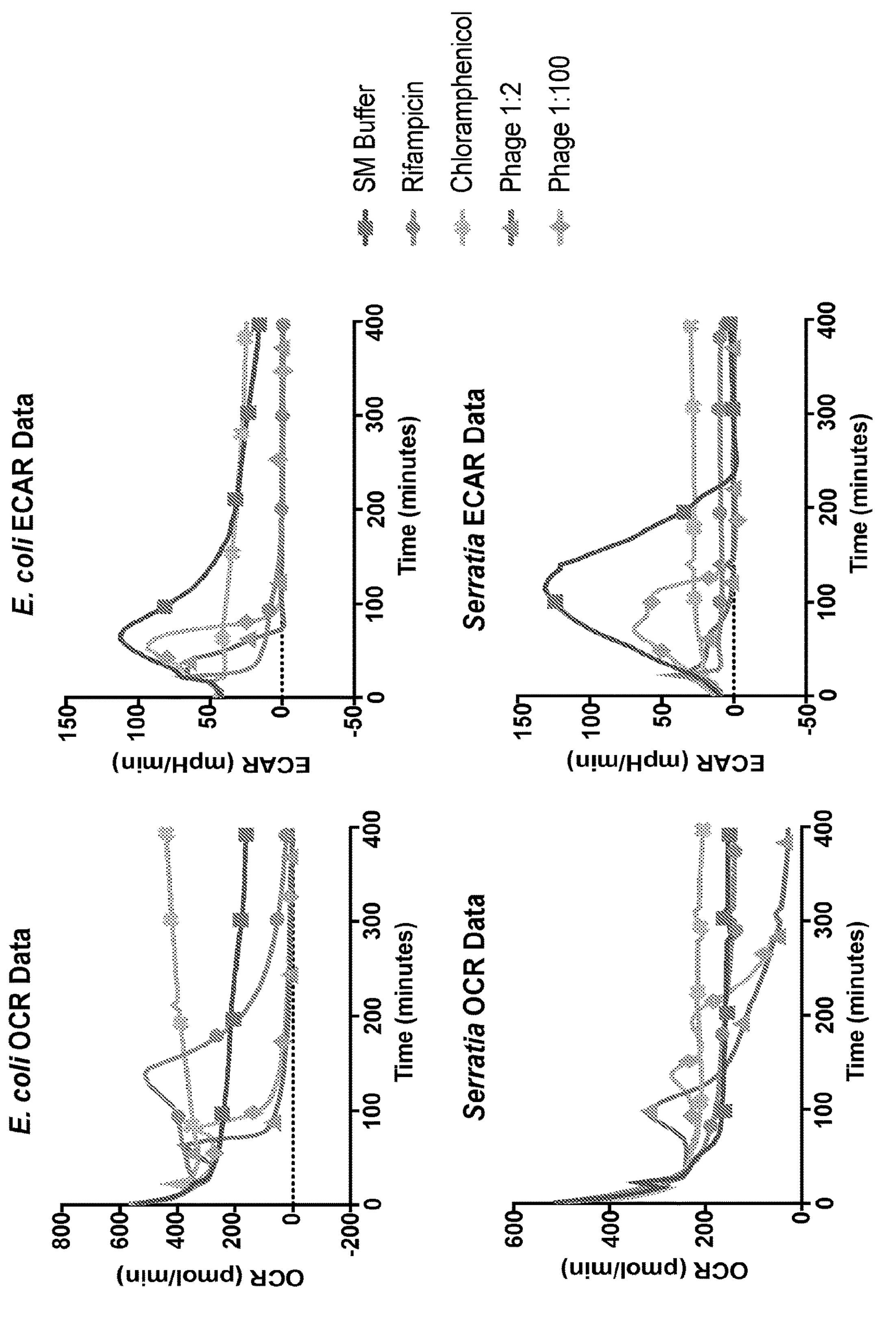

FIG. 64 is a panel of graphs showing the results of a Seahorse flux assay for bacterial respiration. Bacteria were grown to logarithmic phase and loaded into Seahorse XFe96 plates for temporal measurements of oxygen consumption rate (OCR) and extracellular acidification rate (ECAR) as described in methods. Treatments were injected into the wells after approximately 20 minutes and bacteria were monitored to detect changes in growth. Rifampicin=100 μg/mL; Chloramphenicol=25 μg/mL; Phages (T7 for *E. coli* and ϕSmVL-C1 for *S. marcescens*) were lysates diluted either 1:2 or 1:100 in SM Buffer. The markers on each line are solely provided as indicators of the condition to which each line corresponds, and are not indicative of data points.

Figure 65:
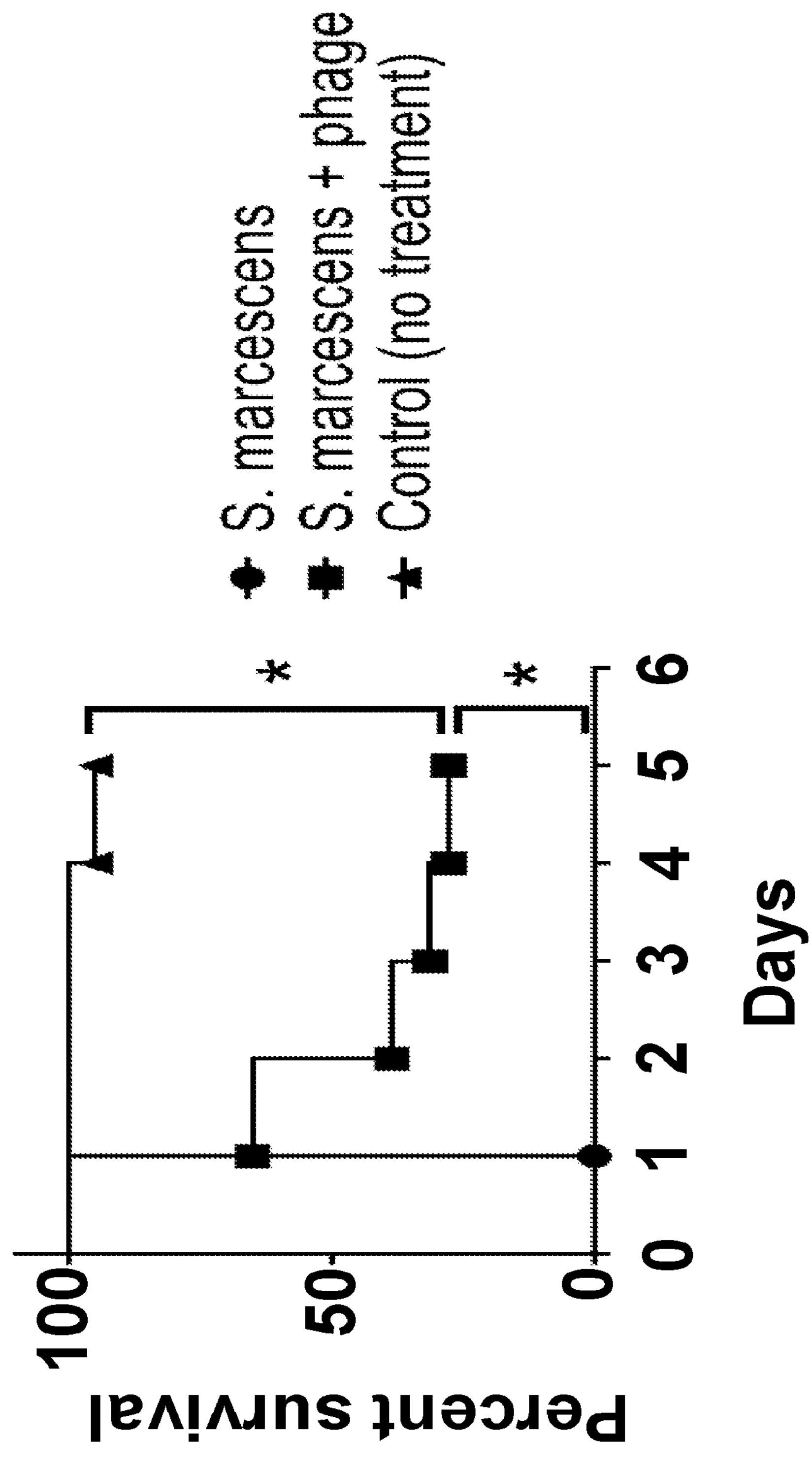

FIG. 65 is a graph showing phage against *S. marcescens* reduced fly mortality. Flies that were pricked with *S. marcescens* were all dead within a day, whereas a sizeable portion of the flies that were pricked with both *S. marcescens* and the phage survived for five days after the treatment. Almost all of the control flies which were not treated in anyway survived till the end of the experiment. Log-rank test was used to compare the curves for statistical significance, asterisk denotes $p<0.0001$.

DETAILED DESCRIPTION

Provided herein are methods and compositions useful for human health, e.g., for altering a level, activity, or metabolism of one or more microorganisms resident in a host insect (e.g., arthropod, e.g., insect, e.g., a human pathogen vector, e.g., mosquito, mite, louse, or tick), the alteration resulting in a decrease in the fitness of the host. The invention features a composition that includes a modulating agent (e.g., phage, peptide, small molecule, antibiotic, or combinations thereof) that can alter the host's microbiota in a manner that is detrimental to the host. By disrupting microbial levels, microbial activity, microbial metabolism, or microbial diversity, the modulating agent described herein may be used to decrease the fitness of a variety of insects that carry vector-borne pathogens that cause disease in humans.

The methods and compositions described herein are based in part on the examples provided herein, which illustrate how modulating agents, for example antibiotics (e.g., oxytetracycline, doxycycline, or a combination thereof) can be used to target symbiotic microorganisms in a host (e.g., endosymbionts e.g., endosymbiotic *Wolbachia* in mosquitos or *Rickettsia* in ticks) in insect vectors of human pathogens, to decrease the fitness of the host by altering the level, activity, or metabolism of the microorganisms within the hosts. Oxytetracycline and doxycycline are representative examples of antibiotics useful for this purpose. On this basis the present disclosure describes a variety of different approaches for the use of agents that alter a level, activity, or metabolism of one or more microorganisms resident in a host (e.g., a vector of a human pathogen, e.g., a mosquito, mite, louse or a tick) the alteration resulting in a decrease in the host's fitness.

I. Hosts i. Insects

The methods and compositions provided herein may be used with any insect host that is considered a vector for a pathogen that is capable of causing disease in humans For example, the insect host may include, but is not limited to those with piercing-sucking mouthparts, as found in Hemiptera and some Hymenoptera and Diptera such as mosquitoes, bees, wasps, midges, lice, tsetse fly, fleas and ants, as well as members of the Arachnidae such as ticks and mites; order, class or family of Acarina (ticks and mites) e.g. representatives of the families Argasidae, Dermanyssidae, Ixodidae, Psoroptidae or Sarcoptidae and representatives of the species *Amblyomma* spp., *Anocenton* spp., *Argas* spp., *Boophilus* spp., *Cheyletiella* spp., *Chorioptes* spp., *Demodex* spp., *Dermacentorspp., Denmanyssus* spp., *Haemophysalis* spp., *Hyalomma* spp., *Ixodes* spp., *Lynxacarus* spp., *Mesostigmata* spp., *Notoednes* spp., *Ornithodoros* spp., *Ornithonyssus* spp., *Otobius* spp., *otodectes* spp., *Pneumonyssus* spp., *Psoroptes* spp., *Rhipicephalus* spp., *Sancoptes* spp., or *Trombicula* spp.; *Anoplura* (*sucking* and *biting lice*) e.g. *representatives of the* species *Bovicola* spp., *Haematopinus* spp., *Linognathus* spp., *Menopon* spp., *Pediculus* spp., *Pemphigus* spp., *Phylloxera* spp., or *Solenopotes* spp.; Diptera (flies) e.g. representatives of the species *Aedes* spp., *Anopheles* spp., *Calliphora* spp., *Chrysomyia* spp., *Chrysops* spp., *Cochliomyia* spp., *Cw/ex* spp., *Culicoides* spp., *Cuterebra* spp., *Dermatobia* spp., *Gastrophilus* spp., *Glossina* spp., *Haematobia* spp., *Haematopota* spp., *Hippobosca* spp., *Hypoderma* spp., *Lucilia* spp., *Lyperosia* spp., *Melophagus* spp., *Oestrus* spp., *Phaenicia* spp., *Phlebotomus* spp., *Phormia* spp., *Acari* (*sarcoptic mange*) e.g., *Sarcoptidae* spp., *Sarcophaga* spp., *Simulium* spp., *Stomoxys* spp., *Tabanus* spp., *Tannia* spp. or *Zzpu/alpha* spp.; *Mallophaga* (*biting lice*) e.g. *representatives of the* species *Damalina* spp., *Felicola* spp., *Heterodoxus* spp. or *Trichodectes* spp.; or *Siphonaptera* (*wingless insects*) e.g. *representatives of the* species *Ceratophyllus* spp., *Xenopsylla* spp; *Cimicidae* (*true bugs*) e.g. representatives of the species *Cimex* spp., *Tritominae* spp., *Rhodinius* spp., or *Triatoma* spp.

In some instances, the insect is a blood-sucking insect from the order Diptera (e.g., suborder Nematocera, e.g., family Colicidae). In some instances, the insect is from the subfamilies Culicinae, Corethrinae, Ceratopogonidae, or Simuliidae. In some instances, the insect is of a *Culex* spp., *Theobaldia* spp., *Aedes* spp., *Anopheles* spp., *Aedes* spp., *Forciponiyia* spp., *Culicoides* spp., or *Helea* spp.

In certain instances, the insect is a mosquito. In certain instances, the insect is a tick. In certain instances, the insect is a mite. In certain instances, the insect is a biting louse.

ii. Host Fitness

The methods and compositions provided herein may be used to decrease the fitness of any of the hosts described herein. The decrease in fitness may arise from any alterations in microorganisms resident in the host, wherein the alterations are a consequence of administration of a modulating agent and have detrimental effects on the host.

In some instances, the decrease in host fitness may manifest as a deterioration or decline in the physiology of the host (e.g., reduced health or survival) as a consequence of administration of a modulating agent. In some instances, the fitness of an organism may be measured by one or more parameters, including, but not limited to, reproductive rate, lifespan, mobility, fecundity, body weight, metabolic rate or activity, or survival in comparison to a host organism to which the modulating agent has not been administered. For example, the methods or compositions provided herein may be effective to decrease the overall health of the host or to decrease the overall survival of the host. In some instances, the decreased survival of the host is about 2%, 5%, 10%, 20%, 30%, 40%, 50%, 60%, 70%, 80%, 90%, 100%, or greater than 100% greater relative to a reference level (e.g., a level found in a host that does not receive a modulating agent). In some instances, the methods and compositions are effective to decrease host reproduction (e.g., reproductive rate) in comparison to a host organism to which the modulating agent has not been administered. In some instances, the methods and compositions are effective to decrease other physiological parameters, such as mobility, body weight, life span, fecundity, or metabolic rate, by about 2%, 5%, 10%, 20%, 30%, 40%, 50%, 60%, 70%, 80%, 90%, 100%, or greater than 100% relative to a reference level (e.g., a level found in a host that does not receive a modulating agent).

In some instances, the decrease in host fitness may manifest as a decrease in the production of one or more nutrients in the host (e.g., vitamins, carbohydrates, amino acids, or polypeptides). In some instances, the methods or compositions provided herein may be effective to decrease the production of nutrients in the host (e.g., vitamins, carbohydrates, amino acids, or polypeptides) by about 2%, 5%, 10%, 20%, 30%, 40%, 50%, 60%, 70%, 80%, 90%, 100%, or greater than 100% relative to a reference level (e.g., a level found in a host that does not receive a modulating agent). In some instances, the methods or compositions provided herein may decrease nutrients in the host by decreasing the production of nutrients by one or more microorganisms (e.g., endosymbiont) in the host in comparison to a host organism to which the modulating agent has not been administered.

In some instances, the decrease in host fitness may manifest as an increase in the host's sensitivity to a pesticidal agent (e.g., a pesticide listed in Table 12) and/or a decrease in the host's resistance to a pesticidal agent (e.g., a pesticide listed in Table 12) in comparison to a host organism to which the modulating agent has not been administered. In some instances, the methods or compositions provided herein may be effective to increase the host's sensitivity to a pesticidal agent (e.g., a pesticide listed in Table 12) by about 2%, 5%, 10%, 20%, 30%, 40%, 50%, 60%, 70%, 80%, 90%, 100%, or greater than 100% relative to a reference level (e.g., a level found in a host that does not receive a modulating agent). The pesticidal agent may be any pesticidal agent known in the art, including insecticidal agents. In some instances, the methods or compositions provided herein may increase the host's sensitivity to a pesticidal agent (e.g., a pesticide listed in Table 12) by decreasing the host's ability to metabolize or degrade the pesticidal agent into usable substrates.

In some instances, the decrease in host fitness may manifest as an increase in the host's sensitivity to an allelochemical agent and/or a decrease in the host's resistance to an allelochemical agent in comparison to a host organism to which the modulating agent has not been administered. In some instances, the methods or compositions provided herein may be effective to decrease the host's resistance to an allelochemical agent by about 2%, 5%, 10%, 20%, 30%, 40%, 50%, 60%, 70%, 80%, 90%, 100%, or greater than 100% relative to a reference level (e.g., a level found in a host that does not receive a modulating agent). In some instances, the allelochemical agent is caffeine, soyacystatin N, monoterpenes, diterpene acids, or phenolic compounds. In some instances, the methods or compositions provided herein may increase the host's sensitivity to an allelochemical agent by decreasing the host's ability to metabolize or degrade the allelochemical agent into usable substrates in comparison to a host organism to which the modulating agent has not been administered.

In some instances, the methods or compositions provided herein may be effective to decease the host's resistance to parasites or pathogens (e.g., fungal, bacterial, or viral pathogens or parasites) in comparison to a host organism to which the modulating agent has not been administered. In some instances, the methods or compositions provided herein may be effective to decrease the host's resistance to a pathogen or parasite (e.g., fungal, bacterial, or viral pathogens; or parasitic mites) by about 2%, 5%, 10%, 20%, 30%, 40%, 50%, 60%, 70%, 80%, 90%, 100%, or greater than 100% relative to a reference level (e.g., a level found in a host that does not receive a modulating agent).

In some instances, the decrease in host fitness may manifest as other fitness disadvantages, such as decreased tolerance to certain environmental factors (e.g., a high or low temperature tolerance), decreased ability to survive in certain habitats, or a decreased ability to sustain a certain diet in comparison to a host organism to which the modulating agent has not been administered. In some instances, the methods or compositions provided herein may be effective to decrease host fitness in any plurality of ways described herein. Further, the modulating agent may decrease host fitness in any number of host classes, orders, families, genera, or species (e.g., 1 host species, 2, 3, 4, 5, 6, 7, 8, 9, 10, 15, 20, 30, 40, 50, 60, 70, 80, 90, 100, 150, 200, 200, 250, 500, or more host species). In some instances, the modulating agent acts on a single host class, order, family, genus, or species.

Host fitness may be evaluated using any standard methods in the art. In some instances, host fitness may be evaluated by assessing an individual host. Alternatively, host fitness may be evaluated by assessing a host population. For example, a decrease in host fitness may manifest as a decrease in successful competition against other insects, thereby leading to a decrease in the size of the host population.

iii. Host Insects in Disease Transmission

By decreasing the fitness of host insects that carry human pathogens, the modulating agents provided herein are effective to reduce the spread of vector-borne diseases. The modulating agent may be delivered to the insects using any of the formulations and delivery methods described herein, in an amount and for a duration effective to reduce transmission of the disease, e.g., reduce vertical or horizontal transmission between vectors and/or reduce transmission to humans. For example, the modulating agent described herein may reduce vertical or horizontal transmission of a vector-borne pathogen by about 2%, 5%, 10%, 20%, 30%, 40%, 50%, 60%, 70%, 80%, 90%, 100%, or more in comparison to a host organism to which the modulating agent has not been administered. As an another example, the modulating agent described herein may reduce vectorial competence of an insect vector by about 2%, 5%, 10%, 20%, 30%, 40%, 50%, 60%, 70%, 80%, 90%, 100%, or more in comparison to a host organism to which the modulating agent has not been administered.

Non-limiting examples of diseases that may be controlled by the compositions and methods provided herein include diseases caused by Togaviridae viruses (e.g., Chikungunya, Ross River fever, Mayaro, Onyon-nyong fever, Sindbis fever, Eastern equine enchephalomyeltis, Wesetern equine encephalomyelitis, Venezualan equine encephalomyelitis, or Barmah forest); diseases caused by Flavivirdae viruses (e.g., Dengue fever, Yellow fever, Kyasanur Forest disease, Omsk haemorrhagic fever, Japaenese encephalitis, Murray Valley encephalitis, Rocio, St. Louis encephalitis, West Nile encephalitis, or Tick-borne encephalitis); diseases caused by Bunyaviridae viruses (e.g., Sandly fever, Rift Valley fever, La Crosse encephalitis, California encephalitis, Crimean-Congo haemorrhagic fever, or Oropouche fever); disease caused by Rhabdoviridae viruses (e.g., Vesicular stomatitis); disease caused by Orbiviridae (e.g., Bluetongue); diseases caused by bacteria (e.g., Plague, Tularaemia, Q fever, Rocky Mountain spotted fever, Murine typhus, Boutonneuse fever, Queensland tick typhus, Siberian tick typhus, Scrub typhus, Relapsing fever, or Lyme disease); or diseases caused by protozoa (e.g., Malaria, African trypanosomiasis, Nagana, Chagas disease, Leishmaniasis, Piroplasmosis, Bancroftian filariasis, or Brugian filariasis).

II. Target Microorganisms

The microorganisms targeted by the modulating agent described herein may include any microorganism resident in or on the host, including, but not limited to, any bacteria and/or fungi described herein. Microorganisms resident in the host may include, for example, symbiotic (e.g., endosymbiotic microorganisms that provide beneficial nutrients or enzymes to the host), commensal, pathogenic, or parasitic microorganisms. An endosymbiotic microorganism may be a primary endosymbiont or a secondary endosymbiont. A symbiotic microorganism (e.g., bacteria or fungi) may be an obligate symbiont of the host or a facultative symbiont of the host. Microorganisms resident in the host may be acquired by any mode of transmission, including vertical, horizontal, or multiple origins of transmission.

i. Bacteria

Exemplary bacteria that may be targeted in accordance with the methods and compositions provided herein, include, but are not limited to, *Xenorhabdus* spp, *Photorhabdus* spp, *Candidatus* spp, *Buchnera* spp, *Blattabacterium* spp, *Baumania* spp, *Wigglesworthia* spp, *Wolbachia* spp, *Rickettsia* spp, *Orientia* spp, *Sodalis* spp, *Burkholderia* spp, *Cupriavidus* spp, *Frankia* spp, *Snirhizobium* spp, *Streptococcus* spp, *Wolinella* spp, *Xylella* spp, *Erwinia* spp, *Agrobacterium* spp, *Bacillus* spp, *Paenibacillus* spp, *Streptomyces* spp, *Micrococcus* spp, *Corynebacterium* spp, *Acetobacter* spp, *Cyanobacteria* spp, *Salmonella* spp, *Rhodococcus* spp, *Pseudomonas* spp, *Lactobacillus* spp, *Entero-*

*coccus* spp, *Alcaligenes* spp, *Klebsiella* spp, *Paenibacillus* spp, *Arthrobacter* spp, *Corynebacterium* spp, *Brevibacterium* spp, *Thermus* spp, *Pseudomonas* spp, *Clostridium* spp, and *Escherichia* spp. Non-limiting examples of bacteria that may be targeted by the methods and compositions provided herein are shown in Table 1. In some instances, the 16S rRNA sequence of the bacteria targeted by the modulating agent has at least 50%, 60%, 70%, 80%, 85%, 90%, 95%, 97%, 99%, 99.9%, or 100% identity with a sequence listed in Table 1.

TABLE 1

Examples of Target Bacteria and Host Insects

| Primary endosymbiont | Host | Location | 16S rRNA |
|---|---|---|---|
| Gamma proteobacteria | | | |
| *Carsonella ruddii* | Psyllids (Psylloidea) | bacteriocytes | TATCCAGCCACAGGTTCCCCTAC<br>AGCTACCTTGTTACGACTTCACC<br>CCAGTTACAAATCATACCGTTGT<br>AATAGTAAAATTACTTATGATACA<br>ATTTACTTCCATGGTGTGACGGG<br>CGGTGTGTACAAGGCTCGAGAA<br>CGTATTCACCGTAACATTCTGAT<br>TTACGATTACTAGCGATTCCAAC<br>TTCATGAAATCGAGTTACAGATT<br>TCAATCCGAACTAAGAATATTTTT<br>TAAGATTAGCATTATGTTGCCAT<br>ATAGCATATAACTTTTTGTAATAC<br>TCATTGTAGCACGTGTGTAGCCC<br>TACTTATAAGGGCCATGATGACT<br>TGACGTCGTCCTCACCTTCCTCC<br>AATTTATCATTGGCAGTTTCTTAT<br>TAGTTCTAATATATTTTTAGTAAA<br>ATAAGATAAGGGTTGCGCTCGTT<br>ATAGGACTTAACCCAACATTTCA<br>CAACACGAGCTGACGACAGCCA<br>TGCAGCACCTGTCTCAAAGCTAA<br>AAAAGCTTTATTATTTCTAATAAA<br>TTCTTTGGATGTCAAAAGTAGGT<br>AAGATTTTTCGTGTTGTATCGAA<br>TTAAACCACATGCTCCACCGCTT<br>GTGCGAGCCCCCGTCAATTCAT<br>TTGAGTTTTAACCTTGCGGTCGT<br>AATCCCCAGGCGGTCAACTTAA<br>CGCGTTAGCTTTTTCACTAAAAA<br>TATATAACTTTTTTTCATAAAACA<br>AAATTACAATTATAATATTTAATA<br>AATAGTTGACATCGTTTACTGCA<br>TGGACTACCAGGGTATCTAATCC<br>TGTTTGCTCCCCATGCTTTCGTG<br>TATTAGTGTCAGTATTAAAATAG<br>AAATACGCCTTCGCCACTAGTAT<br>TCTTTCAGATATCTAAGCATTTCA<br>CTGCTACTCCTGAAATTCTAATT<br>TCTTCTTTTATACTCAAGTTTATA<br>AGTATTAATTTCAATATTAAATTA<br>CTTTAATAAATTTAAAAATTAATT<br>TTTAAAAACAACCTGCACACCCT<br>TTACGCCCAATAATTCCGATTAA<br>CGCTTGCACCCCTCGTATTACC<br>GCGGCTGCTGGCACGAAGTTAG<br>CCGGTGCTTCTTTTACAAATAAC<br>GTCAAAGATAATATTTTTTTATTA<br>TAAAATCTCTTCTTACTTTGTTGA<br>AAGTGTTTTACAACCCTAAGGCC<br>TTCTTCACACACGCGATATAGCT<br>GGATCAAGCTTTCGCTCATTGTC<br>CAATATCCCCCACTGCTGCCTTC<br>CGTAAAAGTTTGGGCCGTGTCT<br>CAGTCCCAATGTGGTTGTTCATC<br>CTCTAAGATCAACTACGAATCAT<br>AGTCTTGTTAAGCTTTTACTTTAA<br>CAACTAACTAATTCGATATAAGC<br>TCTTCTATTAGCGAACGACATTC<br>TCGTTCTTTATCCATTAGGATAC<br>ATATTGAATTACTATACATTTCTA<br>TATACTTTTCTAATACTAATAGGT<br>AGATTCTTATATATTACTCACCC<br>GTTCGCTGCTAATTATTTTTTTAA<br>TAATTCGCACAACTTGCATGTGT<br>TAAGCTTATCGCTAGCGTTCAAT<br>CTGAGCTATGATCAAACTCA |

TABLE 1-continued

| Examples of Target Bacteria and Host Insects | | | |
|---|---|---|---|
| | | | (SEQ ID NO: 1) |
| *Portiera aleyrodidarum* BT-B | whiteflyes (Aleyrodoidea) | bacteriocytes | AAGAGTTTGATCATGGCTCAGAT TGAACGCTAGCGGCAGACATAA CACATGCAAGTCGAGCGGCATC ATACAGGTTGGCAAGCGGCGCA CGGGTGAGTAATACATGTAAATA TACCTAAAAGTGGGGAATAACGT ACGGAAACGTACGCTAATACCG CATAATTATTACGAGATAAAGCA GGGGCTTGATAAAAAAAATCAAC CTTGCGCTTTTAGAAAATTACAT GCCGGATTAGCTAGTTGGTAGA GTAAAAGCCTACCAAGGTAACG ATCCGTAGCTGGTCTGAGAGGA TGATCAGCCACACTGGGACTGA GAAAAGGCCCAGACTCCTACGG GAGGCAGCAGTGGGGAATATTG GACAATGGGGGGAACCCTGATC CAGTCATGCCGCGTGTGTGAAG AAGGCCTTTGGGTTGTAAAGCA CTTTCAGCGAAGAAGAAAAGTTA GAAAATAAAAAGTTATAACTATG ACGGTACTCGCAGAAGAAGCAC CGGCTAACTCCGTGCCAGCAGC CGCGGTAAGACGGAGGGTGCAA GCGTTAATCAGAATTACTGGGC GTAAAGGGCATGTAGGTGGTTT GTTAAGCTTTATGTGAAAGCCCT ATGCTTAACATAGGAACGGAATA AAGAACTGACAAACTAGAGTGCA GAAGAGGAAGGTAGAATTCCCG GTGTAGCGGTGAAATGCGTAGA TATCTGGAGGAATACCAGTTGC GAAGGCGACCTTCTGGGCTGAC ACTGACACTGAGATGCGAAAGC GTGGGGAGCAAACAGGATTAGA TACCCTGGTAGTCCACGCTGTAA ACGATATCAACTAGCCGTTGGAT TCTTAAAGAATTTTGTGGCGTAG CTAACGCGATAAGTTGATCGCCT GGGGAGTACGGTCGCAAGGCTA AAACTCAAATGAATTGACGGGG GCCCGCACAAGCGGTGGAGCAT GTGGTTTAATTCGATGCAACGCG CAAAACCTTACCTACTCTTGACA TCCAAAGTACTTTCCAGAGATGG AAGGGTGCCTTAGGGAACTTTG AGACAGGTGCTGCATGGCTGTC GTCAGCTCGTGTTGTGAAATGTT GGGTTAAGTCCCGTAACGAGCG CAACCCTTGTCCTTAGTTGCCAA CGCATAAGGCGGGAACTTTAAG GAGACTGCTGGTGATAAACCGG AGGAAGGTGGGGACGACGTCAA GTCATCATGGCCCTTAAGAGTAG GGCAACACACGTGCTACAATGG CAAAAACAAAGGGTCGCAAAAT GGTAACATGAAGCTAATCCCAAA AAAATTGTCTTAGTTCGGATTGG AGTCTGAAACTCGACTCCATAAA GTCGGAATCGCTAGTAATCGTG AATCAGAATGTCACGGTGAATAC GTTCTCGGGCCTTGTACACACC GCCCGTCACACCATGGAAGTGA AATGCACCAGAAGTGGCAAGTTT AACCAAAAAACAGGAGAACAGT CACTACGGTGTGGTTCATGACT GGGGTGAAGTCGTAACAAGGTA GCTGTAGGGGAACCTGTGGCTG GATCACCTCCTTAA |
| | | | (SEQ ID NO: 2) |
| *Buchnera aphidicola* str. *APS* (*Acyrthosiphon pisum*) | Aphids (Aphidoidea) | bacteriocytes | AGAGTTTGATCATGGCTCAGATT GAACGCTGGCGGCAAGCCTAAC ACATGCAAGTCGAGCGGCAGCG AGAAGAGAGCTTGCTCTCTTTGT CGGCAAGCGGCAAACGGGTGA |

TABLE 1-continued

| Examples of Target Bacteria and Host Insects | | | |
|---|---|---|---|
| | | | GTAATATCTGGGGATCTACCCAA<br>AAGAGGGGGATAACTACTAGAA<br>ATGGTAGCTAATACCGCATAATG<br>TTGAAAAACCAAAGTGGGGGAC<br>CTTTTGGCCTCATGCTTTTGGAT<br>GAACCCAGACGAGATTAGCTTG<br>TTGGTAGAGTAATAGCCTACCAA<br>GGCAACGATCTCTAGCTGGTCT<br>GAGAGGATAACCAGCCACACTG<br>GAACTGAGACACGGTCCAGACT<br>CCTACGGGAGGCAGCAGTGGG<br>GAATATTGCACAATGGGCGAAA<br>GCCTGATGCAGCTATGCCGCGT<br>GTATGAAGAAGGCCTTAGGGTT<br>GTAAAGTACTTTCAGCGGGGAG<br>GAAAAAAATAAAACTAATAATTTT<br>ATTTCGTGACGTTACCCGCAGAA<br>GAAGCACCGGCTAACTCCGTGC<br>CAGCAGCCGCGGTAATACGGAG<br>GGTGCAAGCGTTAATCAGAATTA<br>CTGGGCGTAAAGAGCGCGTAGG<br>TGGTTTTTTAAGTCAGGTGTGAA<br>ATCCCTAGGCTCAACCTAGGAA<br>CTGCATTTGAAACTGGAAAACTA<br>GAGTTTCGTAGAGGGAGGTAGA<br>ATTCTAGGTGTAGCGGTGAAATG<br>CGTAGATATCTGGAGGAATACC<br>CGTGGCGAAAGCGGCCTCCTAA<br>ACGAAAACTGACACTGAGGCGC<br>GAAAGCGTGGGGAGCAAACAGG<br>ATTAGATACCCTGGTAGTCCATG<br>CCGTAAACGATGTCGACTTGGA<br>GGTTGTTTCCAAGAGAAGTGACT<br>TCCGAAGCTAACGCATTAAGTCG<br>ACCGCCTGGGGAGTACGGCCG<br>CAAGGCTAAAACTCAAATGAATT<br>GACGGGGGCCCGCACAAGCGG<br>TGGAGCATGTGGTTTAATTCGAT<br>GCAACGCGAAAAACCTTACCTG<br>GTCTTGACATCCACAGAATTCTT<br>TAGAAATAAAGAAGTGCCTTCGG<br>GAGCTGTGAGACAGGTGCTGCA<br>TGGCTGTCGTCAGCTCGTGTTG<br>TGAAATGTTGGGTTAAGTCCCGC<br>AACGAGCGCAACCCTTATCCCC<br>TGTTGCCAGCGGTTCGGCCGGG<br>AACTCAGAGGAGACTGCCGGTT<br>ATAAACCGGAGGAAGGTGGGGA<br>CGACGTCAAGTCATCATGGCCC<br>TTACGACCAGGGCTACACACGT<br>GCTACAATGGTTTATACAAAGAG<br>AAGCAAATCTGCAAAGACAAGCA<br>AACCTCATAAAGTAAATCGTAGT<br>CCGGACTGGAGTCTGCAACTCG<br>ACTCCACGAAGTCGGAATCGCT<br>AGTAATCGTGGATCAGAATGCCA<br>CGGTGAATACGTTCCCGGGCCT<br>TGTACACACCGCCCGTCACACC<br>ATGGGAGTGGGTTGCAAAAGAA<br>GCAGGTATCCTAACCCTTTAAAA<br>GGAAGGCGCTTACCACTTTGTG<br>ATTCATGACTGGGGTGAAGTCG<br>TAACAAGGTAACCGTAGGGGAA<br>CCTGCGGTTGGATCACCTCCTT<br>(SEQ ID NO: 3) |
| *Buchnera aphidicola* str. *Sg* (*Schizaphis graminum*) | Aphids (Aphidoidea) | bacteriocytes | AAACTGAAGAGTTTGATCATGGC<br>TCAGATTGAACGCTGGCGGCAA<br>GCCTAACACATGCAAGTCGAGC<br>GGCAGCGAAAAGAAAGCTTGCT<br>TTCTTGTCGGCGAGCGGCAAAC<br>GGGTGAGTAATATCTGGGGATC<br>TGCCCAAAAGAGGGGGATAACT<br>ACTAGAAATGGTAGCTAATACCG<br>CATAAAGTTGAAAAACCAAAGTG<br>GGGGACCTTTTTTAAAGGCCTCA<br>TGCTTTTGGATGAACCCAGACGA<br>GATTAGCTTGTTGGTAAGGTAAA |

TABLE 1-continued

Examples of Target Bacteria and Host Insects

| | | | |
|---|---|---|---|
| | | | AGCTTACCAAGGCAACGATCTCT AGCTGGTCTGAGAGGATAACCA GCCACACTGGAACTGAGACACG GTCCAGACTCCTACGGGAGGCA GCAGTGGGGAATATTGCACAAT GGGCGAAAGCCTGATGCAGCTA TGCCGCGTGTATGAAGAAGGCC TTAGGGTTGTAAAGTACTTTCAG CGGGGAGGAAAAAATTAAAACTA ATAATTTTATTTTGTGACGTTACC CGCAGAAGAAGCACCGGCTAAC TCCGTGCCAGCAGCCGCGGTAA TACGGAGGGTGCGAGCGTTAAT CAGAATTACTGGGCGTAAAGAG CACGTAGGTGGTTTTTTAAGTCA GATGTGAAATCCCTAGGCTTAAC CTAGGAACTGCATTTGAAACTGA AATGCTAGAGTATCGTAGAGGG AGGTAGAATTCTAGGTGTAGCG GTGAAATGCGTAGATATCTGGA GGAATACCCGTGGCGAAAGCGG CCTCCTAAACGAATACTGACACT GAGGTGCGAAAGCGTGGGGAG CAAACAGGATTAGATACCCTGGT AGTCCATGCCGTAAACGATGTC GACTTGGAGGTTGTTTCCAAGA GAAGTGACTTCCGAAGCTAACG CGTTAAGTCGACCGCCTGGGGA GTACGGCCGCAAGGCTAAAACT CAAATGAATTGACGGGGGCCCG CACAAGCGGTGGAGCATGTGGT TTAATTCGATGCAACGCGAAAAA CCTTACCTGGTCTTGACATCCAC AGAATTTTTTAGAAATAAAAAAGT GCCTTCGGGAACTGTGAGACAG GTGCTGCATGGCTGTCGTCAGC TCGTGTTGTGAAATGTTGGGTTA AGTCCCGCAACGAGCGCAACCC TTATCCCCTGTTGCCAGCGGTTC GGCCGGGAACTCAGAGGAGACT GCCGGTTATAAACCGGAGGAAG GTGGGGACGACGTCAAGTCATC ATGGCCCTTACGACCAGGGCTA CACACGTGCTACAATGGTTTATA CAAAGAGAAGCAAATCTGTAAAG ACAAGCAAACCTCATAAAGTAAA TCGTAGTCCGGACTGGAGTCTG CAACTCGACTCCACGAAGTCGG AATCGCTAGTAATCGTGGATCAG AATGCCACGGTGAATACGTTCC CGGGCCTTGTACACACCGCCCG TCACACCATGGGAGTGGGTTGC AAAAGAAGCAGATTTCCTAACCA CGAAAGTGGAAGGCGTCTACCA CTTTGTGATTCATGACTGGGGTG AAGTCGTAACAAGGTAACCGTA GGGGAACCTGCGGTTGGATCAC CTCCTTA (SEQ ID NO: 4) |
| *Buchnera aphidicola* str. *Bp* (*Baizongia pistaciae*) | Aphids (Aphidoidea) | bacteriocytes | ACTTAAAATTGAAGAGTTTGATC ATGGCTCAGATTGAACGCTGGC GGCAAGCTTAACACATGCAAGT CGAGCGGCATCGAAGAAAAGTT TACTTTTCTGGCGGCGAGCGGC AAACGGGTGAGTAACATCTGGG GATCTACCTAAAAGAGGGGGAC AACCATTGGAAACGATGGCTAAT ACCGCATAATGTTTTTAAATAAA CCAAAGTAGGGGACTAAAATTTT TAGCCTTATGCTTTTAGATGAAC CCAGACGAGATTAGCTTGATGG TAAGGTAATGGCTTACCAAGGC GACGATCTCTAGCTGGTCTGAG AGGATAACCAGCCACACTGGAA CTGAGATACGGTCCAGACTCCT ACGGGAGGCAGCAGTGGGGAAT ATTGCACAATGGGCTAAAGCCT |

TABLE 1-continued

| Examples of Target Bacteria and Host Insects | | | |
|---|---|---|---|
| | | | GATGCAGCTATGCCGCGTGTAT GAAGAAGGCCTTAGGGTTGTAA AGTACTTTCAGCGGGGAGGAAA GAATTATGTCTAATATACATATTT TGTGACGTTACCCGAAGAAGAA GCACCGGCTAACTCCGTGCCAG CAGCCGCGGTAATACGGAGGGT GCGAGCGTTAATCAGAATTACTG GGCGTAAAGAGCACGTAGGCGG TTTATTAAGTCAGATGTGAAATC CCTAGGCTTAACTTAGGAACTGC ATTTGAAACTAATAGACTAGAGT CTCATAGAGGGAGGTAGAATTCT AGGTGTAGCGGTGAAATGCGTA GATATCTAGAGGAATACCCGTG GCGAAAGCGACCTCCTAAATGA AAACTGACGCTGAGGTGCGAAA GCGTGGGGAGCAAACAGGATTA GATACCCTGGTAGTCCATGCTGT AAACGATGTCGACTTGGAGGTT GTTTCCTAGAGAAGTGGCTTCC GAAGCTAACGCATTAAGTCGAC CGCCTGGGGAGTACGGTCGCAA GGCTAAAACTCAAATGAATTGAC GGGGGCCCGCACAAGCGGTGG AGCATGTGGTTTAATTCGATGCA ACGCGAAGAACCTTACCTGGTC TTGACATCCATAGAATTTTTTAGA GATAAAAGAGTGCCTTAGGGAA CTATGAGACAGGTGCTGCATGG CTGTCGTCAGCTCGTGTTGTGAA ATGTTGGGTTAAGTCCCGCAAC GAGCGCAACCCCTATCCTTTGTT GCCATCAGGTTATGCTGGGAAC TCAGAGGAGACTGCCGGTTATA AACCGGAGGAAGGTGGGGATGA CGTCAAGTCATCATGGCCCTTAC GACCAGGGCTACACACGTGCTA CAATGGCATATACAAAGAGATGC AACTCTGCGAAGATAAGCAAACC TCATAAAGTATGTCGTAGTCCGG ACTGGAGTCTGCAACTCGACTC CACGAAGTAGGAATCGCTAGTA ATCGTGGATCAGAATGCCACGG TGAATACGTTCCCGGGCCTTGTA CACACCGCCCGTCACACCATGG GAGTGGGTTGCAAAAGAAGCAG GTAGCTTAACCAGATTATTTTATT GGAGGGCGCTTACCACTTTGTG ATTCATGACTGGGGTGAAGTCG TAACAAGGTAACCGTAGGGGAA CCTGCGGTTGGATCACCTCCTTA (SEQ ID NO: 5) |
| *Buchnera aphidicola* BCc | Aphids (Aphidoidea) | bacteriocytes | ATGAGATCATTAATATATAAAAAT CATGTTCCAATTAAAAAATTAGG ACAAAATTTTTTACAGAATAAAGA AATTATTAATCAGATAATTAATTT AATAAATATTAATAAAAATGATAA TATTATTGAAATAGGATCAGGAT TAGGAGCGTTAACTTTTCCTATT TGTAGAATCATTAAAAAAATGAT AGTATTAGAAATTGATGAAGATC TTGTGTTTTTTTTAACTCAAAGTT TATTTATTAAAAAATTACAAATTA TAATTGCTGATATTATAAAATTTG ATTTTTGTTGTTTTTTTTCTTTAC AGAAATATAAAAAATATAGGTTTA TTGGTAATTTACCATATAATATTG CTACTATATTTTTTTTAAAAACAA TTAAATTTCTTTATAATATAATTG ATATGCATTTTATGTTTCAAAAAG AAGTAGCAAAGAGATTATTAGCT ACTCCTGGTACTAAAGAATATGG TAGATTAAGTATTATTGCACAATA TTTTTATAAGATAGAAACTGTTAT TAATGTTAATAAATTTAATTTTTTT CCTACTCCTAAAGTAGATTCTAC |

TABLE 1-continued

Examples of Target Bacteria and Host Insects

| | | | |
|---|---|---|---|
| | | | TTTTTTACGATTTACTCCTAAATA<br>TTTTAATAGTAAATATAAAATAGA<br>TAAACATTTTTCTGTTTTAGAATT<br>AATTACTAGATTTTCTTTTCAACA<br>TAGAAGAAAATTTTTAAATAATAA<br>TTTAATATCTTTATTTTCTACAAA<br>AGAATTAATTTCTTTAGATATTGA<br>TCCATATTCAAGAGCAGAAAATG<br>TTTCTTTAATTCAATATTGTAAAT<br>TAATGAAATATTATTTGAAAAGAA<br>AAATTTTATGTTTAGATTAA<br>(SEQ ID NO: 6) |
| *Buchnera aphidicola* (*Cinara tujafilina*) | Aphids (Aphidoidea) | bacteriocytes | TTATCTTATTTCACATATACGTAA<br>TATTGCGCTGCGTGCACGAGGA<br>TTTTTTTGAATTTCAGATATATTT<br>GGTTTAATACGTTTAATAAAACG<br>TATTTTTTTTTTTATTTTTCTTATT<br>TGCAATTCAGTAATAGGAAGTTT<br>TTTAGGTATATTTGGATAATTACT<br>GTAATTCTTAATAAAGTTTTTTAC<br>AATCCTATCTTCAATAGAATGAA<br>AACTAATAATAGCAATTTTTTGATC<br>CGGAATGTAATATGTTAATAATA<br>ATTTTTAATATTTTATGTAATTCA<br>TTTATTTCTTGGTTAATATATATT<br>CGAAAAGCTTGAAATGTTCTCGT<br>AGCTGGATGTTTAAATTTGTCAT<br>ATTTTGGGATTGATTTTTTTATGA<br>TTTGAACTAACTCTAACGTGCTT<br>GTTATGGTTTTTTTTTTTTATTTGT<br>AATATGATGGCTCGGGATATTTT<br>TTTTGCGTATTTTTCTTCGCCAAA<br>ATTTTTTATTACCTGTTCTATTGT<br>TTTTTGGTTTGTTTTTTTTAACCA<br>TTGACTAACTGATATTCCAGATT<br>TAGGGTTCATACGCATATCTAAA<br>GGTCCATCATTCATAAATGAAAA<br>TCCTCGGATACTAGAATTTAACT<br>GTATTGAAGAAATACCTAAATCT<br>AATAATATTCCATCTATTTTATCT<br>CTATTTTTTTCTTTTTTTTAATATTT<br>TTTCAATATTAGAAAATTTACCTA<br>AAAATATTTTAAATCGCGAATCTT<br>TTATTTTTTTTCCGATTTTTATAG<br>ATTGTGGGTCTTGATCAATACTA<br>TATAACTTTCCATTAACCCCTAAT<br>TCTTGAAGAATTGCTTTTGAATG<br>ACCACCACCTCCAAATGTACAAT<br>CAACATATGTACCGTCTTTTTTTA<br>TTTTTAAGTATTGTATGATTTCTT<br>TTGTTAAAACAGGTTTATGAATC<br>AT<br>(SEQ ID NO: 7) |
| *Buchnera aphidicola* str. G002 (*Myzus persicae*) | Aphids (Aphidoidea) | bacteriocytes | ATGAAAAGTATAAAAACTTTTAAA<br>AAACACTTTCCTGTGAAAAAATA<br>TGGACAAAATTTTCTTATTAATAA<br>AGAGATCATAAAAAATATTGTTA<br>AAAAAATTAATCCAAATATAGAA<br>CAAACATTAGTAGAAATCGGACC<br>AGGATTAGCTGCATTAACTGAGC<br>CCATATCTCAGTTATTAAAAGAG<br>TTAATAGTTATTGAAATAGACTGT<br>AATCTATTATATTTTTTAAAAAAA<br>CAACCATTTTATTCAAAATTAATA<br>GTTTTTTGTCAAGATGCTTTAAA<br>CTTTAATTATACAAATTTATTTTA<br>TAAAAAAAATAAATTAATTCGTAT<br>TTTTGGTAATTTACCATATAATAT<br>CTCTACATCTTTAATTATTTTTTT<br>ATTTCAACACATTAGAGTAATTC<br>AAGATATGAATTTTATGCTTCAAA<br>AAGAAGTTGCTGCAAGATTAATT<br>GCATTACCTGGAAATAAATATTA<br>CGGTCGTTTGAGCATTATATCTC<br>AATATTATTGTGATATCAAAATTT<br>TATTAAATGTTGCTCCTGAAGAT |

TABLE 1-continued

| Examples of Target Bacteria and Host Insects | | | |
|---|---|---|---|
| | | | TTTTGGCCTATTCCGAGAGTTCA<br>TTCTATATTTGTAAATTTAACACC<br>TCATCATAATTCTCCTTATTTTGT<br>TTATGATATTAATATTTTAAGCCT<br>TATTACAAATAAGGCTTTCCAAA<br>ATAGAAGAAAAATATTACGTCAT<br>AGTTTAAAAAATTTATTTTCTGAA<br>ACAACTTTATTAAATTTAGATATT<br>AATCCCAGATTAAGAGCTGAAAA<br>TATTTCTGTTTTTCAGTATTGTCA<br>ATTAGCTAATTATTTGTATAAAAA<br>AAATTATACTAAAAAAAATTAA<br>(SEQ ID NO: 8) |
| *Buchnera aphidicola* str. *Ak* (*Acyrthosiphon kondoi*) | Aphids (Aphidoidea) | bacteriocytes | ATTATAAAAAATTTTAAAAAACAT<br>TTTCCTTTAAAAAGGTATGGACA<br>AAATTTTCTTGTCAATACAAAAAC<br>TATTCAAAAGATAATTAATATAAT<br>TAATCCAAACACCAAACAAACAT<br>TAGTGGAAATTGGACCTGGATTA<br>GCTGCATTAACAAAACCAATTTG<br>TCAATTATTAGAAGAATTAATTGT<br>TATTGAAATAGATCCTAATTTATT<br>GTTTTTATTAAAAAAACGTTCATT<br>TTATTCAAAATTAACAGTTTTTTA<br>TCAAGACGCTTTAAATTTCAATTA<br>TACAGATTTGTTTTATAAGAAAAA<br>TCAATTAATTCGTGTTTTTGGAAA<br>CTTGCCATATAATATTTCTACATC<br>TTTAATTATTTCTTTATTCAATCA<br>TATTAAAGTTATTCAAGATATGAA<br>TTTTATGTTACAGAAAGAGGTTG<br>CTGAAAGATTAATTTCTATTCCT<br>GGAAATAAATCTTATGGCCGTTT<br>AAGCATTATTTCTCAGTATTATTG<br>TAAAATTAAAATATTATTAAATGT<br>TGTACCTGAAGATTTTCGACCTA<br>TACCGAAAGTGCATTCTGTTTTT<br>ATCAATTTAACTCCTCATACCAAT<br>TCTCCATATTTTGTTTATGATACA<br>AATATCCTCAGTTCTATCACAAG<br>AAATGCTTTTCAAAATAGAAGGA<br>AAATTTTGCGTCATAGTTTAAAAA<br>ATTTATTTTCTGAAAAAGAACTAA<br>TTCAATTAGAAATTAATCCAAATT<br>TACGAGCTGAAAATATTTCTATC<br>TTTCAGTATTGTCAATTAGCTGA<br>TTATTTATATAAAAAATTAAATAA<br>TCTTGTAAAAATCAATTAA<br>(SEQ ID NO: 9) |
| *Buchnera aphidicola* str. *Ua* (*Uroleucon ambrosiae*) | Aphids (Aphidoidea) | bacteriocytes | ATGATACTAAATAAATATAAAAAA<br>TTTATTCCTTTAAAAAGATACGG<br>ACAAAATTTTCTTGTAAATAGAG<br>AAATAATCAAAAATATTATCAAAA<br>TAATTAATCCTAAAAAAACGCAA<br>ACATTATTAGAAATTGGACCGGG<br>TTTAGGTGCGTTAACAAAACCTA<br>TTTGTGAATTTTTAAATGAACTTA<br>TCGTCATTGAAATAGATCCTAAT<br>ATATTATCTTTTTTAAAGAAATGT<br>ATATTTTTTGATAAATTAAAAATA<br>TATTGTCATAATGCTTTAGATTTT<br>AATTATAAAAATATATTCTATAAA<br>AAAAGTCAATTAATTCGTATTTTT<br>GGAAATTTACCATATAATATTTCT<br>ACATCTTTAATAATATATTTATTT<br>CGGAATATTGATATTATTCAAGA<br>TATGAATTTTATGTTACAACAAGA<br>AGTGGCTAAAAGATTAGTTGCTA<br>TTCCTGGTGAAAAACTTTATGGT<br>CGTTTAAGTATTATATCTCAATAT<br>TATTGTAATATTAAAATATTATTA<br>CATATTCGACCTGAAAATTTTCA<br>ACCTATTCCTAAAGTTAATTCAAT<br>GTTTGTAAATTTAACTCCGCATA<br>TTCATTCTCCTTATTTTGTTTATG<br>ATATTAATTTATTAACTAGTATTA |

TABLE 1-continued

| Examples of Target Bacteria and Host Insects | | | |
|---|---|---|---|
| | | | CAAAACATGCTTTTCAACATAGA AGAAAAATATTGCGTCATAGTTT AAGAAATTTTTTTTCTGAGCAAG ATTTAATTCATTTAGAAATTAATC CAAATTTAAGAGCTGAAAATGTT TCTATTATTCAATATTGTCAATTG GCTAATAATTTATATAAAAAACAT AAACAGTTTATTAATAATTAA (SEQ ID NO: 10) |
| *Buchnera aphidicola* (*Aphis glycines*) | Aphids (Aphidoidea) | bacteriocytes | ATGAAAAAGCATATTCCTATAAA AAAATTTAGTCAAAATTTTCTTGT AGATTTGAGTGTGATTAAAAAAA TAATTAAATTTATTAATCCGCAGT TAAATGAAATATTGGTTGAAATT GGACCGGGATTAGCTGCTATCA CTCGACCTATTTGTGATTTGATA GATCATTTAATTGTGATTGAAATT GATAAAATTTTATTAGATAGATTA AAACAGTTCTCATTTTATTCAAAA TTAACAGTATATCATCAAGATGC TTTAGCATTTGATTACATAAAGTT ATTTAATAAAAAAAATAAATTAGT TCGAATTTTTGGTAATTTACCATA TCATGTTTCTACGTCTTTAATATT GCATTTATTTAAAAGAATTAATAT TATTAAAGATATGAATTTTATGCT ACAAAAAGAAGTTGCTGAACGTT TAATTGCAACTCCAGGTAGTAAA TTATATGGTCGTTTAAGTATTATT TCTCAATATTATTGTAATATAAAA GTTTTATTGCATGTGTCTTCAAA ATGTTTTAAACCAGTTCCTAAAG TAGAATCAATTTTTCTTAATTTGA CACCTTATACTGATTATTTCCCTT ATTTTACTTATAATGTAAACGTTC TTAGTTATATTACAAATTTAGCTT TTCAAAAAAGAAGAAAAATATTA CGTCATAGTTTAGGTAAAATATT TTCTGAAAAAGTTTTTATAAAATT AAATATTAATCCCAAATTAAGAC CTGAGAATATTTCTATATTACAAT ATTGTCAGTTATCTAATTATATGA TAGAAAATAATATTCATCAGGAA CATGTTTGTATTTAA (SEQ ID NO: 11) |
| *Annandia pinicola* | (Phylloxeroidea) | bacteriocytes | AGATTGAACGCTGGCGGCATGC CTTACACATGCAAGTCGAACGGT AACAGGTCTTCGGACGCTGACG AGTGGCGAACGGGTGAGTAATA CATCGGAACGTGCCCAGTCGTG GGGGATAACTACTCGAAAGAGT AGCTAATACCGCATACGATCTGA GGATGAAAGCGGGGGACCTTCG GGCCTCGCGCGATTGGAGCGG CCGATGGCAGATTAGGTAGTTG GTGGGATAAAAGCTTACCAAGC CGACGATCTGTAGCTGGTCTGA GAGGACGACCAGCCACACTGGA ACTGAGATACGGTCCAGACTCTT ACGGGAGGCAGCAGTGGGGAAT ATTGCACAATGGGCGCAAGCCT GATGCAGCTATGTCGCGTGTAT GAAGAAGACCTTAGGGTTGTAAA GTACTTTCGATAGCATAAGAAGA TAATGAGACTAATAATTTTATTGT CTGACGTTAGCTATAGAAGAAGC ACCGGCTAACTCCGTGCCAGCA GCCGCGGTAATACGGGGGGTG CTAGCGTTAATCGGAATTACTGG GCGTAAAGAGCATGTAGGTGGT TTATTAAGTCAGATGTGAAATCC CTGGACTTAATCTAGGAACTGCA TTTGAAACTAATAGGCTAGAGTT TCGTAGAGGGAGGTAGAATTCT AGGTGTAGCGGTGAAATGCATA GATATCTAGAGGAATATCAGTGG |

TABLE 1-continued

| Examples of Target Bacteria and Host Insects | | | |
|---|---|---|---|
| | | | CGAAGGCGACCTTCTGGACGAT<br>AACTGACGCTAAAATGCGAAAG<br>CATGGGTAGCAAACAGGATTAG<br>ATACCCTGGTAGTCCATGCTGTA<br>AACGATGTCGACTAAGAGGTTG<br>GAGGTATAACTTTTAATCTCTGT<br>AGCTAACGCGTTAAGTCGACCG<br>CCTGGGGAGTACGGTCGCAAGG<br>CTAAAACTCAAATGAATTGACGG<br>GGGCCTGCACAAGCGGTGGAG<br>CATGTGGTTTAATTCGATGCAAC<br>GCGTAAAACCTTACCTGGTCTTG<br>ACATCCACAGAATTTTACAGAAA<br>TGTAGAAGTGCAATTTGAACTGT<br>GAGACAGGTGCTGCATGGCTGT<br>CGTCAGCTCGTGTTGTGAAATGT<br>TGGGTTAAGTCCCGCAACGAGC<br>GCAACCCTTGTCCTTTGTTACCA<br>TAAGATTTAAGGAACTCAAAGGA<br>GACTGCCGGTGATAAACTGGAG<br>GAAGGCGGGGACGACGTCAAGT<br>CATCATGGCCCTTATGACCAGG<br>GCTACACACGTGCTACAATGGC<br>ATATACAAAGAGATGCAATATTG<br>CGAAATAAAGCCAATCTTATAAA<br>ATATGTCCTAGTTCGGACTGGAG<br>TCTGCAACTCGACTCCACGAAGT<br>CGGAATCGCTAGTAATCGTGGA<br>TCAGCATGCCACGGTGAATATGT<br>TTCCAGGCCTTGTACACACCGC<br>CCGTCACACCATGGAAGTGGAT<br>TGCAAAAGAAGTAAGAAAATTAA<br>CCTTCTTAACAAGGAAATAACTT<br>ACCACTTTGTGACTCATAACTGG<br>GGTGA<br>(SEQ ID NO: 12) |
| *Moranella endobia* | (Coccoidea) | bacteriocytes | TCTTTTTGGTAAGGAGGTGATCC<br>AACCGCAGGTTCCCCTACGGTT<br>ACCTTGTTACGACTTCACCCCAG<br>TCATGAATCACAAAGTGGTAAGC<br>GCCCTCCTAAAAGGTTAGGCTA<br>CCTACTTCTTTTGCAACCCACTT<br>CCATGGTGTGACGGGCGGTGTG<br>TACAAGGCCCGGGAACGTATTC<br>ACCGTGGCATTCTGATCCACGAT<br>TACTAGCGATTCCTACTTCATGG<br>AGTCGAGTTGCAGACTCCAATC<br>CGGACTACGACGCACTTTATGA<br>GGTCCGCTAACTCTCGCGAGCT<br>TGCTTCTCTTTGTATGCGCCATT<br>GTAGCACGTGTGTAGCCCTACT<br>CGTAAGGGCCATGATGACTTGA<br>CGTCATCCCCACCTTCCTCCGG<br>TTTATCACCGGCAGTCTCCTTTG<br>AGTTCCCGACCGAATCGCTGGC<br>AAAAAAGGATAAGGGTTGCGCT<br>CGTTGCGGGACTTAACCCAACA<br>TTTCACAACACGAGCTGACGACA<br>GCCATGCAGCACCTGTCTCAGA<br>GTTCCCGAAGGTACCAAAACATC<br>TCTGCTAAGTTCTCTGGATGTCA<br>AGAGTAGGTAAGGTTCTTCGCG<br>TTGCATCGAATTAAACCACATGC<br>TCCACCGCTTGTGCGGGCCCCC<br>GTCAATTCATTTGAGTTTTAACCT<br>TGCGGCCGTACTCCCCAGGCGG<br>TCGATTTAACGCGTTAACTACGA<br>AAGCCACAGTTCAAGACCACAG<br>CTTTCAAATCGACATAGTTTACG<br>GCGTGGACTACCAGGGTATCTA<br>ATCCTGTTTGCTCCCCACGCTTT<br>CGTACCTGAGCGTCAGTATTCGT<br>CCAGGGGGCCGCCTTCGCCACT<br>GGTATTCCTCCAGATATCTACAC<br>ATTTCACCGCTACACCTGGAATT<br>CTACCCCCCTCTACGAGACTCTA<br>GCCTATCAGTTTCAAATGCAGTT |

TABLE 1-continued

| Examples of Target Bacteria and Host Insects | | | |
|---|---|---|---|
| | | | CCTAGGTTAAGCCCAGGGATTT<br>CACATCTGACTTAATAAACCGCC<br>TACGTACTCTTTACGCCCAGTAA<br>TTCCGATTAACGCTTGCACCCTC<br>CGTATTACCGCGGCTGCTGGCA<br>CGGAGTTAGCCGGTGCTTCTTC<br>TGTAGGTAACGTCAATCAATAAC<br>CGTATTAAGGATATTGCCTTCCT<br>CCCTACTGAAAGTGCTTTACAAC<br>CCGAAGGCCTTCTTCACACACG<br>CGGCATGGCTGCATCAGGGTTT<br>CCCCCATTGTGCAATATTCCCCA<br>CTGCTGCCTCCCGTAGGAGTCT<br>GGACCGTGTCTCAGTTCCAGTG<br>TGGCTGGTCATCCTCTCAGACC<br>AGCTAGGGATCGTCGCCTAGGT<br>AAGCTATTACCTCACCTACTAGC<br>TAATCCCATCTGGGTTCATCTGA<br>AGGTGTGAGGCCAAAAGGTCCC<br>CCACTTTGGTCTTACGACATTAT<br>GCGGTATTAGCTACCGTTTCCAG<br>CAGTTATCCCCCTCCATCAGGCA<br>GATCCCCAGACTTTACTCACCCG<br>TTCGCTGCTCGCCGGCAAAAAA<br>GTAAACTTTTTTCCGTTGCCGCT<br>CAACTTGCATGTGTTAGGCCTGC<br>CGCCAGCGTTCAATCTGAGCCA<br>TGATCAAACTCTTCAATTAAA<br>(SEQ ID NO: 13) |
| *Ishikawaella capsulata* Mpkobe | (Heteroptera) | bacteriocytes | AAATTGAAGAGTTTGATCATGGC<br>TCAGATTGAACGCTAGCGGCAA<br>GCTTAACACATGCAAGTCGAAC<br>GGTAACAGAAAAAAGCTTGCTTT<br>TTTGCTGACGAGTGGCGGACGG<br>GTGAGTAATGTCTGGGGATCTA<br>CCTAATGGCGGGGGATAACTAC<br>TGGAAACGGTAGCTAATACCGC<br>ATAATGTTGTAAAACCAAAGTGG<br>GGGACCTTATGGCCTCACACCA<br>TTAGATGAACCTAGATGGGATTA<br>GCTTGTAGGTGGGGTAAAGGCT<br>CACCTAGGCAACGATCCCTAGC<br>TGGTCTGAGAGGATGACCAGCC<br>ACACTGGAACTGAGATACGGTC<br>CAGACTCCTACGGGAGGCAGCA<br>GTGGGGAATCTTGCACAATGGG<br>CGCAAGCCTGATGCAGCTATGT<br>CGCGTGTATGAAGAAGGCCTTA<br>GGGTTGTAAAGTACTTTCATCGG<br>GGAAGAAGGATATGAGCCTAAT<br>ATTCTCATATATTGACGTTACCT<br>GCAGAAGAAGCACCGGCTAACT<br>CCGTGCCAGCAGCCGCGGTAAC<br>ACGGAGGGTGCGAGCGTTAATC<br>GGAATTACTGGGCGTAAAGAGC<br>ACGTAGGTGGTTTATTAAGTCAT<br>ATGTGAAATCCCTGGGCTTAACC<br>TAGGAACTGCATGTGAAACTGAT<br>AAACTAGAGTTTCGTAGAGGGA<br>GGTGGAATTCCAGGTGTAGCGG<br>TGAAATGCGTAGATATCTGGAG<br>GAATATCAGAGGCGAAGGCGAC<br>CTTCTGGACGAAAACTGACACTC<br>AGGTGCGAAAGCGTGGGGAGCA<br>AACAGGATTAGATACCCTGGTAG<br>TCCACGCTGTAAACAATGTCGAC<br>TAAAAAACTGTGAGCTTGACTTG<br>TGGTTTTTGTAGCTAACGCATTA<br>AGTCGACCGCCTGGGGAGTACG<br>GCCGCAAGGTTAAAACTCAAATG<br>AATTGACGGGGGTCCGCACAAG<br>CGGTGGAGCATGTGGTTTAATTC<br>GATGCAACGCGAAAAACCTTAC<br>CTGGTCTTGACATCCAGCGAATT<br>ATATAGAAATATATAAGTGCCTTT<br>CGGGGAACTCTGAGACGCTGCA<br>TGGCTGTCGTCAGCTCGTGTTG |

TABLE 1-continued

| Examples of Target Bacteria and Host Insects | | | |
|---|---|---|---|
| | | | TGAAATGTTGGGTTAAGTCCCGC AACGAGCGCCCTTATCCTCTGTT GCCAGCGGCATGGCCGGGAACT CAGAGGAGACTGCCAGTATTAA ACTGGAGGAAGGTGGGGATGAC GTCAAGTCATCATGGCCCTTATG ACCAGGGCTACACACGTGCTAC AATGGTGTATACAAAGAGAAGCA ATCTCGCAAGAGTAAGCAAAACT CAAAAAGTACATCGTAGTTCGGA TTAGAGTCTGCAACTCGACTCTA TGAAGTAGGAATCGCTAGTAATC GTGGATCAGAATGCCACGGTGA ATACGTTCTCTGGCCTTGTACAC ACCGCCCGTCACACCATGGGAG TAAGTTGCAAAAGAAGTAGGTAG CTTAACCTTTATAGGAGGGCGCT TACCACTTTGTGATTTATGACTG GGGTGAAGTCGTAACAAGGTAA CTGTAGGGGAACCTGTGGTTGG ATTACCTCCTTA (SEQ ID NO: 14) |
| *Baumannia cicadellinicola* | sharpshooter leafhoppers (Cicadellinae) | bacteriocytes | TTCAATTGAAGAGTTTGATCATG GCTCAGATTGAACGCTGGCGGT AAGCTTAACACATGCAAGTCGAG CGGCATCGGAAAGTAAATTAATT ACTTTGCCGGCAAGCGGCGAAC GGGTGAGTAATATCTGGGGATC TACCTTATGGAGAGGGATAACTA TTGGAAACGATAGCTAACACCG CATAATGTCGTCAGACCAAAATG GGGGACCTAATTTAGGCCTCAT GCCATAAGATGAACCCAGATGA GATTAGCTAGTAGGTGAGATAAT AGCTCACCTAGGCAACGATCTCT AGTTGGTCTGAGAGGATGACCA GCCACACTGGAACTGAGACACG GTCCAGACTCCTACGGGAGGCA GCAGTGGGGAATCTTGCACAAT GGGGGAAACCCTGATGCAGCTA TACCGCGTGTGTGAAGAAGGCC TTCGGGTTGTAAAGCACTTTCAG CGGGGAAGAAAATGAAGTTACT AATAATAATTGTCAATTGACGTTA CCCGCAAAAGAAGCACCGGCTA ACTCCGTGCCAGCAGCCGCGGT AAGACGGAGGGTGCAAGCGTTA ATCGGAATTACTGGGCGTAAAG CGTATGTAGGCGGTTTATTTAGT CAGGTGTGAAAGCCCTAGGCTT AACCTAGGAATTGCATTTGAAAC TGGTAAGCTAGAGTCTCGTAGA GGGGGGGAGAATTCCAGGTGTA GCGGTGAAATGCGTAGAGATCT GGAAGAATACCAGTGGCGAAGG CGCCCCCCTGGACGAAAACTGA CGCTCAAGTACGAAAGCGTGGG GAGCAAACAGGATTAGATACCCT GGTAGTCCACGCTGTAAACGAT GTCGATTTGAAGGTTGTAGCCTT GAGCTATAGCTTTCGAAGCTAAC GCATTAAATCGACCGCCTGGGG AGTACGACCGCAAGGTTAAAACT CAAATGAATTGACGGGGGCCCG CACAAGCGGTGGAGCATGTGGT TTAATTCGATACAACGCGAAAAA CCTTACCTACTCTTGACATCCAG AGTATAAAGCAGAAAAGCTTTAG TGCCTTCGGGAACTCTGAGACA GGTGCTGCATGGCTGTCGTCAG CTCGTGTTGTGAAATGTTGGGTT AAGTCCCGCAACGAGCGCAACC CTTATCCTTTGTTGCCAACGATT AAGTCGGGAACTCAAAGGAGAC TGCCGGTGATAAACCGGAGGAA GGTGAGGATAACGTCAAGTCAT CATGGCCCTTACGAGTAGGGCT |

TABLE 1-continued

| Examples of Target Bacteria and Host Insects | | | |
|---|---|---|---|
| | | | ACACACGTGCTACAATGGTGCAT ACAAAGAGAAGCAATCTCGTAAG AGTTAGCAAACCTCATAAAGTGC ATCGTAGTCCGGATTAGAGTCTG CAACTCGACTCTATGAAGTCGGA ATCGCTAGTAATCGTGGATCAGA ATGCCACGGTGAATACGTTCCC GGGCCTTGTACACACCGCCCGT CACACCATGGGAGTGTATTGCA AAAGAAGTTAGTAGCTTAACTCA TAATACGAGAGGGCGCTTACCA CTTTGTGATTCATAACTGGGGTG AAGTCGTAACAAGGTAACCGTA GGGGAACCTGCGGTTGGATCAC CTCCTTACACTAAA (SEQ ID NO: 15) |
| *Sodalis like* | *Rhopalus sapporensis* | wider tissue tropism | ATTGAACGCTGGCGGCAGGCCT AACACATGCAAGTCGAGCGGCA GCGGGAAGAAGCTTGCTTCTTT GCCGGCGAGCGGCGGACGGGT GAGTAATGTCTGGGGATCTGCC CGATGGAGGGGGATAACTACTG GAAACGGTAGCTAATACCGCATA ACGTCGCAAGACCAAAGTGGGG GACCTTCGGGCCTCACACCATC GGATGAACCCAGGTGGGATTAG CTAGTAGGTGGGGTAATGGCTC ACCTAGGCGACGATCCCTAGCT GGTCTGAGAGGATGACCAGTCA CACTGGAACTGAGACACGGTCC AGACTCCTACGGGAGGCAGCAG TGGGGAATATTGCACAATGGGG GAAACCCTGATGCAGCCATGCC GCGTGTGTGAAGAAGGCCTTCG GGTTGTAAAGCACTTTCAGCGG GGAGGAAGGCGATGGCGTTAAT AGCGCTATCGATTGACGTTACCC GCAGAAGAAGCACCGGCTAACT CCGTGCCAGCAGCCGCGGTAAT ACGGAGGGTGCGAGCGTTAATC GGAATTACTGGGCGTAAAGCGT ACGCAGGCGGTCTGTTAAGTCA GATGTGAAATCCCCGGGCTCAA CCTGGGAACTGCATTTGAAACTG GCAGGCTAGAGTCTCGTAGAGG GGGGTAGAATTCCAGGTGTAGC GGTGAAATGCGTAGAGATCTGG AGGAATACCGGTGGCGAAGGCG GCCCCCTGGACGAAGACTGACG CTCAGGTACGAAAGCGTGGGGA GCAAACAGGATTAGATACCCTG GTAGTCCACGCTGTAAACGATGT CGATTTGAAGGTTGTGGCCTTGA GCCGTGGCTTTCGGAGCTAACG TGTTAAATCGACCGCCTGGGGA GTACGGCCGCAAGGTTAAAACT CAAATGAATTGACGGGGGCCCG CACAAGCGGTGGAGCATGTGGT TTAATTCGATGCAACGCGAAGAA CCTTACCTACTCTTGACATCCAG AGAACTTGGCAGAGATGCTTTG GTGCCTTCGGGAACTCTGAGAC AGGTGCTGCATGGCTGTCGTCA GCTCGTGTTGTGAAATGTTGGGT TAAGTCCCGCAACGAGCGCAAC CCTTATCCTTTATTGCCAGCGAT TCGGTCGGGAACTCAAAGGAGA CTGCCGGTGATAAACCGGAGGA AGGTGGGGATGACGTCAAGTCA TCATGGCCCTTACGAGTAGGGC TACACACGTGCTACAATGGCGC ATACAAAGAGAAGCGATCTCGC GAGAGTCAGCGGACCTCATAAA GTGCGTCGTAGTCCGGATTGGA GTCTGCAACTCGACTCCATGAA GTCGGAATCGCTAGTAATCGTG GATCAGAATGCCACGGTGAATA |

TABLE 1-continued

| Examples of Target Bacteria and Host Insects | | | |
|---|---|---|---|
| | | | CGTTCCCGGGCCTTGTACACAC CGCCCGTCACACCATGGGAGTG GGTTGCAAAAGAAGTAGGTAGC TTAACCTTCGGGAGGGCGCTTA CCACTTTGTGATTCATGACTGGG GTG (SEQ ID NO: 16) |
| *Hartigia pinicola* | The pine bark adelgid | bacteriocytes | AGATTTAACGCTGGCGGCAGGC CTAACACATGCAAGTCGAGCGG TACCAGAAGAAGCTTGCTTCTTG CTGACGAGCGGCGGACGGGTG AGTAATGTATGGGGATCTGCCC GACAGAGGGGGATAACTATTGG AAACGGTAGCTAATACCGCATAA TCTCTGAGGAGCAAAGCAGGGG AACTTCGGTCCTTGCGCTATCG GATGAACCCATATGGGATTAGCT AGTAGGTGAGGTAATGGCTCCC CTAGGCAACGATCCCTAGCTGG TCTGAGAGGATGATCAGCCACA CTGGGACTGAGACACGGCCCAG ACTCCTACGGGAGGCAGCAGTG GGGAATATTGCACAATGGGCGA AAGCCTGATGCAGCCATGCCGC GTGTATGAAGAAGGCTTTAGGG TTGTAAAGTACTTTCAGTCGAGA GGAAAACATTGATGCTAATATCA TCAATTATTGACGTTTCCGACAG AAGAAGCACCGGCTAACTCCGT GCCAGCAGCCGCGGTAATACGG AGGGTGCAAGCGTTAATCGGAA TTACTGGGCGTAAAGCGCACGC AGGCGGTTAATTAAGTTAGATGT GAAAGCCCCGGGCTTAACCCAG GAATAGCATATAAAACTGGTCAA CTAGAGTATTGTAGAGGGGGGT AGAATTCCATGTGTAGCGGTGAA ATGCGTAGAGATGTGGAGGAAT ACCAGTGGCGAAGGCGGCCCC CTGGACAAAAACTGACGCTCAAA TGCGAAAGCGTGGGGAGCAAAC AGGATTAGATACCCTGGTAGTCC ATGCTGTAAACGATGTCGATTTG GAGGTTGTTCCCTTGAGGAGTA GCTTCCGTAGCTAACGCGTTAAA TCGACCGCCTGGGGGAGTACGA CTGCAAGGTTAAAACTCAAATGA ATTGACGGGGGCCCGCACAAGC GGTGGAGCATGTGGTTTAATTC GATGCAACGCGAAAAACCTTAC CTACTCTTGACATCCAGATAATT TAGCAGAAATGCTTTAGTACCTT CGGGAAATCTGAGACAGGTGCT GCATGGCTGTCGTCAGCTCGTG TTGTGAAATGTTGGGTTAAGTCC CGCAACGAGCGCAACCCTTATC CTTTGTTGCCAGCGATTAGGTCG GGAACTCAAAGGAGACTGCCGG TGATAAACCGGAGGAAGGTGGG GATGACGTCAAGTCATCATGGC CCTTACGAGTAGGGCTACACAC GTGCTACAATGGCATATACAAAG GGAAGCAACCTCGCGAGAGCAA GCGAAACTCATAAATTATGTCGT AGTTCAGATTGGAGTCTGCAACT CGACTCCATGAAGTCGGAATCG CTAGTAATCGTAGATCAGAATGC TACGGTGAATACGTTCCCGGGC CTTGTACACACCGCCCGTCACA CCATGGGAGTGGGTTGCAAAAG AAGTAGGTAACTTAACCTTATGG AAAGCGCTTACCACTTTGTGATT CATAACTGGGGTG (SEQ ID NO: 17) |

TABLE 1-continued

| Examples of Target Bacteria and Host Insects | | | |
|---|---|---|---|
| *Wigglesworthia glossinidia* | tsetse fly (Diptera: Glossinidae) | bacteriocytes | |
| Beta proteobacteria | | | |
| *Tremblaya phenacola* | *Phenacoccus avenae* (TPPAVE). | bacteriomes | AGGTAATCCAGCCACACCTTCCA<br>GTACGGCTACCTTGTTACGACTT<br>CACCCCAGTCACAACCCTTACCT<br>TCGGAACTGCCCTCCTCACAACT<br>CAAACCACCAAACACTTTTAAAT<br>CAGGTTGAGAGAGGTTAGGCCT<br>GTTACTTCTGGCAAGAATTATTT<br>CCATGGTGTGACGGGCGGTGTG<br>TACAAGACCCGAGAACATATTCA<br>CCGTGGCATGCTGATCCACGAT<br>TACTAGCAATTCCAACTTCATGC<br>ACTCGAGTTTCAGAGTACAATCC<br>GAACTGAGGCCGGCTTTGTGAG<br>ATTAGCTCCCTTTTGCAAGTTGG<br>CAACTCTTTGGTCCGGCCATTGT<br>ATGATGTGTGAAGCCCCACCCA<br>TAAAGGCCATGAGGACTTGACG<br>TCATCCCCACCTTCCTCCAACTT<br>ATCGCTGGCAGTCTCTTTAAGGT<br>AACTGACTAATCCAGTAGCAATT<br>AAAGACAGGGGTTGCGCTCGTT<br>ACAGGACTTAACCCAACATCTCA<br>CGACACGAGCTGACGACAGCCA<br>TGCAGCACCTGTGCACTAATTCT<br>CTTTCAAGCACTCCCGCTTCTCA<br>ACAGGATCTTAGCCATATCAAAG<br>GTAGGTAAGGTTTTTCGCGTTGC<br>ATCGAATTAATCCACATCATCCA<br>CTGCTTGTGCGGGTCCCCGTCA<br>ATTCCTTTGAGTTTTAACCTTGC<br>GGCCGTACTCCCCAGGCGGTCG<br>ACTTGTGCGTTAGCTGCACCACT<br>GAAAAGGAAAACTGCCCAATGG<br>TTAGTCAACATCGTTTAGGGCAT<br>GGACTACCAGGGTATCTAATCCT<br>GTTTGCTCCCCATGCTTTAGTGT<br>CTGAGCGTCAGTAACGAACCAG<br>GAGGCTGCCTACGCTTTCGGTA<br>TTCCTCCACATCTCTACACATTT<br>CACTGCTACATGCGGAATTCTAC<br>CTCCCCCTCTCGTACTCCAGCCT<br>GCCAGTAACTGCCGCATTCTGA<br>GGTTAAGCCTCAGCCTTTCACAG<br>CAATCTTAACAGGCAGCCTGCA<br>CACCCTTTACGCCCAATAAATCT<br>GATTAACGCTCGCACCCTACGTA<br>TTACCGCGGCTGCTGGCACGTA<br>GTTTGCCGGTGCTTATTCTTTCG<br>GTACAGTCACACCACCAAATTGT<br>TAGTTGGGTGGCTTTCTTTCCGA<br>ACAAAAGTGCTTTACAACCCAAA<br>GGCCTTCTTCACACACGCGGCA<br>TTGCTGGATCAGGCTTCCGCCC<br>ATTGTCCAAGATTCCTCACTGCT<br>GCCTTCCTCAGAAGTCTGGGCC<br>GTGTCTCAGTCCCAGTGTGGCT<br>GGCCGTCCTCTCAGACCAGCTA<br>CCGATCATTGCCTTGGGAAGCC<br>ATTACCTTTCCAACAAGCTAATC<br>AGACATCAGCCAATCTCAGAGC<br>GCAAGGCAATTGGTCCCCTGCT<br>TTCATTCTGCTTGGTAGAGAACT<br>TTATGCGGTATTAATTAGGCTTT<br>CACCTAGCTGTCCCCCACTCTG<br>AGGCATGTTCTGATGCATTACTC<br>ACCCGTTTGCCACTTGCCACCAA<br>GCCTAAGCCCGTGTTGCCGTTC<br>GACTTGCATGTGTAAGGCATGC<br>CGCTAGCGTTCAATCTGAGCCA<br>GGATCAAACTCT<br>(SEQ ID NO: 18) |

TABLE 1-continued

| Examples of Target Bacteria and Host Insects | | | |
|---|---|---|---|
| *Tremblaya princeps* | citrus mealybug *Planococcus citri* | bacteriomes | AGAGTTTGATCCTGGCTCAGATT GAACGCTAGCGGCATGCATTAC ACATGCAAGTCGTACGGCAGCA CGGGCTTAGGCCTGGTGGCGAG TGGCGAACGGGTGAGTAACGCC TCGGAACGTGCCTTGTAGTGGG GGATAGCCTGGCGAAAGCCAGA TTAATACCGCATGAAGCCGCACA GCATGCGCGGTGAAAGTGGGG GATTCTAGCCTCACGCTACTGGA TCGGCCGGGGTCTGATTAGCTA GTTGGCGGGGTAATGGCCCACC AAGGCTTAGATCAGTAGCTGGT CTGAGAGGACGATCAGCCACAC TGGGACTGAGACACGGCCCAGA CTCCTACGGGAGGCAGCAGTGG GGAATCTTGGACAATGGGCGCA AGCCTGATCCAGCAATGCCGCG TGTGTGAAGAAGGCCTTCGGGT CGTAAAGCACTTTTGTTCGGGAT GAAGGGGGGCGTGCAAACACCA TGCCCTCTTGACGATACCGAAA GAATAAGCACCGGCTAACTACG TGCCAGCAGCCGCGGTAATACG TAGGGTGCGAGCGTTAATCGGA ATCACTGGGCGTAAAGGGTGCG CGGGTGGTTTGCCAAGACCCCT GTAAAATCCTACGGCCCAACCG TAGTGCTGCGGAGGTTACTGGT AAGCTTGAGTATGGCAGAGGGG GGTAGAATTCCAGGTGTAGCGG TGAAATGCGTAGATATCTGGAG GAATACCGAAGGCGAAGGCAAC CCCCTGGGCCATCACTGACACT GAGGCACGAAAGCGTGGGGAG CAAACAGGATTAGATACCCTGGT AGTCCACGCCCTAAACCATGTC GACTAGTTGTCGGGGGGAGCCC TTTTTCCTCGGTGACGAAGCTAA CGCATGAAGTCGACCGCCTGGG GAGTACGACCGCAAGGTTAAAA CTCAAAGGAATTGACGGGGACC CGCACAAGCGGTGGATGATGTG GATTAATTCGATGCAACGCGAAA AACCTTACCTACCCTTGACATGG CGGAGATTCTGCCGAGAGGCGG AAGTGCTCGAAAGAGAATCCGT GCACAGGTGCTGCATGGCTGTC GTCAGCTCGTGTCGTGAGATGT TGGGTTAAGTCCCATAACGAGC GCAACCCCCGTCTTTAGTTGCTA CCACTGGGGCACTCTATAGAGA CTGCCGGTGATAAACCGGAGGA AGGTGGGGACGACGTCAAGTCA TCATGGCCTTTATGGGTAGGGC TTCACACGTCATACAATGGCTGG AGCAAAGGGTCGCCAACTCGAG AGAGGGAGCTAATCCCACAAAC CCAGCCCCAGTTCGGATTGCAC TCTGCAACTCGAGTGCATGAAGT CGGAATCGCTAGTAATCGTGGA TCAGCATGCCACGGTGAATACG TTCTCGGGTCTTGTACACACCGC CCGTCACACCATGGGAGTAAGC CGCATCAGAAGCAGCCTCCCTA ACCCTATGCTGGGAAGGAGGCT GCGAAGGTGGGGTCTATGACTG GGGTGAAGTCGTAACAAGGTAG CCGTACCGGAAGGTGCGGCTGG ATTACCT (SEQ ID NO: 19) |

TABLE 1-continued

| Examples of Target Bacteria and Host Insects | | | |
|---|---|---|---|
| *Vidania* | | bacteriomes | |
| *Nasuia deltocephalinicola* | pestiferous insect host, *Macrosteles quadripunctulatus* (Hemiptera: Cicadellidae) | bacteriomes | AGTTTAATCCTGGCTCAGATTTAACGCTTGCGACATGCCTAACACATGCAAGTTGAACGTTGAAAATATTTCAAAGTAGCGTATAGGTGAGTATAACATTTAAACATACCTTAAAGTTCGGAATACCCCGATGAAAATCGGTATAATACCGTATAAAAGTATTTAAGAATTAAAGCGGGGAAAACCTCGTGCTATAAGATTGTTAAATGCCTGATTAGTTTGTTGGTTTTTAAGGTAAAAGCTTACCAAGACTTTGATCAGTAGCTATTCTGTGAGGATGTATAGCCACATTGGGATTGAAATAATGCCCAAACCTCTACGGAGGGCAGCAGTGGGGAATATTGGACAATGAGCGAAAGCTTGATCCAGCAATGTCGCGTGTGCGATTAAGGGAAACTGTAAAGCACTTTTTTTTAAGAATAAGAAATTTTAATTAATAATTAAAATTTTTGAATGTATTAAAAGAATAAGTACCGACTAATCACGTGCCAGCAGTCGCGGTAATACGTGGGGTGCGAGCGTTAATCGGATTTATTGGGCGTAAAGTGTATTCAGGCTGCTTAAAAAGATTTATATTAAATATTTAAATTAAATTTAAAAAATGTATAAATTACTATTAAGCTAGAGTTTAGTATAAGAAAAAAGAATTTTATGTGTAGCAGTGAAATGCGTTGATATATAAAGGAACGCCGAAAGCGAAAGCATTTTTCTGTAATAGAACTGACGCTTATATACGAAAGCGTGGGTAGCAAACAGGATTAGATACCCTGGTAGTCCACGCCCTAAACTATGTCAATTAACTATTAGAATTTTTTTTAGTGGTGTAGCTAACGCGTTAAATTGACCGCCTGGGTATTACGATCGCAAGATTAAAACTCAAAGGAATTGACGGGGACCAGCACAAGCGGTGGATGATGTGGATTAATTCGATGATACGCGAAAAACCTTACCTGCCCTTGACATGGTTAGAATTTTATTGAAAAATAAAAGTGCTTGGAAAAGAGCTAACACACAGGTGCTGCATGGCTGTCGTCAGCTCGTGTCGTGAGATGTTGGGTTAAGTCCCGCAACGAGCGCAACCCCTACTCTTAGTTGCTAATTAAAGAACTTTAAGAGAACAGCTAACAATAAGTTTAGAGGAAGGAGGGGATGACTTCAAGTCCTCATGGCCCTTATGGGCAGGGCTTCACACGTCATACAATGGTTAATACAAAAAGTTGCAATATCGTAAGATTGAGCTAATCTTTAAAATTAATCTTAGTTCGGATTGTACTCTGCAACTCGAGTACATGAAGTTGGAATCGCTAGTAATCGCGGATCAGCATGCCGCGGTGAATAGTTTAACTGGTCTTGTACACACCGCCCGTCACACCATGGAAATAAATCTTGTTTTAAATGAAGTAATATATTTTATCAAAACAGGTTTTGTAACCGGGGTGAAGTCGTAACA (SEQ ID NO: 20) |
| *Zinderia insecticola* CARI | spittlebug *Clastoptera arizonana* | bacteriocytes | ATATAAATAAGAGTTTGATCCTGGCTCAGATTGAACGCTAGCGGTATGCTTTACACATGCAAGTCGAACGACAATATTAAAGCTTGCTTTAATATAAAGTGGCGAACGGGTGAGTAATATATCAAAACGTACCTTAAAGTGGGGGATAACTAATTGAAAAATTAGATAATACCGCATATTAATCTTAGGATGAAAATAGGAATAATATCTTATGCTTTTAGATCGGTTG |

TABLE 1-continued

| Examples of Target Bacteria and Host Insects | | | |
|---|---|---|---|
| | | | ATATCTGATTAGCTAGTTGGTAG GGTAAATGCTTACCAAGGCAATG ATCAGTAGCTGGTTTTAGCGAAT GATCAGCCACACTGGAACTGAG ACACGGTCCAGACTTCTACGGA AGGCAGCAGTGGGGAATATTGG ACAATGGGAGAAATCCTGATCCA GCAATACCGCGTGAGTGATGAA GGCCTTAGGGTCGTAAAACTCTT TTGTTAGGAAAGAAATAATTTTAA ATAATATTTAAAATTGATGACGG TACCTAAAGAATAAGCACCGGCT AACTACGTGCCAGCAGCCGCGG TAATACGTAGGGTGCAAGCGTTA ATCGGAATTATTGGGCGTAAAGA GTGCGTAGGCTGTTATATAAGAT AGATGTGAAATACTTAAGCTTAA CTTAAGAACTGCATTTATTACTG TTTAACTAGAGTTTATTAGAGAG AAGTGGAATTTTATGTGTAGCAG TGAAATGCGTAGATATATAAAGG AATATCGATGGCGAAGGCAGCT TCTTGGAATAATACTGACGCTGA GGCACGAAAGCGTGGGGAGCAA ACAGGATTAGATACCCTGGTAGT CCACGCCCTAAACTATGTCTACT AGTTATTAAATTAAAAATAAAATT TAGTAACGTAGCTAACGCATTAA GTAGACCGCCTGGGGAGTACGA TCGCAAGATTAAAACTCAAAGGA ATTGACGGGGACCCGCACAAGC GGTGGATGATGTGGATTAATTCG ATGCAACACGAAAAACCTTACCT ACTCTTGACATGTTTGGAATTTT AAAGAAATTTAAAAGTGCTTGAA AAAGAACCAAAACACAGGTGCT GCATGGCTGTCGTCAGCTCGTG TCGTGAGATGTTGGGTTAAGTCC CGCAACGAGCGCAACCCTTGTT ATTATTTGCTAATAAAAAGAACTT TAATAAGACTGCCAATGACAAAT TGGAGGAAGGTGGGGATGACGT CAAGTCCTCATGGCCCTTATGAG TAGGGCTTCACACGTCATACAAT GATATATACAATGGGTAGCAAAT TTGTGAAAATGAGCCAATCCTTA AAGTATATCTTAGTTCGGATTGT AGTCTGCAACTCGACTACATGAA GTTGGAATCGCTAGTAATCGCG GATCAGCATGCCGCGGTGAATA CGTTCTCGGGTCTTGTACACACC GCCCGTCACACCATGGAAGTGA TTTTTACCAGAAATTATTTGTTTA ACCTTTATTGGAAAAAAATAATTA AGGTAGAATTCATGACTGGGGT GAAGTCGTAACAAGGTAGCAGT ATCGGAAGGTGCGGCTGGATTA CATTTTAAAT (SEQ ID NO: 21) |
| *Profftella armatura* | *Diaphorina citri*, the Asian citrus psyllid | bacteriomes | |
| Alpha proteobacteria | | | |
| *Hodgkinia* | Cicada *Diceroprocta semicincta* | bacteriome | AATGCTGGCGGCAGGCCTAACA CATGCAAGTCGAGCGGACAACG TTCAAACGTTGTTAGCGGCGAAC GGGTGAGTAATACGTGAGAATC TACCCATCCCAACGTGATAACAT AGTCAACACCATGTCAATAACGT ATGATTCCTGCAACAGGTAAAGA TTTTATCGGGGATGGATGAGCTC ACGCTAGATTAGCTAGTTGGTGA GATAAAAGCCCACCAAGGCCAA GATCTATAGCTGGTCTGGAAGG ATGGACAGCCACATTGGGACTG |

TABLE 1-continued

Examples of Target Bacteria and Host Insects

| | | | |
|---|---|---|---|
| | | | AGACAAGGCCCAACCCTCTAAG GAGGGCAGCAGTGAGGAATATT GGACAATGGGCGTAAGCCTGAT CCAGCCATGCCGCATGAGTGAT TGAAGGTCCAACGGACTGTAAA ACTCTTTTCTCCAGAGATCATAA ATGATAGTATCTGGTGATATAAG CTCCGGCCAACTTCGTGCCAGC AGCCGCGGTAATACGAGGGGAG CGAGTATTGTTCGGTTTTATTGG GCGTAAAGGGTGTCCAGGTTGC TAAGTAAGTTAACAACAAAATCT TGAGATTCAACCTCATAACGTTC GGTTAATACTACTAAGCTCGAGC TTGGATAGAGACAAACGGAATTC CGAGTGTAGAGGTGAAATTCGTT GATACTTGGAGGAACACCAGAG GCGAAGGCGGTTTGTCATACCA AGCTGACACTGAAGACACGAAA GCATGGGGAGCAAACAGGATTA GATACCCTGGTAGTCCATGCCC TAAACGTTGAGTGCTAACAGTTC GATCAAGCCACATGCTATGATCC AGGATTGTACAGCTAACGCGTTA AGCACTCCGCCTGGGTATTACG ACCGCAAGGTTAAAACTCAAAG GAATTGACGGAGACCCGCACAA GCGGTGGAGCATGTGGTTTAAT TCGAAGCTACACGAAGAACCTTA CCAGCCCTTGACATACCATGGC CAACCATCCTGGAAACAGGATG TTGTTCAAGTTAAACCCTTGAAA TGCCAGGAACAGGTGCTGCATG GCTGTTGTCAGTTCGTGTCGTGA GATGTATGGTTAAGTCCCAAAAC GAACACAACCCTCACCCATAGTT GCCATAAACACAATTGGGTTCTC TATGGGTACTGCTAACGTAAGTT AGAGGAAGGTGAGGACCACAAC AAGTCATCATGGCCCTTATGGG CTGGGCCACACACATGCTACAA TGGTGGTTACAAAGAGCCGCAA CGTTGTGAGACCGAGCAAATCT CCAAAGACCATCTCAGTCCGGA TTGTACTCTGCAACCCGAGTACA TGAAGTAGGAATCGCTAGTAATC GTGGATCAGCATGCCACGGTGA ATACGTTCTCGGGTCTTGTACAC GCCGCCCGTCACACCATGGGAG CTTCGCTCCGATCGAAGTCAAGT TACCCTTGACCACATCTTGGCAA GTGACCGA (SEQ ID NO: 22) |
| *Wolbachia* sp. *wPip* | Mosquito *Culex quinquefasciatus* | bacteriome | AAATTTGAGAGTTTGATCCTGGC TCAGAATGAACGCTGGCGGCAG GCCTAACACATGCAAGTCGAAC GGAGTTATATTGTAGCTTGCTAT GGTATAACTTAGTGGCAGACGG GTGAGTAATGTATAGGAATCTAC CTAGTAGTACGGAATAATTGTTG GAAACGACAACTAATACCGTATA CGCCCTACGGGGGAAAAATTTA TTGCTATTAGATGAGCCTATATT AGATTAGCTAGTTGGTGGGGTA ATAGCCTACCAAGGTAATGATCT ATAGCTGATCTGAGAGGATGATC AGCCACACTGGAACTGAGATAC GGTCCAGACTCCTACGGGAGGC AGCAGTGGGGAATATTGGACAA TGGGCGAAAGCCTGATCCAGCC ATGCCGCATGAGTGAAGAAGGC CTTTGGGTTGTAAAGCTCTTTTA GTGAGGAAGATAATGACGGTAC TCACAGAAGAAGTCCTGGCTAA CTCCGTGCCAGCAGCCGCGGTA ATACGGAGAGGGCTAGCGTTAT TCGGAATTATTGGGCGTAAAGG |

TABLE 1-continued

| Examples of Target Bacteria and Host Insects | | | |
|---|---|---|---|
| | | | GCGCGTAGGCTGGTTAATAAGT TAAAAGTGAAATCCCGAGGCTTA ACCTTGGAATTGCTTTTAAAACT ATTAATCTAGAGATTGAAAGAGG ATAGAGGAATTCCTGATGTAGAG GTAAAATTCGTAAATATTAGGAG GAACACCAGTGGCGAAGGCGTC TATCTGGTTCAAATCTGACGCTG AAGCGCGAAGGCGTGGGGAGC AAACAGGATTAGATACCCTGGTA GTCCACGCTGTAAACGATGAAT GTTAAATATGGGGAGTTTACTTT CTGTATTACAGCTAACGCGTTAA ACATTCCGCCTGGGGACTACGG TCGCAAGATTAAAACTCAAAGGA ATTGACGGGGACCCGCACAAGC GGTGGAGCATGTGGTTTAATTC GATGCAACGCGAAAAACCTTAC CACTTCTTGACATGAAAATCATA CCTATTCGAAGGGATAGGGTCG GTTCGGCCGGATTTTACACAAGT GTTGCATGGCTGTCGTCAGCTC GTGTCGTGAGATGTTGGGTTAA GTCCCGCAACGAGCGCAACCCT CATCCTTAGTTGCCATCAGGTAA TGCTGAGTACTTTAAGGAAACTG CCAGTGATAAGCTGGAGGAAGG TGGGGATGATGTCAAGTCATCAT GGCCTTTATGGAGTGGGCTACA CACGTGCTACAATGGTGTCTACA ATGGGCTGCAAGGTGCGCAAGC CTAAGCTAATCCCTAAAAGACAT CTCAGTTCGGATTGTACTCTGCA ACTCGAGTACATGAAGTTGGAAT CGCTAGTAATCGTGGATCAGCAT GCCACGGTGAATACGTTCTCGG GTCTTGTACACACTGCCCGTCAC GCCATGGGAATTGGTTTCACTC GAAGCTAATGGCCTAACCGCAA GGAAGGAGTTATTTAAAGTGGG ATCAGTGACTGGGGTGAAGTCG TAACAAGGTAGCAGTAGGGGAA TCTGCAGCTGGATTACCTCCTTA (SEQ ID NO: 23) |
| Bacteroidetes | | | |
| *Uzinura diaspidicola* | armoured scale insects | bacteriocytes | AAAGGAGATATTCCAACCACACC TTCCGGTACGGTTACCTTGTTAC GACTTAGCCCTAGTCATCAAGTT TACCTTAGGCAGACCACTGAAG GATTACTGACTTCAGGTACCCCC GACTCCCATGGCTTGACGGGCG GTGTGTACAAGGTTCGAGAACAT ATTCACCGCGCCATTGCTGATG CGCGATTACTAGCGATTCCTGCT TCATAGAGTCGAATTGCAGACTC CAATCCGAACTGAGACTGGTTTT AGAGATTAGCTCCTGATCACCCA GTGGCTGCCCTTTGTAACCAGC CATTGTAGCACGTGTGTAGCCC AAGGCATAGAGGCCATGATGAT TTGACATCATCCCCACCTTCCTC ACAGTTTACACCGGCAGTTTTGT TAGAGTCCCCGGCTTTACCCGA TGGCAACTAACAATAGGGGTTG CGCTCGTTATAGGACTTAACCAA ACACTTCACAGCACGAACTGAA GACAACCATGCAGCACCTTGTAA TACGTCGTATAGACTAAGCTGTT TCCAGCTTATTCGTAATACATTTA AGCCTTGGTAAGGTTCCTCGCG TATCATCGAATTAAACCACATGC TCCACCGCTTGTGCGAACCCCC GTCAATTCCTTTGAGTTTCAATC TTGCGACTGTACTTCCCAGGTG GATCACTTATCGCTTTCGCTAAG CCACTGAATATCGTTTTTCCAAT |

TABLE 1-continued

Examples of Target Bacteria and Host Insects

AGCTAGTGATCATCGTTTAGGGC
GTGGACTACCAGGGTATCTAATC
CTGTTTGCTCCCCACGCTTTCGT
GCACTGAGCGTCAGTAAAGATTT
AGCAACCTGCCTTCGCTATCGG
TGTTCTGTATGATATCTATGCATT
TCACCGCTACACCATACATTCCA
GATGCTCCAATCTTACTCAAGTT
TACCAGTATCAATAGCAATTTTA
CAGTTAAGCTGTAAGCTTTCACT
ACTGACTTAATAAACAGCCTACA
CACCCTTTAAACCCAATAAATCC
GAATAACGCTTGTGTCATCCGTA
TTGCCGCGGCTGCTGGCACGGA
ATTAGCCGACACTTATTCGTATA
GTACCTTCAATCTCCTATCACGT
AAGATATTTTATTTCTATACAAAA
GCAGTTTACAACCTAAAAGACCT
TCATCCTGCACGCGACGTAGCT
GGTTCAGAGTTTCCTCCATTGAC
CAATATTCCTCACTGCTGCCTCC
CGTAGGAGTCTGGTCCGTGTCT
CAGTACCAGTGTGGAGGTACAC
CCTCTTAGGCCCCCTACTGATCA
TAGTCTTGGTAGAGCCATTACCT
CACCAACTAACTAATCAAACGCA
GGCTCATCTTTTGCCACCTAAGT
TTTAATAAAGGCTCCATGCAGAA
ACTTTATATTATGGGGGATTAAT
CAGAATTTCTTCTGGCTATACCC
CAGCAAAAGGTAGATTGCATAC
GTGTTACTCACCCATTCGCCGGT
CGCCGACAAATTAAAAATTTTTC
GATGCCCCTCGACTTGCATGTG
TTAAGCTCGCCGCTAGCGTTAAT
TCTGAGCCAGGATCAAACTCTTC
GTTGTAG
(SEQ ID NO: 24)

| | | | |
|---|---|---|---|
| *Sulcia muelleri* | Blue-Green Sharpshooter and several other leafhopper species | bacteriocytes | CTCAGGATAAACGCTAGCGGAG
GGCTTAACACATGCAAGTCGAG
GGGCAGCAAAAATAATTATTTTT
GGCGACCGGCAAACGGGTGAGT
AATACATACGTAACTTTCCTTAT
GCTGAGGAATAGCCTGAGGAAA
CTTGGATTAATACCTCATAATAC
AATTTTTTAGAAAGAAAAATTGTT
AAAGTTTTATTATGGCATAAGAT
AGGCGTATGTCCAATTAGTTAGT
TGGTAAGGTAATGGCTTACCAAG
ACGATGATTGGTAGGGGGCCTG
AGAGGGGCGTTCCCCCACATTG
GTACTGAGACACGGACCAAACT
TCTACGGAAGGCTGCAGTGAGG
AATATTGGTCAATGGAGGAAACT
CTGAACCAGCCACTCCGCGTGC
AGGATGAAAGAAAGCCTTATTGG
TTGTAAACTGCTTTTGTATATGAA
TAAAAAATTCTAATTATAGAAATA
ATTGAAGGTAATATACGAATAAG
TATCGACTAACTCTGTGCCAGCA
GTCGCGGTAAGACAGAGGATAC
AAGCGTTATCCGGATTTATTGGG
TTTAAAGGGTGCGTAGGCGGTT
TTTAAAGTCAGTAGTGAAATCTT
AAAGCTTAACTTTAAAAGTGCTA
TTGATACTGAAAAACTAGAGTAA
GGTTGGAGTAACTGGAATGTGT
GGTGTAGCGGTGAAATGCATAG
ATATCACACAGAACACCGATAGC
GAAAGCAAGTTACTAACCCTATA
CTGACGCTGAGTCACGAAAGCA
TGGGGAGCAAACAGGATTAGAT
ACCCTGGTAGTCCATGCCGTAA
ACGATGATCACTAACTATTGGGT
TTTATACGTTGTAATTCAGTGGT
GAAGCGAAAGTGTTAAGTGATC
CACCTGAGGAGTACGACCGCAA |

TABLE 1-continued

| Examples of Target Bacteria and Host Insects | | | |
|---|---|---|---|
| | | | GGTTGAAACTCAAAGGAATTGAC GGGGGCCCGCACAATCGGTGG AGCATGTGGTTTAATTCGATGAT ACACGAGGAACCTTACCAAGAC TTAAATGTACTACGAATAAATTG GAAACAATTTAGTCAAGCGACG GAGTACAAGGTGCTGCATGGTT GTCGTCAGCTCGTGCCGTGAGG TGTAAGGTTAAGTCCTTTAAACG AGCGCAACCCTTATTATTAGTTG CCATCGAGTAATGTCAGGGGAC TCTAATAAGACTGCCGGCGCAA GCCGAGAGGAAGGTGGGGATG ACGTCAAATCATCACGGCCCTTA CGTCTTGGGCCACACACGTGCT ACAATGATCGGTACAAAAGGGA GCGACTGGGTGACCAGGAGCAA ATCCAGAAAGCCGATCTAAGTTC GGATTGGAGTCTGAAACTCGAC TCCATGAAGCTGGAATCGCTAGT AATCGTGCATCAGCCATGGCAC GGTGAATATGTTCCCGGGCCTT GTACACACCGCCCGTCAAGCCA TGGAAGTTGGAAGTACCTAAAGT TGGTTCGCTACCTAAGGTAAGTC TAATAACTGGGGCTAAGTCGTAA CAAGGTA (SEQ ID NO: 25) |
| Yeast like | | | |
| *Symbiotaphrina buchneri* voucher JCM9740 | Anobiid beetles *Stegobium paniceum* | mycetome between the foregut and midgut | AGATTAAGCCATGCAAGTCTAAG TATAAGNAATCTATACNGTGAAA CTGCGAATGGCTCATTAAATCAG TTATCGTTTATTTGATAGTACCTT ACTACATGGATAACCGTGGTAAT TCTAGAGCTAATACATGCTAAAA ACCCCGACTTCGGAAGGGGTGT ATTTATTAGATAAAAAACCAATG CCCTTCGGGGCTCCTTGGTGAT TCATGATAACTTAACGAATCGCA TGGCCTTGCGCCGGCGATGGTT CATTCAAATTTCTGCCCTATCAA CTTTCGATGGTAGGATAGTGGC CTACCATGGTTTTAACGGGTAAC GGGGAATTAGGGTTCGATTCCG GAGAGGGAGCCTGAGAAACGGC TACCACATCCAAGGAAGGCAGC AGGCGCGCAAATTACCCAATCC CGACACGGGGAGGTAGTGACAA TAAATACTGATACAGGGCTCTTT TGGGTCTTGTAATTGGAATGAGT ACAATTTAAATCCCTTAACGAGG AACAATTGGAGGGCAAGTCTGG TGCCAGCAGCCGCGGTAATTCC AGCTCCAATAGCGTATATTAAAG TTGTTGCAGTTAAAAAGCTCGTA GTTGAACCTTGGGCCTGGCTGG CCGGTCCGCCTAACCGCGTGTA CTGGTCCGGCCGGGCCTTTCCT TCTGGGGAGCCGCATGCCCTTC ACTGGGTGTGTCGGGGAACCAG GACTTTTACTTTGAAAAAATTAGA GTGTTCAAAGCAGGCCTATGCT CGAATACATTAGCATGGAATAAT AGAATAGGACGTGCGGTTCTATT TTGTTGGTTTCTAGGACCGCCGT AATGATTAATAGGGATAGTCGGG GGCATCAGTATTCAATTGTCAGA GGTGAAATTCTTGGATTTATTGA AGACTAACTACTGCGAAAGCATT TGCCAAGGATGTTTTCATTAATC AGTGAACGAAAGTTAGGGGATC GAAGACGATCAGATACCGTCGT AGTCTTAACCATAAACTATGCCG ACTAGGGATCGGGCGATGTTAT TATTTTGACTCGCTCGGCACCTT ACGAGAAATCAAAGTCTTTGGGT |

TABLE 1-continued

| Examples of Target Bacteria and Host Insects | | | |
|---|---|---|---|
| | | | TCTGGGGGGAGTATGGTCGCAA GGCTGAAACTTAAAGAAATTGAC GGAAGGGCACCACCAGGAGTG GAGCCTGCGGCTTAATTTGACTC AACACGGGGAAACTCACCAGGT CCAGACACATTAAGGATTGACAG ATTGAGAGCTCTTTCTTGATTAT GTGGGTGGTGGTGCATGGCCGT TCTTAGTTGGTGGAGTGATTTGT CTGCTTAATTGCGATAACGAACG AGACCTTAACCTGCTAAATAGCC CGGTCCGCTTTGGCGGGCCGCT GGCTTCTTAGAGGGACTATCGG CTCAAGCCGATGGAAGTTTGAG GCAATAACAGGTCTGTGATGCC CTTAGATGTTCTGGGCCGCACG CGCGCTACACTGACAGAGCCAA CGAGTAAATCACCTTGGCCGGA AGGTCTGGGTAATCTTGTTAAAC TCTGTCGTGCTGGGGATAGAGC ATTGCAATTATTGCTCTTCAACG AGGAATTCCTAGTAAGCGCAAGT CATCAGCTTGCGCTGATTACGTC CCTGCCCTTTGTACACACCGCC CGTCGCTACTACCGATTGAATG GCTCAGTGAGGCCTTCGGACTG GCACAGGGACGTTGGCAACGAC GACCCAGTGCCGGAAAGTTGGT CAAACTTGGTCATTTAGAGGAAG TAAAAGTCGTAACAAGGTTTCCG TAGGTGAACCTGCGGAAGGATC ATTA (SEQ ID NO: 26) |
| *Symbiotaphrina kochii* voucher CBS 589.63 | Anobiid beetles *Lasioderma serricorne* | mycetome | TACCTGGTTGATTCTGCCAGTAG TCATATGCTTGTCTCAAAGATTA AGCCATGCAAGTCTAAGTATAAG CAATCTATACGGTGAAACTGCGA ATGGCTCATTAAATCAGTTATCG TTTATTTGATAGTACCTTACTACA TGGATAACCGTGGTAATTCTAGA GCTAATACATGCTAAAAACCTCG ACTTCGGAAGGGGTGTATTTATT AGATAAAAAACCAATGCCCTTCG GGGCTCCTTGGTGATTCATGATA ACTTAACGAATCGCATGGCCTTG CGCCGGCGATGGTTCATTCAAA TTTCTGCCCTATCAACTTTCGAT GGTAGGATAGTGGCCTACCATG GTTTCAACGGGTAACGGGGAAT TAGGGTTCGATTCCGGAGAGGG AGCCTGAGAAACGGCTACCACA TCCAAGGAAGGCAGCAGGCGCG CAAATTACCCAATCCCGACACG GGGAGGTAGTGACAATAAATACT GATACAGGGCTCTTTTGGGTCTT GTAATTGGAATGAGTACAATTTA AATCCCTTAACGAGGAACAATTG GAGGGCAAGTCTGGTGCCAGCA GCCGCGGTAATTCCAGCTCCAA TAGCGTATATTAAAGTTGTTGCA GTTAAAAAGCTCGTAGTTGAACC TTGGGCCTGGCTGGCCGGTCCG CCTAACCGCGTGTACTGGTCCG GCCGGGCCTTTCCTTCTGGGGA GCCGCATGCCCTTCACTGGGTG TGTCGGGGAACCAGGACTTTTA CTTTGAAAAAATTAGAGTGTTCA AAGCAGGCCTATGCTCGAATAC ATTAGCATGGAATAATAGAATAG GACGTGTGGTTCTATTTTGTTGG TTTCTAGGACCGCCGTAATGATT AATAGGGATAGTCGGGGGCATC AGTATTCAATTGTCAGAGGTGAA ATTCTTGGATTTATTGAAGACTA ACTACTGCGAAAGCATTTGCCAA GGATGTTTTCATTAATCAGTGAA CGAAAGTTAGGGGATCGAAGAC |

TABLE 1-continued

| Examples of Target Bacteria and Host Insects | | | |
|---|---|---|---|
| | | | GATCAGATACCGTCGTAGTCTTA ACCATAAACTATGCCGACTAGG GATCGGGCGATGTTATTATTTTG ACTCGCTCGGCACCTTACGAGA AATCAAAGTCTTTGGGTTCTGGG GGGAGTATGGTCGCAAGGCTGA AACTTAAAGAAATTGACGGAAGG GCACCACCAGGAGTGGAGCCTG CGGCTTAATTTGACTCAACACGG GGAAACTCACCAGGTCCAGACA CATTAAGGATTGACAGATTGAGA GCTCTTTCTTGATTATGTGGGTG GTGGTGCATGGCCGTTCTTAGTT GGTGGAGTGATTTGTCTGCTTAA TTGCGATAACGAACGAGACCTTA ACCTGCTAAATAGCCCGGTCCG CTTTGGCGGGCCGCTGGCTTCT TAGAGGGACTATCGGCTCAAGC CGATGGAAGTTTGAGGCAATAA CAGGTCTGTGATGCCCTTAGAT GTTCTGGGCCGCACGCGCGCTA CACTGACAGAGCCAACGAGTAC ATCACCTTGGCCGGAAGGTCTG GGTAATCTTGTTAAACTCTGTCG TGCTGGGGATAGAGCATTGCAA TTATTGCTCTTCAACGAGGAATT CCTAGTAAGCGCAAGTCATCAG CTTGCGCTGATTACGTCCCTGC CCTTTGTACACACCGCCCGTCG CTACTACCGATTGAATGGCTCAG TGAGGCCTTCGGACTGGCACAG GGACGTTGGCAACGACGACCCA GTGCCGGAAAGTTCGTCAAACTT GGTCATTTAGAGGAAGNNNAAG TCGTAACAAGGTTTCCGTAGGTG AACCTGCGGAAGGATCATTA (SEQ ID NO: 27) |
| **Primary extracelullar symbiont** | **Host** | **location** | **16 rRNA** |
| fenitrothion-degrading bacteria | | | |
| *Burkholderia* sp. SFA1 | *Riptortus pedestris* | Gut | AGTTTGATCCTGGCTCAGATTGA ACGCTGGCGGCATGCCTTACAC ATGCAAGTCGAACGGCAGCACG GGGGCAACCCTGGTGGCGAGT GGCGAACGGGTGAGTAATACAT CGGAACGTGTCCTGTAGTGGGG GATAGCCCGGCGAAAGCCGGAT TAATACCGCATACGACCTAAGG GAGAAAGCGGGGGATCTTCGGA CCTCGCGCTATAGGGGCGGCCG ATGGCAGATTAGCTAGTTGGTG GGGTAAAGGCCTACCAAGGCGA CGATCTGTAGCTGGTCTGAGAG GACGACCAGCCACACTGGGACT GAGACACGGCCCAGACTCCTAC GGGAGGCAGCAGTGGGGAATTT TGGACAATGGGGGCAACCCTGA TCCAGCAATGCCGCGTGTGTGA AGAAGGCTTCGGGTTGTAAAGC ACTTTTGTCCGGAAAGAAAACTT CGTCCCTAATATGGATGGAGGA TGACGGTACCGGAAGAATAAGC ACCGGCTAACTACGTGCCAGCA GCCGCGGTAATACGTAGGGTGC GAGCGTTAATCGGAATTACTGG GCGTAAAGCGTGCGCAGGCGGT CTGTTAAGACCGATGTGAAATCC CCGGGCTTAACCTGGGAACTGC ATTGGTGACTGGCAGGCTTTGA GTGTGGCAGAGGGGGGTAGAAT TCCACGTGTAGCAGTGAAATGC GTAGAGATGTGGAGGAATACCG ATGGCGAAGGCAGCCCCCTGGG CCAACTACTGACGCTCATGCAC |

TABLE 1-continued

| Examples of Target Bacteria and Host Insects | | | |
|---|---|---|---|
| | | | GAAAGCGTGGGGAGCAAACAGG ATTAGATACCCTGGTAGTCCACG CCCTAAACGATGTCAACTAGTTG TTGGGGATTCATTTCCTTAGTAA CGTAGCTAACGCGTGAAGTTGA CCGCCTGGGGAGTACGGTCGCA AGATTAAAACTCAAAGGAATTGA CGGGGACCCGCACAAGCGGTG GATGATGTGGATTAATTCGATGC AACGCGAAAAACCTTACCTACCC TTGACATGGTCGGAACCCTGCT GAAAGGTGGGGGTGCTCGAAAG AGAACCGGCGCACAGGTGCTGC ATGGCTGTCGTCAGCTCGTGTC GTGAGATGTTGGGTTAAGTCCC GCAACGAGCGCAACCCTTGTCC TTAGTTGCTACGCAAGAGCACTC TAAGGAGACTGCCGGTGACAAA CCGGAGGAAGGTGGGGATGAC GTCAAGTCCTCATGGCCCTTATG GGTAGGGCTTCACACGTCATAC AATGGTCGGAACAGAGGGTTGC CAAGCCGCGAGGTGGAGCCAAT CCCAGAAAACCGATCGTAGTCC GGATCGCAGTCTGCAACTCGAC TGCGTGAAGCTGGAATCGCTAG TAATCGCGGATCAGCATGCCGC GGTGAATACGTTCCCGGGTCTT GTACACACCGCCCGTCACACCA TGGGAGTGGGTTTCACCAGAAG TAGGTAGCCTAACCGCAAGGAG GGCGCTTACCACGGTGGGATTC ATGACTGGGGTGAAGTCGTAAC AAGGTAGC (SEQ ID NO: 28) |
| *Burkholderia* sp. KM-A | *Riptortus pedestris* | Gut | GCAACCCTGGTGGCGAGTGGCG AACGGGTGAGTAATACATCGGA ACGTGTCCTGTAGTGGGGGATA GCCCGGCGAAAGCCGGATTAAT ACCGCATACGATCTACGGAAGA AAGCGGGGGATCCTTCGGGACC TCGCGCTATAGGGGCGGCCGAT GGCAGATTAGCTAGTTGGTGGG GTAAAGGCCTACCAAGGCGACG ATCTGTAGCTGGTCTGAGAGGA CGACCAGCCACACTGGGACTGA GACACGGCCCAGACTCCTACGG GAGGCAGCAGTGGGGAATTTTG GACAATGGGGGCAACCCTGATC CAGCAATGCCGCGTGTGTGAAG AAGGCCTTCGGGTTGTAAAGCA CTTTTGTCCGGAAAGAAAACGTC TTGGTTAATACCTGAGGCGGAT GACGGTACCGGAAGAATAAGCA CCGGCTAACTACGTGCCAGCAG CCGCGGTAATACGTAGGGTGCG AGCGTTAATCGGAATTACTGGG CGTAAAGCGTGCGCAGGCGGTC TGTTAAGACCGATGTGAAATCCC CGGGCTTAACCTGGGAACTGCA TTGGTGACTGGCAGGCTTTGAG TGTGGCAGAGGGGGGTAGAATT CCACGTGTAGCAGTGAAATGCG TAGAGATGTGGAGGAATACCGA TGGCGAAGGCAGCCCCCTGGG CCAACACTGACGCTCATGCACG AAAGCGTGGGGAGCAAACAGGA TTAGATACCCTGGTAGTCCACGC CCTAAACGATGTCAACTAGTTGT TGGGGATTCATTTCCTTAGTAAC GTAGCTAACGCGTGAAGTTGAC CGCCTGGGGAGTACGGTCGCAA GATTAAAACTCAAAGGAATTGAC GGGGACCCGCACAAGCGGTGG ATGATGTGGATTAATTCGATGCA ACGCGAAAAACCTTACCTACCCT TGACATGGTCGGAAGTCTGCTG |

TABLE 1-continued

| Examples of Target Bacteria and Host Insects | | | |
|---|---|---|---|
| | | | AGAGGTGGACGTGCTCGAAAGA GAACCGGCGCACAGGTGCTGCA TGGCTGTCGTCAGCTCGTGTCG TGAGATGTTGGGTTAAGTCCCG CAACGAGCGCAACCCTTGTCCT TAGTTGCTACGCAAGAGCACTCT AAGGAGACTGCCGGTGACAAAC CGGAGGAAGGTGGGGATGACGT CAAGTCCTCATGGCCCTTATGG GTAGGGCTTCACACGTCATACAA TGGTCGGAACAGAGGGTTGCCA AGCCGCGAGGTGGAGCCAATCC CAGAAAACCGATCGTAGTCCGG ATCGCAGTCTGCAACTCGACTG CGTGAAGCTGGAATCGCTAGTA ATCGCGGATCAGCATGCCGCGG TGAATACGTTCCCGGGTCTTGTA CACACCGCCCGTCACACCATGG GAGTGGGTTTCACCAGAAGTAG GTAGCCTAACCGCAAGGAGGGC GCTTACCACGGTGGGATTCATG ACTGGGGTGAAGT (SEQ ID NO: 29) |
| *Burkholderia* sp. KM-G | *Riptortus pedestris* | Gut | GCAACCCTGGTGGCGAGTGGCG AACGGGTGAGTAATACATCGGA ACGTGTCCTGTAGTGGGGGATA GCCCGGCGAAAGCCGGATTAAT ACCGCATACGACCTAAGGGAGA AAGCGGGGGATCTTCGGACCTC GCGCTATAGGGGCGGCCGATG GCAGATTAGCTAGTTGGTGGGG TAAAGGCCTACCAAGGCGACGA TCTGTAGCTGGTCTGAGAGGAC GACCAGCCACACTGGGACTGAG ACACGGCCCAGACTCCTACGGG AGGCAGCAGTGGGGAATTTTGG ACAATGGGGGCAACCCTGATCC AGCAATGCCGCGTGTGTGAAGA AGGCCTTCGGGTTGTAAAGCAC TTTTGTCCGGAAAGAAAACTTCG AGGTTAATACCCTTGGAGGATGA CGGTACCGGAAGAATAAGCACC GGCTAACTACGTGCCAGCAGCC GCGGTAATACGTAGGGTGCGAG CGTTAATCGGAATTACTGGGCGT AAAGCGTGCGCAGGCGGTCTGT TAAGACCGATGTGAAATCCCCG GGCTTAACCTGGGAACTGCATT GGTGACTGGCAGGCTTTGAGTG TGGCAGAGGGGGGTAGAATTCC ACGTGTAGCAGTGAAATGCGTA GAGATGTGGAGGAATACCGATG GCGAAGGCAGCCCCCTGGGCC AACACTGACGCTCATGCACGAA AGCGTGGGGAGCAAACAGGATT AGATACCCTGGTAGTCCACGCC CTAAACGATGTCAACTAGTTGTT GGGGATTCATTTCCTTAGTAACG TAGCTAACGCGTGAAGTTGACC GCCTGGGGAGTACGGTCGCAAG ATTAAAACTCAAAGGAATTGACG GGGACCCGCACAAGCGGTGGAT GATGTGGATTAATTCGATGCAAC GCGAAAAACCTTACCTACCCTTG ACATGGTCGGAAGTCTGCTGAG AGGTGGACGTGCTCGAAAGAGA ACCGGCGCACAGGTGCTGCATG GCTGTC GTCAGCTCGTGTCGTGAGATGT TGGGTTAAGTCCCGCAACGAGC GCAACCCTTGTCCTTAGTTGCTA CGCAAGAGCACTCTAAGGAGAC TGCCGGTGACAAACCGGAGGAA GGTGGGGATGACGTCAAGTCCT CATGGCCCTTATGGGTAGGGCT TCACACGTCATACAATGGTCGGA ACAGAGGGTTGCCAAGCCGCGA |

TABLE 1-continued

| Examples of Target Bacteria and Host Insects | | | |
|---|---|---|---|
| | | | GGTGGAGCCAATCCCAGAAAAC CGATCGTAGTCCGGATCGCAGT CTGCAACTCGACTGCGTGAAGC TGGAATCGCTAGTAATCGCGGA TCAGCATGCCGCGGTGAATACG TTCCCGGGTCTTGTACACACCG CCCGTCACACCATGGGAGTGGG TTTCACCAGAAGTAGGTAGCCTA ACCTGCAAAGGAGGGCGCTTAC CACG (SEQ ID NO: 30) |
| Bees | | | |
| *Snodgrassella alvi* | Honeybee (*Apis mellifera*) and *Bombus* spp. | Ileum | GAGAGTTTGATCCTGGCTCAGAT TGAACGCTGGCGGCATGCCTTA CACATGCAAGTCGAACGGCAGC ACGGAGAGCTTGCTCTCTGGTG GCGAGTGGCGAACGGGTGAGTA ATGCATCGGAACGTACCGAGTA ATGGGGGATAACTGTCCGAAAG GATGGCTAATACCGCATACGCC CTGAGGGGGAAAGCGGGGGAT CGAAAGACCTCGCGTTATTTGAG CGGCCGATGTTGGATTAGCTAG TTGGTGGGGTAAAGGCCTACCA AGGCGACGATCCATAGCGGGTC TGAGAGGATGATCCGCCACATT GGGACTGAGACACGGCCCAAAC TCCTACGGGAGGCAGCAGTGGG GAATTTTGGACAATGGGGGGAA CCCTGATCCAGCCATGCCGCGT GTCTGAAGAAGGCCTTCGGGTT GTAAAGGACTTTTGTTAGGGAAG AAAAGCCGGGTGTTAATACCATC TGGTGCTGACGGTACCTAAAGA ATAAGCACCGGCTAACTACGTG CCAGCAGCCGCGGTAATACGTA GGGTGCGAGCGTTAATCGGAAT TACTGGGCGTAAAGCGAGCGCA GACGGTTAATTAAGTCAGATGTG AAATCCCCGAGCTCAACTTGGG ACGTGCATTTGAAACTGGTTAAC TAGAGTGTGTCAGAGGGAGGTA GAATTCCACGTGTAGCAGTGAAA TGCGTAGAGATGTGGAGGAATA CCGATGGCGAAGGCAGCCTCCT GGGATAACACTGACGTTCATGCT CGAAAGCGTGGGTAGCAAACAG GATTAGATACCCTGGTAGTCCAC GCCCTAAACGATGACAATTAGCT GTTGGGACACTAGATGTCTTAGT AGCGAAGCTAACGCGTGAAATT GTCCGCCTGGGGAGTACGGTCG CAAGATTAAAACTCAAAGGAATT GACGGGGACCCGCACAAGCGG TGGATGATGTGGATTAATTCGAT GCAACGCGAAGAACCTTACCTG GTCTTGACATGTACGGAATCTCT TAGAGATAGGAGAGTGCCTTCG GGAACCGTAACACAGGTGCTGC ATGGCTGTCGTCAGCTCGTGTC GTGAGATGTTGGGTTAAGTCCC GCAACGAGCGCAACCCTTGTCA TTAGTTGCCATCATTAAGTTGGG CACTCTAATGAGACTGCCGGTG ACAAACCGGAGGAAGGTGGGGA TGACGTCAAGTCCTCATGGCCC TTATGACCAGGGCTTCACACGTC ATACAATGGTCGGTACAGAGGG TAGCGAAGCCGCGAGGTGAAGC CAATCTCAGAAAGCCGATCGTA GTCCGGATTGCACTCTGCAACT CGAGTGCATGAAGTCGGAATCG CTAGTAATCGCAGGTCAGCATAC TGCGGTGAATACGTTCCCGGGT CTTGTACACACCGCCCGTCACA CCATGGGAGTGGGGGATACCAG |

TABLE 1-continued

| Examples of Target Bacteria and Host Insects | | | |
|---|---|---|---|
| | | | AATTGGGTAGACTAACCGCAAG GAGGTCGCTTAACACGGTATGC TTCATGACTGGGGTGAAGTCGT AACAAGGTAGCCGTAG (SEQ ID NO: 31) |
| *Gilliamella apicola* | honeybee (*Apis mellifera*) and *Bombus* spp. | Ileum | TTAAATTGAAGAGTTTGATCATG GCTCAGATTGAACGCTGGCGGC AGGCTTAACACATGCAAGTCGAA CGGTAACATGAGTGCTTGCACTT GATGACGAGTGGCGGACGGGT GAGTAAAGTATGGGGATCTGCC GAATGGAGGGGGACAACAGTTG GAAACGACTGCTAATACCGCATA AAGTTGAGAGACCAAAGCATGG GACCTTCGGGCCATGCGCCATT TGATGAACCCATATGGGATTAGC TAGTTGGTAGGGTAATGGCTTAC CAAGGCGACGATCTCTAGCTGG TCTGAGAGGATGACCAGCCACA CTGGAACTGAGACACGGTCCAG ACTCCTACGGGAGGCAGCAGTG GGGAATATTGCACAATGGGGGA AACCCTGATGCAGCCATGCCGC GTGTATGAAGAAGGCCTTCGGG TTGTAAAGTACTTTCGGTGATGA GGAAGGTGGTGTATCTAATAGG TGCATCAATTGACGTTAATTACA GAAGAAGCACCGGCTAACTCCG TGCCAGCAGCCGCGGTAATACG GAGGGTGCGAGCGTTAATCGGA ATGACTGGGCGTAAAGGGCATG TAGGCGGATAATTAAGTTAGGTG TGAAAGCCCTGGGCTCAACCTA GGAATTGCACTTAAAACTGGTTA ACTAGAGTATTGTAGAGGAAGGT AGAATTCCACGTGTAGCGGTGA AATGCGTAGAGATGTGGAGGAA TACCGGTGGCGAAGGCGGCCTT CTGGACAGATACTGACGCTGAG ATGCGAAAGCGTGGGGAGCAAA CAGGATTAGATACCCTGGTAGTC CACGCTGTAAACGATGTCGATTT GGAGTTTGTTGCCTAGAGTGAT GGGCTCCGAAGCTAACGCGATA AATCGACCGCCTGGGGAGTACG GCCGCAAGGTTAAAACTCAAATG AATTGACGGGGGCCCGCACAAG CGGTGGAGCATGTGGTTTAATTC GATGCAACGCGAAGAACCTTAC CTGGTCTTGACATCCACAGAATC TTGCAGAGATGCGGGAGTGCCT TCGGGAACTGTGAGACAGGTGC TGCATGGCTGTCGTCAGCTCGT GTTGTGAAATGTTGGGTTAAGTC CCGCAACGAGCGCAACCCTTAT CCTTTGTTGCCATCGGTTAGGCC GGGAACTCAAAGGAGACTGCCG TTGATAAAGCGGAGGAAGGTGG GGACGACGTCAAGTCATCATGG CCCTTACGACCAGGGCTACACA CGTGCTACAATGGCGTATACAAA GGGAGGCGACCTCGCGAGAGC AAGCGGACCTCATAAAGTACGT CTAAGTCCGGATTGGAGTCTGC AACTCGACTCCATGAAGTCGGA ATCGCTAGTAATCGTGAATCAGA ATGTCACGGTGAATACGTTCCC GGGCCTTGTACACACCGCCCGT CACACCATGGGAGTGGGTTGCA CCAGAAGTAGATAGCTTAACCTT CGGGAGGGCGTTTACCACGGTG TGGTCCATGACTGGGGTGAAGT CGTAACAAGGTAACCGTAGGGG AACCTGCGGTTGGATCACCTCC TTAC (SEQ ID NO: 32) |

TABLE 1-continued

| Examples of Target Bacteria and Host Insects | | | |
|---|---|---|---|
| *Bartonella apis* | honeybee (*Apis mellifera*) | Gut | AAGCCAAAATCAAATTTTCAACT<br>TGAGAGTTTGATCCTGGCTCAGA<br>ACGAACGCTGGCGGCAGGCTTA<br>ACACATGCAAGTCGAACGCACTT<br>TTCGGAGTGAGTGGCAGACGGG<br>TGAGTAACGCGTGGGAATCTAC<br>CTATTTCTACGGAATAACGCAGA<br>GAAATTTGTGCTAATACCGTATA<br>CGTCCTTCGGGAGAAAGATTTAT<br>CGGAGATAGATGAGCCCGCGTT<br>GGATTAGCTAGTTGGTGAGGTA<br>ATGGCCCACCAAGGCGACGATC<br>CATAGCTGGTCTGAGAGGATGA<br>CCAGCCACATTGGGACTGAGAC<br>ACGGCCCAGACTCCTACGGGAG<br>GCAGCAGTGGGGAATATTGGAC<br>AATGGGCGCAAGCCTGATCCAG<br>CCATGCCGCGTGAGTGATGAAG<br>GCCCTAGGGTTGTAAAGCTCTTT<br>CACCGGTGAAGATAATGACGGT<br>AACCGGAGAAGAAGCCCCGGCT<br>AACTTCGTGCCAGCAGCCGCGG<br>TAATACGAAGGGGGCTAGCGTT<br>GTTCGGATTTACTGGGCGTAAA<br>GCGCACGTAGGOGGATATTTAA<br>GTCAGGGGTGAAATCCCGGGGC<br>TCAACCCCGGAACTGCCTTTGAT<br>ACTGGATATCTTGAGTATGGAAG<br>AGGTAAGTGGAATTCCGAGTGT<br>AGAGGTGAAATTCGTAGATATTC<br>GGAGGAACACCAGTGGCGAAGG<br>CGGCTTACTGGTCCATTACTGAC<br>GCTGAGGTGCGAAAGCGTGGG<br>GAGCAAACAGGATTAGATACCCT<br>GGTAGTCCACGCTGTAAACGAT<br>GAATGTTAGCCGTTGGACAGTTT<br>ACTGTTCGGTGGCGCAGCTAAC<br>GCATTAAACATTCCGCCTGGGG<br>AGTACGGTCGCAAGATTAAAACT<br>CAAAGGAATTGACGGGGGCCCG<br>CACAAGCGGTGGAGCATGTGGT<br>TTAATTCGAAGCAACGCGCAGAA<br>CCTTACCAGCCCTTGACATCCC<br>GATCGCGGATGGTGGAGACACC<br>GTCTTTCAGTTCGGCTGGATCG<br>GTGACAGGTGCTGCATGGCTGT<br>CGTCAGCTCGTGTCGTGAGATG<br>TTGGGTTAAGTCCCGCAACGAG<br>CGCAACCCTCGCCCTTAGTTGC<br>CATCATTTAGTTGGGCACTCTAA<br>GGGGACTGCCGGTGATAAGCCG<br>AGAGGAAGGTGGGGATGACGTC<br>AAGTCCTCATGGCCCTTACGGG<br>CTGGGCTACACACGTGCTACAA<br>TGGTGGTGACAGTGGGCAGCGA<br>GACCGCGAGGTCGAGCTAATCT<br>CCAAAAGCCATCTCAGTTCGGAT<br>TGCACTCTGCAACTCGAGTGCAT<br>GAAGTTGGAATCGCTAGTAATCG<br>TGGATCAGCATGCCACGGTGAA<br>TACGTTCCCGGGCCTTGTACAC<br>ACCGCCCGTCACACCATGGGAG<br>TTGGTTTTACCCGAAGGTGCTGT<br>GCTAACCGCAAGGAGGCAGGCA<br>ACCACGGTAGGGTCAGCGACTG<br>GGGTGAAGTCGTAACAAGGTAG<br>CCGTAGGGGAACCTGCGGCTGG<br>ATCACCTCCTTTCTAAGGAAGAT<br>GAAGAATTGGAA<br>(SEQ ID NO: 33) |
| *Parasaccharibacter apium* | honeybee (*Apis mellifera*) | Gut | CTACCATGCAAGTCGCACGAAA<br>CCTTTCGGGGTTAGTGGCGGAC<br>GGGTGAGTAACGCGTTAGGAAC<br>CTATCTGGAGGTGGGGGATAAC<br>ATCGGGAAACTGGTGCTAATAC<br>CGCATGATGCCTGAGGGCCAAA<br>GGAGAGATCCGCCATTGGAGGG |

TABLE 1-continued

| Examples of Target Bacteria and Host Insects | | | |
|---|---|---|---|
| | | | GCCTGCGTTCGATTAGCTAGTTG<br>GTTGGGTAAAGGCTGACCAAGG<br>CGATGATCGATAGCTGGTTTGA<br>GAGGATGATCAGCCACACTGGG<br>ACTGAGACACGGCCCAGACTCC<br>TACGGGAGGCAGCAGTGGGGAA<br>TATTGGACAATGGGGGCAACCC<br>TGATCCAGCAATGCCGCGTGTG<br>TGAAGAAGGTCTTCGGATTGTAA<br>AGCACTTTCACTAGGGAAGATGA<br>TGACGGTACCTAGAGAAGAAGC<br>CCCGGCTAACTTCGTGCCAGCA<br>GCCGCGGTAATACGAAGGGGGC<br>TAGCGTTGCTCGGAATGACTGG<br>GCGTAAAGGGCGCGTAGGCTGT<br>TTGTACAGTCAGATGTGAAATCC<br>CCGGGCTTAACCTGGGAACTGC<br>ATTTGATACGTGCAGACTAGAGT<br>CCGAGAGAGGGTTGTGGAATTC<br>CCAGTGTAGAGGTGAAATTCGTA<br>GATATTGGGAAGAACACCGGTT<br>GCGAAGGCGGCAACCTGGCTNN<br>NNNNNNNNNNNNNNNNNNNNNN<br>NNNNNNNNNNNNNNNNNNNNNN<br>NNNNNNNNNNNNNNNNNNNNNN<br>NNNNNNNNNNNNNNNNNNNNNN<br>NNNNNNNNNNNNNNNNNNNNNN<br>NNGAGCTAACGCGTTAAGCACA<br>CCGCCTGGGGAGTACGGCCGC<br>AAGGTTGAAACTCAAAGGAATTG<br>ACGGGGGCCCGCACAAGCGGT<br>GGAGCATGTGGTTTAATTCGAAG<br>CAACGCGCAGAACCTTACCAGG<br>GCTTGCATGGGGAGGCTGTATT<br>CAGAGATGGATATTTCTTCGGAC<br>CTCCCGCACAGGTGCTGCATGG<br>CTGTCGTCAGCTCGTGTCGTGA<br>GATGTTGGGTTAAGTCCCGCAA<br>CGAGCGCAACCCTTGTCTTTAGT<br>TGCCATCACGTCTGGGTGGGCA<br>CTCTAGAGAGACTGCCGGTGAC<br>AAGCCGGAGGAAGGTGGGGAT<br>GACGTCAAGTCCTCATGGCCCT<br>TATGTCCTGGGCTACACACGTG<br>CTACAATGGCGGTGACAGAGGG<br>ATGCTACATGGTGACATGGTGCT<br>GATCTCAAAAAACCGTCTCAGTT<br>CGGATTGTACTCTGCAACTCGA<br>GTGCATGAAGGTGGAATCGCTA<br>GTAATCGCGGATCAGCATGCCG<br>CGGTGAATACGTTCCCGGGCCT<br>TGTACACACCGCCCGTCACACC<br>ATGGGAGTTGGTTTGACCTTAAG<br>CCGGTGAGCGAACCGCAAGGAA<br>CGCAGCCGACCACCGGTTCGGG<br>TTCAGCGACTGGGGGA<br>(SEQ ID NO: 34) |
| *Lactobacillus kunkeei* | honeybee (*Apis mellifera*) | Gut | TTCCTTAGAAAGGAGGTGATCCA<br>GCCGCAGGTTCTCCTACGGCTA<br>CCTTGTTACGACTTCACCCTAAT<br>CATCTGTCCCACCTTAGACGACT<br>AGCTCCTAAAAGGTTACCCCATC<br>GTCTTTGGGTGTTACAAACTCTC<br>ATGGTGTGACGGGCGGTGTGTA<br>CAAGGCCCGGGAACGTATTCAC<br>CGTGGCATGCTGATCCACGATT<br>ACTAGTGATTCCAACTTCATGCA<br>GGCGAGTTGCAGCCTGCAATCC<br>GAACTGAGAATGGCTTTAAGAGA<br>TTAGCTTGACCTCGCGGTTTCGC<br>GACTCGTTGTACCATCCATTGTA<br>GCACGTGTGTAGCCCAGCTCAT<br>AAGGGGCATGATGATTTGACGT<br>CGTCCCCACCTTCCTCCGGTTTA<br>TCACCGGCAGTCTCACTAGAGT<br>GCCCAACTAAATGCTGGCAACTA<br>ATAATAAGGGTTGCGCTCGTTGC |

TABLE 1-continued

Examples of Target Bacteria and Host Insects

| | | | |
|---|---|---|---|
| | | | GGGACTTAACCCAACATCTCAC<br>GACACGAGCTGACGACAACCAT<br>GCACCACCTGTCATTCTGTCCCC<br>GAAGGGAACGCCCAATCTCTTG<br>GGTTGGCAGAAGATGTCAAGAG<br>CTGGTAAGGTTCTTCGCGTAGC<br>ATCGAATTAAACCACATGCTCCA<br>CCACTTGTGCGGGCCCCCGTCA<br>ATTCCTTTGAGTTTCAACCTTGC<br>GGTCGTACTCCCCAGGCGGAAT<br>ACTTAATGCGTTAGCTGCGGCA<br>CTGAAGGGCGGAAACCCTCCAA<br>CACCTAGTATTCATCGTTTACGG<br>CATGGACTACCAGGGTATCTAAT<br>CCTGTTCGCTACCCATGCTTTCG<br>AGCCTCAGCGTCAGTAACAGAC<br>CAGAAAGCCGCCTTCGCCACTG<br>GTGTTCTTCCATATATCTACGCA<br>TTTCACCGCTACACATGGAGTTC<br>CACTTTCCTCTTCTGTACTCAAG<br>TTTTGTAGTTTCCACTGCACTTC<br>CTCAGTTGAGCTGAGGGCTTTC<br>ACAGCAGACTTACAAAACCGCCT<br>GCGCTCGCTTTACGCCCAATAAA<br>TCCGGACAACGCTTGCCACCTA<br>CGTATTACCGCGGCTGCTGGCA<br>CGTAGTTAGCCGTGGCTTTCTG<br>GTTAAATACCGTCAAAGTGTTAA<br>CAGTTACTCTAACACTTGTTCTT<br>CTTTAACAACAGAGTTTTACGAT<br>CCGAAAACCTTCATCACTCACGC<br>GGCGTTGCTCCATCAGACTTTC<br>GTCCATTGTGGAAGATTCCCTAC<br>TGCTGCCTCCCGTAGGAGTCTG<br>GGCCGTGTCTCAGTCCCAATGT<br>GGCCGATTACCCTCTCAGGTCG<br>GCTACGTATCATCGTCTTGGTGG<br>GCTTTTATCTCACCAACTAACTA<br>ATACGGCGCGGGTCCATCCCAA<br>AGTGATAGCAAAGCCATCTTTCA<br>AGTTGGAACCATGCGGTTCCAA<br>CTAATTATGCGGTATTAGCACTT<br>GTTTCCAAATGTTATCCCCCGCT<br>TCGGGGCAGGTTACCCACGTGT<br>TACTCACCAGTTCGCCACTCGCT<br>CCGAATCCAAAAATCATTTATGC<br>AAGCATAAAATCAATTTGGGAGA<br>ACTCGTTCGACTTGCATGTATTA<br>GGCACGCCGCCAGCGTTCGTCC<br>TGAGCCAGGATCAAACTCTCATC<br>TTAA<br>(SEQ ID NO: 35) |
| *Lactobacillus* Firm-4 | honeybee (*Apis mellifera*) | Gut | ACGAACGCTGGCGGCGTGCCTA<br>ATACATGCAAGTCGAGCGCGGG<br>AAGTCAGGGAAGCCTTCGGGTG<br>GAACTGGTGGAACGAGCGGCG<br>GATGGGTGAGTAACACGTAGGT<br>AACCTGCCCTAAAGCGGGGGAT<br>ACCATCTGGAAACAGGTGCTAAT<br>ACCGCATAAACCCAGCAGTCAC<br>ATGAGTGCTGGTTGAAAGACGG<br>CTTCGGCTGTCACTTTAGGATGG<br>ACCTGCGGCGTATTAGCTAGTT<br>GGTGGAGTAACGGTTCACCAAG<br>GCAATGATACGTAGCCGACCTG<br>AGAGGGTAATCGGCCACATTGG<br>GACTGAGACACGGCCCAAACTC<br>CTACGGGAGGCAGCAGTAGGGA<br>ATCTTCCACAATGGACGCAAGTC<br>TGATGGAGCAACGCCGCGTGGA<br>TGAAGAAGGTCTTCGGATCGTAA<br>AATCCTGTTGTTGAAGAAGAACG<br>GTTGTGAGAGTAACTGCTCATAA<br>CGTGACGGTAATCAACCAGAAA<br>GTCACGGCTAACTACGTGCCAG<br>CAGCCGCGGTAATACGTAGGTG<br>GCAAGCGTTGTCCGGATTTATTG |

TABLE 1-continued

| Examples of Target Bacteria and Host Insects | | | |
|---|---|---|---|
| | | | GGCGTAAAGGGAGCGCAGGCG<br>GTCTTTTAAGTCTGAATGTGAAA<br>GCCCTCAGCTTAACTGAGGAAG<br>AGCATCGGAAACTGAGAGACTT<br>GAGTGCAGAAGAGGAGAGTGGA<br>ACTCCATGTGTAGCGGTGAAAT<br>GCGTAGATATATGGAAGAACAC<br>CAGTGGCGAAGGCGGCTCTCTG<br>GTCTGTTACTGACGCTGAGGCT<br>CGAAAGCATGGGTAGCGAACAG<br>GATTAGATACCCTGGTAGTCCAT<br>GCCGTAAACGATGAGTGCTAAG<br>TGTTGGGAGGTTTCCGCCTCTC<br>AGTGCTGCAGCTAACGCATTAA<br>GCACTCCGCCTGGGGAGTACGA<br>CCGCAAGGTTGAAACTCAAAGG<br>AATTGACGGGGGCCCGCACAAG<br>CGGTGGAGCATGTGGTTTAATTC<br>GAAGCAACGCGAAGAACCTTAC<br>CAGGTCTTGACATCTCCTGCAAG<br>CCTAAGAGATTAGGGGTTCCCTT<br>CGGGGACAGGAAGACAGGTGGT<br>GCATGGTTGTCGTCAGCTCGTG<br>TCGTGAGATGTTGGGTTAAGTCC<br>CGCAACGAGCGCAACCCTTGTT<br>ACTAGTTGCCAGCATTAAGTTGG<br>GCACTCTAGTGAGACTGCCGGT<br>GACAAACCGGAGGAAGGTGGG<br>GACGACGTCAAATCATCATGCC<br>CCTTATGACCTGGGCTACACAC<br>GTGCTACAATGGATGGTACAATG<br>AGAAGCGAACTCGCGAGGGGAA<br>GCTGATCTCTGAAAACCATTCTC<br>AGTTCGGATTGCAGGCTGCAAC<br>TCGCCTGCATGAAGCTGGAATC<br>GCTAGTAATCGCGGATCAGCAT<br>GCCGCGGTGAATACGTTCCCGG<br>GCCTTGTACACACCGCCC<br>(SEQ ID NO: 36) |
| Silk worm | | | |
| *Enterococcus* | *Bombyx mori* | Gut | AGGTGATCCAGCCGCACCTTCC<br>GATACGGCTACCTTGTTACGACT<br>TCACCCCAATCATCTATCCCACC<br>TTAGGCGGCTGGCTCCAAAAAG<br>GTTACCTCACCGACTTCGGGTG<br>TTACAAACTCTCGTGGTGTGACG<br>GGCGGTGTGTACAAGGCCCGG<br>GAACGTATTCACCGCGGCGTGC<br>TGATCCGCGATTACTAGCGATTC<br>CGGCTTCATGCAGGCGAGTTGC<br>AGCCTGCAATCCGAACTGAGAG<br>AAGCTTTAAGAGATTTGCATGAC<br>CTCGCGGTCTAGCGACTCGTTG<br>TACTTCCCATTGTAGCACGTGTG<br>TAGCCCAGGTCATAAGGGGCAT<br>GATGATTTGACGTCATCCCCACC<br>TTCCTCCGGTTTGTCACCGGCA<br>GTCTCGCTAGAGTGCCCAACTA<br>AATGATGGCAACTAACAATAAGG<br>GTTGCGCTCGTTGCGGGACTTA<br>ACCCAACATCTCACGACACGAG<br>CTGACGACAACCATGCACCACC<br>TGTCACTTTGTCCCCGAAGGGA<br>AAGCTCTATCTCTAGAGTGGTCA<br>AAGGATGTCAAGACCTGGTAAG<br>GTTCTTCGCGTTGCTTCGAATTA<br>AACCACATGCTCCACCGCTTGT<br>GCGGGCCCCCGTCAATTCCTTT<br>GAGTTTCAACCTTGCGGTCGTAC<br>TCCCCAGGCGGAGTGCTTAATG<br>CGTTTGCTGCAGCACTGAAGGG<br>CGGAAACCCTCCAACACTTAGC<br>ACTCATCGTTTACGGCGTGGACT<br>ACCAGGGTATCTAATCCTGTTTG<br>CTCCCCACGCTTTCGAGCCTCA<br>GCGTCAGTTACAGACCAGAGAG |

TABLE 1-continued

| Examples of Target Bacteria and Host Insects | | | |
|---|---|---|---|
| | | | CCGCCTTCGCCACTGGTGTTCC<br>TCCATATATCTACGCATTTCACC<br>GCTACACATGGAATTCCACTCTC<br>CTCTTCTGCACTCAAGTCTCCCA<br>GTTTCCAATGACCCTCCCCGGTT<br>GAGCCGGGGGCTTTCACATCAG<br>ACTTAAGAAACCGCCTGCGCTC<br>GCTTTACGCCCAATAAATCCGGA<br>CAACGCTTGCCACCTACGTATTA<br>CCGCGGCTGCTGGCACGTAGTT<br>AGCCGTGGCTTTCTGGTTAGATA<br>CCGTCAGGGGACGTTCAGTTAC<br>TAACGTCCTTGTTCTTCTCTAAC<br>AACAGAGTTTTACGATCCGAAAA<br>CCTTCTTCACTCACGCGGCGTT<br>GCTCGGTCAGACTTTCGTCCATT<br>GCCGAAGATTCCCTACTGCTGC<br>CTCCCGTAGGAGTCTGGGCCGT<br>GTCTCAGTCCCAGTGTGGCCGA<br>TCACCCTCTCAGGTCGGCTATG<br>CATCGTGGCCTTGGTGAGCCGT<br>TACCTCACCAACTAGCTAATGCA<br>CCGCGGGTCCATCCATCAGCGA<br>CACCCGAAAGCGCCTTTCACTCT<br>TATGCCATGCGGCATAAACTGTT<br>ATGCGGTATTAGCACCTGTTTCC<br>AAGTGTTATCCCCCTCTGATGGG<br>TAGGTTACCCACGTGTTACTCAC<br>CCGTCCGCCACTCCTCTTTCCAA<br>TTGAGTGCAAGCACTCGGGAGG<br>AAAGAAGCGTTCGACTTGCATGT<br>ATTAGGCACGCCGCCAGCGTTC<br>GTCCTGAGCCAGGATCAAACTCT<br>(SEQ ID NO: 37) |
| *Delftia* | *Bombyx mori* | Gut | CAGAAAGGAGGTGATCCAGCCG<br>CACCTTCCGATACGGCTACCTTG<br>TTACGACTTCACCCCAGTCACGA<br>ACCCCGCCGTGGTAAGCGCCCT<br>CCTTGCGGTTAGGCTACCTACTT<br>CTGGCGAGACCCGCTCCCATGG<br>TGTGACGGGCGGTGTGTACAAG<br>ACCCGGGAACGTATTCACCGCG<br>GCATGCTGATCCGCGATTACTA<br>GCGATTCCGACTTCACGCAGTC<br>GAGTTGCAGACTGCGATCCGGA<br>CTACGACTGGTTTTATGGGATTA<br>GCTCCCCCTCGCGGGTTGGCAA<br>CCCTCTGTACCAGCCATTGTATG<br>ACGTGTGTAGCCCCACCTATAA<br>GGGCCATGAGGACTTGACGTCA<br>TCCCCACCTTCCTCCGGTTTGTC<br>ACCGGCAGTCTCATTAGAGTGC<br>TCAACTGAATGTAGCAACTAATG<br>ACAAGGGTTGCGCTCGTTGCGG<br>GACTTAACCCAACATCTCACGAC<br>ACGAGCTGACGACAGCCATGCA<br>GCACCTGTGTGCAGGTTCTCTTT<br>CGAGCACGAATCCATCTCTGGA<br>AACTTCCTGCCATGTCAAAGGTG<br>GGTAAGGTTTTTCGCGTTGCATC<br>GAATTAAACCACATCATCCACCG<br>CTTGTGCGGGTCCCCGTCAATT<br>CCTTTGAGTTTCAACCTTGCGGC<br>CGTACTCCCCAGGCGGTCAACT<br>TCACGCGTTAGCTTCGTTACTGA<br>GAAAACTAATTCCCAACAACCAG<br>TTGACATCGTTTAGGGCGTGGA<br>CTACCAGGGTATCTAATCCTGTT<br>TGCTCCCCACGCTTTCGTGCAT<br>GAGCGTCAGTACAGGTCCAGGG<br>GATTGCCTTCGCCATCGGTGTTC<br>CTCCGCATATCTACGCATTTCAC<br>TGCTACACGCGGAATTCCATCC<br>CCCTCTACCGTACTCTAGCCATG<br>CAGTCACAAATGCAGTTCCCAG<br>GTTGAGCCCGGGGATTTCACAT<br>CTGTCTTACATAACCGCCTGCGC |

TABLE 1-continued

| Examples of Target Bacteria and Host Insects | | | |
|---|---|---|---|
| | | | ACGCTTTACGCCCAGTAATTCCG ATTAACGCTCGCACCCTACGTAT TACCGCGGCTGCTGGCACGTAG TTAGCCGGTGCTTATTCTTACGG TACCGTCATGGGCCCCCTGTATT AGAAGGAGCTTTTTCGTTCCGTA CAAAAGCAGTTTACAACCCGAAG GCCTTCATCCTGCACGCGGCAT TGCTGGATCAGGCTTTCGCCCA TTGTCCAAAATTCCCCACTGCTG CCTCCCGTAGGAGTCTGGGCCG TGTCTCAGTCCCAGTGTGGCTG GTCGTCCTCTCAGACCAGCTAC AGATCGTCGGCTTGGTAAGCTTT TATCCCACCAACTACCTAATCTG CCATCGGCCGCTCCAATCGCGC GAGGCCCGAAGGGCCCCCGCTT TCATCCTCAGATCGTATGCGGTA TTAGCTACTCTTTCGAGTAGTTA TCCCCCACGACTGGGCACGTTC CGATGTATTACTCACCCGTTCGC CACTCGTCAGCGTCCGAAGACC TGTTACCGTTCGACTTGCATGTG TAAGGCATGCCGCCAGCGTTCA ATCTGAGCCAGGATCAAACTCTA CAGTTCGATCT (SEQ ID NO: 38) |
| *Pelomonas* | *Bombyx mori* | Gut | ATCCTGGCTCAGATTGAACGCT GGCGGCATGCCTTACACATGCA AGTCGAACGGTAACAGGTTAAG CTGACGAGTGGCGAACGGGTGA GTAATATATCGGAACGTGCCCA GTCGTGGGGGATAACTGCTCGA AAGAGCAGCTAATACCGCATAC GACCTGAGGGTGAAAGCGGGG GATCGCAAGACCTCGCNNGATT GGAGCGGCCGATATCAGATTAG GTAGTTGGTGGGGTAAAGGCCC ACCAAGCCAACGATCTGTAGCT GGTCTGAGAGGACGACCAGCCA CACTGGGACTGAGACACGGCCC AGACTCCTACGGGAGGCAGCAG TGGGGAATTTTGGACAATGGGC GCAAGCCTGATCCAGCCATGCC GCGTGCGGGAAGAAGGCCTTCG GGTTGTAAACCGCTTTTGTCAGG GAAGAAAAGGTTCTGGTTAATAC CTGGGACTCATGACGGTACCTG AAGAATAAGCACCGGCTAACTAC GTGCCAGCAGCCGCGGTAATAC GTAGGGTGCAAGCGTTAATCGG AATTACTGGGCGTAAAGCGTGC GCAGGCGGTTATGCAAGACAGA GGTGAAATCCCCGGGCTCAACC TGGGAACTGCCTTTGTGACTGC ATAGCTAGAGTACGGTAGAGGG GGATGGAATTCCGCGTGTAGCA GTGAAATGCGTAGATATGCGGA GGAACACCGATGGCGAAGGCAA TCCCCTGGACCTGTACTGACGC TCATGCACGAAAGCGTGGGGAG CAAACAGGATTAGATACCCTGGT AGTCCACGCCCTAAACGATGTC AACTGGTTGTTGGGAGGGTTTCT TCTCAGTAACGTANNTAACGCGT GAAGTTGACCGCCTGGGGAGTA CGGCCGCAAGGTTGAAACTCAA AGGAATTGACGGGGACCCGCAC AAGCGGTGGATGATGTGGTTTA ATTCGATGCAACGCGAAAAACCT TACCTACCCTTGACATGCCAGGA ATCCTGAAGAGATTTGGGAGTG CTCGAAAGAGAACCTGGACACA GGTGCTGCATGGCCGTCGTCAG CTCGTGTCGTGAGATGTTGGGT TAAGTCCCGCAACGAGCGCAAC CCTTGTCATTAGTTGCTACGAAA |

TABLE 1-continued

| Examples of Target Bacteria and Host Insects | |
|---|---|
| | GGGCACTCTAATGAGACTGCCG GTGACAAACCGGAGGAAGGTGG GGATGACGTCAGGTCATCATGG CCCTTATGGGTAGGGCTACACA CGTCATACAATGGCCGGGACAG AGGGCTGCCAACCCGCGAGGG GGAGCTAATCCCAGAAACCCGG TCGTAGTCCGGATCGTAGTCTG CAACTCGACTGCGTGAAGTCGG AATCGCTAGTAATCGCGGATCA GCTTGCCGCGGTGAATACGTTC CCGGGTCTTGTACACACCGCCC GTCACACCATGGGAGCGGGTTC TGCCAGAAGTAGTTAGCCTAACC GCAAGGAGGGCGATTACCACGG CAGGGTTCGTGACTGGGGTGAA GTCGTAACAAGGTAGCCGTATC GGAAGGTGCGGCTGGATCAC (SEQ ID NO: 39) |

For example, a mosquito (e.g., *Aedes* spp. or *Anopheles* spp.) harbors symbiotic bacteria that modulate the mosquito's immune response and influence vectorial competence to pathogens. The modulating agent described herein may be useful in targeting bacteria resident in the mosquito, including, but not limited to, *EspZ, Seratia* spp (*e.g., Serratia marcescens*), *Enterbacterioaceae* spp., *Enterobacter* spp. (*e.g., Enterobacter cloacae, Enterobacter amnigenus, Enterobacter ludwigii*), *Proteus* spp., *Acinetobacter* spp., *Wigglesworthia* spp. (*Wigglesworthia gloosinidia*), *Xanthomonas* spp. (*e.g., Xanthomonas maltophilia*), *Pseudomonas* spp. (*e.g., Pseudomonas aeruginosa, Pseudomonas stutzeri, Pseudomonas rhodesiae*), *Escherichia* spp. (*e.g., Escherchia Cedecea* spp. (*e.g., Cedecea lapagei*), *Ewingella* spp. (*e.g., Ewingella americana*), *Bacillus* spp. (*e.g., Bacillus pumilus*), *Comamonas* spp., or *Vagococcus* spp. (*e.g., Vagococcus salmoninarium*), or *Wolbachia* spp. (e.g., *Wolbachia*-wMel, *Wolbachia*-wAlbB, *Wolbachia*-wMelPop, *Wolbachia*-wMelPop-CLA).

Any number of bacterial species may be targeted by the compositions or methods described herein. For example, in some instances, the modulating agent may target a single bacterial species. In some instances, the modulating agent may target at least about any of 1, 2, 3, 4, 5, 6, 7, 8, 9, 10, 15, 20, 30, 40, 50, 60, 70, 80, 90, 100, 150, 200, 250, 500, or more distinct bacterial species. In some instances, the modulating agent may target any one of about 1 to about 5, about 5 to about 10, about 10 to about 20, about 20 to about 50, about 50 to about 100, about 100 to about 200, about 200 to about 500, about 10 to about 50, about 5 to about 20, or about 10 to about 100 distinct bacterial species. In some instances, the modulating agent may target at least about any of 1, 2, 3, 4, 5, 6, 7, 8, 9, 10, 15, 20, 30, 40, 50, 60, 70, 80, 90, 100, or more phyla, classes, orders, families, or genera of bacteria.

In some instances, the modulating agent may increase a population of one or more bacteria (e.g., pathogenic bacteria, toxin-producing bacteria) by at least about any of 10%, 20%, 30%, 40%, 50%, 60%, 70%, 80%, 90% or more in the host in comparison to a host organism to which the modulating agent has not been administered. In some instances, the modulating agent may reduce the population of one or more bacteria (e.g., symbiotic bacteria, a pesticide-degrading bacterium, e.g., a bacterium that degrades a pesticide listed in Table 12) by at least about any of 10%, 20%, 30%, 40%, 50%, 60%, 70%, 80%, 90%, or more in the host in comparison to a host organism to which the modulating agent has not been administered. In some instances, the modulating agent may eradicate the population of a bacterium (e.g., symbiotic bacteria, a pesticide-degrading bacterium) in the host. In some instances, the modulating agent may increase the level of one or more pathogenic bacteria by at least about any of 10%, 20%, 30%, 40%, 50%, 60%, 70%, 80%, 90% or more in the host and/or decreases the level of one or more symbiotic bacteria by at least about any of 10%, 20%, 30%, 40%, 50%, 60%, 70%, 80%, 90%, or more in the host in comparison to a host organism to which the modulating agent has not been administered.

In some instances, the modulating agent may alter the bacterial diversity and/or bacterial composition of the host. In some instances, the modulating agent may increase the bacterial diversity in the host relative to a starting diversity by at least about any of 10%, 20%, 30%, 40%, 50%, 60%, 70%, 80%, 90%, or more in comparison to a host organism to which the modulating agent has not been administered. In some instances, the modulating agent may decrease the bacterial diversity in the host relative to a starting diversity by at least about any of 10%, 20%, 30%, 40%, 50%, 60%, 70%, 80%, 90%, or more in comparison to a host organism to which the modulating agent has not been administered.

In some instances, the modulating agent may alter the function, activity, growth, and/or division of one or more bacterial cells. For example, the modulating agent may alter the expression of one or genes in the bacteria. In some instances, the modulating agent may alter the function of one or more proteins in the bacteria. In some instances, the modulating agent may alter the function of one or more cellular structures (e.g., the cell wall, the outer or inner membrane) in the bacteria. In some instances, the modulating agent may kill (e.g., lyse) the bacteria.

The target bacterium may reside in one or more parts of the insect. Further, the target bacteria may be intracellular or extracellular. In some instances, the bacteria reside in or on one or more parts of the host gut, including, e.g., the foregut, midgut, and/or hindgut. In some instances, the bacteria reside as an intracellular bacteria within a cell of the host insect. In some instances, the bacteria reside in a bacteriocyte of the host insect.

Changes to the populations of bacteria in the host may be determined by any methods known in the art, such as microarray, polymerase chain reaction (PCR), real-time PCR, flow cytometry, fluorescence microscopy, transmission electron microscopy, fluorescence in situ hybridization (e.g., FISH), spectrophotometry, matrix-assisted laser desorption ionization-mass spectrometry (MALDI-MS), and DNA sequencing. In some instances, a sample of the host treated with a modulating agent is sequenced (e.g., by metagenomics sequencing of 16S rRNA or rDNA) to determine the microbiome of the host after delivery or administration of the modulating agent. In some instances, a sample of a host that did not receive the modulating agent is also sequenced to provide a reference.

ii. Fungi

Exemplary fungi that may be targeted in accordance with the methods and compositions provided herein, include, but are not limited to *Amylostereum areolatum, Epichloe* spp, *Pichia pinus, Hansenula capsulate, Daldinia decipien, Ceratocytis* spp, *Ophiostoma* spp, and *Attamyces bromatificus*. Non-limiting examples of yeast and yeast-like symbionts found in insects include *Candida, Metschnikowia, Debaromyces, Scheffersomyces shehatae and Scheffersomyces stipites, Starmerella, Pichia, Trichosporon, Cryptococcus, Pseudozyma*, and yeast-like symbionts from the subphylum Pezizomycotina (e.g., *Symbiotaphrina bucneri* and *Symbiotaphrina kochii*). Non-limiting examples of yeast that may be targeted by the methods and compositions herein are listed in Table 2.

TABLE 2

| Insect Species | Order: Family | Yeast Location (Species) |
|---|---|---|
| *Stegobium paniceum* (=*Sitodrepa panicea*) | Coleoptera: Anobiidae | Mycetomes (*Saccharomyces*)<br>Cecae (*Torulopsis buchnerii*)<br>Mycetome between foregut and midgut<br>Mycetomes (*Symbiotaphrina buchnerii*)<br>Mycetomes and digestive tube (*Torulopsis buchnerii*)<br>Gut cecae (*Symbiotaphrina buchnerii*) |
| *Lasioderma serricorne* | Coleoptera: Anobiidae | Mycetome between foregut and midgut (*Symbiotaphrina kochii*) |
| *Ernobius abietis* | Coleoptera: Anobiidae | Mycetomes (*Torulopsis karawaiewii*) (*Candida karawaiewii*) |
| *Ernobius mollis* | Coleoptera: Anobiidae | Mycetomes (*Torulopsis ernobii*) (*Candida ernobii*) |
| *Hemicoelus gibbicollis* | Coleoptera: Anobiidae | Larval mycetomes |
| *Xestobium plumbeum* | Coleoptera: Anobiidae | Mycetomes (*Torulopsis xestobii*) (*Candida xestobii*) |
| *Criocephalus rusticus* | Coleoptera: Cerambycidae | Mycetomes |
| *Phoracantha semipunctata* | Coleoptera: Cerambycidae | Alimentary canal (*Candida guilliermondii*, *C. tenuis*)<br>Cecae around midgut (*Candida guilliermondii*) |
| *Harpium inquisitor* | Coleoptera: Cerambycidae | Mycetomes (*Candida rhagii*) |
| *Harpium mordax*<br>*H. sycophanta* | Coleoptera: Cerambycidae | Cecae around midgut (*Candida tenuis*) |
| *Gaurotes virginea* | Coleoptera: Cerambycidae | Cecae around midgut (*Candida rhagii*) |
| *Leptura rubra* | Coleoptera: Cerambycidae | Cecae around midgut (*Candida tenuis*)<br>Cecae around midgut (*Candida parapsilosis*) |
| *Leptura maculicornis*<br>*L. cerambyciformis* | Coleoptera: Cerambycidae | Cecae around midgut (*Candida parapsilosis*) |
| *Leptura sanguinolenta* | Coleoptera: Cerambycidae | Cecae around midgut (*Candida* sp.) |
| *Rhagium bifasciatum* | Coleoptera: Cerambycidae | Cecae around midgut (*Candida tenuis*) |
| *Rhagium inquisitor* | Coleoptera: Cerambycidae | Cecae around midgut (*Candida guilliermondii*) |
| *Rhagium mordax* | Coleoptera: Cerambycidae | Cecae around midgut (*Candida*) |
| *Carpophilus hemipterus* | Coleoptera: Nitidulidae | Intestinal tract (10 yeast species) |
| *Odontotaenius disjunctus* | Coleoptera: Passalidae | Hindgut (*Enteroramus dimorphus*) |
| *Odontotaenius disjunctus*<br>*Verres sternbergianus* | Coleoptera: Passalidae | Gut (*Pichia stipitis*, *P. segobiensis*, *Candida shehatae*)<br>(*C. ergatensis*) |
| *Scarabaeus semipunctatus*<br>*Chironitis furcifer* | Coleoptera: Scarabaeidae | Digestive tract (10 yeast species) |
| Unknown species | Coleoptera: Scarabaeidae | Guts (*Trichosporon cutaneum*) |
| *Dendroctonus* and *Ips* spp. | Coleoptera: Scolytidae | Alimentary canal (13 yeast species) |
| *Dendroctonus frontalis* | Coleoptera: Scolytidae | Midgut (*Candida* sp.) |
| *Ips sexdentatus* | Coleoptera: Scolytidae | Digestive tract (*Pichia bovis*, *P. rhodanensis*)<br>*Hansenula holstii* (*Candida rhagii*)<br>Digestive tract (*Candida pulcherina*) |

TABLE 2-continued

| Insect Species | Order: Family | Yeast Location (Species) |
|---|---|---|
| *Ips typographus* | Coleoptera: Scolytidae | Alimentary canal<br>Alimentary tracts (*Hansenula capsulata*, *Candida parapsilosis*)<br>Guts and beetle homogenates (*Hansenula holstii*, *H. capsulata*, *Candida diddensii*, *C. mohschtana*, *C. nitratophila*, *Cryptococcus albidus*, *C. laurentii*) |
| *Trypodendron lineatum* | Coleoptera: Scolytidae | Not specified |
| *Xyloterinus politus* | Coleoptera: Scolytidae | Head, thorax, abdomen (*Candida*, *Pichia*, *Saccharomycopsis*) |
| *Periplaneta americana* | Dictyoptera: Blattidae | Hemocoel (*Candida* sp. nov.) |
| *Blatta orientalis* | Dictyoptera: Blattidae | Intestinal tract (*Kluyveromyces blattae*) |
| *Blatella germanica* | Dictyoptera: Blattellidae | Hemocoel |
| *Cryptocercus punctulatus* | Dictyoptera: Cryptocercidae | Hindgut (1 yeast species) |
| *Philophylla heraclei* | Diptera: Tephritidae | Hemocoel |
| *Aedes* (4 species) | Diptera: Culicidae | Internal microflora (9 yeast genera) |
| *Drosophila pseudoobscura* | Diptera: Drosophilidae | Alimentary canal (24 yeast species) |
| *Drosophila* (5 spp.) | Diptera: Drosophilidae | Crop (42 yeast species) |
| *Drosophila melanogaster* | Diptera: Drosophilidae | Crop (8 yeast species) |
| *Drosophila* (4 spp.) | Diptera: Drosophilidae | Crop (7 yeast species) |
| *Drosophila* (6 spp.) | Diptera: Drosophilidae | Larval gut (17 yeast species) |
| *Drosophila* (20 spp.) | Diptera: Drosophilidae | Crop (20 yeast species) |
| *Drosophila* (8 species groups) | Diptera: Drosophilidae | Crop (*Kloeckera*, *Candida*, *Kluyveromyces*) |
| *Drosophila serido* | Diptera: Drosophilidae | Crop (18 yeast species) |
| *Drosophila* (6 spp.) | Diptera: Drosophilidae | Intestinal epithelium (*Coccidiascus legeri*) |
| *Protaxymia melanoptera* | Diptera | Unknown (*Candida*, *Cryptococcus*, *Sporoblomyces*) |
| *Astegopteryx styraci* | Homoptera: Aphididae | Hemocoel and fat body |
| *Tuberaphis* sp.<br>*Hamiltonaphis styraci*<br>*Glyphinaphis bambusae*<br>*Cerataphis* sp. | Homoptera: Aphididae | Tissue sections |
| *Hamiltonaphis styraci* | Homoptera: Aphididae | Abdominal hemocoel |
| *Cofana unimaculata* | Homoptera: Cicadellidae | Fat body |
| *Leofa unicolor* | Homoptera: Cicadellidae | Fat body |
| *Lecaniines*, etc. | Homoptera: Coccoidea d | Hemolymph, fatty tissue, etc. |
| *Lecanium* sp. | Homoptera: Coccidae | Hemolymph, adipose tissue |
| *Ceroplastes* (4 sp.) | Homoptera: Coccidae | Blood smears |
| *Laodelphax striatellus* | Homoptera: Delphacidae | Fat body<br>Eggs<br>Eggs (*Candida*) |
| *Nilaparvata lugens* | Homoptera: Delphacidae | Fat body<br>Eggs (2 unidentified yeast species)<br>Eggs, nymphs (*Candida*)<br>Eggs (7 unidentified yeast species)<br>Eggs (*Candida*) |
| *Nisia nervosa*<br>*Nisia grandiceps*<br>*Perkinsiella* spp.<br>*Sardia rostrata*<br>*Sogatella furcifera* | Homoptera: Delphacidae | Fat body |
| *Sogatodes orizicola* | Homoptera: Delphacidae | Fat body |
| *Amrasca devastans* | Homoptera: Jassidae | Eggs, mycetomes, hemolymph |
| *Tachardina lobata* | Homoptera: Kerriidae | Blood smears (*Torulopsis*) |
| *Laccifer* (=*Lakshadia*) sp. | Homoptera: Kerriidae | Blood smears (*Torula variabilis*) |
| *Comperia merceti* | Hymenoptera: Encyrtidae | Hemolymph, gut, poison gland |
| *Solenopsis invicta*<br><br>*S. quinquecuspis* | Hymenoptera: Formicidae | Hemolymph (*Myrmecomyces annellisae*) |
| *Solenopsis invicta* | Hymenoptera: Formicidae | Fourth instar larvae (*Candida parapsilosis*, *Yarrowia lipolytica*)<br>Gut and hemolymph (*Candida parapsilosis*, *C. lipolytica*, *C. guillermondii*, *C. rugosa*, *Debaryomyces hansenii*) |
| *Apis mellifera* | Hymenoptera: Apidae | Digestive tracts (*Torulopsis* sp.)<br>Intestinal tract (*Torulopsis apicola*)<br>Digestive tracts (8 yeast species)<br>Intestinal contents (12 yeast species) |

TABLE 2-continued

| Insect Species | Order: Family | Yeast Location (Species) |
|---|---|---|
| | | Intestinal contents (7 yeast species)<br>Intestines (14 yeast species)<br>Intestinal tract (Pichia melissophila)<br>Intestinal tracts (7 yeast species)<br>Alimentary canal (*Hansenula silvicola*)<br>Crop and gut (13 yeast species) |
| *Apis mellifera* | Hymenoptera: Apidae | Midguts (9 yeast genera) |
| *Anthophora occidentalis* | Hymenoptera: Anthophoridae | |
| *Nomia melanderi* | Hymenoptera: Halictidae | |
| *Halictus rubicundus* | Hymenoptera: Halictidae | |
| *Megachile rotundata* | Hymenoptera: Megachilidae | |

Any number of fungal species may be targeted by the compositions or methods described herein. For example, in some instances, the modulating agent may target a single fungal species. In some instances, the modulating agent may target at least about any of 1, 2, 3, 4, 5, 6, 7, 8, 9, 10, 15, 20, 30, 40, 50, 60, 70, 80, 90, 100, 150, 200, 250, 500, or more distinct fungal species. In some instances, the modulating agent may target any one of about 1 to about 5, about 5 to about 10, about 10 to about 20, about 20 to about 50, about 50 to about 100, about 100 to about 200, about 200 to about 500, about 10 to about 50, about 5 to about 20, or about 10 to about 100 distinct fungal species. In some instances, the modulating agent may target at least about any of 1, 2, 3, 4, 5, 6, 7, 8, 9, 10, 15, 20, 30, 40, 50, 60, 70, 80, 90, 100, or more phyla, classes, orders, families, or genera of fungi.

In some instances, the modulating agent may increase a population of one or more fungi (e.g., pathogenic or parasitic fungi) by at least about any of 10%, 20%, 30%, 40%, 50%, 60%, 70%, 80%, 90% or more in the host in comparison to a host organism to which the modulating agent has not been administered. In some instances, the modulating agent may reduce the population of one or more fungi (e.g., symbiotic fungi) by at least about any of 10%, 20%, 30%, 40%, 50%, 60%, 70%, 80%, 90% or more in the host in comparison to a host organism to which the modulating agent has not been administered. In some instances, the modulating agent may eradicate the population of a fungi (e.g., symbiotic fungi) in the host. In some instances, the modulating agent may increase the level of one or more symbiotic fungi by at least about any of 10%, 20%, 30%, 40%, 50%, 60%, 70%, 80%, 90% or more in the host and/or may decrease the level of one or more symbiotic fungi by at least about any of 10%, 20%, 30%, 40%, 50%, 60%, 70%, 80%, 90% or more in the host in comparison to a host organism to which the modulating agent has not been administered.

In some instances, the modulating agent may alter the fungal diversity and/or fungal composition of the host. In some instances, the modulating agent may increase the fungal diversity in the host relative to a starting diversity by at least about any of 10%, 20%, 30%, 40%, 50%, 60%, 70%, 80%, 90%, or more in comparison to a host organism to which the modulating agent has not been administered. In some instances, the modulating agent may decrease the fungal diversity in the host relative to a starting diversity by at least about any of 10%, 20%, 30%, 40%, 50%, 60%, 70%, 80%, 90%, or more in comparison to a host organism to which the modulating agent has not been administered.

In some instances, the modulating agent may alter the function, activity, growth, and/or division of one or more fungi. For example, the modulating agent may alter the expression of one or more genes in the fungus. In some instances, the modulating agent may alter the function of one or more proteins in the fungus. In some instances, the modulating agent may alter the function of one or more cellular components in the fungus. In some instances, the modulating agent may kill the fungus.

Further, the target fungus may reside in one or more parts of the insect. In some instances, the fungus resides in or on one or more parts of the insect gut, including, e.g., the foregut, midgut, and/or hindgut. In some instances, the fungus lives extracellularly in the hemolymph, fat bodies or in specialized structures in the host.

Changes to the population of fungi in the host may be determined by any methods known in the art, such as microarray, polymerase chain reaction (PCR), real-time PCR, flow cytometry, fluorescence microscopy, transmission electron microscopy, fluorescence in situ hybridization (e.g., FISH), spectrophotometry, matrix-assisted laser desorption ionization-mass spectrometry (MALDI-MS), and DNA sequencing. In some instances, a sample of the host treated with a modulating agent is sequenced (e.g., by metagenomics sequencing) to determine the microbiome of the host after delivery or administration of the modulating agent. In some instances, a sample of a host that did not receive the modulating agent is also sequenced to provide a reference.

III. Modulating Agents

The modulating agent of the methods and compositions provided herein may include a phage, a polypeptide, a small molecule, an antibiotic, a secondary metabolite, a bacterium, a fungus, or any combination thereof.

i. Phage

The modulating agent described herein may include a phage (e.g., a lytic phage or a non-lytic phage). In some instances, an effective concentration of any phage described herein may alter a level, activity, or metabolism of one or more microorganisms (as described herein) resident in a host described herein (e.g., a vector of a human pathogen, e.g., a mosquito, a mite, a biting louse, or a tick), the modulation resulting in a decrease in the host's fitness (e.g., as outlined herein). In some instances, the modulating agent includes at least one phage selected from the order Tectiviridae, Myoviridae, Siphoviridae, Podoviridae, Caudovirales, Lipothrixviridae, Rudiviridae, or Ligamenvirales. In some instances, the composition includes at least one phage selected from the family Myoviridae, Siphoviridae, Podoviridae, Lipothrixviridae, Rudiviridae, Ampullaviridae, Bicaudaviridae, Clavaviridae, Corticoviridae, Cystoviridae, Fuselloviridae, Gluboloviridae, Guttaviridae, Inoviridae, Leviviridae, Microviridae, Plasmaviridae, and Tectiviridae. Further non-limiting examples of phages useful in the methods and compositions are listed in Table 3.

TABLE 3

Examples of Phage and Targeted Bacteria

| Phage and Accession # | Target bacteria | Target host |
|---|---|---|
| SA1(NC_027991), phiP68 (NC_004679) | Staphylococcus sp. | Apidae family |
| WO (AB036666.1) | Wolbachia sp. | Aedes aegypt; Drosophila melanogaster; Plasmodium sp; Teleogryllus taiwanemma; Bombyx mori |
| KL1 (NC_018278), BcepNazgul (NC_005091) PhiE125 (NC_003309) | Burkholderia sp. | Riptortus sp.; Pyrrhocoris apterus. |
| Fern (NC_028851), Xenia (NC_028837), HB10c2 (NC_028758) | Paenibacillus larvae | bumble bees: Bombus sp.; honey bees: A. mellifera |
| CP2 (NC_020205), XP10 (NC_004902), XP15 (NC_007024), phiL7 (NC_012742) | Xanthomonas sp. | Plebeina denoiti; Apidae family; Apis mellifera; Drosphilidae family; and Chloropidae family |
| PP1 (NC_019542), PM1 (NC_023865) | Pectobacterium carotovorum subsp. carotovorum | Apidae family |
| φRSA1 (NC_009382), φRSB1 (NC_011201), φRSL1 (NC_010811), RSM1 (NC_008574) | Ralstonia solanacearum | Bombyx mori |
| SF1(NC_028807) | Streptomyces scabies | Philantus sp.; Trachypus sp |
| ECML-4 (NC_025446), ECML-117 (NC_025441), ECML-134 (NC_025449) | Escherichia coli | Apidae family; Varroa destructor |
| SSP5(JX274646.1), SSP6 (NC_004831), SFP10 (NC_016073), F18SE (NC_028698) | Salmonella sp. | Drosphilidae family |
| γ (NC_001416), Bcp1 (NC_024137) | Bacillus sp. | Gypsy moth; Lymantria dispar; Varroa destructor |
| Phi1 (NC_009821) | Enterococcus sp. | Schistocerca gragaria |
| φKMV (NC_005045), φEL(AJ697969.1), ¢KZ (NC_004629) | Pseudomonas sp. | Lymantria dispar; Apidae family |
| A2 (NC_004112), phig1e (NC_004305) | Lactobacilli sp. | Apidae family; Drosophila family; Varroa destructor |
| KLPN1 (NC_028760) | Klebsiella sp | C. capitata |
| vB_AbaM_Acibel004 (NC_025462), vB_AbaP_Acibel007 (NC_025457) | Acinetobacter sp. | Schistocerca gragaria |

In some instances, a modulating agent includes a lytic phage. Thus, after delivery of the lytic phage to a bacterial cell resident in the host, the phage causes lysis in the target bacterial cell. In some instances, the lytic phage targets and kills a bacterium resident in a host insect to decrease the fitness of the host. Alternatively or additionally, the phage of the modulating agent may be a non-lytic phage (also referred to as lysogenic or temperate phage). Thus, after delivery of the non-lytic phage to a bacterial cell resident in the host, the bacterial cell may remain viable and able to stably maintain expression of genes encoded in the phage genome. In some instances, a non-lytic phage is used to alter gene expression in a bacterium resident in a host insect to decrease the fitness of the host. In some instances, the modulating agent includes a mixture of lytic and non-lytic phage.

In certain instances, the phage is a naturally occurring phage. For example, a naturally occurring phage may be isolated from an environmental sample containing a mixture of different phages. The naturally occurring phage may be isolated using methods known in the art to isolate, purify, and identify phage that target a particular microorganism (e.g., a bacterial endosymbiont in an insect host). Alternatively, in certain instances, the phage may be engineered based on a naturally occurring phage.

The modulating agent described herein may include phage with either a narrow or broad bacterial target range. In some instances, the phage has a narrow bacterial target range. In some instances, the phage is a promiscuous phage with a large bacterial target range. For example, the promiscuous phage may target at least about any of 5, 10, 20, 30, 40, 50, or more bacterium resident in the host. A phage with a narrow bacterial target range may target a specific bacterial strain in the host without affecting another, e.g., non-targeted, bacterium in the host. For example, the phage may target no more than about any of 50, 40, 30, 20, 10, 8, 6, 4, 2, or 1 bacterium resident in the host. For example, the phage described herein may be useful in targeting one or more bacteria resident in the mosquito, including, but not limited to, EspZ, Seratia spp (e.g., Serratia marcescens), Enterbacterioaceae spp., Enterobacter spp. (e.g., Enterobacter cloacae, Enterobacter amnigenus, Enterobacter ludwigii), Proteus spp., Acinetobacter spp., Wigglesworthia spp. (Wigglesworthia gloosinidia), Xanthomonas spp. (e.g., Xanthomonas maltophilia), Pseudomonas spp. (e.g., Pseudomonas aeruginosa, Pseudomonas stutzeri, Pseudomonas rhodesiae), Escherichia spp. (e.g., Escherchia coli), Cedecea spp. (e.g., Cedecea lapagei), Ewingella spp. (e.g., Ewingella americana), Bacillus spp. (e.g., Bacillus pumilus), Comamonas spp., or Vagococcus spp. (e.g., Vagococcus salmoninarium), or Wolbachia spp. (e.g., Wolbachia-wMel, Wolbachia-wAlbB, Wolbachia-wMelPop, Wolbachia-wMelPop-CLA).

The compositions described herein may include any number of phage, such as at least about any one of 1, 2, 3, 4, 5, 10, 15, 20, 30, 40, 50, 100, or more phage. In some instances, the composition includes phage from one or more (e.g., 2, 3, 4, 5, 6, 7, 8, 9, 10, or more phage) families, one or more orders (e.g., 2, 3, 4, 5, 6, 7, 8, 9, 10, or more phage), or one or more species (e.g., 1, 2, 3, 4, 5, 10, 15, 20, 30, 40, 50, 100, or more phage). Compositions including one or more phage are also referred herein as "phage cocktails." Phage cocktails are useful because they allow for targeting of a wider host range of bacteria. Furthermore, they allow for each bacterial strain (i.e. subspecies) to be targeted by multiple orthogonal phages, thereby preventing or significantly delaying the onset of resistance. In some instances, a cocktail includes multiple phages targeting one bacterial species. In some instances, a cocktail includes multiple phages targeting multiple bacterial species. In some instances, a one-phage "cocktail" includes a single promiscuous phage (i.e. a phage with a large host range) targeting many strains within a species.

Suitable concentrations of the phage in the modulating agent described herein depends on factors such as efficacy, survival rate, transmissibility of the phage, number of distinct phage, and/or lysin types in the compositions, formulation, and methods of application of the composition. In some instances, the phage is in a liquid or a solid formulation. In some instances, the concentration of each phage in any of the compositions described herein is at least about any of $10^2$, $10^3$, $10^4$, $10^5$, $10^6$, $10^7$, $\mathbf{10^8}$, $10^9$, $10^{10}$ or more pfu/ml. In some instances, the concentration of each phage in any of the compositions described herein is no more than about any of $10^2$, $10^3$, $10^4$, $10^5$, $10^6$, $10^7$, $\mathbf{10^8}$, $10^9$ pfu/ml. In some instances, the concentration of each phage in the composition is any of about $10^2$ to about $10^3$, about $10^3$ to about $10^4$, about $10^4$ to about $10^5$, about $10^5$ to about $10^6$, about $10^7$ to about $10^8$, about $10^8$ to about $10^9$, about $10^2$ to about $10^4$, about $10^4$ to about $10^6$, about $10^6$ to about $10^9$, or about $10^3$ to about $10^8$ pfu/ml. In some instances, wherein the composition includes at least two types of phages, the concentration of each type of the phages may be the same or different. For example, in some instances, the concentration of one phage in the cocktail is about $10^8$ pfu/ml and the concentration of a second phage in the cocktail is about $10^6$ pfu/ml.

A modulating agent including a phage as described herein can be contacted with the target host in an amount and for a time sufficient to: (a) reach a target level (e.g., a predetermined or threshold level) of phage concentration inside a target host; (b) reach a target level (e.g., a predetermined or threshold level) of phage concentration inside a target host gut; (c) reach a target level (e.g., a predetermined or threshold level) of phage concentration inside a target host bacteriocyte; (d) modulate the level, or an activity, of one or more microorganism (e.g., endosymbiont) in the target host; or/and (e) modulate fitness of the target host.

As illustrated by Examples 5-7 and 28, phages (e.g., one or more naturally occurring phage) can be used as modulating agents that target an endosymbiotic bacterium in an insect host to decrease the fitness of the host (e.g., as outlined herein).

ii. Polypeptides

Numerous polypeptides (e.g., a bacteriocin, R-type bacteriocin, nodule C-rich peptide, antimicrobial peptide, lysin, or bacteriocyte regulatory peptide) may be used in the compositions and methods described herein. In some instances, an effective concentration of any peptide or polypeptide described herein may alter a level, activity, or metabolism of one or more microorganisms (as described herein, e.g., a *Wolbachia* spp. or a *Rickettsia* spp.) resident in a host (e.g., a vector of a human pathogen, e.g., a mosquito, mite, biting louse, or tick), the modulation resulting in a decrease in the host's fitness (e.g., as outlined herein). Polypeptides included herein may include naturally occurring polypeptides or recombinantly produced variants. For example, the polypeptide may be a functionally active variant of any of the polypeptides described herein with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a polypeptide described herein or a naturally occurring polypeptide.

A modulating agent comprising a polypeptide as described herein can be contacted with the target host in an amount and for a time sufficient to: (a) reach a target level (e.g., a predetermined or threshold level) of concentration inside a target host; (b) reach a target level (e.g., a predetermined or threshold level) of concentration inside a target host gut; (c) reach a target level (e.g., a predetermined or threshold level) of concentration inside a target host bacteriocyte; (d) modulate the level, or an activity, of one or more microorganism (e.g., endosymbiont) in the target host; or/and (e) modulate fitness of the target host.

The polypeptide modulating agents discussed hereinafter, namely bacteriocins, lysins, antimicrobial peptides, nodule C-rich peptides, and bacteriocyte regulatory peptides, can be used to alter the level, activity, or metabolism of target microorganisms (e.g., *Rickettsia* or Wolbochia) as indicated in the section for decreasing the fitness of host insects (e.g., a vector of a human pathogen, e.g., a mosquito, a mite, a biting louse, or a tick).

(a) Bacteriocins

The modulating agent described herein may include a bacteriocin. In some instances, the bacteriocin is naturally produced by Gram-positive bacteria, such as *Pseudomonas, Streptomyces, Bacillus, Staphylococcus*, or lactic acid bacteria (LAB, such as *Lactococcus lactis*). In some instances, the bacteriocin is naturally produced by Gram-negative bacteria, such as Hafnia *alvei, Citrobacter freundii, Klebsiella oxytoca, Klebsiella pneumonia, Enterobacter cloacae, Serratia* plymithicum, *Xanthomonas campestris, Erwinia carotovora, Ralstonia solanacearum*, or *Escherichia coli*. Exemplary bacteriocins include, but are not limited to, Class I-IV LAB antibiotics (such as lantibiotics), colicins, microcins, and pyocins. Non-limiting examples of bacteriocins are listed in Table 4.

TABLE 4

Examples of Bacteriocins

| Class | Name | Producer | Targets | Sequence |
|---|---|---|---|---|
| Class I | Nisin | *Lactococcus lactis* | Active on Gram-positive bacteria: *Enterococcus*, | ITSISLCTPGCKT GALMGCNMKTA TCHCSIHVSK |

TABLE 4-continued

| Examples of Bacteriocins | | | | |
|---|---|---|---|---|
| Class | Name | Producer | Targets | Sequence |
| | | | *Lactobacillus*, *Lactococcus*, *Leuconostoc*, *Listeria*, *Clostridium* | (SEQ ID NO: 40) |
| | Epidermin | *Staphylococcus epidermis* | Gram-positive bacteria | IASKFICTPGCA KTGSFNSYCC (SEQ ID NO: 41) |
| Class II | | | | |
| Class II a | Pediocin PA-1 | *Pediococcus acidilactici* | *Pediococci*, *Lactobacilli*, *Leuconostoc*, *Brochothrix thermosphacta*, *Propionibacteria*, *Bacilli*, *Enterococci*, *Staphylococci*, *Listeria clostridia*, *Listeria monocytogenes*, *Listeria innocua* | KYYGNGVTCG KHSCSVDWGK ATTCIINNGAMA WATGGHQGNH KC (SEQ ID NO: 42) |
| Class II b | Enterocin P | *Enterococcus faecium* | *Lactobacillus sakei*, *Enterococcus faecium* | ATRSYGNGVYC NNSKCWVNWG EAKENIAGIVISG WASGLAGMGH (SEQ ID NO: 43) |
| Class II c | lactococcin G | *Streptococcus lactis* | Gram-positive bacteria | GTWDDIGQGIG RVAYWVGKAM GNMSDVNQAS RINRKKKH (SEQ ID NO: 44) |
| Class II d | Lactacin-F | *Lactobacillus johnsonii* | *Lactobacilli*, *Enterococcus faecalis* | NRWGDTVLSAA SGAGTGIKACK SFGPWGMAICG VGGAAIGGYFG YTHN (SEQ ID NO: 45) |
| Class III | | | | |
| Class III a | Enterocin AS-48 | *Enterococcus faecalis* | Broad spectrum: Gram positive and Gram negative bacteria. | MAKEFGIPAAVA GTVLNVVEAGG WVTTIVSILTAV GSGGLSLLAAA GRESIKAYLKKE IKKKGKRAVIAW (SEQ ID NO: 46) |
| Class III b | aureocin A70 | *Staphylococcus aureus* | Broad spectrum: Gram positive and Gram negative bacteria. | MSWLNFLKYIAK YGKKAVSAAWK YKGKVLEWLNV GPTLEWVWQKL KKIAGL (SEQ ID NO: 47) |
| Class IV | Garvicin A | *Lactococcus garvieae* | Broad spectrum: Gram positive and Gram negative bacteria. | IGGALGNALNGL GTWANMMNGG GFVNQWQVYA NKGKINQYRPY (SEQ ID NO: 48) |
| Unclassified | Colicin V | *Escherichia coli* | Active against *Escherichia coli* (also closely related bacteria); Enterobacteriaceae | MRTLTLNELDS VSGGASGRDIA MAIGTLSGQFV AGGIGAAAGGV AGGAIYDYAST HKPNPAMSPSG LGGTIKQKPEGI PSEAWNYAAGR LCNWSPNNLSD VCL (SEQ ID NO: 49) |

In some instances, the bacteriocin is a colicin, a pyocin, or a microcin produced by Gram-negative bacteria. In some instances, the bacteriocin is a colicin. The colicin may be a group A colicin (e.g., uses the Tol system to penetrate the outer membrane of a target bacterium) or a group B colicin (e.g., uses the Ton system to penetrate the outer membrane of a target bacterium). In some instances, the bacteriocin is a microcin. The microcin may be a class I microcin (e.g., <5 kDa, has post-translational modifications) or a class II microcin (e.g., 5-10 kDa, with or without post-translational modifications). In some instances, the class II microcin is a class IIa microcin (e.g., requires more than one genes to synthesize and assemble functional peptides) or a class IIb microcin (e.g., linear peptides with or without post-translational modifications at C-terminus). In some instances, the bacteriocin is a pyocin. In some instances, the pyocin is an R-pyocin, F-pyocin, or S-pyocin.

In some instances, the bacteriocin is a class I, class II, class III, or class IV bacteriocin produced by Gram-positive bacteria. In some instances, the modulating agent includes a Class I bacteriocin (e.g., lanthionine-containing antibiotics (lantibiotics) produced by a Gram-positive bacteria). The class I bacteriocins or lantibiotic may be a low molecular weight peptide (e.g., less than about 5 kDa) and may possess post-translationally modified amino acid residues (e.g., lanthionine, β-methyllanthionine, or dehydrated amino acids).

In some instances, the bacteriocin is a Class II bacteriocin (e.g., non-lantibiotics produced by Gram-positive bacteria). Many are positively charged, non-lanthionine-containing peptides, which unlike lantibiotics, do not undergo extensive post-translational modification. The Class II bacteriocin may belong to one of the following subclasses: "pediocin-like" bacteriocins (e.g., pediocin PA-1 and carnobacteriocin X (Class IIa)); two-peptide bacteriocins (e.g., lactacin F and ABP-118 (Class IIb)); circular bacteriocins (e.g., carnocyclin A and enterocin AS-48 (Class IIc)); or unmodified, linear, non-pediocin-like bacteriocins (e.g., epidermicin NI01 and lactococcin A (Class IId)).

In some instances, the bacteriocin is a Class III bacteriocin (e.g., produced by Gram-positive bacteria). Class III bacteriocins may have a molecular weight greater than 10 kDa and may be heat unstable proteins. The Class III bacteriocins can be further subdivided into Group IIIA and Group IIIB bacteriocins. The Group IIIA bacteriocins include bacteriolytic enzymes which kill sensitive strains by lysis of the cell well, such as Enterolisin A. Group IIIB bacteriocins include non-lytic proteins, such as Caseicin 80, Helveticin J, and lactacin B.

In some instances, the bacteriocin is a Class IV bacteriocin (e.g., produced by Gram-positive bacteria). Class IV bacteriocins are a group of complex proteins, associated with other lipid or carbohydrate moieties, which appear to be required for activity. They are relatively hydrophobic and heat stable. Examples of Class IV bacteriocins leuconocin S, lactocin 27, and lactocin S.

In some instances, the bacteriocin is an R-type bacteriocin. R-type bacteriocins are contractile bacteriocidal protein complexes. Some R-type bacteriocins have a contractile phage-tail-like structure.

The C-terminal region of the phage tail fiber protein determines target-binding specificity. They may attach to target cells through a receptor-binding protein, e.g., a tail fiber. Attachment is followed by sheath contraction and insertion of the core through the envelope of the target bacterium. The core penetration results in a rapid depolarization of the cell membrane potential and prompt cell death. Contact with a single R-type bacteriocin particle can result in cell death. An R-type bacteriocin, for example, may be thermolabile, mild acid resistant, trypsin resistant, sedimentable by centrifugation, resolvable by electron microscopy, or a combination thereof. Other R-type bacteriocins may be complex molecules including multiple proteins, polypeptides, or subunits, and may resemble a tail structure of bacteriophages of the myoviridae family. In naturally occurring R-type bacteriocins, the subunit structures may be encoded by a bacterial genome, such as that of *C. difficile* or *P. aeruginosa* and form R-type bacteriocins to serve as natural defenses against other bacteria. In some instances, the R-type bacteriocin is a pyocin. In some instances, the pyocin is an R-pyocin, F-pyocin, or S-pyocin.

In some instances, the bacteriocin is a functionally active variant of the bacteriocins described herein. In some instances, the variant of the bacteriocin has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a bacteriocin described herein or a naturally occurring bacteriocin.

In some instances, the bacteriocin may be bioengineered, according to standard methods, to modulate their bioactivity, e.g., increase or decrease or regulate, or to specify their target microorganisms. In other instances, the bacteriocin is produced by the translational machinery (e.g. a ribosome, etc.) of a microbial cell. In some instances, the bacteriocin is chemically synthesized. Some bacteriocins can be derived from a polypeptide precursor. The polypeptide precursor can undergo cleavage (e.g., processing by a protease) to yield the polypeptide of the bacteriocin itself. As such, in some instances, the bacteriocin is produced from a precursor polypeptide. In some other instances, the bacteriocin includes a polypeptide that has undergone post-translational modifications, for example, cleavage, or the addition of one or more functional groups.

The bacteriocins described herein may be formulated in a composition for any of the uses described herein. The compositions disclosed herein may include any number or type (e.g., classes) of bacteriocins, such as at least about any one of 1 bacteriocin, 2, 3, 4, 5, 10, 15, 20, 30, 40, 50, 100, or more bacteriocins. Suitable concentrations of each bacteriocin in the compositions described herein depends on factors such as efficacy, stability of the bacteriocin, number of distinct bacteriocin types in the compositions, formulation, and methods of application of the composition. In some instances, each bacteriocin in a liquid composition is from about 0.01 ng/ml to about 100 mg/mL. In some instances, each bacteriocin in a solid composition is from about 0.01 ng/g to about 100 mg/g. In some instances, wherein the composition includes at least two types of bacteriocins, the concentration of each type of the bacteriocins may be the same or different. In some instances, the bacteriocin is provided in a composition including a bacterial cell that secretes the bacteriocin. In some instances, the bacteriocin is provided in a composition including a polypeptide (e.g., a polypeptide isolated from a bacterial cell).

Bacteriocins may neutralize (e.g., kill) at least one microorganism other than the individual bacterial cell in which the polypeptide is made, including cells clonally related to the bacterial cell and other microbial cells. As such, a bacterial cell may exert cytotoxic or growth-inhibiting effects on a plurality of microbial organisms by secreting bacteriocins. In some instances, the bacteriocin targets and kills one or more species of bacteria resident in the host via cytoplasmic membrane pore formation, cell wall interference (e.g., peptidoglycanase activity), or nuclease activity (e.g., DNase activity, 16S rRNase activity, or tRNase activity).

In some instances, the bacteriocin has a neutralizing activity. Neutralizing activity of bacteriocins may include, but is not limited to, arrest of microbial reproduction, or cytotoxicity. Some bacteriocins have cytotoxic activity, and thus can kill microbial organisms, for example bacteria, yeast, algae, and the like. Some bacteriocins can inhibit the reproduction of microbial organisms, for example bacteria, yeast, algae, and the like, for example by arresting the cell cycle.

In some instances, the bacteriocin has killing activity. The killing mechanism of bacteriocins is specific to each group of bacteriocins. In some instances, the bacteriocin has narrow-spectrum bioactivity. Bacteriocins are known for their very high potency against their target strains. Some bacteriocin activity is limited to strains that are closely related to the bacteriocin producer strain (narrow-spectrum bioactivity). In some instances, the bacteriocin has broad-spectrum bioactivity against a wide range of genera.

In some instances, bacteriocins interact with a receptor molecule or a docking molecule on the target bacterial cell membrane. For example, nisin is extremely potent against its target bacterial strains, showing antimicrobial activity even at a single-digit nanomolar concentration. The nisin molecule has been shown to bind to lipid II, which is the main transporter of peptidoglycan subunits from the cytoplasm to the cell wall In some instances, the bacteriocin has anti-fungal activity. A number of bacteriocins with anti-yeast or anti-fungal activity have been identified. For example, bacteriocins from *Bacillus* have been shown to have neutralizing activity against some yeast strains (see, for example, Adetunji and Olaoye, Malaysian Journal of Microbiology 9:130-13, 2013). In another example, an *Enterococcus faecalis* peptide has been shown to have neutralizing activity against *Candida* species (see, for example, Shekh and Roy, *BMC* Microbiology 12:132, 2012). In another example, bacteriocins from *Pseudomonas* have been shown to have neutralizing activity against fungi, such as Curvularia lunata, *Fusarium* species, *Helminthosporium* species, and Biopolaris species (see, for example, Shalani and Srivastava, The Internet Journal of Microbiology Volume 5 Number 2, 2008). In another example, botrycidin AJ1316 and alirin B1 from *B. subtilis* have been shown to have antifungal activities.

A modulating agent including a bacteriocin as described herein can be contacted with the target host in an amount and for a time sufficient to: (a) reach a target level (e.g., a predetermined or threshold level) of bacteriocin concentration inside a target host; (b) reach a target level (e.g., a predetermined or threshold level) of bacteriocin concentration inside a target host gut; (c) reach a target level (e.g., a predetermined or threshold level) of bacteriocin concentration inside a target host bacteriocyte; (d) modulate the level, or an activity, of one or more microorganism (e.g., endosymbiont) in the target host; or/and (e) modulate fitness of the target host.

As illustrated by Examples 8, 9, and 16, bacteriocins (e.g., colA or nisin) can be used as modulating agents that target an endosymbiotic bacterium in an insect host to decrease the fitness of the host (e.g., as outlined herein).

(b) Lysins

The modulating agent described herein may include a lysin (e.g., also known as a murein hydrolase or peptidoglycan autolysin). Any lysin suitable for inhibiting a bacterium resident in the host may be used. In some instances, the lysin is one that can be naturally produced by a bacterial cell. In some instances, the lysin is one that can be naturally produced by a bacteriophage. In some instances, the lysin is obtained from a phage that inhibits a bacterium resident in the host. In some instances, the lysin is engineered based on a naturally occurring lysin. In some instances, the lysin is engineered to be secreted by a host bacterium, for example, by introducing a signal peptide to the lysin. In some instances, the lysin is used in combination with a phage holin. In some instances, a lysin is expressed by a recombinant bacterium host that is not sensitive to the lysin. In some instances, the lysin is used to inhibit a Gram-positive or Gram-negative bacterium resident in the host.

The lysin may be any class of lysin and may have one or more substrate specificities. For example, the lysin may be a glycosidase, an endopeptidase, a carboxypeptidase, or a combination thereof. In some instances, the lysin cleaves the β-1-4 glycosidic bond in the sugar moiety of the cell wall, the amide bond connecting the sugar and peptide moieties of the bacterial cell wall, and/or the peptide bonds between the peptide moieties of the cell wall. The lysin may belong to one or more specific lysin groups, depending on the cleavage site within the peptidoglycan. In some instances, the lysin is a N-acetyl-β-D-muramidase (e.g., lysozyme), lytic transglycosylase, N-acetyl-β-D-glucosaminidase, N-acetylmuramyl-L-alanine amidase, L,D-endopeptidase, D,D-endopeptidase, D,D-carboxypeptidase, L,D-carboxypeptidase, or L,D-transpeptidase. Non-limiting examples of lysins and their activities are listed in Table 5.

TABLE 5

Examples of Lysins

| Target Bacteria | Producer | Lysins | Activity | Sequence |
|---|---|---|---|---|
| *S. pneumoniae* | Cp1 | Cpl-1 | Muramidase | MVKKNDLFVDVS<br>SHNGYDITGILEQ<br>MGTTNTIIKISEST<br>TYLNPCLSAQVEQ<br>SNPIGFYHFARFG<br>GDVAEAEREAQF<br>FLDNVPMQVKYLV<br>LDYEDDPSGDAQ<br>ANTNACLRFMQMI<br>ADAGYKPIYYSYK<br>PFTHDNVDYQQIL<br>AQFPNSLWIAGYG<br>LNDGTANFEYFPS<br>MDGIRWWQYSSN<br>PFDKNIVLLDDEE<br>DDKPKTAGTWKQ<br>DSKGWWFRRNN<br>GSFPYNKWEKIG<br>GVWYYFDSKGYC<br>LTSEWLKDNEKW |

TABLE 5-continued

| Examples of Lysins | | | | |
|---|---|---|---|---|
| Target Bacteria | Producer | Lysins | Activity | Sequence |
| | | | | YYLKDNGAMATG WVLVGSEWYYMD DSGAMVTGWVKY KNNWYYMTNERG NMVSNEFIKSGKG WYFMNTNGELAD NPSFTKEPDGLIT VA (SEQ ID NO: 50) |
| *S. pneumoniae* | Dp-1 | Pal | Amidase | MGVDIEKGVAWM QARKGRVSYSMD FRDGPDSYDCSS SMYYALRSAGAS SAGWAVNTEYMH AWLIENGYELISE NAPWDAKRGDIFI WGRKGASAGAG GHTGMFIDSDNIIH CNYAYDGISVNDH DERWYYAGQPYY YVYRLTNANAQPA EKKLGWQKDATG FWYARANGTYPK DEFEYIEENKSWF YFDDQGYMLAEK WLKHTDGNWYW FDRDGYMATSWK RIGESWYYFNRD GSMVTGWIKYYD NWYYCDATNGDM KSNAFIRYNDGW YLLLPDGRLADKP QFTVEPDGLITAKV (SEQ ID NO: 51) |
| *S. pyogenes* | C1 | C1 | Amidase | N/A |
| *B. anthracis* | γ | PlyG | Amidase | MEIQKKLVDPSKY GTKCPYTMKPKYI TVHNTYNDAPAE NEVSYMISNNNEV SFHIAVDDKKAIQ GIPLERNAWACG DGNGSGNRQSIS VEICYSKSGGDRY YKAEDNAVDVVR QLMSMYNIPIENV RTHQSWSGKYCP HRMLAEGRWGAF IQKVKNGNVATTS PTKQNIIQSGAFS PYETPDVMGALTS LKMTADFILQSDG LTYFISKPTSDAQL KAMKEYLDRKGW WYEVK (SEQ ID NO: 52) |
| *B. anthracis* | Ames prophage | PlyPH | Amidase | N/A |
| *E. faecalis* and *E. faecium* | Phi1 | PlyV12 | Amidase | N/A |
| *S. aureus* | ΦMR11 | MV-L | Endopeptidase and amidase | MQAKLTKKEFIEW LKTSEGKQFNVDL WYGFQCFDYANA GWKVLFGLLLKGL GAKDIPFANNFDG LATVYQNTPDFLA QPGDMVVFGSNY GAGYGHVAWVIE ATLDYIIVYEQNWL GGGWTDRIEQPG WGWEKVTRRQH |

TABLE 5-continued

| Examples of Lysins | | | | |
|---|---|---|---|---|
| Target Bacteria | Producer | Lysins | Activity | Sequence |
| | | | | AYDFPMWFIRPNF KSETAPRSIQSPT QASKKETAKPQP KAVELKIIKDVVKG YDLPKRGGNPKGI VIHNDAGSKGATA EAYRNGLVNAPLS RLEAGIAHSYVSG NTVWQALDESQV GWHTANQLGNKY YYGIEVCQSMGA DNATFLKNEQATF QECARLLKKWGL PANRNTIRLHNEF TSTSCPHRSSVLH TGFDPVTRGLLPE DKQLQLKDYFIKQI RVYMDGKIPVATV SNESSASSNTVKP VASAWKRNKYGT YYMEENARFTNG NQPITVRKIGPFLS CPVAYQFQPGGY CDYTEVMLQDGH VWVGYTWEGQR YYLPIRTWNGSAP PNQILGDLWGEIS (SEQ ID NO: 53) |
| *S. pyogenes* | C1 | PlyC | Amidase | N/A |
| *S. agalactiae* | B30 | GBS lysin | Muramidase and endopeptidase | MVINIEQAIAWMA SRKGKVTYSMDY RNGPSSYDCSSS VYFALRSAGASDN GWAVNTEYEHDW LIKNGYVLIAENTN WNAQRGDIFIWG KRGASAGAFGHT GMFVDPDNIIHCN YGYNSITVNNHDE IWGYNGQPYVYA YRYSGKQSNAKV DNKSVVSKFEKEL DVNTPLSNSNMP YYEATISEDYYVE SKPDVNSTDKELL VAGTRVRVYEKV KGWARIGAPQSN QWVEDAYLIDATDM (SEQ ID NO: 54) |
| *S. aureus* | P68 | Lys16 | Endopeptidase | N/A |
| *S. aureus* | K | LysK | Amidase and endopeptidase | MAKTQAEINKRLD AYAKGTVDSPYR VKKATSYDPSFGV MEAGAIDADGYY HAQCQDLITDYVL WLTDNKVRTWGN AKDQIKQSYGTGF KIHENKPSTVPKK GWIAVFTSGSYEQ WGHIGIVYDGGNT STFTILEQNWNGY ANKKPTKRVDNY YGLTHFIEIPVKAG TTVKKETAKKSAS KTPAPKKKATLKV SKNHINYTMDKRG KKPEGMVIHNDA GRSSGQQYENSL ANAGYARYANGIA HYYGSEGYVWEA IDAKNQIAWHTGD GTGANSGNFRFA |

TABLE 5-continued

| Examples of Lysins | | | | |
|---|---|---|---|---|
| Target Bacteria | Producer | Lysins | Activity | Sequence |
| | | | | GIEVCQSMSASDA QFLKNEQAVFQFT AEKFKEWGLTPN RKTVRLHMEFVPT ACPHRSMVLHTG FNPVTQGRPSQAI MNKLKDYFIKQIK NYMDKGTSSSTV VKDGKTSSASTPA TRPVTGSWKKNQ YGTWYKPENATF VNGNQPIVTRIGS PFLNAPVGGNLPA GATIVYDEVCIQA GHIWIGYNAYNGN RVYCPVRTCQGV PPNQIPGVAWGV FK (SEQ ID NO: 55) |
| *L. monocytogenes* | A118 | Ply118 | Amidase | MTSYYYSRSLANV NKLADNTKAAARK LLDWSESNGIEVLI YETIRTKEQQAAN VNSGASQTMRSY HLVGQALDFVMA KGKTVDWGAYRS DKGKKFVAKAKSL GFEWGGDWSGF VDNPHLQFNYKG YGTDTFGKGAST SNSSKPSADTNTN SLGLVDYMNLNKL DSSFANRKKLATS YGIKNYSGTATQN TTLLAKLKAGKPH TPASKNTYYTENP RKVKTLVQCDLYK SVDFTTKNQTGG TFPPGTVFTISGM GKTKGGTPRLKTK SGYYLTANTKFVK KI (SEQ ID NO: 56) |
| *L. monocytogenes* | A511 | Ply511 | Amidase | MVKYTVENKIIAGL PKGKLKGANFVIA HETANSKSTIDNE VSYMTRNWKNAF VTHFVGGGGRVV QVANVNYVSWGA GQYANSYSYAQV ELCRTSNATTFKK DYEVYCQLLVDLA KKAGIPITLDSGSK TSDKGIKSHKWVA DKLGGTTHQDPY AYLSSWGISKAQF ASDLAKVSGGGN TGTAPAKPSTPAP KPSTPSTNLDKLG LVDYMNAKKMDS SYSNRDKLAKQY GIANYSGTASQNT TLLSKIKGGAPKP STPAPKPSTSTAK KIYFPPNKGNWSV YPTNKAPVKANAI GAINPTKFGGLTY TIQKDRGNGVYEI QTDQFGRVQVYG APSTGAVIKK (SEQ ID NO: 57) |

TABLE 5-continued

| Examples of Lysins | | | | |
|---|---|---|---|---|
| Target Bacteria | Producer | Lysins | Activity | Sequence |
| *L. monocytogenes* | A500 | Ply500 | Endopeptidase | MALTEAWLIEKAN RKLNAGGMYKITS DKTRNVIKKMAKE GIYLCVAQGYRST AEQNALYAQGRT KPGAIVTNAKGGQ SNHNYGVAVDLC LYTNDGKDVIWES TTSRWKKVVAAM KAEGFKWGGDW KSFKDYPHFELCD AVSGEKIPAATQN TNTNSNRYEGKVI DSAPLLPKMDFKS SPFRMYKVGTEFL VYDHNQYWYKTYI DDKLYYMYKSFC DVVAKKDAKGRIK VRIKSAKDLRIPV WNNIKLNSGKIKW YAPNVKLAWYNY RRGYLELWYPND GWYYTAEYFLK (SEQ ID NO: 58) |
| *S. pneumoniae* | ΦDp-1 | Pal, S | Endopeptidase and amidase | N/A |
| *S. agalactiae* | LambdaSa1 prophage | LambdaSa1 | Glycosidase | MVINIEQAIAWMA SRKGKVTYSMDY RNGPSSYDCSSS VYFALRSAGASDN GWAVNTEYEHDW LIKNGYVLIAENTN WNAQRGDIFIWG KRGASAGAFGHT GMFVDPDNIIHCN YGYNSITVNNHDE IWGYNGQPYVYA YRYARKQSNAKV DNQSVVSKFEKEL DVNTPLSNSNMP YYEATISEDYYVE SKPDVNSTDKELL VAGTRVRVYEKV KGWARIGAPQSN QWVEDAYLIDATDM (SEQ ID NO: 59) |
| *S. agalactiae* | LambdaSa2 prophage | LambdaSa2 | Glycosidase and endopeptidase | MEINTEIAIAWMSA RQGKVSYSMDYR DGPNSYDCSSSV YYALRSAGASSA GWAVNTEYMHD WLIKNGYELIAEN VDWNAVRGDIAIW GMRGHSSGAGG HVVMFIDPENIIHC NWANNGITVNNY NQTAAASGWMYC YVYRLKSGASTQ GKSLDTLVKETLA GNYGNGEARKAV LGNQYEAVMSVIN GKTTTNQKTVDQL VQEVIAGKHGNG EARKKSLGSQYD AVQKRVTELLKKQ PSEPFKAQEVNKP TETKTSQTELTGQ ATATKEEGDLSFN GTILKKAVLDKILG NCKKHDILPSYAL TILHYEGLWGTSA VGKADNNWGGM TWTGQGNRPSGV |

TABLE 5-continued

| Examples of Lysins | | | | |
|---|---|---|---|---|
| Target Bacteria | Producer | Lysins | Activity | Sequence |
| | | | | TVTQGSARPSNE GGHYMHYASVDD FLTDWFYLLRAGG SYKVSGAKTFSEA IKGMFKVGGAVYD YAASGFDSYIVGA SSRLKAIEAENGS LDKFDKATDIGDG SKDKIDITIEGIEVT INGITYELTKKPV (SEQ ID NO: 60) |
| *S. uberis* | (ATCC700407) prophage | Ply700 | Amidase | MTDSIQEMRKLQS IPVRYDMGDRYG NDADRDGRIEMD CSSAVSKALGISM TNNTETLQQALPA IGYGKIHDAVDGT FDMQAYDVIIWAP RDGSSSLGAFGH VLIATSPTTAIHCN YGSDGITENDYNY IWEINGRPREIVFR KGVTQTQATVTS QFERELDVNARLT VSDKPYYEATLSE DYYVEAGPRIDSQ DKELIKAGTRVRV YEKLNGWSRINHP ESAQWVEDSYLV DATEM (SEQ ID NO: 61) |
| *S. suis* | SMP | LySMP | Glycosidase and endopeptidase | N/A |
| *B. anthracis* | Bcp1 | PlyB | Muramidase | N/A |
| *S. aureus* | Phi11 and Phi12 | Phi11 lysin | Amidase and endopeptidase | MQAKLTKNEFIEW LKTSEGKQFNVDL WYGFQCFDYANA GWKVLFGLLLKGL GAKDIPFANNFDG LATVYQNTPDFLA QPGDMVVFGSNY GAGYGHVAWVIE ATLDYIIVYEQNWL GGGWTDGIEQPG WGWEKVTRRQH AYDFPMWFIRPNF KSETAPRSVQSPT QAPKKETAKPQP KAVELKIIKDVVKG YDLPKRGSNPKGI VIHNDAGSKGATA EAYRNGLVNAPLS RLEAGIAHSYVSG NTVWQALDESQV GWHTANQIGNKY YYGIEVCQSMGA DNATFLKNEQATF QECARLLKKWGL PANRNTIRLHNEF TSTSCPHRSSVLH TGFDPVTRGLLPE DKRLQLKDYFIKQI RAYMDGKIPVATV SNESSASSNTVKP VASAWKRNKYGT YYMEESARFTNG NQPITVRKVGPFL |

TABLE 5-continued

Examples of Lysins

| Target Bacteria | Producer | Lysins | Activity | Sequence |
| --- | --- | --- | --- | --- |
| | | | | SCPVGYQFQPGG YCDYTEVMLQDG HVWVGYTWEGQ RYYLPIRTWNGSA PPNQILGDLWGEIS (SEQ ID NO: 62) |
| *S. aureus* | ΦH5 | LysH5 | Amidase and endopeptidase | MQAKLTKKEFIEW LKTSEGKQYNAD GWYGFQCFDYAN AGWKALFGLLLKG VGAKDIPFANNFD GLATVYQNTPDFL AQPGDMVVFGSN YGAGYGHVAWVI EATLDYIIVYEQN WLGGGWTDGVQ QPGSGWEKVTRR QHAYDFPMWFIR PNFKSETAPRSVQ SPTQASKKETAKP QPKAVELKIIKDVV KGYDLPKRGSNP NFIVIHNDAGSKG ATAEAYRNGLVNA PLSRLEAGIAHSY VSGNTVWQALDE SQVGWHTANQIG NKYGYGIEVCQS MGADNATFLKNE QATFQECARLLKK WGLPANRNTIRLH NEFTSTSCPHRSS VLHTGFDPVTRGL LPEDKRLQLKDYF IKQIRAYMDGKIPV ATVSNDSSASSNT VKPVASAWKRNK YGTYYMEESARF TNGNQPITVRKVG PFLSCPVGYQFQ PGGYCDYTEVML QDGHVWVGYTW EGQRYYLPIRTWN GSAPPNQILGDLW GEIS (SEQ ID NO: 63) |
| *S. warneri* | ΦWMY | LysWMY | Amidase and endopeptidase | MKTKAQAKSWIN SKIGKGIDWDGMY GYQCMDEAVDYI HHVTDGKVTMWG NAIDAPKNNFQGL CTVYTNTPEFRPA YGDVIVWSYGTFA TYGHIAIVVNPDPY GDLQYITVLEQNW NGNGIYKTEFATIR THDYTGVSHFIRP KFADEVKETAKTV NKLSVQKKIVTPK NSVERIKNYVKTS GYINGEHYELYNR GHKPKGVVIHNTA GTASATQEGQRL TNMTFQQLANGV AHVYIDKNTIYETL PEDRIAWHVAQQ YGNTEFYGIEVCG SRNTDKEQFLANE QVAFQEAARRLK SWGMRANRNTVR LHHTFSSTECPDM SMLLHTGYSMKN GKPTQDITNKCAD YFMKQINAYIDGK |

TABLE 5-continued

Examples of Lysins

| Target Bacteria | Producer | Lysins | Activity | Sequence |
|---|---|---|---|---|
| | | | | QPTSTVVGSSSS NKLKAKNKDKSTG WNTNEYGTLWKK EHATFTCGVRQGI VTRTTGPFTSCPQ AGVLYYGQSVNY DTVCKQDGYVWI SWTTSDGYDVW MPIRTWDRSTDK VSEIWGTIS (SEQ ID NO: 64) |
| *Streptococci* (GBS) | ΦNCTC 11261 | PlyGBS | Muramidase and endopeptidase | MATYQEYKSRSN GNAYDIDGSFGA QCWDGYADYCKY LGLPYANCTNTGY ARDIWEQRHENGI LNYFDEVEVMQA GDVAIFMVVDGVT PYSHVAIFDSDAG GGYGWFLGQNQ GGANGAYNIVKIP YSATYPTAFRPKV FKNAVTVTGNIGL NKGDYFIDVSAYQ QADLTTTCQQAG TTKTIIKVSESIAW LSDRHQQQANTS DPIGYYHFGRFGG DSALAQREADLFL SNLPSKKVSYLVI DYEDSASADKQA NTNAVIAFMDKIAS AGYKPIYYSYKPF TLNNIDYQKIIAKY PNSIWIAGYPDYE VRTEPLWEFFPS MDGVRWWQFTS VGVAGGLDKNIVL LADDSSKMDIPKV DKPQELTFYQKLA TNTKLDNSNVPYY EATLSTDYYVESK PNASSADKEFIKA GTRVRVYEKVNG WSRINHPESAQW VEDSYLVNATDM (SEQ ID NO: 65) |
| *C. perfringens* | Φ3626 | Ply3626 | Amidase | N/A |
| *C. difficile* | ΦCD27 | CD27 lysin | Amidase | N/A |
| *E. faecalis* | Φ1 | PlyV12 | Amidase | N/A |
| *A. naeslundii* | ΦAV-1- | Av-1 lysin | Putative amidase/muramidase | N/A |
| *L. gasseri* | ΦgaY | LysgaY | Muramidase | N/A |
| *S. aureus* | ΦSA4 | LysSA4 | Amidase and endopeptidase | N/A |
| *S. haemolyticus* | ΦSH2 | SH2 | Amidase and endopeptidase | N/A |
| *B. thuringiensis* | ΦBtCS33 | PlyBt33 | Amidase | N/A |
| *L. monocytogenes* | ΦP40 | PlyP40 | Amidase | N/A |
| *L. monocytogenes* | ΦFWLLm3 | LysZ5 | Amidase | MVKYTVENKIIAGL PKGKLKGANFVIA HETANSKSTIDNE VSYMTRNWQNAF VTHFVGGGGRVV |

TABLE 5-continued

| Examples of Lysins | | | | |
|---|---|---|---|---|
| Target Bacteria | Producer | Lysins | Activity | Sequence |
| | | | | QVANVNYVSWGA GQYANSYSYAQV ELCRTSNATTFKK DYEVYCQLLVDLA KKAGIPITLDSGSK TSDKGIKSHKWVA DKLGGTTHQDPY AYLSSWGISKAQF ASDLAKVSGGGN TGTAPAKPSTPST NLDKLGLVDYMN AKKMDSSYSNRA KLAKQYGIANYSG TASQNTTLLSKIK GGAPKPSTPAPK PSTSTAKKIYFPP NKGNWSVYPTNK APVKANAIGAINPT KFGGLTYTIQKDR GNGVYEIQTDQF GRVQVYGAPSTG AVIKK (SEQ ID NO: 66) |
| *B. cereus* | ΦBPS13 | LysBPS13 | Amidase | MAKREKYIFDVEA EVGKAAKSIKSLE AELSKLQKLNKEI DATGGDRTEKEM LATLKAAKEVNAE YQKMQRILKDLSK YSGKVSRKEFND SKVINNAKTSVQG GKVTDSFGQMLK NMERQINSVNKQ FDNHRKAMVDRG QQYTPHLKTNRK DSQGNSNPSMM GRNKSTTQDMEK AVDKFLNGQNEA TTGLNQALYQLKE ISKLNRRSESLSR RASASGYMSFQQ YSNFTGDRRTVQ QTYGGLKTANRE RVLELSGQATGIS KELDRLNSKKGLT AREGEERKKLMR QLEGIDAELTARK KLNSSLDETTSNM EKFNQSLVDAQV SVKPERGTMRGM MYERAPAIALAIG GAITATIGKLYSEG GNHSKAMRPDEM YVGQQTGAVGAN WRPNRTATMRSG LGNHLGFTGQEM MEFQSNYLSANG YHGAEDMKAATT GQATFARATGLG SDEVKDFFNTAYR SGGIDGNQTKQF QNAFLGAMKQSG AVGREKDQLKAL NGILSSMSQNRTV SNQDMMRTVGLQ SAISSSGVASLQG TKGGALMEQLDN GIREGFNDPQMR VLFGQGTKYQGM GGRAALRKQMEK GISDPDNLNTLIDA SKASAGQDPAEQ AEVLATLASKMGV NMSSDQARGLIDL QPSGKLTKENIDK |

TABLE 5-continued

| Examples of Lysins | | | | |
|---|---|---|---|---|
| Target Bacteria | Producer | Lysins | Activity | Sequence |
| | | | | VMKEGLKEGSIES AKRDKAYSESKAS IDNSSEAATAKQA TELNDMGSKLRQ ANAALGGLPAPLY TAIAAVVAFTAAVA GSALMFKGASWL KGGMASKYGGKG GKGGKGGGTGG GGGAGGAAATGA GAAAGAGGVGAA AAGEVGAGVAAG GAAAGAAAGGSK LAGVGKGFMKGA GKLMLPLGILMGA SEIMQAPEEAKGS AIGSAVGGIGGGI AGGAATGAIAGSF LGPIGTAVGGIAG GIAGGFAGSSLGE TIGGWFDSGPKE DASAADKAKADA SAAALAAAAGTSG AVGSSALQSQMA QGITGAPNMSQV GSMASALGISSGA MASALGISSGQEN QIQTMTDKENTNT KKANEAKKGDNL SYERENISMYERV LTRAEQILAQARA QNGIMGVGGGGT AGAGGGINGFTG GGKLQFLAAGQK WSSSNLQQHDLG FTDQNLTAEDLDK WIDSKAPQGSMM RGMGATFLKAGQ EYGLDPRYLIAHA AEESGWGTSKIAR DKGNFFGIGAFDD SPYSSAYEFKDGT GSAAERGIMGGA KWISEKYYGKGNT TLDKMKAAGYAT NASWAPNIASIMA GAPTGSGSGNVT ATINVNVKGDEKV SDKLKNSSDMKK AGKDIGSLLGFYS REMTIA (SEQ ID NO: 67) |
| *S. aureus* | ΦGH15 | LysGH15 | Amidase and endopeptidase | MAKTQAEINKRLD AYAKGTVDSPYRI KKATSYDPSFGV MEAGAIDADGYY HAQCQDLITDYVL WLTDNKVRTWGN AKDQIKQSYGTGF KIHENKPSTVPKK GWIAVFTSGSYQ QWGHIGIVYDGG NTSTFTILEQNWN GYANKKPTKRVD NYYGLTHFIEIPVK AGTTVKKETAKKS ASKTPAPKKKATL KVSKNHINYTMDK RGKKPEGMVIHN DAGRSSGQQYEN SLANAGYARYAN GIAHYYGSEGYV WEAIDAKNQIAWH TGDGTGANSGNF RFAGIEVCQSMSA |

TABLE 5-continued

Examples of Lysins

| Target Bacteria | Producer | Lysins | Activity | Sequence |
|---|---|---|---|---|
| | | | | SDAQFLKNEQAVF<br>QFTAEKFKEWGL<br>TPNRKTVRLHMEF<br>VPTACPHRSMVL<br>HTGFNPVTQGRP<br>SQAIMNKLKDYFIK<br>QIKNYMDKGTSSS<br>TVVKDGKTSSAST<br>PATRPVTGSWKK<br>NQYGTWYKPENA<br>TFVNGNQPIVTRI<br>GSPFLNAPVGGN<br>LPAGATIVYDEVCI<br>QAGHIWIGYNAYN<br>GDRVYCPVRTCQ<br>GVPPNHIPGVAW<br>GVFK<br>(SEQ ID NO: 68) |
| *S. aureus* | ΦvB SauS-PLA88 | HydH5 | Endopeptidase and glycosidase | N/A |
| *E. faecalis* | ΦF168/08 | Lys168 | Endopeptidase | N/A |
| *E. faecalis* | ΦF170/08 | Lys170 | Amidase | N/A |
| *S. aureus* | ΦP-27/HP | P-27/HP | Nonspecified | N/A |
| *C. perfringens* | ΦSM101 | Psm | Muramidase | N/A |
| *C. sporogenes* | Φ8074-B1 | CS74L | Amidase | MKIGIDMGHTLSG<br>ADYGVVGLRPES<br>VLTREVGTKVIYKL<br>QKLGHVVVNCTV<br>DKASSVSESLYTR<br>YYRANQANVDLFI<br>SIHFNATPGGTGT<br>EVYTYAGRQLGE<br>ATRIRQEFKSLGL<br>RDRGTKDGSGLA<br>VIRNTKAKAMLVE<br>CCFCDNPNDMKL<br>YNSESFSNAIVKGI<br>TGKLPNGESGNN<br>NQGGNKVKAVVIY<br>NEGADRRGAEYL<br>ADYLNCPTISNSR<br>TFDYSCVEHVYAV<br>GGKKEQYTKYLKT<br>LLSGANRYDTMQ<br>QILNFINGGK<br>(SEQ ID NO: 69) |
| *S. typhimurium* | ΦSPN1S | SPN1S | Glycosidase | MDINQFRRASGIN<br>EQLAARWFPHITT<br>AMNEFGITKPDDQ<br>AMFIAQVGHESG<br>GFTRLQENFNYSV<br>NGLSGFIRAGRIT<br>PDQANALGRKTY<br>EKSLPLERQRAIA<br>NLVYSKRMGNNG<br>PGDGWNYRGRG<br>LIQITGLNNYRDC<br>GNGLKVDLVAQP<br>ELLAQDEYAARSA<br>AWFFSSKGCMKY<br>TGDLVRVTQIING<br>GQNGIDDRRTRY<br>AAARKVLAL<br>(SEQ ID NO: 70) |
| *C. michiganensis* | ΦCMP1 | CMP1 | Peptidase | N/A |

TABLE 5-continued

Examples of Lysins

| Target Bacteria | Producer | Lysins | Activity | Sequence |
|---|---|---|---|---|
| *C. michiganensis* | ΦCN77 | CN77 | Peptidase | MGYWGYPNGQIP NDKMALYRGCLL RADAAAQAYALQ DAYTRATGKPLVI LEGYRDLTRQKYL RNLYLSGRGNIAA VPGLSNHGWGLA CDFAAPLNSSGSE EHRWMRQNAPLF GFDWARGKADNE PWHWEYGNVPVS RWASLDVTPIDRN DMADITEGQMQRI AVILLDTEIQTPLG PRLVKHALGDALL LGQANANSIAEVP DKTWDVLVDHPL AKNEDGTPLKVRL GDVAKYEPLEHQ NTRDAIAKLGTLQ FTDKQLATIGAGV KPIDEASLVKKIVD GVRALFGRAAA (SEQ ID NO: 71) |
| *A. baumannii* | ΦAB2 | LysAB2 | Glycosidase | MILTKDGFSIIRNE LFGGKLDQTQVD AINFIVAKATESGL TYPEAAYLLATIYH ETGLPSGYRTMQ PIKEAGSDSYLRS KKYYPYIGYGYVQ LTWKENYERIGKLI GVDLIKNPEKALE PLIAIQIAIKGMLNG WFTGVGFRRKRP VSKYNKQQYVAA RNIINGKDKAELIA KYAIIFERALRSL (SEQ ID NO: 72) |
| *B. cereus* | ΦB4 | LysB4 | Endopeptidase | MAMALQTLIDKAN RKLNVSGMRKDV ADRTRAVITQMHA QGIYICVAQGFRS FAEQNALYAQGR TKPGSIVTNARGG QSNHNYGVAVDL CLYTQDGSDVIWT VEGNFRKVIAAMK AQGFKWGGDWV SFKDYPHFELYDV VGGQKPPADNGG AVDNGGGSGSTG GSGGGSTGGGST GGGYDSSWFTKE TGTFVTNTSIKLRT APFTSADVIATLPA GSPVNYNGFGIEY DGYVWIRQPRSN GYGYLATGESKG GKRQNYWGTFK (SEQ ID NO: 73) |
| *P. aeruginosa* | ΦKMV | KMV45 | Nonspecified | N/A |
| *C. tyrobutyricum* | ΦCTP1 | Ctp1I | Glycosidase | MKKIADISNLNGN VDVKLLFNLGYIGII AKASEGGTFVDK YYKQNYTNTKAQ GKITGAYHFANFS TIAKAQQEANFFL NCIAGTTPDFVVL DLEQQCTGDITDA CLAFLNIVAKKFKC VVYCNSSFIKEHL |

TABLE 5-continued

| Examples of Lysins | | | | |
|---|---|---|---|---|
| Target Bacteria | Producer | Lysins | Activity | Sequence |
| | | | | NSKICAYPLWIAN YGVATPAFTLWTK YAMWQFTEKGQV SGISGYIDFSYITD EFIKYIKGEDEVEN LVVYNDGADQRA AEYLADRLACPTI NNARKFDYSNVK NVYAVGGNKEQY TSYLTTLIAGSTRY TTMQAVLDYIKNLK (SEQ ID NO: 74) |
| *P. aeruginosa* | ΦEL | EL188 | Transglycosylase | N/A |
| *P. aeruginosa* | ΦKZ | KZ144 | Transglycosylase | N/A |
| *S. aureus* | | Ply187 | Cell Wall Hydrolase | MALPKTGKPTAK QVVDWAINLIGSG VDVDGYYGRQC WDLPNYIFNRYW NFKTPGNARDMA WYRYPEGFKVFR NTSDFVPKPGDIA VWTGGNYNWNT WGHTGIVVGPST KSYFYSVDQNWN NSNSYVGSPAAKI KHSYFGVTHFVRP AYKAEPKPTPPAQ NNPAPKDPEPSK KPESNKPIYKVVT KILFTTAHIEHVKA NRFVHYITKSDNH NNKPNKIVIKNTNT ALSTIDVYRYRDE LDKDEIPHFFVDR LNVWACRPIEDSI NGYHDSVVLSITE TRTALSDNFKMNE IECLSLAESILKAN NKKMSASNIIVDN KAWRTFKLHTGK DSLKSSSFTSKDY QKAVNELIKLEND KDKLLNNKPKDVV ERIRIRTIVKENTK FVPSELKPRNNIR DKQDSKIDRVINN YTLKQALNIQYKL NPKPQTSNGVSW YNASVNQIKSAMD TTKIFNNNVQVYQ FLKLNQYQGIPVD KLNKLLVGKGTLA NQGHAFADGCKK YNINEIYLIAHRFLE SANGTSFFASGKT GVYNYFGIGAFDN NPNNAMAFARSH GWTSPTKAIIGGA EFVGKGYFNVGQ NTLYRMRWNPQK PGTHQYATDISWA KVQAQMISAMYK EIGLTGDYFIYDQY KK (SEQ ID NO: 75) |
| *P. uorescens* | ΦOBP | OBPgp279 | Glycosidase | N/A |
| *L. monocytogenes* | ΦP35 | PlyP35 | Amidase | MARKFTKAELVAK AEKKVGGLKPDV KKAVLSAVKEAYD RYGIGIIVSQGYRS IAEQNGLYAQGRT |

TABLE 5-continued

| Examples of Lysins | | | | |
|---|---|---|---|---|
| Target Bacteria | Producer | Lysins | Activity | Sequence |
| | | | | KPGNIVTNAKGGQ SNHNFGVAVDFAI DLIDDGKIDSWQP SATIVNMMKRRGF KWGGDWKSFTDL PHFEACDWYRGE RKYKVDTSEWKK KENINIVIKDVGYF QDKPQFLNSKSV RQWKHGTKVKLT KHNSHWYTGVVK DGNKSVRGYIYHS MAKVTSKNSDGS VNATINAHAFCWD NKKLNGGDFINLK RGFKGITHPASDG FYPLYFASRKKTF YIPRYMFDIKK (SEQ ID NO: 76) |
| *L. fermentum* | ΦPYB5 | Lyb5 | Muramidase | N/A |
| *S. pneumoniae* | ΦCP-7 | Cpl-7 | Muramidase | MVKKNDLFVDVA SHQGYDISGILEE AGTTNTIIKVSEST SYLNPCLSAQVSQ SNPIGFYHFAWFG GNEEEAEAEARY FLDNVPTQVKYLV LDYEDHASASVQ RNTTACLRFMQIIA EAGYTPIYYSYKP FTLDNVDYQQILA QFPNSLWIAGYGL NDGTANFEYFPS MDGIRWWQYSSN PFDKNIVLLDDEK EDNINNENTLKSL TTVANEVIQGLWG NGQERYDSLANA GYDPQAVQDKVN EILNAREIADLTTV ANEVIQGLWGNG QERYDSLANAGY DPQAVQDKVNEIL NAREIADLTTVAN EVIQGLWGNGQE RYDSLANAGYDP QAVQDKVNELLS (SEQ ID NO: 77) |
| *P. chlororaphis*201 | Φ2-1 | 201φ2-1gp229 | Glycosidase | N/A |
| *S. enterica* | ΦPVP-SE1) | PVP-SE1gp146 | Glycosidase | N/A |
| *Corynebacterium* | ΦBFK20 | BKF20 | Amidase | N/A |
| E. *faecalis* | ΦEFAP-1 | EFAL-1 | Amidase | MKLKGILLSVVTTF GLLFGATNVQAYE VNNEFNLQPWEG SQQLAYPNKIILHE TANPRATGRNEA TYMKNNWFNAHT TAIVGDGGIVYKV APEGNVSWGAGN ANPYAPVQIELQH TNDPELFKANYKA |

TABLE 5-continued

| Examples of Lysins | | | | |
|---|---|---|---|---|
| Target Bacteria | Producer | Lysins | Activity | Sequence |
| | | | | YVDYTRDMGKKF GIPMTLDQGGSL WEKGVVSHQWVT DFVWGDHTDPYG YLAKMGISKAQLA HDLANGVSGNTA TPTPKPDKPKPTQ PSKPSNKKRFNY RVDGLEYVNGMW QIYNEHLGKIDFN WTENGIPVEVVDK VNPATGQPTKDQ VLKVGDYFNFQE NSTGVVQEQTPY MGYTLSHVQLPN EFIWLFTDSKQAL MYQ (SEQ ID NO: 78) |
| *Lactobacilli* | lamdaSA2 | LysA, LysA2, and Lysga Y | Nonspecified | N/A |
| *S. aureus* | | SAL-1 | Nonspecified | N/A |

In some instances, the lysin is a functionally active variant of the lysins described herein. In some instances, the variant of the lysin has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a lysin described herein or a naturally occurring lysin.

In some instances, the lysin may be bioengineered to modulate its bioactivity, e.g., increase or decrease or regulate, or to specify a target microorganism. In some instances, the lysin is produced by the translational machinery (e.g. a ribosome, etc.) of a microbial cell. In some instances, the lysin is chemically synthesized. In some instances, the lysin is derived from a polypeptide precursor. The polypeptide precursor can undergo cleavage (for example, processing by a protease) to yield the polypeptide of the lysin itself. As such, in some instances, the lysin is produced from a precursor polypeptide. In some instances, the lysin includes a polypeptide that has undergone post-translational modifications, for example, cleavage, or the addition of one or more functional groups.

The lysins described herein may be formulated in a composition for any of the uses described herein. The compositions disclosed herein may include any number or type (e.g., classes) of lysins, such as at least about any one of 1 lysin, 2, 3, 4, 5, 10, 15, 20, or more lysins. A suitable concentration of each lysin in the composition depends on factors such as efficacy, stability of the lysin, number of distinct lysin, the formulation, and methods of application of the composition. In some instances, each lysin in a liquid composition is from about 0.1 ng/mL to about 100 mg/mL. In some instances, each lysin in a solid composition is from about 0.1 ng/g to about 100 mg/g. In some instances, wherein the composition includes at least two types of lysins, the concentration of each type of lysin may be the same or different.

A modulating agent including a lysin as described herein can be contacted with the target host in an amount and for a time sufficient to: (a) reach a target level (e.g., a predetermined or threshold level) of lysin concentration inside a target host; (b) reach a target level (e.g., a predetermined or threshold level) of lysin concentration inside a target host gut; (c) reach a target level (e.g., a predetermined or threshold level) of lysin concentration inside a target host bacteriocyte; (d) modulate the level, or an activity, of one or more microorganism (e.g., endosymbiont) in the target host; or/and (e) modulate fitness of the target host.

(c) Antimicrobial Peptides

The modulating agent described herein may include an antimicrobial peptide (AMP). Any AMP suitable for inhibiting a microorganism resident in the host may be used. AMPs are a diverse group of molecules, which are divided into subgroups on the basis of their amino acid composition and structure. The AMP may be derived or produced from any organism that naturally produces AMPs, including AMPs derived from plants (e.g., copsin), insects (e.g., drosocin, scorpion peptide (e.g., Uy192, UyCT3, D3, D10, Uy17, Uy192), mastoparan, poneratoxin, cecropin, moricin, melittin), frogs (e.g., magainin, dermaseptin, aurein), and mammals (e.g., cathelicidins, defensins and protegrins). For example, the AMP may be a scorpion peptide, such as Uy192 (5'-FLSTIWNGIKGLL-3'; SEQ ID NO: 246), UyCT3 (5'-LSAIWSGIKSLF-3; SEQ ID NO: 228), D3 (5'-LWGKLWEGVKSLI-3'; SEQ ID NO: 229), and D10 (5'-FPFLKLSLKIPKSAIKSAIKRL-3'; SEQ ID NO: 230), Uy17 (5'-ILSAIWSGIKGLL-3'; SEQ ID NO: 231), or a combination thereof. In some instances, the antimicrobial peptide may be one having at least 90% sequence identity (e.g., at least 90%, 92%, 94%, 96%, 98%, or 100% sequence identity) with one or more of the following: cecropin (SEQ ID NO: 82), melittin, copsin, drosomycin (SEQ ID NO: 93), dermcidin (SEQ ID NO: 81), andropin (SEQ ID NO: 83), moricin (SEQ ID NO: 84), ceratotoxin (SEQ ID NO: 85), abaecin (SEQ ID NO: 86), apidaecin (SEQ ID NO: 87), prophenin (SEQ ID NO: 88), indolicidin (SEQ ID NO: 89), protegrin (SEQ ID NO: 90), tachyplesin (SEQ ID NO: 91), or defensin (SEQ ID NO: 92) to a vector of a human pathogen. Non-limiting examples of AMPs are listed in Table 6.

TABLE 6

Examples of Antimicrobial Peptides

| Type | Characteristic | Example AMP | Sequence |
|---|---|---|---|
| Anionic peptides | rich in glutamic and aspartic acid | dermcidin | SSLLEKGLDGAKKAVGGLGKL GKDAVEDLESVGKGAVHDVKD VLDSVL (SEQ ID NO: 79) |
| Linear cationic α-helical peptides | lack cysteine | cecropin A | KWKLFKKIEKVGQNIRDGIIKAG PAVAVVGQATQIAK (SEQ ID NO: 80) |
| | | andropin | MKYFSVLVVLTLILAIVDQSDAFI NLLDKVEDALHTGAQAGFKLIR PVERGATPKKSEKPEK (SEQ ID NO: 81) |
| | | moricin | MNILKFFFVFIVAMSLVSCSTAA PAKIPIKAIKTVGKAVGKGLRAI NIASTANDVFNFLKPKKRKH (SEQ ID NO: 82) |
| | | ceratotoxin | MANLKAVFLICIVAFIALQCVVA EPAAEDSVVVKRSIGSALKKAL PVAKKIGKIALPIAKAALPVAAG LVG (SEQ ID NO: 83) |
| Cationic peptide enriched for specific amino acid | rich in proline, arginine, phenylalanine, glycine, tryptophan | abaecin | MKVVIFIFALLATICAAFAYVPLP NVPQPGRRPFPTFPGQGPFNP KIKWPQGY (SEQ ID NO: 84) |
| | | apidaecins | KNFALAILVVTFVVAVFGNTNLD PPTRPTRLRREAKPEAEPGNN RPVYIPQPRPPHPRLRREAEPE AEPGNNRPVYIPQPRPPHPRL RREAELEAEPGNNRPVYISQP RPPHPRLRREAEPEAEPGNNR PVYIPQPRPPHPRLRREAELEA EPGNNRPVYISQPRPPHPRLR REAEPEAEPGNNRPVYIPQPR PPHPRLRREAEPEAEPGNNRP VYIPQPRPPHPRLRREAEPEAE PGNNRPVYIPQPRPPHPRLRR EAKPEAKPGNNRPVYIPQPRP PHPRI (SEQ ID NO: 85) |
| | | prophenin | METQRASLCLGRWSLWLLLLA LVVPSASAQALSYREAVLRAVD RLNEQSSEANLYRLLELDQPPK ADEDPGTPKPVSFTVKETVCP RPTRRPPELCDFKENGRVKQC VGTVTLDQIKDPLDITCNEGVR RFPWWWPFLRRPRLRRQAFP PPNVPGPRFPPPNVPGPRFPP PNFPGPRFPPPNFPGPRFPPP NFPGPPFPPPIFPGPWFPPPPP FRPPPFGPPRFPGRR (SEQ ID NO: 86) |
| | | indolicidin | MQTQRASLSLGRWSLWLLLLG LVVPSASAQALSYREAVLRAVD QLNELSSEANLYRLLELDPPPK DNEDLGTRKPVSFTVKETVCP RTIQQPAEQCDFKEKGRVKQC VGTVTLDPSNDQFDLNCNELQ SVILPWKWPWWPWRRG (SEQ ID NO: 87) |
| Anionic and cationic peptides that contain cysteine and form disulfide bonds | contain 1-3 disulfide bond | protegrin | METQRASLCLGRWSLWLLLLA LVVPSASAQALSYREAVLRAVD RLNEQSSEANLYRLLELDQPPK ADEDPGTPKPVSFTVKETVCP RPTRQPPELCDFKENGRVKQC VGTVTLDQIKDPLDITCNEVQG VRGGRLCYCRRRFCVCVGRG (SEQ ID NO: 88) |
| | | tachyplesins | KWCFRVCYRGICYRRCR (SEQ ID NO: 89) |
| | | defensin | MKCATIVCTIAVVLAATLLNGSV QAAPQEEAALSGGANLNTLLD ELPEETHHAALENYRAKRATC |

TABLE 6-continued

| Examples of Antimicrobial Peptides | | | |
|---|---|---|---|
| Type | Characteristic | Example AMP | Sequence |
| | | | DLASGFGVGSSLCAAHCIARR YRGGYCNSKAVCVCRN (SEQ ID NO: 90) |
| | | drosomycin | MMQIKYLFALFAVLMLVVLGAN EADADCLSGRYKGPCAVWDN ETCRRVCKEEGRSSGHCSPSL KCWCEGC (SEQ ID NO: 91) |

The AMP may be active against any number of target microorganisms. In some instances, the AMP may have antibacterial and/or antifungal activities. In some instances, the AMP may have a narrow-spectrum bioactivity or a broad-spectrum bioactivity. For example, some AMPs target and kill only a few species of bacteria or fungi, while others are active against both gram-negative and gram-positive bacteria as well as fungi.

Further, the AMP may function through a number of known mechanisms of action. For example, the cytoplasmic membrane is a frequent target of AMPs, but AMPs may also interfere with DNA and protein synthesis, protein folding, and cell wall synthesis. In some instances, AMPs with net cationic charge and amphipathic nature disrupt bacterial membranes leading to cell lysis. In some instances, AMPs may enter cells and interact with intracellular target to interfere with DNA, RNA, protein, or cell wall synthesis. In addition to killing microorganisms, AMPs have demonstrated a number of immunomodulatory functions that are involved in the clearance of infection, including the ability to alter host gene expression, act as chemokines and/or induce chemokine production, inhibit lipopolysaccharide induced pro-inflammatory cytokine production, promote wound healing, and modulating the responses of dendritic cells and cells of the adaptive immune response.

In some instances, the AMP is a functionally active variant of the AMPs described herein. In some instances, the variant of the AMP has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of an AMP described herein or a naturally derived AMP.

In some instances, the AMP may be bioengineered to modulate its bioactivity, e.g., increase or decrease or regulate, or to specify a target microorganism. In some instances, the AMP is produced by the translational machinery (e.g. a ribosome, etc.) of a cell. In some instances, the AMP is chemically synthesized. In some instances, the AMP is derived from a polypeptide precursor. The polypeptide precursor can undergo cleavage (for example, processing by a protease) to yield the polypeptide of the AMP itself. As such, in some instances, the AMP is produced from a precursor polypeptide. In some instances, the AMP includes a polypeptide that has undergone post-translational modifications, for example, cleavage, or the addition of one or more functional groups.

The AMPs described herein may be formulated in a composition for any of the uses described herein. The compositions disclosed herein may include any number or type (e.g., classes) of AMPs, such as at least about any one of 1 AMP, 2, 3, 4, 5, 10, 15, 20, or more AMPs. For example, the compositions may include a cocktail of AMPs (e.g., a cocktail of scorpion peptides, e.g., UyCT3, D3, D10, and Uy17). A suitable concentration of each AMP in the composition depends on factors such as efficacy, stability of the AMP, number of distinct AMP in the composition, the formulation, and methods of application of the composition. In some instances, each AMP in a liquid composition is from about 0.1 ng/mL to about 100 mg/mL (about 0.1 ng/mL to about 1 ng/mL, about 1 ng/mL to about 10 ng/mL, about 10 ng/mL to about 100 ng/mL, about 100 ng/mL to about 1000 ng/mL, about 1 mg/mL to about 10 mg/mL, about 10 mg/mL to about 100 mg/mL). In some instances, each AMP in a solid composition is from about 0.1 ng/g to about 100 mg/g (about 0.1 ng/g to about 1 ng/g, about 1 ng/g to about 10 ng/g, about 10 ng/g to about 100 ng/g, about 100 ng/g to about 1000 ng/g, about 1 mg/g to about 10 mg/g, about 10 mg/g to about 100 mg/g). In some instances, wherein the composition includes at least two types of AMPs, the concentration of each type of AMP may be the same or different.

A modulating agent including an AMP as described herein can be contacted with the target host in an amount and for a time sufficient to: (a) reach a target level (e.g., a predetermined or threshold level) of AMP concentration inside a target host; (b) reach a target level (e.g., a predetermined or threshold level) of AMP concentration inside a target host gut; (c) reach a target level (e.g., a predetermined or threshold level) of AMP concentration inside a target host bacteriocyte; (d) modulate the level, or an activity, of one or more microorganism (e.g., endosymbiont) in the target host; or/and (e) modulate fitness of the target host.

As illustrated by Examples 20-22, AMPs, such as scorpion peptides, can be used as modulating agents that target an endosymbiotic bacterium in an insect host to decrease the fitness of the host (e.g., as outlined herein).

(d) Nodule C-Rich Peptides

The modulating agent described herein may include a nodule C-rich peptide (NCR peptide). NCR peptides are produced in certain leguminous plants and play an important role in the mutualistic, nitrogen-fixing symbiosis of the plants with bacteria from the Rhizobiaceae family (*rhizobia*), resulting in the formation of root nodules where plant cells contain thousands of intracellular endosymbionts. NCR peptides possess anti-microbial properties that direct an irreversible, terminal differentiation process of bacteria, e.g., to permeabilize the bacterial membrane, disrupt cell division, or inhibit protein synthesis. For example, in *Medicago truncatula* nodule cells infected with *Sinorhizobium meliloti*, hundreds of NCR peptides are produced which direct irreversible differentiation of the bacteria into large polyploid nitrogen-fixing bacteroids). Non-limiting examples of NCR peptides are listed in Table 7.

TABLE 7

Examples of NCR Peptides

| NAME | Peptide sequence | Producer |
|---|---|---|
| >gi\|152218086\|gb\|ABS31477.1\|NCR 340 | MTKIVVFIYVVILLLTIFHVSAKKKRYI ECETHEDCSQVFMPPFVMRCVIHE CKIFNGEHLRY (SEQ ID NO: 92) | *Medicago truncatula* |
| >gi\|152218084\|gb\|ABS31476.1\|NCR 339 | MAKIMKFVYNMIPFLSIFIITLQVNVV VCEIDADCPQICMPPYEVRCVNHRC GWVNTDDSLFLTQEFTRSKQYIIS (SEQ ID NO: 93) | *Medicago truncatula* |
| >gi\|152218082\|gb\|ABS31475.1\|NCR 338 | MYKVVESIFIRYMHRKPNMTKFFKF VYTMFILISLFLVVTNANAHNCTDISD CSSNHCSYEGVSLCMNGQCICIYE (SEQ ID NO: 94) | *Medicago truncatula* |
| >gi\|152218080\|gb\|ABS31474.1\|NCR 337 | MVETLRLFYIMILFVSLCLVVVDGES KLEQTCSEDFECYIKNPHVPFGHLR CFEGFCQQLNGPA (SEQ ID NO: 95) | *Medicago truncatula* |
| >gi\|152218078\|gb\|ABS31473.1\|NCR 336 | MAKIVNFVYSMIVFLFLFLVATKAAR GYLCVTDSHCPPHMCPPGMEPRCV RRMCKCLPIGWRKYFVP (SEQ ID NO: 96) | *Medicago truncatula* |
| >gi\|152218076\|gb\|ABS31472.1\|NCR 335 | MQIGKNMVETPKLDYVIIFFFLYFFF RQMIILRLNTTFRPLNFKMLRFWGQ NRNIMKHRGQKVHFSLILSDCKTNK DCPKLRRANVRCRKSYCVPI (SEQ ID NO: 97) | *Medicago truncatula* |
| >gi\|152218074\|gb\|ABS31471.1\|NCR 334 | MLRLYLVSYFLLKRTLLVSYFSYFST YIIECKTDNDCPISQLKIYAWKCVKN GCHLFDVIPMMYE (SEQ ID NO: 98) | *Medicago truncatula* |
| >gi\|152218072\|gb\|ABS31470.1\|NCR 333 | MAEILKFVYIVILFVSLLLIVVASEREC VTDDDCEKLYPTNEYRMMCDSGYC MNLLNGKIIYLLCLKKKKFLIIISVLL (SEQ ID NO: 99) | *Medicago truncatula* |
| >gi\|152218070\|gb\|ABS31469.1\|NCR 332 | MAEIIKFVYIMILCVSLLLIEVAGEECV TDADCDKLYPDIRKPLMCSIGECYSL YKGKFSLSIISKTSFSLMVYNVVTLVI CLRLAYISLLLKFL (SEQ ID NO: 100) | *Medicago truncatula* |
| >gi\|152218068\|gb\|ABS31468.1\|NCR 331 | MAEILKDFYAMNLFIFLIILPAKIRGET LSLTHPKCHHIMLPSLFITEVFQRVT DDGCPKPVNHLRVVKCIEHICEYGY NYRPDFASQIPESTKMPRKRE (SEQ ID NO: 101) | *Medicago truncatula* |
| >gi\|152218066\|gb\|ABS31467.1\|NCR 330 | MVEILKNFYAMNLFIFLIILAVKIRGAH FPCVTDDDCPKPVNKLRVIKCIDHIC QYARNLPDFASEISESTKMPCKGE (SEQ ID NO: 102) | *Medicago truncatula* |
| >gi\|152218064\|gb\|ABS31466.1\|NCR 329 | MFHAQAENMAKVSNFVCIMILFLALF FITMNDAARFECREDSHCVTRIKCV LPRKPECRNYACGCYDSNKYR (SEQ ID NO: 103) | *Medicago truncatula* |
| >gi\|152218062\|gb\|ABS31465.1\|NCR 328 | MQMRQNMATILNFVFVIILFISLLLVV TKGYREPFSSFTEGPTCKEDIDCPSI SCVNPQVPKCIMFECHCKYIPTTLK (SEQ ID NO: 104) | *Medicago truncatula* |
| >gi\|152218060\|gb\|ABS31464.1\|NCR 327 | MATILMYVYITILFISILTVLTEGLYEPL YNFRRDPDCRRNIDCPSYLCVAPKV PRCIMFECHCKDIPSDH (SEQ ID NO: 105) | *Medicago truncatula* |

TABLE 7-continued

Examples of NCR Peptides

| NAME | Peptide sequence | Producer |
|---|---|---|
| >gi\|152218058\|gb\|ABS31463.1\|NCR 326 | MTTSLKFVYVAILFLSLLLVVMGGIR RFECRQDSDCPSYFCEKLTVPKCF WSKCYCK (SEQ ID NO: 106) | *Medicago truncatula* |
| >gi\|152218056\|gb\|ABS31462.1\|NCR 325 | MTTSLKFVYVAILFLSLLLVVMGGIR KKECRQDSDCPSYFCEKLTIAKCIHS TCLCK (SEQ ID NO: 107) | *Medicago truncatula* |
| >gi\|152218054\|gb\|ABS31461.1\|NCR 324 | MQIGKNMVETPKLVYFIILFLSIFLCIT VSNSSFSQIFNSACKTDKDCPKFGR VNVRCRKGNCVPI (SEQ ID NO: 108) | *Medicago truncatula* |
| >gi\|152218046\|gb\|ABS31457.1\|NCR 320 | MTAILKKFINAVFLFIVLFLATTNVED FVGGSNDECVYPDVFQCINNICKCV SHHRT (SEQ ID NO: 109) | *Medicago truncatula* |
| >gi\|152218044\|gb\|ABS31456.1\|NCR 319 | MQKRKNMAQIIFYVYALIILFSPFLAA RLVFVNPEKPCVTDADCDRYRHES AIYSDMFCKDGYCFIDYHHDPYP (SEQ ID NO: 110) | *Medicago truncatula* |
| >gi\|152218042\|gb\|ABS31455.1\|NCR 318 | MQMRKNMAQILFYVYALLILFTPFLV ARIMVVNPNNPCVTDADCQRYRHK LATRMICNQGFCLMDFTHDPYAPSLP (SEQ ID NO: 111) | *Medicago truncatula* |
| >gi\|152218040\|gb\|ABS31454.1\|NCR 317 | MNHISKFVYALIIFLSIYLVVLDGLPIS CKDHFECRRKINILRCIYRQEKPMCI NSICTCVKLL (SEQ ID NO: 112) | *Medicago truncatula* |
| >gi\|152218038\|gb\|ABS31453.1\|NCR 316 | MQREKNMAKIFEFVYAMIIFILLFLVE KNVVAYLKFECKTDDDCQKSLLKTY VWKCVKNECYFFAKK (SEQ ID NO: 113) | *Medicago truncatula* |
| >gi\|152218036\|gb\|ABS31452.1\|NCR 315 | MAGIIKFVHVLIIFLSLFHVVKNDDGS FCFKDSDCPDEMCPSPLKEMCYFL QCKCGVDTIA (SEQ ID NO: 114) | *Medicago truncatula* |
| >gi\|152218034\|gb\|ABS31451.1\|NCR 314 | MANTHKLVSMILFIFLFLASNNVEGY VNCETDADCPPSTRVKRFKCVKGE CRWTRMSYA (SEQ ID NO: 115) | *Medicago truncatula* |
| >gi\|152218032\|gb\|ABS31450.1\|NCR 313 | MQRRKKKAQVVMFVHDLIICIYLFIVI TTRKTDIRCRFYYDCPRLEYHFCECI EDFCAYIRLN (SEQ ID NO: 116) | *Medicago truncatula* |
| >gi\|152218030\|gb\|ABS31449.1\|NCR 312 | MAKVYMFVYALIIFVSPFLLATFRTRL PCEKDDDCPEAFLPPVMKCVNRFC QYEILE (SEQ ID NO: 117) | *Medicago truncatula* |
| >gi\|152218028\|gb\|ABS31448.1\|NCR 310 | MIKQFSVCYIQMRRNMTTILKFPYIM VICLLLLHVAAYEDFEKEIFDCKKDG DCDHMCVTPGIPKCTGYVCFCFENL (SEQ ID NO: 118) | *Medicago truncatula* |
| >gi\|152218026\|gb\|ABS31447.1\|NCR 309 | MQRSRNMTTIFKFAYIMIICVFLLNIA AQEIENGIHPCKKNEDCNHMCVMP GLPWCHENNLCFCYENAYGNTR (SEQ ID NO: 119) | *Medicago truncatula* |
| >gi\|152218024\|gb\|ABS31446.1\|NCR 304 | MTIIIKFVNVLIIFLSLFHVAKNDDNKL LLSFIEEGFLCFKDSDCPYNMCPSP LKEMCYFIKCVCGVYGPIRERRLYQ SHNPMIQ (SEQ ID NO: 120) | *Medicago truncatula* |

TABLE 7-continued

Examples of NCR Peptides

| NAME | Peptide sequence | Producer |
|---|---|---|
| >gi\|152218022\|gb\|ABS31445.1\|NCR 303 | MRKNMTKILMIGYALMIFIFLSIAVSIT GNLARASRKKPVDVIPCIYDHDCPR KLYFLERCVGRVCKYL (SEQ ID NO: 121) | *Medicago truncatula* |
| >gi\|152218020\|gb\|ABS31444.1\|NCR 301 | MAHKLVYAITLFIFLFLIANNIEDDIFCI TDNDCPPNTLVQRYRCINGKCNLSF VSYG (SEQ ID NO: 122) | *Medicago truncatula* |
| >gi\|152218018\|gb\|ABS31443.1\|NCR 300 | MDETLKFVYILILFVSLCLVVADGVK NINRECTQTSDCYKKYPFIPWGKVR CVKGRCRLDM (SEQ ID NO: 123) | *Medicago truncatula* |
| >gi\|152218016\|gb\|ABS31442.1\|NCR 290 | MAKIIKFVYVLAIFFSLFLVAKNVNG WTCVEDSDCPANICQPPMQRMCFY GECACVRSKFCT (SEQ ID NO: 124) | *Medicago truncatula* |
| >gi\|152218014\|gb\|ABS31441.1\|NCR 289 | MVKIIKFVYFMTLFLSMLLVTTKEDG SVECIANIDCPQIFMLPFVMRCINFR CQIVNSEDT (SEQ ID NO: 125) | *Medicago truncatula* |
| >gi\|152218012\|gb\|ABS31440.1\|NCR 286 | MDEILKFVYTLIIFFSLFFAANNVDANI MNCQSTFDCPRDMCSHIRDVICIFK KCKCAGGRYMPQVP (SEQ ID NO: 126) | *Medicago truncatula* |
| >gi\|152218008\|gb\|ABS31438.1\|NCR 278 | MQRRKNMANNHMLIYAMIICLFPYL VVTFKTAITCDCNEDCLNFFTPLDNL KCIDNVCEVFM (SEQ ID NO: 127) | *Medicago truncatula* |
| >gi\|152218006\|gb\|ABS31437.1\|NCR 266 | MVNILKFIYVIIFFILMFFVLIDVDGHV LVECIENRDCEKGMCKFPFIVRCLM DQCKCVRIHNLI (SEQ ID NO: 128) | *Medicago truncatula* |
| >gi\|152218004\|gb\|ABS31436.1\|NCR 265 | MIIQFSIYYMQRRKLNMVEILKFSHA LIIFLFLSALVTNANIFFCSTDEDCTW NLCRQPWVQKCRLHMCSCEKN (SEQ ID NO: 129) | *Medicago truncatula* |
| >gi\|152218002\|gb\|ABS31435.1\|NCR 263 | MDEVFKFVYVMIIFPFLILDVATNAEK IRRCFNDAHCPPDMCTLGVIPKCSR FTICIC (SEQ ID NO: 130) | *Medicago truncatula* |
| >gi\|152218000\|gb\|ABS31434.1\|NCR 244 | MHRKPNMTKFFKFVYTMFILISLFLV VTNANANNCTDTSDCSSNHCSYEG VSLCMNGQCICIYE (SEQ ID NO: 131) | *Medicago truncatula* |
| >gi\|152217998\|gb\|ABS31433.1\|NCR 239 | MQMKKMATILKFVYLIILLIYPLLVVTE ESHYMKFSICKDDTDCPTLFCVLPN VPKCIGSKCHCKLMVN (SEQ ID NO: 132) | *Medicago truncatula* |
| >gi\|152217996\|gb\|ABS31432.1\|NCR 237 | MVETLRLFYIMILFVSLYLVVVDGVS KLAQSCSEDFECYIKNPHAPFGQLR CFEGYCQRLDKPT (SEQ ID NO: 133) | *Medicago truncatula* |
| >gi\|152217994\|gb\|ABS31431.1\|NCR 228 | MTTFLKVAYIMIICVFVLHLAAQVDS QKRLHGCKEDRDCDNICSVHAVTK CIGNMCRCLANVK (SEQ ID NO: 134) | *Medicago truncatula* |
| >gi\|152217992\|gb\|ABS31430.1\|NCR 224 | MRINRTPAIFKFVYTIIIYLFLLRVVAK DLPFNICEKDEDCLEFCAHDKVAKC MLNICFCF (SEQ ID NO: 135) | *Medicago truncatula* |

TABLE 7-continued

Examples of NCR Peptides

| NAME | Peptide sequence | Producer |
|---|---|---|
| >gi\|152217990\|gb\|ABS31429.1\|NCR 221 | MAEILKILYVFIIFLSLILAVISQHPFTP CETNADCKCRNHKRPDCLWHKCYCY (SEQ ID NO: 136) | *Medicago truncatula* |
| >gi\|152217988\|gb\|ABS31428.1\|NCR 217 | MRKSMATILKFVYVIMLFIYSLFVIES FGHRFLIYNNCKNDTECPNDCGPHE QAKCILYACYCVE (SEQ ID NO: 137) | *Medicago truncatula* |
| >gi\|152217986\|gb\|ABS31427.1\|NCR 209 | MNTILKFIFVVFLFLSIFLSAGNSKSY GPCTTLQDCETHNWFEVCSCIDFEC KCWSLL (SEQ ID NO: 138) | *Medicago truncatula* |
| >gi\|152217984\|gb\|ABS31426.1\|NCR 206 | MAEIIKFVYIMILCVSLLLIAEASGKEC VTDADCENLYPGNKKPMFCNNTGY CMSLYKEPSRYM (SEQ ID NO: 139) | *Medicago truncatula* |
| >gi\|152217982\|gb\|ABS31425.1\|NCR 201 | MAKIIKFVYIMILCVSLLLIVEAGGKEC VTDVDCEKIYPGNKKPLICSTGYCYS LYEEPPRYHK (SEQ ID NO: 140) | *Medicago truncatula* |
| >gi\|152217980\|gb\|ABS31424.1\|NCR 200 | MAKVTKFGYIIIHFLSLFFLAMNVAG GRECHANSHCVGKITCVLPQKPEC WNYACVCYDSNKYR (SEQ ID NO: 141) | *Medicago truncatula* |
| >gi\|152217978\|gb\|ABS31423.1\|NCR 192 | MAKIFNYVYALIMFLSLFLMGTSGMK NGCKHTGHCPRKMCGAKTTKCRN NKCQCV (SEQ ID NO: 142) | *Medicago truncatula* |
| >gi\|152217976\|gb\|ABS31422.1\|NCR 189 | MTEILKFVCVMIIFISSFIVSKSLNGG GKDKCFRDSDCPKHMCPSSLVAKCI NRLCRCRRPELQVQLNP (SEQ ID NO: 143) | *Medicago truncatula* |
| >gi\|152217974\|gb\|ABS31421.1\|NCR 187 | MAHIIMFVYALIYALIIFSSLFVRDGIP CLSDDECPEMSHYSFKCNNKICEYD LGEMSDDDYYLEMSRE (SEQ ID NO: 144) | *Medicago truncatula* |
| >gi\|152217972\|gb\|ABS31420.1\|NCR 181 | MYREKNMAKTLKFVYVIVLFLSLFLA AKNIDGRVSYNSFIALPVCQTAADC PEGTRGRTYKCINNKCRYPKLLKPIQ (SEQ ID NO: 145) | *Medicago truncatula* |
| >gi\|152217970\|gb\|ABS31419.1\|NCR 176 | MAHIFNYVYALLVFLSLFLMVTNGIHI GCDKDRDCPKQMCHLNQTPKCLKN ICKCV (SEQ ID NO: 146) | *Medicago truncatula* |
| >gi\|152217968\|gb\|ABS31418.1\|NCR 175 | MAEILKCFYTMNLFIFLIILPAKIREHI QCVIDDDCPKSLNKLLIIKCINHVCQY VGNLPDFASQIPKSTKMPYKGE (SEQ ID NO: 147) | *Medicago truncatula* |
| >gi\|152217966\|gb\|ABS31417.1\|NCR 173 | MAYISRIFYVLIIFLSLFFVVINGVKSL LLIKVRSFIPCQRSDDCPRNLCVDQII PTCVWAKCKCKNYND (SEQ ID NO: 148) | *Medicago truncatula* |
| >gi\|152217964\|gb\|ABS31416.1\|NCR 172 | MANVTKFVYIAIYFLSLFFIAKNDATA TFCHDDSHCVTKIKCVLPRTPQCRN EACGCYHSNKFR (SEQ ID NO: 149) | *Medicago truncatula* |
| >gi\|152217962\|gb\|ABS31415.1\|NCR 171 | MGEIMKFVYVMIIYLFMFNVATGSEF IFTKKLTSCDSSKDCRSFLCYSPKFP VCKRGICECI (SEQ ID NO: 150) | *Medicago truncatula* |

TABLE 7-continued

Examples of NCR Peptides

| NAME | Peptide sequence | Producer |
|---|---|---|
| >gi\|152217960\|gb\|ABS31414.1\|NCR 169 | MGEMFKFIYTFILFVHLFLVVIFEDIG HIKYCGIVDDCYKSKKPLFKIWKCVE NVCVLWYK (SEQ ID NO: 151) | *Medicago truncatula* |
| >gi\|152217958\|gb\|ABS31413.1\|NCR 165 | MARTLKFVYSMILFLSLFLVANGLKIF CIDVADCPKDLYPLLYKCIYNKCIVFT RIPFPFDWI (SEQ ID NO: 152) | *Medicago truncatula* |
| >gi\|152217956\|gb\|ABS31412.1\|NCR 159 | MANITKFVYIAILFLSLFFIGMNDAAIL ECREDSHCVTKIKCVLPRKPECRNN ACTCYKGGFSFHH (SEQ ID NO: 153) | *Medicago truncatula* |
| >gi\|152217954\|gb\|ABS31411.1\|NCR 147 | MQRVKKMSETLKFVYVLILFISIFHVV IVCDSIYFPVSRPCITDKDCPNMKHY KAKCRKGFCISSRVR (SEQ ID NO: 154) | *Medicago truncatula* |
| >gi\|152217952\|gb\|ABS31410.1\|NCR 146 | MQIRKIMSGVLKFVYAIILFLFLFLVA REVGGLETIECETDGDCPRSMIKM WNKNYRHKCIDGKCEWIKKLP (SEQ ID NO: 155) | *Medicago truncatula* |
| >gi\|152217950\|gb\|ABS31409.1\|NCR 145 | MFVYDLILFISLILVVTGINAEADTSC HSFDDCPWVAHHYRECIEGLCAYRI LY (SEQ ID NO: 156) | *Medicago truncatula* |
| >gi\|152217948\|gb\|ABS31408.1\|NCR 144 | MQRRKKSMAKMLKFFFAIILLLSLFL VATEVGGAYIECEVDDDCPKPMKN SHPDTYYKCVKHRCQWAWK (SEQ ID NO: 157) | *Medicago truncatula* |
| >gi\|152217946\|gb\|ABS31407.1\|NCR 140 | MFVYTLIIFLFPSHVITNKIAIYCVSDD DCLKTFTPLDLKCVDNVCEFNLRCK GKCGERDEKFVFLKALKKMDQKLVL EEQGNAREVKIPKKLLFDRIQVPTPA TKDQVEEDDYDDDDEEEEEEEDDV DMWFHLPDVVCH (SEQ ID NO: 158) | *Medicago truncatula* |
| >gi\|152217944\|gb\|ABS31406.1\|NCR 138 | MAKFSMFVYALINFLSLFLVETAITNI RCVSDDDCPKVIKPLVMKCIGNYCY FFMIYEGP (SEQ ID NO: 159) | *Medicago truncatula* |
| >gi\|152217942\|gb\|ABS31405.1\|NCR 136 | MAHKFVYAIILFIFLFLVAKNVKGYVV CRTVDDCPPDTRDLRYRCLNGKCK SYRLSYG (SEQ ID NO: 160) | *Medicago truncatula* |
| >gi\|152217940\|gb\|ABS31404.1\|NCR 129 | MQRKKNMGQILIFVFALINFLSPILVE MTTTTIPCTFIDDCPKMPLVVKCIDN FCNYFEIK (SEQ ID NO: 161) | *Medicago truncatula* |
| >gi\|152217938\|gb\|ABS31403.1\|NCR 128 | MAQTLMLVYALIIFTSLFLVVISRQTD IPCKSDDACPRVSSHHIECVKGFCT YWKLD (SEQ ID NO: 162) | *Medicago truncatula* |
| >gi\|152217936\|gb\|ABS31402.1\|NCR 127 | MLRRKNTVQILMFVSALLIYIFLFLVIT SSANIPCNSDSDCPWKIYYTYRCND GFCVYKSIDPSTIPQYMTDLIFPR (SEQ ID NO: 163) | *Medicago truncatula* |
| >gi\|152217934\|gb\|ABS31401.1\|NCR 122 | MAVILKFVYIMIIFLFLLYVVNGTRCN RDEDCPFICTGPQIPKCVSHICFCLS SGKEAY (SEQ ID NO: 164) | *Medicago truncatula* |

TABLE 7-continued

Examples of NCR Peptides

| NAME | Peptide sequence | Producer |
|---|---|---|
| >gi\|152217932\|gb\|ABS31400.1\|NCR 121 | MDAILKFIYAMFLFLFLFVTTRNVEAL FECNRDFVCGNDDECVYPYAVQCI HRYCKCLKSRN (SEQ ID NO: 165) | *Medicago truncatula* |
| >gi\|152217930\|gb\|ABS31399.1\|NCR 119 | MQIGRKKMGETPKLVYVIILFLSIFLC TNSSFSQMINFRGCKRDKDCPQFR GVNIRCRSGFCTPIDS (SEQ ID NO: 166) | *Medicago truncatula* |
| >gi\|152217928\|gb\|ABS31398.1\|NCR 118 | MQMRKNMAQILFYVYALLILFSPFLV ARIMVVNPNNPCVTDADCQRYRHK LATRMVCNIGFCLMDFTHDPYAPSLP (SEQ ID NO: 167) | *Medicago truncatula* |
| >gi\|152217926\|gb\|ABS31397.1\|NCR 111 | MYVYYIQMGKNMAQRFMFIYALIIFL SQFFVVINTSDIPNNSNRNSPKEDVF CNSNDDCPTILYYVSKCVYNFCEYW (SEQ ID NO: 168) | *Medicago truncatula* |
| >gi\|152217924\|gb\|ABS31396.1\|NCR 103 | MAKIVNFVYSMIIFVSLFLVATKGGS KPFLTRPYPCNTGSDCPQNMCPPG YKPGCEDGYCNHCYKRW (SEQ ID NO: 169) | *Medicago truncatula* |
| >gi\|152217922\|gb\|ABS31395.1\|NCR 101 | MVRTLKFVYVIILILSLFLVAKGGGKK IYCENAASCPRLMYPLVYKCLDNKC VKFMMKSRFV (SEQ ID NO: 170) | *Medicago truncatula* |
| >gi\|152217920\|gb\|ABS31394.1\|NCR 96 | MARTLKFVYAVILFLSLFLVAKGDDV KIKCVVAANCPDLMYPLVYKCLNGIC VQFTLTFPFV (SEQ ID NO: 171) | *Medicago truncatula* |
| >gi\|152217918\|gb\|ABS31393.1\|NCR 94 | MSNTLMFVITFIVLVTLFLGPKNVYA FQPCVTTADCMKTLKTDENIWYECI NDFCIPFPIPKGRK (SEQ ID NO: 172) | *Medicago truncatula* |
| >gi\|152217916\|gb\|ABS31392.1\|NCR 93 | MKRVVNMAKIVKYVYVIIIFLSLFLVA TKIEGYYYKCFKDSDCVKLLCRIPLR PKCMYRHICKCKVVLTQNNYVLT (SEQ ID NO: 173) | *Medicago truncatula* |
| >gi\|152217914\|gb\|ABS31391.1\|NCR 90 | MKRGKNMSKILKFIYATLVLYLFLVV TKASDDECKIDGDCPISWQKFHTYK CINQKCKWVLRFHEY (SEQ ID NO: 174) | *Medicago truncatula* |
| >gi\|152217912\|gb\|ABS31390.1\|NCR 88 | MAKTLNFMFALILFISLFLVSKNVAIDI FVCQTDADCPKSELSMYTWKCIDN ECNLFKVMQQMV (SEQ ID NO: 175) | *Medicago truncatula* |
| >gi\|152217910\|gb\|ABS31389.1\|NCR 86 | MANTHKLVSMILFIFLFLVANNVEGY VNCETDADCPPSTRVKRFKCVKGE CRWTRMSYA (SEQ ID NO: 176) | *Medicago truncatula* |
| >gi\|152217908\|gb\|ABS31388.1\|NCR 77 | MAHFLMFVYALITCLSLFLVEMGHLS IHCVSVDDCPKVEKPITMKCINNYCK YFVDHKL (SEQ ID NO: 177) | *Medicago truncatula* |
| >gi\|152217906\|gb\|ABS31387.1\|NCR 76 | MNQIPMFGYTLIIFFSLFPVITNGDRI PCVTNGDCPVMRLPLYMRCITYSCE LFFDGPNLCAVERI (SEQ ID NO: 178) | *Medicago truncatula* |
| >gi\|152217904\|gb\|ABS31386.1\|NCR 74 | MRKDMARISLFVYALIIFFSLFFVLTN GELEIRCVSDADCPLFPLPLHNRCID DVCHLFTS (SEQ ID NO: 179) | *Medicago truncatula* |

TABLE 7-continued

Examples of NCR Peptides

| NAME | Peptide sequence | Producer |
|---|---|---|
| >gi\|152217902\|gb\|ABS31385.1\|NCR 68 | MAQILMFVYFLIIFLSLFLVESIKIFTE HRCRTDADCPARELPEYLKCQGGM CRLLIKKD (SEQ ID NO: 180) | *Medicago truncatula* |
| >gi\|152217900\|gb\|ABS31384.1\|NCR 65 | MARVISLFYALIIFLFLFLVATNGDLS PCLRSGDCSKDECPSHLVPKCIGLT CYCI (SEQ ID NO: 181) | *Medicago truncatula* |
| >gi\|152217898\|gb\|ABS31383.1\|NCR 62 | MQRRKNMAQILLFAYVFIISISLFLVV TNGVKIPCVKDTDCPTLPCPLYSKC VDGFCKMLSI (SEQ ID NO: 182) | *Medicago truncatula* |
| >gi\|152217896\|gb\|ABS31382.1\|NCR 57 | MNHISKFVYALIIFLSVYLVVLDGRPV SCKDHYDCRRKVKIVGCIFPQEKPM CINSMCTCIREIVP (SEQ ID NO: 183) | *Medicago truncatula* |
| >gi\|152217894\|gb\|ABS31381.1\|NCR 56 | MKSQNHAKFISFYKNDLFKIFQNND SHFKVFFALIIFLYTYLHVTNGVFVSC NSHIHCRVNNHKIGCNIPEQYLLCVN LFCLWLDY (SEQ ID NO: 184) | *Medicago truncatula* |
| >gi\|152217892\|gb\|ABS31380.1\|NCR 54 | MTYISKVVYALIIFLSIYVGVNDCMLV TCEDHFDCRQNVQQVGCSFREIPQ CINSICKCMKG (SEQ ID NO: 185) | *Medicago truncatula* |
| >gi\|152217890\|gb\|ABS31379.1\|NCR 53 | MTHISKFVFALIIFLSIYVGVNDCKRIP CKDNNDCNNNWQLLACRFEREVPR CINSICKCMPM (SEQ ID NO: 186) | *Medicago truncatula* |
| >gi\|152217888\|gb\|ABS31378.1\|NCR 43 | MVQTPKLVYVIVLLLSIFLGMTICNSS FSHFFEGACKSDKDCPKLHRSNVR CRKGQCVQI (SEQ ID NO: 187) | *Medicago truncatula* |
| >gi\|152217886\|gb\|ABS31377.1\|NCR 28 | MTKILMLFYAMIVFHSIFLVASYTDEC STDADCEYILCLFPIIKRCIHNHCKCV PMGSIEPMSTIPNGVHKFHIINN (SEQ ID NO: 188) | *Medicago truncatula* |
| >gi\|152217884\|gb\|ABS31376.1\|NCR 26 | MAKTLNFVCAMILFISLFLVSKNVAL YIIECKTDADCPISKLNMYNWRCIKS SCHLYKVIQFMV (SEQ ID NO: 189) | *Medicago truncatula* |
| >gi\|152217882\|gb\|ABS31375.1\|NCR 24 | MQKEKNMAKTFEFVYAMIIFILLFLVE NNFAAYIIECQTDDDCPKSQLEMFA WKCVKNGCHLFGMYEDDDDP (SEQ ID NO: 190) | *Medicago truncatula* |
| >gi\|152217880\|gb\|ABS31374.1\|NCR 21 | MAATRKFIYVLSHFLFLFLVTKITDAR VCKSDKDCKDIIIYRYILKCRNGECV KIKI (SEQ ID NO: 191) | *Medicago truncatula* |
| >gi\|152217878\|gb\|ABS31373.1\|NCR 20 | MQRLDNMAKNVKFIYVIILLLFIFLVII VCDSAFVPNSGPCTTDKDCKQVKG YIARCRKGYCMQSVKRTWSSYSR (SEQ ID NO: 192) | *Medicago truncatula* |
| >gi\|152217876\|gb\|ABS31372.1\|NCR 19 | MKFIYIMILFLSLFLVQFLTCKGLTVP CENPTTCPEDFCTPPMITRCINFICL CDGPEYAEPEYDGPEPEYDHKGDF LSVKPKIINENMMMRERHMMKEIEV (SEQ ID NO: 193) | *Medicago truncatula* |
| >gi\|152217874\|gb\|ABS31371.1\|NCR 12 | MAQFLMFIYVLIIFLYLFYVEAAMFEL TKSTIRCVTDADCPNVVKPLKPKCV DGFCEYT (SEQ ID NO: 194) | *Medicago truncatula* |

TABLE 7-continued

| Examples of NCR Peptides | | |
|---|---|---|
| NAME | Peptide sequence | Producer |
| >gi\|152217872\|gb\|ABS31370.1\|NCR 10 | MKMRIHMAQIIMFFYALIIFLSPFLVD RRSFPSSFVSPKSYTSEIPCKATRD CPYELYYETKCVDSLCTY (SEQ ID NO: 195) | *Medicago truncatula* |

Any NCR peptide known in the art is suitable for use in the methods or compositions described herein. NCR peptide-producing plants include but are not limited to *Pisum sativum* (*pea*), *Astragalus sinicus* (IRLC legumes), *Phaseolus vulgaris* (bean), *Vigna unguiculata* (cowpea), *Medicago truncatula* (barrelclover), and *Lotus japonicus*. For example, over 600 potential NCR peptides are predicted from the *M. truncatula* genome sequence and almost 150 different NCR peptides have been detected in cells isolated from root nodules by mass spectrometry.

The NCR peptides described herein may be mature or immature NCR peptides. Immature NCR peptides have a C-terminal signal peptide that is required for translocation into the endoplasmic reticulum and cleaved after translocation. The N-terminus of a NCR peptide includes a signal peptide, which may be cleavable, for targeting to a secretory pathway. NCR peptides are generally small peptides with disulfide bridges that stabilize their structure. Mature NCR peptides have a length in the range of about 20 to about 60 amino acids, about 25 to about 55 amino acids, about 30 to about 50 amino acids, about 35 to about 45 amino acids, or any range therebetween. NCR peptides may include a conserved sequence of cysteine residues with the rest of the peptide sequence highly variable. NCR peptides generally have about four or eight cysteines.

NCR peptides may be anionic, neutral, or cationic. In some instances, synthetic cationic NCR peptides having a pI greater than about eight possess antimicrobial activities. For example, NCR247 (pI=10.15) (RNGCIVDPRCPYQQCRRPLYCRRR; SEQ ID NO: 196) and NCR335 (pI=11.22) (MAQFLLFVYSLIIFLSLFFGEAAFERTETRMLTIPCTSDDNCPKVISPCHTKCFDGFCGWYIEGSYEGP; SEQ ID NO: 197) are both effective against gram-negative and gram-positive bacteria as well as fungi. In some instances, neutral and/or anionic NCR peptides, such as NCR001, do not possess antimicrobial activities at a pI greater than about 8.

In some instances, the NCR peptide is effective to kill bacteria. In some instances, the NCR peptide is effective to kill *S. meliloti, Xenorhabdus* spp, *Photorhabdus* spp, *Candidatus* spp, *Buchnera* spp, *Blattabacterium* spp, *Baumania* spp, *Wigglesworthia* spp, *Wolbachia* spp, *Rickettsia* spp, *Orientia* spp, *Sodalis* spp, *Burkholderia* spp, *Cupriavidus* spp, *Frankia* spp, *Snirhizobium* spp, *Streptococcus* spp, *Wolinella* spp, *Xylella* spp, *Erwinia* spp, *Agrobacterium* spp, *Bacillus* spp, *Paenibacillus* spp, *Streptomyces* spp, *Micrococcus* spp, *Corynebacterium* spp, *Acetobacter* spp, *Cyanobacteria* spp, *Salmonella* spp, *Rhodococcus* spp, *Pseudomonas* spp, *Lactobacillus* spp, *Enterococcus* spp, *Alcaligenes* spp, *Klebsiella* spp, *Paenibacillus* spp, *Arthrobacter* spp, *Corynebacterium* spp, *Brevibacterium* spp, *Thermus* spp, *Pseudomonas* spp, *Clostridium* spp, or *Escherichia* spp.

In some instances, the NCR peptide is a functionally active variant of a NCR peptide described herein. In some instances, the variant of the NCR peptide has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a NCR peptide described herein or naturally derived NCR peptide.

In some instances, the NCR peptide may be bioengineered to modulate its bioactivity, e.g., increase or decrease or regulate, or to specify a target microorganism. In some instances, the NCR peptide is produced by the translational machinery (e.g. a ribosome, etc.) of a cell. In some instances, the NCR peptide is chemically synthesized. In some instances, the NCR peptide is derived from a polypeptide precursor. The polypeptide precursor can undergo cleavage (for example, processing by a protease) to yield the NCR peptide itself. As such, in some instances, the NCR peptide is produced from a precursor polypeptide. In some instances, the NCR peptide includes a polypeptide that has undergone post-translational modifications, for example, cleavage, or the addition of one or more functional groups.

The NCR peptide described herein may be formulated in a composition for any of the uses described herein. The compositions disclosed herein may include any number or type of NCR peptides, such as at least about any one of 1 NCR peptide, 2, 3, 4, 5, 10, 15, 20, 30, 40, 50, 100, or more NCR peptides. A suitable concentration of each NCR peptide in the composition depends on factors such as efficacy, stability of the NCR peptide, number of distinct NCR peptide, the formulation, and methods of application of the composition. In some instances, each NCR peptide in a liquid composition is from about 0.1 ng/mL to about 100 mg/mL. In some instances, each NCR peptide in a solid composition is from about 0.1 ng/g to about 100 mg/g. In some instances, wherein the composition includes at least two types of NCR peptides, the concentration of each type of NCR peptide may be the same or different.

A modulating agent including a NCR peptide as described herein can be contacted with the target host in an amount and for a time sufficient to: (a) reach a target level (e.g., a predetermined or threshold level) of NCR peptide concentration inside a target host; (b) reach a target level (e.g., a predetermined or threshold level) of NCR peptide concentration inside a target host gut; (c) reach a target level (e.g., a predetermined or threshold level) of NCR peptide concentration inside a target host bacteriocyte; (d) modulate the level, or an activity, of one or more microorganism (e.g., endosymbiont) in the target host; or/and (e) modulate fitness of the target host.

(e) Bacteriocyte Regulatory Peptides

The modulating agent described herein may include a bacteriocyte regulatory peptide (BRP). BRPs are peptides expressed in the bacteriocytes of insects. These genes are expressed first at a developmental time point coincident with the incorporation of symbionts and their bacteriocyte-specific expression is maintained throughout the insect's life. In some instances, the BRP has a hydrophobic amino terminal domain, which is predicted to be a signal peptide. In addition, some BRPs have a cysteine-rich domain. In some instances, the bacteriocyte regulatory peptide is a bacteriocyte-specific cysteine rich (BCR) protein. Bacteriocyte regulatory peptides have a length between about 40 and 150 amino acids. In some instances, the bacteriocyte regulatory peptide has a length in the range of about 45 to about 145, about 50 to about 140, about 55 to about 135, about 60 to about 130, about 65 to about 125, about 70 to about 120, about 75 to about 115, about 80 to about 110, about 85 to about 105, or any range therebetween. Non-limiting examples of BRPs and their activities are listed in Table 8.

TABLE 8

Examples of Bacteriocyte Regulatory Peptides

| Name | Peptide Sequence |
|---|---|
| Bacteriocyte-specific cysteine rich proteins BCR family, peptide BCR1 | MKLLHGFLIIMLTMHLSIQYAYGGPFLTKYLCDRVC HKLCGDEFVCSCIQYKSLKGLWFPHCPTGKASVV LHNFLTSP (SEQ ID NO: 198) |
| Bacteriocyte-specific cysteine rich proteins BCR family, peptide BCR2 | MKLLYGFLIIMLTIHLSVQYFESPFETKYNCDTHCN KLCGKIDHCSCIQYHSMEGLWFPHCRTGSAAQML HDFLSNP (SEQ ID NO: 199) |
| Bacteriocyte-specific cysteine rich proteins BCR family, peptide BCR3 | MSVRKNVLPTMFVVLLIMSPVTPTSVFISAVCYSG CGSLALVCFVSNGITNGLDYFKSSAPLSTSETSCG EAFDTCTDHCLANFKF (SEQ ID NO: 200) |
| Bacteriocyte-specific cysteine rich proteins BCR family, peptide BCR4 | MRLLYGFLIIMLTIYLSVQDFDPTEFKGPFPTIEICS KYCAVVCNYTSRPCYCVEAAKERDQWFPYCYD (SEQ ID NO: 201) |
| Bacteriocyte-specific cysteine rich proteins BCR family, peptide BCR5 | MRLLYGFLIIMLTIHLSVQDIDPNTLRGPYPTKEICS KYCEYNVVCGASLPCICVQDARQLDHWFACCYD GGPEMLM (SEQ ID NO: 202) |
| Secreted proteins SP family, peptide SP1 | MKLFVVVVLVAVGIMFVFASDTAAAPTDYEDTND MISLSSLVGDNSPYVRVSSADSGGSSKTSSKNPIL GLLKSVIKLLTKIFGTYSDAAPAMPPIPPALRKNRG MLA (SEQ ID NO: 203) |
| Secreted proteins SP family, peptide SP2 | MVACKVILAVAVVFVAAVQGRPGGEPEWAAPIFA ELKSVSDNITNLVGLDNAGEYATAAKNNLNAFAES LKTEAAVFSKSFEGKASASDVFKESTKNFQAVVD TYIKNLPKDLTLKDFTEKSEQALKYMVEHGTEITKK AQGNTETEKEIKEFFKKQIENLIGQGKALQAKIAEA KKA (SEQ ID NO: 204) |
| Secreted proteins SP family, peptide SP3 | MKTSSSKVFASCVAIVCLASVANALPVQKSVAATT ENPIVEKHGCRAHKNLVRQNVVDLKTYDSMLITNE VVQKQSNEVQSSEQSNEGQNSEQSNEGQNSEQ SNEVQSSEHSNEGQNSKQSNEGQNSEQSNEVQ SSEHSNEGQNSEQSNEVQSSEHSNEGQNSKQS NEGQNSKQSNEVQSSEHWNEGONSKQSNEDQN SEQSNEGQNSKQSNEGQNSKQSNEDQNSEQSN EGQNSKQSNEVQSSEQSNEGQNSKQSNEGQSS EQSNEGQNSKQSNEVQSPEEHYDLPDPESSYES EETKGSHESGDDSEHR (SEQ ID NO: 205) |
| Secreted proteins SP family, peptide SP4 | MKTIILGLCLFGALFWSTQSMPVGEVAPAVPAVPS EAVPQKQVEAKPETNAASPVSDAKPESDSKPVDA EVKPTVSEVKAESEQKPSGEPKPESDAKPVVASE SKPESDPKPAAVVESKPENDAVAPETNNDAKPEN AAAPVSENKPATDAKAETELIAQAKPESKPASDLK AEPEAAKPNSEVPVALPLNPTETKATQQSVETNQ VEQAAPAAAQADPAAAPAADPAPAPAAAPVAAEE AKLSESAPSTENKAAEEPSKPAEQQSAKPVEDAV PAASEISETKVSPAVPAVPEVPASPSAPAVADPVS APEAEKNAEPAKAANSAEPAVQSEAKPAEDIQKS GAVVSAENPKPVEEQKPAEVAKPAEQSKSEAPAE APKPTEQSAAEEPKKPESANDEKKEQHSVNKRDA TKEKKPTDSIMKKQKQKKAN (SEQ ID NO: 206) |

TABLE 8-continued

| Examples of Bacteriocyte Regulatory Peptides | |
|---|---|
| Name | Peptide Sequence |
| Secreted proteins SP family, peptide SP5a | MNGKIVLCFAVVFIGQAMSAATGTTPEVEDIKKVA EQMSQTFMSVANHLVGITPNSADAQKSIEKIRTIM NKGFTDMETEANKMKDIVRKNADPKLVEKYDELE KELKKHLSTAKDMFEDKVVKPIGEKVELKKITENVI KTTKDMEATMNKAIDGFKKQ (SEQ ID NO: 207) |
| Secreted proteins SP family, peptide SP6 | MHLFLALGLFIVCGMVDATFYNPRSQTFNQLMER RQRSIPIPYSYGYHYNPIEPSINVLDSLSEGLDSRI NTFKPIYQNVKMSTQDVNSVPRTQYQPKNSLYDS EYISAKDIPSLFPEEDSYDYKYLGSPLNKYLTRPST QESGIAINLVAIKETSVFDYGFPTYKSPYSSDSVW NFGSKIPNTVFEDPQSVESDPNTFKVSSPTIKIVKL LPETPEQESIITTTKNYELNYKTTQETPTEAELYPIT SEEFQTEDEWHPMVPKENTTKDESSFITTEEPLTE DKSNSITIEKTQTEDESNSIEFNSIRTEEKSNSITTE ENQKEDDESMSTTSQETTTAFNLNDTFDTNRYSS SHESLMLRIRELMKNIADQQNKSQFRTVDNIPAKS QSNLSSDESTNQQFEPQLVNGADTYK (SEQ ID NO: 208) |
| Colepotericin A, ColA peptide | MTRTMLFLACVAALYVCISATAGKPEEFAKLSDEA PSNDQAMYESIQRYRRFVDGNRYNGGQQQQQQ PKQWEVRPDLSRDQRGNTKAQVEINKKGDNHDI NAGWGKNINGPDSHKDTWHVGGSVRW (SEQ ID NO: 209) |
| RIpA type I | MKETTVVWAKLFLILIILAKPLGLKAVNECKRLGNN SCRSHGECCSGFCFIEPGWALGVCKRLGTPKKS DDSNNGKNIEKNNGVHERIDDVFERGVCSYYKGP SITANGDVFDENEMTAAHRTLPFNTMVKVEGMGT SVVVKINDRKTAADGKVMLLSRAAAESLNIDENTG PVQCQLKFVLDGSGCTPDYGDTCVLHHECCSQN CFREMFSDKGFCLPK (SEQ ID NO: 210) |

In some instances, the BRP alters the growth and/or activity of one or more bacteria resident in the bacteriocyte of the host. In some instances, the BRP may be bioengineered to modulate its bioactivity (e.g., increase, decrease, or regulate) or to specify a target microorganism. In some instances, the BRP is produced by the translational machinery (e.g. a ribosome, etc.) of a cell. In some instances, the BRP is chemically synthesized. In some instances, the BRP is derived from a polypeptide precursor. The polypeptide precursor can undergo cleavage (for example, processing by a protease) to yield the polypeptide of the BRP itself. As such, in some instances, the BRP is produced from a precursor polypeptide. In some instances, the BRP includes a polypeptide that has undergone post-translational modifications, for example, cleavage, or the addition of one or more functional groups.

Functionally active variants of the BRPs as described herein are also useful in the compositions and methods described herein. In some instances, the variant of the BRP has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a BRP described herein or naturally derived BRP.

The BRP described herein may be formulated in a composition for any of the uses described herein. The compositions disclosed herein may include any number or type (e.g., classes) of BRPs, such as at least about any one of 1 BRP, 2, 3, 4, 5, 10, 15, 20, or more BRPs. A suitable concentration of each BRP in the composition depends on factors such as efficacy, stability of the BRP, number of distinct BRP, the formulation, and methods of application of the composition. In some instances, each BRP in a liquid composition is from about 0.1 ng/mL to about 100 mg/mL. In some instances, each BRP in a solid composition is from about 0.1 ng/g to about 100 mg/g. In some instances, wherein the composition includes at least two types of BRPs, the concentration of each type of BRP may be the same or different.

A modulating agent including a BRP as described herein can be contacted with the target host in an amount and for a time sufficient to: (a) reach a target level (e.g., a predetermined or threshold level) of BRP concentration inside a target host; (b) reach a target level (e.g., a predetermined or threshold level) of BRP concentration inside a target host gut; (c) reach a target level (e.g., a predetermined or threshold level) of BRP concentration inside a target host bacteriocyte; (d) modulate the level, or an activity, of one or more microorganism (e.g., endosymbiont) in the target host; or/and (e) modulate fitness of the target host.

iii. Small Molecules

Numerous small molecules (e.g., an antibiotic or a metabolite) may be used in the compositions and methods described herein. In some instances, an effective concentration of any small molecule described herein may alter the level, activity, or metabolism of one or more microorganisms (as described herein) resident in a host, the alteration resulting in a decrease in the host's fitness.

A modulating agent comprising a small molecule as described herein can be contacted with the target host in an amount and for a time sufficient to: (a) reach a target level (e.g., a predetermined or threshold level) of a small molecule concentration inside a target host; (b) reach a target level (e.g., a predetermined or threshold level) of small molecule concentration inside a target host gut; (c) reach a target level (e.g., a predetermined or threshold level) of a small molecule concentration inside a target host bacteriocyte; (d) modulate the level, or an activity, of one or more microorganism (e.g., endosymbiont) in the target host; or/and (e) modulate fitness of the target host.

The small molecules discussed hereinafter, namely antibiotics and secondary metabolites, can be used to alter the level, activity, or metabolism of target microorganisms as indicated in the sections for decreasing the fitness of a host insect (e.g., vector of a human pathogen), such as a mosquito, a mite, a louse, or a tick.

(a) Antibiotics

The modulating agent described herein may include an antibiotic. Any antibiotic known in the art may be used. Antibiotics are commonly classified based on their mechanism of action, chemical structure, or spectrum of activity.

The antibiotic described herein may target any bacterial function or growth processes and may be either bacteriostatic (e.g., slow or prevent bacterial growth) or bactericidal (e.g., kill bacteria). In some instances, the antibiotic is a bactericidal antibiotic. In some instances, the bactericidal antibiotic is one that targets the bacterial cell wall (e.g., penicillins and cephalosporins); one that targets the cell membrane (e.g., polymyxins); or one that inhibits essential bacterial enzymes (e.g., rifamycins, lipiarmycins, quinolones, and sulfonamides). In some instances, the bactericidal antibiotic is an aminoglycoside. In some instances, the antibiotic is a bacteriostatic antibiotic. In some instances the bacteriostatic antibiotic targets protein synthesis (e.g., macrolides, lincosamides and tetracyclines). Additional classes of antibiotics that may be used herein include cyclic lipopeptides (such as daptomycin), glycylcyclines (such as tigecycline), oxazolidinones (such as linezolid), or lipiarmycins (such as fidaxomicin). Examples of antibiotics include oxytetracycline, doxycycline, rifampicin, ciprofloxacin, ampicillin, and polymyxin B. Other non-limiting examples of antibiotics are found in Table 9.

TABLE 9

Examples of Antibiotics

| Antibiotics | Action |
|---|---|
| Penicillins, cephalosporins, vancomycin | Cell wall synthesis |
| Polymixin, gramicidin | Membrane active agent, disrupt cell membrane |
| Tetracyclines, macrolides, chloramphenicol, clindamycin, spectinomycin | Inhibit protein synthesis |
| Sulfonamides | Inhibit folate-dependent pathways |
| Ciprofloxacin | Inhibit DNA-gyrase |
| Isoniazid, rifampicin, pyrazinamide, ethambutol, (myambutol)l, streptomycin | Antimycobacterial agents |

The antibiotic described herein may have any level of target specificity (e.g., narrow- or broad-spectrum). In some instances, the antibiotic is a narrow-spectrum antibiotic, and thus targets specific types of bacteria, such as gram-negative or gram-positive bacteria. Alternatively, the antibiotic may be a broad-spectrum antibiotic that targets a wide range of bacteria.

The antibiotics described herein may be formulated in a composition for any of the uses described herein. The compositions disclosed herein may include any number or type (e.g., classes) of antibiotics, such as at least about any one of 1 antibiotic, 2, 3, 4, 5, 10, 15, 20, or more antibiotics (e.g., a combination of rifampicin and doxycycline, or a combination of ampicillin and rifampicin). A suitable concentration of each antibiotic in the composition depends on factors such as efficacy, stability of the antibiotic, number of distinct antibiotics, the formulation, and methods of application of the composition. In some instances, wherein the composition includes at least two types of antibiotics, the concentration of each type of antibiotic may be the same or different.

A modulating agent including an antibiotic as described herein can be contacted with the target host in an amount and for a time sufficient to: (a) reach a target level (e.g., a predetermined or threshold level) of antibiotic concentration inside a target host; (b) reach a target level (e.g., a predetermined or threshold level) of antibiotic concentration inside a target host gut; (c) reach a target level (e.g., a predetermined or threshold level) of antibiotic concentration inside a target host bacteriocyte; (d) modulate the level, or an activity, of one or more microorganism (e.g., endosymbiont) in the target host; or/and (e) modulate fitness of the target host.

As illustrated by Examples 1-4, 10, 14, 26, and 27, antibiotics (e.g., doxycycline, oxytetracycline, azithromycin, ciprofloxacin, or rifampicin) can be used as modulating agents that target an endosymbiotic bacterium, such as a *Wolbachia* spp., in an insect host (e.g., an insect vector of an animal pathogen), such as a mosquito or mite or tick or biting louse, to decrease the fitness of the host (e.g., as outlined herein). As illustrated by Example 3, antibiotics such as oxytetracycline can be used as modulating agents that target an endosymbiotic bacterium, such as a *Rickettsia* spp., in an insect host, such as ticks, to decrease the fitness of the host (e.g., as outlined herein).

(b) Secondary Metabolites

In some instances, the modulating agent of the compositions and methods described herein includes a secondary metabolite. Secondary metabolites are derived from organic molecules produced by an organism. Secondary metabolites may act (i) as competitive agents used against bacteria, fungi, amoebae, plants, insects, and large animals; (ii) as metal transporting agents; (iii) as agents of symbiosis between microbes and plants, insects, and higher animals; (iv) as sexual hormones; and (v) as differentiation effectors. Non-limiting examples of secondary metabolites are found in Table 10.

TABLE 10

Examples of Secondary Metabolites

| Phenylpropanoids | Alkaloids | Terpenoids | Quinones | Steroids | Polyketides |
|---|---|---|---|---|---|
| Anthocyanins | Acridines | Carotenes | Anthroquinones | Cardiac | Erythromycin |

TABLE 10-continued

| Examples of Secondary Metabolites | | | | | |
|---|---|---|---|---|---|
| Phenyl-propanoids | Alkaloids | Terpenoids | Quinones | Steroids | Polyketides |
| Coumarins | Betalaines | Monoterpenes | Bezo-quinones | Glycosides | Lovastatin and other statins |
| Flavonoids | Quinolozidines | Sesquiterpenes | Naphtho-quinones | Pregnen-olone | Discoder-molide |
| Hydroxy-cinnamoyl | Furono-quinones | Diterpenes | | Derivatives | Aflatoxin B1 |
| Derivatives | Harring-tonines | Triterpenes | | | Avermectins |
| Isoflavonoids | Isoquino-lines | | | | Nystatin |
| Lignans | Indoles | | | | Rifamycin |
| Phenolenones | Purines | | | | |
| Proantho-cyanidins | Pyridines | | | | |
| Stilbenes | Tropane | | | | |
| Tanins | Alkaloids | | | | |

The secondary metabolite used herein may include a metabolite from any known group of secondary metabolites. For example, secondary metabolites can be categorized into the following groups: alkaloids, terpenoids, flavonoids, glycosides, natural phenols (e.g., gossypol acetic acid), enals (e.g., trans-cinnamaldehyde), phenazines, biphenols and dibenzofurans, polyketides, fatty acid synthase peptides, nonribosomal peptides, ribosomally synthesized and post-translationally modified peptides, polyphenols polysaccharides (e.g., chitosan), and biopolymers. For an in-depth review of secondary metabolites see, for example, Vining, Annu. Rev. Microbiol. 44:395-427, 1990.

Secondary metabolites useful for compositions and methods described herein include those that alter a natural function of an endosymbiont (e.g., primary or secondary endosymbiont), bacteriocyte, or extracellular symbiont. In some instances, one or more secondary metabolites described herein is isolated from a high throughput screening (HTS) for antimicrobial compounds. For example, a HTS screen identified 49 antibacterial extracts that have specificity against gram positive and gram negative bacteria from over 39,000 crude extracts from organisms growing in diverse ecosystems of one specific region. In some instances, the secondary metabolite is transported inside a bacteriocyte.

In some instances, the small molecule is an inhibitor of vitamin synthesis. In some instances, the vitamin synthesis inhibitor is a vitamin precursor analog. In certain instances, the vitamin precursor analog is pantothenol.

In some instances, the small molecule is an amino acid analog. In certain instances, the amino acid analog is L-canvanine, D-arginine, D-valine, D-methionine, D-phenylalanine, D-histidine, D-tryptophan, D-threonine, D-leucine, L-NG-nitroarginine, or a combination thereof.

In some instances the small molecule is a natural antimicrobial compound, such as propionic acid, levulinic acid, trans-cinnemaldehdye, nisin, or low molecular weight chitosan.

The secondary metabolite described herein may be formulated in a composition for any of the uses described herein. The compositions disclosed herein may include any number or type (e.g., classes) of secondary metabolites, such as at least about any one of 1 secondary metabolite, 2, 3, 4, 5, 10, 15, 20, or more secondary metabolites. A suitable concentration of each secondary metabolite in the composition depends on factors such as efficacy, stability of the secondary metabolite, number of distinct secondary metabolites, the formulation, and methods of application of the composition. In some instances, wherein the composition includes at least two types of secondary metabolites, the concentration of each type of secondary metabolite may be the same or different.

A modulating agent including a secondary metabolite as described herein can be contacted with the target host in an amount and for a time sufficient to: (a) reach a target level (e.g., a predetermined or threshold level) of secondary metabolite concentration inside a target host; (b) reach a target level (e.g., a predetermined or threshold level) of secondary metabolite concentration inside a target host gut; (c) reach a target level (e.g., a predetermined or threshold level) of secondary metabolite concentration inside a target host bacteriocyte; (d) modulate the level, or an activity, of one or more microorganism (e.g., endosymbiont) in the target host; or/and (e) modulate fitness of the target host.

As illustrated by Example 15, secondary metabolites (e.g., gossypol) can be used as modulating agents that target an endosymbiotic bacterium in an insect host to decrease the fitness of the host (e.g., as outlined herein). As further illustrated by Examples 11-13, 17-19, 23, and 24, small molecules, such as trans-cinnemaldehyde, levulinic acid, chitosan, vitamin analogs, or amino acid transport inhibitors, can also be used as modulating agents that target an endosymbiotic bacterium in an insect host to decrease the fitness of the host (e.g., as outlined herein).

iv. Bacteria as Modulating Agents

In some instances, the modulating agent described herein includes one or more bacteria. Numerous bacteria are useful in the compositions and methods described herein. In some instances, the agent is a bacterial species endogenously found in the host. In some instances, the bacterial modulating agent is an endosymbiotic bacterial species. Non-limiting examples of bacteria that may be used as modulating agents include all bacterial species described herein in Section II of the detailed description and those listed in Table 1. For example, the modulating agent may be a bacterial species from any bacterial phyla present in insect guts, including Gammaproteobacteria, Alphaproteobacteria, Betaproteobacteria, Bacteroidetes, Firmicutes (e.g., *Lactobacillus* and *Bacillus* spp.), Clostridia, Actinomycetes, Spirochetes, Verrucomicrobia, and Actinobacteria.

In some instances, the modulating agent is a bacterium that disrupts microbial diversity or otherwise alters the microbiota of the host in a manner detrimental to the host. In one instance, bacteria may be provided to disrupt the microbiota of mosquitos. For example, the bacterial modulating agent may compete with, displace, and/or reduce a population of symbiotic bacteria in a mosquito.

In another instance, bacteria may be provided to disrupt the microbiota of mites. For example, the bacterial modulating agent may compete with, displace, and/or reduce a population of symbiotic bacteria in a mite.

In another instance, bacteria may be provided to disrupt the microbiota of biting louse. For example, the bacterial modulating agent may compete with, displace, and/or reduce a population of symbiotic bacteria in a biting louse.

In another instance, bacteria may be provided to disrupt the microbiota of ticks. For example, the bacterial modulating agent may compete with, displace, and/or reduce a population of symbiotic bacteria in a tick.

The bacterial modulating agents discussed herein can be used to alter the level, activity, or metabolism of target microorganisms as indicated in the sections for decreasing the fitness of a host insect (e.g., a vector of a human pathogen), such as a mosquito a mite, a biting louse, or a tick.

v. Modifications to Modulating Agents (a) Fusions

Any of the modulating agents described herein may be fused or linked to an additional moiety. In some instances, the modulating agent includes a fusion of one or more additional moieties (e.g., 1 additional moiety, 2, 3, 4, 5, 6, 7, 8, 9, 10, or more additional moieties). In some instances, the additional moiety is any one of the modulating agents described herein (e.g., a peptide, polypeptide, small molecule, or antibiotic). Alternatively, the additional moiety may not act as modulating agent itself but may instead serve a secondary function. For example, the additional moiety may to help the modulating agent access, bind, or become activated at a target site in the host (e.g., at a host gut or a host bacteriocyte) or at a target microorganism resident in the host (e.g., a vector of a human pathogen, e.g., a mosquito, a mite, a biting louse, or a tick).

In some instances, the additional moiety may help the modulating agent penetrate a target host cell or target microorganism resident in the host. For example, the additional moiety may include a cell penetrating peptide. Cell penetrating peptides (CPPs) may be natural sequences derived from proteins; chimeric peptides that are formed by the fusion of two natural sequences; or synthetic CPPs, which are synthetically designed sequences based on structure-activity studies. In some instances, CPPs have the capacity to ubiquitously cross cellular membranes (e.g., prokaryotic and eukaryotic cellular membranes) with limited toxicity. Further, CPPs may have the capacity to cross cellular membranes via energy-dependent and/or independent mechanisms, without the necessity of a chiral recognition by specific receptors. CPPs can be bound to any of the modulating agents described herein. For example, a CPP can be bound to an antimicrobial peptide (AMP), e.g., a scorpion peptide, e.g., UY192 fused to a cell penetrating peptide (e.g., YGRKKRRQRRRFLSTIWNGIKGLLFAM; SEQ ID NO: 232). Non-limiting examples of CPPs are listed in Table 11.

TABLE 1

Examples of Cell Penetrating Peptides (CPPs)

| Peptide | Origin | Sequence |
|---|---|---|
| Protein-derived | | |
| Penetratin | Antennapedia | RQIKIWFQNRRMKWKK (SEQ ID NO: 213) |
| Tat peptide | Tat | GRKKRRQRRRPPQ (SEQ ID NO: 214) |
| pVEC | Cadherin | LLIILRRRIRKQAHAHSK (SEQ ID NO: 215) |
| Chimeric | | |
| Transportan | Galanine/ Mastoparan | GWTLNSAGYLLGKINLKALAA LAKKIL (SEQ ID NO: 216) |
| MPG | HIV-gp41/SV40 T-antigen | GALFLGFLGAAGSTMGAWSQP KKKRKV (SEQ ID NO: 217) |
| Pep-1 | HIV-reverse transcriptase/ SV40 T-antigen | KETWWETWWTEWSQPKKKRKV (SEQ ID NO: 218) |
| Synthetic | | |
| Poly-arginines | Based on Tat peptide | $(R)_n$; 6 < n < 12 |
| MAP | de novo | KLALKLALKALKAALKLA (SEQ ID NO: 219) |
| $R_6W_3$ | Based on penetratin | RRWWRRWRR (SEQ ID NO: 220) |

In other instances, the additional moiety helps the modulating agent bind a target microorganism (e.g., a fungi or bacterium) resident in the host. The additional moiety may include one or more targeting domains. In some instances, the targeting domain may target the modulating agent to one or more microorganisms (e.g., bacterium or fungus) resident in the gut of the host. In some instances, the targeting domain may target the modulating agent to a specific region of the host (e.g., host gut or bacteriocyte) to access microorganisms that are generally present in said region of the host. For example, the targeting domain may target the modulating agent to the foregut, midgut, or hindgut of the host. In other instances, the targeting domain may target the modulating agent to a bacteriocyte in the host and/or one or more specific bacteria resident in a host bacteriocyte. For example, the targeting domain may be *Galanthus nivalis* lectin or agglutinin (GNA) bound to a modulating agent described herein, e.g., an AMP, e.g., a scorpion peptide, e.g., Uy192.

(b) Pre- or Pro-Domains

In some instances, the modulating agent may include a pre- or pro-amino acid sequence. For example, the modulating agent may be an inactive protein or peptide that can be activated by cleavage or post-translational modification of a pre- or pro-sequence. In some instances, the modulating agent is engineered with an inactivating pre- or pro-sequence. For example, the pre- or pro-sequence may obscure an activation site on the modulating agent, e.g., a receptor binding site, or may induce a conformational change in the modulating agent. Thus, upon cleavage of the pre- or pro-sequence, the modulating agent is activated.

Alternatively, the modulating agent may include a pre- or pro-small molecule, e.g., an antibiotic. The modulating agent may be an inactive small molecule described herein that can be activated in a target environment inside the host. For example, the small molecule may be activated upon reaching a certain pH in the host gut.

(c) Linkers

In instances where the modulating agent is connected to an additional moiety, the modulating agent may further include a linker. For example, the linker may be a chemical bond, e.g., one or more covalent bonds or non-covalent bonds. In some instances, the linker may be a peptide linker (e.g., 2, 3, 4, 5, 6, 8, 10, 12, 14, 16, 20, 25, 30, 35, 40, or more amino acids longer). The linker may be include any flexible, rigid, or cleavable linkers described herein.

A flexible peptide linker may include any of those commonly used in the art, including linkers having sequences having primarily Gly and Ser residues ("GS" linker). Flexible linkers may be useful for joining domains that require a certain degree of movement or interaction and may include small, non-polar (e.g. Gly) or polar (e.g. Ser or Thr) amino acids.

Alternatively, a peptide linker may be a rigid linker. Rigid linkers are useful to keep a fixed distance between moieties and to maintain their independent functions. Rigid linkers may also be useful when a spatial separation of the domains is critical to preserve the stability or bioactivity of one or more components in the fusion. Rigid linkers may, for example, have an alpha helix-structure or Pro-rich sequence, $(XP)_n$, with X designating any amino acid, preferably Ala, Lys, or Glu.

In yet other instances, a peptide linker may be a cleavable linker. In some instances, linkers may be cleaved under specific conditions, such as the presence of reducing reagents or proteases. In vivo cleavable linkers may utilize the reversible nature of a disulfide bond. One example includes a thrombin-sensitive sequence (e.g., PRS) between two Cys residues. In vitro thrombin treatment of CPRSC results in the cleavage of the thrombin-sensitive sequence, while the reversible disulfide linkage remains intact. Such linkers are known and described, e.g., in Chen et al., *Adv. Drug Deliv. Rev.* 65(10):1357-1369, 2013. Cleavage of linkers in fusions may also be carried out by proteases that are expressed in vivo under conditions in specific cells or tissues of the host or microorganisms resident in the host. In some instances, cleavage of the linker may release a free functional, modulating agent upon reaching a target site or cell.

Fusions described herein may alternatively be linked by a linking molecule, including a hydrophobic linker, such as a negatively charged sulfonate group; lipids, such as a poly ($-CH_2-$) hydrocarbon chains, such as polyethylene glycol (PEG) group, unsaturated variants thereof, hydroxylated variants thereof, amidated or otherwise N-containing variants thereof, non-carbon linkers; carbohydrate linkers; phosphodiester linkers, or other molecule capable of covalently linking two or more molecules, e.g., two modulating agents. Non-covalent linkers may be used, such as hydrophobic lipid globules to which the modulating agent is linked, for example, through a hydrophobic region of the modulating agent or a hydrophobic extension of the modulating agent, such as a series of residues rich in leucine, isoleucine, valine, or perhaps also alanine, phenylalanine, or even tyrosine, methionine, glycine, or other hydrophobic residue. The modulating agent may be linked using charge-based chemistry, such that a positively charged moiety of the modulating agent is linked to a negative charge of another modulating agent or an additional moiety.

IV. Formulations and Compositions

The compositions described herein may be formulated either in pure form (e.g., the composition contains only the modulating agent) or together with one or more additional agents (such as excipient, delivery vehicle, carrier, diluent, stabilizer, etc.) to facilitate application or delivery of the compositions. Examples of suitable excipients and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate, and mineral oil.

In some instances, the composition includes a delivery vehicle or carrier. In some instances, the delivery vehicle includes an excipient. Exemplary excipients include, but are not limited to, solid or liquid carrier materials, solvents, stabilizers, slow-release excipients, colorings, and surface-active substances (surfactants). In some instances, the delivery vehicle is a stabilizing vehicle. In some instances, the stabilizing vehicle includes a stabilizing excipient. Exemplary stabilizing excipients include, but are not limited to, epoxidized vegetable oils, antifoaming agents, e.g. silicone oil, preservatives, viscosity regulators, binding agents and tackifiers. In some instances, the stabilizing vehicle is a buffer suitable for the modulating agent. In some instances, the composition is microencapsulated in a polymer bead delivery vehicle. In some instances, the stabilizing vehicle protects the modulating agent against UV and/or acidic conditions. In some instances, the delivery vehicle contains a pH buffer. In some instances, the composition is formulated to have a pH in the range of about 4.5 to about 9.0, including for example pH ranges of about any one of 5.0 to about 8.0, about 6.5 to about 7.5, or about 6.5 to about 7.0.

Depending on the intended objectives and prevailing circumstances, the composition may be formulated into emulsifiable concentrates, suspension concentrates, directly sprayable or dilutable solutions, coatable pastes, diluted emulsions, spray powders, soluble powders, dispersible powders, wettable powders, dusts, granules, encapsulations in polymeric substances, microcapsules, foams, aerosols, carbon dioxide gas preparations, tablets, resin preparations, paper preparations, nonwoven fabric preparations, or knitted or woven fabric preparations. In some instances, the composition is a liquid. In some instances, the composition is a solid. In some instances, the composition is an aerosol, such as in a pressurized aerosol can. In some instances, the composition is present in the waste (such as feces) of the pest. In some instances, the composition is present in or on a live pest.

In some instances, the delivery vehicle is the food or water of the host. In other instances, the delivery vehicle is a food source for the host. In some instances, the delivery vehicle is a food bait for the host. In some instances, the composition is a comestible agent consumed by the host. In some instances, the composition is delivered by the host to a second host, and consumed by the second host. In some instances, the composition is consumed by the host or a second host, and the composition is released to the surrounding of the host or the second host via the waste (such as feces) of the host or the second host. In some instances, the modulating agent is included in food bait intended to be consumed by a host or carried back to its colony.

In some instances, the modulating agent may make up about 0.1% to about 100% of the composition, such as any one of about 0.01% to about 100%, about 1% to about 99.9%, about 0.1% to about 10%, about 1% to about 25%, about 10% to about 50%, about 50% to about 99%, or about 0.1% to about 90% of active ingredients (such as phage, lysin or bacteriocin). In some instances, the composition includes at least any of 0.1%, 0.5%, 1%, 5%, 10%, 20%, 30%, 40%, 50%, 60%, 70%, 80%, 90%, 95%, or more active ingredients (such as phage, lysin or bacteriocin). In some instances, the concentrated agents are preferred as commercial products, the final user normally uses diluted agents, which have a substantially lower concentration of active ingredient.

Any of the formulations described herein may be used in the form of a bait, a coil, an electric mat, a smoking preparation, a fumigant, or a sheet.

i. Liquid Formulations

The compositions provided herein may be in a liquid formulation. Liquid formulations are generally mixed with water, but in some instances may be used with crop oil, diesel fuel, kerosene or other light oil as a carrier. The amount of active ingredient often ranges from about 0.5 to about 80 percent by weight.

An emulsifiable concentrate formulation may contain a liquid active ingredient, one or more petroleum-based solvents, and an agent that allows the formulation to be mixed with water to form an emulsion. Such concentrates may be used in agricultural, ornamental and turf, forestry, structural, food processing, livestock, and public health pest formulations. These may be adaptable to application equipment from small portable sprayers to hydraulic sprayers, low-volume ground sprayers, mist blowers, and low-volume aircraft sprayers. Some active ingredients are readily dissolve in a liquid carrier. When mixed with a carrier, they form a solution that does not settle out or separate, e.g., a homogenous solution. Formulations of these types may include an active ingredient, a carrier, and one or more other ingredients. Solutions may be used in any type of sprayer, indoors and outdoors.

In some instances, the composition may be formulated as an invert emulsion. An invert emulsion is a water-soluble active ingredient dispersed in an oil carrier. Invert emulsions require an emulsifier that allows the active ingredient to be mixed with a large volume of petroleum-based carrier, usually fuel oil. Invert emulsions aid in reducing drift. With other formulations, some spray drift results when water droplets begin to evaporate before reaching target surfaces; as a result the droplets become very small and lightweight. Because oil evaporates more slowly than water, invert emulsion droplets shrink less and more active ingredient reaches the target. Oil further helps to reduce runoff and improve rain resistance. It further serves as a sticker-spreader by improving surface coverage and absorption. Because droplets are relatively large and heavy, it is difficult to get thorough coverage on the undersides of foliage. Invert emulsions are most commonly used along rights-of-way where drift to susceptible non-target areas can be a problem.

A flowable or liquid formulation combines many of the characteristics of emulsifiable concentrates and wettable powders. Manufacturers use these formulations when the active ingredient is a solid that does not dissolve in either water or oil. The active ingredient, impregnated on a substance such as clay, is ground to a very fine powder. The powder is then suspended in a small amount of liquid. The resulting liquid product is quite thick. Flowables and liquids share many of the features of emulsifiable concentrates, and they have similar disadvantages. They require moderate agitation to keep them in suspension and leave visible residues, similar to those of wettable powders.

Flowables/liquids are easy to handle and apply. Because they are liquids, they are subject to spilling and splashing. They contain solid particles, so they contribute to abrasive wear of nozzles and pumps. Flowable and liquid suspensions settle out in their containers. Because flowable and liquid formulations tend to settle, packaging in containers of five gallons or less makes remixing easier.

Aerosol formulations contain one or more active ingredients and a solvent. Most aerosols contain a low percentage of active ingredients. There are two types of aerosol formulations—the ready-to-use type commonly available in pressurized sealed containers and those products used in electrical or gasoline-powered aerosol generators that release the formulation as a smoke or fog.

Ready to use aerosol formulations are usually small, self-contained units that release the formulation when the nozzle valve is triggered. The formulation is driven through a fine opening by an inert gas under pressure, creating fine droplets. These products are used in greenhouses, in small areas inside buildings, or in localized outdoor areas. Commercial models, which hold five to 5 pounds of active ingredient, are usually refillable.

Smoke or fog aerosol formulations are not under pressure. They are used in machines that break the liquid formulation into a fine mist or fog (aerosol) using a rapidly whirling disk or heated surface.

ii. Dry or Solid Formulations

Dry formulations can be divided into two types: ready-to-use and concentrates that must be mixed with water to be applied as a spray. Most dust formulations are ready to use and contain a low percentage of active ingredients (less than about 10 percent by weight), plus a very fine, dry inert carrier made from talc, chalk, clay, nut hulls, or volcanic ash. The size of individual dust particles varies. A few dust formulations are concentrates and contain a high percentage of active ingredients. Mix these with dry inert carriers before applying. Dusts are always used dry and can easily drift to non-target sites.

iii. Granule or Pellet Formulations

In some instances, the composition is formulated as granules. Granular formulations are similar to dust formulations, except granular particles are larger and heavier. The coarse particles may be made from materials such as clay, corncobs, or walnut shells. The active ingredient either coats the outside of the granules or is absorbed into them. The amount of active ingredient may be relatively low, usually ranging from about 0.5 to about 15 percent by weight. Granular formulations are most often used to apply to the soil, insects living in the soil, or absorption into plants through the roots. Granular formulations are sometimes applied by airplane or helicopter to minimize drift or to penetrate dense vegetation. Once applied, granules may release the active ingredient slowly. Some granules require soil moisture to release the active ingredient. Granular formulations also are used to control larval mosquitoes and other aquatic pests. Granules are used in agricultural, structural, ornamental, turf, aquatic, right-of-way, and public health (biting insect) pest-control operations.

In some instances, the composition is formulated as pellets. Most pellet formulations are very similar to granular formulations; the terms are used interchangeably. In a pellet formulation, however, all the particles are the same weight and shape. The uniformity of the particles allows use with precision application equipment.

iv. Powders

In some instances, the composition is formulated as a powder. In some instances, the composition is formulated as a wettable powder. Wettable powders are dry, finely ground formulations that look like dusts. They usually must be mixed with water for application as a spray. A few products, however, may be applied either as a dust or as a wettable powder—the choice is left to the applicator. Wettable powders have about 1 to about 95 percent active ingredient by weight; in some cases more than about 50 percent. The particles do not dissolve in water. They settle out quickly unless constantly agitated to keep them suspended. They can be used for most pest problems and in most types of spray equipment where agitation is possible. Wettable powders have excellent residual activity. Because of their physical properties, most of the formulation remains on the surface of treated porous materials such as concrete, plaster, and untreated wood. In such cases, only the water penetrates the material.

In some instances, the composition is formulated as a soluble powder. Soluble powder formulations look like wettable powders. However, when mixed with water, soluble powders dissolve readily and form a true solution. After they are mixed thoroughly, no additional agitation is necessary. The amount of active ingredient in soluble powders ranges from about 15 to about 95 percent by weight; in some cases more than about 50 percent. Soluble powders have all the advantages of wettable powders and none of the disadvantages, except the inhalation hazard during mixing.

In some instances, the composition is formulated as a water-dispersible granule. Water-dispersible granules, also known as dry flowables, are like wettable powders, except instead of being dust-like, they are formulated as small, easily measured granules. Water-dispersible granules must be mixed with water to be applied. Once in water, the granules break apart into fineparticles similar to wettable powders. The formulation requires constant agitation to keep it suspended in water. The percentage of active ingredient is high, often as much as 90 percent by weight. Water-dispersible granules share many of the same advantages and disadvantages of wettable powders, except they are more easily measured and mixed. Because of low dust, they cause less inhalation hazard to the applicator during handling v. Bait In some instances, the composition includes a bait. The bait can be in any suitable form, such as a solid, paste, pellet or powdered form. The bait can also be carried away by the host back to a population of said host (e.g., a colony or hive). The bait can then act as a food source for other members of the colony, thus providing an effective modulating agent for a large number of hosts and potentially an entire host colony.

The baits can be provided in a suitable "housing" or "trap." Such housings and traps are commercially available and existing traps can be adapted to include the compositions described herein. The housing or trap can be box-shaped for example, and can be provided in pre-formed condition or can be formed of foldable cardboard for example. Suitable materials for a housing or trap include plastics and cardboard, particularly corrugated cardboard. The inside surfaces of the traps can be lined with a sticky substance in order to restrict movement of the host once inside the trap. The housing or trap can contain a suitable trough inside which can hold the bait in place. A trap is distinguished from a housing because the host cannot readily leave a trap following entry, whereas a housing acts as a "feeding station" which provides the host with a preferred environment in which they can feed and feel safe from predators.

vi. Attractants

In some instances, the composition includes an attractant (e.g., a chemoattractant). The attractant may attract an adult host or immature host (e.g., larva) to the vicinity of the composition.

Attractants include pheromones, a chemical that is secreted by an animal, especially an insect, which influences the behavior or development of others of the same species. Other attractants include sugar and protein hydrolysate syrups, yeasts, and rotting meat. Attractants also can be combined with an active ingredient and sprayed onto foliage or other items in the treatment area.

Various attractants are known which influence host behavior as a host's search for food, oviposition or mating sites, or mates. Attractants useful in the methods and compositions described herein include, for example, eugenol, phenethyl propionate, ethyl dimethylisobutyl-cyclopropane carboxylate, propyl benszodioxancarboxylate, cis-7,8-epoxy-2-methyloctadecane, trans-8,trans-0-dodecadienol, cis-9-tetradecenal (with cis-11-hexadecenal), trans-11-tetradecenal, cis-11-hexadecenal, (Z)-11,12-hexadecadienal, cis-7-dodecenyl acetate, cis-8-dodecenyul acetate, cis-9-dodecenyl acetate, cis-9-tetradecenyl acetate, cis-11-tetradecenyl acetate, trans-11-tetradecenyl acetate (with cis-11), cis-9, trans-11-tetradecadienyl acetate (with cis-9,trans-12), cis-9, trans-1 2-tetradecadienyl acetate, cis-7,cis-11-hexadecadienyl acetate (with cis-7,trans-11), cis-3,cis-13-octadecadienyl acetate, trans-3,cis-13-octadecadienyl acetate, anethole and isoamyl salicylate.

Means other than chemoattractants may also be used to attract insects, including lights in various wavelengths or colors.

vii. Nanocapsules/Microencapsulation/Liposomes

In some instances, the composition is provided in a microencapsulated formulation. Microencapsulated formulations are mixed with water and sprayed in the same manner as other sprayable formulations. After spraying, the plastic coating breaks down and slowly releases the active ingredient.

viii. Carriers

Any of the compositions described herein may be formulated to include the modulating agent described herein and an inert carrier. Such carrier can be a solid carrier, a liquid carrier, a gel carrier, and/or a gaseous carrier. In certain instances, the carrier can be a seed coating. The seed coating is any non-naturally occurring formulation that adheres, in whole or part, to the surface of the seed. The formulation may further include an adjuvant or surfactant. The formulation can also include one or more modulating agents to enlarge the action spectrum.

A solid carrier used for formulation includes finely-divided powder or granules of clay (e.g. kaolin clay, diatomaceous earth, bentonite, Fubasami clay, acid clay, etc.), synthetic hydrated silicon oxide, talc, ceramics, other inorganic minerals (e.g., sericite, quartz, sulfur, activated carbon, calcium carbonate, hydrated silica, etc.), a substance which can be sublimated and is in the solid form at room temperature (e.g., 2,4,6-triisopropyl-1,3,5-trioxane, naphthalene, p-dichlorobenzene, camphor, adamantan, etc.); wool; silk; cotton; hemp; pulp; synthetic resins (e.g., polyethylene resins such as low-density polyethylene, straight low-density polyethylene and high-density polyethylene; ethylene-vinyl ester copolymers such as ethylene-vinyl acetate copolymers; ethylene-methacrylic acid ester copolymers such as ethylene-methyl methacrylate copolymers and ethylene-ethyl methacrylate copolymers; ethylene-acrylic acid ester copolymers such as ethylene-methyl acrylate copolymers and ethylene-ethyl acrylate copolymers; ethylene-vinylcarboxylic acid copolymers such as ethylene-acrylic acid copolymers; ethylene-tetracyclododecene copolymers; polypropylene resins such as propylene homopolymers and propylene-ethylene copolymers; poly-4-methylpentene-1, polybutene-1, polybutadiene, polystyrene; acrylonitrile-styrene resins; styrene elastomers such as acrylonitrile-butadiene-styrene resins, styrene-conjugated diene block copolymers, and styrene-conjugated diene block copolymer hydrides; fluororesins; acrylic resins such as poly(methyl methacrylate); polyamide resins such as nylon 6 and nylon 66; polyester resins such as polyethylene terephthalate, polyethylene naphthalate, polybutylene terephthalate, and polycyclohexylenedimethylene terephthalate; polycarbonates, polyacetals, polyacrylsulfones, polyarylates, hydroxybenzoic acid polyesters, polyetherimides, polyester carbonates, polyphenylene ether resins, polyvinyl chloride, polyvinylidene chloride, polyurethane, and porous resins such as foamed polyurethane, foamed polypropylene, or foamed ethylene, etc.), glasses, metals, ceramics, fibers, cloths, knitted fabrics, sheets, papers, yarn, foam, porous substances, and multifilaments.

A liquid carrier may include, for example, aromatic or aliphatic hydrocarbons (e.g., xylene, toluene, alkylnaphthalene, phenylxylylethane, kerosine, gas oil, hexane, cyclohexane, etc.), halogenated hydrocarbons (e.g., chlorobenzene, dichloromethane, dichloroethane, trichloroethane, etc.), alcohols (e.g., methanol, ethanol, isopropyl alcohol, butanol, hexanol, benzyl alcohol, ethylene glycol, etc.), ethers (e.g., diethyl ether, ethylene glycol dimethyl ether, diethylene glycol monomethyl ether, diethylene glycol monoethyl ether, propylene glycol monomethyl ether, tetrahydrofuran, dioxane, etc.), esters (e.g., ethyl acetate, butyl acetate, etc.), ketones (e.g., acetone, methyl ethyl ketone, methyl isobutyl ketone, cyclohexanone, etc.), nitriles (e.g., acetonitrile, isobutyronitrile, etc.), sulfoxides (e.g., dimethyl sulfoxide, etc.), amides (e.g., N,N-dimethylformamide, N,N-dimethylacetamide, cyclic imides (e.g. N-methylpyrrolidone) alkylidene carbonates (e.g., propylene carbonate, etc.), vegetable oil (e.g., soybean oil, cottonseed oil, etc.), vegetable essential oils (e.g., orange oil, hyssop oil, lemon oil, etc.), or water.

A gaseous carrier may include, for example, butane gas, flon gas, liquefied petroleum gas (LPG), dimethyl ether, and carbon dioxide gas.

ix. Adjuvants

In some instances, the composition provided herein may include an adjuvant. Adjuvants are chemicals that do not possess activity. Adjuvants are either pre-mixed in the formulation or added to the spray tank to improve mixing or application or to enhance performance. They are used extensively in products designed for foliar applications. Adjuvants can be used to customize the formulation to specific needs and compensate for local conditions. Adjuvants may be designed to perform specific functions, including wetting, spreading, sticking, reducing evaporation, reducing volatilization, buffering, emulsifying, dispersing, reducing spray drift, and reducing foaming. No single adjuvant can perform all these functions, but compatible adjuvants often can be combined to perform multiple functions simultaneously.

Among nonlimiting examples of adjuvants included in the formulation are binders, dispersants and stabilizers, specifically, for example, casein, gelatin, polysaccharides (e.g., starch, gum arabic, cellulose derivatives, alginic acid, etc.), lignin derivatives, bentonite, sugars, synthetic water-soluble polymers (e.g., polyvinyl alcohol, polyvinylpyrrolidone, polyacrylic acid, etc.), PAP (acidic isopropyl phosphate), BHT (2,6-di-t-butyl-4-methylphenol), BHA (a mixture of 2-t-butyl-4-methoxyphenol and 3-t-butyl-4-methoxyphenol), vegetable oils, mineral oils, fatty acids and fatty acid esters.

x. Surfactants

In some instances, the composition provided herein includes a surfactant. Surfactants, also called wetting agents and spreaders, physically alter the surface tension of a spray droplet. For a formulation to perform its function properly, a spray droplet must be able to wet the foliage and spread out evenly over a leaf. Surfactants enlarge the area of formulation coverage, thereby increasing the pest's exposure to the chemical. Surfactants are particularly important when applying a formulation to waxy or hairy leaves. Without proper wetting and spreading, spray droplets often run off or fail to cover leaf surfaces adequately. Too much surfactant, however, can cause excessive runoff and reduce efficacy.

Surfactants are classified by the way they ionize or split apart into electrically charged atoms or molecules called ions. A surfactant with a negative charge is anionic. One with a positive charge is cationic, and one with no electrical charge is nonionic. Formulation activity in the presence of a nonionic surfactant can be quite different from activity in the presence of a cationic or anionic surfactant. Selecting the wrong surfactant can reduce the efficacy of a pesticide product and injure the target plant. Anionic surfactants are most effective when used with contact pesticides (pesticides that control the pest by direct contact rather than being absorbed systemically). Cationic surfactants should never be used as stand-alone surfactants because they usually are phytotoxic.

Nonionic surfactants, often used with systemic pesticides, help pesticide sprays penetrate plant cuticles. Nonionic surfactants are compatible with most pesticides, and most EPA-registered pesticides that require a surfactant recommend a nonionic type. Adjuvants include, but are not limited to, stickers, extenders, plant penetrants, compatibility agents, buffers or pH modifiers, drift control additives, defoaming agents, and thickeners.

Among nonlimiting examples of surfactants included in the compositions described herein are alkyl sulfate ester salts, alkyl sulfonates, alkyl aryl sulfonates, alkyl aryl ethers and polyoxyethylenated products thereof, polyethylene glycol ethers, polyvalent alcohol esters and sugar alcohol derivatives.

xi. Combinations

In formulations and in the use forms prepared from these formulations, the modulating agent may be in a mixture with other active compounds, such as pesticidal agents (e.g., insecticides, sterilants, acaricides, nematicides, molluscicides, or fungicides; see, e.g., pesticides listed in Table 12), attractants, growth-regulating substances, or herbicides. As used herein, the term "pesticidal agent" refers to any substance or mixture of substances intended for preventing, destroying, repelling, or mitigating any pest.

A pesticide can be a chemical substance or biological agent used against pests including insects, pathogens, weeds, and microbes that compete with humans for food, destroy property, spread disease, or are a nuisance. The term "pesticidal agent" may further encompass other bioactive molecules such as antibiotics, antivirals pesticides, antifungals, antihelminthics, nutrients, pollen, sucrose, and/or agents that stun or slow insect movement.

In instances where the modulating agent is applied to plants, a mixture with other known compounds, such as herbicides, fertilizers, growth regulators, safeners, semiochemicals, or else with agents for improving plant properties is also possible.

V. Delivery

A host described herein can be exposed to any of the compositions described herein in any suitable manner that permits delivering or administering the composition to the insect. The modulating agent may be delivered either alone or in combination with other active or inactive substances and may be applied by, for example, spraying, microinjection, through plants, pouring, dipping, in the form of concentrated liquids, gels, solutions, suspensions, sprays, powders, pellets, briquettes, bricks and the like, formulated to deliver an effective concentration of the modulating agent. Amounts and locations for application of the compositions described herein are generally determined by the habits of the host, the lifecycle stage at which the microorganisms of the host can be targeted by the modulating agent, the site where the application is to be made, and the physical and functional characteristics of the modulating agent. The modulating agents described herein may be administered to the insect by oral ingestion, but may also be administered by means which permit penetration through the cuticle or penetration of the insect respiratory system.

In some instances, the insect can be simply "soaked" or "sprayed" with a solution including the modulating agent. Alternatively, the modulating agent can be linked to a food component (e.g., comestible) of the insect for ease of delivery and/or in order to increase uptake of the modulating agent by the insect. Methods for oral introduction include, for example, directly mixing a modulating agent with the insect's food, spraying the modulating agent in the insect's habitat or field, as well as engineered approaches in which a species that is used as food is engineered to express a modulating agent, then fed to the insect to be affected. In some instances, for example, the modulating agent composition can be incorporated into, or overlaid on the top of, the insects diet. For example, the modulating agent composition can be sprayed onto a field of crops which an insect inhabits.

In some instances, the composition is sprayed directly onto a plant e.g., crops, by e.g., backpack spraying, aerial spraying, crop spraying/dusting etc. In instances where the modulating agent is delivered to a plant, the plant receiving the modulating agent may be at any stage of plant growth. For example, formulated modulating agents can be applied as a seed-coating or root treatment in early stages of plant growth or as a total plant treatment at later stages of the crop cycle. In some instances, the modulating agent may be applied as a topical agent to a plant, such that the host insect ingests or otherwise comes in contact with the plant upon interacting with the plant.

Further, the modulating agent may be applied (e.g., in the soil in which a plant grows, or in the water that is used to water the plant) as a systemic agent that is absorbed and distributed through the tissues (e.g., stems or leafs) of a plant or animal host, such that an insect feeding thereon will obtain an effective dose of the modulating agent. In some instances, plants or food organisms may be genetically transformed to express the modulating agent such that a host feeding upon the plant or food organism will ingest the modulating agent.

Delayed or continuous release can also be accomplished by coating the modulating agent or a composition containing the modulating agent(s) with a dissolvable or bioerodable coating layer, such as gelatin, which coating dissolves or erodes in the environment of use, to then make the modulating agent available, or by dispersing the agent in a dissolvable or erodable matrix. Such continuous release and/or dispensing means devices may be advantageously employed to consistently maintain an effective concentration of one or more of the modulating agents described herein in a specific host habitat.

The modulating agent can also be incorporated into the medium in which the insect grows, lives, reproduces, feeds, or infests. For example, a modulating agent can be incorporated into a food container, feeding station, protective wrapping, or a hive. For some applications the modulating agent may be bound to a solid support for application in powder form or in a "trap" or "feeding station." As an example, for applications where the composition is to be used in a trap or as bait for a particular host insect, the compositions may also be bound to a solid support or encapsulated in a time-release material. For example, the compositions described herein can be administered by delivering the composition to at least one habitat where a vector (e.g., a vector of a human pathogen, e.g., a mosquito, mite, biting louse, or tick) grows, lives, reproduces, feeds, or infests.

VI. Screening

Included herein are methods for screening for modulating agents that are effective to alter the microbiota of a host (e.g., insect) and thereby decrease host fitness. The screening assays provided herein may be effective to identify one or more modulating agents (e.g., phage) that target symbiotic microorganisms resident in the host and thereby decrease the fitness of the host. For example, the identified modulating agent (e.g., phage) may be effective to decrease the viability of pesticide- or allelochemical-degrading microorganisms (e.g., bacteria e.g., a bacterium that degrades a pesticide listed in Table 12), thereby increasing the hosts sensitivity to a pesticide (e.g., sensitivity to a pesticide listed in Table 12) or allelochemical agent.

For example, a phage library may be screened to identify a phage that targets a specific endosymbiotic microorganism resident in a host. In some instances, the phage library may be provided in the form of one or more environmental samples (e.g., soil, pond sediments, or sewage water). Alternatively, the phage library may be generated from laboratory isolates. The phage library may be co-cultured with a target bacterial strain. After incubation with the bacterial strain, phage that successfully infect and lyse the target bacteria are enriched in the culture media. The phage-enriched culture may be sub-cultured with additional bacteria any number of times to further enrich for phage of interest. The phage may be isolated for use as a modulating agent in any of the methods or compositions described herein, wherein the phage alters the microbiota of the host in a manner that decreases host fitness.

TABLE 12

| Pesticides |
|---|
| Aclonifen |
| Acetamiprid |
| Alanycarb |
| Amidosulfuron |
| Aminocyclopyrachlor |
| Amisulbrom |
| Anthraquinone |
| Asulam, sodium salt |
| Benfuracarb |
| Bensulide |

TABLE 12-continued

| Pesticides |
|---|
| beta-HCH; beta-BCH |
| Bioresmethrin |
| Blasticidin-S |
| Borax; disodium tetraborate |
| Boric acid |
| Bromoxynil heptanoate |
| Bromoxynil octanoate |
| Carbosulfan |
| Chlorantraniliprole |
| Chlordimeform |
| Chlorfluazuron |
| Chlorphropham |
| Climbazole |
| Clopyralid |
| Copper (II) hydroxide |
| Cyflufenamid |
| Cyhalothrin |
| Cyhalothrin, gamma |
| Decahydrate |
| Diafenthiuron |
| Dimefuron |
| Dimoxystrobin |
| Dinotefuran |
| Diquat dichloride |
| Dithianon |
| E-Phosphamidon |
| EPTC |
| Ethaboxam |
| Ethirimol |
| Fenchlorazole-ethyl |
| Fenothiocarb |
| Fenitrothion |
| Fenpropidin |
| Fluazolate |
| Flufenoxuron |
| Flumetralin |
| Fluxapyroxad |
| Fuberidazole |
| Glufosinate-ammonium |
| Glyphosate |
| Group: Borax, borate salts (see |
| Group: Paraffin oils, Mineral |
| Halfenprox |
| Imiprothrin |
| Imidacloprid |
| Ipconazole |
| Isopyrazam |
| Isopyrazam |
| Lenacil |
| Magnesium phosphide |
| Metaflumizone |
| Metazachlor |
| Metazachlor |
| Metobromuron |
| Metoxuron |
| Metsulfuron-methyl |
| Milbemectin |
| Naled |
| Napropamide |
| Nicosulfuron |
| Nitenpyram |
| Nitrobenzene |
| o-phenylphenol |
| oils |
| Oxadiargyl |
| Oxycarboxin |
| Paraffin oil |
| Penconazole |
| Pendimethalin |
| Penflufen |
| Penflufen |
| Pentachlorbenzene |
| Penthiopyrad |
| Penthiopyrad |
| Pirimiphos-methyl |
| Prallethrin |
| Profenofos |
| Proquinazid |

TABLE 12-continued

| Pesticides |
|---|
| Prothiofos |
| Pyraclofos |
| Pyrazachlor |
| Pyrazophos |
| Pyridaben |
| Pyridalyl |
| Pyridiphenthion |
| Pyrifenox |
| Quinmerac |
| Rotenone |
| Sedaxane |
| Sedaxane |
| Silafluofen |
| Sintofen |
| Spinetoram |
| Sulfoxaflor |
| Temephos |
| thiocloprid |
| Thiamethoxam |
| Tolfenpyrad |
| Tralomethrin |
| Tributyltin compounds |
| Tridiphane |
| Triflumizole |
| Validamycin |
| Zinc phosphide |

EXAMPLES

The following is an example of the methods of the invention. It is understood that various other embodiments may be practiced, given the general description provided above.

Example 1: Treatment of the *Anopheles* Mosquito with Azithromycin Solutions This example demonstrates the ability to kill or decrease the fitness of the *Anopheles coluzzii* mosquitoes and decrease the transmission rate of parasites by treatment with azithromycin, relatively broad but shallow antibacterial activity. It inhibits some Gram-positive bacteria, some Gram-negative bacteria, and many atypical bacteria. The effect of azithromycin on mosquitoes is mediated through the modulation of bacterial populations endogenous to the mosquito that are sensitive to azithromycin. One targeted bacterial strain is Asaia.

The mosquito has been described as the most dangerous animal in the world and malaria is one mosquito-borne disease that detrimentally impacts humans. There are about 3,500 mosquito species and those that transmit malaria all belong to a sub-set called the *Anopheles*. Approximately 40 *Anopheles* species are able to transmit malaria that significantly impacts human health.

Therapeutic design: Blood meals mixed with azithromycin solutions are formulated with final antibiotic concentrations of 0 (negative control), 0.1, 1, or 5 μg/ml in 1 mL of blood.

Experimental Design:

To prepare for the treatment, mosquitoes are grown in a lab environment and medium.

Experiments are performed with female mosquitoes from an *Anopheles* coluzzii Ngousso colony, originally established from field mosquitoes collected in Cameroon, maintained on human blood and fed as adults with 5% fructose. Larvae are fed tetramin fish food. Temperature is maintained at 28° C. (±1° C.), 70-80% humidity on a 12 hr light/dark cycle.

Human Blood Feeding and *Plasmodium* Infections:

*Plasmodium falciparum* NF54 gametocytes are cultured in RPMI medium (GIBCO) including 300 mg. L-1 L-glutamine supplemented with 50 mg/L hypoxanthine, 25 mM HEPES plus 10% heat-inactivated human serum without antibiotics. Two 25-mL cultures are started 17 and 14 days before the infection at 0.5% parasitemia in 6% v/v washed O+ red blood cells (RBCs). Media is changed daily. Before mosquito infection, centrifuged RBCs are pooled and supplemented with 20% fresh washed RBCs and human serum (2:3 v/v ratio between RBCs and serum). Mosquitoes are offered a blood meal from a membrane-feeding device (2 ml Eppendorf tube) covered with Parafilm and kept at 37° C.

Azithromycin solutions are made by dissolving azithromycin (SIGMA-ALDRICH, PZ0007) in DMSO. Different volumes of azithromycin solution are added to fresh blood to total 1 mL in preparation for blood meals. The final azithromycin concentrations in the blood are 0 (just solvent as control solution), 0.1, 1, or 5 μg/ml.

For each *Plasmodium* infection, at least 100 age-matched, 2- to 3-day-old, mosquitoes per condition are offered a control or experimental blood meal from a membrane-feeding device (2 ml Eppendorf tube) covered with parafilm and kept at 37° C. and nonengorged mosquitoes are removed. Meals are given every four days for a total of three blood meals. Between the blood meals, mosquitoes are provided with a cotton pad moistened with distilled water for oviposition. Unfed mosquitoes are not removed after the second and later blood meals. Deaths are counted daily and carcasses are removed and stored for Asaia analysis as described herein. At least 50 mosquitoes per concentration of azithromycin are used for each replicate. At the end of the last blood meal, mosquitoes are kept for 12 hours before dissection.

Microbiota Analysis by Quantitative Polymerase Chain Reaction:

Before dissection, mosquitoes are immersed in 70% ethanol for 5 minutes then rinsed 3 times in sterile phosphate-buffered saline (PBS) to kill and remove surface bacteria, thus minimizing sample contamination with cuticle bacteria during dissection. The midgut of each mosquitoe (control and azithromycin treatment) is removed and frozen immediately on dry ice and stored at 20° C. until processing. Midguts are only excluded from analysis if they burst and a substantial amount of the gut content is lost. Samples are homogenized in phenol-chloroform in a Precellys 24 homogenizer (Bertin) using 0.5 mm-wide glass beads (Bertin) for 30 seconds at 6800 rpm and deoxy-ribonucleic acid (DNA) is extracted with phenol-chloroform. The 16S ribosomal DNA (rDNA) is used for Asaia quantification and is shown as a ratio of the *Anopheles* housekeeping gene 40S ribosomal protein S7 (Vector-Base gene ID AGAP010592). Primer sequences for Asaia are: forward 5'-GTGCCGATCTCTAAAAGCCGTCTCA-3' (SEQ ID NO: 219) and reverse 5'-TTCGCTCACCGGCTTCGGGT-3' (SEQ ID NO: 220), and for S7: forward 5'-GTGCGCGAGTTGGAGAAGA-3' (SEQ ID NO: 221) and reverse 5'-ATCGGTTTGGGCAGAATGC-3' (SEQ ID NO: 222). Quantitative polymerase chain reaction (qPCR) is performed on a 7500 Fast Real-Time thermocycler (Applied Biosystems) using the SYBR Premix Ex Taq kit (Takara), following the manufacturer's instructions. Azithromycin treated mosquitoes show a reduction of Asaia specific genes.

The survival rates of mosquitoes treated with azithromycin are compared to the mosquitoes treated with the negative control. The survival rate of mosquitoes treated with azithromycin solution is decreased compared to the control.

Example 2: Treatment of the *Aedes vexans* Mosquito with an Antibiotic Solution This Example demonstrates the ability to kill or decrease the fitness of the *Aedes vexans* mosquitoes by treatment with doxycycline, a broad spectrum antibiotic that inhibits protein production. The effect of doxycycline on mosquitoes is mediated through the modulation of bacterial populations endogenous to the mosquito that are sensitive to doxycycline. One targeted bacterial strain is *Wolbachia.*

Successful control and eradication of porcine reproductive and respiratory syndrome virus (PRRSV) is of great importance to the global swine industry today. To reduce the risk of PRRSV entry, swine producers utilize stringent measures to enhance the biosecurity of their farms; however, infection of PRRSV in swine herds still frequently occurs. One vector of transmission of PRRSV is the *Aedes vexans* mosquito. *Aedes vexans* is a cosmopolitan and common pest mosquito. On top of PRRSV, it is also a known vector of *Dirofilaria immitis* (dog heartworm); Myxomatosis (deadly rabbit virus disease) and Eastern equine encephalitis (deadly horse virus disease in the USA). *Aedes vexans* is the most common mosquito in Europe, often composing more than 80% the European mosquito community. Its abundance depends upon availability of floodwater pools. In summer, mosquito traps can collect up to 8,000 mosquitoes per trap per night.

Therapeutic design: Blood meals mixed with doxycycline solutions are formulated with final antibiotic concentrations of 0 (negative control), 1, 10, or 50 μg/ml in 1 mL of blood Experimental Design:

To prepare for the treatment, mosquitoes are grown in a lab environment and medium. Experiments are performed with female mosquitoes from an *Aedes vexans*, originally established from field mosquitoes collected on a field of the University of Minnesota St. Paul campus, maintained on human blood and fed as adults with 5% fructose. Doxycycline solutions are made by dissolving doxycycline (SIGMA-ALDRICH, D9891) in sterile water. Different volumes of a doxycycline solution are added to fresh blood to total 1 mL in preparation for blood meals. The final doxycycline concentrations in the blood are approximately 0 (control solution), 1, 10 or 50 μg/ml.

For each replicate, age-matched, 2- to 3-day-old mosquitoes are offered a control or experimental blood meal from a membrane-feeding device (2 ml Eppendorf tube) covered with parafilm and kept at 37° C. Nonengorged mosquitoes are discarded. Meals are given every four days for a total of three blood meals. Between the blood meals, mosquitoes are provided with a cotton pad moistened with distilled water for oviposition. Unfed mosquitoes are not removed after the second and later blood meals. Deaths are counted daily and carcasses are removed and stored for *Wolbachia* analysis as described herein. At least 50 mosquitoes per concentration of doxycycline are used for each replicate. At the end of the last blood meal, mosquitoes are kept for 12 hours before dissection.

Microbiota Analysis by Quantitative Polymerase Chain Reaction:

Before dissection, mosquitoes are immersed in 70% ethanol for 5 minutes then rinsed 3 times in sterile phosphate-buffered saline (PBS) to kill and remove surface bacteria, thus minimizing sample contamination with cuticle bacteria during dissection. The midgut of each mosquito (control and doxycycline treatment) is removed and frozen immediately on dry ice and stored at 20° C. until processing. Midguts are only excluded from analysis if they burst and a substantial amount of the gut content is lost. Samples are homogenized in phenol-chloroform in a Precellys 24 homogenizer (Bertin) using 0.5 mm wide glass beads (Bertin) for 30 seconds at 6800 rpm and deoxy-ribonucleic acid (DNA) is extracted with phenol-chloroform. The 16S ribosomal DNA (rDNA) is used for *Wolbachia* quantification and is shown as a ratio of the *Aedes* housekeeping gene 40S ribosomal protein S7 (Vector—Base gene ID AAEL009496). Primer sequences for *Wolbachia* are: forward primer 5'-TCAGCCACACTGGAACTGAG-3' (SEQ ID NO: 225) and reverse primer 5'-TAACGCTAGCCCTCTCCGTA-3' (SEQ ID NO: 226), and for S7: forward 5'-AAGGTCGACACCTTCACGTC-3' (SEQ ID NO: 227) and reverse 5'-CCGTTTGGTGAGGGTCTTTA-3' (SEQ ID NO: 228). Quantitative polymerase chain reaction (qPCR) is performed on a 7500 Fast Real-Time thermocycler (Applied Biosystems) using the SYBR Premix Ex Taq kit (Takara), following the manufacturer's instructions. Doxycycline treated mosquitoes show a reduction of *Wolbachia* specific genes.

The survival rates of mosquitoes treated with doxycycline solution are compared to the mosquitoes treated with the negative control. The survival rate of mosquitoes treated with doxycycline solution is decreased compared to the control.

Example 3: Treatment of the *Dermacentor andersoni*, with an Antibiotic Solution This Example demonstrates the ability to kill or decrease the fitness of the tick, *Dermacentor andersoni*, by treatment with Liquamycin LA-200 oxytetracycline, a broad spectrum antibiotic commonly used to treat a broad range of bacterial infections in cattle. The effect of Liquamycin LA-200 oxytetracycline on ticks is mediated through the modulation of bacterial populations endogenous to the tick that are sensitive to Liquamycin LA-200 oxytetracycline. One targeted bacterial strain is *Rickettsia.*

Ticks are obligate hematophagous arthropods that feed on vertebrates and cause great economic losses to livestock due to their ability to transmit diseases to humans and animals. In particular, ticks transmit pathogens throughout all continents and are labeled as principle vectors of zoonotic pathogens. In fact, 415 new tick-borne bacterial pathogens have been discovered since Lyme disease was characterized in 1982. *Dermacentor andersoni*, the Rocky Mountain wood tick, has been labeled a 'veritable Pandora's box of disease-producing agents' and transmits several pathogens, including *Rickettsia rickettsii* and *Francisella tularensis*. It is also a vector of *Anaplasma* marginale, the agent of anaplasmosis, and the most widespread tick-borne pathogen of livestock worldwide (Gall et al., *The ISME Journal* 10:1846-1855, 2016). Economic losses due to anaplasmosis in cattle are estimated to be $300 million per year in the United States (Rochon et al., *J. Med. Entomol.* 49:253-261, 2012). Therapeutic design: A therapeutic dose (11 mg/kg of body weight) of Liquamycin LA-200 oxytetracycline injection on −4, −1, +3 and +5 days post application of ticks.

Experimental Design:

Questing adult *D. andersoni* are collected by flag and drag techniques at sites in Burns, Oregon and Lake Como, Montana as described in (Scoles et al., *J. Med. Entomol.* 42:153-162, 2005). Field collected ticks are used to establish laboratory colonies. For tick bacteria analysis, a cohort of adult F1 or F2 male ticks from each colony is fed on a Holstein calf and dissected to collect midguts (MG) and salivary glands (SG) for genomic DNA isolation and bacteria quantification as follows:

A cohort of F1 ticks are fed on either antibiotic-treated calves or untreated calves (control). The antibiotic-treated calves received a therapeutic dose (11 mg/kg of body weight) of Liquamycin LA-200 oxytetracycline injections on −4, −1, +3 and +5 days post application of ticks, whereas untreated calves did not receive any injections (untreated control). Females ticks are allowed to oviposit to continue a second generation of the untreated and treated ticks (F2 generation). The F2 treated generation arose from F1 adults that are exposed to antibiotics. The F2 ticks are not subjected to antibiotics.

F1 and F2 generation adult male ticks are fed for 7 days and then dissected within 24 h. Deaths are counted daily and ticks are removed and stored for *Rickettsia* analysis as described herein. Before dissection, the ticks are surface sterilized and all dissection tools are sterilized between each dissection. Tick MG and SG are dissected and pooled in groups of 30 with three biological replicates. Tissues are stored in Cell Lysis Solution (Qiagen, Valencia, Calif., USA) and Proteinase K (1.25 mg/ml). Genomic DNA is isolated using the PureGene Extraction kit (Qiagen) according to the manufacturer's specifications.

Quantitative analysis of *Rickettsia bellii:*

To quantify *Rickettsia*, rickA gene copy numbers are measured using SYBR Green quantitative PCR of non-treated and antibiotic treated in F1 and F2 ticks. The quantity of *Rickettsia* is determined using Forward (5'-TACGCCACTCCCTGTGT CA-3'; SEQ ID NO: 229) and Reverse (5'-GATGTAACGGTATTAC ACCAACAG-3'; SEQ ID NO: 230) primers. The bacterial quantity is measured in F1 and F2 MG and SG of the pooled samples. Quantitative polymerase chain reaction (qPCR) is performed on a 7500 Fast Real-Time thermocycler (Applied Biosystems) using the SYBR Premix Ex Taq kit (Takara), following the manufacturer's instructions. Liquamycin LA-200 oxytetracycline treated ticks show a reduction of *Rickettsia* specific genes.

The survival rates of ticks treated with antibiotic solution are compared to the ticks untreated. The survival rate of ticks treated with Liquamycin LA-200 oxytetracycline solution is decreased compared to the untreated.

Example 4: Treatment of Mites that Infect Livestock with Rifampicin Solutions This Example demonstrates the ability to kill or decrease the fitness of mites by treating them with an antibiotic solution. This Example demonstrates that the effect of oxytetracycline on mites is mediated through the modulation of bacterial populations endogenous, such as *Bacillus*, to the mites that are sensitive to oxytetracycline.

Sarcoptic mange is caused by mites that infest animals by burrowing deeply into the skin and laying eggs inside the burrows. The eggs hatch into the larval stage. The larval mites then leave the burrows, move up to the skin surface, and begin forming new burrows in healthy skin tissue. Development from egg to adult is completed in about 2 weeks. The lesions resulting from infestations by these mites are a consequence of the reaction of the animals' immune system to the mites' presence. Because of the intensity of the animals' immunological response, it takes only a small number of mites to produce widespread lesions and generalized dermatitis. While mites can be killed with chemically synthesized miticides, these types of chemicals must sprayed on every animal in the herd with high-pressure hydraulic spray equipment to ensure penetration by the spray into the skin. Furthermore, these types of chemical pesticides may have detrimental ecological and/or agricultural effects.

Therapeutic design: Oxytetracycline solution is formulated with 0 (negative control), 1, 10, or 50 μg/ml in 10 mL of sterile water with 0.5% sucrose and essential amino acids.

Experimental Design:

To determine whether adult mites at the reproductive stage have different susceptibility compared to phoretic mites or their offspring because their cuticle is not hardened, mites living on livestock and mites associated with larvae and pupae are collected. This assay tests antibiotic solutions on different types of mites and determines how their fitness is altered by targeting endogenous microbes, such as *Bacillus*.

The brood mites are collected from mite-infested pigs. Skin samples are collected by gently scraping and lifting off encrusted areas from the inner ear area of the pig with a sharpened teaspoon and subsequently examined for mites.

Mites are grouped per age and assayed separately. The age is determined based on the morphology and pigmentation of the larva or the pupa as follows: mites collected from spinning larvae that are small enough to move around are grouped into Group 1; mites collected from stretched larvae, which are too big to lay in the cell and start to stretch upright with their mouth in the direction of the cell opening, are grouped into Group 2; and mites collected from pupae are grouped into Group 3. Mites are stored on their host larva or pupa in glass Petri dishes until 50 units are collected. This ensures their feeding routine and physiological status remains unchanged. To prevent mites from straying from their host larva or pupa or climbing onto one another, only hosts at the same development stage are kept in the same dish.

The equipment—a stainless steel ring (56 mm inner diameter, 2-3 mm height) and 2 glass circles (62 mm diameter)—is cleaned with acetone and hexane or pentane to form the testing arena. The oxytetracycline solutions and control solution are applied on the equipment by spraying the glass disks and ring of the arena homogeneously. For this, a reservoir is loaded with 1 ml of the solutions; the distance of the sprayed surface from the bottom end of the tube is set at 11 mm and a 0.0275 inch nozzle is used. The pressure is adjusted (usually in the range 350-500 h Pa) until the amount of solution deposited is 1±0.05 mg/cm2. The antibiotic solutions are poured in their respective dishes, covering the whole bottom of the dishes, and residual liquid is evaporated under a fume hood. The ring is placed between the glass circles to build a cage. The cages are used within 60 hr of preparation, for not more than three assays, in order to control the exposure of mites to antibiotic solutions. 10 to 15 mites are introduced in this cage and the equipment pieces are bound together with droplets of melted wax. Mites collected from spinning larvae, stretched larvae, white eyed pupae and dark eyed with white and pale body are used.

After 4 hours, mites are transferred into a clean glass Petri dish (60 mm diameter) with two or three white eye pupae (4-5 days after capping) to feed on. The mites are observed under a dissecting microscope at 4 hr, 24 hr, and 48 hr after being treated with the antibiotic or the control solutions, and classified according to the following categories:

Mobile: they walk around when on their legs, whether after being poked by a needle.

Paralyzed: they move one or more appendages, unstimulated or after stimulation, but they cannot move around.

Dead: immobile and do not react to 3 subsequent stimulations.

A sterile toothpick or needle is used to stimulate the mites by touching their legs. New tooth picks or sterile needles are used for stimulating each group to avoid contamination between mite groups.

The assays are carried out at 32.5° C. and 60-70% relative humidity. If the mortality in the controls exceeds 30%, the replicate is excluded. Each experiment is replicated with four series of cages.

The status of *Bacillus* in mite groups is assessed by PCR. Total DNA is isolated from control (non-oxytetracycline treated) and oxytetracyline treated individuals (whole body) using a DNA Kit (OMEGA, Bio-tek) according to the manufacturer's protocol. The primers for *Bacillus*, forward primer 5'-GAGGTAGACGAAGCGACCTG-3' (SEQ ID NO: 231) and reverse primer 5'-TTCCCTCACGGTACTGGTTC-3' (SEQ ID NO: 232), are designed based on 23S-5S rRNA sequences obtained from the *Bacillus* genome (Accession Number: AP007209.1) (Takeno et al., *J. Bacteriol.* 194(17):4767-4768, 2012) using Primer 5.0 software (Primer-E Ltd., Plymouth, UK). The PCR amplification cycles included an initial denaturation step at 95° C. for 5 min, 35 cycles of 95° C. for 1 min, 59° C. for 1 min, and 72° C. for 2 min, and a final extension step of 5 min at 72° C. Amplification products from oxytetracyline treated and control samples are analyzed on 1% agarose gels, stained with SYBR safe, and visualized using an imaging System.

The survival rates of mites treated with an oxytetracyline solution are compared to the *Varroa* mites treated with the negative control.

The survival rate and the mobility of mites treated with oxytetracyline solution are expected to be decreased compared to the control.

Example 5: Production of a Phage Library

This Example demonstrates the acquisition of a phage collection from environmental samples.

Therapeutic design: Phage library collection having the following phage families: Myoviridae, Siphoviridae, Podoviridae, Lipothrixviridae, Rudiviridae, Ampullaviridae, Bicaudaviridae, Clavaviridae, Corticoviridae, Cystoviridae, Fuselloviridae, Globoloviridae, Guttaviridae, Inoviridae, Leviviridae, Microviridae, Plasmaviridae, Tectiviridae Experimental Design:

Multiple environmental samples (soil, pond sediments, sewage water) are collected in sterile 1 L flasks over a period of 2 weeks and are immediately processed as described below after collection and stored thereafter at 4° C. Solid samples are homogenized in sterile double-strength difco luria broth (LB) or tryptic soy broth (TSB) supplemented with 2 mM $CaCl_2$) to a final volume of 100 mL. The pH and phosphate levels are measured using phosphate test strips. For purification, all samples are centrifuged at 3000-6000 g in a Megafuge 1.0 R, Heraeus, or in Eppendorf centrifuge 5702 R, for 10-15 min at +4° C., and filtered through 0.2-μm low protein filters to remove all remaining bacterial cells. The supernatant is stored at 4° C. in the presence of chloroform in a glass bottle.

Example 6: Identification of Target Specific Phage

This Example demonstrates the isolation, purification, and identification of single target specific phages from a heterogeneous phage library.

Experimental Design:

20-30 ml of the phage library described in Example 5 is diluted to a volume of 30-40 ml with LB-broth. The target bacterial strain, e.g., *Buchnera*, is added (50-200 µl overnight culture grown in LB-broth) to enrich phages that target this specific bacterial strain in the culture. This culture is incubated overnight at +37° C., shaken at 230 rpm. Bacteria from this enrichment culture are removed by centrifugation (3000-6000 g in Megafuge 1.0 R, Heraeus, or in Eppendorf centrifuge 5702 R, 15-20 min, +4° C.) and filtered (0.2 or 0.45 µm filter). 2.5 ml of the bacteria free culture is added to 2.5 ml of LB-broth and 50-100 µl of the target bacteria to enrich the phages. The enrichment culture is grown overnight as above. A sample from this enrichment culture is centrifuged at 13,000 g for 15 min at room temperature and 10 µl of the supernatant is plated on a LB-agar containing petri dish along with 100-300 µl of the target bacteria and 3 ml of melted 0.7% soft-agar. The plates are incubated overnight at +37° C. Each of the plaques observed on the bacterial lawn are picked and transferred into 500 µl of LB-broth. A sample from this plaque-stock is further plated on the target bacteria. Plaque-purification is performed three times for all discovered phages in order to isolate a single homogenous phage from the heterogeneous phage mix.

Lysates from plates with high-titer phages (>1×10^10 PFU/ml) are prepared by harvesting overlay plates of a host bacterium strain exhibiting confluent lysis. After being flooded with 5 ml of buffer, the soft agar overlay is macerated, clarified by centrifugation, and filter sterilized. The resulting lysates are stored at 4° C. High-titer phage lysates are further purified by isopycnic CsCl centrifugation, as described in (Summer et al., *J. Bacteriol.* 192:179-190, 2010).

DNA is isolated from CsCl-purified phage suspensions as described in (Summer, *Methods Mol. Biol.* 502:27-46, 2009). An individual isolated phage is sequenced as part of two pools of phage genomes by using a 454 pyrosequencing method. Phage genomic DNA is mixed in equimolar amounts to a final concentration of about 100 ng/L. The pooled DNA is sheared, ligated with a multiplex identifier (MID) tag specific for each of the pools, and sequenced by pyrosequencing using a full-plate reaction on a Roche FLX Titanium sequencer according to the manufacturer's protocols. The pooled phage DNA is present in two sequencing reactions. The trimmed FLX Titanium flow-gram output corresponding to each of the pools is assembled individually by using Newbler Assembler version 2.5.3 (454 Life Sciences), by adjusting the settings to include only reads containing a single MID per assembly. The identity of individual contigs is determined by PCR using primers generated against contig sequences and individual phage genomic DNA preparations as the template. Sequencher 4.8 (Gene Codes Corporation) is used for sequence assembly and editing. Phage chromosomal end structures are determined experimentally. Cohesive (cos) ends for phages are determined by sequencing off the ends of the phage genome and sequencing the PCR products derived by amplification through the ligated junction of circularized genomic DNA, as described in (Summer, *Methods Mol. Biol.* 502:27-46, 2009). Protein-coding regions are initially predicted using GeneMark.hmm (Lukashin et al. *Nucleic Acids Res.* 26:1107-1115, 1998), refined through manual analysis in Artemis (Rutherford et al., *Bioinformatics* 16:944-945, 2000), and analyzed through the use of BLAST (E value cutoff of 0.005) (Camacho et al., *BMC Bioinformatics* 10:421, 2009). Proteins of particular interest are additionally analyzed by InterProScan (Hunter et al., *Nucleic Acids Res.* 40:D306-D312, 2012).

Electron microscopy of CsCl-purified phage (>1×10^11 PFU/ml) that lysed the endosymbiotic bacteria, *Buchnera*, is performed by diluting stock with the tryptic soy broth buffer. Phages are applied onto thin 400-mesh carbon-coated Formvar grids, stained with 2% (wt/vol) uranyl acetate, and air dried. Specimens are observed on a JEOL 1200EX transmission electron microscope operating at an acceleration voltage of 100 kV. Five virions of each phage are measured to calculate mean values and standard deviations for dimensions of capsid and tail, where appropriate.

Example 7: Treatment of Aphids with a Solution of Purified Phages

This Example demonstrates the ability to kill or decrease the fitness of aphids by treating them with a phage solution. This Example demonstrates that the effect of phage on aphids is mediated through the modulation of bacterial populations endogenous to the aphid that are sensitive to phages. One targeted bacterial strain is *Buchnera* with the phage identified in Example 6.

Aphids are representative species for testing microbiota modulating agents and effects on fitness of the aphids.

Therapeutic Design:

Phage solutions are formulated with 0 (negative control), $10^2$, $10^5$, or $10^8$ plaque-forming units (pfu)/ml phage from Example 6 in 10 mL of sterile water with 0.5% sucrose and essential amino acids.

Experimental Design:

To prepare for the treatment, aphids are grown in a lab environment and medium. In a climate-controlled room (16 h light photoperiod; 60±5% RH; 20±2° C.), fava bean plants are grown in a mixture of vermiculite and perlite at 24° C. with 16 h of light and 8 h of darkness. To limit maternal effects or health differences between plants, 5-10 adults from different plants are distributed among 10 two-week-old plants, and allowed to multiply to high density for 5-7 days. For experiments, second and third instar aphids are collected from healthy plants and divided into treatments so that each treatment receives approximately the same number of individuals from each of the collection plants.

Phage solutions are prepared as described herein. Wells of a 96-well plate are filled with 200 µl of artificial aphid diet (Febvay et al., *Canadian Journal of Zoology* 66(11):2449-2453, 1988) and the plate is covered with parafilm to make a feeding sachet. Artificial diet is either mixed with sterile water and with 0.5% sucrose and essential amino acids as a negative control or phage solutions with varying concentrations of phages. Phage solutions are mixed with artificial diet to get final concentrations of phages between $10^2$ to $10^8$ (pfu)/ml.

For each replicate treatment, 30-50 second and third instar aphids are placed individually in wells of a 96-well plate and a feeding sachet plate is inverted above them, allowing the insects to feed through the parafilm and keeping them restricted to individual wells. Experimental aphids are kept under the same environmental conditions as aphid colonies. After the aphids are fed for 24 hr, the feeding sachet is replaced with a new one containing sterile artificial diet and a new sterile sachet is provided every 24 h for 4 days. At the time that the sachet is replaced, aphids are also checked for mortality. An aphid is counted as dead if it had turned brown or is at the bottom of the well and does not move during the observation. If an aphid is on the parafilm of the feeding sachet but not moving, it is assumed to be feeding and alive.

The status of *Buchnera* in aphid samples is assessed by PCR. Aphids adults from the negative control (non-phage treated) and phage treated groups are first surface-sterilized with 70% ethanol for 1 min, 10% bleach for 1 min and three washes of ultrapure water for 1 min. Total DNA is extracted from each individual (whole body) using an Insect DNA Kit (OMEGA, Bio-tek) according to the manufacturer's protocol. The primers for *Buchnera*, forward primer 5'-GTCGGCTCATCACATCC-3' (SEQ ID NO: 233) and reverse primer 5'-TTCCGTCTGTATTATCTCCT-3' (SEQ ID NO: 234), are designed based on 23S-5S rRNA sequences obtained from the *Buchnera* genome (Accession Number: GCA_000009605.1) (Shigenobu et al., *Nature* 407:81-86, 2000) using Primer 5.0 software (Primer-E Ltd., Plymouth, UK). The PCR amplification cycles included an initial denaturation step at 95° C. for 5 min, 35 cycles of 95° C. for 30s, 55° C. for 30s, and 72° C. for 60s, and a final extension step of 10 min at 72° C. Amplification products from rifampicin treated and control samples are analyzed on 1% agarose gels, stained with SYBR safe, and visualized using an imaging System. Phage treated aphids show a reduction of *Buchnera* specific genes.

The survival rates of aphids treated with *Buchnera* specific phages are compared to the aphids treated with the negative control. The survival rate of aphids treated with *Buchnera* specific phages is decreased as compared to the control treated aphids.

Example 8: Production of a colA Bacteriocin Solution

This Example demonstrates the production and purification of colA bacteriocin.
Construct Sequence:
catatgatgacccgcac-
catgctgtttctggcgtgcgtggcggcgctgtatgtgtgcatt-
agcgcgaccgcgggcaaaccggaagaatttgcgaaac tgagcgat-
gaagcgccgagcaacgatcaggcgatgtatgaaagcattcagc
gctatcgccgctttgtggatggcaaccgctataacggcggccat catcat-
catcatcatccgaaacagtgggaagtgcgcccggatctgagccgc-
gatcagcgcggcaacaccaagcgcaggtggaaattaac aaaaaaggc-
gataaccatgatattaacgcgggctggggcaaaaacattaacggccc-
ggatagccataaagatacctggcatgtgggcggcagc
gtgcgctggctcgag (SEQ ID NO: 235)
Experimental Design:

DNA is generated by PCR with specific primers with upstream (NdeI) and downstream (XhoI) restriction sites. Forward primer GTATCTATTCCCGTCTACGAA-CATATGGAATTCC (SEQ ID NO: 236) and reverse primer CCGCTCGAGCCATCTGACACTTCCTCCAA (SEQ ID NO: 237). Purified PCR fragments (Nucleospin Extract II-Macherey Nagel) are digested with NdeI or XhoI and then the fragments are ligated. For colA cloning, the ligated DNA fragment is cloned into per2.1 (GenBank database accession number EY122872) vector (Anselme et al., *BMC Biol.* 6:43, 2008). The nucleotide sequence is systematically checked (Cogenics).

The plasmid with colA sequence is expressed in BL21 (DE3)/pLys. Bacteria are grown in LB broth at 30° C. At an OD600 of 0.9, isopropyl β-D-1-thiogalactopyranoside (IPTG) is added to a final concentration of 1 mM and cells were grown for 6 h. Bacteria are lysed by sonication in 100 mM NaCL, 1% Triton X-100, 100 mM Tris-base pH 9.5, and proteins are loaded onto a HisTrap HP column (GE Healthcare). The column is washed successively with 100 mM NaCl, 100 mM Tris-HCl pH 6.8, and PBS. Elution is performed with 0.3M imidazol in PBS. Desalting PD-10 columns (GE Healthcare) are used to eliminate imidazol and PBS solubilized peptides are concentrated on centrifugal filter units (Millipore).
ColA Protein Sequence:
MTRTMLFLAC VAALYVCISA TAGKPEEFAK
LSDEAPSNDQ AMYESIQRYR RFVDGNRYNG
GQQQQQQPKQ WEVRPDLSRD QRGNTKAQVE
INKKGDNHDI NAGWGKNING PDSHKDTWHV
GGSVRW (SEQ ID NO: 211)

Example 9: Treatment of Aphids with a Solution of colA Bacteriocin

This Example demonstrates the ability to kill or decrease the fitness of aphids by treating them with a bacteriocin solution. This Example demonstrates that the effect of bacteriocins on aphids is mediated through the modulation of bacterial populations endogenous to the aphid that are sensitive to ColA bacteriocin. One targeted bacterial strain is *Buchnera* with the bacteriocin produced in Example 8.
Therapeutic Design:

ColA solutions are formulated with 0 (negative control), 0.6, 1, 50 or 100 mg/ml of ColA from Example 8 in 10 mL of sterile water with 0.5% sucrose and essential amino acids.
Experimental Design:

To prepare for the treatment, aphids are grown in a lab environment and medium. In a climate-controlled room (16 h light photoperiod; 60±5% RH; 20±2° C.), plants are grown in a mixture of vermiculite and perlite and are infested with aphids. In the same climatic conditions, *E. balteatus* larvae are obtained from a mass production; the hoverflies are reared with sugar, pollen, and water; and the oviposition is induced by the introduction of infested host plants in the rearing cage during 3 h. The complete life cycle takes place on the host plants that are daily re-infested with aphids.

Wells of a 96-well plate are filled with 200 µl of artificial aphid diet (Febvay et al., *Canadian Journal of Zoology* 66(11):2449-2453, 1988) and the plate is covered with parafilm to make a feeding sachet. Artificial diet is either mixed with the solution of sterile water with 0.5% sucrose and essential amino acids as a negative control or ColA solutions with varying concentrations of ColA. ColA solutions are mixed with artificial diet to obtain final concentrations between 0.6 to 100 mg/ml.

For each replicate treatment, 30-50 second and third instar aphids are placed individually in wells of a 96-well plate and a feeding sachet plate is inverted above them, allowing the insects to feed through the parafilm and keeping them restricted to individual wells. Experimental aphids are kept under the same environmental conditions as aphid colonies. After the aphids are fed for 24 hr, the feeding sachet is replaced with a new one containing sterile artificial diet and a new sterile sachet is provided every 24 h for 4 days. At the time that the sachet is replaced, aphids are also checked for mortality. An aphid is counted as dead if it had turned brown or is at the bottom of the well and does not move during the observation. If an aphid is on the parafilm of the feeding sachet but not moving, it is assumed to be feeding and alive.

The status of *Buchnera* in aphid samples is assessed by PCR. Aphids adults from the negative control and phage treated are first surface-sterilized with 70% ethanol for 1 min, 10% bleach for 1 min and three washes of ultrapure water for 1 min. Total DNA is extracted from each individual (whole body) using an Insect DNA Kit (OMEGA, Bio-tek) according to the manufacturer's protocol. The primers for

*Buchnera*, forward primer 5'-GTCGGCTCATCACATCC-3' (SEQ ID NO: 233) and reverse primer 5'-TTCCGTCTGTATTATCTCCT-3' (SEQ ID NO: 234), are designed based on 23S-5S rRNA sequences obtained from the *Buchnera* genome (Accession Number: GCA_000009605.1) (Shigenobu, et al., *Nature* 200.407, 81-86) using Primer 5.0 software (Primer-E Ltd., Plymouth, UK). The PCR amplification cycles included an initial denaturation step at 95° C. for 5 min, 35 cycles of 95° C. for 30s, 55° C. for 30s, and 72° C. for 60s, and a final extension step of 10 min at 72° C. Amplification products from rifampicin treated and control samples are analyzed on 1% agarose gels, stained with SYBR safe, and visualized using an imaging System. ColA treated aphids show a reduction of *Buchnera* specific genes.

The survival rates of aphids treated with *Buchnera* specific ColA bacteriocin are compared to the aphids treated with the negative control. The survival rate of aphids treated with *Buchnera* specific ColA bacteriocin is decreased as compared to the control treated aphids.

Example 10: Treatment of Aphids with Rifampicin Solutions

This Example demonstrates the ability to kill or decrease the fitness of aphids by treating them with rifampicin, a narrow spectrum antibiotic that inhibits DNA-dependent RNA synthesis by inhibiting a bacterial RNA polymerase. This Example demonstrates that the effect of rifampicin on aphids is mediated through the modulation of bacterial populations endogenous to the aphid that are sensitive to rifampicin. One targeted bacterial strain is *Buchnera*.

Therapeutic Design:

The antibiotic solutions are formulated with 0 (negative control), 1, 10, or 50 μg/ml of rifampicin in 10 mL of sterile water with 0.5% sucrose and essential amino acids.

Experimental Design:

To prepare for the treatment, aphids are grown in a lab environment and medium. In a climate-controlled room (16 h light photoperiod; 60±5% RH; 20±2° C.), fava bean plants are grown in a mixture of vermiculite and perlite at 24° C. with 16 h of light and 8 h of darkness. To limit maternal effects or health differences between plants, 5-10 adults from different plants are distributed among 10 two-week-old plants, and allowed to multiply to high density for 5-7 days. For experiments, second and third instar aphids are collected from healthy plants and divided into treatments so that each treatment receives approximately the same number of individuals from each of the collection plants.

Rifampicin solutions are made by dissolving rifampicin (SIGMA-ALDRICH, 557303) in sterile water with 0.5% sucrose and essential aminoacids. Wells of a 96-well plate are filled with 200 pl of artificial aphid diet (Febvay et al., *Canadian Journal of Zoology* 66(11):2449-2453, 1988) and the plate is covered with parafilm to make a feeding sachet. Artificial diet is either mixed with sterile water and with 0.5% sucrose and essential aminoacids as a negative control or a rifampicin solution with one of the concentrations of rifampicin. Rifampicin solutions are mixed with artificial diet to get final concentrations of the antibiotic between 1 and 50 μg/mL.

For each replicate treatment, 30-50 second and third instar aphids are placed individually in wells of a 96-well plate and a feeding sachet plate is inverted above them, allowing the insects to feed through the parafilm and keeping them restricted to individual wells. Experimental aphids are kept under the same environmental conditions as aphid colonies. After the aphids are fed for 24 hr, the feeding sachet is replaced with a new one containing sterile artificial diet and a new sterile sachet is provided every 24 h for four days. At the time that the sachet is replaced, aphids are also checked for mortality. An aphid is counted as dead if it had turned brown or is at the bottom of the well and does not move during the observation. If an aphid is on the parafilm of the feeding sachet but not moving, it is assumed to be feeding and alive.

The status of *Buchnera* in aphid samples is assessed by PCR. Total DNA is isolated from control (non-rifampicin treated) and rifampicin treated individuals using an Insect DNA Kit (OMEGA, Bio-tek) according to the manufacturer's protocol. The primers for *Buchnera*, forward primer 5'-GTCGGCTCATCACATCC-3' (SEQ ID NO: 233) and reverse primer 5'-TTCCGTCTGTATTATCTCCT-3' (SEQ ID NO: 234), are designed based on 23S-5S rRNA sequences obtained from the *Buchnera* genome (Accession Number: GCA_000009605.1) (Shigenobu et al., *Nature* 407:81-86, 2000) using Primer 5.0 software (Primer-E Ltd., Plymouth, UK). The PCR amplification cycles included an initial denaturation step at 95° C. for 5 min, 35 cycles of 95° C. for 30s, 55° C. for 30s, and 72° C. for 60s, and a final extension step of 10 min at 72° C. Amplification products from rifampicin treated and control samples are analyzed on 1% agarose gels, stained with SYBR safe, and visualized using an imaging System. Rifampicin treated aphids show a reduction of *Buchnera* specific genes.

The survival rates of aphids treated with rifampicin solution are compared to the aphids treated with the negative control. The survival rate of aphids treated with rifampicin solution is decreased compared to the control.

Example 11: High Throughput Screening (HTS) for *Buchnera* Targeting Molecules This Example demonstrates the identification of molecules that target *Buchnera*.

Experimental design: A HTS to identify inhibitors of targeted bacterial strains, *Buchnera*, uses sucrose fermentation in pH-MMSuc medium (Ymele-Leki et al., *PLoS ONE* 7(2):e31307, 2012) to decrease the pH of the medium. pH indicators in the medium monitor medium acidification spectrophotometrically through a change in absorbance at 615 nm (A615). A target bacterial strain, *Buchnera*, derived from a glycerol stock, is plated on an LB-agar plate and incubated overnight at 37° C. A loopful of cells is harvested, washed three times with PBS, and then resuspended in PBS at an optical density of 0.015.

For the HTS, 10 μL of this bacterial cell suspension is aliquoted into the wells of a 384-well plate containing 30 μL of pH-MMSuc medium and 100 nL of a test compound fraction from a natural product library of pre-fractionated extracts (39,314 extracts arrayed in 384-well plates) from microbial sources, such as fungal endophytes, bacterial endophytes, soil bacteria, and marine bacteria, described in (Ymele-Leki et al., *PLoS ONE* 7(2):e31307, 2012). For each assay, the A615 is measured after incubation at room temperature at 6 hr and 20 hr. This step is automated and validated in the 384-well plate format using an EnVision™ multi-well spectrophotometer to test all fractions from the library. Fractions that demonstrate delayed medium acidification by sucrose fermentation and inhibited cell growth are selected for further purification and identification.

Example 12: Isolation and Identification of *Buchnera* Specific Molecules

This Example demonstrates the isolation and identification of an isolate from the fraction described in Example 11 that blocks sucrose fermentation and inhibits cell growth of *Buchnera*.

Experimental Design:

The fraction described in Example 11 is resuspended in 90% water/methanol and passed over a C18 SPE column to get fraction I. The column is then washed with methanol to get fraction II. Fraction II is separated on an Agilent 1100 series HPLC with a preparative Phenyl-hexyl column (Phenomenex, Luna, 25 cm610 mm, 5 mm particle size) using an elution buffer with 20% acetonitrile/water with 0.1% formic acid at a flow rate of 2 mL/min for 50 minutes. This yields multiple compounds at different elution times. Spectra for each compound is obtained on an Alpha FT-IR mass spectrometer (Bruker), an Ultrospec™ 5300 pro UV/Visible Spectrophotometer (Amersham Biosciences), and an INOVA 600 MHz nuclear magnetic resonance spectrometer (Varian).

Example 13: Treatment of Aphids with a Solution of a *Buchnera* Specific Molecule This Example demonstrates the ability to kill or decrease the fitness of aphids by treating them with one of the compounds identified in Example 12 through the modulation of bacterial populations endogenous to the aphid that are sensitive to this compound. One targeted bacterial strain is *Buchnera*.

Therapeutic Design:

Each compound from Example 12 is formulated at 0 (negative control), 0.6, 1, 20 or 80 µg/ml in 10 mL of sterile water with 0.5% sucrose and essential amino acids.

Experimental Design:

To prepare for the treatment, aphids are grown in a lab environment and medium. In a climate-controlled room (16 h light photoperiod; 60±5% RH; 20±2° C.), fava bean plants are grown in a mixture of vermiculite and perlite at 24° C. with 16 h of light and 8 h of darkness. To limit maternal effects or health differences between plants, 5-10 adults from different plants are distributed among 10 two-week-old plants, and allowed to multiply to high density for 5-7 days. For experiments, second and third instar aphids are collected from healthy plants and divided into treatments so that each treatment receives approximately the same number of individuals from each of the collection plants.

Wells of a 96-well plate are filled with 200 µl of artificial aphid diet (Febvay et al., *Canadian Journal of Zoology* 66(11):2449-2453, 1988) and the plate is covered with parafilm to make a feeding sachet. Artificial diet is either mixed with sterile water with 0.5% sucrose and essential amino acids as a negative control or solutions with varying concentrations of the compound.

For each replicate treatment, 30-50 second and third instar aphids are placed individually in wells of a 96-well plate and a feeding sachet plate is inverted above them, allowing the insects to feed through the parafilm and keeping them restricted to individual wells. Experimental aphids are kept under the same environmental conditions as aphid colonies. After the aphids are fed for 24 hr, the feeding sachet is replaced with a new one containing sterile artificial diet and a new sterile sachet is provided every 24 h for 4 days. At the time that the sachet is replaced, aphids are also checked for mortality. An aphid is counted as dead if it had turned brown or is at the bottom of the well and does not move during the observation. If an aphid is on the parafilm of the feeding sachet but not moving, it is assumed to be feeding and alive.

The status of *Buchnera* in aphid samples is assessed by PCR. Aphids from the negative control and compound 1 treated are first surface-sterilized with 70% ethanol for 1 min, 10% bleach for 1 min and three washes of ultrapure water for 1 min. Total DNA is extracted from each individual (whole body) using an Insect DNA Kit (OMEGA, Bio-tek) according to the manufacturer's protocol. The primers for *Buchnera*, forward primer 5'-GTCGGCTCATCACATCC-3' (SEQ ID NO: 233) and reverse primer 5'-TTCCGTCTGTATTATCTCCT-3' (SEQ ID NO: 234), are designed based on 23S-5S rRNA sequences obtained from the *Buchnera* genome (Accession Number: GCA_000009605.1) (Shigenobu et al., *Nature* 407:81-86, 2000) using Primer 5.0 software (Primer-E Ltd., Plymouth, UK). The PCR amplification cycles included an initial denaturation step at 95° C. for 5 min, 35 cycles of 95° C. for 30s, 55° C. for 30s, and 72° C. for 60s, and a final extension step of 10 min at 72° C. Amplification products from compound 1 treated and control samples are analyzed on 1% agarose gels, stained with SYBR safe, and visualized using an imaging System. Reduction of *Buchnera* specific genes indicates antimicrobial activity of compound 1.

The survival rate of aphids treated with the compound is compared to the aphids treated with the negative control. A decrease in the survival rate of aphids treated with the compound is expected to indicate antimicrobial activity of the compound.

Example 14: Insects Treated with an Antibiotic Solution

This Example demonstrates the treatment of aphids with rifampicin, a narrow spectrum antibiotic that inhibits DNA-dependent RNA synthesis by inhibiting a bacterial RNA polymerase. This Example demonstrates that the effect of rifampicin on a model insect species, aphids, was mediated through the modulation of bacterial populations endogenous to the insect that were sensitive to rifampicin. One targeted bacterial strain is *Buchnera*.

Therapeutic Design

The antibiotic solution was formulated according to the means of delivery, as follows (FIG. 1A-1G):

1) Through the plants: with 0 (negative control) or 100 µg/ml of rifampicin formulated in an artificial diet (based on Akey and Beck, 1971; see Experimental Design) with and without essential amino acids (2 mg/ml histidine, 2 mg/ml isoleucine, 2 mg/ml leucine, 2 mg/ml lysine, 1 mg/ml methionine, 1.62 mg/ml phenylalanine, 2 mg/ml threonine, 1 mg/ml tryptophan, and 2 mg/ml valine).
2) Leaf coating: 100 µl of 0.025% nonionic organosilicone surfactant solvent Silwet L-77 in water (negative control) or 100 µl of 50 µg/ml of rifampicin formulated in solvent solution was applied directly to the leaf surface and allowed to dry.
3) Microinjection: injection solutions were either 0.025% nonionic organosilicone surfactant solvent Silwet L-77 in water (negative control), or 50 µg/ml of rifampicin formulated in solvent solution.
4) Topical delivery: 100 µl of 0.025% nonionic organosilicone surfactant solvent Silwet L-77 (negative control), or 50 µg/ml of rifampicin formulated in solvent solution were sprayed using a 30 mL spray bottle.
5) Leaf injection method A—Leaf perfusion and cutting: leaves were injected with approximately 1 ml of 50 µg/ml of rifampicin in water with food coloring or approximately 1 ml of negative control with water and food coloring. Leaves were cut into 2×2 cm squared pieces and aphids were placed on the leaf pieces.
6) Leaf perfusion and delivery through plant: Leaves were injected with approximately 1 ml of 100 µg/ml of rifampicin in water plus food coloring or approximately 1 ml of negative control with water and food coloring. The stem of injected leaf was then placed into an Eppendorf tube with 1 ml of 100 μg/ml of rifampicin plus water and food coloring or 1 ml of negative control with only water and food coloring.

7) Combination delivery method: a) Topical delivery to aphid and plant: via spraying both aphids and plants with 0.025% nonionic organosilicone surfactant solvent Silwet L-77 in water (negative control) or 100 μg/ml of rifampicin formulated in solvent solution using a 30 mL, b) Delivery through plant: water only (negative control) or 100 μg/ml of rifampicin formulated in water.

Plant Delivery Experimental Design:

Aphids (LSR-1 strain, *Acyrthosiphon pisum*) were grown on fava bean plants (*Vroma vicia* faba from Johnny's Selected Seeds) in a climate-controlled incubator (16 h light/8 h dark photoperiod; 60±5% RH; 25±2° C.). Prior to being used for aphid rearing, fava bean plants were grown in potting soil at 24° C. with 16 h of light and 8 h of darkness. To limit maternal effects or health differences between plants, 5-10 adults from different plants were distributed among 10 two-week-old plants, and allowed to multiply to high density for 5-7 days. For experiments, first instar aphids were collected from healthy plants and divided into 3 different treatment groups: 1) artificial diet alone without essential amino acids, 2) artificial diet alone without essential amino acids and 100 μg/ml rifampicin, and 3) artificial diet with essential amino acids and 100 μg/ml rifampicin). Each treatment group received approximately the same number of individuals from each of the collection plants.

The artificial diet used was made as previously published (Akey and Beck, 1971 Continuous Rearing of the Pea Aphid, *Acyrthosiphon pisum*, on a Holidic Diet), with and without the essential amino acids (2 mg/ml histidine, 2 mg/ml isoleucine, 2 mg/ml leucine, 2 mg/ml lysine, 1 mg/ml methionine, 1.62 mg/ml phenylalanine, 2 mg/ml threonine, 1 mg/ml tryptophan, and 2 mg/ml valine), except neither diet included homoserine or beta-alanyltyrosine. The pH of the diets was adjusted to 7.5 with KOH and diets were filter sterilized through a 0.22 μm filter and stored at 4° C. for short term (<7 days) or at −80° C. for long term.

Rifampicin (Tokyo Chemical Industry, LTD) stock solutions were made at 25 mg/ml in methanol, sterilized by passing through a 0.22 μm syringe filter, and stored at −20° C. For treatments (see Therapeutic design), the appropriate amount of stock solution was added to the artificial diet with or without essential amino acids to obtain a final concentration of 100 μg/ml rifampicin. The diet was then placed into a 1.5 ml Eppendorf tube with a fava bean stem with a leaf and the opening of the tube was closed using parafilm. This artificial diet feeding system was then placed into a deep petri dish (Fisher Scientific, Cat #FB0875711) and aphids were applied to the leaves of the plant.

For each treatment, 33 aphids were placed onto each leaf. Artificial diet feeding systems were changed every 2-3 days throughout the experiment. Aphids were monitored daily for survival and dead aphids were removed from the deep petri dish housing the artificial feeding system when they were discovered.

In addition, the developmental stage ($1^{st}$, $2^{nd}$, $3^{rd}$, $4^{th}$, $5^{th}$ instar) was determined daily throughout the experiment. Once an aphid reached the 4th instar stage, they were given their own artificial feeding system in a deep petri dish so that fecundity could be monitored once they reached adulthood.

For adult aphids, new nymphs were counted daily and then discarded. At the end of the experiments, fecundity was determined as the mean number of offspring produced daily once the aphid reached adulthood. Pictures of aphids were taken throughout the experiment to evaluate size differences between treatment groups.

After 7 days of treatment, DNA was extracted from multiple aphids from each treatment group. Briefly, the aphid body surface was sterilized by dipping the aphid into a 6% bleach solution for approximately 5 seconds. Aphids were then rinsed in sterile water and DNA was extracted from each individual aphid using a DNA extraction kit (Qiagen, DNeasy kit) according to manufacturer's instructions. DNA concentration was measured using a nanodrop nucleic acid quantification, and *Buchnera* and aphid DNA copy numbers were measured by qPCR. The primers used for *Buchnera* were Buch_groES_18F (CATGATCGTGTGCTTGTTAAG; SEQ ID NO: 238) and Buch_groES_98R (CTGTTCCTCGAGTCGATTTCC; SEQ ID NO: 239) (Chong and Moran, 2016 PNAS). The primers used for aphid were ApEF1a 107F (CTGATTGTGCCGTGCTTATTG; SEQ ID NO: 240) and ApEF1a 246R (TATGGTGGTTCAGTAGAGTCC; SEQ ID NO: 241) (Chong and Moran, 2016 PNAS). qPCR was performed using a qPCR amplification ramp of 1.6 degrees C./s and the following conditions: 1) 95° C. for 10 minutes, 2) 95° C. for 15 seconds, 3) 55° C. for 30 seconds, 4) repeat steps 2-3 40×, 5) 95° C. for 15 seconds, 6) 55° C. for 1 minute, 7) ramp change to 0.15 degrees C./s, 8) 95° C. for 1 second. qPCR data was analyzed using analytic (Thermo Fisher Scientific, QuantStudio Design and Analysis) software.

Antibiotic Treatment Delays and Stops Progression of Aphid Development

Figure 2A:
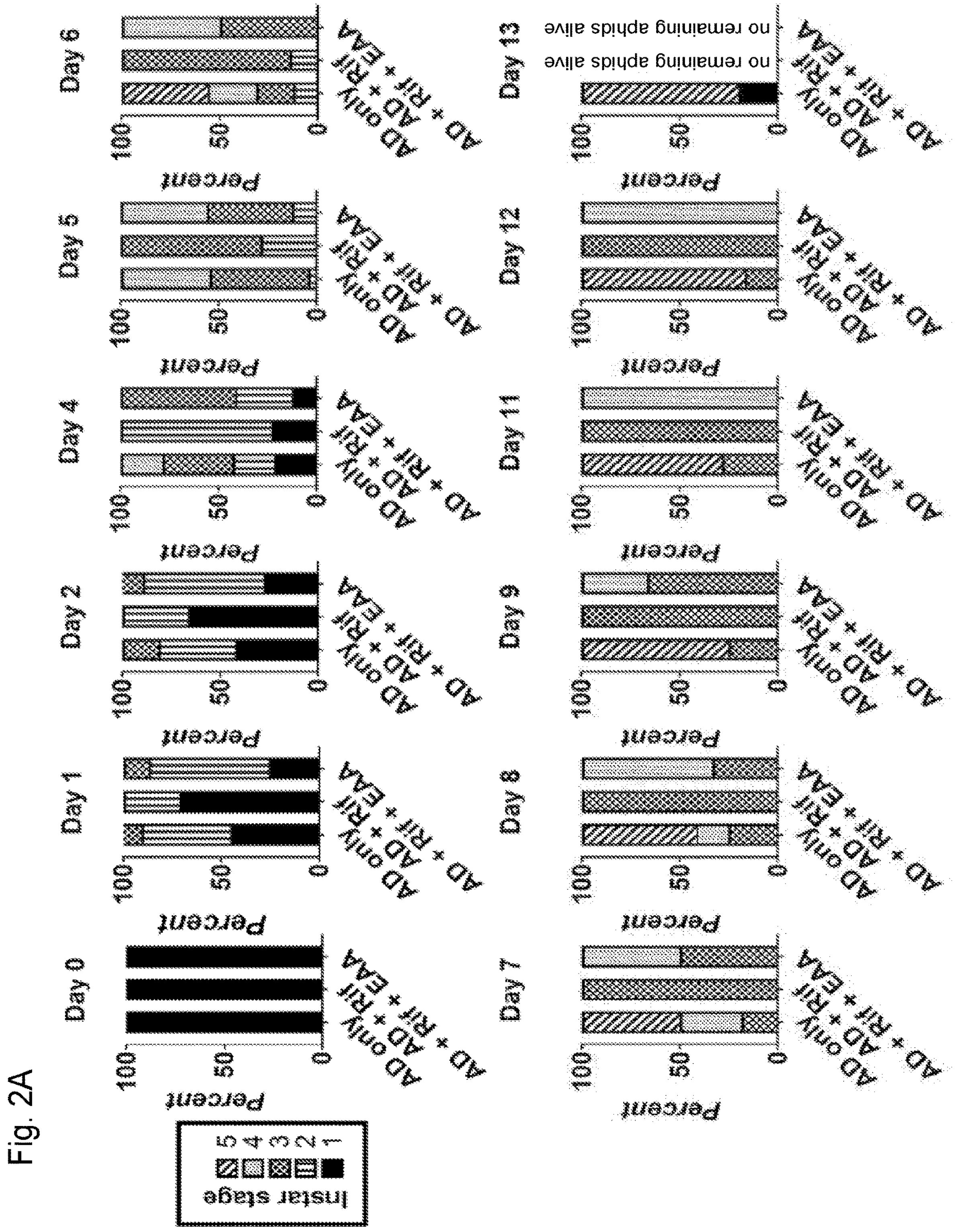
FIG. 2A-2C show the delay in aphid development during rifampicin treatment in first instar LSR-1 aphids treated by delivery through plants with three different conditions: artificial diet without essential amino acids (AD only), artificial diet without essential amino acids with 100 μg/ml rifampicin (AD+Rif), and artificial diet with 100 μg/ml rifampicin and essential amino acids (AD+Rif+EAA).

LSR-1 $1^{st}$ instar aphids were divided into three separate treatment groups as defined in Experimental Design (above). Aphids were monitored daily and the number of aphids at each developmental stage was determined. Aphids treated with artificial diet alone without essential amino acids began reaching maturity (5th instar stage) at approximately 6 days (FIG. 2A). Development was delayed in aphids treated with rifampicin, and by 6 days of treatment, most aphids did not mature further than the $3^{rd}$ instar stage, even after 12 days and their size is drastically affected (FIGS. 2A-2C).

Figure 2B:
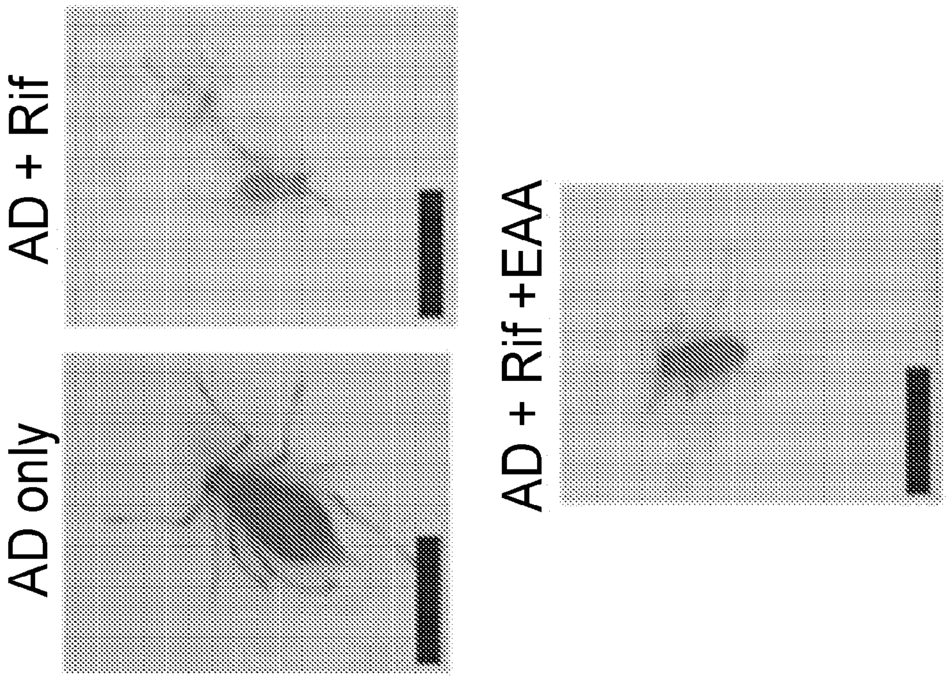
Figure 2C:
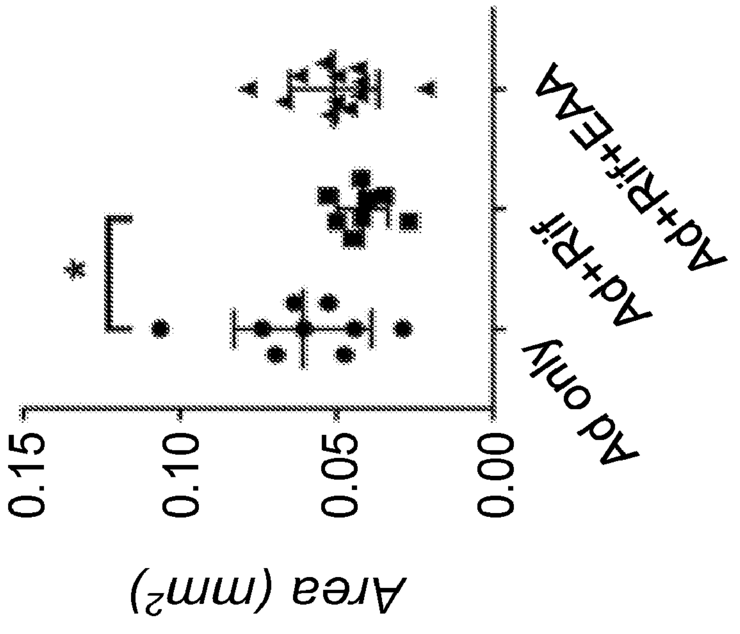

In contrast, aphids treated with artificial diet with rifampicin supplemented with essential amino acids developed faster and to higher instar stages as compared to aphids treated with rifampicin alone, but not as quickly as aphids treated with artificial diet without essential amino acids (FIGS. 2A-2C). These data indicate that treatment with rifampicin impaired aphid development. Adding back essential amino acids partially rescued this defect in development.

Antibiotic Treatment Increased Aphid Mortality

Figure 3:
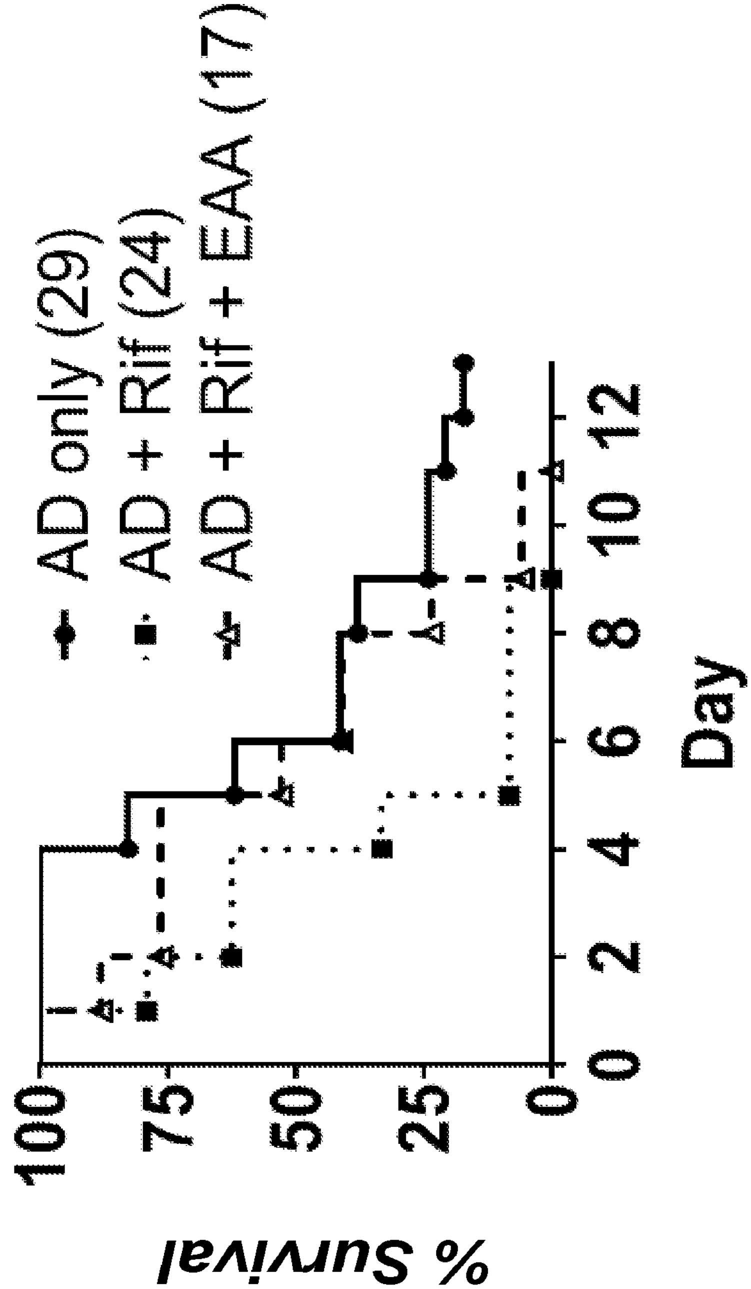
FIG. 3 shows that rifampicin treatment resulted in aphid death. Survival was monitored daily for LSR-1 aphids treated by delivery through plants with artificial diet without essential amino acids (AD only), artificial diet without essential amino acids with 100 ug/ml rifampicin (AD+Rif), and artificial diet with 100 ug/ml rifampicin and (AD+Rif+EAA). Number in parentheses represents number of aphids in each group. Statistical significance was determined by Log-Rank Test and the following statistically significant differences were determined: AD only vs. AD+Rif, $p<0.0001$ and AD+Rif vs. AD+Rif+EAA, 1)=0.017.

Survival rate of aphids was also measured during the treatments. The majority of the aphids treated with artificial diet alone without essential amino acids were alive at 5 days post-treatment (FIG. 3). After 5 days, aphids began gradually dying, and some survived beyond 13 days post-treatment.

In contrast, aphids treated with rifampicin without essential amino acids had lower survival rates than aphids treated with artificial diet alone (p<0.00001). Rifampicin-treated aphids began dying after 1 day of treatment and all aphids succumbed to treatment by 9 days. Aphids treated with both rifampicin and essential amino acids survived longer than those treated with rifampicin alone (p=0.017). These data indicate that rifampicin treatment affected aphid survival.

Antibiotic Treatment Decreased Aphid Reproduction

Figure 4:
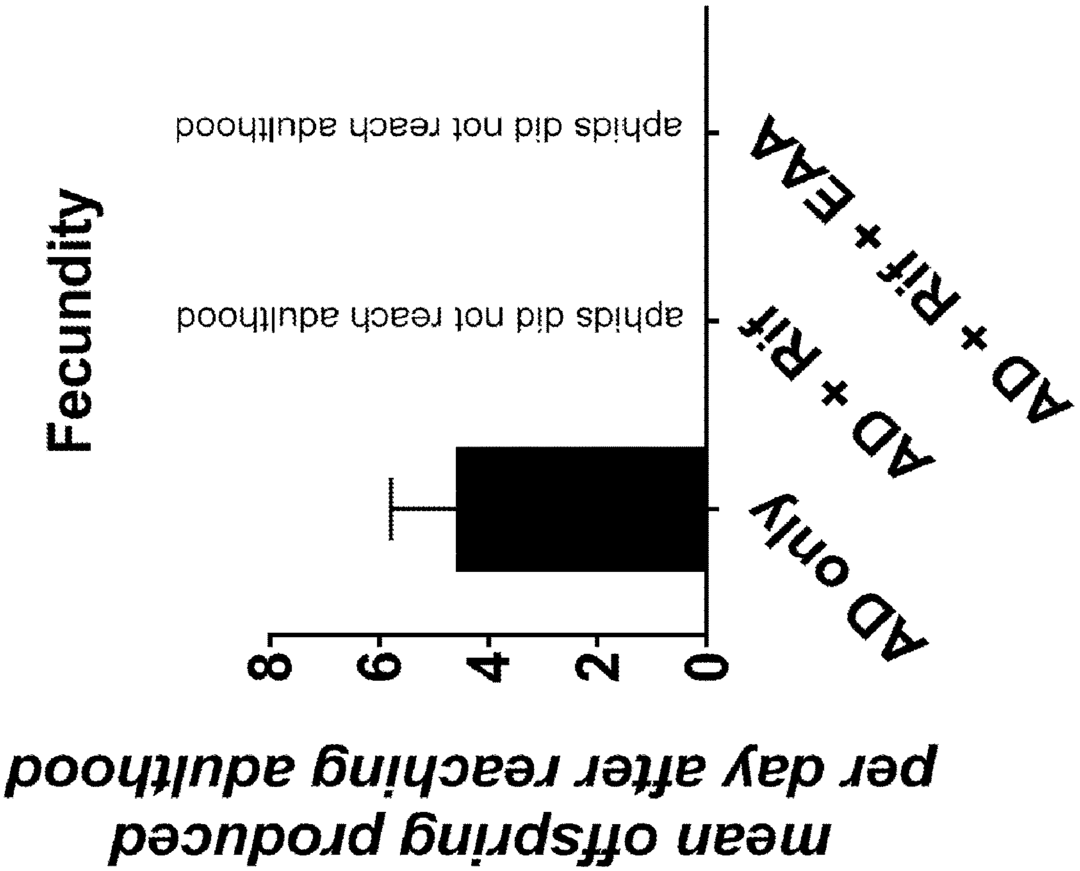
FIG. 4 is a graph showing that rifampicin treatment resulted in loss of reproduction in aphids. First instar LSR-1 aphids were treated by delivery through plants with artificial diet without essential amino acids (AD only), artificial diet without essential amino acids with 100 ug/ml rifampicin (AD+Rif), and artificial diet with 100 ug/ml rifampicin and (AD+Rif+EAA) and the number of offspring produced each day after aphid reached adulthood was measured. Shown is the mean number of offspring produced per day after aphid reached adulthood±S.D.

Fecundity was also monitored in aphids during the treatments. By days 7 and 8 post-treatment, the majority of the adult aphids treated with artificial diet without essential amino acids began reproducing. The mean number of offspring produced daily after maturity by aphids treated with artificial diet without essential amino acids was approximately 4 (FIG. 4). In contrast, aphids treated with rifampicin with or without essential amino acids were unable to reach adulthood and produce offspring. These data indicate that rifampicin treatment resulted in a loss of aphid reproduction.

Antibiotic Treatment Decreased *Buchnera* in Aphids

Figure 5:
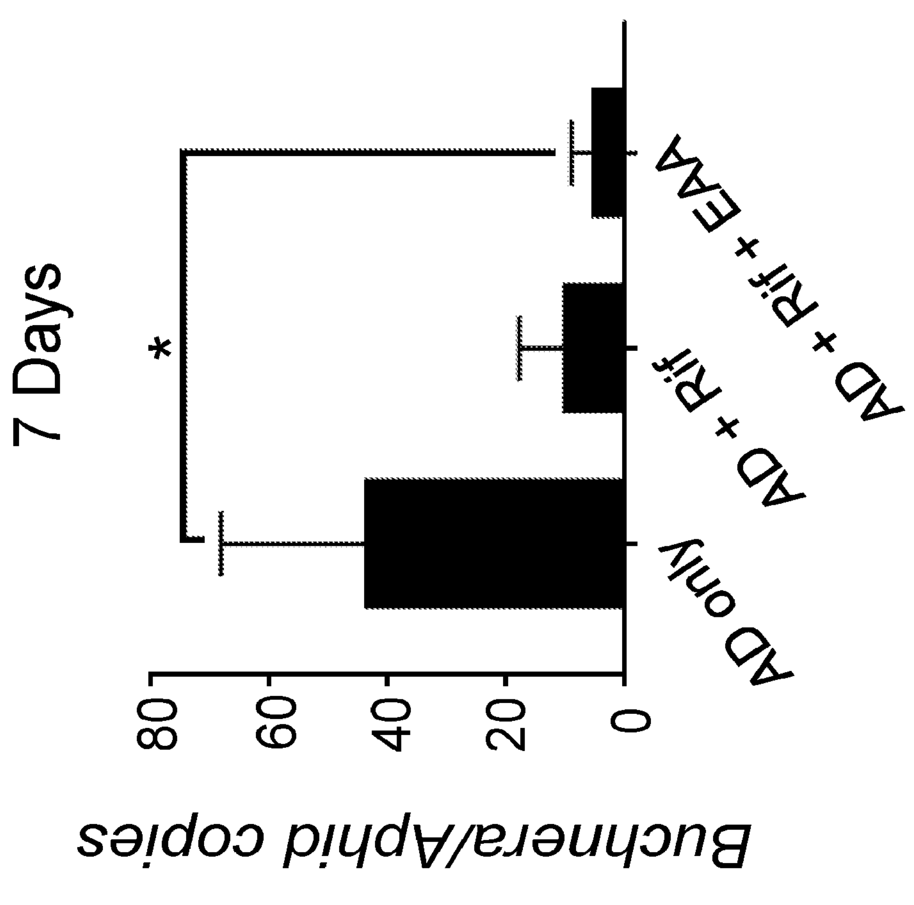
FIG. 5 is a graph showing that rifampicin treatment eliminated endosymbiotic *Buchnera*. Symbiont titer was determined for the different conditions at 7 days post-treatment. DNA from aphids was extracted and qPCR was performed to determine the ratio of *Buchnera* DNA to aphid DNA. Shown is the mean ratio of *Buchnera* DNA to aphid DNA±SD of 3 aphids per group. Statistically significant differences were determined using a one-way-ANOVA followed by Tukey's Post-Test; *, $p<0.05$.

To test whether rifampicin, specifically resulted in loss of *Buchnera* in aphids, and that this loss impacted aphid fitness, DNA was extracted from aphids in each treatment group after 7 days of treatment and qPCR was performed to determine the *Buchnera*/aphid copy numbers. Aphids treated with artificial diet alone without essential amino acids had high ratios of *Buchnera*/aphid DNA copies. In contrast, aphids treated with rifampicin had ~4-fold less *Buchnera*/aphid DNA copies (FIG. 5), indicating that rifampicin treatment decreased *Buchnera* levels.

Leaf Coating Delivery Experimental Design

Rifampicin stock solution was added to 0.025% of a nonionic organosilicone surfactant solvent, Silwet L-77, to obtain a final concentration of 50 μg/ml rifampicin. Aphids (eNASCO strain, *Acyrthosiphon pisum*) were grown on fava bean plants as described in a previous Example. For experiments, first instar aphids were collected from healthy plants and divided into 2 different treatment groups: leaves were sprayed with 1) negative control (solvent solution only), 2) 50 μg/ml rifampicin in solvent. Solutions were absorbed onto a 2×2 cm piece of fava bean leaf.

Each treatment group received approximately the same number of individuals from each of the collection plant. For each treatment, 20 aphids were placed onto each leaf. Aphids were monitored daily for survival and dead aphids were removed when they were discovered. In addition, the developmental stage ($1^{st}$, $2^{nd}$, $3^{rd}$, $4^{th}$, $5^{th}$ instar, and 5 R, representing a reproducing 5th instar) was determined daily throughout the experiment. Pictures of aphids were taken throughout the experiment to evaluate size differences between treatment groups.

After 6 days of treatment, DNA was extracted from multiple aphids from each treatment group and qPCR for quantifying *Buchnera* levels was done as described in the previous Example.

Figure 6A:
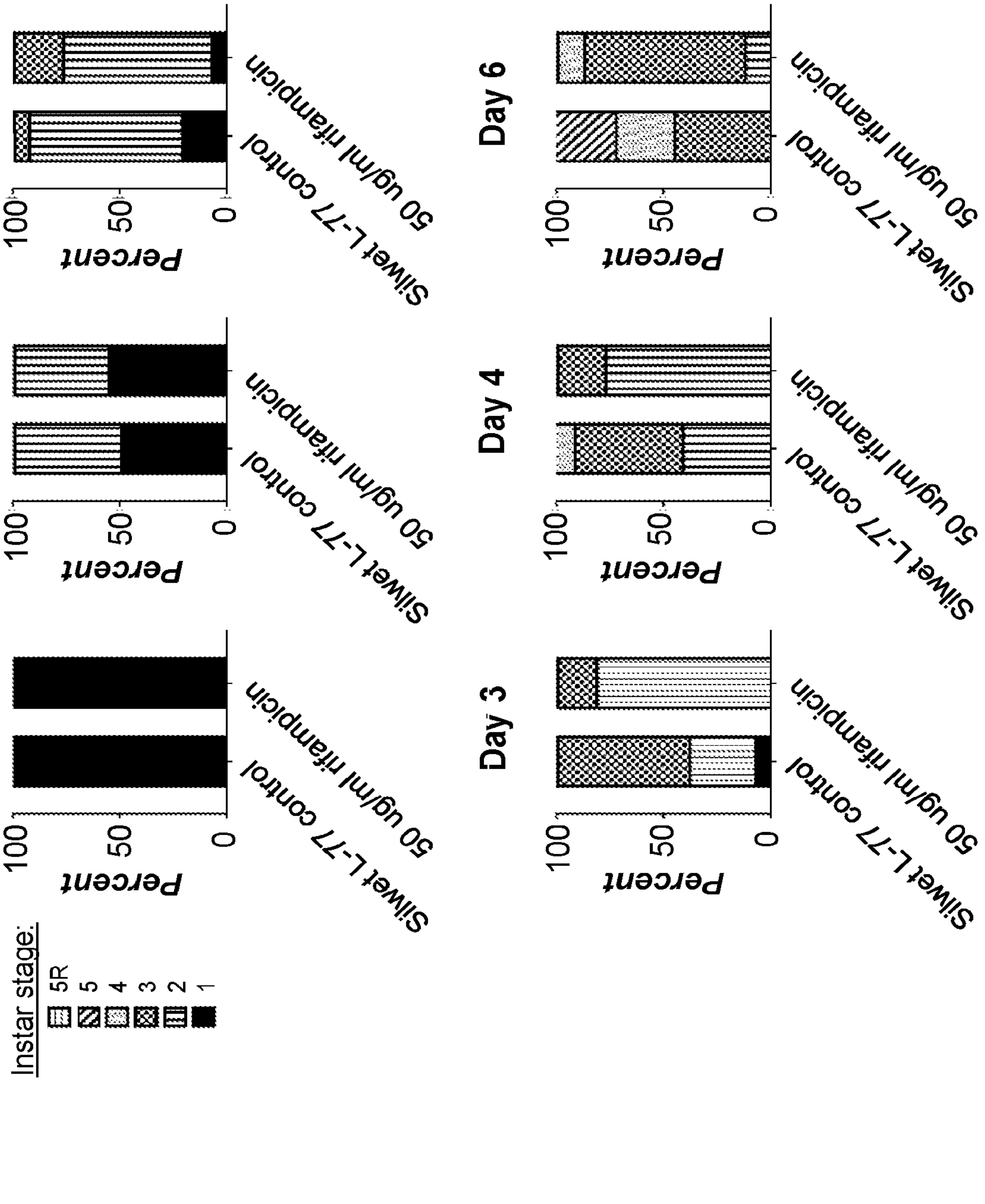
FIGS. 6A and 6B show that rifampicin treatment delivered through leaf coating delayed aphid development. First instar eNASCO aphids were treated by coating leaves with 100 μl of two different solutions:solvent control (0.025% Silwet L-77), and 50 μg/ml rifampicin.
Figure 6B:
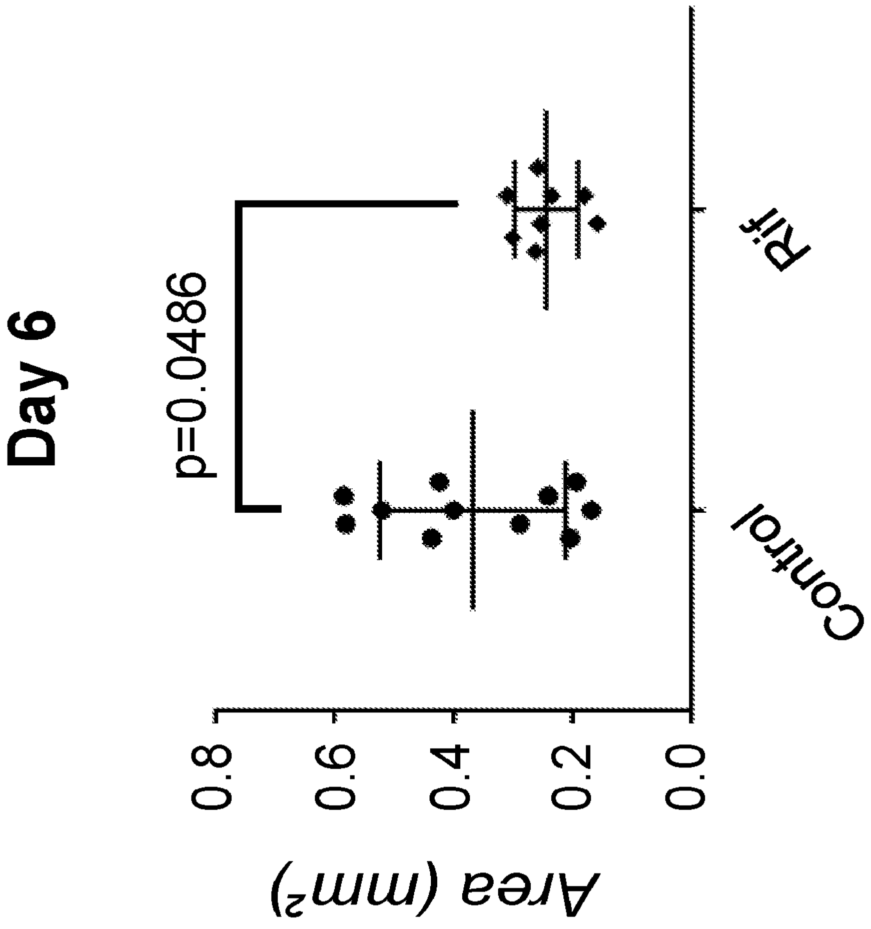

Antibiotic Treatment Delivered Through Leaf Coating Delays and Stops Progression of Aphid Development LSR-1 $1^{st}$ instar aphids were divided into two separate treatment groups as defined in the Experimental Design described herein. Aphids were monitored daily and the number of aphids at each developmental stage was determined. Aphids placed on coated leaves treated with control began reaching maturity ($5^{th}$ instar reproducing stage; 5 R) at approximately 6 days (FIG. 6A). Development was delayed in aphids placed on coated leaves with rifampicin, and by 6 days of treatment, most aphids did not mature further than the $3^{rd}$ instar stage, even after 12 days, and their size is drastically affected (FIGS. 6A and 6B).

These data indicate that leaf coating with rifampicin impaired aphid development.

Antibiotic Treatment Delivered Through Leaf Coating Increased Aphid Mortality

Figure 7:
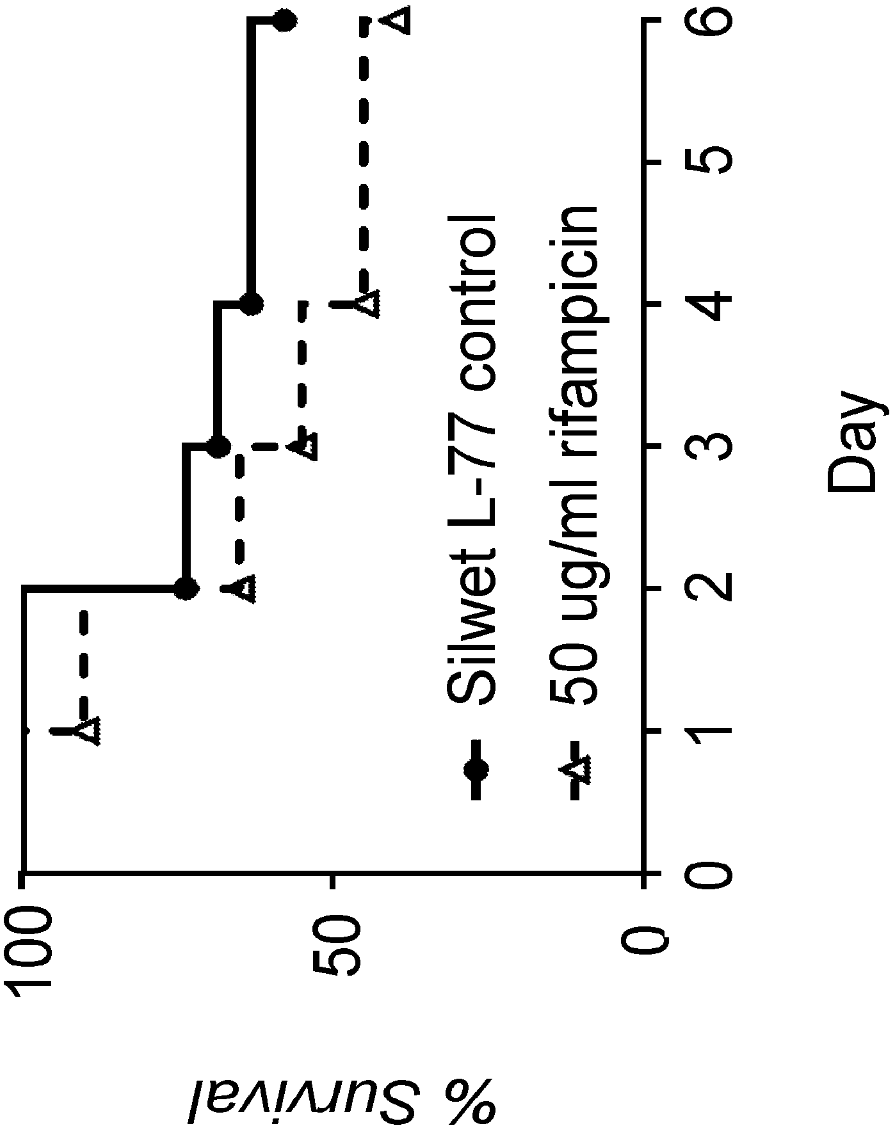
FIG. 7 shows that rifampicin treatment delivered through leaf coating resulted in aphid death. Survival was monitored daily for eNASCO aphids treated by coating leaves with 100 μl of two different solutions:solvent control (Silwet L-77), and 50 μg/ml rifampicin. Treatment affects survival rate of aphids.

Survival rate of aphids was also measured during the leaf coating treatments. Aphids placed on coated leaves with rifampicin had lower survival rates than aphids placed on coated leaves with the control (FIG. 7). These data indicate that rifampicin treatment delivered through leaf coating affected aphid survival.

Antibiotic Treatment Delivered Through Leaf Coating Decreased *Buchnera* in Aphids To test whether rifampicin delivered through leaf coating, specifically resulted in loss of *Buchnera* in aphids, and that this loss impacted aphid fitness, DNA was extracted from aphids in each treatment group after 6 days of treatment and qPCR was performed to determine the *Buchnera*/aphid copy numbers.

Figure 8:
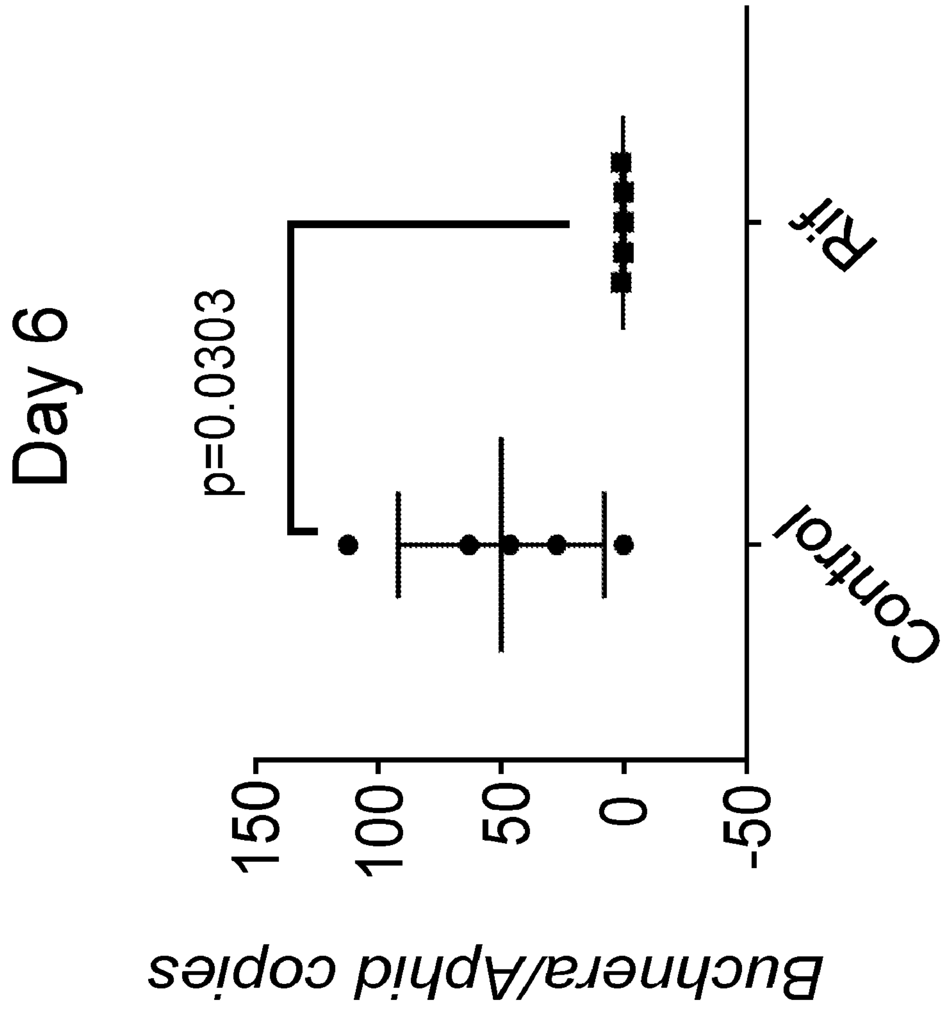
FIG. 8 shows that rifampicin treatment delivered through leaf coating eliminated endosymbiotic *Buchnera*. Symbiont titer was determined for the two conditions at 6 days post-treatment. DNA from aphids was extracted and qPCR was performed to determine the ratio of *Buchnera* DNA to aphid DNA. Shown is the mean ratio of *Buchnera* DNA to aphid DNA±SD. Statistically significant differences were determined using a one-way-ANOVA followed by Tukey's Post-Test; *, $p<0.05$.

Aphids placed on leaves treated with control had high ratios of *Buchnera*/aphid DNA copies. In contrast, aphids placed on leaves treated with rifampicin had a drastic reduction of *Buchnera*/aphid DNA copies (FIG. 8), indicating that rifampicin leaf coating treatment eliminated endosymbiotic *Buchnera.*

Figure 1A:
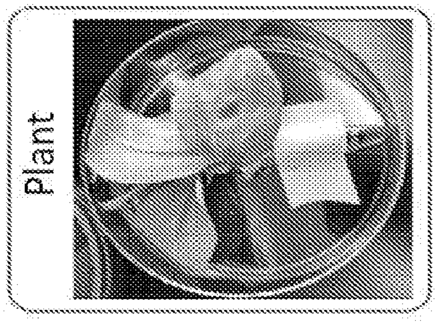
FIG. 1A-1G show images of different antibiotic delivery systems. First instar LSR-1 aphids were treated with different therapeutic solutions by delivery through plants (FIG. 1A), leaf coating (FIG. 1B), microinjection (FIG. 10), topical delivery (FIG. 1D), leaf perfusion and cutting (FIG. 1E), leaf perfusion and through plant (FIG. 1F), and combination treatment of spraying both plant and aphid, and delivery though plant (FIG. 1G).
Figure 1B:
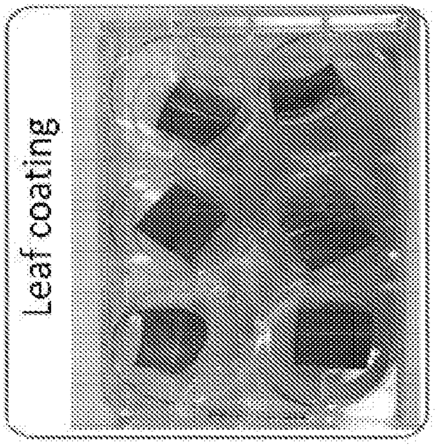
Figure 1C:
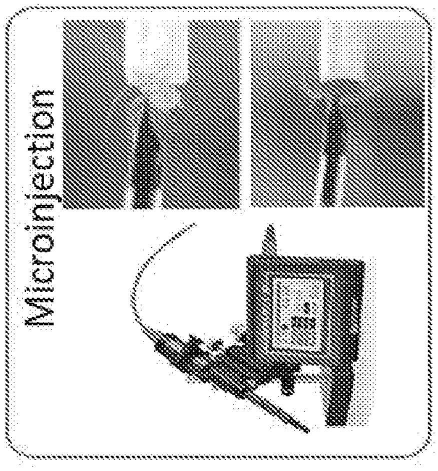
Figure 1D:
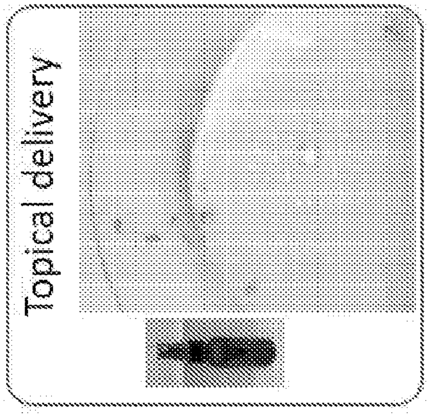
Figure 1E:
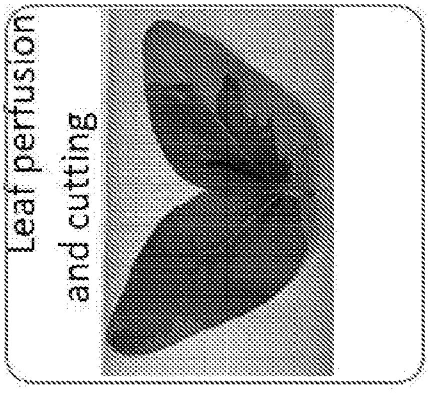
Figure 1F:
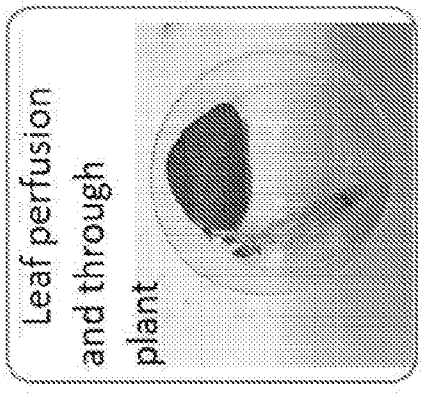
Figure 1G:
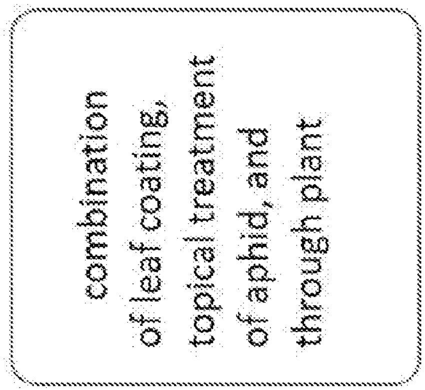

Microinjection Delivery Experimental Design:

Microinjection was performed using NanoJet III Auto-Nanoliter Injector with the in-house pulled borosilicate needle (Drummond Scientific; Cat #3-000-203-G/XL). Aphids (eNASCO strain, *Acyrthosiphon pisum*) were grown on fava bean plants as described in a previous Example. Aphids are transferred using a paint brush to a tubing system connected to vacuum (FIG. 1C). The injection site was at the ventral thorax of the aphid. The injection solutions were either the organosilicone surfactant solvent 0.025% Silwet L-77 (Lehle Seeds, Cat No VIS-01) in water (negative control), or 50 μg/ml of rifampicin formulated in solvent solution. The injection volume was 10 nl for nymph and 20 nl for adult (both at a rate of 2 nl/sec). Each treatment group had approximately the same number of individuals injected from each of the collection plants. After injection, aphids were released into a petri dish with fava bean leaves, whose stems are in 2% agar.

Microinjection with Antibiotic Treatment Decreased *Buchnera* in Aphids

To test whether rifampicin delivered by microinjection results in loss of *Buchnera* in aphids, and that this loss impacts aphid fitness as demonstrated in previous Examples, DNA was extracted from aphids in each treatment group after 4 days of treatment and qPCR was performed as described in a previous Example to determine the *Buchnera*/aphid copy numbers.

Figure 9:
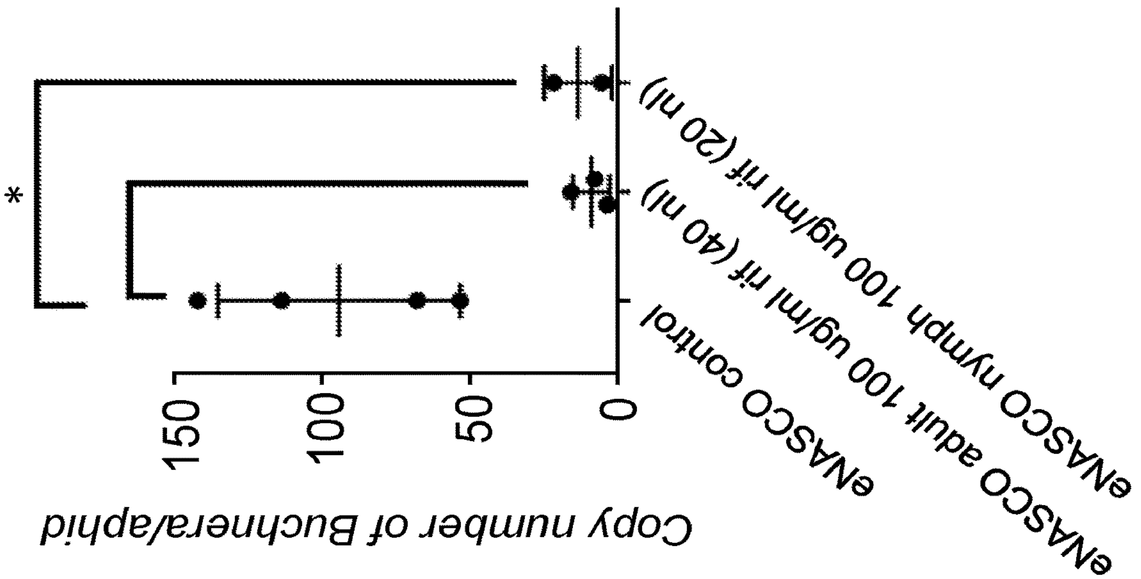
FIG. 9 is a graph showing rifampicin treatment by microinjection eliminated endosymbiotic *Buchnera*. Symbiont titer was determined 4 days post-injection with the indicated conditions. Control sample is the solvent, 0.025% Silwet L-77 described before. DNA from aphids was extracted and qPCR was performed to determine the ratio of *Buchnera* DNA to aphid DNA. Shown is the mean ratio of *Buchnera* DNA to aphid DNA±SD. Statistically significant differences were determined using a one-way-ANOVA followed by Tukey's Post-Test; *, $p<0.05$.

Aphids microinjected with negative control had high ratios of *Buchnera*/aphid DNA copies. In contrast, aphid nymphs and adults microinjected with rifampicin had a drastic reduction of *Buchnera*/aphid DNA copies (FIG. 9), indicating that rifampicin microinjection treatment decreased the presence of endosymbiotic *Buchnera.*

Topical Delivery Experimental Design:

Aphids (LSR-1 strain, *Acyrthosiphon pisum*) were grown on fava bean plants as described in a previous Example. Spray bottles were filled with 2 ml of control (0.025% Silwet L-77) or rifampicin solutions (50 μg/ml of in solvent solution). Aphids (number=10) were transferred to the bottom of a clean petri dish and gathered to the corner of the petri dish using a paint brush. Subsequently, aphids were separated into two cohorts and sprayed with ~100 μl of either control or rifampicin solutions. Immediately after spraying, the petri dish was covered with a lid. Five minutes after spraying, aphids were released into a petri dish with fava bean leaves with stems in 2% agar.

Topical Delivery of Antibiotic Treatment Decreased *Buchnera* in Aphids

To test whether rifampicin delivered by topical delivery results in loss of *Buchnera* in aphids, and that this loss impacts aphid fitness as demonstrated in previous Examples, DNA was extracted from aphids in each treatment group after 3 days of treatment and qPCR as described in a previous Example was performed to determine the *Buchnera*/aphid copy numbers.

Figure 10:
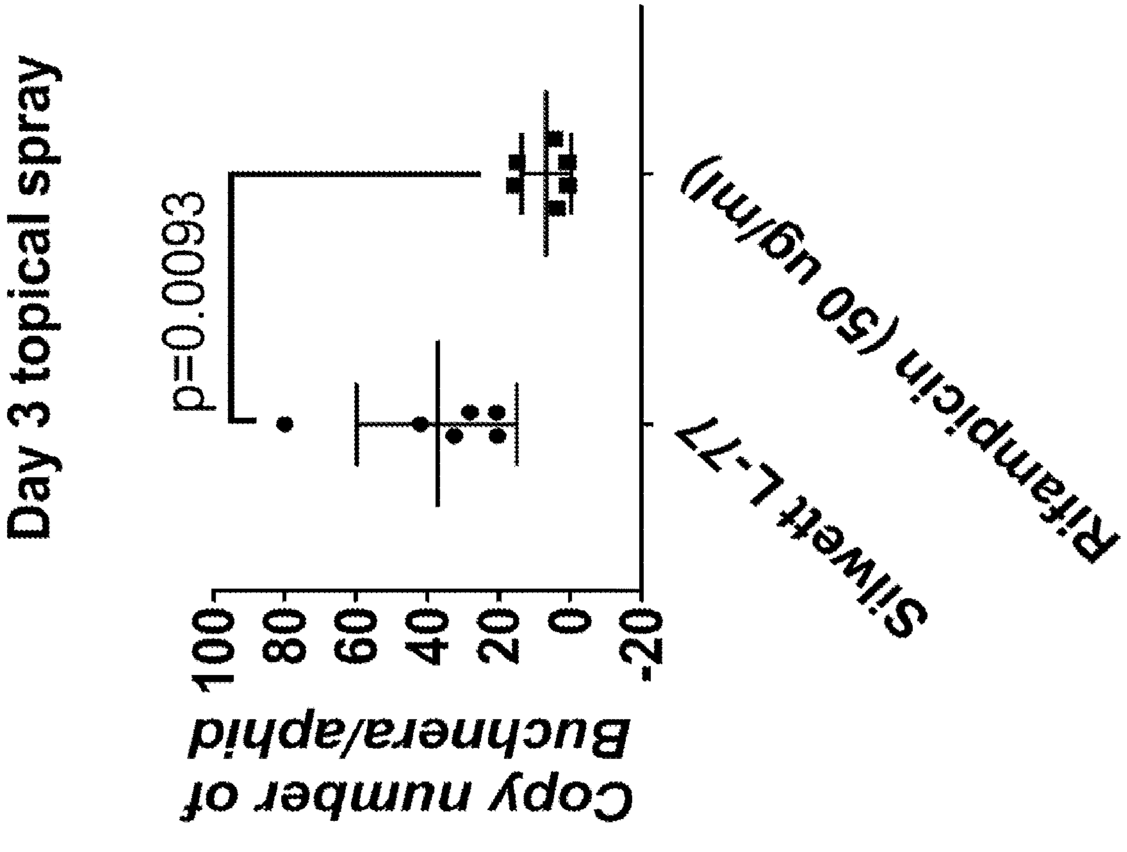
FIG. 10 is a graph showing that rifampicin treatment delivered through topical treatment eliminated endosymbiotic *Buchnera*. Symbiont titer was determined 3 days post-spraying with: solvent (silwet L-77) or the rifampicin solution diluted in solvent. DNA from aphids was extracted and qPCR was performed to determine the ratio of *Buchnera*

Aphids sprayed with the control solution had high ratios of *Buchnera*/aphid DNA copies. In contrast, aphids sprayed with rifampicin had a drastic reduction of *Buchnera*/aphid DNA copies (FIG. 10), indicating that rifampicin treatment delivered through topical treatment decreases the presence of endosymbiotic *Buchnera*.

Leaf Injection Method A—Leaf Perfusion and Cutting Experimental Design:

Aphids LSR-1 (which harbor only *Buchnera*), *Acyrthosiphon pisum* were grown on fava bean plants (*Vroma vicia* faba from Johnny's Selected Seeds) in a climate-controlled incubator (16 h light/8 h dark photoperiod; 60±5% RH; 25±2° C.). Prior to being used for aphid rearing, fava bean plants were grown in potting soil at 24° C. with 16 h of light and 8 h of darkness. To limit maternal effects or health differences between plants, 5-10 adults from different plants were distributed among 10 two-week-old plants, and allowed to multiply to high density for 5-7 days. For experiments, first and second instar aphids were collected from healthy plants and divided into 2 different treatment groups: 1) negative control (leaf injected with water plus blue food coloring) and 2) leaf injected with 50 μg/ml rifampicin in water plus blue food coloring. Each treatment group received approximately the same number of individuals from each of the collection plants. For treatment, rifampicin stock solution (25 mg/ml in 100% methanol) was diluted to 50 μg/ml in water plus blue food coloring. The solution was then placed into a 1.5 ml Eppendorf tube with a fava bean stem perfused with the solutions and the opening of the tube was closed using parafilm. This feeding system was then placed into a deep petri dish (Fisher Scientific, Cat #FB0875711) and aphids were applied to the leaves of the plant. For each treatment, 74-81 aphids were placed onto each leaf. The feeding systems were changed every 2-3 days throughout the experiment. Aphids were monitored daily for survival and dead aphids were removed from the deep petri dish when they were discovered. In addition, the developmental stage ($1^{st}$, $2^{nd}$, $3^{rd}$, $4^{th}$, $5^{th}$ and 5 R (5th that has reproduced) instar) was determined daily throughout the experiment.

Antibiotic Treatment Delivered Through Leaf Injection Method a Delays and Stops Progression of Aphid Development LSR-1 1st and 2nd instar aphids were divided into two separate treatment groups as defined in Leaf injection method A—Leaf perfusion and cutting Experimental Design (described herein). Aphids were monitored daily and the number of aphids at each developmental stage was determined. Aphids treated with water plus food coloring began reaching maturity (5th instar stage) at approximately 6 days (FIG. 11). Development was delayed in aphids feeding on rifampicin injected leaves, and by 6 days of treatment, most aphids did not mature further than the 4th instar stage. Even after 8 days, the development of aphids feeding on rifampicin injected leaves was drastically delayed (FIG. 11). These data indicate that rifampicin treatment via leaf perfusion impaired aphid development.

Antibiotic Treatment Delivered Through Leaf Injection Method a Increased Aphid Mortality Survival rate of aphids was also measured during the leaf perfusion experiments. Aphids placed on leaves injected with rifampicin had lower survival rates than aphids placed on leaves injected with the control solution (FIG. 12). These data indicate that rifampicin treatment delivered through leaf injection affected aphid survival.

Antibiotic Treatment Delivered Thorough Leaf Injection Method a Results in Decreased Levels of *Buchnera*

To test whether rifampicin delivered via leaf perfusion results in loss of *Buchnera* in aphids, and that this loss impacts aphid fitness as demonstrated in previous Examples, DNA was extracted from aphids in each treatment group after 8 days of treatment and qPCR as described in a previous Example was performed to determine the *Buchnera*/aphid copy numbers.

Aphids feeding on leaves injected with the control solution had high ratios of *Buchnera*/aphid DNA copies. In contrast, aphids feeding on leaves injected with rifampicin had a reduction of *Buchnera*/aphid DNA copies (FIG. 13), indicating that rifampicin treatment delivered via leaf injection decreases the presence of endosymbiotic *Buchnera*, as shown in previous Examples, and resulted in a fitness decrease.

Leaf Perfusion and Delivery Through Plant Experimental Design:

Aphids LSR-1 (which harbor only *Buchnera*), *Acyrthosiphon pisum* were grown on fava bean plants (*Vroma vicia* faba from Johnny's Selected Seeds) in a climate-controlled incubator (16 h light/8 h dark photoperiod; 60±5% RH; 25±2° C.). Prior to being used for aphid rearing, fava bean plants were grown in potting soil at 24° C. with 16 h of light and 8 h of darkness.

To limit maternal effects or health differences between plants, 5-10 adults from different plants were distributed among 10 two-week-old plants, and allowed to multiply to high density for 5-7 days. For experiments, first and second instar aphids were collected from healthy plants and divided into 2 different treatment groups: 1) aphids placed on leaves injected with the negative control solution (water and food coloring) and placed into an Eppendorf tube with the negative control solution, or 2) aphids placed on leaves that were injected with 100 ug/ml rifampicin in water plus food coloring and put into an Eppendorf tube with 100 ug/ml rifampicin in water. Each treatment group received approximately the same number of individuals from each of the collection plants.

For treatment, rifampicin stock solution (25 mg/ml in 100% methanol) was diluted to 100 μg/ml in water plus blue food coloring. The solution was then placed into a 1.5 ml Eppendorf tube with a fava bean stem with a leaf also perfused with the solutions and the opening of the tube was closed using parafilm. This feeding system was then placed into a deep petri dish (Fisher Scientific, Cat #FB0875711) and aphids were applied to the leaves of the plant.

For each treatment, 49-50 aphids were placed onto each leaf. The feeding systems were changed every 2-3 days throughout the experiment. Aphids were monitored daily for survival and dead aphids were removed from the deep petri dish when they were discovered.

In addition, the developmental stage ($1^{st}$ $2^{nd}$, $3^{rd}$, $4^{th}$, $5^{th}$ and 5 R ($5^{th}$ that has reproduced) instar) was determined daily throughout the experiment.

Antibiotic Treatment Delivered Through Leaf Injection and Delivery Through Plant Delays and Stops Progression of Aphid Development LSR-1 $1^{st}$ and $2^{nd}$ instar aphids were divided into two separate treatment groups as defined in Leaf perfusion and delivery through plant Experimental Design (described herein). Aphids were monitored daily and the number of aphids at each developmental stage was determined. Aphids treated with the control solution (water plus food coloring only) began reaching maturity ($5^{th}$ instar stage) at approximately 6 days (FIG. 14).

Development was delayed in aphids treated with rifampicin, and by 6 days of treatment, most aphids did not mature further than the 3rd instar stage. Even after 8 days, their development was drastically delayed (FIG. 14). These data indicate that rifampicin treatment via leaf perfusion impaired aphid development.

Antibiotic treatment delivered through leaf injection and delivery through plant increased aphid mortality Survival rate of aphids was also measured during the experiments where aphids were treated with either control solution or rifampicin delivered via leaf perfusion and through the plant. Aphids feeding on leaves perfused and treated with rifampicin had lower survival rates than aphids feeding on leaves perfused and treated with the control solution (FIG. 15). These data indicate that rifampicin treatment delivered through leaf perfusion and through the plant negatively impacted aphid survival.

Antibiotic Treatment Delivered Via Leaf Injection and Through the Plant Results in Decreased Levels of *Buchnera*

To test whether rifampicin delivered via leaf perfusion and through the plant results in loss of *Buchnera* in aphids, and that this loss impacts aphid fitness as demonstrated in previous Examples, DNA was extracted from aphids in each treatment group after 6 and 8 days of treatment and qPCR was performed to determine the *Buchnera*/aphid copy numbers, as described in previous Examples.

Aphids feeding on leaves injected and treated with the control solution had high ratios of *Buchnera*/aphid DNA copies. In contrast, aphids feeding on leaves perfused and treated with rifampicin had a statistically significant reduction of *Buchnera*/aphid DNA copies at both time points (p=0.0037 and p=0.0025 for days 6 and 8, respectively) (FIGS. 16A and 16B), indicating that rifampicin treatment delivered via leaf perfusion and through the plant decreased the presence of endosymbiotic *Buchnera*, and as shown in previous Examples, and resulted in a fitness decrease.

Combination Delivery Method

Experimental Design:

Aphids LSR-1 (which harbor only *Buchnera*), *Acyrthosiphon pisum* were grown on fava bean plants (*Vroma vicia* faba from Johnny's Selected Seeds) in a climate-controlled incubator (16 h light/8 h dark photoperiod; 60±5% RH; 20±2° C.). Prior to being used for aphid rearing, fava bean plants were grown in potting soil at 24° C. with 16 h of light and 8 h of darkness. To limit maternal effects or health differences between plants, 5-10 adults from different plants were distributed among 10 two-week-old plants, and allowed to multiply to high density for 5-7 days.

For experiments, first and second instar aphids were collected from healthy plants and divided into 2 different treatment groups: 1) treatment with Silwet-L77 or water control solutions or 2) treatment with rifampicin diluted in silwet L-77 or water. Each treatment group received approximately the same number of individuals from each of the collection plants. The combination of delivery methods was as follows: a) Topical delivery to aphid and plant by spraying 0.025% nonionic organosilicone surfactant solvent Silwet L-77 (negative control) or 100 μg/ml of rifampicin formulated in solvent solution using a 30 mL spray bottle and b) Delivery through plant with either water (negative control) or 100 μg/ml of rifampicin formulated in water. For treatment, rifampicin stock solution (25 mg/ml in 100% methanol) was diluted to 100 μg/ml in Silwet L-77 (for topical treatment to aphid and coating the leaf) or water (for delivery through plant). The solution was then placed into a 1.5 ml Eppendorf tube with a fava bean stem with a leaf also perfused with the solutions and the opening of the tube was closed using parafilm. This feeding system was then placed into a deep petri dish (Fisher Scientific, Cat #FB0875711) and aphids were applied to the leaves of the plant.

For each treatment, 76-80 aphids were placed onto each leaf. The feeding systems were changed every 2-3 days throughout the experiment. Aphids were monitored daily for survival and dead aphids were removed from the deep petri dish when they were discovered.

In addition, the developmental stage ($1^{st}$, $2^{nd}$, $3^{rd}$, $4^{th}$, $5^{th}$, and 5 R (5th that has reproduced) instar) was determined daily throughout the experiment.

Combination Antibiotic Treatment Delays Aphid Development

LSR-1 $1^{st}$ and $2^{nd}$ instar aphids were divided into two separate treatment groups as defined in Combination delivery method Experimental Design (described herein). Aphids were monitored daily and the number of aphids at each developmental stage was determined. Control treated aphids began reaching maturity (5th instar stage) at approximately 6 days (FIG. 17). Development was delayed in aphids treated with rifampicin, and by 6 days of treatment, most aphids did not mature further than the 3rd instar stage, even after 7 days their development was drastically delayed (FIG. 17). These data indicate that a combination of rifampicin treatments impaired aphid development.

Combination Antibiotic Treatment Results in Increased Aphid Mortality

Survival rate of aphids was also measured during the experiments where aphids were treated with a combination of rifampicin treatments. Rifampicin treated aphids had slightly lower survival rates than aphids treated with control solutions (FIG. 18). These data indicate that rifampicin treatment delivered through a combination of treatments affected aphid survival.

Combination Antibiotic Treatment in Decreased Levels of *Buchnera*

To test whether rifampicin delivered via a combination of methods results in loss of *Buchnera* in aphids, and that this loss impacts aphid fitness as demonstrated in previous Examples, DNA was extracted from aphids in each treatment group after 7 days of treatment and qPCR as described in a previous Example was performed to determine the *Buchnera*/aphid copy numbers.

Aphids treated with the control solutions had high ratios of *Buchnera*/aphid DNA copies. In contrast, aphids treated with rifampicin had a statistically significant and drastic reduction of *Buchnera*/aphid DNA copies (p=0.227; FIG. 19), indicating that rifampicin treatment delivered via a combination of methods decreases the presence of endosymbiotic *Buchnera*, and as shown in previous Examples, this resulted in a fitness decrease.

Together this data described in the previous Examples demonstrate the ability to kill and decrease the development, reproductive ability, longevity, and endogenous bacterial populations, e.g., fitness, of aphids by treating them with an antibiotic through multiple delivery methods.

Example 15: Insects Treated with a Natural Antimicrobial Polysacharide

This Example demonstrates the treatment of aphids with Chitosan, a natural cationic linear polysaccharide of deacetylated beta-1,4-D-glucosamine derived from chitin. Chitin is the structural element in the exoskeleton of insects, crustaceans (mainly shrimp and crabs) and cell walls of fungi, and the second most abundant natural polysaccharide after cellulose. This Example demonstrates that the effect of chitosan on insects was mediated through the modulation of bacterial populations endogenous to the insect that were sensitive to chitosan. One targeted bacterial strain is *Buchnera aphidicola*.

Therapeutic Design

The chitosan solution was formulated using a combination of leaf perfusion and delivery through plants (FIG. 20). The control solution was leaf injected with water+blue food coloring and water in tube. The treatment solution with 300 ug/ml chitosan in water (low molecular weight) via leaf injection (with blue food coloring) and through plant (in Eppendorf tube).

Leaf Perfusion-Plant Delivery Experimental Design:

Aphids LSR-1 (which harbor only *Buchnera*), *Acyrthosiphon pisum* were grown on fava bean plants (*Vroma vicia* faba from Johnny's Selected Seeds) in a climate-controlled incubator (16 h light/8 h dark photoperiod; 60±5% RH; 25±2° C.). Prior to being used for aphid rearing, fava bean plants were grown in potting soil at 24° C. with 16 h of light and 8 h of darkness. To limit maternal effects or health differences between plants, 5-10 adults from different plants were distributed among 10 two-week-old plants, and allowed to multiply to high density for 5-7 days. For experiments, first and second instar aphids were collected from healthy plants and divided into 2 different treatment groups: 1) negative control (water treated), 2) The treatment solution included 300 ug/ml chitosan in water (low molecular weight). Each treatment group received approximately the same number of individuals from each of the collection plants.

Chitosan (Sigma, catalog number 448869-50G) stock solution was made at 1% in acetic acid, sterilized autoclaving, and stored at 4° C. For treatment (see Therapeutic design), the appropriate amount of stock solution was diluted with water to obtain the final treatment concentration of chitosan. The solution was then placed into a 1.5 ml Eppendorf tube with a fava bean stem with a leaf also perfused with the solutions and the opening of the tube was closed using parafilm. This feeding system was then placed into a deep petri dish (Fisher Scientific, Cat #FB0875711) and aphids were applied to the leaves of the plant.

For each treatment, 50-51 aphids were placed onto each leaf. The feeding systems were changed every 2-3 days throughout the experiment. Aphids were monitored daily for survival and dead aphids were removed from the deep petri dish when they were discovered.

In addition, the developmental stage ($1^{st}$, $2^{nd}$, $3^{rd}$, $4^{th}$, $5^{th}$ and 5 R ($5^{th}$ that has reproduced) instar) was determined daily throughout the experiment.

After 8 days of treatment, DNA was extracted from multiple aphids from each treatment group. Briefly, the aphid body surface was sterilized by dipping the aphid into a 6% bleach solution for approximately 5 seconds. Aphids were then rinsed in sterile water and DNA was extracted from each individual aphid using a DNA extraction kit (Qiagen, DNeasy kit) according to manufacturer's instructions. DNA concentration was measured using a nanodrop nucleic acid quantification, and *Buchnera* and aphid DNA copy numbers were measured by qPCR. The primers used for *Buchnera* were Buch_groES_18F (CATGATCGTGTGCTTGTTAAG; SEQ ID NO: 238) and Buch_groES_98R (CTGTTCCTCGAGTCGATTTCC; SEQ ID NO: 239) (Chong and Moran, 2016 PNAS). The primers used for aphid were ApEF1a 107F (CTGATTGTGCCGTGCTTATTG; SEQ ID NO: 240) and ApEF1a 246R (TATGGTGGTTCAGTAGAGTCC; SEQ ID NO: 241) (Chong and Moran, 2016 PNAS). qPCR was performed using a qPCR amplification ramp of 1.6 degrees C./s and the following conditions: 1) 95° C. for 10 minutes, 2) 95° C. for 15 seconds, 3) 55° C. for 30 seconds, 4) repeat steps 2-3 40×, 5) 95° C. for 15 seconds, 6) 55° C. for 1 minute, 7) ramp change to 0.15 degrees C./s, 8) 95° C. for 1 second. qPCR data was analyzed using analytic (Thermo Fisher Scientific, QuantStudio Design and Analysis) software.

There was a negative response on insect fitness upon treatment with the natural antimicrobial polysaccharide LSR-1 *A. pisum* $1^{st}$ and $2^{nd}$ instar aphids were divided into two separate treatment groups as defined in Experimental Design (above). Aphids were monitored daily and the number of aphids at each developmental stage was determined. Aphids treated with the negative control alone began reaching maturity (5" instar stage) at approximately 6 days (FIG. 21). Development was delayed in aphids treated with chitosan solution, and by 6 days of treatment with chitosan, most aphids did not mature further than the $4^{rd}$ instar stage. These data indicate that treatment with chitosan delayed and stopped progression of aphid development.

Chitosan Treatment Increased Aphid Mortality

Survival rate of aphids was also measured during the treatments. The majority of the aphids treated with the control alone were alive at 3 days post-treatment (FIG. 22). After 4 days, aphids began gradually dying, and some survived beyond 7 days post-treatment.

In contrast, aphids treated with chitosan solution had lower survival rates than aphids treated with control. These data indicate that there was a decrease in survival upon treatment with the natural antimicrobial polysaccharide.

Chitosan Treatment Decreased *Buchnera* in Aphids

To test whether the chitosan solution treatment, specifically resulted in loss of *Buchnera* in aphids, and that this loss impacted aphid fitness, DNA was extracted from aphids in each treatment group after 8 days of treatment and qPCR was performed to determine the *Buchnera*/aphid copy numbers. Aphids treated with control alone had high ratios of *Buchnera*/aphid DNA copies. In contrast, aphids treated with 300 ug/ml chitosan in water had ~5-fold less *Buchnera*/aphid DNA copies (FIG. 23), indicating that chitosan treatment decreased *Buchnera* levels.

Together this data described previously demonstrated the ability to kill and decrease the development, longevity, and endogenous bacterial populations, e.g., fitness, of aphids by treating them with a natural antimicrobial polysaccharide.

Example 16: Insects Treated with Nisin, a Natural Antimicrobial Peptide

This Example demonstrates the treatment of aphids with the natural, "broad spectrum," polycyclic antibacterial peptide produced by the bacterium *Lactococcus lactis* that is commonly used as a food preservative. The antibacterial activity of nisin is mediated through its ability to generate pores in the bacterial cell membrane and interrupt bacterial cell-wall biosynthesis through a specific lipid II interaction. This Example demonstrates that the negative effect of nisin on insect fitness is mediated through the modulation of bacterial populations endogenous to the insect that were sensitive to nisin. One targeted bacterial strain is *Buchnera aphidicola*.

Therapeutic Design:

Nisin was formulated using a combination of leaf perfusion and delivery through plants. The control solution (water) or treatment solution (nisin) was injected into the leaf and placed in the Eppendorf tube. The treatment solutions consisted of 1.6 or 7 mg/ml nisin in water.

Leaf Perfusion-Plant Delivery Experimental Design:

LSR-1 aphids, *Acyrthosiphon pisum* were grown on fava bean plants (*Vroma vicia* faba from Johnny's Selected Seeds) in a climate-controlled incubator (16 h light/8 h dark photoperiod; 60±5% RH; 25±2° C.). Prior to being used for aphid rearing, fava bean plants were grown in potting soil at 24° C. with 16 h of light and 8 h of darkness. To limit maternal effects or health differences between plants, 5-10 adults from different plants were distributed among 10 two-week-old plants, and allowed to multiply to high density for 5-7 days. For experiments, first and second instar aphids were collected from healthy plants and divided into 2 different treatment groups: 1) negative control (water treated), 2) nisin treated with either 1.6 or 7 mg/ml nisin in water. Each treatment group received approximately the same number of individuals from each of the collection plants.

For treatment (see Therapeutic design), nisin (Sigma, product number: N5764) solution was made at 1.6 or 7 mg/ml (w/v) in water and filter sterilized using a 0.22 um syringe filter. The solution was then injected into the leaf of the plant and the stem of the plant was placed into a 1.5 ml Eppendorf tube. The opening of the tube was closed using parafilm. This feeding system was then placed into a deep petri dish (Fisher Scientific, Cat #FB0875711) and aphids were applied to the leaves of the plant.

For each treatment, 56-59 aphids were placed onto each leaf. The feeding systems were changed every 2-3 days throughout the experiment. Aphids were monitored daily for survival and dead aphids were removed from the deep petri dish when they were discovered.

In addition, the developmental stage (1st, 2nd, 3rd, 4th, 5th, and 5 R (5th instar aphids that are reproducing) instar) was determined daily throughout the experiment.

After 8 days of treatment, DNA was extracted from the remaining aphids in each treatment group. Briefly, the aphid body surface was sterilized by dipping the aphid into a 6% bleach solution for approximately 5 seconds. Aphids were then rinsed in sterile water and DNA was extracted from each individual aphid using a DNA extraction kit (Qiagen, DNeasy kit) according to manufacturer's instructions. DNA concentration was measured using a nanodrop nucleic acid quantification, and *Buchnera* and aphid DNA copy numbers were measured by qPCR. The primers used for *Buchnera* were Buch_groES_18F (CATGATCGTGTGCTTGTTAAG; SEQ ID NO: 238) and Buch_groES_98R (CTGTTCCTCGAGTCGATTTCC; SEQ ID NO: 239) (Chong and Moran, 2016 PNAS). The primers used for aphid were ApEF1a 107F (CTGATTGTGCCGTGCTTATTG; SEQ ID NO: 240) and ApEF1a 246R (TATGGTGGTTCAGTAGAGTCC; SEQ ID NO: 241) (Chong and Moran, 2016 PNAS). qPCR was performed using a qPCR amplification ramp of 1.6 degrees C./s and the following conditions: 1) 95° C. for 10 minutes, 2) 95° C. for 15 seconds, 3) 55° C. for 30 seconds, 4) repeat steps 2-3 40×, 5) 95° C. for 15 seconds, 6) 55° C. for 1 minute, 7) ramp change to 0.15 degrees C./s, 8) 95° C. for 1 second. qPCR data was analyzed using analytic (Thermo Fisher Scientific, QuantStudio Design and Analysis) software.

There was a dose-dependent negative response on insect fitness upon treatment with nisin LSR-1 *A. pisum* 1st and 2nd instar aphids were divided into three separate treatment groups as defined in Experimental Design (above). Aphids were monitored daily and the number of aphids at each developmental stage was determined. Aphids treated with the negative control solution (water) began reaching maturity (5th instar stage) at approximately 6 days, and reproducing (5 R stage) by 7 days (FIG. 24). Development was severely delayed in aphids treated with 7 mg/ml nisin. Aphids treated with 7 mg/ml nisin only developed to the 2nd instar stage by day 3, and by day 6, all aphids in the group were dead (FIG. 24). Development was slightly delayed in aphids treated with the lower concentration of nisin (1.6 mg/ml) and at each time point assessed, there were more less-developed aphids compared to water-treated controls (FIG. 24). These data indicate that treatment with nisin delayed and stopped progression of aphid development and this delay in development was dependent on the dose of nisin administered.

However, it is important to note that treatment with 7 mg/ml of nisin also had a negative impact on the health of the leaves used in the assay. Shortly after leaf perfusion of 7 mg/ml of nisin it started turning brown. After two days, the leaves perfused with 7 mg/ml turned black. There was no noticeable difference in the condition of the leaves treated with 1.6 mg/ml nisin.

Treatment with Nisin Resulted in Increased Aphid Mortality

Survival rate of aphids was also measured during the treatments. Approximately 50% of aphids treated with the control alone survived the 8-day experiment (FIG. 25). In contrast, survival was significantly less for aphids treated with 7 mg/ml nisin ($p<0.0001$, by Log-Rank Mantel Cox test), and all aphids in this group succumbed to the treatment by 6 days (FIG. 25). Aphids treated with the lower dose of nisin (1.6 mg/ml) had higher mortality compared to control treated aphids, although the difference did not reach statistical significance ($p=0.0501$ by Log-Rank Mantel Cox test). These data indicate that there was a dose-dependent decrease in survival upon treatment with nisin.

Treatment with Nisin Resulted in Decreased *Buchnera* in Aphids

To test whether treatment with nisin, specifically resulted in loss of *Buchnera* in aphids, and that this loss impacted aphid fitness, DNA was extracted from aphids in each treatment group after 8 days of treatment and qPCR was performed to determine the *Buchnera*/aphid copy numbers. Aphids treated with control alone had high ratios of *Buchnera*/aphid DNA copies. In contrast, aphids treated with 1.6 mg/ml nisin had ~1.4-fold less *Buchnera*/aphid DNA copies after 8 days of treatment (FIG. 26). No aphids were alive in the group treated with 7 mg/ml nisin, and therefore, *Buchnera*/aphid DNA copies was not assessed in this group. These data indicate that nisin treatment decreased *Buchnera* levels.

Together this data described previously demonstrate the ability to kill and decrease the development, longevity, and endogenous bacterial populations, e.g., fitness, of aphids by treating them with the antimicrobial peptide nisin.

Example 17: Insects Treated with Levulinic Acid Decreases Insect Fitness

This Example demonstrates the treatment of aphids with levulinic acid, a keto acid produced by heating a carbohydrate with hexose (e.g., wood, starch, wheat, straw, or cane sugar) with the addition of a dilute mineral acid reduces insect fitness. Levulinic acid has previously been tested as an antimicrobial agent against *Escherichia coli* and *Salmonella* in meat production (Carpenter et al., 2010, Meat Science; Savannah G. Hawkins, 2014, University of Tennessee Honors Thesis). This Example demonstrates that the effect of levulinic acid on insects was mediated through the modulation of bacterial populations endogenous to the insect that were sensitive to levulinic acid. One targeted bacterial strain is *Buchnera aphidicola.*

Therapeutic Design:

The levulinic acid was formulated using a combination of leaf perfusion and delivery through plants. The control solution was leaf injected with water and water was placed in the Eppendorf tube. The treatment solutions included 0.03 or 0.3% levulinic acid in water via leaf injection and through plant (in Eppendorf tube).

Leaf Perfusion-Plant Delivery Experimental Design:

eNASCO aphids, *Acyrthosiphon pisum* were grown on fava bean plants (*Vroma vicia* faba from Johnny's Selected Seeds) in a climate-controlled incubator (16 h light/8 h dark photoperiod; 60±5% RH; 25±2° C.). Prior to being used for aphid rearing, fava bean plants were grown in potting soil at 24° C. with 16 h of light and 8 h of darkness. To limit maternal effects or health differences between plants, 5-10 adults from different plants were distributed among 10 two-week-old plants, and allowed to multiply to high density for 5-7 days. For experiments, first and second instar aphids were collected from healthy plants and divided into 2 different treatment groups: 1) negative control (water treated), 2) The treatment solution included 0.03 or 0.3% levulinic acid in water. Each treatment group received approximately the same number of individuals from each of the collection plants.

For treatment (see Therapeutic design), levulinic acid (Sigma, product number: W262706) was diluted to either 0.03 or 0.3% in water. The solution was then placed into a 1.5 ml Eppendorf tube with a fava bean stem with a leaf also perfused with the solutions and the opening of the tube was closed using parafilm. This feeding system was then placed into a deep petri dish (Fisher Scientific, Cat #FB0875711) and aphids were applied to the leaves of the plant.

For each treatment, 57-59 aphids were placed onto each leaf. The feeding systems were changed every 2-3 days throughout the experiment. Aphids were monitored daily for survival and dead aphids were removed from the deep petri dish when they were discovered.

In addition, the developmental stage ($1^{st}$, $2^{nd}$, $3^{rd}$ $4^{th}$ and $5^{th}$ instar) was determined daily throughout the experiment.

After 7 of treatment, DNA was extracted from the remaining aphids in each treatment group. Briefly, the aphid body surface was sterilized by dipping the aphid into a 6% bleach solution for approximately 5 seconds. Aphids were then rinsed in sterile water and DNA was extracted from each individual aphid using a DNA extraction kit (Qiagen, DNeasy kit) according to manufacturer's instructions. DNA concentration was measured using a nanodrop nucleic acid quantification, and *Buchnera* and aphid DNA copy numbers were measured by qPCR. The primers used for *Buchnera* were Buch_groES_18F (CATGATCGTGTGCTTGTTAAG; SEQ ID NO: 238) and Buch_groES_98R (CTGTTCCTCGAGTCGATTTCC; SEQ ID NO: 239) (Chong and Moran, 2016 PNAS). The primers used for aphid were ApEF1a 107F (CTGATTGTGCCGTGCTTATTG; SEQ ID NO: 240) and ApEF1a 246R (TATGGTGGTTCAGTAGAGTCC; SEQ ID NO: 241) (Chong and Moran, 2016 PNAS). qPCR was performed using a qPCR amplification ramp of 1.6 degrees C./s and the following conditions: 1) 95° C. for 10 minutes, 2) 95° C. for 15 seconds, 3) 55° C. for 30 seconds, 4) repeat steps 2-3 40×, 5) 95° C. for 15 seconds, 6) 55° C. for 1 minute, 7) ramp change to 0.15 degrees C./s, 8) 95° C. for 1 second. qPCR data was analyzed using analytic (Thermo Fisher Scientific, QuantStudio Design and Analysis) software.

There was a dose-dependent negative response on insect fitness upon treatment with levulinic acid eNASCO *A. pisum* $1^{st}$ and $2^{nd}$ instar aphids were divided into three separate treatment groups as defined in Experimental Design (above). Aphids were monitored daily and the number of aphids at each developmental stage was determined. Aphids treated with the negative control alone began reaching maturity (5th instar stage) at approximately 7 days (FIG. 27). Development was delayed in aphids treated with levulinic acid and by 11 days post-treatment, nearly all control treated aphids reached maturity while ~23 and 63% aphids treated with 0.03 and 0.3% levulinic acid, respectively, did not mature further than the $4^{rd}$ instar stage. These data indicate that treatment with levulinic acid delayed and stopped progression of aphid development and this delay in development is dependent on the dose of levulinic acid administered.

Treatment with Levulinic Acid Results in Increased Aphid Mortality

Survival rate of aphids was also measured during the treatments. Approximately 50% of aphids treated with the control alone survived the 11-day experiment (FIG. 28). In contrast, survival was significantly less for aphids treated with 0.3% levulinic acid ($p<0.01$). Aphids treated with the low dose of levulinic acid (0.03%) had higher mortality compared to control treated aphids, although the difference did not reach statistical significance. These data indicate that there was a dose-dependent decrease in survival upon treatment with levulinic acid.

Treatment with Levulinic Acid Results in Decreased *Buchnera* in Aphids

To test whether treatment with levulinic acid, specifically resulted in loss of *Buchnera* in aphids, and that this loss impacted aphid fitness, DNA was extracted from aphids in each treatment group after 7 days of treatment and qPCR was performed to determine the *Buchnera*/aphid copy numbers. Aphids treated with control alone had high ratios of *Buchnera*/aphid DNA copies. In contrast, aphids treated with 0.03 or 0.3% levulinic acid in water had ~6-fold less *Buchnera*/aphid DNA copies after 7 days of treatment (FIG. 29, left panel). These data indicate that levulinic acid treatment decreased *Buchnera* levels.

Together this data described previously demonstrated the ability to kill and decrease the development, longevity, and endogenous bacterial populations, e.g., fitness, of aphids by treating them with levulinic acid.

Example 18: Insects Treated with a Plant Derived Secondary Metabolite Solution This Example demonstrates the treatment of aphids with gossypol acetic acid, a natural phenol derived from the cotton plant (genus *Gossypium*) that permeates cells and acts as an inhibitor for several dehydrogenase enzymes. This Example demonstrates that the effect of gossypol on insects was mediated through the modulation of bacterial populations endogenous to the insect that were sensitive to gossypol. One targeted bacterial strain is *Buchnera* aphid/cola.

Therapeutic Design: The gossypol solution was formulated depending on the delivery method:

1) Through the plants: with 0 (negative control) or 0.5%, 0.25%, and 0.05% of gossypol formulated in an artificial diet (based on Akey and Beck, 1971; see Experimental Design)

without essential amino acids (histidine, isoleucine, leucine, lysine, methionine, phenylalanine, threonine, tryptophan, and valine).

2) Microinjection: injection solutions were either 0.5% of gossypol or artificial diet only (negative control).

Plant Delivery Experimental Design:

Aphids (either eNASCO (which harbor both *Buchnera* and *Serratia* primary and secondary symbionts, respectively) or LSR-1 (which harbor only *Buchnera*) strains, *Acyrthosiphon pisum*) were grown on fava bean plants (Vroma viola *faba* from Johnny's Selected Seeds) in a climate-controlled incubator (16 h light/8 h dark photoperiod; 60±5% RH; 25±2° C.). Prior to being used for aphid rearing, fava bean plants were grown in potting soil at 24° C. with 16 h of light and 8 h of darkness. To limit maternal effects or health differences between plants, 5-10 adults from different plants were distributed among 10 two-week-old plants, and allowed to multiply to high density for 5-7 days. For experiments, first and second instar aphids were collected from healthy plants and divided into 4 different treatment groups: 1) artificial diet alone without essential amino acids, 2) artificial diet alone without essential amino acids and 0.05% of gossypol, 3) artificial diet alone without essential amino acids and 0.25% of gossypol, and 4) artificial diet alone without essential amino acids and 0.5% of gossypol. Each treatment group received approximately the same number of individuals from each of the collection plants.

The artificial diet used was made as previously published (Akey and Beck, 1971 Continuous Rearing of the Pea Aphid, *Acyrthosiphon pisum*, on a Holidic Diet), with and without the essential amino acids (2 mg/ml histidine, 2 mg/ml isoleucine, 2 mg/ml leucine, 2 mg/ml lysine, 1 mg/ml methionine, 1.62 mg/ml phenylalanine, 2 mg/ml threonine, 1 mg/ml tryptophan, and 2 mg/ml valine), except neither diet included homoserine or beta-alanyltyrosine. The pH of the diets was adjusted to 7.5 with KOH and diets were filter sterilized through a 0.22 μm filter and stored at 4° C. for short term (<7 days) or at −80° C. for long term.

Gossypol acetic acid (Sigma, Cat #G4382-250MG) stock solution was made at 5% in methanol and sterilized by passing through a 0.22 μM syringe filter, and stored at 4° C. For treatments (see Therapeutic design), the appropriate amount of stock solution was added to the artificial diet to obtain the different final concentrations of gossypol. The diet was then placed into a 1.5 ml Eppendorf tube with a fava bean stem with a leaf and the opening of the tube was closed using parafilm. This feeding system was then placed into a deep petri dish (Fisher Scientific, Cat #FB0875711) and aphids were applied to the leaves of the plant.

For each treatment, 15-87 aphids were placed onto each leaf. Artificial diet feeding systems were changed every 2-3 days throughout the experiment. Aphids were monitored daily for survival and dead aphids were removed from the deep petri dish housing the artificial feeding system when they were discovered.

In addition, the developmental stage (1st, $2^{nd}$, $3^{rd}$, $4^{th}$, $5^{th}$, and 5 R (5th that has reproduced) instar) was determined daily throughout the experiment. Once an aphid reached the 4th instar stage, they were given their own artificial feeding system in a deep petri dish so that fecundity could be monitored once they reached adulthood.

For adult aphids, new nymphs were counted daily and then discarded. At the end of the experiments, fecundity was measured in two ways: 1) the mean day at which the first offspring for the treatment group was determined and 2) the mean number of offspring produced daily once the aphid reached adulthood. Pictures of aphids were taken throughout the experiment to evaluate size differences between treatment groups.

After 5 or 13 days of treatment, DNA was extracted from multiple aphids from each treatment group. Briefly, the aphid body surface was sterilized by dipping the aphid into a 6% bleach solution for approximately 5 seconds. Aphids were then rinsed in sterile water and DNA was extracted from each individual aphid using a DNA extraction kit (Qiagen, DNeasy kit) according to manufacturer's instructions. DNA concentration was measured using a nanodrop nucleic acid quantification, and *Buchnera* and aphid DNA copy numbers were measured by qPCR. The primers used for *Buchnera* were Buch_groES_18F (CATGATCGTGTGCTTGTTAAG; SEQ ID NO: 238) and Buch_groES_98R (CTGTTCCTCGAGTCGATTTCC; SEQ ID NO: 239) (Chong and Moran, 2016 PNAS). The primers used for aphid were ApEF1a 107F (CTGATTGTGCCGTGCTTATTG; SEQ ID NO: 240) and ApEF1a 246R (TATGGTGGTTCAGTAGAGTCC; SEQ ID NO: 241) (Chong and Moran, 2016 PNAS). qPCR was performed using a qPCR amplification ramp of 1.6 degrees C./s and the following conditions: 1) 95° C. for 10 minutes, 2) 95° C. for 15 seconds, 3) 55° C. for 30 seconds, 4) repeat steps 2-3 40×, 5) 95° C. for 15 seconds, 6) 55° C. for 1 minute, 7) ramp change to 0.15 degrees C./s, 8) 95° C. for 1 second. qPCR data was analyzed using analytic (Thermo Fisher Scientific, QuantStudio Design and Analysis) software.

There was a dose-dependent negative response on insect fitness upon treatment with the allelochemical gossypol eNASCO and LSR-1 *A. pisum* $1^{st}$ and $2^{nd}$ instar aphids were divided into four separate treatment groups as defined in Experimental Design (described herein). Aphids were monitored daily and the number of aphids at each developmental stage was determined. Aphids treated with artificial diet alone began reaching maturity ($5^{th}$ instar stage) at approximately 3 days (FIG. 30A). Development was delayed in aphids treated with gossypol, and by 5 days of treatment with 0.5% of gossypol, most aphids did not mature further than the $3^{rd}$ instar stage, and their size is also affected (FIGS. 30A and 30B). These data indicate that treatment with gossypol delayed and stopped progression of aphid development, and that this response was dose dependent.

Gossypol Treatment Increased Aphid Mortality

Survival rate of aphids was also measured during the treatments. The majority of the aphids treated with artificial diet alone without essential amino acids were alive at 2 days post-treatment (FIG. 31). After 4 days, aphids began gradually dying, and some survived beyond 7 days post-treatment. In contrast, aphids treated with 0.25 (not significantly different than control, p=0.2794) and 0.5% of gossypol had lower survival rates than aphids treated with artificial diet alone, with 0.5% gossypol treatment being significantly different than AD no EAA control (p=0.002). 0.5% gossypol-treated aphids began dying after 2 days of treatment and all aphids succumbed to treatment by 4 days. Aphids treated with 0.25% survived a bit longer than those treated with 0.5% but were also drastically affected. These data indicate that there was a dose-dependent decrease in survival upon treatment with the allelochemical gossypol.

Gossypol Treatment Decreased Aphid Reproduction

Fecundity was also monitored in aphids during the treatments. By days 7 and 8 post-treatment, the majority of the adult aphids treated with artificial diet without essential amino acids began reproducing. The mean number of offspring produced daily after maturity by aphids treated with artificial diet without essential amino acids was approximately 5 (FIGS. 32A and 32B).

In contrast, aphids treated with 0.25% of gossypol show a reduction to reach adulthood and produce offspring. These data indicate that gossypol treatment resulted in a decrease of aphid reproduction.

Gossypol Treatment Decreased *Buchnera* in Aphids

To test whether different concentrations of gossypol, specifically resulted in loss of *Buchnera* in aphids, and that this loss impacted aphid fitness, DNA was extracted from aphids in each treatment group after 5 or 13 days of treatment and qPCR was performed to determine the *Buchnera*/aphid copy numbers. Aphids treated with artificial diet alone without essential amino acids (control) had high ratios of *Buchnera*/aphid DNA copies. In contrast, aphids treated with 0.25 and 0.5% of gossypol had ~4-fold less *Buchnera*/aphid DNA copies (FIG. 33), indicating that gossypol treatment decreased *Buchnera* levels, and that this decrease was concentration dependent.

Microinjection Delivery Experimental Design:

Microinjection was performed using NanoJet III Auto-Nanoliter Injector with the in-house pulled borosilicate needle (Drummond Scientific; Cat #3-000-203-G/XL). Aphids (LSR-1 strain, *A. pisum*) were grown on fava bean plants as described in a previous Example. Each treatment group had approximately the same number of individuals injected from each of the collection plants. Nymph aphids (<3$^{rd}$ instar stage) were transferred using a paint brush to a tubing system connected to vacuum and microinjected into the ventral thorax with 20 nl of either artificial diet without essential amino acids (negative control) or 0.05% of gossypol solution in artificial diet without essential amino acids. After injection, aphids were placed in a deep petri dish with a fava bean leaf with stem in 2% agar.

Microinjection with Antibiotic Treatment Decreased *Buchnera* in Aphids

To test whether gossypol delivered by microinjection results in loss of *Buchnera* in aphids, and that this loss impacts aphid fitness as demonstrated in previous Examples, DNA was extracted from aphids in each treatment group after 4 days of treatment and qPCR was performed as described in a previous Example to determine the *Buchnera*/aphid copy numbers.

Aphids microinjected with negative control had high ratios of *Buchnera*/aphid DNA copies. In contrast, aphid nymphs and adults microinjected with gossypol had a drastic reduction of *Buchnera*/aphid DNA copies (FIG. 34), indicating that gossypol microinjection treatment decreases the presence of endosymbiotic *Buchnera*, and as shown in previous Examples this resulted in a fitness decrease.

Together this data described in the previous Examples demonstrated the ability to kill and decrease the development, reproductive ability, longevity, and endogenous bacterial populations, e.g., fitness, of aphids by treating them with plant secondary metabolite solution through multiple delivery methods.

Example 19: Insects Treated with Natural Plant Derived Antimicrobial Compound, Trans-Cinnemaldehyde This Example demonstrates the treatment of aphids with trans-cinnemaldehyde, a natural aromatic aldehyde that is the major component of bark extract of cinnamon (*Cinnamomum zeylandicum*) results in decreased fitness. Trans-cinnemaldehyde has been shown to have antimicrobial activity against both gram-negative and gram-positive organisms, although the exact mechanism of action of its antimicrobial activity remains unclear. Trans-cinnemaldehyde may damage bacterial cell membranes and inhibit of specific cellular processes or enzymes (Gill and Holley, 2004 Applied Environmental Microbiology). This Example demonstrates that the effect of trans-cinnemaldehyde on insects was mediated through the modulation of bacterial populations endogenous to the insect that were sensitive to trans-cinnemaldehyde. One targeted bacterial strain is *Buchnera aphidicola.*

Therapeutic Design:

Trans-cinnemaldehyde was diluted to 0.05%, 0.5%, or 5% in water and was delivered through leaf perfusion (~1 ml was injected into leaves) and through plants.

Experimental Design:

Aphids (LSR-1 (which harbor only *Buchnera*) strains, *Acyrthosiphon pisum*) were grown on fava bean plants (*Vroma vicia* faba from Johnny's Selected Seeds) in a climate-controlled incubator (16 h light/8 h dark photoperiod; 60±5% RH; 25±2° C.). Prior to being used for aphid rearing, fava bean plants were grown in potting soil at 24° C. with 16 h of light and 8 h of darkness. To limit maternal effects or health differences between plants, 5-10 adults from different plants were distributed among 10 two-week-old plants, and allowed to multiply to high density for 5-7 days. For experiments, first and second instar aphids were collected from healthy plants and divided into four different treatment groups: 1) water treated controls, 2) 0.05% trans-cinnemaldehyde in water, 3) 0.5% trans-cinnemaldehyde in water, and 4) 5% trans-cinnemaldehyde in water. Each treatment group received approximately the same number of individuals from each of the collection plants.

Trans-cinnemaldehyde (Sigma, Cat #C80687) was diluted to the appropriate concentration in water (see Therapeutic design), sterilized by passing through a 0.22 μm syringe filter, and stored at 4° C. Fava bean leaves were injected with approximately 1 ml of the treatment and then the leaf was placed in a 1.5 ml Eppendorf tube containing the same treatment solution. The opening of the tube where the fava bean stem was placed was closed using parafilm. This treatment feeding system was then placed into a deep petri dish (Fisher Scientific, Cat #FB0875711) and aphids were applied to the leaves of the plant.

For each treatment, 40-49 aphids were placed onto each leaf. Treatment feeding systems were changed every 2-3 days throughout the experiment. Aphids were monitored daily for survival and dead aphids were removed from the deep petri dish housing the treatment feeding system when they were discovered.

In addition, the developmental stage (1st, 2$^{nd}$, 3$^{rd}$, 4$^{th}$, 5$^{th}$, and 5 R (5th that has reproduced) instar) was determined daily throughout the experiment.

After 3 days of treatment, DNA was extracted from the remaining living aphids from each treatment group. Briefly, the aphid body surface was sterilized by dipping the aphid into a 6% bleach solution for approximately 5 seconds. Aphids were then rinsed in sterile water and DNA was extracted from each individual aphid using a DNA extraction kit (Qiagen, DNeasy kit) according to manufacturer's instructions. DNA concentration was measured using a nanodrop nucleic acid quantification, and *Buchnera* and aphid DNA copy numbers were measured by qPCR. The primers used for *Buchnera* were Buch_groES_18F (CATGATCGTGTGCTTGTTAAG; SEQ ID NO: 238) and Buch_groES_98R (CTGTTCCTCGAGTCGATTTCC; SEQ ID NO: 239) (Chong and Moran, 2016 PNAS). The primers used for aphid were ApEF1a 107F (CTGAT- TGTGCCGTGCTTATTG; SEQ ID NO: 240) and ApEF1a 246R (TATGGTGGTTCAGTAGAGTCC; SEQ ID NO: 241) (Chong and Moran, 2016 PNAS). qPCR was performed using a qPCR amplification ramp of 1.6 degrees C./s and the following conditions: 1) 95° C. for 10 minutes, 2) 95° C. for 15 seconds, 3) 55° C. for 30 seconds, 4) repeat steps 2-3 40×, 5) 95° C. for 15 seconds, 6) 55° C. for 1 minute, 7) ramp change to 0.15 degrees C./s, 8) 95° C. for 1 second. qPCR data was analyzed using analytic (Thermo Fisher Scientific, QuantStudio Design and Analysis) software.

There was a Dose-Dependent Negative Response on Insect Fitness Upon Treatment with the Natural Antimicrobial Trans-Cinnemaldehyde LSR-1 *A. pisum* 1st and 2nd instar aphids were divided into four separate treatment groups as defined in Experimental Design (described herein). Aphids were monitored daily and the number of aphids at each developmental stage was determined. Aphids treated with water alone began reaching the 3rd instar stage at 3 days post-treatment (FIG. 35). Development was delayed in aphids treated with trans-cinnemaldehyde, and by 3 days of treatment with each the three of the trans-cinnemaldehyde concentrations, none of the aphids matured past the second instar stage (FIG. 35). Moreover, all the aphids treated with the highest concentration of trans-cinnemaldehyde (5%) remained at the 1st instar stage throughout the course of the experiment. These data indicate that treatment with trans-cinnemaldehyde delays and stops progression of aphid development, and that this response is dose dependent.

Trans-Cinnemaldehyde Treatment Increased Aphid Mortality

Survival rate of aphids was also measured during the treatments. Approximately 75 percent of the aphids treated with water alone were alive at 3 days post-treatment (FIG. 36). In contrast, aphids treated with 0.05%, 0.5%, and 5% trans-cinnemaldehyde had significantly lower ($p<0.0001$ for each treatment group compared to water treated control) survival rates than aphids treated with water alone. These data indicate that there was a dose-dependent decrease in survival upon treatment with the natural antimicrobial trans-cinnemaldehyde.

Trans-Cinnemaldehyde Treatment Decreased *Buchnera* in Aphids

To test whether different concentrations of trans-cinnemaldehyde, specifically resulted in loss of *Buchnera* in aphids, and that this loss impacted aphid fitness, DNA was extracted from aphids in each treatment group after 3 days of treatment and qPCR was performed to determine the *Buchnera*/aphid copy numbers. Aphids treated with water alone (control) had high ratios of *Buchnera*/aphid DNA copies. Similarly, aphids treated with the lowest concentration of trans-cinnemaldehyde (0.5%) had high ratios of *Buchnera*/aphid DNA copies.

In contrast, aphids treated with 0.5 and 5% of trans-cinnemaldehyde had ~870-fold less *Buchnera*/aphid DNA copies (FIG. 37), indicating that trans-cinnemaldehyde treatment decreased *Buchnera* levels, and that this decrease was concentration dependent.

Together this data described in the previous Examples demonstrate the ability to kill and decrease the development, reproductive ability, longevity, and endogenous bacterial populations, e.g., fitness, of aphids by treating them with plant secondary metabolite solution through multiple delivery methods.

Example 20: Insects Treated with Scorpion Antimicrobial Peptides

This Example demonstrates the treatment of aphids with multiple scorpion antimicrobial peptides (AMP), of which several are identified AMPs in the venom gland transcriptome of the scorpion Urodacus yaschenkoi (Luna-Ramirez et al., 2017, Toxins). AMPs typically have a net positive charge and hence, a high affinity for bacterial membranes. This Example demonstrates that the effect of the AMP on insects was mediated through the modulation of bacterial populations endogenous to the insect that were sensitive to AMP peptides. One targeted bacterial strain is *Buchnera aphidicola*, an obligate symbiont of aphids.

Therapeutic Design:

The Uy192 solution was formulated using a combination of leaf perfusion and delivery through plants. The control solution was leaf injected with water+blue food coloring and water in tube. The treatment solution consisted of 100 ug/ml Uy192 in water via leaf injection (with blue food coloring) and through plant (in Eppendorf tube).

Leaf Perfusion-Plant Delivery Experimental Design:

Aphids LSR-1 (which harbor only *Buchnera*), *Acyrthosiphon pisum* were grown on fava bean plants (*Vroma vicia* faba from Johnny's Selected Seeds) in a climate-controlled incubator (16 h light/8 h dark photoperiod; 60±5% RH; 20±2° C.). Prior to being used for aphid rearing, fava bean plants were grown in potting soil at 24° C. with 16 h of light and 8 h of darkness. To limit maternal effects or health differences between plants, 5-10 adults from different plants were distributed among 10 two-week-old plants, and allowed to multiply to high density for 5-7 days. For experiments, first and second instar aphids were collected from healthy plants and divided into 2 different treatment groups: 1) negative control (water treated), 2) The treatment solution of 100 ug/ml AMP in water. Each treatment group received approximately the same number of individuals from each of the collection plants.

Uy192 was synthesized by Bio-Synthesis at >75% purity. 1 mg of lyophilized peptide was reconstituted in 500 ul of 80% acetonitrile, 20% water, and 0.1% TFA, 100 ul (100 ug) was aliquoted into 10 individual Eppendorf tubes, and allowed to dry. For treatment (see Therapeutic design), 1 ml of water was added to a 100 ug aliquot of peptide to obtain the final concentration of Uy192 (100 ug/ml). The solution was then placed into a 1.5 ml Eppendorf tube with a fava bean stem with a leaf also perfused with the solutions and the opening of the tube was closed using parafilm. This feeding system was then placed into a deep petri dish (Fisher Scientific, Cat #FB0875711) and aphids were applied to the leaves of the plant.

For each treatment, 50 aphids were placed onto each leaf. The feeding systems were changed every 2-3 days throughout the experiment. Aphids were monitored daily for survival and dead aphids were removed from the deep petri dish when they were discovered.

In addition, the developmental stage (1st, 2nd, 3rd 4th 5th and 5 R (5th that has reproduced) instar) was determined daily throughout the experiment.

After 8 days of treatment, DNA was extracted from the remaining aphids in each treatment group. Briefly, the aphid body surface was sterilized by dipping the aphid into a 6% bleach solution for approximately 5 seconds. Aphids were then rinsed in sterile water and DNA was extracted from each individual aphid using a DNA extraction kit (Qiagen, DNeasy kit) according to manufacturer's instructions. DNA concentration was measured using a nanodrop nucleic acid quantification, and *Buchnera* and aphid DNA copy numbers were measured by qPCR. The primers used for *Buchnera* were Buch_groES_18F (CATGATCGTGTGCTTGTTAAG; SEQ ID NO: 238) and Buch_groES_98R (CTGTTCCTCGAGTCGATTTCC; SEQ ID NO: 239) (Chong and Moran, 2016 PNAS). The primers used for aphid were ApEF1a 107F (CTGATTGTGCCGTGCTT-ATTG; SEQ ID NO: 240) and ApEF1a 246R (TATGGTGGTTCAGTAGAGTCC; SEQ ID NO: 241) (Chong and Moran, 2016 PNAS). qPCR was performed using a qPCR amplification ramp of 1.6 degrees C./s and the following conditions: 1) 95° C. for 10 minutes, 2) 95° C. for 15 seconds, 3) 55° C. for 30 seconds, 4) repeat steps 2-3 40×, 5) 95° C. for 15 seconds, 6) 55° C. for 1 minute, 7) ramp change to 0.15 degrees C./s, 8) 95° C. for 1 second. qPCR data was analyzed using analytic (Thermo Fisher Scientific, QuantStudio Design and Analysis) software.

There was a negative response on insect fitness upon treatment with the scorpion AMPs LSR-1 *A. pisum* $1^{st}$ and $2^{nd}$ instar aphids were divided into two separate treatment groups as defined in Experimental Design (above). Aphids were monitored daily and the number of aphids at each developmental stage was determined. Aphids treated with the negative control alone began reaching maturity (5th instar stage) at approximately 6 days (FIG. 38). Development was delayed in aphids treated with Uy192, and after 8 days of treatment, aphids did not mature further than the $4^{rd}$ instar stage. These data indicate that treatment with Uy192 delayed and stopped progression of aphid development.

Treatment with Scorpion AMPs Results in Increased Aphid Mortality

Survival rate of aphids was also measured during the treatments. The majority of the aphids treated with the control alone were alive at 3 days post-treatment (FIG. 39). After 4 days, aphids began gradually dying, and some survived beyond 7 days post-treatment.

In contrast, aphids treated with Uy192 had lower survival rates than aphids treated with control. These data indicate that there was a decrease in survival upon treatment with the scorpion AMP Uly192.

Treatment with Scorpion AMP Uy192 Results in Decreased *Buchnera* in Aphids

To test whether treatment with Uy192, specifically resulted in loss of *Buchnera* in aphids, and that this loss impacted aphid fitness, DNA was extracted from aphids in each treatment group after 8 days of treatment and qPCR was performed to determine the *Buchnera*/aphid copy numbers. Aphids treated with control alone had high ratios of *Buchnera*/aphid DNA copies. In contrast, aphids treated with 100 ug/ml Uy192 in water had ~7-fold less *Buchnera*/ aphid DNA copies (FIG. 40), indicating that Uy192 treatment decreased *Buchnera* levels.

Together this data described previously demonstrated the ability to kill and decrease the development, longevity, and endogenous bacterial populations, e.g., fitness, of aphids by treating them with a natural scorpion antimicrobial peptide.

Example 21: Insects Treated with Scorpion Antimicrobial Peptides

This Example demonstrates the treatment of aphids with several scorpion antimicrobial peptides (AMPs) D10, D3, Uyct3, and Uy17, which have been recently identified AMPs in the venom gland transcriptome of the scorpion Urodacus yaschenkoi (Luna-Ramirez et al., 2017, Toxins). AMPs typically have a net positive charge and hence, a high affinity for bacterial membranes. This Example demonstrates that the effect of the AMPs on insects was mediated through the modulation of bacterial populations endogenous to the insect that were sensitive to AMP peptides. One targeted bacterial strain is *Buchnera aphidicola*, an obligate symbiont of aphids.

Aphids are agricultural insect pests causing direct feeding damage to the plant and serving as vectors of plant viruses. In addition, aphid honeydew promotes the growth of sooty mold and attracts nuisance ants. The use of chemical treatments, unfortunately still widespread, leads to the selection of resistant individuals whose eradication becomes increasingly difficult.

Therapeutic Design:

The indicated peptide or peptide cocktail (see Aphid Microinjection Experimental Design and Leaf perfusion-Plant Experimental Design sections for details below) was directly microinjected into aphids or delivered using a combination of leaf perfusion and delivery through plants. As a negative control, aphids were microinjected with water (for microinjection experiments) or placed on leaves injected with water and water in tube (for leaf perfusion and plant delivery experiments). The treatment solutions consisted of 20 nl of 5 μg/μl of D3 or D10 dissolved in water (for aphid microinjections) or 40 μg/ml of a cocktail of D10, Uy17, D3, and UyCt3 in water via leaf injection and through plant (in Eppendorf tube).

Aphid Microinjection Experimental Design

Microinjection was performed using NanoJet III Auto-Nanoliter Injector with the in-house pulled borosilicate needle (Drummond Scientific; Cat #3-000-203-G/XL). Aphids (LSR-1 strain, *Acyrthosiphon pisum*) were grown on fava bean plants (*Vroma vicia* faba from Johnny's Selected Seeds) in a climate-controlled incubator (16 h light/8 h dark photoperiod; 60±5% RH; 25±2° C.). Prior to being used for aphid rearing, fava bean plants were grown in potting soil at 24° C. with 16 h of light and 8 h of darkness. To limit maternal effects or health differences between plants, 5-10 adults from different plants were distributed among 10 two-week-old plants, and allowed to multiply to high density for 5-7 days. Each treatment group had approximately the same number of individuals injected from each of the collection plants. Adult aphids were microinjected into the ventral thorax with 20 nl of either water or 100 ng (20 ul of a 5 ug/ml solution of peptide D3 or D10. The microinjection rate as 5 nl/sec. After injection, aphids were placed in a deep petri dish containing a fava bean leaf with stem in 2% agar.

Peptides were synthesized by Bio-Synthesis at >75% purity. 1 mg of lyophilized peptide was reconstituted in 500 μl of 80% acetonitrile, 20% water, and 0.1% TFA, 100 μl (100 μg) was aliquoted into 10 individual Eppendorf tubes, and allowed to dry.

After 5 days of treatment, DNA was extracted from the remaining aphids in each treatment group. Briefly, the aphid body surface was sterilized by dipping the aphid into a 6% bleach solution for approximately 5 seconds. Aphids were then rinsed in sterile water and DNA was extracted from each individual aphid using a DNA extraction kit (Qiagen, DNeasy kit) according to manufacturer's instructions. DNA concentration was measured using a nanodrop nucleic acid quantification, and *Buchnera* and aphid DNA copy numbers were measured by qPCR. The primers used for *Buchnera* were Buch_groES_18F (CATGATCGTGTGCTTGTTAAG; SEQ ID NO: 238) and Buch_groES_98R (CTGTTCCTCGAGTCGATTTCC; SEQ ID NO: 239) (Chong and Moran, 2016 PNAS). The primers used for aphid were ApEF1a 107F (CTGATTGTGCCGTGCTT- ATTG; SEQ ID NO: 240) and ApEF1a 246R (TATGGTGGTTCAGTAGAGTCC; SEQ ID NO: 241) (Chong and Moran, 2016 PNAS). qPCR was performed using a qPCR amplification ramp of 1.6 degrees C./s and the following conditions: 1) 95° C. for 10 minutes, 2) 95° C. for 15 seconds, 3) 55° C. for 30 seconds, 4) repeat steps 2-3 40×, 5) 95° C. for 15 seconds, 6) 55° C. for 1 minute, 7) ramp change to 0.15 degrees C./s, 8) 95° C. for 1 second. qPCR data was analyzed using analytic (Thermo Fisher Scientific, QuantStudio Design and Analysis) software.

Microinjection of Aphids with Scorpion Peptides D3 and D10 Results in Decreased Insect Survival LSR-1 *A. pisum* $1^{st}$ and $2^{nd}$ instar aphids were divided into three separate treatment groups as defined in Experimental Design (described herein). Aphids were monitored daily and survival rate was determined. After 5 days of treatment, the aphids injected with the scorpion peptides had lower survival rates compared to water injected controls (9, 35, and 45% survival for injection with D3, D10, and water, respectively) (FIG. 41). These data indicate that there was a decrease in survival upon treatment with the scorpion AMPs D3 and D10.

Microinjection of Aphids with Scorpion Peptides D3 and D10 Results in a Reduction of *Buchnera* Endosymbionts To test whether injection with the scorpion AMPs D3 and D10, specifically resulted in loss of *Buchnera* in aphids, and that this loss impacted aphid fitness, DNA was extracted from aphids in each treatment group 5 days after injection and qPCR was performed to determine the *Buchnera*/aphid copy numbers. Aphids injected with water alone had high ratios of *Buchnera*/aphid DNA (47.4) while aphids injected with D3 and D10 had lower ratios of *Buchnera*/aphid DNA (25.3 and 30.9, respectively) (FIG. 42). These data indicate that treatment with scorpion peptides D3 and D10 resulted in decreased levels of the bacterial symbiont *Buchnera*.

Leaf Perfusion-Plant Delivery Experimental Design:

eNASCO Aphids (which harbor *Buchnera* and *Serratia*), *Acyrthosiphon pisum* were grown on fava bean plants (*Vroma vicia* faba from Johnny's Selected Seeds) as described above. For experiments, first and second instar aphids were collected from healthy plants and divided into 2 different treatment groups: 1) negative control (water treated), 2) The treatment solution consisted of 40 μg/ml of each D10, Uy17, D3, and UyCt3 in water. Each treatment group received approximately the same number of individuals from each of the collection plants.

Peptides were synthesized, dissolved, and aliquoted, as described above. For treatment (see Therapeutic design), water was added to a 100 pg aliquot of peptide to obtain the desired final concentration (40 μg/ml). The four peptides were combined to make the peptide cocktail solution. This solution was used to perfuse into leaves via injection. Following injection, the stems of the injected leaves were placed into a 1.5 ml Eppendorf tube which was then sealed with parafilm. This feeding system was then placed into a deep petri dish (Fisher Scientific, Cat #FB0875711) and aphids were applied to the leaves of the plant.

For each treatment, 41-49 aphids were placed onto each leaf. The feeding systems were changed every 2-3 days throughout the experiment. Aphids were monitored daily for survival and dead aphids were removed from the deep petri dish when they were discovered.

Treatment with Cocktail of Scorpion Peptides Results in Increased Aphid Mortality Survival rate of aphids was also measured during the treatments. After 6 days of treatment, aphids treated with the peptide cocktail had lower survival rates compared to those treated with water, and after 9 days the effect is more evident (16 and 29% survival for peptide cocktail and water treated, respectively) (FIG. 43). These data indicate that there was a decrease in survival upon treatment with the cocktail of scorpion AMPs, and as shown in previous Examples these AMP decreased the endosymbiont levels in the aphids.

Together this data described previously demonstrated the ability to kill and decrease the longevity and endogenous bacterial populations, e.g., fitness, of aphids by treating them with single natural scorpion antimicrobial peptides or a peptide cocktail.

Example 22: Insects Treated with an Antimicrobial Peptide Fused to a Cell Penetrating Peptide This Example demonstrates the treatment of aphids with a fused scorpion antimicrobial peptide (AMP) (Uy192) to a cell penetrating peptide derived from a virus. The AMP Uy192 is one of several recently identified AMPs in the venom gland transcriptome of the scorpion Urodacus yaschenkoi (Luna-Ramirez et al., 2017, Toxins). AMPs typically have a net positive charge and hence, a high affinity for bacterial membranes. To enhance the delivery of the scorpion peptide Uy192 into aphid cells, the peptide was synthesized fused to a portion of the transactivator of transcription (TAT) protein of human immunodeficiency virus I (HIV-1). Previous studies have shown that conjugating this cell penetrating peptide (CPP) to other molecules increased their uptake into cells via transduction (Zhou et al., 2015 Journal of Insect Science and Cermenati et al., 2011 Journal of Insect Physiology). This Example demonstrates that the effect of the fused peptide on insects was mediated through the modulation of bacterial populations endogenous to the insect that were sensitive to the antimicrobial peptide. One targeted bacterial strain is *Buchnera*.

Therapeutic Design

The scorpion peptide conjugated to the cell penetrating peptide and fluorescently tagged with 6FAM (Uy192+CPP+FAM) was formulated using a combination of leaf perfusion and delivery through plants. The control solution (water) or treatment solution (Uy192+CPP+FAM) was injected into the leaf and placed in the Eppendorf tube. The treatment solution included 100 μg/ml Uy192+CPP+FAM in water.

Leaf Perfusion-Plant Delivery Experimental Design

LSR-1 aphids, *Acyrthosiphon pisum* were grown on fava bean plants (*Vroma vicia* faba from Johnny's Selected Seeds) in a climate-controlled incubator (16 h light/8 h dark photoperiod; 60±5% RH; 25±2° C.). Prior to being used for aphid rearing, fava bean plants were grown in potting soil at 24° C. with 16 h of light and 8 h of darkness. To limit maternal effects or health differences between plants, 5-10 adults from different plants were distributed among 10 two-week-old plants, and allowed to multiply to high density for 5-7 days. For experiments, first instar aphids were collected from healthy plants and divided into 2 different treatment groups: 1) negative control (water treated), 2) Uy192+CPP+FAM treated with 100 μg/ml Uy192+CPP+FAM in water. Each treatment group received approximately the same number of individuals from each of the collection plants.

For treatment (see Therapeutic design), Uy192+CPP+FAM (amino acid sequence: YGRKKRRQRRRFL-STIWNGIKGLL-FAM; SEQ ID NOS: 246 and 247 (YGRKKRRQRRR) was synthesized by Bio-Synthesis at >75% purity. 5 mg of lyophilized peptide was reconstituted in 1 ml of 80% acetonitrile, 20% water, and 0.1% TFA, 50 μl (100 μg) was aliquoted into individual Eppendorf tubes, and allowed to dry. For treatment (see Therapeutic design), 1 ml of sterile water was added to a 100 μg aliquot of peptide to obtain the final concentration of Uy192+CPP+FAM (100 μg/ml). The solution was then injected into the leaf of the plant and the stem of the plant was placed into a 1.5 ml Eppendorf tube. The opening of the tube was closed using parafilm. This feeding system was then placed into a deep petri dish (Fisher Scientific, Cat #FB0875711) and aphids were applied to the leaves of the plant. Epi fluorescence imaging of the leaf confirmed that the leaves contained the green fluorescently tagged peptide in their vascular system.

For each treatment, 30 aphids were placed onto each leaf in triplicate. The feeding systems were changed every 2-3 days throughout the experiment. Aphids were monitored daily for survival and dead aphids were removed from the deep petri dish when they were discovered. In addition, the developmental stage (1st, 2nd, 3rd, 4th, 5th, and 5 R (5th instar aphids that are reproducing) instar) was determined daily throughout the experiment.

At 5 days post-treatment, DNA was extracted from several aphids in each treatment group. Briefly, the aphid body surface was sterilized by dipping the aphid into a 6% bleach solution for approximately 5 seconds. Aphids were then rinsed in sterile water and DNA was extracted from each individual aphid using a DNA extraction kit (Qiagen, DNeasy kit) according to manufacturer's instructions. DNA concentration was measured using a nanodrop nucleic acid quantification, and *Buchnera* and aphid DNA copy numbers were measured by qPCR. The primers used for *Buchnera* were Buch_groES_18F (CATGATCGTGTGCTTGTTAAG; SEQ ID NO: 238) and Buch_groES_98R (CTGTTCCTCGAGTCGATTTCC; SEQ ID NO: 239) (Chong and Moran, 2016 PNAS). The primers used for aphid were ApEF1a 107F (CTGATTGTGCCGTGCTTATTG; SEQ ID NO: 240) and ApEF1a 246R (TATGGTGGTTCAGTAGAGTCC; SEQ ID NO: 241) (Chong and Moran, 2016 PNAS). qPCR was performed using a qPCR amplification ramp of 1.6 degrees C./s and the following conditions: 1) 95° C. for 10 minutes, 2) 95° C. for 15 seconds, 3) 55° C. for 30 seconds, 4) repeat steps 2-3 40×, 5) 95° C. for 15 seconds, 6) 55° C. for 1 minute, 7) ramp change to 0.15 degrees C./s, 8) 95° C. for 1 second. qPCR data was analyzed using analytic (Thermo Fisher Scientific, QuantStudio Design and Analysis) software.

Treatment with Scorpion Peptide Uy192 Fused to a Cell Penetrating Peptide Delayed and Stopped Progression of Aphid Development LSR-1 *A. pisum* 1st instar aphids were divided into three separate treatment groups as defined in Experimental Design (above). Aphids were monitored daily and the number of aphids at each developmental stage was determined. Development for both aphids treated with water and those treated with the scorpion peptide fused to the cell penetrating peptide was similar for days 0 and 1 (FIG. 44). By day 2, however, control treated aphids developed to either in the second or third instar stage, while some aphids treated with the scorpion peptide fused to the cell penetrating peptide remained in the first instar stage (FIG. 44). Even at 3 days post-treatment, some aphids treated with the scorpion peptide fused to the cell penetrating peptide remained in the first instar stage (FIG. 44). By 7 days post-treatment, the majority of the water treated aphids developed to the 5th or 5th reproducing instar stage. In contrast, only 50 percent of aphids treated with the scorpion peptide fused to the cell penetrating peptide developed to the 5th instar stage, while ~42 and ~8 percent of aphids remained at the 3rd or 4th instar stage, respectively (FIG. 44). These data indicate that treatment with the scorpion peptide Uy192 fused to the cell penetrating peptide delayed and stopped progression of aphid development.

Treatment with the Scorpion Peptide Uy192 Fused to a Cell Penetrating Peptide Resulted in Increased Aphid Mortality Survival rate of aphids was also measured during the treatments. Approximately 40% of aphids treated with the control alone survived the 7-day experiment (FIG. 45). In contrast, survival was significantly less for aphids treated with 100 μg/ml Uy192+CPP+FAM (p=0.0036, by Log-Rank Mantel Cox test), with only 16% of aphids surviving to day 7 (FIG. 45). These data indicate that there was a decrease in survival upon treatment with the scorpion peptide Uy192 fused to a cell penetrating peptide.

Treatment with a Scorpion Peptide Fused to a Cell Penetrating Peptide Resulted in Decreased *Buchnera*/Aphid DNA Ratios To test whether treatment with treatment with Uy192+CPP+FAM, specifically resulted in loss of *Buchnera* in aphids, and that this loss impacted aphid fitness, DNA was extracted from aphids in each group after 5 days of treatment, and qPCR was performed to determine the *Buchnera*/aphid copy numbers. Aphids treated with water had high ratios (~134) of *Buchnera*/aphid DNA. In contrast, aphids treated with the scorpion peptide fused to the cell penetrating peptide had ~1.8-fold less *Buchnera*/aphid DNA copies after 5 days of treatment (FIG. 46). These data indicate that treatment with the scorpion peptide fused to a cell penetrating peptide decreased endosymbiont levels.

The Scorpion Peptide Fused to a Cell Penetrating Peptide Freely Entered the Bacteriocytes to Act Against *Buchnera*

To test whether the cell penetrating peptide aids in the delivery of the scorpion peptide into the bacteriocytes directly, isolated bacteriocytes were directly exposed to the fusion protein and imaged. The bacteriocytes were dissected from the aphids in Schneider's medium supplemented with 1% w/v BSA (Schneider-BSA medium), and placed in an imaging well containing 20 ul of schneider's medium. A 100 ug lyophilized aliquot of the scorpion peptide was resuspended in 100 ul of the schneider's medium to produce 1 mg/ml solution, and 5 ul of this solution was mixed in to the well containing bacteriocytes. After 30 min of incubation at room temperature, the bacteriocytes were thoroughly washed to eliminate any excess free peptide in the solution. Images of the bacteriocytes were captured before and after the incubation (FIG. 47). The fusion peptide penetrated the bacteriocyte membranes and was directly available to *Buchnera.*

Together, this data demonstrates the ability to kill and decrease the development, longevity, and endogenous bacterial populations, e.g., fitness, of aphids by treating them with the scorpion antimicrobial peptide Uy192 fused to a cell penetrating peptide.

Example 23: Insects Treated with Vitamin Analogs

This Example demonstrates the treatment of aphids with the provitamin pantothenol which is the alcohol analog of pantothenic acid (Vitamin B5). Aphids have obligate endosymbiont bacteria, *Buchnera*, that help them make essential amino acids and vitamins, including Vitamin B5. A previous study has shown that pantothenol inhibits the growth of *Plasmodium falciparium* by inhibition of the specific parasite kinases (Saliba et al., 2005). It was hypothesized that treating insects with pantothenol would be detrimental for the bacterial-insect symbiosis therefore affecting insect fitness. This Example demonstrates that the treatment with pantothenol decreased insect fitness.

Therapeutic Design:

Pantothenol Solutions were Formulated Depending on the Delivery Method:

1) In artificial diet through the plants: with 0 (negative control) or 10 or 100 uM pantothenol formulated in an artificial diet (based on Akey and Beck, 1971; see Experimental Design) without essential amino acids (2 mg/ml histidine, 2 mg/ml isoleucine, 2 mg/ml leucine, 2 mg/ml lysine, 1 mg/ml methionine, 1.62 mg/ml phenylalanine, 2 mg/ml threonine, 1 mg/mil tryptophan, and 2 mg/ml valine).
2) Leaf coating: 100 µl of 0.025% nonionic organosilicone surfactant solvent Silwet L-77 in water (negative control) or 100 µl of 50 µg/ml of rifampicin formulated in solvent solution was applied directly to the leaf surface and allowed to dry.

Plant Delivery Experimental Design

Aphids (eNASCO, *Acyrthosiphon pisum*) were grown on fava bean plants (*Vroma vicia* faba from Johnny's Selected Seeds) in a climate-controlled incubator (16 h light/8 h dark photoperiod; 60±5% RH; 25±2° C.). Prior to being used for aphid rearing, fava bean plants were grown in potting soil at 24° C. with 16 h of light and 8 h of darkness. To limit maternal effects or health differences between plants, 5-10 adults from different plants were distributed among 10 two-week-old plants, and allowed to multiply to high density for 5-7 days. For experiments, first and second instar aphids were collected from healthy plants and divided into 3 different treatment groups: 1) artificial diet alone without essential amino acids, 2) artificial diet alone without essential amino acids and 10 uM pantothenol, and 3) artificial diet alone without essential amino acids and 100 uM pantothenol. Each treatment group received approximately the same number of individuals from each of the collection plants.

The artificial diet used was made as previously published (Akey and Beck, 1971 Continuous Rearing of the Pea Aphid, *Acyrthosiphon pisum*, on a Holidic Diet), with and without the essential amino acids (2 mg/ml histidine, 2 mg/ml isoleucine, 2 mg/ml leucine, 2 mg/ml lysine, 1 mg/ml methionine, 1.62 mg/ml phenylalanine, 2 mg/ml threonine, 1 mg/ml tryptophan, and 2 mg/ml valine), except neither diet included homoserine or beta-alanyltyrosine. The pH of the diets was adjusted to 7.5 with KOH and diets were filter sterilized through a 0.22 µm filter and stored at 4° C. for short term (<7 days) or at −80° C. for long term.

Pantothenol (Sigma Cat #295787) solutions were made at 10 uM and 100 uM in artificial diet without essential amino acids, sterilized by passing through a 0.22 µm syringe filter, and stored at −20° C. For treatments (see Therapeutic design), the appropriate amount of stock solution was added to the artificial diet without essential amino acids to obtain a final concentration of 10 or 100 uM pantothenol. The diet was then placed into a 1.5 ml Eppendorf tube with a fava bean stem with a leaf and the opening of the tube was closed using parafilm. This artificial diet feeding system was then placed into a deep petri dish (Fisher Scientific, Cat #FB0875711) and aphids were applied to the leaves of the plant.

For each treatment, 16-20 aphids were placed onto each leaf. Artificial diet feeding systems were changed every 2-3 days throughout the experiment. Aphids were monitored daily for survival and dead aphids were removed from the deep petri dish housing the artificial feeding system when they were discovered.

In addition, the developmental stage (1st, 2nd, 3rd, 4th, 5th instar) was determined daily throughout the experiment. Once an aphid reached the 4th instar stage, they were given their own artificial feeding system in a deep petri dish so that fecundity could be monitored once they reached adulthood.

For adult aphids, new nymphs were counted daily and then discarded. At the end of the experiments, fecundity was determined as the mean number of offspring produced daily once the aphid reached adulthood. Pictures of aphids were taken throughout the experiment to evaluate size differences between treatment groups.

After 8 days of treatment, DNA was extracted from multiple aphids from each treatment group. Briefly, the aphid body surface was sterilized by dipping the aphid into a 6% bleach solution for approximately 5 seconds. Aphids were then rinsed in sterile water and DNA was extracted from each individual aphid using a DNA extraction kit (Qiagen, DNeasy kit) according to manufacturer's instructions. DNA concentration was measured using a nanodrop nucleic acid quantification, and *Buchnera* and aphid DNA copy numbers were measured by qPCR. The primers used for *Buchnera* were Buch_groES_18F (CATGATCGTGTGCTTGTTAAG; SEQ ID NO: 238) and Buch_groES_98R (CTGTTCCTCGAGTCGATTTCC; SEQ ID NO: 239) (Chong and Moran, 2016 PNAS). The primers used for aphid were ApEF1a 107F (CTGATTGTGCCGTGCTTATTG; SEQ ID NO: 240) and ApEF1a 246R (TATGGTGGTTCAGTAGAGTCC; SEQ ID NO: 241) (Chong and Moran, 2016 PNAS). qPCR was performed using a qPCR amplification ramp of 1.6 degrees C./s and the following conditions: 1) 95° C. for 10 minutes, 2) 95° C. for 15 seconds, 3) 55° C. for 30 seconds, 4) repeat steps 2-3 40×, 5) 95° C. for 15 seconds, 6) 55° C. for 1 minute, 7) ramp change to 0.15 degrees C./s, 8) 95° C. for 1 second. qPCR data was analyzed using analytic (Thermo Fisher Scientific, QuantStudio Design and Analysis) software.

Vitamin Analog Treatment Delays Aphid Development eNASCO 1st and 2nd instar aphids were divided into three separate treatment groups as defined in Plant Delivery Experimental Design (described herein). Aphids were monitored daily and the number of aphids at each developmental stage was determined. Aphids treated with artificial diet alone without essential amino acids began reaching maturity (5th instar stage) at approximately 5 days (FIG. 48A). Development was delayed in aphids treated with pantothenol, especially at days two and three post-treatment (FIG. 48A), indicating that treatment with pantothenol impairs aphid development. Eventually, most aphids from each treatment group reached maturity and began reproducing. In addition to monitoring developmental stage of aphids over time, aphids were also imaged and aphid area was determined. All aphids were the same size after 1 day of treatment, however, by 3 days post-treatment, aphids treated with pantothenol were smaller in area than untreated controls. Moreover, aphids treated with pantothenol had much less of an increase in body size (as determined by area) over the course of the experiment, compared to aphids treated with artificial diet alone without essential amino acids (FIG. 48B).

Vitamin Analog Treatment Increased Aphid Mortality

Survival rate of aphids was also measured during the treatments. Aphids reared on artificial diet alone without essential amino acids had higher survival rates compared to aphids treated with 10 or 100 uM pantothenol (FIG. 49), indicating that pantothenol treatment negatively affected aphid fitness.

Treatment with Pantothenol Decreases Aphid Fecundity

Fecundity was also monitored in aphids during the treatments. The fraction of aphids surviving to maturity and reproducing was determined. Approximately one quarter of aphids treated with artificial diet without essential amino acids survived to reach maturity by 8 days post-treatment (FIG. 50A). In contrast, only a little over ⅒th of aphids treated with 10 or 100 uM pantothenol survived to reach maturity and reproduce by 8 days post-treatment. The mean day aphids in each treatment group began reproducing was also measured and for all treatment groups, the mean day aphids began reproducing was 7 days (FIG. 50B). Additionally, the mean number of offspring per day produced by mature, reproducing aphids was also monitored. Aphids treated with artificial diet alone without essential amino acids produced approximately 7 offspring/day. In contrast, aphids treated with 10 and 100 uM pantothenol only produced approximately 4 and 5 offspring/day, respectively, shown in FIG. 50C. Taken together, these data indicate that pantothenol treatment resulted in a loss of aphid reproduction.

Pantothenol Treatment does not Affect *Buchnera* in Aphids

To test whether treatment with pantothenol, specifically resulted in loss of *Buchnera* in aphids, and that this loss impacted aphid fitness, DNA was extracted from aphids in each treatment group after 8 days of treatment and qPCR was performed to determine the *Buchnera*/aphid copy numbers. Aphids treated with artificial diet alone without essential amino acids had high ratios of *Buchnera*/aphid DNA copies as did aphids treated with each of the two concentrations of pantothenol (FIG. 51). These data indicate that pantothenol treatment does not affect *Buchnera*/aphid DNA copy number directly.

Leaf Coating Delivery Experimental Design:

Pantothenol powder was added to 0.025% of a nonionic organosilicone surfactant solvent, Silwet L-77, to obtain a final concentration of 10 uM pantothenol. The treatment was filter sterilized using a 0.22 urn filter and stored at 4 degrees C. Aphids (eNASCO strain, *Acyrthosiphon pisum*) were grown on fava bean plants as described in a previous Example. For experiments, first instar aphids were collected from healthy plants and divided into 2 different treatment groups: 1) negative control (solvent solution only) and 2) 10 uM pantothenol in solvent. 100 ul of the solution was absorbed onto a 2×2 cm piece of fava bean leaf.

Each treatment group received approximately the same number of individuals from each of the collection plant. For each treatment, 20 aphids were placed onto each leaf. Aphids were monitored daily for survival and dead aphids were removed when they were discovered. In addition, the developmental stage (1st, 2nd, 3rd, 4th, 5th instar, and 5 R, representing a reproducing 5th instar) was determined daily throughout the experiment.

Pantothenol Treatment Delivered Through Leaf Coating does not Affect Aphid Development eNASCO 1st instar aphids were divided into two separate treatment groups as defined in the Experimental Design described herein. Aphids were monitored daily and the number of aphids at each developmental stage was determined. Aphids placed on coated leaves treated with either the control or pantothenol solution matured at similar rates up to two days post-treatment (FIG. 52). These data indicate that leaf coating with pantothenol did not affect aphid development.

Pantothenol Treatment Delivered Through Leaf Coating Increased Aphid Mortality

Survival rate of aphids was also measured during the leaf coating treatments. Aphids placed on coated leaves with pantothenol had lower survival rates than aphids placed on coated leaves with the control solution (FIG. 53). These data indicate that pantothenol treatment delivered through leaf coating significantly (p=0.0019) affected aphid survival. All aphids died in this experiment and there were no remaining aphids left to extract DNA from and determine *Buchnera*/aphid DNA ratios.

Together this data described in the previous Examples demonstrate the ability to kill and decrease the development, reproductive ability, longevity, and endogenous bacterial populations, e.g., fitness, of aphids by treating them with pantothenol through multiple delivery methods.

Example 24: Insects Treated with a Cocktail of Amino Acid Transporters Inhibitors This Example demonstrates the treatment of aphids with a cocktail of amino acid analogs. The objective of this treatment was to inhibit uptakes of glutamine into the bacteriocytes through the ApGLNT1 glutamine transporter. It has previously been shown that arginine inhibits glutamine uptake by the glutamine transporter (Price et al., 2014 PNAS), and we hypothesized that treatment with analogs of arginine, or other amino acid analogs, may also inhibit uptake of essential amino acids into the aphid bacteriocytes. This Example demonstrates that the decrease in fitness upon treatment was mediated through the modulation of bacterial populations endogenous to the insect that were sensitive to amino acid analogs. One targeted bacterial strain is *Buchnera.*

Therapeutic Design:

The amino acid cocktail was formulated for delivery through leaf perfusion and through the plant. This delivery method consisted of injecting leaves with approximately 1 ml of the amino acid cocktail in water (see below for list of components in the cocktail) or 1 ml of the negative control solution containing water only.

Leaf Perfusion and Delivery Through Plants Experimental Design:

Aphids LSR-1 (which harbor only *Buchnera*), *Acyrthosiphon pisum* were grown on fava bean plants (*Vroma vicia* faba from Johnny's Selected Seeds) in a climate-controlled incubator (16 h light/8 h dark photoperiod; 60±5% RH; 25±2° C.). Prior to being used for aphid rearing, fava bean plants were grown in potting soil at 24° C. with 16 h of light and 8 h of darkness. To limit maternal effects or health differences between plants, 5-10 adults from different plants were distributed among 10 two-week-old plants, and allowed to multiply to high density for 5-7 days. For experiments, first instar aphids were collected from healthy plants and divided into 2 different treatment groups: 1) negative control (water treatment) and 2) amino acid cocktail treatment. The amino acid cocktail contained each of the following agents at the indicated final concentrations: 330 μM L-NNA (N-nitro-L-Arginine; Sigma), 0.1 mg/ml L-canavanine (Sigma), 0.5 mg/ml D-arginine (Sigma), 0.5 mg/ml D-phenylalanine (Sigma), 0.5 mg/ml D-histidine (Sigma), 0.5 mg/ml D-tryptophan (Sigma), 0.5 mg/ml D-threonine (Sigma), 0.5 mg/ml D-valine (Sigma), 0.5 mg/ml D-methionine (Sigma), 0.5 mg/ml D-leucine, and 6 μM L-NMMA (citrate) (Cayman Chemical). ~1 ml of the treatment solution was perfused into the fava bean leaf via injection and the stem of the plant was put into a 1.5 ml Eppendorf tube containing the treatment solution. The opening of the tube was closed using parafilm. This feeding system was then placed into a deep petri dish (Fisher Scientific, Cat #FB0875711) and aphids were applied to the leaves of the plant. For each treatment, a total of 56-58 aphids were placed onto each leaf (each treatment consisted of two replicates of 28-31 aphids). Each treatment group received approximately the same number of individuals from each of the collection plants. The feeding systems were changed every 2-3 days throughout the experiment. Aphids were monitored daily for survival and dead aphids were removed from the deep petri dish when they were discovered. The aphid developmental stage (1st, 2nd, 3rd, 4th, and 5th instar) was determined daily throughout the experiment and microscopic images were taken of the aphids on day 5 to determine aphid area measurements.

Stock solutions of L-NNA were made at 5 mM in water, sterilized by passing through a 0.22 μm syringe filter, and stored at −20° C. Stock solutions of L-canavanine were made at 100 mg/ml in water, sterilized by passing through a 0.22 μm syringe filter, and stored at 4° C. Stock solutions of D-arginine and D-threonine were made at 50 mg/ml in water, sterilized by passing through a 0.22 μm syringe filter, and stored at 4° C. Stock solutions of D-valine and D-methionine were made at 25 mg/ml in water, sterilized by passing through a 0.22 μm syringe filter, and stored at 4° C. Stock solutions of D-leucine were made at 12 mg/ml in water, sterilized by passing through a 0.22 μm syringe filter, and stored at 4° C. Stock solutions of D-phenylalanine and D-histidine were made at 50 mg/ml in 1M HCl, sterilized by passing through a 0.22 μm syringe filter, and stored at 4° C. Stock solutions of D-tryptophan were made at 50 mg/ml in 0.5M HCl, sterilized by passing through a 0.22 μm syringe filter, and stored at 4° C. Stock solutions of L-NMMA were made at 6 mg/ml in sterile PBS, sterilized by passing through a 0.22 μm syringe filter, and stored at −20° C. For treatments (see Therapeutic design), the appropriate amount of stock solution was added to water to obtain the final concentration of the agent in the cocktail as indicated above.

After 6 days of treatment, DNA was extracted from multiple aphids from each treatment group. Briefly, the aphid body surface was sterilized by dipping the aphid into a 6% bleach solution for approximately 5 seconds. Aphids were then rinsed in sterile water and DNA was extracted from each individual aphid using a DNA extraction kit (Qiagen, DNeasy kit) according to manufacturer's instructions. DNA concentration was measured using a nanodrop nucleic acid quantification, and *Buchnera* and aphid DNA copy numbers were measured by qPCR. The primers used for *Buchnera* were Buch_groES_18F (CATGATCGTGTGCTTGTTAAG; SEQ ID NO: 238) and Buch_groES_98R (CTGTTCCTCGAGTCGATTTCC; SEQ ID NO: 239) (Chong and Moran, 2016 PNAS). The primers used for aphid were ApEF1a 107F (CTGATTGTGCCGTGCTTATTG; SEQ ID NO: 240) and ApEF1a 246R (TATGGTGGTTCAGTAGAGTCC; SEQ ID NO: 241) (Chong and Moran, 2016 PNAS). qPCR was performed using a qPCR amplification ramp of 1.6 degrees C./s and the following conditions: 1) 95° C. for 10 minutes, 2) 95° C. for 15 seconds, 3) 55° C. for 30 seconds, 4) repeat steps 2-3 40×, 5) 95° C. for 15 seconds, 6) 55° C. for 1 minute, 7) ramp change to 0.15 degrees C./s, 8) 95° C. for 1 second. qPCR data was analyzed using analytic (Thermo Fisher Scientific, QuantStudio Design and Analysis) software.

Treatment with a Cocktail of Amino Acid Analogs Delayed and Stopped Progression of Aphid Development LSR-1 1st instar aphids were divided into two separate treatment groups as defined in Leaf perfusion and delivery through plants experimental design (described herein). Aphids were monitored daily and the number of aphids at each developmental stage was determined. Aphids treated with water began reaching maturity (5th instar stage) at day 5 post-treatment (FIG. 54A). By 6 days post-treatment, ~20 percent of aphids treated with water reached the 5th instar stage. In contrast, less than 3 percent of the aphids treated with the amino acid cocktail reached the 5th instar stage, even after 6 days (FIG. 54A). This delay in development upon treatment with the amino acid cocktail was further exemplified by aphid size measurements taken at 5 days post-treatment. Aphids treated with water alone were approximately 0.45 mm2, whereas aphids treated with the amino acid cocktail were approximately 0.33 mm2 (FIG. 54B). These data indicate that treatment with the amino acid cocktail delayed aphid development, negatively impacting aphid fitness.

Treatment with an Amino Acid Analog Cocktail Resulted in Decreased *Buchnera* in Aphids To test whether treatment with the amino acid analog cocktail specifically resulted in loss of *Buchnera* in aphids, and that this loss impacted aphid fitness, DNA was extracted from aphids in each treatment group after 6 days of treatment and qPCR was performed to determine the *Buchnera*/aphid copy numbers. Aphids placed on control solution had high ratios of *Buchnera*/aphid DNA copies. In contrast, aphids placed on AA cocktail treatment had a drastic reduction of *Buchnera*/aphid DNA copies (FIG. 55), indicating that the AA analog cocktail treatment eliminated endosymbiotic *Buchnera*.

Together, this data demonstrates the ability to decrease the development and endogenous bacterial populations, e.g., fitness, of aphids by treating them with a cocktail of amino acid analogs.

Example 25: Insects Treated with a Combination of Agents (Antibiotic, Peptide, and Natural Antimicrobial)

This Example demonstrates the treatment of insects with a combination of three antimicrobial agents—an antibiotic (rifampicin), a peptide (the scorpion peptide Uy192), and a natural antimicrobial (low molecular weight chitosan). In other Examples, each of these agents administered individually resulted in decreased aphid fitness and reduced endosymbiont levels. This Example demonstrates that through the delivery of a combination of treatments, insect fitness and endosymbiont levels were reduced as well as, or better than, treatment with each individual agent alone.

Therapeutic Design

The combination treatment was formulated for delivery through leaf perfusion and through the plant. This delivery method consisted of injecting leaves with approximately 1 ml of the combination treatment in water (with final concentrations of 100 μg/ml rifampicin, 100 μg/ml Uy192, and 300 μg/ml chitosan) or 1 ml of the negative control solution containing water only.

Leaf Perfusion and Delivery Through Plants Experimental Design

Aphids LSR-1 (which harbor only *Buchnera*), *Acyrthosiphon pisum* were grown on fava bean plants (*Vroma vicia* faba from Johnny's Selected Seeds) in a climate-controlled incubator (16 h light/8 h dark photoperiod; 60±5% RH; 25±2° C.). Prior to being used for aphid rearing, fava bean plants were grown in potting soil at 24° C. with 16 h of light and 8 h of darkness. To limit maternal effects or health differences between plants, 5-10 adults from different plants were distributed among 10 two-week-old plants, and allowed to multiply to high density for 5-7 days. For experiments, first instar aphids were collected from healthy plants and divided into 2 different treatment groups: 1) negative control (water treatment) and 2) a combination of 100 μg/ml rifampicin, 100 μg/ml Uy192, and 300 μg/ml chitosan treatment. ~1 ml of the treatment solution was perfused into the fava bean leaf via injection and the stem of the plant was put into a 1.5 ml Eppendorf tube containing the treatment solution. The opening of the tube was closed using parafilm. This treatment system was then placed into a deep petri dish (Fisher Scientific, Cat #FB0875711) and aphids were applied to the leaves of the plant. For each treatment, a total of 56 aphids were placed onto each leaf (each treatment consisted of two replicates of 28 aphids). Each treatment group received approximately the same number of individuals from each of the collection plants. The feeding systems were changed every 2-3 days throughout the experiment. Aphids were monitored daily for survival and dead aphids were removed from the deep petri dish when they were discovered. The aphid developmental stage ($1^{st}$, $2^{nd}$, $3^{rd}$, $4^{th}$ and $5^{th}$ instar) was determined daily throughout the experiment and microscopic images were taken of the aphids on day 5 to determine aphid area measurements.

Rifampicin (Tokyo Chemical Industry, LTD) stock solution was made at 25 mg/ml in methanol, sterilized by passing through a 0.22 μm syringe filter, and stored at −20° C. For treatment, the appropriate amount of stock solution was added to water to obtain a final concentration of 100 μg/ml rifampicin. Uy192 was synthesized by Bio-Synthesis at >75% purity. 1 mg of lyophilized peptide was reconstituted in 500 μl of 80% acetonitrile, 20% water, and 0.1% TFA. 100 μl (100 μg) was aliquoted into 10 individual Eppendorf tubes and allowed to dry. For treatment, 1 ml of water was added to a 100 μg aliquot of peptide to obtain the final concentration of 100 μg/ml Uy192. Chitosan (Sigma, catalog number 448869-50G) stock solution was made at 1% in acetic acid, sterilized autoclaving, and stored at 4° C. For treatments the appropriate amount of stock solution was added to water to obtain the final concentration of 300 μg/ml chitosan.

After 6 days of treatment, DNA was extracted from multiple aphids from each treatment group. Briefly, the aphid body surface was sterilized by dipping the aphid into a 6% bleach solution for approximately 5 seconds. Aphids were then rinsed in sterile water and DNA was extracted from each individual aphid using a DNA extraction kit (Qiagen, DNeasy kit) according to manufacturer's instructions. DNA concentration was measured using a nanodrop nucleic acid quantification, and *Buchnera* and aphid DNA copy numbers were measured by qPCR. The primers used for *Buchnera* were Buch_groES_18F (CATGATCGTGTGCTTGTTAAG; SEQ ID NO: 238) and Buch_groES_98R (CTGTTCCTCGAGTCGATTTCC; SEQ ID NO: 239) (Chong and Moran, 2016 PNAS). The primers used for aphid were ApEF1a 107F (CTGATTGTGCCGTGCTTATTG; SEQ ID NO: 240) and ApEF1a 246R (TATGGTGGTTCAGTAGAGTCC; SEQ ID NO: 241) (Chong and Moran, 2016 PNAS). qPCR was performed using a qPCR amplification ramp of 1.6 degrees C./s and the following conditions: 1) 95° C. for 10 minutes, 2) 95° C. for 15 seconds, 3) 55° C. for 30 seconds, 4) repeat steps 2-3 40×, 5) 95° C. for 15 seconds, 6) 55° C. for 1 minute, 7) ramp change to 0.15 degrees C./s, 8) 95° C. for 1 second. qPCR data was analyzed using analytic (Thermo Fisher Scientific, QuantStudio Design and Analysis) software.

Treatment with a Combination of Three Antimicrobial Agents Delayed and Stopped Progression of Aphid Development LSR-1 $1^{st}$ instar aphids were divided into two separate treatment groups as defined in Leaf perfusion and delivery through plants experimental design (described herein). Aphids were monitored daily and the number of aphids at each developmental stage was determined. Aphids treated with water began reaching maturity (5th instar stage) at day 5 post-treatment (FIG. 56A). By 6 days post-treatment, ~20 percent of aphids treated with water reached the 5th instar stage. In contrast, no aphids treated with the combination of three agents reached the 5th instar stage, even after 6 days (FIG. 56A). This delay in development upon combination treatment was further exemplified by aphid size measurements taken at 5 days post-treatment. Aphids treated with water alone were approximately 0.45 $mm^2$, whereas aphids treated with the 3-agent combination were approximately 0.26 $mm^2$ (FIG. 56B). These data indicate that treatment with a combination of agents delayed aphid development, negatively impacting aphid fitness.

Treatment with a Combination of Three Antimicrobial Agents Increased Aphid Mortality Survival was also monitored daily after treatment. At 2 days post-treatment, approximately 75 percent of aphids treated with water were alive, whereas only 62 percent of aphids treated with the combination of agents were alive. This trend of more aphids surviving treatment in the control (water-treated) group continued for the duration of the experiment. At 6 days post-treatment, 64 percent of control (water-treated) aphids survived, whereas 58 percent of aphids treated with a combination of rifampicin, Uy192, and chitosan survived (FIG. 57). These data indicate that the combination of treatments negatively affected aphid survival.

Treatment with a Combination of Three Agents Resulted in Decreased *Buchnera* in Aphids To test whether treatment with a combination of a peptide, antibiotic, and natural antimicrobial specifically resulted in loss of *Buchnera* in aphids, and that this loss impacted aphid fitness, DNA was extracted from aphids in each treatment group after 6 days of treatment and qPCR was performed to determine the *Buchnera*/aphid copy numbers. Aphids treated with water alone ratios of approximately 2.3 *Buchnera*/aphid DNA (FIG. 58). In contrast, aphids treated with the combination of a peptide, antibiotic, and natural antimicrobial had approximately 2-fold lower ratios of *Buchnera*/aphid DNA (FIG. 58). These data indicate that combination treatment reduced endosymbiont levels, which resulted in decreased aphid fitness.

Together, this data demonstrates the ability to decrease the development and endogenous bacterial populations, e.g., fitness, of aphids by treating them with a combination of a peptide, antibiotic, and natural antimicrobial.

Example 26: Insects Treated with an Antibiotic Solution

This Example demonstrates the effects of treatment of weevils with ciprofloxacin, a bactericidal antibiotic that inhibits the activity of DNA gyrase and topoisomerase, two enzymes essential for DNA replication. This Example demonstrates that the phenotypic effect of ciprofloxacin on another model insect, weevils, was mediated through the modulation of bacterial populations endogenous to the insects that were sensitive to ciprofloxacin. One targeted bacterial strain is *Sitophilus* primary endosymbiont (SPE, *Candidatus Sodalis pierantonius*).

Experimental Design:

*Sitophilus* maize weevils (*Sitophilus zeamais*) were reared on organic corn at 27.5° C. and 70% relative humidity. Prior to being used for weevil rearing, corn was frozen for 7 days and then tempered to 10% humidity with sterile water. For experiments, adult male/female mating pairs were divided into 3 different treatment groups that were done in triplicate: 1) water control, 2) 250 μg/ml ciprofloxacin, and 3) 2.5 mg/ml ciprofloxacin. Ciprofloxacin (Sigma) stock solutions were made at 25 mg/ml in 0.1 N HCl, sterilized by passing through a 0.22 μm syringe filter, and stored at −20° C. For treatments, the appropriate amount of stock solution was diluted in sterile water.

The weevils were subjected to three successive treatments:

1. The first treatment included soaking 25 g of corn with each of the three treatment groups listed above: 1) water control, 2) 250 μg/ml ciprofloxacin, and 3) 2.5 mg/ml ciprofloxacin. Briefly, 25 g of corn was placed into a 50 ml conical tube and each of the treatment was added to fill the tube completely. The tube was put on a shaker for 1.5 hours after which, the corn was removed and placed into a deep petri dish and air dried. Male/Female mating pairs were then added to each treatment group and allowed to feed for 4 days.
2. After 4 days, mating pairs were removed and subjected to a second treatment by putting them onto 25 g of new corn treated with 1) water control, 2) 250 μg/ml ciprofloxacin, and
3) 2.5 mg/ml ciprofloxacin. Mating pairs fed and laid eggs on this corn for 7 days. The corn from the second treatment was assessed for the emergence of offspring (see assessment of offspring, below)
3. Mating pairs were subjected to a final treatment which included a combination of submerging them into the treatment (1) water control, 2) 250 μg/ml ciprofloxacin, and 3) 2.5 mg/ml ciprofloxacin for 5 seconds and then placing them in a vial with 10 corn kernels that had been coated with 1 ml of 1) water control, 2) 250 μg/ml ciprofloxacin, and 3) 2.5 mg/ml ciprofloxacin.

Weevil survival was monitored daily for 18 days, after which DNA was extracted from the remaining weevils in each group. Briefly, the weevil body was surface sterilized by dipping the weevil into a 6% bleach solution for approximately 5 seconds. Weevils were then rinsed in sterile water and DNA was extracted from each individual aphid using a DNA extraction kit (Qiagen, DNeasy kit) according to manufacturer's instructions. DNA concentration was measured using a nanodrop nucleic acid quantification, and SPE and weevil DNA copy numbers were measured by qPCR. The primers used for SPE were qPCR_Sod_F (ATAGCTGTCCAGACGTTTCG; SEQ ID NO: 242) and qPCR_Sod_R (ATGTCGTCGAGGCGATTACC; SEQ ID NO: 243). The primers used for weevil ((3-actin) were SACT144_FOR (GGTGTTGGCGTACAAGTCCT; SEQ ID NO: 244) and SACT314_REV (GAATTGCCTGATGGACAGGT; SEQ ID NO: 245) (Login et al., 2011). qPCR was performed using a qPCR amplification ramp of 1.6 degrees C./s and the following conditions: 1) 95° C. for 10 minutes, 2) 95° C. for 15 seconds, 3) 57° C. for 30 seconds, 4) repeat steps 2-3 40×, 5) 95° C. for 15 seconds, 6) 55° C. for 1 minute, 7) ramp change to 0.15 degrees C./s, 8) 95° C. for 1 second. qPCR data was analyzed using analytic (Thermo Fisher Scientific, QuantStudio Design and Analysis) software.

Assessment of Offspring:

After 25 days, one replicate of the corn kernels from the second treatment of the adult mating pairs was dissected (see Experimental Design, above) to check for the presence of any developing larvae, pupae, or adult weevils. Most of the development of *Sitophilus* weevils takes place within the grain/rice/corn and adults emerge from the kernels once their development is complete. Corn kernels were gently dissected open with a scalpel and any developing weevils were collected and the percent of adults, pupae, and larvae were determined. The weevils from the dissection were then surface sterilized and the levels of SPE were determined by qPCR. Corn kernels from the remaining two replicates of each of the groups from the second treatment were not dissected but checked daily for the emergence of adult weevils.

Assessment of Antibiotic Penetration into Corn 25 mg of corn kernels was placed into a 50 ml conical tube and water or 2.5 mg/ml or 0.25 mg/ml ciprofloxacin in water was added to fill the tube. The kernels were soaked for 1.5 hours as described herein. After soaking, kernels were air dried and assayed to determine whether the antibiotic was able to coat and penetrate the kernel. To test this, a concentrated sample of *Escherichia coli* DH5a in water was spread onto 5 Luria Broth (LB) plates. To each plate the following was done, 1) a corn kernel soaked in water was added, 2) an entire corn kernel that had been soaked with 2.5 or 0.25 mg/ml ciprofloxacin was added, and 3) a half of corn kernel that had been soaked with 2.5 or 0.25 mg/ml ciprofloxacin was added and placed inside down on the plate. The plates were incubated overnight at 37 degrees C. and bacterial growth and/or zone(s) of inhibition were assessed the next day.

Soaking Corn Kernels in Antibiotics Allowed Antibiotics to Coat the Surface and Penetrate Corn Kernels.

To test whether ciprofloxacin could coat the surface of a corn kernel after a kernel, corn kernels were soaked in water without antibiotics or water with 2.5 or 0.25 mg/ml ciprofloxacin (as described above). A concentrated culture of *E. coli* was then spread onto LB plates and one of the coated kernels was then placed onto the center of the plate. The plates were incubated overnight, and bacterial growth was assessed the next day.

A lawn of bacteria grew on the entire plate with the corn kernel that had been coated in water without any antibiotics (FIG. 56A). In contrast, no bacteria grew on plates with entire corn kernels that had been soaked in either of the two concentrations of ciprofloxacin (FIG. 56B, left panels). These data show that the coating method employed in these experiments allowed for ciprofloxacin to successfully coat the surface of corn kernels and inhibit bacterial growth.

To test whether ciprofloxacin could penetrate the corn kernel, corn kernels soaked in 2.5 or 0.25 mg/ml ciprofloxacin were cut in half and placed cut side down on an LB plate with a concentrated culture of *E. coli*. The plates were incubated overnight and the next day bacterial growth was assessed. No bacterial growth was present on the plates with the kernels soaked in either concentration of antibiotic, indicating that ciprofloxacin penetrated the corn kernel (FIG. 56B, right panels). Together, these data indicate that the method of corn kernel soaking used for these experiments successfully coated and penetrated the kernels with the antibiotic.

Antibiotic Treatment Decreases SPE Levels in the F0 Generation.

*S. zeamais* mating pairs were divided into three separate treatment groups as defined in Experimental Design (above).

Weevils were monitored daily and all weevils remained alive for the course of the experiment. After 18 days of treatment, weevils were surface sterilized, genomic DNA was extracted, and SPE levels were measured by qPCR. Weevils treated with water only had approximately 4 and 8-fold higher amounts of SPE compared to weevils treated with 250 ug/ml and 2.5 mg/ml ciprofloxacin, respectively (FIG. 57). These data indicate that treatment of weevils with ciprofloxacin resulted in decreased levels of SPE.

Antibiotic Treatment Delays the Development and Decreases the SPE Levels of the F1 Generation of Weevils.

The development of the F1 generation of weevils was assessed by dissecting corn kernels that F0 mating pairs had oviposited on for 7 days and were subsequently removed. After 25 days, 12 offspring were found in water/control-treated corn with the majority (~67%) of offspring being in the pupae form (FIG. 58A). 13 and 20 offspring were found in weevils treated with 250 ug/ml and 2.5 mg/ml ciprofloxacin, respectively. Interestingly, weevils treated with antibiotic showed a delay in development compared to control treated weevils with the majority (38 and 65% for 250 ug/ml and 2.5 mg/ml ciprofloxacin, respectively) of the offspring being in the larval form (FIG. 58A).

Genomic DNA was extracted from weevils dissected from the corn kernels and qPCR was performed to measure the levels of SPE. Water treated F1 weevils had approximately 4-fold higher levels of SPE compared to weevils treated with 2.5 mg/ml ciprofloxacin (FIG. 58B). These data indicate that treatment with ciprofloxacin reduced the levels of the SPE in weevils which led to a delay in development.

Antibiotic Treatment Decreased Weevil Reproduction

The number of weevils that emerged over the course of 43 days after the initial mating pairs were removed from the second treatment was used a measure for the fecundity FIGS. 59A and 59B). The first weevil emerged on day 29, and the total number of weevils that emerged till day 43 were counted. While weevils treated with water and 250 ug/ml had similar amount of F1 offspring, there were much less offspring that emerged from the 2.5 mg/ml treatment group, indicating that antibiotic treatment decreased SPE levels affected weevil fecundity.

Together with the previous Examples, this data demonstrate the ability to kill and decrease the development, reproductive ability, longevity, and endogenous bacterial populations, e.g., fitness, of weevils by treating them with an antibiotic through multiple delivery methods.

Example 27: Mites Treated with an Antibiotic Solution

This Example demonstrates the ability to kill, decrease the fitness of two-spotted spider mites by treating them with rifampicin, a narrow spectrum antibiotic that inhibits DNA-dependent RNA synthesis by inhibiting a bacterial RNA polymerase, and doxycycline, a broad-spectrum antibiotic that prevents bacterial reproduction by inhibiting protein synthesis. The effect of rifampicin and doxycycline on mites was mediated through the modulation of bacterial populations endogenous to the mites that were sensitive to the antibiotics.

Insects, such as mosquitoes, and arachnids, such as ticks, can function as vectors for pathogens causing severe diseases in humans and animals such as Lyme disease, dengue, trypanosomiases, and malaria. Vector-borne diseases cause millions of human deaths every year. Also, vector-borne diseases that infect animals, such as livestock, represent a major global public health burden. Thus, there is a need for methods and compositions to control insects and arachnids that carry vector-borne diseases. Two-spotted spider mites are arachnids in the same subclass as ticks. Therefore, this Example demonstrates methods and compositions used to decrease the fitness of two-spotted spider mites and provide insight into decreasing tick fitness.

Therapeutic Design

Two treatments were used for these experiments 1) 0.025% Silwet L-77 (negative control) or 2) a cocktail of antibiotics containing 250 μg/ml rifampicin and 500 μg/ml doxycycline. Rifampicin (Tokyo Chemical Industry, LTD) stock solutions were made at 25 mg/ml in methanol, sterilized by passing through a 0.22 μm syringe filter, and stored at −20° C. Doxcycline (manufacturer) stock solutions were made at 50 mg/mL in water, sterilized by passing through a 0.22 μm syringe filter, and stored at −20° C.

Experimental Design:

This assay tested an antibiotic solution on two-spotted spider mites and determined how their fitness was altered by targeting endogenous microbes.

Kidney plants were grown in potting soil at 24° C. with 16 h of light and 8 h of darkness. Mites were reared on kidney bean plants at 26° C. and 15-20% relative humidity. For treatments, one-inch diameter leaf disks were cut from kidney bean leaves and sprayed with either 0.025% Silwet L-77 (negative control) or the antibiotic cocktail (250 μg/ml rifampicin and 500 μg/ml doxycycline in 0.025% Silwet L-77) using a Master Airbrush Brand Compressor Model C-16-B Black Mini Airbrush Air Compressor. The compressor was cleaned with ethanol before, after, and between treatments. The liquid was feed through the compressor using a quarter inch tube. A new tube was used for each treatment.

After leaf discs dried, four of each treatment were placed in a cup on top of a wet cotton ball covered with a piece of kimwipe. Each treatment setup was done in duplicate. 25 adult female mites were then placed in the cup. On day 4, the females were removed from the cup and the eggs and larvae were left on the leaf discs.

On day 11, mites at the protonymph stage and the deutonymph stage were taken from the cups and placed in their own tube so survival could be measured. Each tube contained a moist cotton ball covered with a piece of kimwipe with a half inch leaf disc treated with the negative control or the cocktail.

The mites were observed under a dissecting microscope daily after feeding on a leaf treated with the antibiotic or the control solutions, and classified according to the following categories:

- Alive: they walked around when on their legs or moved after being poked by a paint brush.
- Dead: immobile and did not react to stimulation from a paint brush A sterile paint brush was used to stimulate the mites by touching their legs. Mites classified as dead were kept throughout the assay and rechecked for movement daily. The assays were carried out at 26° C. and 15-20% relative humidity.

Antibiotic Treatment Increased Mite Mortality

The survival rates of the two-spotted spider mites treated with the antibiotic cocktail were compared to the mites treated with the negative control. The survival rates of the mites treated with the cocktail were decreased compared to the control (FIG. 60).

This data demonstrates the ability to decrease fitness of mites by treating them with a solution of antibiotics.

Example 28: Insects Treated with a Solution of Purified Phage

This Example demonstrates the isolation and purification of phages from environmental samples that targeted specific insect bacteria. This Example also demonstrates the efficacy of isolated phages against the target bacteria in vitro by plaque assays, by measuring their oxygen consumption rate, and the extracellular acidification rate. Finally, this Example demonstrates the efficacy of the phages in vivo, by measuring the ability of the phage to the target bacteria from flies by treating them with a phage isolated against the bacteria. This Eample demonstrates that a pathogenic bacterium that decreased the fitness of an insect can be cleared using a phage to target the bacteria. Specifically, *Serratia marcescens* which is a pathogenic bacterium in flies can be cleared with the use of a phage that was isolated from garden compost.

Experimental Design

Isolation of Specific Bacteriophages from Natural Samples:

Bacteriophages against target bacteria were isolated from environmental source material. Briefly, a saturated culture of *Serratia marcescens* was diluted into fresh double-strength tryptic soy broth (TSB) and grown for −120 minutes to early log-phase at 24-26° C., or into double-strength Luria-Bertani (LB) broth and grown for −90 min at 37° C. Garden compost was prepared by homogenization in PBS and sterilized by 0.2 μm filtration. Raw sewage was sterilized by 0.2 μm filtration. One volume of filtered source material was added to log-phase bacterial cultures and incubation was continued for 24 h. Enriched source material was prepared by pelleting cultures and filtering supernatant fluid through 0.45 μm membranes.

Phages were isolated by plating samples onto double-agar bacterial lawns. Stationary bacterial cultures were combined with molten 0.6% agar LB or TSB and poured onto 1.5% agar LB or TSB plates. After solidification, 2.5 μL of phage sample dilutions were spotted onto the double-agar plates and allowed to absorb. Plates were then wrapped and incubated overnight at 25° C. (TSA) or 37° C. (LB), then assessed for the formation of visible plaques. Newly isolated plaques were purified by serial passaging of individual plaques on the target strain by picking plaques into SM Buffer (50 mM Tris-HCl [pH 7.4], 10 mM MgSO4, 100 mM NaCl) and incubating for 15 min at 55° C., then repeating the double-agar spotting method from above using the plaque suspension.

Bacteriophages were successfully isolated from both sewage and compost, as detailed above. Plaque formation was clearly evident after spotting samples onto lawns of the *S. marcescens* bacteria used for the enrichments.

Passaging, Quantification, and Propagation of Bacteriophages:

Propagation and generation of phage lysates for use in subsequent experiments was performed using bacteriophages isolated and purified as above. Briefly, saturated bacterial cultures were diluted 100-fold into fresh medium and grown for 60-120 minutes to achieve an early-logarithmic growth state for effective phage infection. Phage suspensions or lysates were added to early log phase cultures and incubation was continued until broth clearing, indicative of phage propagation and bacterial lysis, was observed, or until up to 24 h post-infection. Lysates were harvested by pelleting cells at 7,197×g for 20 min, then filtering the supernatant fluid through 0.45 or 0.2 μm membranes. Filtered lysates were stored at 4° C.

Enumeration of infective phage particles was performed using the double-agar spotting method. Briefly, a 1:10 dilution series of samples was performed in PBS and dilutions were spotted onto solidified double-agar plates prepared with the host bacteria as above. Plaque-forming units (PFU) were counted after overnight incubation to determine the approximate titer of samples.

In Vitro Analysis of Isolated Phages Measuring Bacterial Respiration:

A Seahorse XFe96 Analyzer (Agilent) was used to measure the effects of phages on bacteria by monitoring oxygen consumption rate (OCR) and extracellular acidification rate (ECAR) during infection. XFe96 plates were coated the day prior to experiments by 15 μL of a 1 mg/mL poly-L-lysine stock per well and dried overnight at 28° C. and XFe96 probes were equilibrated by placing into wells containing 200 μL of XF Calibrant and incubating in the dark at room temperature. The following day, poly-L-lysine coated plates were washed twice with ddH2O. Saturated overnight cultures of *E. coli* BL21 (LB, 37° C.) or *S. marcescens* (TSB, 25° C.) were subcultured at 1:100 into the same media and grown with aeration for ~2.5 h at 30° C. Cultures were then diluted to O.D.600 nm-0.02 using the same media. Treatments were prepared by diluting stocks into SM Buffer at 10× final concentration and loading 20 μL of the 10× solutions into the appropriate injection ports of the probe plate. While the probes were equilibrating in the XFe96 Flux Analyzer, bacterial plates were prepared by adding 90 μL of bacterial suspensions or media controls and spun at 3,000 rpm for 10 min. Following centrifugation, an additional 90 μL of the appropriate media were added gently to the wells so as not to disturb bacterial adherence, bringing the total volume to 180 μL per well.

The XFe96 Flux Analyzer was run at −30° C., following a Mix, Wait, Read cycling of 1:00, 0:30, 3:00. Four cycles were completed to permit equilibration/normalization of bacteria, then the 20 μL treatments were injected and cycling continued as above, for a total time of approximately 6 h. Data were analyzed using the Seahorse XFe96 Wave software package.

The effects of isolated bacteriophages were assayed by measuring oxygen consumption rate (OCR) and extracellular acidification rate (ECAR) of bacteria with a Seahorse XFe96 Analyzer. When *E. coli* was infected with phage T7 and *S. marcescens* infected with the newly isolated ϕSmVL-C1, dramatic decreases in OCR were observed following brief bursts in this rate (FIG. 64). For both phages with both host organisms, the Seahorse assay permitted the detection of successful phage infection without the need for plaque assays. Thus, this method is applicable for detecting phage infection of a host organism not amenable to traditional phage detection methods.

SYBR Gold Transduction Assay for Infection Identification:

Bacteriophage preparations were prepared for staining by pretreating with nucleases to remove extraviral nucleic acids that could interfere with fluorescent signal interpretation. Briefly, MgCl2 was added to 10 mL of phage lysate at 10 mM final concentration, and RNase A (Qiagen) and DNase I (Sigma) were both added to final concentrations of 10 μg/mL. Samples were incubated for 1 h at room temperature. After nuclease treatment, 5 mL of lysates were combined with 1 μL of SYBR Gold (Thermo, 10,000×) and incubated at room temperature for ~1.5 h. Excess dye was subsequently removed from samples using Amicon ultrafiltration columns. Briefly, Amicon columns (15 mL, 10 k MWCO)

were washed by adding 10 mL of SM Buffer and spinning at 5,000×g, 4° C. for 5 min. Labeled phage samples were then spun through the columns at 5,000×g, 4° C. until the volume had decreased by approximately 10-fold (15-30 min). To wash samples, 5 mL SM Buffer was added to each reservoir and the spin repeated, followed by two additional washes. After the third wash, the retained samples were pipetted out from the Amicon reservoirs and brought up to approximately 1 mL using SM Buffer. To remove larger contaminants, washed and labeled phage samples were spun at 10,000×g for 2 min, and the supernatants were subsequently filtered through 0.2 μm membranes into black microtubes and stored at 4° C.

Saturated bacterial cultures (*E. coli* MG1655 grown in LB at 37° C., *S. marcescens* and S. *symbiotica* grown in TSB at 26° C.) were prepared by spinning down 1 mL aliquots and washing once with 1 mL PBS before a final resuspension using 1 mL PBS. Positive control labeled bacteria were stained by combining 500 μL of washed bacteria with 1 μL of SYBR Gold and incubating for 1 h in the dark at room temperature. Bacteria were pelleted by spinning at 8,000×g for 5 min and washed twice with an equal volume of PBS, followed by resuspension in a final volume of 500 μL PBS. A volume of 25 μL of stained bacteria was combined with 25 μL of SM Buffer in a black microtube, to which 50 μL of 10% formalin (5% final volume, ~2% formaldehyde) was added and mixed by flicking. Samples were fixed at room temperature for ~3 h and then washed using Amicon ultrafiltration columns. Briefly, 500 μL of picopure water was added to Amicon columns (0.5 mL, 100 k MWCO) and spun at 14,000×g for 5 min to wash membranes. Fixed samples were diluted by adding 400 μL of PBS and then transferred to pre-washed spin columns and spun at 14,000×g for 10 min. Columns were transferred to fresh collection tubes, and 500 μL of PBS was added to dilute out fixative remaining in the retentate. Subsequently, two additional PBS dilutions were performed, for a total of three washes. The final retentates were diluted to roughly 100 μL, then columns were inverted into fresh collection tubes and spun at 1,000×g for 2 min to collect samples. Washed samples were transferred to black microtubes and stored at 4° C.

For transduction experiments and controls, 25 μL of bacteria (or PBS) and 25 μL of SYBR Gold labeled phage (or SM Buffer) were combined in black microtubes and incubated static for 15-20 min at room temperature to permit phage adsorption and injection into recipient bacteria. Immediately after incubation, 50 μL of 10% formalin was added to samples and fixation was performed at room temperature for ~4 h. Samples were washed with PBS using Amicon columns, as above.

Injection of bacteriophage nucleic acid was required for a phage to successfully infect a host bacterial cell. Coliphage P1kc labeled with SYBR Gold and co-incubated with *S. marcescens* revealed the presence of fluorescent bacteria by microscopy, validating the use of this assay in a phage isolation pipeline. As with the Seahorse assay, this approach provided an alternative to traditional phage methods to permit expansion to organisms not amenable to plaque assay. Additionally, the SYBR Gold transduction assay did not require bacterial growth, so is applicable to analysis of phages targeting difficult or even non-culturable organisms, including endosymbionts such as *Buchnera.*

Testing In Vivo Efficacy of the Phages Against *S. marcescens* in *Drosophila melanogaster* Flies

*S. marcescens* cultures were grown in Tryptic Soy Broth (TSB) at 30° C. with constant shaking at 200 rpm.

The media used to rear fly stocks was cornmeal, molasses and yeast medium (11 g/I yeast, 54 g/I yellow cornmeal, 5 g/I agar, 66 ml/l molasses, and 4.8 ml/l propionic acid). All the components of the diet except propionic acid were heated together to 80° C. in deionized water with constant mixing for 30 minutes and let to cool to 60° C. Propionic acid was then mixed in and 50 ml of the diet was aliquoted into individual bottles and allowed to cool down and solidify. The flies were raised at 26° C., 16:8 hour light:dark cycle, at around 60% humidity.

To infect the flies with *S. marcescens*, a fine needle (About 10 um wide tip) was dipped in a dense overnight stationary phase culture and the thorax of the flies was punctured. For this experiment, four replicates of 10 males and 10 females each were infected with *S. marcescens* using the needle puncturing method as the positive control for fly mortality. For the treatment group, four replicates of 10 males and 10 females each were pricked with *S. marcescens* and a phage solution containing about 108 phage particles/ml. Finally, two replicates of 10 males and 10 females each that were not pricked or treated in anyway were used as a negative control for mortality.

Flies in all conditions were placed in food bottles and incubated at 26° C., 16:8 light:dark cycle, at 60% humidity. The number of alive and dead flies were counted every day for four days after the pricking. All The flies pricked with *S. marcescens* alone were all dead within 24 hours of the treatment. In comparison, more than 60% of the flies in the phage treatment group, and all the flies in the untreated control group were alive at that time point (FIG. 65). Further, most of the flies in the phage treatment group and the negative control group went on to survive for four more days when the experiment was terminated.

To ascertain the reason of death of the flies, dead flies from both the *S. marcescens* and *S. marcescens*+phage pricked flies were homogenized and plated out. Four dead flies from each of the four replicates of both the *S. marcescens* and the *S. marcescens*+phage treatment were homogenized in 100 ul of TSB. A 1:100 dilution was also produced by diluting the homogenate in TSB. 10 ul of the concentrated homogenate as well as the 1:100 dilution was plated out onto TSA plates, and incubated overnight at 30° C. Upon inspection of the plates for bacteria growth, all the plates from the dead *S. marcescens* pricked flies had a lawn of bacteria growing on them, whereas the plates from the dead *S. marcescens*+phage pricked flies had no bacteria on them. This shows that in the absence of the phage, *S. marcescens* likely induced septic shock in the flies leading to their fatality. However, in the presence of the phage, the mortality may have been due to injury caused by the pricking with the needle.

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A composition comprising a cell penetrating peptide and an antimicrobial peptide having at least 90% sequence identity with one or more of the following: scorpion peptide Uy192, cecropin, melittin, copsin, drosomycin, dermcidin, andropin, moricin, ceratotoxin, abaecin, apidaecin, prophenin, indolicidin, protegrin, tachyplesin, or defensin, wherein the composition is formulated for targeting a microorganism in a vector for a human pathogen.

2. The composition of claim 1, wherein the antimicrobial peptide is at a concentration of about 0.1 ng/g to about 100 mg/g in the composition.

3. The composition of claim 1, wherein the antimicrobial peptide further comprises a targeting domain.

4. A method of decreasing fitness of a vector for a human pathogen, the method comprising: delivering a fusion peptide comprising a cell penetrating peptide and an antimicrobial peptide to the vector, wherein the antimicrobial peptide is cecropin (SEQ ID NO: 82), and wherein the cell penetrating peptide has an amino acid sequence selected from the group consisting of SEQ ID NOs: 213, 214, 215, 216, 217, 218, 219, 220, and 247, thereby decreasing fitness of the vector for the human pathogen.

5. The method of claim 4, wherein the delivery comprises delivering the fusion peptide to at least one habitat where the vector grows, lives, reproduces, feeds, or infests.

6. The method of claim 4, wherein the fusion peptide is delivered in an insect comestible composition for ingestion by the vector.

7. The method of claim 4, wherein the fusion peptide is formulated as a liquid, a solid, an aerosol, a paste, a gel, or a gas composition.

8. The method of claim 4, wherein the vector is an insect.

9. The method of claim 4, wherein the fusion peptide further comprises a targeting domain.

10. The method of claim 8, wherein the insect is a mosquito.

11. The method of claim 6, wherein the insect comestible composition comprises the fusion peptide at a concentration of about 0.1 ng/g to about 100 mg/g.

* * * * *

SEQUENCE LISTING

<160> NUMBER OF SEQ ID NOS: 247

<210> SEQ ID NO 1
<211> LENGTH: 1526
<212> TYPE: DNA
<213> ORGANISM: Carsonella ruddii

<400> SEQUENCE: 1
tatccagcca caggttcccc tacagctacc ttgttacgac ttcaccccag ttacaaatca 60
taccgttgta atagtaaaat tacttatgat acaatttact tccatggtgt gacgggcggt 120
gtgtacaagg ctcgagaacg tattcaccgt aacattctga tttacgatta ctagcgattc 180
caacttcatg aaatcgagtt acagatttca atccgaacta agaatatttt ttaagattag 240
cattatgttg ccatatagca tataactttt tgtaatactc attgtagcac gtgtgtagcc 300
ctacttataa gggccatgat gacttgacgt cgtcctcacc ttcctccaat ttatcattgg 360
cagtttctta ttagttctaa tatattttta gtaaaataag ataagggttg cgctcgttat 420
aggacttaac ccaacatttc acaacacgag ctgacgacag ccatgcagca cctgtctcaa 480
agctaaaaaa gctttattat ttctaataaa ttctttggat gtcaaaagta ggtaagattt 540
ttcgtgttgt atcgaattaa accacatgct ccaccgcttg tgcgagcccc cgtcaattca 600
tttgagtttt aaccttgcgg tcgtaatccc caggcggtca acttaacgcg ttagcttttt 660
cactaaaaat atataacttt ttttcataaa acaaaattac aattataata tttaataaat 720
agttgacatc gtttactgca tggactacca gggtatctaa tcctgtttgc tccccatgct 780
ttcgtgtatt agtgtcagta ttaaaataga aatacgcctt cgccactagt attctttcag 840
atatctaagc atttcactgc tactcctgaa attctaattt cttcttttat actcaagttt 900
ataagtatta atttcaatat taaattactt taataaattt aaaaattaat ttttaaaaac 960
aacctgcaca ccctttacgc ccaataattc cgattaacgc ttgcacccct cgtattaccg 1020
cggctgctgg cacgaagtta gccggtgctt cttttacaaa taacgtcaaa gataatattt 1080
ttttattata aaatctcttc ttactttgtt gaaagtgttt tacaacccta aggccttctt 1140
cacacacgcg atatagctgg atcaagcttt cgctcattgt ccaatatccc ccactgctgc 1200
cttccgtaaa agtttgggcc gtgtctcagt cccaatgtgg ttgttcatcc tctaagatca 1260
actacgaatc atagtcttgt taagctttta ctttaacaac taactaattc gatataagct 1320
cttctattag cgaacgacat tctcgttctt tatccattag gatacatatt gaattactat 1380
acatttctat atacttttct aatactaata ggtagattct tatatattac tcacccgttc 1440
gctgctaatt atttttttaa taattcgcac aacttgcatg tgttaagctt atcgctagcg 1500
ttcaatctga gctatgatca aactca 1526

<210> SEQ ID NO 2
<211> LENGTH: 1536
<212> TYPE: DNA
<213> ORGANISM: aleyrodidarum BT-B

<400> SEQUENCE: 2
aagagtttga tcatggctca gattgaacgc tagcggcaga cataacacat gcaagtcgag 60
cggcatcata caggttggca agcggcgcac gggtgagtaa tacatgtaaa tatacctaaa 120
agtggggaat aacgtacgga aacgtacgct aataccgcat aattattacg agataaagca 180
ggggcttgat aaaaaaaatc aaccttgcgc ttttagaaaa ttacatgccg gattagctag 240
ttggtagagt aaaagcctac caaggtaacg atccgtagct ggtctgagag gatgatcagc 300

```
cacactggga ctgagaaaag gcccagactc ctacgggagg cagcagtggg gaatattgga    360

caatgggggg aaccctgatc cagtcatgcc gcgtgtgtga agaaggcctt tgggttgtaa    420

agcactttca gcgaagaaga aaagttagaa aataaaaagt tataactatg acggtactcg    480

cagaagaagc accggctaac tccgtgccag cagccgcggt aagacggagg gtgcaagcgt    540

taatcagaat tactgggcgt aaagggcatg taggtggttt gttaagcttt atgtgaaagc    600

cctatgctta acataggaac ggaataaaga actgacaaac tagagtgcag aagaggaagg    660

tagaattccc ggtgtagcgg tgaaatgcgt agatatctgg aggaatacca gttgcgaagg    720

cgaccttctg ggctgacact gacactgaga tgcgaaagcg tggggagcaa acaggattag    780

ataccctggt agtccacgct gtaaacgata tcaactagcc gttggattct taaagaattt    840

tgtggcgtag ctaacgcgat aagttgatcg cctggggagt acggtcgcaa ggctaaaact    900

caaatgaatt gacgggggcc cgcacaagcg gtggagcatg tggtttaatt cgatgcaacg    960

cgcaaaacct tacctactct tgacatccaa agtactttcc agagatggaa gggtgcctta   1020

gggaactttg agacaggtgc tgcatggctg tcgtcagctc gtgttgtgaa atgttgggtt   1080

aagtcccgta acgagcgcaa cccttgtcct tagttgccaa cgcataaggc gggaacttta   1140

aggagactgc tggtgataaa ccggaggaag gtggggacga cgtcaagtca tcatggccct   1200

taagagtagg gcaacacacg tgctacaatg gcaaaaacaa agggtcgcaa aatggtaaca   1260

tgaagctaat cccaaaaaaa ttgtcttagt tcggattgga gtctgaaact cgactccata   1320

aagtcggaat cgctagtaat cgtgaatcag aatgtcacgg tgaatacgtt ctcgggcctt   1380

gtacacaccg cccgtcacac catggaagtg aaatgcacca gaagtggcaa gtttaaccaa   1440

aaaacaggag aacagtcact acggtgtggt tcatgactgg ggtgaagtcg taacaaggta   1500

gctgtagggg aacctgtggc tggatcacct ccttaa                             1536
```

<210> SEQ ID NO 3
<211> LENGTH: 1540
<212> TYPE: DNA
<213> ORGANISM: Buchnera aphidicola str. APS (Acyrthosiphon pisum)

<400> SEQUENCE: 3

```
agagtttgat catggctcag attgaacgct ggcggcaagc ctaacacatg caagtcgagc     60

ggcagcgaga agagagcttg ctctctttgt cggcaagcgg caaacgggtg agtaatatct    120

ggggatctac ccaaaagagg gggataacta ctagaaatgg tagctaatac cgcataatgt    180

tgaaaaacca aagtggggga ccttttggcc tcatgctttt ggatgaaccc agacgagatt    240

agcttgttgg tagagtaata gcctaccaag gcaacgatct ctagctggtc tgagaggata    300

accagccaca ctggaactga gacacggtcc agactcctac gggaggcagc agtggggaat    360

attgcacaat gggcgaaagc ctgatgcagc tatgccgcgt gtatgaagaa ggccttaggg    420

ttgtaaagta ctttcagcgg ggaggaaaaa aataaaacta ataattttat ttcgtgacgt    480

tacccgcaga agaagcaccg gctaactccg tgccagcagc cgcggtaata cggagggtgc    540

aagcgttaat cagaattact gggcgtaaag agcgcgtagg tggtttttta agtcaggtgt    600

gaaatcccta ggctcaacct aggaactgca tttgaaactg gaaaactaga gtttcgtaga    660

gggaggtaga attctaggtg tagcggtgaa atgcgtagat atctggagga atacccgtgg    720

cgaaagcggc ctcctaaacg aaaactgaca ctgaggcgcg aaagcgtggg gagcaaacag    780

gattagatac cctggtagtc catgccgtaa acgatgtcga cttggaggtt gtttccaaga    840
```

-continued

```
gaagtgactt ccgaagctaa cgcattaagt cgaccgcctg gggagtacgg ccgcaaggct    900

aaaactcaaa tgaattgacg ggggcccgca caagcggtgg agcatgtggt ttaattcgat    960

gcaacgcgaa aaaccttacc tggtcttgac atccacagaa ttctttagaa ataaagaagt   1020

gccttcggga gctgtgagac aggtgctgca tggctgtcgt cagctcgtgt tgtgaaatgt   1080

tgggttaagt cccgcaacga gcgcaaccct tatcccctgt tgccagcggt tcggccggga   1140

actcagagga gactgccggt tataaaccgg aggaaggtgg ggacgacgtc aagtcatcat   1200

ggcccttacg accagggcta cacacgtgct acaatggttt atacaaagag aagcaaatct   1260

gcaaagacaa gcaaacctca taaagtaaat cgtagtccgg actggagtct gcaactcgac   1320

tccacgaagt cggaatcgct agtaatcgtg gatcagaatg ccacggtgaa tacgttcccg   1380

ggccttgtac acaccgcccg tcacaccatg ggagtgggtt gcaaaagaag caggtatcct   1440

aaccctttaa aaggaaggcg cttaccactt tgtgattcat gactggggtg aagtcgtaac   1500

aaggtaaccg taggggaacc tgcggttgga tcacctcctt                         1540
```

<210> SEQ ID NO 4
<211> LENGTH: 1552
<212> TYPE: DNA
<213> ORGANISM: Buchnera aphidicola str. Sg (Schizaphis graminum)

<400> SEQUENCE: 4

```
aaactgaaga gtttgatcat ggctcagatt gaacgctggc ggcaagccta acacatgcaa     60

gtcgagcggc agcgaaaaga aagcttgctt tcttgtcggc gagcggcaaa cgggtgagta    120

atatctgggg atctgcccaa aagaggggga taactactag aaatggtagc taataccgca    180

taaagttgaa aaaccaaagt gggggacctt ttttaaaggc ctcatgcttt tggatgaacc    240

cagacgagat tagcttgttg gtaaggtaaa agcttaccaa ggcaacgatc tctagctggt    300

ctgagaggat aaccagccac actggaactg agacacggtc cagactccta cgggaggcag    360

cagtggggaa tattgcacaa tgggcgaaag cctgatgcag ctatgccgcg tgtatgaaga    420

aggccttagg gttgtaaagt actttcagcg gggaggaaaa aattaaaact aataatttta    480

ttttgtgacg ttacccgcag aagaagcacc ggctaactcc gtgccagcag ccgcggtaat    540

acggagggtg cgagcgttaa tcagaattac tgggcgtaaa gagcacgtag gtggtttttt    600

aagtcagatg tgaaatccct aggcttaacc taggaactgc atttgaaact gaaatgctag    660

agtatcgtag agggaggtag aattctaggt gtagcggtga aatgcgtaga tatctggagg    720

aatacccgtg gcgaaagcgg cctcctaaac gaatactgac actgaggtgc gaaagcgtgg    780

ggagcaaaca ggattagata ccctggtagt ccatgccgta aacgatgtcg acttggaggt    840

tgtttccaag agaagtgact tccgaagcta acgcgttaag tcgaccgcct ggggagtacg    900

gccgcaaggc taaaactcaa atgaattgac gggggcccgc acaagcggtg gagcatgtgg    960

tttaattcga tgcaacgcga aaaaccttac ctggtcttga catccacaga attttttaga   1020

aataaaaaag tgccttcggg aactgtgaga caggtgctgc atggctgtcg tcagctcgtg   1080

ttgtgaaatg ttgggttaag tcccgcaacg agcgcaaccc ttatcccctg ttgccagcgg   1140

ttcggccggg aactcagagg agactgccgg ttataaaccg gaggaaggtg gggacgacgt   1200

caagtcatca tggcccttac gaccagggct acacacgtgc tacaatggtt tatacaaaga   1260

gaagcaaatc tgtaaagaca agcaaacctc ataaagtaaa tcgtagtccg gactggagtc   1320

tgcaactcga ctccacgaag tcggaatcgc tagtaatcgt ggatcagaat gccacggtga   1380

atacgttccc gggccttgta cacaccgccc gtcacaccat gggagtgggt tgcaaaagaa   1440
```

gcagatttcc taaccacgaa agtggaaggc gtctaccact ttgtgattca tgactggggt 1500
gaagtcgtaa caaggtaacc gtaggggaac ctgcggttgg atcacctcct ta 1552

<210> SEQ ID NO 5
<211> LENGTH: 1566
<212> TYPE: DNA
<213> ORGANISM: Buchnera aphidicola str. Bp (Baizongia pistaciae)

<400> SEQUENCE: 5
acttaaaatt gaagagtttg atcatggctc agattgaacg ctggcggcaa gcttaacaca 60
tgcaagtcga gcggcatcga agaaaagttt acttttctgg cggcgagcgg caaacgggtg 120
agtaacatct ggggatctac ctaaaagagg gggacaacca ttggaaacga tggctaatac 180
cgcataatgt ttttaaataa accaaagtag ggactaaaa tttttagcct tatgctttta 240
gatgaaccca gacgagatta gcttgatggt aaggtaatgg cttaccaagg cgacgatctc 300
tagctggtct gagaggataa ccagccacac tggaactgag atacggtcca gactcctacg 360
ggaggcagca gtggggaata ttgcacaatg ggctaaagcc tgatgcagct atgccgcgtg 420
tatgaagaag gccttagggt tgtaaagtac tttcagcggg gaggaaagaa ttatgtctaa 480
tatacatatt ttgtgacgtt acccgaagaa gaagcaccgg ctaactccgt gccagcagcc 540
gcggtaatac ggagggtgcg agcgttaatc agaattactg ggcgtaaaga gcacgtaggc 600
ggtttattaa gtcagatgtg aaatccctag gcttaactta ggaactgcat ttgaaactaa 660
tagactagag tctcatagag ggaggtagaa ttctaggtgt agcggtgaaa tgcgtagata 720
tctagaggaa tacccgtggc gaaagcgacc tcctaaatga aaactgacgc tgaggtgcga 780
aagcgtgggg agcaaacagg attagatacc ctggtagtcc atgctgtaaa cgatgtcgac 840
ttggaggttg tttcctagag aagtggcttc cgaagctaac gcattaagtc gaccgcctgg 900
ggagtacggt cgcaaggcta aaactcaaat gaattgacgg gggcccgcac aagcggtgga 960
gcatgtggtt taattcgatg caacgcgaag aaccttacct ggtcttgaca tccatagaat 1020
tttttagaga taaaagagtg ccttagggaa ctatgagaca ggtgctgcat ggctgtcgtc 1080
agctcgtgtt gtgaaatgtt gggttaagtc ccgcaacgag cgcaacccct atcctttgtt 1140
gccatcaggt tatgctggga actcagagga gactgccggt tataaaccgg aggaaggtgg 1200
ggatgacgtc aagtcatcat ggcccttacg accagggcta cacacgtgct acaatggcat 1260
atacaaagag atgcaactct gcgaagataa gcaaacctca taaagtatgt cgtagtccgg 1320
actggagtct gcaactcgac tccacgaagt aggaatcgct agtaatcgtg gatcagaatg 1380
ccacggtgaa tacgttcccg ggccttgtac acaccgcccg tcacaccatg ggagtgggtt 1440
gcaaaagaag caggtagctt aaccagatta ttttattgga gggcgcttac cactttgtga 1500
ttcatgactg ggtgaagtc gtaacaaggt aaccgtaggg gaacctgcgg ttggatcacc 1560
tcctta 1566

<210> SEQ ID NO 6
<211> LENGTH: 828
<212> TYPE: DNA
<213> ORGANISM: Buchnera aphidicola BCc

<400> SEQUENCE: 6
atgagatcat taatatataa aaatcatgtt ccaattaaaa aattaggaca aaattttta 60 cagaataaag aaattattaa tcagataatt aatttaataa atattaataa aaatgataat 120

```
attattgaaa taggatcagg attaggagcg ttaacttttc ctatttgtag aatcattaaa    180

aaaatgatag tattagaaat tgatgaagat cttgtgtttt ttttaactca aagtttattt    240

attaaaaaat tacaaattat aattgctgat attataaaat ttgattttg ttgtttttt    300

tctttacaga aatataaaaa atataggttt attggtaatt taccatataa tattgctact    360

atattttttt taaaaacaat taaatttctt tataatataa ttgatatgca ttttatgttt    420

caaaaagaag tagcaaagag attattagct actcctggta ctaaagaata tggtagatta    480

agtattattg cacaatattt ttataagata gaaactgtta ttaatgttaa taaatttaat    540

ttttttccta ctcctaaagt agattctact tttttacgat ttactcctaa atattttaat    600

agtaaatata aaatagataa acatttttct gttttagaat taattactag atttctttt    660

caacatagaa gaaaattttt aaataataat ttaatatctt tattttctac aaaagaatta    720

atttctttag atattgatcc atattcaaga gcagaaaatg tttctttaat tcaatattgt    780

aaattaatga aatattattt gaaaagaaaa attttatgtt tagattaa                828
```

<210> SEQ ID NO 7
<211> LENGTH: 921
<212> TYPE: DNA
<213> ORGANISM: Buchnera aphidicola (Cinara tujafilina)

<400> SEQUENCE: 7

```
ttatcttatt tcacatatac gtaatattgc gctgcgtgca cgaggatttt tttgaatttc     60

agatatattt ggtttaatac gtttaataaa acgtattttt tttttattt ttcttatttg    120

caattcagta ataggaagtt ttttaggtat atttggataa ttactgtaat tcttaataaa    180

gttttttaca atcctatctt caatagaatg aaaactaata atagcaattt ttgatccgga    240

atgtaatatg ttaataataa tttttaatat tttatgtaat tcatttattt cttggttaat    300

atatattcga aaagcttgaa atgttctcgt agctggatgt ttaaatttgt catattttgg    360

gattgatttt tttatgattt gaactaactc taacgtgctt gttatggttt tttttttat    420

ttgtaatatg atggctcggg atattttttt tgcgtatttt tcttcgccaa aatttttat    480

tacctgttct attgtttttt ggtttgtttt ttttaaccat tgactaactg atattccaga    540

tttagggttc atacgcatat ctaaaggtcc atcattcata aatgaaaatc ctcggatact    600

agaatttaac tgtattgaag aaatacctaa atctaataat attccatcta ttttatctct    660

atttttttct tttttaata ttttttcaat attagaaaat ttacctaaaa atattttaaa    720

tcgcgaatct tttatttttt ttccgatttt tatagattgt gggtcttgat caatactata    780

taactttcca ttaaccccta attcttgaag aattgctttt gaatgaccac cacctccaaa    840

tgtacaatca acatatgtac cgtctttttt tatttttaag tattgtatga tttcttttgt    900

taaaacaggt ttatgaatca t                                              921
```

<210> SEQ ID NO 8
<211> LENGTH: 822
<212> TYPE: DNA
<213> ORGANISM: Buchnera aphidicola str. G002 (Myzus persicae)

<400> SEQUENCE: 8

```
atgaaaagta taaaaacttt taaaaaacac tttcctgtga aaaaatatgg acaaaatttt     60

cttattaata aagagatcat aaaaaatatt gttaaaaaaa ttaatccaaa tatagaacaa    120

acattagtag aaatcggacc aggattagct gcattaactg agcccatatc tcagttatta    180

aaagagttaa tagttattga aatagactgt aatctattat attttttaaa aaaacaacca    240
```

```
ttttattcaa aattaatagt tttttgtcaa gatgctttaa actttaatta tacaaattta    300

ttttataaaa aaaataaatt aattcgtatt tttggtaatt taccatataa tatctctaca    360

tctttaatta tttttttatt tcaacacatt agagtaattc aagatatgaa ttttatgctt    420

caaaaagaag ttgctgcaag attaattgca ttacctggaa ataaatatta cggtcgtttg    480

agcattatat ctcaatatta ttgtgatatc aaaattttat taaatgttgc tcctgaagat    540

ttttggccta ttccgagagt tcattctata tttgtaaatt taacacctca tcataattct    600

ccttattttg tttatgatat taatatttta agccttatta caaataaggc tttccaaaat    660

agaagaaaaa tattacgtca tagtttaaaa aatttatttt ctgaaacaac tttattaaat    720

ttagatatta atcccagatt aagagctgaa aatatttctg tttttcagta ttgtcaatta    780

gctaattatt tgtataaaaa aaattatact aaaaaaaatt aa                       822
```

```
<210> SEQ ID NO 9
<211> LENGTH: 822
<212> TYPE: DNA
<213> ORGANISM: Buchnera aphidicola str. Ak (Acyrthosiphon kondoi)

<400> SEQUENCE: 9

attataaaaa attttaaaaa acattttcct ttaaaaaggt atggacaaaa ttttcttgtc     60

aatacaaaaa ctattcaaaa gataattaat ataattaatc caaacaccaa acaaacatta    120

gtggaaattg gacctggatt agctgcatta acaaaaccaa tttgtcaatt attagaagaa    180

ttaattgtta ttgaaataga tcctaattta ttgtttttat taaaaaaacg ttcattttat    240

tcaaaattaa cagtttttta tcaagacgct ttaaatttca attatacaga tttgttttat    300

aagaaaaatc aattaattcg tgtttttgga aacttgccat ataatatttc tacatcttta    360

attatttctt tattcaatca tattaaagtt attcaagata tgaattttat gttacagaaa    420

gaggttgctg aaagattaat ttctattcct ggaaataaat cttatggccg tttaagcatt    480

atttctcagt attattgtaa aattaaaata ttattaaatg ttgtacctga agattttcga    540

cctataccga aagtgcattc tgtttttatc aatttaactc ctcataccaa ttctccatat    600

tttgtttatg atacaaatat cctcagttct atcacaagaa atgcttttca aaatagaagg    660

aaaattttgc gtcatagttt aaaaaattta ttttctgaaa aagaactaat tcaattagaa    720

attaatccaa atttacgagc tgaaaatatt tctatctttc agtattgtca attagctgat    780

tatttatata aaaaattaaa taatcttgta aaaatcaatt aa                       822
```

```
<210> SEQ ID NO 10
<211> LENGTH: 822
<212> TYPE: DNA
<213> ORGANISM: Buchnera aphidicola str. Ua (Uroleucon ambrosiae)

<400> SEQUENCE: 10

atgatactaa ataaatataa aaaatttatt cctttaaaaa gatacggaca aaattttctt     60

gtaaatagag aaataatcaa aaatattatc aaaataatta atcctaaaaa aacgcaaaca    120

ttattagaaa ttggaccggg tttaggtgcg ttaacaaaac ctatttgtga atttttaaat    180

gaacttatcg tcattgaaat agatcctaat atattatctt ttttaaagaa atgtatattt    240

tttgataaat taaaaatata ttgtcataat gctttagatt ttaattataa aaatatattc    300

tataaaaaaa gtcaattaat tcgtattttt ggaaatttac catataatat ttctacatct    360

ttaataatat atttatttcg gaatattgat attattcaag atatgaattt tatgttacaa    420
```

-continued caagaagtgg ctaaaagatt agttgctatt cctggtgaaa aactttatgg tcgtttaagt 480
attatatctc aatattattg taatattaaa atattattac atattcgacc tgaaaatttt 540
caacctattc ctaaagttaa ttcaatgttt gtaaatttaa ctccgcatat tcattctcct 600
tattttgttt atgatattaa tttattaact agtattacaa aacatgcttt tcaacataga 660
agaaaaatat tgcgtcatag tttaagaaat ttttttctg agcaagattt aattcattta 720
gaaattaatc caaatttaag agctgaaaat gtttctatta ttcaatattg tcaattggct 780
aataatttat ataaaaaaca taaacagttt attaataatt aa 822

<210> SEQ ID NO 11
<211> LENGTH: 816
<212> TYPE: DNA
<213> ORGANISM: Buchnera aphidicola (Aphis glycines)

<400> SEQUENCE: 11
atgaaaaagc atattcctat aaaaaaattt agtcaaaatt ttcttgtaga tttgagtgtg 60
attaaaaaaa taattaaatt tattaatccg cagttaaatg aaatattggt tgaaattgga 120
ccgggattag ctgctatcac tcgacctatt tgtgatttga tagatcattt aattgtgatt 180
gaaattgata aaattttatt agatagatta aaacagttct cattttattc aaaattaaca 240
gtatatcatc aagatgcttt agcatttgat tacataaagt tatttaataa aaaaaataaa 300
ttagttcgaa tttttggtaa tttaccatat catgtttcta cgtctttaat attgcattta 360
tttaaaagaa ttaatattat taaagatatg aattttatgc tacaaaaaga agttgctgaa 420
cgtttaattg caactccagg tagtaaatta tatggtcgtt taagtattat ttctcaatat 480
tattgtaata taaaagtttt attgcatgtg tcttcaaaat gttttaaacc agttcctaaa 540
gtagaatcaa tttttcttaa tttgacacct tatactgatt atttccctta ttttacttat 600
aatgtaaacg ttcttagtta tattacaaat ttagcttttc aaaaaagaag aaaaatatta 660
cgtcatagtt taggtaaaat attttctgaa aaagttttta taaaattaaa tattaatccc 720
aaattaagac ctgagaatat ttctatatta caatattgtc agttatctaa ttatatgata 780
gaaaataata ttcatcagga acatgtttgt atttaa 816

<210> SEQ ID NO 12
<211> LENGTH: 1463
<212> TYPE: DNA
<213> ORGANISM: Annandia pinicola

<400> SEQUENCE: 12
agattgaacg ctggcggcat gccttacaca tgcaagtcga acggtaacag gtcttcggac 60
gctgacgagt ggcgaacggg tgagtaatac atcggaacgt gcccagtcgt gggggataac 120
tactcgaaag agtagctaat accgcatacg atctgaggat gaaagcgggg gaccttcggg 180
cctcgcgcga ttggagcggc cgatggcaga ttaggtagtt ggtgggataa aagcttacca 240
agccgacgat ctgtagctgg tctgagagga cgaccagcca cactggaact gagatacggt 300
ccagactctt acgggaggca gcagtgggga atattgcaca atgggcgcaa gcctgatgca 360
gctatgtcgc gtgtatgaag aagaccttag ggttgtaaag tactttcgat agcataagaa 420
gataatgaga ctaataattt tattgtctga cgttagctat agaagaagca ccggctaact 480
ccgtgccagc agccgcggta atacgggggg tgctagcgtt aatcggaatt actgggcgta 540
aagagcatgt aggtggttta ttaagtcaga tgtgaaatcc ctggacttaa tctaggaact 600
gcatttgaaa ctaataggct agagtttcgt agagggaggt agaattctag gtgtagcggt 660
gaaatgcata gatatctaga ggaatatcag tggcgaaggc gaccttctgg acgataactg 720
acgctaaaat gcgaaagcat gggtagcaaa caggattaga taccctggta gtccatgctg 780
taaacgatgt cgactaagag gttggaggta taacttttaa tctctgtagc taacgcgtta 840
agtcgaccgc ctggggagta cggtcgcaag gctaaaactc aaatgaattg acgggggcct 900
gcacaagcgg tggagcatgt ggtttaattc gatgcaacgc gtaaaacctt acctggtctt 960
gacatccaca gaattttaca gaaatgtaga agtgcaattt gaactgtgag acaggtgctg 1020
catggctgtc gtcagctcgt gttgtgaaat gttgggttaa gtcccgcaac gagcgcaacc 1080
cttgtccttt gttaccataa gatttaagga actcaaagga gactgccggt gataaactgg 1140
aggaaggcgg ggacgacgtc aagtcatcat ggcccttatg accagggcta cacacgtgct 1200
acaatggcat atacaaagag atgcaatatt gcgaaataaa gccaatctta taaaatatgt 1260
cctagttcgg actggagtct gcaactcgac tccacgaagt cggaatcgct agtaatcgtg 1320
gatcagcatg ccacggtgaa tatgtttcca ggccttgtac acaccgcccg tcacaccatg 1380
gaagtggatt gcaaaagaag taagaaaatt aaccttctta acaaggaaat aacttaccac 1440
tttgtgactc ataactgggg tga 1463

<210> SEQ ID NO 13
<211> LENGTH: 1554
<212> TYPE: DNA
<213> ORGANISM: Moranella endobia

<400> SEQUENCE: 13
tctttttggt aaggaggtga tccaaccgca ggttccccta cggttacctt gttacgactt 60
caccccagtc atgaatcaca aagtggtaag cgccctccta aaaggttagg ctacctactt 120
cttttgcaac ccacttccat ggtgtgacgg gcggtgtgta caaggcccgg gaacgtattc 180
accgtggcat tctgatccac gattactagc gattcctact tcatggagtc gagttgcaga 240
ctccaatccg gactacgacg cactttatga ggtccgctaa ctctcgcgag cttgcttctc 300
tttgtatgcg ccattgtagc acgtgtgtag ccctactcgt aagggccatg atgacttgac 360
gtcatcccca ccttcctccg gtttatcacc ggcagtctcc tttgagttcc cgaccgaatc 420
gctggcaaaa aaggataagg gttgcgctcg ttgcgggact taacccaaca tttcacaaca 480
cgagctgacg acagccatgc agcacctgtc tcagagttcc cgaaggtacc aaaacatctc 540
tgctaagttc tctggatgtc aagagtaggt aaggttcttc gcgttgcatc gaattaaacc 600
acatgctcca ccgcttgtgc gggcccccgt caattcattt gagttttaac cttgcggccg 660
tactccccag gcggtcgatt taacgcgtta actacgaaag ccacagttca agaccacagc 720
tttcaaatcg acatagttta cggcgtggac taccagggta tctaatcctg tttgctcccc 780
acgctttcgt acctgagcgt cagtattcgt ccagggggcc gccttcgcca ctggtattcc 840
tccagatatc tacacatttc accgctacac ctggaattct accccccctct acgagactct 900 agcctatcag tttcaaatgc agttcctagg ttaagcccag ggatttcaca tctgacttaa 960
taaaccgcct acgtactctt tacgcccagt aattccgatt aacgcttgca ccctccgtat 1020
taccgcggct gctggcacgg agttagccgg tgcttcttct gtaggtaacg tcaatcaata 1080
accgtattaa ggatattgcc ttcctcccta ctgaaagtgc tttacaaccc gaaggccttc 1140
ttcacacacg cggcatggct gcatcagggt ttcccccatt gtgcaatatt ccccactgct 1200
gcctcccgta ggagtctgga ccgtgtctca gttccagtgt ggctggtcat cctctcagac 1260

-continued cagctaggga tcgtcgccta ggtaagctat tacctcacct actagctaat cccatctggg 1320
ttcatctgaa ggtgtgaggc caaaaggtcc cccactttgg tcttacgaca ttatgcggta 1380
ttagctaccg tttccagcag ttatccccct ccatcaggca gatccccaga ctttactcac 1440
ccgttcgctg ctcgccggca aaaaagtaaa cttttttccg ttgccgctca acttgcatgt 1500
gttaggcctg ccgccagcgt tcaatctgag ccatgatcaa actcttcaat taaa 1554

<210> SEQ ID NO 14
<211> LENGTH: 1539
<212> TYPE: DNA
<213> ORGANISM: Ishikawaella capsulata Mpkobe

<400> SEQUENCE: 14
aaattgaaga gtttgatcat ggctcagatt gaacgctagc ggcaagctta acacatgcaa 60
gtcgaacggt aacagaaaaa agcttgcttt tttgctgacg agtggcggac gggtgagtaa 120
tgtctgggga tctacctaat ggcgggggat aactactgga aacggtagct aataccgcat 180
aatgttgtaa aaccaaagtg gggggacctta tggcctcaca ccattagatg aacctagatg 240
ggattagctt gtaggtgggg taaaggctca cctaggcaac gatccctagc tggtctgaga 300
ggatgaccag ccacactgga actgagatac ggtccagact cctacgggag gcagcagtgg 360
ggaatcttgc acaatgggcg caagcctgat gcagctatgt cgcgtgtatg aagaaggcct 420
tagggttgta aagtactttc atcggggaag aaggatatga gcctaatatt ctcatatatt 480
gacgttacct gcagaagaag caccggctaa ctccgtgcca gcagccgcgg taacacggag 540
ggtgcgagcg ttaatcggaa ttactgggcg taaagagcac gtaggtggtt tattaagtca 600
tatgtgaaat ccctgggctt aacctaggaa ctgcatgtga aactgataaa ctagagtttc 660
gtagagggag gtggaattcc aggtgtagcg gtgaaatgcg tagatatctg gaggaatatc 720
agaggcgaag gcgaccttct ggacgaaaac tgacactcag gtgcgaaagc gtggggagca 780
aacaggatta gataccctgg tagtccacgc tgtaaacaat gtcgactaaa aaactgtgag 840
cttgacttgt ggtttttgta gctaacgcat taagtcgacc gcctggggag tacggccgca 900
aggttaaaac tcaaatgaat tgacgggggt ccgcacaagc ggtggagcat gtggtttaat 960
tcgatgcaac gcgaaaaacc ttacctggtc ttgacatcca gcgaattata tagaaatata 1020
taagtgcctt tcggggaact ctgagacgct gcatggctgt cgtcagctcg tgttgtgaaa 1080
tgttgggtta agtcccgcaa cgagcgccct tatcctctgt tgccagcggc atggccggga 1140
actcagagga gactgccagt attaaactgg aggaaggtgg ggatgacgtc aagtcatcat 1200
ggcccttatg accagggcta cacacgtgct acaatggtgt atacaaagag aagcaatctc 1260
gcaagagtaa gcaaaactca aaaagtacat cgtagttcgg attagagtct gcaactcgac 1320
tctatgaagt aggaatcgct agtaatcgtg gatcagaatg ccacggtgaa tacgttctct 1380
ggccttgtac acaccgcccg tcacaccatg ggagtaagtt gcaaaagaag taggtagctt 1440
aacctttata ggagggcgct taccactttg tgatttatga ctggggtgaa gtcgtaacaa 1500
ggtaactgta ggggaacctg tggttggatt acctcctta 1539

<210> SEQ ID NO 15
<211> LENGTH: 1561
<212> TYPE: DNA
<213> ORGANISM: Baumannia cicadellinicola

<400> SEQUENCE: 15
ttcaattgaa gagtttgatc atggctcaga ttgaacgctg gcggtaagct taacacatgc 60
aagtcgagcg gcatcggaaa gtaaattaat tactttgccg gcaagcggcg aacgggtgag 120
taatatctgg ggatctacct tatggagagg gataactatt ggaaacgata gctaacaccg 180
cataatgtcg tcagaccaaa atgggggacc taatttaggc ctcatgccat aagatgaacc 240
cagatgagat tagctagtag gtgagataat agctcaccta ggcaacgatc tctagttggt 300
ctgagaggat gaccagccac actggaactg agacacggtc cagactccta cgggaggcag 360
cagtggggaa tcttgcacaa tgggggaaac cctgatgcag ctataccgcg tgtgtgaaga 420
aggccttcgg gttgtaaagc actttcagcg gggaagaaaa tgaagttact aataataatt 480
gtcaattgac gttacccgca aaagaagcac cggctaactc cgtgccagca gccgcggtaa 540
gacggagggt gcaagcgtta atcggaatta ctgggcgtaa agcgtatgta ggcggtttat 600
ttagtcaggt gtgaaagccc taggcttaac ctaggaattg catttgaaac tggtaagcta 660
gagtctcgta gaggggggga gaattccagg tgtagcggtg aaatgcgtag agatctggaa 720
gaataccagt ggcgaaggcg gcccccctgga cgaaaactga cgctcaagta cgaaagcgtg 780
gggagcaaac aggattagat accctggtag tccacgctgt aaacgatgtc gatttgaagg 840
ttgtagcctt gagctatagc tttcgaagct aacgcattaa atcgaccgcc tggggagtac 900
gaccgcaagg ttaaaactca aatgaattga cgggggcccg cacaagcggt ggagcatgtg 960
gtttaattcg atacaacgcg aaaaacctta cctactcttg acatccagag tataaagcag 1020
aaaagcttta gtgccttcgg gaactctgag acaggtgctg catggctgtc gtcagctcgt 1080
gttgtgaaat gttgggttaa gtcccgcaac gagcgcaacc cttatccttt gttgccaacg 1140
attaagtcgg gaactcaaag gagactgccg gtgataaacc ggaggaaggt gaggataacg 1200
tcaagtcatc atggccctta cgagtagggc tacacacgtg ctacaatggt gcatacaaag 1260
agaagcaatc tcgtaagagt tagcaaacct cataaagtgc atcgtagtcc ggattagagt 1320
ctgcaactcg actctatgaa gtcggaatcg ctagtaatcg tggatcagaa tgccacggtg 1380
aatacgttcc cgggccttgt acacaccgcc cgtcacacca tgggagtgta ttgcaaaaga 1440
agttagtagc ttaactcata atacgagagg gcgcttacca ctttgtgatt cataactggg 1500
gtgaagtcgt aacaaggtaa ccgtagggga acctgcggtt ggatcacctc cttacactaa 1560
a 1561

<210> SEQ ID NO 16
<211> LENGTH: 1464
<212> TYPE: DNA
<213> ORGANISM: Sodalis like

<400> SEQUENCE: 16
attgaacgct ggcggcaggc ctaacacatg caagtcgagc ggcagcggga agaagcttgc 60
ttctttgccg gcgagcggcg gacgggtgag taatgtctgg ggatctgccc gatggagggg 120
gataactact ggaaacggta gctaataccg cataacgtcg caagaccaaa gtgggggacc 180
ttcgggcctc acaccatcgg atgaacccag gtgggattag ctagtaggtg gggtaatggc 240
tcacctaggc gacgatccct agctggtctg agaggatgac cagtcacact ggaactgaga 300
cacggtccag actcctacgg gaggcagcag tggggaatat tgcacaatgg gggaaaccct 360
gatgcagcca tgccgcgtgt gtgaagaagg ccttcgggtt gtaaagcact ttcagcgggg 420
aggaaggcga tggcgttaat agcgctatcg attgacgtta cccgcagaag aagcaccggc 480
taactccgtg ccagcagccg cggtaatacg gagggtgcga gcgttaatcg gaattactgg 540
gcgtaaagcg tacgcaggcg gtctgttaag tcagatgtga aatccccggg ctcaacctgg 600
gaactgcatt tgaaactggc aggctagagt ctcgtagagg ggggtagaat tccaggtgta 660
gcggtgaaat gcgtagagat ctggaggaat accggtggcg aaggcggccc cctggacgaa 720
gactgacgct caggtacgaa agcgtgggga gcaaacagga ttagataccc tggtagtcca 780
cgctgtaaac gatgtcgatt tgaaggttgt ggccttgagc cgtggctttc ggagctaacg 840
tgttaaatcg accgcctggg gagtacggcc gcaaggttaa aactcaaatg aattgacggg 900
ggcccgcaca agcggtggag catgtggttt aattcgatgc aacgcgaaga accttaccta 960
ctcttgacat ccagagaact tggcagagat gctttggtgc cttcgggaac tctgagacag 1020
gtgctgcatg gctgtcgtca gctcgtgttg tgaaatgttg ggttaagtcc cgcaacgagc 1080
gcaaccctta tcctttattg ccagcgattc ggtcgggaac tcaaaggaga ctgccggtga 1140
taaaccggag gaaggtgggg atgacgtcaa gtcatcatgg cccttacgag tagggctaca 1200
cacgtgctac aatggcgcat acaaagagaa gcgatctcgc gagagtcagc ggacctcata 1260
aagtgcgtcg tagtccggat tggagtctgc aactcgactc catgaagtcg gaatcgctag 1320
taatcgtgga tcagaatgcc acggtgaata cgttcccggg ccttgtacac accgcccgtc 1380
acaccatggg agtgggttgc aaaagaagta ggtagcttaa ccttcgggag ggcgcttacc 1440
actttgtgat tcatgactgg ggtg 1464

<210> SEQ ID NO 17
<211> LENGTH: 1465
<212> TYPE: DNA
<213> ORGANISM: Hartigia pinicola

<400> SEQUENCE: 17
agatttaacg ctggcggcag gcctaacaca tgcaagtcga gcggtaccag aagaagcttg 60
cttcttgctg acgagcggcg gacgggtgag taatgtatgg ggatctgccc gacagagggg 120
gataactatt ggaaacggta gctaataccg cataatctct gaggagcaaa gcaggggaac 180
ttcggtcctt gcgctatcgg atgaacccat atgggattag ctagtaggtg aggtaatggc 240
tcccctaggc aacgatccct agctggtctg agaggatgat cagccacact gggactgaga 300
cacggcccag actcctacgg gaggcagcag tggggaatat tgcacaatgg gcgaaagcct 360
gatgcagcca tgccgcgtgt atgaagaagg ctttagggtt gtaaagtact ttcagtcgag 420
aggaaaacat tgatgctaat atcatcaatt attgacgttt ccgacagaag aagcaccggc 480
taactccgtg ccagcagccg cggtaatacg gagggtgcaa gcgttaatcg gaattactgg 540
gcgtaaagcg cacgcaggcg gttaattaag ttagatgtga aagccccggg cttaacccag 600
gaatagcata taaaactggt caactagagt attgtagagg ggggtagaat tccatgtgta 660
gcggtgaaat gcgtagagat gtggaggaat accagtggcg aaggcggccc cctggacaaa 720
aactgacgct caaatgcgaa agcgtgggga gcaaacagga ttagataccc tggtagtcca 780
tgctgtaaac gatgtcgatt tggaggttgt tcccttgagg agtagcttcc gtagctaacg 840
cgttaaatcg accgcctggg ggagtacgac tgcaaggtta aaactcaaat gaattgacgg 900
gggcccgcac aagcggtgga gcatgtggtt taattcgatg caacgcgaaa aaccttacct 960
actcttgaca tccagataat ttagcagaaa tgctttagta ccttcgggaa atctgagaca 1020
ggtgctgcat ggctgtcgtc agctcgtgtt gtgaaatgtt gggttaagtc ccgcaacgag 1080
cgcaaccctt atcctttgtt gccagcgatt aggtcgggaa ctcaaaggag actgccggtg 1140
ataaaccgga ggaaggtggg gatgacgtca agtcatcatg gcccttacga gtagggctac 1200

```
acacgtgcta caatggcata tacaaaggga agcaacctcg cgagagcaag cgaaactcat   1260

aaattatgtc gtagttcaga ttggagtctg caactcgact ccatgaagtc ggaatcgcta   1320

gtaatcgtag atcagaatgc tacggtgaat acgttcccgg gccttgtaca caccgcccgt   1380

cacaccatgg gagtgggttg caaaagaagt aggtaactta accttatgga aagcgcttac   1440

cactttgtga ttcataactg gggtg                                         1465
```

```
<210> SEQ ID NO 18
<211> LENGTH: 1571
<212> TYPE: DNA
<213> ORGANISM: Tremblaya phenacola

<400> SEQUENCE: 18

aggtaatcca gccacacctt ccagtacggc taccttgtta cgacttcacc ccagtcacaa     60

cccttacctt cggaactgcc ctcctcacaa ctcaaaccac caaacacttt taaatcaggt    120

tgagagaggt taggcctgtt acttctggca agaattattt ccatggtgtg acgggcggtg    180

tgtacaagac ccgagaacat attcaccgtg gcatgctgat ccacgattac tagcaattcc    240

aacttcatgc actcgagttt cagagtacaa tccgaactga ggccggcttt gtgagattag    300

ctcccttttg caagttggca actctttggt ccggccattg tatgatgtgt gaagccccac    360

ccataaaggc catgaggact tgacgtcatc cccaccttcc tccaacttat cgctggcagt    420

ctctttaagg taactgacta atccagtagc aattaaagac aggggttgcg ctcgttacag    480

gacttaaccc aacatctcac gacacgagct gacgacagcc atgcagcacc tgtgcactaa    540

ttctctttca agcactcccg cttctcaaca ggatcttagc catatcaaag gtaggtaagg    600

tttttcgcgt tgcatcgaat taatccacat catccactgc ttgtgcgggt ccccgtcaat    660

tcctttgagt tttaaccttg cggccgtact ccccaggcgg tcgacttgtg cgttagctgc    720

accactgaaa aggaaaactg cccaatggtt agtcaacatc gtttagggca tggactacca    780

gggtatctaa tcctgtttgc tccccatgct ttagtgtctg agcgtcagta acgaaccagg    840

aggctgccta cgctttcggt attcctccac atctctacac atttcactgc tacatgcgga    900

attctacctc cccctctcgt actccagcct gccagtaact gccgcattct gaggttaagc    960

ctcagccttt cacagcaatc ttaacaggca gcctgcacac cctttacgcc caataaatct   1020

gattaacgct cgcaccctac gtattaccgc ggctgctggc acgtagtttg ccggtgctta   1080

ttctttcggt acagtcacac caccaaattg ttagttgggt ggctttcttt ccgaacaaaa   1140

gtgctttaca acccaaaggc cttcttcaca cacgcggcat tgctggatca ggcttccgcc   1200

cattgtccaa gattcctcac tgctgccttc ctcagaagtc tgggccgtgt ctcagtccca   1260

gtgtggctgg ccgtcctctc agaccagcta ccgatcattg ccttgggaag ccattacctt   1320

tccaacaagc taatcagaca tcagccaatc tcagagcgca aggcaattgg tcccctgctt   1380

tcattctgct tggtagagaa ctttatgcgg tattaattag gctttcacct agctgtcccc   1440

cactctgagg catgttctga tgcattactc acccgtttgc cacttgccac caagcctaag   1500

cccgtgttgc cgttcgactt gcatgtgtaa ggcatgccgc tagcgttcaa tctgagccag   1560

gatcaaactc t                                                        1571
```

```
<210> SEQ ID NO 19
<211> LENGTH: 1535
<212> TYPE: DNA
<213> ORGANISM: Tremblaya princeps
```

<400> SEQUENCE: 19
agagtttgat cctggctcag attgaacgct agcggcatgc attacacatg caagtcgtac 60
ggcagcacgg gcttaggcct ggtggcgagt ggcgaacggg tgagtaacgc ctcggaacgt 120
gccttgtagt gggggatagc ctggcgaaag ccagattaat accgcatgaa gccgcacagc 180
atgcgcggtg aaagtggggg attctagcct cacgctactg gatcggccgg ggtctgatta 240
gctagttggc ggggtaatgg cccaccaagg cttagatcag tagctggtct gagaggacga 300
tcagccacac tgggactgag acacggccca gactcctacg ggaggcagca gtggggaatc 360
ttggacaatg ggcgcaagcc tgatccagca atgccgcgtg tgtgaagaag gccttcgggt 420
cgtaaagcac ttttgttcgg gatgaagggg ggcgtgcaaa caccatgccc tcttgacgat 480
accgaaagaa taagcaccgg ctaactacgt gccagcagcc gcggtaatac gtagggtgcg 540
agcgttaatc ggaatcactg ggcgtaaagg gtgcgcgggt ggtttgccaa gacccctgta 600
aaatcctacg gcccaaccgt agtgctgcgg aggttactgg taagcttgag tatggcagag 660
gggggtagaa ttccaggtgt agcggtgaaa tgcgtagata tctggaggaa taccgaaggc 720
gaaggcaacc ccctgggcca tcactgacac tgaggcacga aagcgtgggg agcaaacagg 780
attagatacc ctggtagtcc acgccctaaa ccatgtcgac tagttgtcgg ggggagccct 840
ttttcctcgg tgacgaagct aacgcatgaa gtcgaccgcc tggggagtac gaccgcaagg 900
ttaaaactca aaggaattga cggggacccg cacaagcggt ggatgatgtg gattaattcg 960
atgcaacgcg aaaaacctta cctacccttg acatggcgga gattctgccg agaggcggaa 1020
gtgctcgaaa gagaatccgt gcacaggtgc tgcatggctg tcgtcagctc gtgtcgtgag 1080
atgttgggtt aagtcccata acgagcgcaa cccccgtctt tagttgctac cactggggca 1140
ctctatagag actgccggtg ataaaccgga ggaaggtggg gacgacgtca agtcatcatg 1200
gcctttatgg gtagggcttc acacgtcata caatggctgg agcaaagggt cgccaactcg 1260
agagagggag ctaatcccac aaacccagcc ccagttcgga ttgcactctg caactcgagt 1320
gcatgaagtc ggaatcgcta gtaatcgtgg atcagcatgc cacggtgaat acgttctcgg 1380
gtcttgtaca caccgcccgt cacaccatgg gagtaagccg catcagaagc agcctcccta 1440
accctatgct gggaaggagg ctgcgaaggt ggggtctatg actggggtga agtcgtaaca 1500
aggtagccgt accggaaggt gcggctggat tacct 1535

<210> SEQ ID NO 20
<211> LENGTH: 1450
<212> TYPE: DNA
<213> ORGANISM: Nasuia deltocephalinicola

<400> SEQUENCE: 20
agtttaatcc tggctcagat ttaacgcttg cgacatgcct aacacatgca agttgaacgt 60
tgaaaatatt tcaaagtagc gtataggtga gtataacatt taaacatacc ttaaagttcg 120
gaataccccg atgaaaatcg gtataatacc gtataaaagt atttaagaat taaagcgggg 180
aaaacctcgt gctataagat tgttaaatgc ctgattagtt tgttggtttt taaggtaaaa 240
gcttaccaag actttgatca gtagctattc tgtgaggatg tatagccaca ttgggattga 300
aataatgccc aaacctctac ggagggcagc agtggggaat attggacaat gagcgaaagc 360
ttgatccagc aatgtcgcgt gtgcgattaa gggaaactgt aaagcacttt tttttaagaa 420
taagaaattt taattaataa ttaaaatttt tgaatgtatt aaaagaataa gtaccgacta 480
atcacgtgcc agcagtcgcg gtaatacgtg ggtgcgagcg ttaatcgga tttattgggc 540

```
gtaaagtgta ttcaggctgc ttaaaaagat ttatattaaa tatttaaatt aaatttaaaa    600

aatgtataaa ttactattaa gctagagttt agtataagaa aaaagaattt tatgtgtagc    660

agtgaaatgc gttgatatat aaaggaacgc cgaaagcgaa agcatttttc tgtaatagaa    720

ctgacgctta tatacgaaag cgtgggtagc aaacaggatt agataccctg gtagtccacg    780

ccctaaacta tgtcaattaa ctattagaat ttttttagt ggtgtagcta acgcgttaaa    840

ttgaccgcct gggtattacg atcgcaagat taaaactcaa aggaattgac ggggaccagc    900

acaagcggtg gatgatgtgg attaattcga tgatacgcga aaaaccttac ctgcccttga    960

catggttaga attttattga aaaataaaag tgcttggaaa agagctaaca cacaggtgct   1020

gcatggctgt cgtcagctcg tgtcgtgaga tgttgggtta agtcccgcaa cgagcgcaac   1080

ccctactctt agttgctaat taaagaactt taagagaaca gctaacaata agtttagagg   1140

aaggagggga tgacttcaag tcctcatggc ccttatgggc agggcttcac acgtcataca   1200

atggttaata caaaaagttg caatatcgta agattgagct aatctttaaa attaatctta   1260

gttcggattg tactctgcaa ctcgagtaca tgaagttgga atcgctagta atcgcggatc   1320

agcatgccgc ggtgaatagt ttaactggtc ttgtacacac cgcccgtcac accatggaaa   1380

taaatcttgt tttaaatgaa gtaatatatt ttatcaaaac aggttttgta accggggtga   1440

agtcgtaaca                                                          1450
```

<210> SEQ ID NO 21
<211> LENGTH: 1536
<212> TYPE: DNA
<213> ORGANISM: Zinderia insecticola CARI

<400> SEQUENCE: 21

```
atataaataa gagtttgatc ctggctcaga ttgaacgcta gcggtatgct ttacacatgc     60

aagtcgaacg acaatattaa agcttgcttt aatataaagt ggcgaacggg tgagtaatat    120

atcaaaacgt accttaaagt gggggataac taattgaaaa attagataat accgcatatt    180

aatcttagga tgaaaatagg aataatatct tatgctttta gatcggttga tatctgatta    240

gctagttggt agggtaaatg cttaccaagg caatgatcag tagctggttt tagcgaatga    300

tcagccacac tggaactgag acacggtcca gacttctacg gaaggcagca gtggggaata    360

ttggacaatg ggagaaatcc tgatccagca ataccgcgtg agtgatgaag gccttagggt    420

cgtaaaactc ttttgttagg aaagaaataa ttttaaataa tatttaaaat tgatgacggt    480

acctaaagaa taagcaccgg ctaactacgt gccagcagcc gcggtaatac gtagggtgca    540

agcgttaatc ggaattattg ggcgtaaaga gtgcgtaggc tgttatataa gatagatgtg    600

aaatacttaa gcttaactta agaactgcat ttattactgt ttaactagag tttattagag    660

agaagtggaa ttttatgtgt agcagtgaaa tgcgtagata tataaaggaa tatcgatggc    720

gaaggcagct tcttggaata atactgacgc tgaggcacga aagcgtgggg agcaaacagg    780

attagatacc ctggtagtcc acgccctaaa ctatgtctac tagttattaa attaaaaata    840

aaatttagta acgtagctaa cgcattaagt agaccgcctg ggagtacga tcgcaagatt    900

aaaactcaaa ggaattgacg gggacccgca caagcggtgg atgatgtgga ttaattcgat    960

gcaacacgaa aaaccttacc tactcttgac atgtttggaa ttttaaagaa atttaaaagt   1020

gcttgaaaaa gaaccaaaac acaggtgctg catggctgtc gtcagctcgt gtcgtgagat   1080

gttgggttaa gtcccgcaac gagcgcaacc cttgttatta tttgctaata aaaagaactt   1140
```

```
taataagact gccaatgaca aattggagga aggtggggat gacgtcaagt cctcatggcc   1200

cttatgagta gggcttcaca cgtcatacaa tgatatatac aatgggtagc aaatttgtga   1260

aaatgagcca atccttaaag tatatcttag ttcggattgt agtctgcaac tcgactacat   1320

gaagttggaa tcgctagtaa tcgcggatca gcatgccgcg gtgaatacgt tctcgggtct   1380

tgtacacacc gcccgtcaca ccatggaagt gatttttacc agaaattatt tgtttaacct   1440

ttattggaaa aaaataatta aggtagaatt catgactggg gtgaagtcgt aacaaggtag   1500

cagtatcgga aggtgcggct ggattacatt ttaaat                             1536
```

<210> SEQ ID NO 22
<211> LENGTH: 1423
<212> TYPE: DNA
<213> ORGANISM: Hodgkinia

<400> SEQUENCE: 22

```
aatgctggcg gcaggcctaa cacatgcaag tcgagcggac aacgttcaaa cgttgttagc     60

ggcgaacggg tgagtaatac gtgagaatct acccatccca acgtgataac atagtcaaca    120

ccatgtcaat aacgtatgat tcctgcaaca ggtaaagatt ttatcgggga tggatgagct    180

cacgctagat tagctagttg gtgagataaa agcccaccaa ggccaagatc tatagctggt    240

ctggaaggat ggacagccac attgggactg agacaaggcc caaccctcta aggagggcag    300

cagtgaggaa tattggacaa tgggcgtaag cctgatccag ccatgccgca tgagtgattg    360

aaggtccaac ggactgtaaa actcttttct ccagagatca taaatgatag tatctggtga    420

tataagctcc ggccaacttc gtgccagcag ccgcggtaat acgaggggag cgagtattgt    480

tcggttttat tgggcgtaaa gggtgtccag gttgctaagt aagttaacaa caaaatcttg    540

agattcaacc tcataacgtt cggttaatac tactaagctc gagcttggat agagacaaac    600

ggaattccga gtgtagaggt gaaattcgtt gatacttgga ggaacaccag aggcgaaggc    660

ggtttgtcat accaagctga cactgaagac acgaaagcat ggggagcaaa caggattaga    720

taccctggta gtccatgccc taaacgttga gtgctaacag ttcgatcaag ccacatgcta    780

tgatccagga ttgtacagct aacgcgttaa gcactccgcc tgggtattac gaccgcaagg    840

ttaaaactca aaggaattga cggagacccg cacaagcggt ggagcatgtg gtttaattcg    900

aagctacacg aagaacctta ccagcccttg acataccatg gccaaccatc ctggaaacag    960

gatgttgttc aagttaaacc cttgaaatgc caggaacagg tgctgcatgg ctgttgtcag   1020

ttcgtgtcgt gagatgtatg gttaagtccc aaaacgaaca caaccctcac ccatagttgc   1080

cataaacaca attgggttct ctatgggtac tgctaacgta agttagagga aggtgaggac   1140

cacaacaagt catcatggcc cttatgggct gggccacaca catgctacaa tggtggttac   1200

aaagagccgc aacgttgtga gaccgagcaa atctccaaag accatctcag tccggattgt   1260

actctgcaac ccgagtacat gaagtaggaa tcgctagtaa tcgtggatca gcatgccacg   1320

gtgaatacgt tctcgggtct tgtacacgcc gcccgtcaca ccatgggagc ttcgctccga   1380

tcgaagtcaa gttacccttg accacatctt ggcaagtgac cga                     1423
```

<210> SEQ ID NO 23
<211> LENGTH: 1504
<212> TYPE: DNA
<213> ORGANISM: Wolbachia sp. wPip

<400> SEQUENCE: 23

```
aaatttgaga gtttgatcct ggctcagaat gaacgctggc ggcaggccta acacatgcaa     60
```

```
gtcgaacgga gttatattgt agcttgctat ggtataactt agtggcagac gggtgagtaa    120

tgtataggaa tctacctagt agtacggaat aattgttgga aacgacaact aataccgtat    180

acgccctacg ggggaaaaat ttattgctat tagatgagcc tatattagat tagctagttg    240

gtggggtaat agcctaccaa ggtaatgatc tatagctgat ctgagaggat gatcagccac    300

actggaactg agatacggtc cagactccta cgggaggcag cagtggggaa tattggacaa    360

tgggcgaaag cctgatccag ccatgccgca tgagtgaaga aggcctttgg gttgtaaagc    420

tcttttagtg aggaagataa tgacggtact cacagaagaa gtcctggcta actccgtgcc    480

agcagccgcg gtaatacgga gagggctagc gttattcgga attattgggc gtaaagggcg    540

cgtaggctgg ttaataagtt aaaagtgaaa tcccgaggct taaccttgga attgctttta    600

aaactattaa tctagagatt gaaagaggat agaggaattc ctgatgtaga ggtaaaattc    660

gtaaatatta ggaggaacac cagtggcgaa ggcgtctatc tggttcaaat ctgacgctga    720

agcgcgaagg cgtggggagc aaacaggatt agataccctg gtagtccacg ctgtaaacga    780

tgaatgttaa atatggggag tttactttct gtattacagc taacgcgtta aacattccgc    840

ctggggacta cggtcgcaag attaaaactc aaaggaattg acggggaccc gcacaagcgg    900

tggagcatgt ggtttaattc gatgcaacgc gaaaaacctt accacttctt gacatgaaaa    960

tcatacctat tcgaagggat agggtcggtt cggccggatt ttacacaagt gttgcatggc   1020

tgtcgtcagc tcgtgtcgtg agatgttggg ttaagtcccg caacgagcgc aaccctcatc   1080

cttagttgcc atcaggtaat gctgagtact ttaaggaaac tgccagtgat aagctggagg   1140

aaggtgggga tgatgtcaag tcatcatggc ctttatggag tgggctacac acgtgctaca   1200

atggtgtcta caatgggctg caaggtgcgc aagcctaagc taatccctaa aagacatctc   1260

agttcggatt gtactctgca actcgagtac atgaagttgg aatcgctagt aatcgtggat   1320

cagcatgcca cggtgaatac gttctcgggt cttgtacaca ctgcccgtca cgccatggga   1380

attggtttca ctcgaagcta atggcctaac cgcaaggaag gagttattta aagtgggatc   1440

agtgactggg gtgaagtcgt aacaaggtag cagtagggga atctgcagct ggattacctc   1500

ctta                                                                1504
```

<210> SEQ ID NO 24
<211> LENGTH: 1532
<212> TYPE: DNA
<213> ORGANISM: Uzinura diaspidicola

<400> SEQUENCE: 24

```
aaaggagata ttccaaccac accttccggt acggttacct tgttacgact tagccctagt     60

catcaagttt accttaggca gaccactgaa ggattactga cttcaggtac ccccgactcc    120

catggcttga cgggcggtgt gtacaaggtt cgagaacata ttcaccgcgc cattgctgat    180

gcgcgattac tagcgattcc tgcttcatag agtcgaattg cagactccaa tccgaactga    240

gactggtttt agagattagc tcctgatcac ccagtggctg ccctttgtaa ccagccattg    300

tagcacgtgt gtagcccaag gcatagaggc catgatgatt tgacatcatc cccaccttcc    360

tcacagttta caccggcagt tttgttagag tccccggctt tacccgatgg caactaacaa    420

taggggttgc gctcgttata ggacttaacc aaacacttca cagcacgaac tgaagacaac    480

catgcagcac cttgtaatac gtcgtataga ctaagctgtt tccagcttat tcgtaataca    540

tttaagcctt ggtaaggttc ctcgcgtatc atcgaattaa accacatgct ccaccgcttg    600
```

```
tgcgaacccc cgtcaattcc tttgagtttc aatcttgcga ctgtacttcc caggtggatc    660

acttatcgct ttcgctaagc cactgaatat cgtttttcca atagctagtg atcatcgttt    720

agggcgtgga ctaccagggt atctaatcct gtttgctccc cacgctttcg tgcactgagc    780

gtcagtaaag atttagcaac ctgccttcgc tatcggtgtt ctgtatgata tctatgcatt    840

tcaccgctac accatacatt ccagatgctc caatcttact caagtttacc agtatcaata    900

gcaattttac agttaagctg taagctttca ctactgactt aataaacagc ctacacaccc    960

tttaaaccca ataaatccga ataacgcttg tgtcatccgt attgccgcgg ctgctggcac   1020

ggaattagcc gacacttatt cgtatagtac cttcaatctc ctatcacgta agatatttta   1080

tttctataca aaagcagttt acaacctaaa agaccttcat cctgcacgcg acgtagctgg   1140

ttcagagttt cctccattga ccaatattcc tcactgctgc ctcccgtagg agtctggtcc   1200

gtgtctcagt accagtgtgg aggtacaccc tcttaggccc cctactgatc atagtcttgg   1260

tagagccatt acctcaccaa ctaactaatc aaacgcaggc tcatcttttg ccacctaagt   1320

tttaataaag gctccatgca gaaactttat attatggggg attaatcaga atttcttctg   1380

gctatacccc agcaaaaggt agattgcata cgtgttactc acccattcgc cggtcgccga   1440

caaattaaaa atttttcgat gcccctcgac ttgcatgtgt taagctcgcc gctagcgtta   1500

attctgagcc aggatcaaac tcttcgttgt ag                                 1532
```

<210> SEQ ID NO 25
<211> LENGTH: 1470
<212> TYPE: DNA
<213> ORGANISM: Carsonella ruddii

<400> SEQUENCE: 25

```
ctcaggataa acgctagcgg agggcttaac acatgcaagt cgaggggcag caaaaataat     60

tatttttggc gaccggcaaa cgggtgagta atacatacgt aactttcctt atgctgagga    120

atagcctgag gaaacttgga ttaatacctc ataatacaat tttttagaaa gaaaaattgt    180

taaagtttta ttatggcata agataggcgt atgtccaatt agttagttgg taaggtaatg    240

gcttaccaag acgatgattg gtagggggcc tgagaggggc gttcccccac attggtactg    300

agacacggac caaacttcta cggaaggctg cagtgaggaa tattggtcaa tggaggaaac    360

tctgaaccag ccactccgcg tgcaggatga aagaaagcct tattggttgt aaactgcttt    420

tgtatatgaa taaaaaattc taattataga aataattgaa ggtaatatac gaataagtat    480

cgactaactc tgtgccagca gtcgcggtaa gacagaggat acaagcgtta tccggattta    540

ttgggtttaa agggtgcgta ggcggttttt aaagtcagta gtgaaatctt aaagcttaac    600

tttaaaagtg ctattgatac tgaaaaacta gagtaaggtt ggagtaactg gaatgtgtgg    660

tgtagcggtg aaatgcatag atatcacaca gaacaccgat agcgaaagca agttactaac    720

cctatactga cgctgagtca cgaaagcatg gggagcaaac aggattagat accctggtag    780

tccatgccgt aaacgatgat cactaactat tgggttttat acgttgtaat tcagtggtga    840

agcgaaagtg ttaagtgatc cacctgagga gtacgaccgc aaggttgaaa ctcaaaggaa    900

ttgacggggg cccgcacaat cggtggagca tgtggtttaa ttcgatgata cacgaggaac    960

cttaccaaga cttaaatgta ctacgaataa attggaaaca atttagtcaa gcgacggagt   1020

acaaggtgct gcatggttgt cgtcagctcg tgccgtgagg tgtaaggtta agtcctttaa   1080

acgagcgcaa cccttattat tagttgccat cgagtaatgt caggggactc taataagact   1140

gccggcgcaa gccgagagga aggtggggat gacgtcaaat catcacggcc cttacgtctt   1200
```

```
gggccacaca cgtgctacaa tgatcggtac aaaagggagc gactgggtga ccaggagcaa   1260

atccagaaag ccgatctaag ttcggattgg agtctgaaac tcgactccat gaagctggaa   1320

tcgctagtaa tcgtgcatca gccatggcac ggtgaatatg ttcccgggcc ttgtacacac   1380

cgcccgtcaa gccatggaag ttggaagtac ctaaagttgg ttcgctacct aaggtaagtc   1440

taataactgg ggctaagtcg taacaaggta                                    1470


<210> SEQ ID NO 26
<211> LENGTH: 1761
<212> TYPE: DNA
<213> ORGANISM: Symbiotaphrina buchneri voucher JCM9740
<220> FEATURE:
<221> NAME/KEY: misc_feature
<222> LOCATION: (30)..(30)
<223> OTHER INFORMATION: n is a, g, c, or t
<220> FEATURE:
<221> NAME/KEY: misc_feature
<222> LOCATION: (40)..(40)
<223> OTHER INFORMATION: n is a, g, c, or t

<400> SEQUENCE: 26

agattaagcc atgcaagtct aagtataagn aatctatacn gtgaaactgc gaatggctca     60

ttaaatcagt tatcgtttat ttgatagtac cttactacat ggataaccgt ggtaattcta    120

gagctaatac atgctaaaaa ccccgacttc ggaaggggtg tatttattag ataaaaaacc    180

aatgcccttc ggggctcctt ggtgattcat gataacttaa cgaatcgcat ggccttgcgc    240

cggcgatggt tcattcaaat ttctgcccta tcaactttcg atggtaggat agtggcctac    300

catggtttta acgggtaacg gggaattagg gttcgattcc ggagagggag cctgagaaac    360

ggctaccaca tccaaggaag gcagcaggcg cgcaaattac ccaatcccga cacggggagg    420

tagtgacaat aaatactgat acagggctct tttgggtctt gtaattggaa tgagtacaat    480

ttaaatccct taacgaggaa caattggagg gcaagtctgg tgccagcagc cgcggtaatt    540

ccagctccaa tagcgtatat taaagttgtt gcagttaaaa agctcgtagt tgaaccttgg    600

gcctggctgg ccggtccgcc taaccgcgtg tactggtccg gccgggcctt tccttctggg    660

gagccgcatg cccttcactg ggtgtgtcgg ggaaccagga cttttacttt gaaaaaatta    720

gagtgttcaa agcaggccta tgctcgaata cattagcatg gaataataga ataggacgtg    780

cggttctatt ttgttggttt ctaggaccgc cgtaatgatt aatagggata gtcgggggca    840

tcagtattca attgtcagag gtgaaattct tggatttatt gaagactaac tactgcgaaa    900

gcatttgcca aggatgtttt cattaatcag tgaacgaaag ttaggggatc gaagacgatc    960

agataccgtc gtagtcttaa ccataaacta tgccgactag ggatcgggcg atgttattat   1020

tttgactcgc tcggcacctt acgagaaatc aaagtctttg ggttctgggg ggagtatggt   1080

cgcaaggctg aaacttaaag aaattgacgg aagggcacca ccaggagtgg agcctgcggc   1140

ttaatttgac tcaacacggg gaaactcacc aggtccagac acattaagga ttgacagatt   1200

gagagctctt tcttgattat gtgggtggtg gtgcatggcc gttcttagtt ggtggagtga   1260

tttgtctgct taattgcgat aacgaacgag accttaacct gctaaatagc ccggtccgct   1320

ttggcgggcc gctggcttct tagagggact atcggctcaa gccgatggaa gtttgaggca   1380

ataacaggtc tgtgatgccc ttagatgttc tgggccgcac gcgcgctaca ctgacagagc   1440

caacgagtaa atcaccttgg ccggaaggtc tgggtaatct tgttaaactc tgtcgtgctg   1500

gggatagagc attgcaatta ttgctcttca acgaggaatt cctagtaagc gcaagtcatc   1560
```

agcttgcgct gattacgtcc ctgccctttg tacacaccgc ccgtcgctac taccgattga 1620
atggctcagt gaggccttcg gactggcaca gggacgttgg caacgacgac ccagtgccgg 1680
aaagttggtc aaacttggtc atttagagga agtaaaagtc gtaacaaggt ttccgtaggt 1740
gaacctgcgg aaggatcatt a 1761

<210> SEQ ID NO 27
<211> LENGTH: 1801
<212> TYPE: DNA
<213> ORGANISM: Symbiotaphrina kochii voucher CBS 589.63
<220> FEATURE:
<221> NAME/KEY: misc_feature
<222> LOCATION: (1753)..(1755)
<223> OTHER INFORMATION: n is a, g, c, or t

<400> SEQUENCE: 27
tacctggttg attctgccag tagtcatatg cttgtctcaa agattaagcc atgcaagtct 60
aagtataagc aatctatacg gtgaaactgc gaatggctca ttaaatcagt tatcgtttat 120
ttgatagtac cttactacat ggataaccgt ggtaattcta gagctaatac atgctaaaaa 180
cctcgacttc ggaaggggtg tatttattag ataaaaaacc aatgcccttc ggggctcctt 240
ggtgattcat gataacttaa cgaatcgcat ggccttgcgc cggcgatggt tcattcaaat 300
ttctgcccta tcaactttcg atggtaggat agtggcctac catggtttca acgggtaacg 360
gggaattagg gttcgattcc ggagagggag cctgagaaac ggctaccaca tccaaggaag 420
gcagcaggcg cgcaaattac ccaatcccga cacggggagg tagtgacaat aaatactgat 480
acagggctct tttgggtctt gtaattggaa tgagtacaat ttaaatccct taacgaggaa 540
caattggagg gcaagtctgg tgccagcagc cgcggtaatt ccagctccaa tagcgtatat 600
taaagttgtt gcagttaaaa agctcgtagt tgaaccttgg gcctggctgg ccggtccgcc 660
taaccgcgtg tactggtccg gccgggcctt tccttctggg gagccgcatg cccttcactg 720
ggtgtgtcgg ggaaccagga cttttacttt gaaaaaatta gagtgttcaa agcaggccta 780
tgctcgaata cattagcatg gaataataga ataggacgtg tggttctatt ttgttggttt 840
ctaggaccgc cgtaatgatt aatagggata gtcgggggca tcagtattca attgtcagag 900
gtgaaattct tggatttatt gaagactaac tactgcgaaa gcatttgcca aggatgtttt 960
cattaatcag tgaacgaaag ttaggggatc gaagacgatc agataccgtc gtagtcttaa 1020
ccataaacta tgccgactag ggatcgggcg atgttattat tttgactcgc tcggcacctt 1080
acgagaaatc aaagtctttg ggttctgggg ggagtatggt cgcaaggctg aaacttaaag 1140
aaattgacgg aagggcacca ccaggagtgg agcctgcggc ttaatttgac tcaacacggg 1200
gaaactcacc aggtccagac acattaagga ttgacagatt gagagctctt tcttgattat 1260
gtgggtggtg gtgcatggcc gttcttagtt ggtggagtga tttgtctgct taattgcgat 1320
aacgaacgag accttaacct gctaaatagc ccggtccgct ttggcgggcc gctggcttct 1380
tagagggact atcggctcaa gccgatggaa gtttgaggca ataacaggtc tgtgatgccc 1440
ttagatgttc tgggccgcac gcgcgctaca ctgacagagc caacgagtac atcaccttgg 1500
ccggaaggtc tgggtaatct tgttaaactc tgtcgtgctg gggatagagc attgcaatta 1560
ttgctcttca acgaggaatt cctagtaagc gcaagtcatc agcttgcgct gattacgtcc 1620
ctgccctttg tacacaccgc ccgtcgctac taccgattga atggctcagt gaggccttcg 1680
gactggcaca gggacgttgg caacgacgac ccagtgccgg aaagttcgtc aaacttggtc 1740
atttagagga agnnnaagtc gtaacaaggt ttccgtaggt gaacctgcgg aaggatcatt 1800
a 1801

<210> SEQ ID NO 28
<211> LENGTH: 1490
<212> TYPE: DNA
<213> ORGANISM: Burkholderia sp. SFA1

<400> SEQUENCE: 28
agtttgatcc tggctcagat tgaacgctgg cggcatgcct tacacatgca agtcgaacgg 60
cagcacgggg gcaaccctgg tggcgagtgg cgaacgggtg agtaatacat cggaacgtgt 120
cctgtagtgg gggatagccc ggcgaaagcc ggattaatac cgcatacgac ctaagggaga 180
aagcggggga tcttcggacc tcgcgctata ggggcggccg atggcagatt agctagttgg 240
tggggtaaag gcctaccaag gcgacgatct gtagctggtc tgagaggacg accagccaca 300
ctgggactga gacacggccc agactcctac gggaggcagc agtggggaat tttggacaat 360
gggggcaacc ctgatccagc aatgccgcgt gtgtgaagaa ggcttcgggt tgtaaagcac 420
ttttgtccgg aaagaaaact tcgtccctaa tatggatgga ggatgacggt accggaagaa 480
taagcaccgg ctaactacgt gccagcagcc gcggtaatac gtagggtgcg agcgttaatc 540
ggaattactg ggcgtaaagc gtgcgcaggc ggtctgttaa gaccgatgtg aaatccccgg 600
gcttaacctg ggaactgcat tggtgactgg caggctttga gtgtggcaga ggggggtaga 660
attccacgtg tagcagtgaa atgcgtagag atgtggagga ataccgatgg cgaaggcagc 720
cccctgggcc aactactgac gctcatgcac gaaagcgtgg ggagcaaaca ggattagata 780
ccctggtagt ccacgcccta aacgatgtca actagttgtt ggggattcat ttccttagta 840
acgtagctaa cgcgtgaagt tgaccgcctg gggagtacgg tcgcaagatt aaaactcaaa 900
ggaattgacg gggacccgca caagcggtgg atgatgtgga ttaattcgat gcaacgcgaa 960
aaaccttacc tacccttgac atggtcggaa ccctgctgaa aggtgggggt gctcgaaaga 1020
gaaccggcgc acaggtgctg catggctgtc gtcagctcgt gtcgtgagat gttgggttaa 1080
gtcccgcaac gagcgcaacc cttgtcctta gttgctacgc aagagcactc taaggagact 1140
gccggtgaca aaccggagga aggtggggat gacgtcaagt cctcatggcc cttatgggta 1200
gggcttcaca cgtcatacaa tggtcggaac agagggttgc caagccgcga ggtggagcca 1260
atcccagaaa accgatcgta gtccggatcg cagtctgcaa ctcgactgcg tgaagctgga 1320
atcgctagta atcgcggatc agcatgccgc ggtgaatacg ttcccgggtc ttgtacacac 1380
cgcccgtcac accatgggag tgggtttcac cagaagtagg tagcctaacc gcaaggaggg 1440
cgcttaccac ggtgggattc atgactgggg tgaagtcgta acaaggtagc 1490

<210> SEQ ID NO 29
<211> LENGTH: 1408
<212> TYPE: DNA
<213> ORGANISM: Burkholderia sp. KM-A

<400> SEQUENCE: 29
gcaaccctgg tggcgagtgg cgaacgggtg agtaatacat cggaacgtgt cctgtagtgg 60
gggatagccc ggcgaaagcc ggattaatac cgcatacgat ctacggaaga aagcggggga 120
tccttcggga cctcgcgcta taggggcggc cgatggcaga ttagctagtt ggtggggtaa 180
aggcctacca aggcgacgat ctgtagctgg tctgagagga cgaccagcca cactgggact 240
gagacacggc ccagactcct acgggaggca gcagtgggga attttggaca atgggggcaa 300
ccctgatcca gcaatgccgc gtgtgtgaag aaggccttcg ggttgtaaag cacttttgtc 360
cggaaagaaa acgtcttggt taatacctga ggcggatgac ggtaccggaa gaataagcac 420
cggctaacta cgtgccagca gccgcggtaa tacgtagggt gcgagcgtta atcggaatta 480
ctgggcgtaa agcgtgcgca ggcggtctgt taagaccgat gtgaaatccc cgggcttaac 540
ctgggaactg cattggtgac tggcaggctt tgagtgtggc agaggggggt agaattccac 600
gtgtagcagt gaaatgcgta gagatgtgga ggaataccga tggcgaaggc agccccctgg 660
gccaacactg acgctcatgc acgaaagcgt ggggagcaaa caggattaga taccctggta 720
gtccacgccc taaacgatgt caactagttg ttggggattc atttccttag taacgtagct 780
aacgcgtgaa gttgaccgcc tggggagtac ggtcgcaaga ttaaaactca aaggaattga 840
cggggacccg cacaagcggt ggatgatgtg gattaattcg atgcaacgcg aaaaacctta 900
cctacccttg acatggtcgg aagtctgctg agaggtggac gtgctcgaaa gagaaccggc 960
gcacaggtgc tgcatggctg tcgtcagctc gtgtcgtgag atgttgggtt aagtcccgca 1020
acgagcgcaa cccttgtcct tagttgctac gcaagagcac tctaaggaga ctgccggtga 1080
caaaccggag gaaggtgggg atgacgtcaa gtcctcatgg cccttatggg tagggcttca 1140
cacgtcatac aatggtcgga acagagggtt gccaagccgc gaggtggagc caatcccaga 1200
aaaccgatcg tagtccggat cgcagtctgc aactcgactg cgtgaagctg gaatcgctag 1260
taatcgcgga tcagcatgcc gcggtgaata cgttcccggg tcttgtacac accgcccgtc 1320
acaccatggg agtgggtttc accagaagta ggtagcctaa ccgcaaggag ggcgcttacc 1380
acggtgggat tcatgactgg ggtgaagt 1408

<210> SEQ ID NO 30
<211> LENGTH: 1383
<212> TYPE: DNA
<213> ORGANISM: Burkholderia sp. KM-G

<400> SEQUENCE: 30
gcaaccctgg tggcgagtgg cgaacgggtg agtaatacat cggaacgtgt cctgtagtgg 60
gggatagccc ggcgaaagcc ggattaatac cgcatacgac ctaagggaga aagcggggga 120
tcttcggacc tcgcgctata ggggcggccg atggcagatt agctagttgg tggggtaaag 180
gcctaccaag gcgacgatct gtagctggtc tgagaggacg accagccaca ctgggactga 240
gacacggccc agactcctac gggaggcagc agtggggaat tttggacaat gggggcaacc 300
ctgatccagc aatgccgcgt gtgtgaagaa ggccttcggg ttgtaaagca cttttgtccg 360
gaaagaaaac ttcgaggtta atacccttgg aggatgacgg taccggaaga ataagcaccg 420
gctaactacg tgccagcagc cgcggtaata cgtagggtgc gagcgttaat cggaattact 480
gggcgtaaag cgtgcgcagg cggtctgtta agaccgatgt gaaatccccg ggcttaacct 540
gggaactgca ttggtgactg gcaggctttg agtgtggcag aggggggtag aattccacgt 600
gtagcagtga aatgcgtaga gatgtggagg aataccgatg gcgaaggcag ccccctgggc 660
caacactgac gctcatgcac gaaagcgtgg ggagcaaaca ggattagata ccctggtagt 720
ccacgcccta aacgatgtca actagttgtt ggggattcat ttccttagta acgtagctaa 780
cgcgtgaagt tgaccgcctg gggagtacgg tcgcaagatt aaaactcaaa ggaattgacg 840
gggacccgca caagcggtgg atgatgtgga ttaattcgat gcaacgcgaa aaaccttacc 900
tacccttgac atggtcggaa gtctgctgag aggtggacgt gctcgaaaga gaaccggcgc 960
acaggtgctg catggctgtc gtcagctcgt gtcgtgagat gttgggttaa gtcccgcaac 1020

-continued gagcgcaacc cttgtcctta gttgctacgc aagagcactc taaggagact gccggtgaca 1080
aaccggagga aggtggggat gacgtcaagt cctcatggcc cttatgggta gggcttcaca 1140
cgtcatacaa tggtcggaac agagggttgc caagccgcga ggtggagcca atcccagaaa 1200
accgatcgta gtccggatcg cagtctgcaa ctcgactgcg tgaagctgga atcgctagta 1260
atcgcggatc agcatgccgc ggtgaatacg ttcccgggtc ttgtacacac cgcccgtcac 1320
accatgggag tgggtttcac cagaagtagg tagcctaacc tgcaaaggag ggcgcttacc 1380
acg 1383

<210> SEQ ID NO 31

<400> SEQUENCE: 31

000

<210> SEQ ID NO 32

<400> SEQUENCE: 32

000

<210> SEQ ID NO 33
<211> LENGTH: 1505
<212> TYPE: DNA
<213> ORGANISM: Snodgrassella alvi

<400> SEQUENCE: 33
gagagtttga tcctggctca gattgaacgc tggcggcatg ccttacacat gcaagtcgaa 60
cggcagcacg gagagcttgc tctctggtgg cgagtggcga acgggtgagt aatgcatcgg 120
aacgtaccga gtaatggggg ataactgtcc gaaaggatgg ctaataccgc atacgccctg 180
agggggaaag cgggggatcg aaagacctcg cgttatttga gcggccgatg ttggattagc 240
tagttggtgg ggtaaaggcc taccaaggcg acgatccata gcgggtctga gaggatgatc 300
cgccacattg ggactgagac acggcccaaa ctcctacggg aggcagcagt ggggaatttt 360
ggacaatggg gggaaccctg atccagccat gccgcgtgtc tgaagaaggc cttcgggttg 420
taaaggactt ttgttaggga agaaaagccg ggtgttaata ccatctggtg ctgacggtac 480
ctaaagaata agcaccggct aactacgtgc cagcagccgc ggtaatacgt agggtgcgag 540
cgttaatcgg aattactggg cgtaaagcga gcgcagacgg ttaattaagt cagatgtgaa 600
atccccgagc tcaacttggg acgtgcattt gaaactggtt aactagagtg tgtcagaggg 660
aggtagaatt ccacgtgtag cagtgaaatg cgtagagatg tggaggaata ccgatggcga 720
aggcagcctc ctgggataac actgacgttc atgctcgaaa gcgtgggtag caaacaggat 780
tagataccct ggtagtccac gccctaaacg atgacaatta gctgttggga cactagatgt 840
cttagtagcg aagctaacgc gtgaaattgt ccgcctgggg agtacggtcg caagattaaa 900
actcaaagga attgacgggg acccgcacaa gcggtggatg atgtggatta attcgatgca 960
acgcgaagaa ccttacctgg tcttgacatg tacggaatct cttagagata ggagagtgcc 1020
ttcgggaacc gtaacacagg tgctgcatgg ctgtcgtcag ctcgtgtcgt gagatgttgg 1080
gttaagtccc gcaacgagcg caacccttgt cattagttgc catcattaag ttgggcactc 1140
taatgagact gccggtgaca aaccggagga aggtggggat gacgtcaagt cctcatggcc 1200
cttatgacca gggcttcaca cgtcatacaa tggtcggtac agagggtagc gaagccgcga 1260
ggtgaagcca atctcagaaa gccgatcgta gtccggattg cactctgcaa ctcgagtgca 1320
tgaagtcgga atcgctagta atcgcaggtc agcatactgc ggtgaatacg ttcccgggtc 1380
ttgtacacac cgcccgtcac accatgggag tgggggatac cagaattggg tagactaacc 1440
gcaaggaggt cgcttaacac ggtatgcttc atgactgggg tgaagtcgta acaaggtagc 1500
cgtag 1505

<210> SEQ ID NO 34
<211> LENGTH: 1541
<212> TYPE: DNA
<213> ORGANISM: Gilliamella apicola

<400> SEQUENCE: 34
ttaaattgaa gagtttgatc atggctcaga ttgaacgctg gcggcaggct taacacatgc 60
aagtcgaacg gtaacatgag tgcttgcact tgatgacgag tggcggacgg gtgagtaaag 120
tatggggatc tgccgaatgg agggggacaa cagttggaaa cgactgctaa taccgcataa 180
agttgagaga ccaaagcatg ggaccttcgg gccatgcgcc atttgatgaa cccatatggg 240
attagctagt tggtagggta atggcttacc aaggcgacga tctctagctg gtctgagagg 300
atgaccagcc acactggaac tgagacacgg tccagactcc tacgggaggc agcagtgggg 360
aatattgcac aatgggggaa accctgatgc agccatgccg cgtgtatgaa gaaggccttc 420
gggttgtaaa gtactttcgg tgatgaggaa ggtggtgtat ctaataggtg catcaattga 480
cgttaattac agaagaagca ccggctaact ccgtgccagc agccgcggta atacggaggg 540
tgcgagcgtt aatcggaatg actgggcgta aagggcatgt aggcggataa ttaagttagg 600
tgtgaaagcc ctgggctcaa cctaggaatt gcacttaaaa ctggttaact agagtattgt 660
agaggaaggt agaattccac gtgtagcggt gaaatgcgta gagatgtgga ggaataccgg 720
tggcgaaggc ggccttctgg acagatactg acgctgagat gcgaaagcgt ggggagcaaa 780
caggattaga taccctggta gtccacgctg taaacgatgt cgatttggag tttgttgcct 840
agagtgatgg gctccgaagc taacgcgata aatcgaccgc ctggggagta cggccgcaag 900
gttaaaactc aaatgaattg acgggggccc gcacaagcgg tggagcatgt ggtttaattc 960
gatgcaacgc gaagaacctt acctggtctt gacatccaca gaatcttgca gagatgcggg 1020
agtgccttcg ggaactgtga gacaggtgct gcatggctgt cgtcagctcg tgttgtgaaa 1080
tgttgggtta agtcccgcaa cgagcgcaac ccttatcctt tgttgccatc ggttaggccg 1140
ggaactcaaa ggagactgcc gttgataaag cggaggaagg tggggacgac gtcaagtcat 1200
catggccctt acgaccaggg ctacacacgt gctacaatgg cgtatacaaa gggaggcgac 1260
ctcgcgagag caagcggacc tcataaagta cgtctaagtc cggattggag tctgcaactc 1320
gactccatga agtcggaatc gctagtaatc gtgaatcaga atgtcacggt gaatacgttc 1380
ccgggccttg tacacaccgc ccgtcacacc atgggagtgg gttgcaccag aagtagatag 1440
cttaaccttc gggagggcgt ttaccacggt gtggtccatg actggggtga agtcgtaaca 1500
aggtaaccgt aggggaacct gcggttggat cacctcctta c 1541

<210> SEQ ID NO 35
<211> LENGTH: 1528
<212> TYPE: DNA
<213> ORGANISM: Bartonella apis

<400> SEQUENCE: 35
aagccaaaat caaattttca acttgagagt ttgatcctgg ctcagaacga acgctggcgg 60

```
caggcttaac acatgcaagt cgaacgcact tttcggagtg agtggcagac gggtgagtaa     120

cgcgtgggaa tctacctatt tctacggaat aacgcagaga aatttgtgct aataccgtat     180

acgtccttcg ggagaaagat ttatcggaga tagatgagcc cgcgttggat tagctagttg     240

gtgaggtaat ggcccaccaa ggcgacgatc catagctggt ctgagaggat gaccagccac     300

attgggactg agacacggcc cagactccta cgggaggcag cagtggggaa tattggacaa     360

tgggcgcaag cctgatccag ccatgccgcg tgagtgatga aggccctagg gttgtaaagc     420

tctttcaccg gtgaagataa tgacggtaac cggagaagaa gccccggcta acttcgtgcc     480

agcagccgcg gtaatacgaa gggggctagc gttgttcgga tttactgggc gtaaagcgca     540

cgtaggcgga tatttaagtc aggggtgaaa tcccggggct caaccccgga actgcctttg     600

atactggata tcttgagtat ggaagaggta agtggaattc cgagtgtaga ggtgaaattc     660

gtagatattc ggaggaacac cagtggcgaa ggcggcttac tggtccatta ctgacgctga     720

ggtgcgaaag cgtggggagc aaacaggatt agataccctg gtagtccacg ctgtaaacga     780

tgaatgttag ccgttggaca gtttactgtt cggtggcgca gctaacgcat taaacattcc     840

gcctggggag tacggtcgca agattaaaac tcaaaggaat tgacgggggc ccgcacaagc     900

ggtggagcat gtggtttaat tcgaagcaac gcgcagaacc ttaccagccc ttgacatccc     960

gatcgcggat ggtggagaca ccgtctttca gttcggctgg atcggtgaca ggtgctgcat    1020

ggctgtcgtc agctcgtgtc gtgagatgtt gggttaagtc ccgcaacgag cgcaaccctc    1080

gcccttagtt gccatcattt agttgggcac tctaagggga ctgccggtga taagccgaga    1140

ggaaggtggg gatgacgtca agtcctcatg gcccttacgg gctgggctac acacgtgcta    1200

caatggtggt gacagtgggc agcgagaccg cgaggtcgag ctaatctcca aaagccatct    1260

cagttcggat tgcactctgc aactcgagtg catgaagttg gaatcgctag taatcgtgga    1320

tcagcatgcc acggtgaata cgttcccggg ccttgtacac accgcccgtc acaccatggg    1380

agttggtttt acccgaaggt gctgtgctaa ccgcaaggag gcaggcaacc acggtagggt    1440

cagcgactgg ggtgaagtcg taacaaggta gccgtagggg aacctgcggc tggatcacct    1500

cctttctaag gaagatgaag aattggaa                                       1528
```

<210> SEQ ID NO 36
<211> LENGTH: 1390
<212> TYPE: DNA
<213> ORGANISM: Parasaccharibacter apium
<220> FEATURE:
<221> NAME/KEY: misc_feature
<222> LOCATION: (643)..(756)
<223> OTHER INFORMATION: n is a, g, c, or t

<400> SEQUENCE: 36

```
ctaccatgca agtcgcacga aacctttcgg ggttagtggc ggacgggtga gtaacgcgtt      60

aggaacctat ctggaggtgg gggataacat cgggaaactg gtgctaatac cgcatgatgc     120

ctgagggcca aaggagagat ccgccattgg aggggcctgc gttcgattag ctagttggtt     180

gggtaaaggc tgaccaaggc gatgatcgat agctggtttg agaggatgat cagccacact     240

gggactgaga cacggcccag actcctacgg gaggcagcag tggggaatat tggacaatgg     300

gggcaaccct gatccagcaa tgccgcgtgt gtgaagaagg tcttcggatt gtaaagcact     360

ttcactaggg aagatgatga cggtacctag agaagaagcc ccggctaact tcgtgccagc     420

agccgcggta atacgaaggg ggctagcgtt gctcggaatg actgggcgta aagggcgcgt     480
```

aggctgtttg tacagtcaga tgtgaaatcc ccgggcttaa cctgggaact gcatttgata 540
cgtgcagact agagtccgag agagggttgt ggaattccca gtgtagaggt gaaattcgta 600
gatattggga agaacaccgg ttgcgaaggc ggcaacctgg ctnnnnnnnn nnnnnnnnnn 660
nnnnnnnnnn nnnnnnnnnn nnnnnnnnnn nnnnnnnnnn nnnnnnnnnn nnnnnnnnnn 720
nnnnnnnnnn nnnnnnnnnn nnnnnnnnnn nnnnnngagc taacgcgtta agcacaccgc 780
ctggggagta cggccgcaag gttgaaactc aaaggaattg acgggggccc gcacaagcgg 840
tggagcatgt ggtttaattc gaagcaacgc gcagaacctt accagggctt gcatggggag 900
gctgtattca gagatggata tttcttcgga cctcccgcac aggtgctgca tggctgtcgt 960
cagctcgtgt cgtgagatgt tgggttaagt cccgcaacga gcgcaaccct tgtctttagt 1020
tgccatcacg tctgggtggg cactctagag agactgccgg tgacaagccg gaggaaggtg 1080
gggatgacgt caagtcctca tggcccttat gtcctgggct acacacgtgc tacaatggcg 1140
gtgacagagg gatgctacat ggtgacatgg tgctgatctc aaaaaaccgt ctcagttcgg 1200
attgtactct gcaactcgag tgcatgaagg tggaatcgct agtaatcgcg gatcagcatg 1260
ccgcggtgaa tacgttcccg ggccttgtac acaccgcccg tcacaccatg ggagttggtt 1320
tgaccttaag ccggtgagcg aaccgcaagg aacgcagccg accaccggtt cgggttcagc 1380
gactggggga 1390

<210> SEQ ID NO 37
<211> LENGTH: 1583
<212> TYPE: DNA
<213> ORGANISM: Lactobacillus kunkeei

<400> SEQUENCE: 37
ttccttagaa aggaggtgat ccagccgcag gttctcctac ggctaccttg ttacgacttc 60
accctaatca tctgtcccac cttagacgac tagctcctaa aaggttaccc catcgtcttt 120
gggtgttaca aactctcatg gtgtgacggg cggtgtgtac aaggcccggg aacgtattca 180
ccgtggcatg ctgatccacg attactagtg attccaactt catgcaggcg agttgcagcc 240
tgcaatccga actgagaatg gctttaagag attagcttga cctcgcggtt tcgcgactcg 300
ttgtaccatc cattgtagca cgtgtgtagc ccagctcata aggggcatga tgatttgacg 360
tcgtccccac cttcctccgg tttatcaccg gcagtctcac tagagtgccc aactaaatgc 420
tggcaactaa taataagggt tgcgctcgtt gcgggactta acccaacatc tcacgacacg 480
agctgacgac aaccatgcac cacctgtcat tctgtccccg aagggaacgc ccaatctctt 540
gggttggcag aagatgtcaa gagctggtaa ggttcttcgc gtagcatcga attaaaccac 600
atgctccacc acttgtgcgg gcccccgtca attcctttga gtttcaacct tgcggtcgta 660
ctccccaggc ggaatactta atgcgttagc tgcggcactg aagggcggaa accctccaac 720
acctagtatt catcgtttac ggcatggact accagggtat ctaatcctgt tcgctaccca 780
tgctttcgag cctcagcgtc agtaacagac cagaaagccg ccttcgccac tggtgttctt 840
ccatatatct acgcatttca ccgctacaca tggagttcca ctttcctctt ctgtactcaa 900
gttttgtagt ttccactgca cttcctcagt tgagctgagg gctttcacag cagacttaca 960
aaaccgcctg cgctcgcttt acgcccaata aatccggaca acgcttgcca cctacgtatt 1020
accgcggctg ctggcacgta gttagccgtg gctttctggt taaataccgt caaagtgtta 1080
acagttactc taacacttgt tcttctttaa caacagagtt ttacgatccg aaaaccttca 1140
tcactcacgc ggcgttgctc catcagactt tcgtccattg tggaagattc cctactgctg 1200
cctcccgtag gagtctgggc cgtgtctcag tcccaatgtg gccgattacc ctctcaggtc 1260
ggctacgtat catcgtcttg gtgggctttt atctcaccaa ctaactaata cggcgcgggt 1320
ccatcccaaa gtgatagcaa agccatcttt caagttggaa ccatgcggtt ccaactaatt 1380
atgcggtatt agcacttgtt tccaaatgtt atcccccgct tcggggcagg ttacccacgt 1440
gttactcacc agttcgccac tcgctccgaa tccaaaaatc atttatgcaa gcataaaatc 1500
aatttgggag aactcgttcg acttgcatgt attaggcacg ccgccagcgt tcgtcctgag 1560
ccaggatcaa actctcatct taa 1583

<210> SEQ ID NO 38
<211> LENGTH: 1395
<212> TYPE: DNA
<213> ORGANISM: Lactobacillus Firm-4

<400> SEQUENCE: 38
acgaacgctg gcggcgtgcc taatacatgc aagtcgagcg cgggaagtca gggaagcctt 60
cgggtggaac tggtggaacg agcggcggat gggtgagtaa cacgtaggta acctgcccta 120
aagcggggga taccatctgg aaacaggtgc taataccgca taaacccagc agtcacatga 180
gtgctggttg aaagacggct tcggctgtca ctttaggatg gacctgcggc gtattagcta 240
gttggtggag taacggttca ccaaggcaat gatacgtagc cgacctgaga gggtaatcgg 300
ccacattggg actgagacac ggcccaaact cctacgggag gcagcagtag ggaatcttcc 360
acaatggacg caagtctgat ggagcaacgc cgcgtggatg aagaaggtct tcggatcgta 420
aaatcctgtt gttgaagaag aacggttgtg agagtaactg ctcataacgt gacggtaatc 480
aaccagaaag tcacggctaa ctacgtgcca gcagccgcgg taatacgtag gtggcaagcg 540
ttgtccggat ttattgggcg taaagggagc gcaggcggtc ttttaagtct gaatgtgaaa 600
gccctcagct taactgagga agagcatcgg aaactgagag acttgagtgc agaagaggag 660
agtggaactc catgtgtagc ggtgaaatgc gtagatatat ggaagaacac cagtggcgaa 720
ggcggctctc tggtctgtta ctgacgctga ggctcgaaag catgggtagc gaacaggatt 780
agataccctg gtagtccatg ccgtaaacga tgagtgctaa gtgttgggag gtttccgcct 840
ctcagtgctg cagctaacgc attaagcact ccgcctgggg agtacgaccg caaggttgaa 900
actcaaagga attgacgggg gcccgcacaa gcggtggagc atgtggttta attcgaagca 960
acgcgaagaa ccttaccagg tcttgacatc tcctgcaagc ctaagagatt aggggttccc 1020
ttcggggaca ggaagacagg tggtgcatgg ttgtcgtcag ctcgtgtcgt gagatgttgg 1080
gttaagtccc gcaacgagcg caacccttgt tactagttgc cagcattaag ttgggcactc 1140
tagtgagact gccggtgaca aaccggagga aggtggggac gacgtcaaat catcatgccc 1200
cttatgacct gggctacaca cgtgctacaa tggatggtac aatgagaagc gaactcgcga 1260
ggggaagctg atctctgaaa accattctca gttcggattg caggctgcaa ctcgcctgca 1320
tgaagctgga atcgctagta atcgcggatc agcatgccgc ggtgaatacg ttcccgggcc 1380
ttgtacacac cgccc 1395

<210> SEQ ID NO 39
<211> LENGTH: 1549
<212> TYPE: DNA
<213> ORGANISM: Enterococcus

<400> SEQUENCE: 39

```
aggtgatcca gccgcacctt ccgatacggc taccttgtta cgacttcacc ccaatcatct     60
atcccacctt aggcggctgg ctccaaaaag gttacctcac cgacttcggg tgttacaaac    120
tctcgtggtg tgacgggcgg tgtgtacaag gcccgggaac gtattcaccg cggcgtgctg    180
atccgcgatt actagcgatt ccggcttcat gcaggcgagt tgcagcctgc aatccgaact    240
gagagaagct ttaagagatt tgcatgacct cgcggtctag cgactcgttg tacttcccat    300
tgtagcacgt gtgtagccca ggtcataagg ggcatgatga tttgacgtca tccccacctt    360
cctccggttt gtcaccggca gtctcgctag agtgcccaac taaatgatgg caactaacaa    420
taagggttgc gctcgttgcg ggacttaacc caacatctca cgacacgagc tgacgacaac    480
catgcaccac ctgtcacttt gtccccgaag ggaaagctct atctctagag tggtcaaagg    540
atgtcaagac ctggtaaggt tcttcgcgtt gcttcgaatt aaaccacatg ctccaccgct    600
tgtgcgggcc cccgtcaatt cctttgagtt tcaaccttgc ggtcgtactc cccaggcgga    660
gtgcttaatg cgtttgctgc agcactgaag ggcggaaacc ctccaacact tagcactcat    720
cgtttacggc gtggactacc agggtatcta atcctgtttg ctccccacgc tttcgagcct    780
cagcgtcagt tacagaccag agagccgcct tcgccactgg tgttcctcca tatatctacg    840
catttcaccg ctacacatgg aattccactc tcctcttctg cactcaagtc tcccagtttc    900
caatgaccct ccccggttga gccgggggct ttcacatcag acttaagaaa ccgcctgcgc    960
tcgctttacg cccaataaat ccggacaacg cttgccacct acgtattacc gcggctgctg   1020
gcacgtagtt agccgtggct ttctggttag ataccgtcag ggacgttca gttactaacg   1080
tccttgttct tctctaacaa cagagtttta cgatccgaaa accttcttca ctcacgcggc   1140
gttgctcggt cagactttcg tccattgccg aagattccct actgctgcct cccgtaggag   1200
tctgggccgt gtctcagtcc cagtgtggcc gatcaccctc tcaggtcggc tatgcatcgt   1260
ggccttggtg agccgttacc tcaccaacta gctaatgcac cgcgggtcca tccatcagcg   1320
acacccgaaa gcgcctttca ctcttatgcc atgcggcata aactgttatg cggtattagc   1380
acctgtttcc aagtgttatc cccctctgat gggtaggtta cccacgtgtt actcacccgt   1440
ccgccactcc tctttccaat tgagtgcaag cactcgggag gaaagaagcg ttcgacttgc   1500
atgtattagg cacgccgcca gcgttcgtcc tgagccagga tcaaactct               1549
```

<210> SEQ ID NO 40
<211> LENGTH: 1541
<212> TYPE: DNA
<213> ORGANISM: Delftia

<400> SEQUENCE: 40

```
cagaaaggag gtgatccagc cgcaccttcc gatacggcta ccttgttacg acttcacccc     60
agtcacgaac cccgccgtgg taagcgccct ccttgcggtt aggctaccta cttctggcga    120
gacccgctcc catggtgtga cgggcggtgt gtacaagacc cgggaacgta ttcaccgcgg    180
catgctgatc cgcgattact agcgattccg acttcacgca gtcgagttgc agactgcgat    240
ccggactacg actggtttta tgggattagc tccccctcgc gggttggcaa ccctctgtac    300
cagccattgt atgacgtgtg tagccccacc tataagggcc atgaggactt gacgtcatcc    360
ccaccttcct ccggtttgtc accggcagtc tcattagagt gctcaactga atgtagcaac    420
taatgacaag ggttgcgctc gttgcgggac ttaacccaac atctcacgac acgagctgac    480
gacagccatg cagcacctgt gtgcaggttc tctttcgagc acgaatccat ctctggaaac    540
ttcctgccat gtcaaaggtg ggtaaggttt ttcgcgttgc atcgaattaa accacatcat    600
```

ccaccgcttg tgcgggtccc cgtcaattcc tttgagtttc aaccttgcgg ccgtactccc 660
caggcggtca acttcacgcg ttagcttcgt tactgagaaa actaattccc aacaaccagt 720
tgacatcgtt tagggcgtgg actaccaggg tatctaatcc tgtttgctcc ccacgctttc 780
gtgcatgagc gtcagtacag gtccagggga ttgccttcgc catcggtgtt cctccgcata 840
tctacgcatt tcactgctac acgcggaatt ccatccccct ctaccgtact ctagccatgc 900
agtcacaaat gcagttccca ggttgagccc ggggatttca catctgtctt acataaccgc 960
ctgcgcacgc tttacgccca gtaattccga ttaacgctcg caccctacgt attaccgcgg 1020
ctgctggcac gtagttagcc ggtgcttatt cttacggtac cgtcatgggc cccctgtatt 1080
agaaggagct tttcgttcc gtacaaaagc agtttacaac ccgaaggcct tcatcctgca 1140
cgcggcattg ctggatcagg ctttcgccca ttgtccaaaa ttccccactg ctgcctcccg 1200
taggagtctg ggccgtgtct cagtcccagt gtggctggtc gtcctctcag accagctaca 1260
gatcgtcggc ttggtaagct tttatcccac caactaccta atctgccatc ggccgctcca 1320
atcgcgcgag gcccgaaggg cccccgcttt catcctcaga tcgtatgcgg tattagctac 1380
tctttcgagt agttatcccc cacgactggg cacgttccga tgtattactc acccgttcgc 1440
cactcgtcag cgtccgaaga cctgttaccg ttcgacttgc atgtgtaagg catgccgcca 1500
gcgttcaatc tgagccagga tcaaactcta cagttcgatc t 1541

<210> SEQ ID NO 41
<211> LENGTH: 1502
<212> TYPE: DNA
<213> ORGANISM: Pelomonas
<220> FEATURE:
<221> NAME/KEY: misc_feature
<222> LOCATION: (192)..(193)
<223> OTHER INFORMATION: n is a, g, c, or t
<220> FEATURE:
<221> NAME/KEY: misc_feature
<222> LOCATION: (832)..(833)
<223> OTHER INFORMATION: n is a, g, c, or t

<400> SEQUENCE: 41
atcctggctc agattgaacg ctggcggcat gccttacaca tgcaagtcga acggtaacag 60
gttaagctga cgagtggcga acgggtgagt aatatatcgg aacgtgccca gtcgtggggg 120
ataactgctc gaaagagcag ctaataccgc atacgacctg agggtgaaag cgggggatcg 180
caagacctcg cnngattgga gcggccgata tcagattagg tagttggtgg ggtaaaggcc 240
caccaagcca acgatctgta gctggtctga gaggacgacc agccacactg ggactgagac 300
acggcccaga ctcctacggg aggcagcagt ggggaatttt ggacaatggg cgcaagcctg 360
atccagccat gccgcgtgcg ggaagaaggc cttcgggttg taaaccgctt ttgtcaggga 420
agaaaaggtt ctggttaata cctgggactc atgacggtac ctgaagaata agcaccggct 480
aactacgtgc cagcagccgc ggtaatacgt agggtgcaag cgttaatcgg aattactggg 540
cgtaaagcgt gcgcaggcgg ttatgcaaga cagaggtgaa atccccgggc tcaacctggg 600
aactgccttt gtgactgcat agctagagta cggtagaggg ggatggaatt ccgcgtgtag 660
cagtgaaatg cgtagatatg cggaggaaca ccgatggcga aggcaatccc ctggacctgt 720
actgacgctc atgcacgaaa gcgtggggag caaacaggat tagataccct ggtagtccac 780
gccctaaacg atgtcaactg gttgttggga gggtttcttc tcagtaacgt anntaacgcg 840
tgaagttgac cgcctgggga gtacggccgc aaggttgaaa ctcaaaggaa ttgacgggga 900

-continued

```
cccgcacaag cggtggatga tgtggtttaa ttcgatgcaa cgcgaaaaac cttacctacc    960

cttgacatgc caggaatcct gaagagattt gggagtgctc gaaagagaac ctggacacag   1020

gtgctgcatg gccgtcgtca gctcgtgtcg tgagatgttg ggttaagtcc cgcaacgagc   1080

gcaacccttg tcattagttg ctacgaaagg gcactctaat gagactgccg gtgacaaacc   1140

ggaggaaggt ggggatgacg tcaggtcatc atggccctta tgggtagggc tacacacgtc   1200

atacaatggc cgggacagag ggctgccaac ccgcgagggg gagctaatcc cagaaacccg   1260

gtcgtagtcc ggatcgtagt ctgcaactcg actgcgtgaa gtcggaatcg ctagtaatcg   1320

cggatcagct tgccgcggtg aatacgttcc cgggtcttgt acacaccgcc cgtcacacca   1380

tgggagcggg ttctgccaga agtagttagc ctaaccgcaa ggagggcgat taccacggca   1440

gggttcgtga ctggggtgaa gtcgtaacaa ggtagccgta tcggaaggtg cggctggatc   1500

ac                                                                  1502
```

<210> SEQ ID NO 42
<211> LENGTH: 34
<212> TYPE: PRT
<213> ORGANISM: Lactococcus lactis

<400> SEQUENCE: 42

```
Ile Thr Ser Ile Ser Leu Cys Thr Pro Gly Cys Lys Thr Gly Ala Leu
1               5                   10                  15

Met Gly Cys Asn Met Lys Thr Ala Thr Cys His Cys Ser Ile His Val
            20                  25                  30

Ser Lys
```

<210> SEQ ID NO 43
<211> LENGTH: 22
<212> TYPE: PRT
<213> ORGANISM: Staphylococcus epidermis

<400> SEQUENCE: 43

```
Ile Ala Ser Lys Phe Ile Cys Thr Pro Gly Cys Ala Lys Thr Gly Ser
1               5                   10                  15

Phe Asn Ser Tyr Cys Cys
            20
```

<210> SEQ ID NO 44
<211> LENGTH: 44
<212> TYPE: PRT
<213> ORGANISM: Pediococcus acidilactici

<400> SEQUENCE: 44

```
Lys Tyr Tyr Gly Asn Gly Val Thr Cys Gly Lys His Ser Cys Ser Val
1               5                   10                  15

Asp Trp Gly Lys Ala Thr Thr Cys Ile Ile Asn Asn Gly Ala Met Ala
            20                  25                  30

Trp Ala Thr Gly Gly His Gln Gly Asn His Lys Cys
        35                  40
```

<210> SEQ ID NO 45
<211> LENGTH: 44
<212> TYPE: PRT
<213> ORGANISM: Enterococcus faecium

<400> SEQUENCE: 45

```
Ala Thr Arg Ser Tyr Gly Asn Gly Val Tyr Cys Asn Asn Ser Lys Cys
1               5                   10                  15
```

```
Trp Val Asn Trp Gly Glu Ala Lys Glu Asn Ile Ala Gly Ile Val Ile
            20                  25                  30

Ser Gly Trp Ala Ser Gly Leu Ala Gly Met Gly His
        35                  40


<210> SEQ ID NO 46
<211> LENGTH: 39
<212> TYPE: PRT
<213> ORGANISM: Streptococcus lactis

<400> SEQUENCE: 46

Gly Thr Trp Asp Asp Ile Gly Gln Gly Ile Gly Arg Val Ala Tyr Trp
1               5                   10                  15

Val Gly Lys Ala Met Gly Asn Met Ser Asp Val Asn Gln Ala Ser Arg
            20                  25                  30

Ile Asn Arg Lys Lys Lys His
        35


<210> SEQ ID NO 47
<211> LENGTH: 48
<212> TYPE: PRT
<213> ORGANISM: Lactobacillus johnsonii

<400> SEQUENCE: 47

Asn Arg Trp Gly Asp Thr Val Leu Ser Ala Ala Ser Gly Ala Gly Thr
1               5                   10                  15

Gly Ile Lys Ala Cys Lys Ser Phe Gly Pro Trp Gly Met Ala Ile Cys
            20                  25                  30

Gly Val Gly Gly Ala Ala Ile Gly Gly Tyr Phe Gly Tyr Thr His Asn
        35                  40                  45


<210> SEQ ID NO 48
<211> LENGTH: 70
<212> TYPE: PRT
<213> ORGANISM: Enterococcus faecalis

<400> SEQUENCE: 48

Met Ala Lys Glu Phe Gly Ile Pro Ala Ala Val Ala Gly Thr Val Leu
1               5                   10                  15

Asn Val Val Glu Ala Gly Gly Trp Val Thr Thr Ile Val Ser Ile Leu
            20                  25                  30

Thr Ala Val Gly Ser Gly Gly Leu Ser Leu Leu Ala Ala Ala Gly Arg
        35                  40                  45

Glu Ser Ile Lys Ala Tyr Leu Lys Lys Glu Ile Lys Lys Lys Gly Lys
    50                  55                  60

Arg Ala Val Ile Ala Trp
65                  70


<210> SEQ ID NO 49
<211> LENGTH: 51
<212> TYPE: PRT
<213> ORGANISM: Staphylococcus aureus

<400> SEQUENCE: 49

Met Ser Trp Leu Asn Phe Leu Lys Tyr Ile Ala Lys Tyr Gly Lys Lys
1               5                   10                  15

Ala Val Ser Ala Ala Trp Lys Tyr Lys Gly Lys Val Leu Glu Trp Leu
            20                  25                  30

Asn Val Gly Pro Thr Leu Glu Trp Val Trp Gln Lys Leu Lys Lys Ile
```

```
        35                  40                  45

Ala Gly Leu
    50


<210> SEQ ID NO 50
<211> LENGTH: 43
<212> TYPE: PRT
<213> ORGANISM: Lactococcus garvieae

<400> SEQUENCE: 50

Ile Gly Gly Ala Leu Gly Asn Ala Leu Asn Gly Leu Gly Thr Trp Ala
1               5                   10                  15

Asn Met Met Asn Gly Gly Gly Phe Val Asn Gln Trp Gln Val Tyr Ala
            20                  25                  30

Asn Lys Gly Lys Ile Asn Gln Tyr Arg Pro Tyr
        35                  40


<210> SEQ ID NO 51
<211> LENGTH: 103
<212> TYPE: PRT
<213> ORGANISM: Escherichia coli

<400> SEQUENCE: 51

Met Arg Thr Leu Thr Leu Asn Glu Leu Asp Ser Val Ser Gly Gly Ala
1               5                   10                  15

Ser Gly Arg Asp Ile Ala Met Ala Ile Gly Thr Leu Ser Gly Gln Phe
            20                  25                  30

Val Ala Gly Gly Ile Gly Ala Ala Ala Gly Gly Val Ala Gly Gly Ala
        35                  40                  45

Ile Tyr Asp Tyr Ala Ser Thr His Lys Pro Asn Pro Ala Met Ser Pro
    50                  55                  60

Ser Gly Leu Gly Gly Thr Ile Lys Gln Lys Pro Glu Gly Ile Pro Ser
65                  70                  75                  80

Glu Ala Trp Asn Tyr Ala Ala Gly Arg Leu Cys Asn Trp Ser Pro Asn
                85                  90                  95

Asn Leu Ser Asp Val Cys Leu
            100


<210> SEQ ID NO 52
<211> LENGTH: 339
<212> TYPE: PRT
<213> ORGANISM: Cp1

<400> SEQUENCE: 52

Met Val Lys Lys Asn Asp Leu Phe Val Asp Val Ser Ser His Asn Gly
1               5                   10                  15

Tyr Asp Ile Thr Gly Ile Leu Glu Gln Met Gly Thr Thr Asn Thr Ile
            20                  25                  30

Ile Lys Ile Ser Glu Ser Thr Thr Tyr Leu Asn Pro Cys Leu Ser Ala
        35                  40                  45

Gln Val Glu Gln Ser Asn Pro Ile Gly Phe Tyr His Phe Ala Arg Phe
    50                  55                  60

Gly Gly Asp Val Ala Glu Ala Glu Arg Glu Ala Gln Phe Phe Leu Asp
65                  70                  75                  80

Asn Val Pro Met Gln Val Lys Tyr Leu Val Leu Asp Tyr Glu Asp Asp
                85                  90                  95

Pro Ser Gly Asp Ala Gln Ala Asn Thr Asn Ala Cys Leu Arg Phe Met
            100                 105                 110
```

```
Gln Met Ile Ala Asp Ala Gly Tyr Lys Pro Ile Tyr Tyr Ser Tyr Lys
        115                 120                 125

Pro Phe Thr His Asp Asn Val Asp Tyr Gln Gln Ile Leu Ala Gln Phe
    130                 135                 140

Pro Asn Ser Leu Trp Ile Ala Gly Tyr Gly Leu Asn Asp Gly Thr Ala
145                 150                 155                 160

Asn Phe Glu Tyr Phe Pro Ser Met Asp Gly Ile Arg Trp Trp Gln Tyr
                165                 170                 175

Ser Ser Asn Pro Phe Asp Lys Asn Ile Val Leu Leu Asp Asp Glu Glu
            180                 185                 190

Asp Asp Lys Pro Lys Thr Ala Gly Thr Trp Lys Gln Asp Ser Lys Gly
        195                 200                 205

Trp Trp Phe Arg Arg Asn Asn Gly Ser Phe Pro Tyr Asn Lys Trp Glu
    210                 215                 220

Lys Ile Gly Gly Val Trp Tyr Tyr Phe Asp Ser Lys Gly Tyr Cys Leu
225                 230                 235                 240

Thr Ser Glu Trp Leu Lys Asp Asn Glu Lys Trp Tyr Tyr Leu Lys Asp
                245                 250                 255

Asn Gly Ala Met Ala Thr Gly Trp Val Leu Val Gly Ser Glu Trp Tyr
            260                 265                 270

Tyr Met Asp Asp Ser Gly Ala Met Val Thr Gly Trp Val Lys Tyr Lys
        275                 280                 285

Asn Asn Trp Tyr Tyr Met Thr Asn Glu Arg Gly Asn Met Val Ser Asn
    290                 295                 300

Glu Phe Ile Lys Ser Gly Lys Gly Trp Tyr Phe Met Asn Thr Asn Gly
305                 310                 315                 320

Glu Leu Ala Asp Asn Pro Ser Phe Thr Lys Glu Pro Asp Gly Leu Ile
                325                 330                 335

Thr Val Ala


<210> SEQ ID NO 53
<211> LENGTH: 296
<212> TYPE: PRT
<213> ORGANISM: Dp-1

<400> SEQUENCE: 53

Met Gly Val Asp Ile Glu Lys Gly Val Ala Trp Met Gln Ala Arg Lys
1               5                   10                  15

Gly Arg Val Ser Tyr Ser Met Asp Phe Arg Asp Gly Pro Asp Ser Tyr
            20                  25                  30

Asp Cys Ser Ser Ser Met Tyr Tyr Ala Leu Arg Ser Ala Gly Ala Ser
        35                  40                  45

Ser Ala Gly Trp Ala Val Asn Thr Glu Tyr Met His Ala Trp Leu Ile
    50                  55                  60

Glu Asn Gly Tyr Glu Leu Ile Ser Glu Asn Ala Pro Trp Asp Ala Lys
65                  70                  75                  80

Arg Gly Asp Ile Phe Ile Trp Gly Arg Lys Gly Ala Ser Ala Gly Ala
                85                  90                  95

Gly Gly His Thr Gly Met Phe Ile Asp Ser Asp Asn Ile Ile His Cys
            100                 105                 110

Asn Tyr Ala Tyr Asp Gly Ile Ser Val Asn Asp His Asp Glu Arg Trp
        115                 120                 125

Tyr Tyr Ala Gly Gln Pro Tyr Tyr Tyr Val Tyr Arg Leu Thr Asn Ala
    130                 135                 140
```

Asn Ala Gln Pro Ala Glu Lys Lys Leu Gly Trp Gln Lys Asp Ala Thr
145 150 155 160

Gly Phe Trp Tyr Ala Arg Ala Asn Gly Thr Tyr Pro Lys Asp Glu Phe
165 170 175

Glu Tyr Ile Glu Glu Asn Lys Ser Trp Phe Tyr Phe Asp Asp Gln Gly
180 185 190

Tyr Met Leu Ala Glu Lys Trp Leu Lys His Thr Asp Gly Asn Trp Tyr
195 200 205

Trp Phe Asp Arg Asp Gly Tyr Met Ala Thr Ser Trp Lys Arg Ile Gly
210 215 220

Glu Ser Trp Tyr Tyr Phe Asn Arg Asp Gly Ser Met Val Thr Gly Trp
225 230 235 240

Ile Lys Tyr Tyr Asp Asn Trp Tyr Tyr Cys Asp Ala Thr Asn Gly Asp
245 250 255

Met Lys Ser Asn Ala Phe Ile Arg Tyr Asn Asp Gly Trp Tyr Leu Leu
260 265 270

Leu Pro Asp Gly Arg Leu Ala Asp Lys Pro Gln Phe Thr Val Glu Pro
275 280 285

Asp Gly Leu Ile Thr Ala Lys Val
290 295

<210> SEQ ID NO 54
<211> LENGTH: 233
<212> TYPE: PRT
<213> ORGANISM: gamma

<400> SEQUENCE: 54

Met Glu Ile Gln Lys Lys Leu Val Asp Pro Ser Lys Tyr Gly Thr Lys
1 5 10 15

Cys Pro Tyr Thr Met Lys Pro Lys Tyr Ile Thr Val His Asn Thr Tyr
20 25 30

Asn Asp Ala Pro Ala Glu Asn Glu Val Ser Tyr Met Ile Ser Asn Asn
35 40 45

Asn Glu Val Ser Phe His Ile Ala Val Asp Asp Lys Lys Ala Ile Gln
50 55 60

Gly Ile Pro Leu Glu Arg Asn Ala Trp Ala Cys Gly Asp Gly Asn Gly
65 70 75 80

Ser Gly Asn Arg Gln Ser Ile Ser Val Glu Ile Cys Tyr Ser Lys Ser
85 90 95

Gly Gly Asp Arg Tyr Tyr Lys Ala Glu Asp Asn Ala Val Asp Val Val
100 105 110

Arg Gln Leu Met Ser Met Tyr Asn Ile Pro Ile Glu Asn Val Arg Thr
115 120 125

His Gln Ser Trp Ser Gly Lys Tyr Cys Pro His Arg Met Leu Ala Glu
130 135 140

Gly Arg Trp Gly Ala Phe Ile Gln Lys Val Lys Asn Gly Asn Val Ala
145 150 155 160

Thr Thr Ser Pro Thr Lys Gln Asn Ile Ile Gln Ser Gly Ala Phe Ser
165 170 175

Pro Tyr Glu Thr Pro Asp Val Met Gly Ala Leu Thr Ser Leu Lys Met
180 185 190

Thr Ala Asp Phe Ile Leu Gln Ser Asp Gly Leu Thr Tyr Phe Ile Ser
195 200 205

Lys Pro Thr Ser Asp Ala Gln Leu Lys Ala Met Lys Glu Tyr Leu Asp

```
    210                 215                 220

Arg Lys Gly Trp Trp Tyr Glu Val Lys
225                 230


<210> SEQ ID NO 55
<211> LENGTH: 481
<212> TYPE: PRT
<213> ORGANISM: MR11

<400> SEQUENCE: 55

Met Gln Ala Lys Leu Thr Lys Lys Glu Phe Ile Glu Trp Leu Lys Thr
1               5                   10                  15

Ser Glu Gly Lys Gln Phe Asn Val Asp Leu Trp Tyr Gly Phe Gln Cys
            20                  25                  30

Phe Asp Tyr Ala Asn Ala Gly Trp Lys Val Leu Phe Gly Leu Leu Leu
        35                  40                  45

Lys Gly Leu Gly Ala Lys Asp Ile Pro Phe Ala Asn Asn Phe Asp Gly
    50                  55                  60

Leu Ala Thr Val Tyr Gln Asn Thr Pro Asp Phe Leu Ala Gln Pro Gly
65                  70                  75                  80

Asp Met Val Val Phe Gly Ser Asn Tyr Gly Ala Gly Tyr Gly His Val
                85                  90                  95

Ala Trp Val Ile Glu Ala Thr Leu Asp Tyr Ile Ile Val Tyr Glu Gln
            100                 105                 110

Asn Trp Leu Gly Gly Gly Trp Thr Asp Arg Ile Glu Gln Pro Gly Trp
        115                 120                 125

Gly Trp Glu Lys Val Thr Arg Arg Gln His Ala Tyr Asp Phe Pro Met
    130                 135                 140

Trp Phe Ile Arg Pro Asn Phe Lys Ser Glu Thr Ala Pro Arg Ser Ile
145                 150                 155                 160

Gln Ser Pro Thr Gln Ala Ser Lys Lys Glu Thr Ala Lys Pro Gln Pro
                165                 170                 175

Lys Ala Val Glu Leu Lys Ile Ile Lys Asp Val Val Lys Gly Tyr Asp
            180                 185                 190

Leu Pro Lys Arg Gly Gly Asn Pro Lys Gly Ile Val Ile His Asn Asp
        195                 200                 205

Ala Gly Ser Lys Gly Ala Thr Ala Glu Ala Tyr Arg Asn Gly Leu Val
    210                 215                 220

Asn Ala Pro Leu Ser Arg Leu Glu Ala Gly Ile Ala His Ser Tyr Val
225                 230                 235                 240

Ser Gly Asn Thr Val Trp Gln Ala Leu Asp Glu Ser Gln Val Gly Trp
                245                 250                 255

His Thr Ala Asn Gln Leu Gly Asn Lys Tyr Tyr Tyr Gly Ile Glu Val
            260                 265                 270

Cys Gln Ser Met Gly Ala Asp Asn Ala Thr Phe Leu Lys Asn Glu Gln
        275                 280                 285

Ala Thr Phe Gln Glu Cys Ala Arg Leu Leu Lys Lys Trp Gly Leu Pro
    290                 295                 300

Ala Asn Arg Asn Thr Ile Arg Leu His Asn Glu Phe Thr Ser Thr Ser
305                 310                 315                 320

Cys Pro His Arg Ser Ser Val Leu His Thr Gly Phe Asp Pro Val Thr
                325                 330                 335

Arg Gly Leu Leu Pro Glu Asp Lys Gln Leu Gln Leu Lys Asp Tyr Phe
            340                 345                 350
```

Ile Lys Gln Ile Arg Val Tyr Met Asp Gly Lys Ile Pro Val Ala Thr
355 360 365

Val Ser Asn Glu Ser Ser Ala Ser Ser Asn Thr Val Lys Pro Val Ala
370 375 380

Ser Ala Trp Lys Arg Asn Lys Tyr Gly Thr Tyr Tyr Met Glu Glu Asn
385 390 395 400

Ala Arg Phe Thr Asn Gly Asn Gln Pro Ile Thr Val Arg Lys Ile Gly
405 410 415

Pro Phe Leu Ser Cys Pro Val Ala Tyr Gln Phe Gln Pro Gly Gly Tyr
420 425 430

Cys Asp Tyr Thr Glu Val Met Leu Gln Asp Gly His Val Trp Val Gly
435 440 445

Tyr Thr Trp Glu Gly Gln Arg Tyr Tyr Leu Pro Ile Arg Thr Trp Asn
450 455 460

Gly Ser Ala Pro Pro Asn Gln Ile Leu Gly Asp Leu Trp Gly Glu Ile
465 470 475 480

Ser

<210> SEQ ID NO 56
<211> LENGTH: 239
<212> TYPE: PRT
<213> ORGANISM: B30

<400> SEQUENCE: 56

Met Val Ile Asn Ile Glu Gln Ala Ile Ala Trp Met Ala Ser Arg Lys
1 5 10 15

Gly Lys Val Thr Tyr Ser Met Asp Tyr Arg Asn Gly Pro Ser Ser Tyr
20 25 30

Asp Cys Ser Ser Ser Val Tyr Phe Ala Leu Arg Ser Ala Gly Ala Ser
35 40 45

Asp Asn Gly Trp Ala Val Asn Thr Glu Tyr Glu His Asp Trp Leu Ile
50 55 60

Lys Asn Gly Tyr Val Leu Ile Ala Glu Asn Thr Asn Trp Asn Ala Gln
65 70 75 80

Arg Gly Asp Ile Phe Ile Trp Gly Lys Arg Gly Ala Ser Ala Gly Ala
85 90 95

Phe Gly His Thr Gly Met Phe Val Asp Pro Asp Asn Ile Ile His Cys
100 105 110

Asn Tyr Gly Tyr Asn Ser Ile Thr Val Asn Asn His Asp Glu Ile Trp
115 120 125

Gly Tyr Asn Gly Gln Pro Tyr Val Tyr Ala Tyr Arg Tyr Ser Gly Lys
130 135 140

Gln Ser Asn Ala Lys Val Asp Asn Lys Ser Val Val Ser Lys Phe Glu
145 150 155 160

Lys Glu Leu Asp Val Asn Thr Pro Leu Ser Asn Ser Asn Met Pro Tyr
165 170 175

Tyr Glu Ala Thr Ile Ser Glu Asp Tyr Tyr Val Glu Ser Lys Pro Asp
180 185 190

Val Asn Ser Thr Asp Lys Glu Leu Leu Val Ala Gly Thr Arg Val Arg
195 200 205

Val Tyr Glu Lys Val Lys Gly Trp Ala Arg Ile Gly Ala Pro Gln Ser
210 215 220

Asn Gln Trp Val Glu Asp Ala Tyr Leu Ile Asp Ala Thr Asp Met
225 230 235

<210> SEQ ID NO 57
<211> LENGTH: 495
<212> TYPE: PRT
<213> ORGANISM: K

<400> SEQUENCE: 57

```
Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
            20                  25                  30

Asp Pro Ser Phe Gly Val Met Glu Ala Gly Ala Ile Asp Ala Asp Gly
        35                  40                  45

Tyr Tyr His Ala Gln Cys Gln Asp Leu Ile Thr Asp Tyr Val Leu Trp
    50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Glu Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys
    130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Lys Ala Thr Leu Lys Val
            180                 185                 190

Ser Lys Asn His Ile Asn Tyr Thr Met Asp Lys Arg Gly Lys Lys Pro
        195                 200                 205

Glu Gly Met Val Ile His Asn Asp Ala Gly Arg Ser Ser Gly Gln Gln
    210                 215                 220

Tyr Glu Asn Ser Leu Ala Asn Ala Gly Tyr Ala Arg Tyr Ala Asn Gly
225                 230                 235                 240

Ile Ala His Tyr Tyr Gly Ser Glu Gly Tyr Val Trp Glu Ala Ile Asp
                245                 250                 255

Ala Lys Asn Gln Ile Ala Trp His Thr Gly Asp Gly Thr Gly Ala Asn
            260                 265                 270

Ser Gly Asn Phe Arg Phe Ala Gly Ile Glu Val Cys Gln Ser Met Ser
        275                 280                 285

Ala Ser Asp Ala Gln Phe Leu Lys Asn Glu Gln Ala Val Phe Gln Phe
    290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
                325                 330                 335

Met Val Leu His Thr Gly Phe Asn Pro Val Thr Gln Gly Arg Pro Ser
            340                 345                 350

Gln Ala Ile Met Asn Lys Leu Lys Asp Tyr Phe Ile Lys Gln Ile Lys
        355                 360                 365

Asn Tyr Met Asp Lys Gly Thr Ser Ser Ser Thr Val Val Lys Asp Gly
    370                 375                 380
```

```
Lys Thr Ser Ser Ala Ser Thr Pro Ala Thr Arg Pro Val Thr Gly Ser
385                 390                 395                 400

Trp Lys Lys Asn Gln Tyr Gly Thr Trp Tyr Lys Pro Glu Asn Ala Thr
                405                 410                 415

Phe Val Asn Gly Asn Gln Pro Ile Val Thr Arg Ile Gly Ser Pro Phe
            420                 425                 430

Leu Asn Ala Pro Val Gly Gly Asn Leu Pro Ala Gly Ala Thr Ile Val
        435                 440                 445

Tyr Asp Glu Val Cys Ile Gln Ala Gly His Ile Trp Ile Gly Tyr Asn
    450                 455                 460

Ala Tyr Asn Gly Asn Arg Val Tyr Cys Pro Val Arg Thr Cys Gln Gly
465                 470                 475                 480

Val Pro Pro Asn Gln Ile Pro Gly Val Ala Trp Gly Val Phe Lys
                485                 490                 495


<210> SEQ ID NO 58
<211> LENGTH: 281
<212> TYPE: PRT
<213> ORGANISM: A118

<400> SEQUENCE: 58

Met Thr Ser Tyr Tyr Tyr Ser Arg Ser Leu Ala Asn Val Asn Lys Leu
1               5                   10                  15

Ala Asp Asn Thr Lys Ala Ala Ala Arg Lys Leu Leu Asp Trp Ser Glu
            20                  25                  30

Ser Asn Gly Ile Glu Val Leu Ile Tyr Glu Thr Ile Arg Thr Lys Glu
        35                  40                  45

Gln Gln Ala Ala Asn Val Asn Ser Gly Ala Ser Gln Thr Met Arg Ser
    50                  55                  60

Tyr His Leu Val Gly Gln Ala Leu Asp Phe Val Met Ala Lys Gly Lys
65                  70                  75                  80

Thr Val Asp Trp Gly Ala Tyr Arg Ser Asp Lys Gly Lys Lys Phe Val
                85                  90                  95

Ala Lys Ala Lys Ser Leu Gly Phe Glu Trp Gly Gly Asp Trp Ser Gly
            100                 105                 110

Phe Val Asp Asn Pro His Leu Gln Phe Asn Tyr Lys Gly Tyr Gly Thr
        115                 120                 125

Asp Thr Phe Gly Lys Gly Ala Ser Thr Ser Asn Ser Ser Lys Pro Ser
    130                 135                 140

Ala Asp Thr Asn Thr Asn Ser Leu Gly Leu Val Asp Tyr Met Asn Leu
145                 150                 155                 160

Asn Lys Leu Asp Ser Ser Phe Ala Asn Arg Lys Lys Leu Ala Thr Ser
                165                 170                 175

Tyr Gly Ile Lys Asn Tyr Ser Gly Thr Ala Thr Gln Asn Thr Thr Leu
            180                 185                 190

Leu Ala Lys Leu Lys Ala Gly Lys Pro His Thr Pro Ala Ser Lys Asn
        195                 200                 205

Thr Tyr Tyr Thr Glu Asn Pro Arg Lys Val Lys Thr Leu Val Gln Cys
    210                 215                 220

Asp Leu Tyr Lys Ser Val Asp Phe Thr Thr Lys Asn Gln Thr Gly Gly
225                 230                 235                 240

Thr Phe Pro Pro Gly Thr Val Phe Thr Ile Ser Gly Met Gly Lys Thr
                245                 250                 255

Lys Gly Gly Thr Pro Arg Leu Lys Thr Lys Ser Gly Tyr Tyr Leu Thr
```

```
            260                 265                 270

Ala Asn Thr Lys Phe Val Lys Lys Ile
        275                 280


<210> SEQ ID NO 59
<211> LENGTH: 341
<212> TYPE: PRT
<213> ORGANISM: A511

<400> SEQUENCE: 59

Met Val Lys Tyr Thr Val Glu Asn Lys Ile Ile Ala Gly Leu Pro Lys
1               5                   10                  15

Gly Lys Leu Lys Gly Ala Asn Phe Val Ile Ala His Glu Thr Ala Asn
            20                  25                  30

Ser Lys Ser Thr Ile Asp Asn Glu Val Ser Tyr Met Thr Arg Asn Trp
        35                  40                  45

Lys Asn Ala Phe Val Thr His Phe Val Gly Gly Gly Gly Arg Val Val
    50                  55                  60

Gln Val Ala Asn Val Asn Tyr Val Ser Trp Gly Ala Gly Gln Tyr Ala
65                  70                  75                  80

Asn Ser Tyr Ser Tyr Ala Gln Val Glu Leu Cys Arg Thr Ser Asn Ala
                85                  90                  95

Thr Thr Phe Lys Lys Asp Tyr Glu Val Tyr Cys Gln Leu Leu Val Asp
            100                 105                 110

Leu Ala Lys Lys Ala Gly Ile Pro Ile Thr Leu Asp Ser Gly Ser Lys
        115                 120                 125

Thr Ser Asp Lys Gly Ile Lys Ser His Lys Trp Val Ala Asp Lys Leu
    130                 135                 140

Gly Gly Thr Thr His Gln Asp Pro Tyr Ala Tyr Leu Ser Ser Trp Gly
145                 150                 155                 160

Ile Ser Lys Ala Gln Phe Ala Ser Asp Leu Ala Lys Val Ser Gly Gly
                165                 170                 175

Gly Asn Thr Gly Thr Ala Pro Ala Lys Pro Ser Thr Pro Ala Pro Lys
            180                 185                 190

Pro Ser Thr Pro Ser Thr Asn Leu Asp Lys Leu Gly Leu Val Asp Tyr
        195                 200                 205

Met Asn Ala Lys Lys Met Asp Ser Ser Tyr Ser Asn Arg Asp Lys Leu
    210                 215                 220

Ala Lys Gln Tyr Gly Ile Ala Asn Tyr Ser Gly Thr Ala Ser Gln Asn
225                 230                 235                 240

Thr Thr Leu Leu Ser Lys Ile Lys Gly Gly Ala Pro Lys Pro Ser Thr
                245                 250                 255

Pro Ala Pro Lys Pro Ser Thr Ser Thr Ala Lys Lys Ile Tyr Phe Pro
            260                 265                 270

Pro Asn Lys Gly Asn Trp Ser Val Tyr Pro Thr Asn Lys Ala Pro Val
        275                 280                 285

Lys Ala Asn Ala Ile Gly Ala Ile Asn Pro Thr Lys Phe Gly Gly Leu
    290                 295                 300

Thr Tyr Thr Ile Gln Lys Asp Arg Gly Asn Gly Val Tyr Glu Ile Gln
305                 310                 315                 320

Thr Asp Gln Phe Gly Arg Val Gln Val Tyr Gly Ala Pro Ser Thr Gly
                325                 330                 335

Ala Val Ile Lys Lys
            340
```

<210> SEQ ID NO 60
<211> LENGTH: 289
<212> TYPE: PRT
<213> ORGANISM: A500

<400> SEQUENCE: 60

Met Ala Leu Thr Glu Ala Trp Leu Ile Glu Lys Ala Asn Arg Lys Leu
1 5 10 15

Asn Ala Gly Gly Met Tyr Lys Ile Thr Ser Asp Lys Thr Arg Asn Val
20 25 30

Ile Lys Lys Met Ala Lys Glu Gly Ile Tyr Leu Cys Val Ala Gln Gly
35 40 45

Tyr Arg Ser Thr Ala Glu Gln Asn Ala Leu Tyr Ala Gln Gly Arg Thr
50 55 60

Lys Pro Gly Ala Ile Val Thr Asn Ala Lys Gly Gly Gln Ser Asn His
65 70 75 80

Asn Tyr Gly Val Ala Val Asp Leu Cys Leu Tyr Thr Asn Asp Gly Lys
85 90 95

Asp Val Ile Trp Glu Ser Thr Thr Ser Arg Trp Lys Lys Val Val Ala
100 105 110

Ala Met Lys Ala Glu Gly Phe Lys Trp Gly Gly Asp Trp Lys Ser Phe
115 120 125

Lys Asp Tyr Pro His Phe Glu Leu Cys Asp Ala Val Ser Gly Glu Lys
130 135 140

Ile Pro Ala Ala Thr Gln Asn Thr Asn Thr Asn Ser Asn Arg Tyr Glu
145 150 155 160

Gly Lys Val Ile Asp Ser Ala Pro Leu Leu Pro Lys Met Asp Phe Lys
165 170 175

Ser Ser Pro Phe Arg Met Tyr Lys Val Gly Thr Glu Phe Leu Val Tyr
180 185 190

Asp His Asn Gln Tyr Trp Tyr Lys Thr Tyr Ile Asp Asp Lys Leu Tyr
195 200 205

Tyr Met Tyr Lys Ser Phe Cys Asp Val Val Ala Lys Lys Asp Ala Lys
210 215 220

Gly Arg Ile Lys Val Arg Ile Lys Ser Ala Lys Asp Leu Arg Ile Pro
225 230 235 240

Val Trp Asn Asn Ile Lys Leu Asn Ser Gly Lys Ile Lys Trp Tyr Ala
245 250 255

Pro Asn Val Lys Leu Ala Trp Tyr Asn Tyr Arg Arg Gly Tyr Leu Glu
260 265 270

Leu Trp Tyr Pro Asn Asp Gly Trp Tyr Tyr Thr Ala Glu Tyr Phe Leu
275 280 285

Lys

<210> SEQ ID NO 61
<211> LENGTH: 239
<212> TYPE: PRT
<213> ORGANISM: LambdaSa1 prophage

<400> SEQUENCE: 61

Met Val Ile Asn Ile Glu Gln Ala Ile Ala Trp Met Ala Ser Arg Lys
1 5 10 15

Gly Lys Val Thr Tyr Ser Met Asp Tyr Arg Asn Gly Pro Ser Ser Tyr
20 25 30

Asp Cys Ser Ser Ser Val Tyr Phe Ala Leu Arg Ser Ala Gly Ala Ser

```
        35                  40                  45

Asp Asn Gly Trp Ala Val Asn Thr Glu Tyr Glu His Asp Trp Leu Ile
    50                  55                  60

Lys Asn Gly Tyr Val Leu Ile Ala Glu Asn Thr Asn Trp Asn Ala Gln
65                  70                  75                  80

Arg Gly Asp Ile Phe Ile Trp Gly Lys Arg Gly Ala Ser Ala Gly Ala
                85                  90                  95

Phe Gly His Thr Gly Met Phe Val Asp Pro Asp Asn Ile Ile His Cys
            100                 105                 110

Asn Tyr Gly Tyr Asn Ser Ile Thr Val Asn Asn His Asp Glu Ile Trp
        115                 120                 125

Gly Tyr Asn Gly Gln Pro Tyr Val Tyr Ala Tyr Arg Tyr Ala Arg Lys
    130                 135                 140

Gln Ser Asn Ala Lys Val Asp Asn Gln Ser Val Val Ser Lys Phe Glu
145                 150                 155                 160

Lys Glu Leu Asp Val Asn Thr Pro Leu Ser Asn Ser Asn Met Pro Tyr
                165                 170                 175

Tyr Glu Ala Thr Ile Ser Glu Asp Tyr Tyr Val Glu Ser Lys Pro Asp
            180                 185                 190

Val Asn Ser Thr Asp Lys Glu Leu Leu Val Ala Gly Thr Arg Val Arg
        195                 200                 205

Val Tyr Glu Lys Val Lys Gly Trp Ala Arg Ile Gly Ala Pro Gln Ser
    210                 215                 220

Asn Gln Trp Val Glu Asp Ala Tyr Leu Ile Asp Ala Thr Asp Met
225                 230                 235


<210> SEQ ID NO 62
<211> LENGTH: 468
<212> TYPE: PRT
<213> ORGANISM: LambdaSa2 prophage

<400> SEQUENCE: 62

Met Glu Ile Asn Thr Glu Ile Ala Ile Ala Trp Met Ser Ala Arg Gln
1               5                   10                  15

Gly Lys Val Ser Tyr Ser Met Asp Tyr Arg Asp Gly Pro Asn Ser Tyr
            20                  25                  30

Asp Cys Ser Ser Ser Val Tyr Tyr Ala Leu Arg Ser Ala Gly Ala Ser
        35                  40                  45

Ser Ala Gly Trp Ala Val Asn Thr Glu Tyr Met His Asp Trp Leu Ile
    50                  55                  60

Lys Asn Gly Tyr Glu Leu Ile Ala Glu Asn Val Asp Trp Asn Ala Val
65                  70                  75                  80

Arg Gly Asp Ile Ala Ile Trp Gly Met Arg Gly His Ser Ser Gly Ala
                85                  90                  95

Gly Gly His Val Val Met Phe Ile Asp Pro Glu Asn Ile Ile His Cys
            100                 105                 110

Asn Trp Ala Asn Asn Gly Ile Thr Val Asn Asn Tyr Asn Gln Thr Ala
        115                 120                 125

Ala Ala Ser Gly Trp Met Tyr Cys Tyr Val Tyr Arg Leu Lys Ser Gly
    130                 135                 140

Ala Ser Thr Gln Gly Lys Ser Leu Asp Thr Leu Val Lys Glu Thr Leu
145                 150                 155                 160

Ala Gly Asn Tyr Gly Asn Gly Glu Ala Arg Lys Ala Val Leu Gly Asn
                165                 170                 175
```

Gln Tyr Glu Ala Val Met Ser Val Ile Asn Gly Lys Thr Thr Thr Asn
180 185 190

Gln Lys Thr Val Asp Gln Leu Val Gln Glu Val Ile Ala Gly Lys His
195 200 205

Gly Asn Gly Glu Ala Arg Lys Lys Ser Leu Gly Ser Gln Tyr Asp Ala
210 215 220

Val Gln Lys Arg Val Thr Glu Leu Leu Lys Lys Gln Pro Ser Glu Pro
225 230 235 240

Phe Lys Ala Gln Glu Val Asn Lys Pro Thr Glu Thr Lys Thr Ser Gln
245 250 255

Thr Glu Leu Thr Gly Gln Ala Thr Ala Thr Lys Glu Glu Gly Asp Leu
260 265 270

Ser Phe Asn Gly Thr Ile Leu Lys Lys Ala Val Leu Asp Lys Ile Leu
275 280 285

Gly Asn Cys Lys Lys His Asp Ile Leu Pro Ser Tyr Ala Leu Thr Ile
290 295 300

Leu His Tyr Glu Gly Leu Trp Gly Thr Ser Ala Val Gly Lys Ala Asp
305 310 315 320

Asn Asn Trp Gly Gly Met Thr Trp Thr Gly Gln Gly Asn Arg Pro Ser
325 330 335

Gly Val Thr Val Thr Gln Gly Ser Ala Arg Pro Ser Asn Glu Gly Gly
340 345 350

His Tyr Met His Tyr Ala Ser Val Asp Asp Phe Leu Thr Asp Trp Phe
355 360 365

Tyr Leu Leu Arg Ala Gly Gly Ser Tyr Lys Val Ser Gly Ala Lys Thr
370 375 380

Phe Ser Glu Ala Ile Lys Gly Met Phe Lys Val Gly Gly Ala Val Tyr
385 390 395 400

Asp Tyr Ala Ala Ser Gly Phe Asp Ser Tyr Ile Val Gly Ala Ser Ser
405 410 415

Arg Leu Lys Ala Ile Glu Ala Glu Asn Gly Ser Leu Asp Lys Phe Asp
420 425 430

Lys Ala Thr Asp Ile Gly Asp Gly Ser Lys Asp Lys Ile Asp Ile Thr
435 440 445

Ile Glu Gly Ile Glu Val Thr Ile Asn Gly Ile Thr Tyr Glu Leu Thr
450 455 460

Lys Lys Pro Val
465

<210> SEQ ID NO 63
<211> LENGTH: 236
<212> TYPE: PRT
<213> ORGANISM: (ATCC700407) prophage

<400> SEQUENCE: 63

Met Thr Asp Ser Ile Gln Glu Met Arg Lys Leu Gln Ser Ile Pro Val
1 5 10 15

Arg Tyr Asp Met Gly Asp Arg Tyr Gly Asn Asp Ala Asp Arg Asp Gly
20 25 30

Arg Ile Glu Met Asp Cys Ser Ser Ala Val Ser Lys Ala Leu Gly Ile
35 40 45

Ser Met Thr Asn Asn Thr Glu Thr Leu Gln Gln Ala Leu Pro Ala Ile
50 55 60

Gly Tyr Gly Lys Ile His Asp Ala Val Asp Gly Thr Phe Asp Met Gln
65 70 75 80

```
Ala Tyr Asp Val Ile Ile Trp Ala Pro Arg Asp Gly Ser Ser Ser Leu
                85                  90                  95

Gly Ala Phe Gly His Val Leu Ile Ala Thr Ser Pro Thr Thr Ala Ile
            100                 105                 110

His Cys Asn Tyr Gly Ser Asp Gly Ile Thr Glu Asn Asp Tyr Asn Tyr
        115                 120                 125

Ile Trp Glu Ile Asn Gly Arg Pro Arg Glu Ile Val Phe Arg Lys Gly
    130                 135                 140

Val Thr Gln Thr Gln Ala Thr Val Thr Ser Gln Phe Glu Arg Glu Leu
145                 150                 155                 160

Asp Val Asn Ala Arg Leu Thr Val Ser Asp Lys Pro Tyr Tyr Glu Ala
                165                 170                 175

Thr Leu Ser Glu Asp Tyr Tyr Val Glu Ala Gly Pro Arg Ile Asp Ser
            180                 185                 190

Gln Asp Lys Glu Leu Ile Lys Ala Gly Thr Arg Val Arg Val Tyr Glu
        195                 200                 205

Lys Leu Asn Gly Trp Ser Arg Ile Asn His Pro Glu Ser Ala Gln Trp
    210                 215                 220

Val Glu Asp Ser Tyr Leu Val Asp Ala Thr Glu Met
225                 230                 235


<210> SEQ ID NO 64
<211> LENGTH: 481
<212> TYPE: PRT
<213> ORGANISM: Phi11 and Phi12

<400> SEQUENCE: 64

Met Gln Ala Lys Leu Thr Lys Asn Glu Phe Ile Glu Trp Leu Lys Thr
1               5                   10                  15

Ser Glu Gly Lys Gln Phe Asn Val Asp Leu Trp Tyr Gly Phe Gln Cys
            20                  25                  30

Phe Asp Tyr Ala Asn Ala Gly Trp Lys Val Leu Phe Gly Leu Leu Leu
        35                  40                  45

Lys Gly Leu Gly Ala Lys Asp Ile Pro Phe Ala Asn Asn Phe Asp Gly
    50                  55                  60

Leu Ala Thr Val Tyr Gln Asn Thr Pro Asp Phe Leu Ala Gln Pro Gly
65                  70                  75                  80

Asp Met Val Val Phe Gly Ser Asn Tyr Gly Ala Gly Tyr Gly His Val
                85                  90                  95

Ala Trp Val Ile Glu Ala Thr Leu Asp Tyr Ile Ile Val Tyr Glu Gln
            100                 105                 110

Asn Trp Leu Gly Gly Gly Trp Thr Asp Gly Ile Glu Gln Pro Gly Trp
        115                 120                 125

Gly Trp Glu Lys Val Thr Arg Arg Gln His Ala Tyr Asp Phe Pro Met
    130                 135                 140

Trp Phe Ile Arg Pro Asn Phe Lys Ser Glu Thr Ala Pro Arg Ser Val
145                 150                 155                 160

Gln Ser Pro Thr Gln Ala Pro Lys Lys Glu Thr Ala Lys Pro Gln Pro
                165                 170                 175

Lys Ala Val Glu Leu Lys Ile Ile Lys Asp Val Val Lys Gly Tyr Asp
            180                 185                 190

Leu Pro Lys Arg Gly Ser Asn Pro Lys Gly Ile Val Ile His Asn Asp
        195                 200                 205

Ala Gly Ser Lys Gly Ala Thr Ala Glu Ala Tyr Arg Asn Gly Leu Val
```

```
    210                 215                 220

Asn Ala Pro Leu Ser Arg Leu Glu Ala Gly Ile Ala His Ser Tyr Val
225                 230                 235                 240

Ser Gly Asn Thr Val Trp Gln Ala Leu Asp Glu Ser Gln Val Gly Trp
                245                 250                 255

His Thr Ala Asn Gln Ile Gly Asn Lys Tyr Tyr Tyr Gly Ile Glu Val
            260                 265                 270

Cys Gln Ser Met Gly Ala Asp Asn Ala Thr Phe Leu Lys Asn Glu Gln
        275                 280                 285

Ala Thr Phe Gln Glu Cys Ala Arg Leu Leu Lys Lys Trp Gly Leu Pro
    290                 295                 300

Ala Asn Arg Asn Thr Ile Arg Leu His Asn Glu Phe Thr Ser Thr Ser
305                 310                 315                 320

Cys Pro His Arg Ser Ser Val Leu His Thr Gly Phe Asp Pro Val Thr
                325                 330                 335

Arg Gly Leu Leu Pro Glu Asp Lys Arg Leu Gln Leu Lys Asp Tyr Phe
            340                 345                 350

Ile Lys Gln Ile Arg Ala Tyr Met Asp Gly Lys Ile Pro Val Ala Thr
        355                 360                 365

Val Ser Asn Glu Ser Ser Ala Ser Ser Asn Thr Val Lys Pro Val Ala
    370                 375                 380

Ser Ala Trp Lys Arg Asn Lys Tyr Gly Thr Tyr Tyr Met Glu Glu Ser
385                 390                 395                 400

Ala Arg Phe Thr Asn Gly Asn Gln Pro Ile Thr Val Arg Lys Val Gly
                405                 410                 415

Pro Phe Leu Ser Cys Pro Val Gly Tyr Gln Phe Gln Pro Gly Gly Tyr
            420                 425                 430

Cys Asp Tyr Thr Glu Val Met Leu Gln Asp Gly His Val Trp Val Gly
        435                 440                 445

Tyr Thr Trp Glu Gly Gln Arg Tyr Tyr Leu Pro Ile Arg Thr Trp Asn
    450                 455                 460

Gly Ser Ala Pro Pro Asn Gln Ile Leu Gly Asp Leu Trp Gly Glu Ile
465                 470                 475                 480

Ser


<210> SEQ ID NO 65
<211> LENGTH: 481
<212> TYPE: PRT
<213> ORGANISM: (Phi)H5

<400> SEQUENCE: 65

Met Gln Ala Lys Leu Thr Lys Lys Glu Phe Ile Glu Trp Leu Lys Thr
1               5                   10                  15

Ser Glu Gly Lys Gln Tyr Asn Ala Asp Gly Trp Tyr Gly Phe Gln Cys
            20                  25                  30

Phe Asp Tyr Ala Asn Ala Gly Trp Lys Ala Leu Phe Gly Leu Leu Leu
        35                  40                  45

Lys Gly Val Gly Ala Lys Asp Ile Pro Phe Ala Asn Asn Phe Asp Gly
    50                  55                  60

Leu Ala Thr Val Tyr Gln Asn Thr Pro Asp Phe Leu Ala Gln Pro Gly
65                  70                  75                  80

Asp Met Val Val Phe Gly Ser Asn Tyr Gly Ala Gly Tyr Gly His Val
                85                  90                  95

Ala Trp Val Ile Glu Ala Thr Leu Asp Tyr Ile Ile Val Tyr Glu Gln
```

```
            100                 105                 110

Asn Trp Leu Gly Gly Gly Trp Thr Asp Gly Val Gln Gln Pro Gly Ser
        115                 120                 125

Gly Trp Glu Lys Val Thr Arg Arg Gln His Ala Tyr Asp Phe Pro Met
    130                 135                 140

Trp Phe Ile Arg Pro Asn Phe Lys Ser Glu Thr Ala Pro Arg Ser Val
145                 150                 155                 160

Gln Ser Pro Thr Gln Ala Ser Lys Lys Glu Thr Ala Lys Pro Gln Pro
                165                 170                 175

Lys Ala Val Glu Leu Lys Ile Ile Lys Asp Val Val Lys Gly Tyr Asp
            180                 185                 190

Leu Pro Lys Arg Gly Ser Asn Pro Asn Phe Ile Val Ile His Asn Asp
        195                 200                 205

Ala Gly Ser Lys Gly Ala Thr Ala Glu Ala Tyr Arg Asn Gly Leu Val
    210                 215                 220

Asn Ala Pro Leu Ser Arg Leu Glu Ala Gly Ile Ala His Ser Tyr Val
225                 230                 235                 240

Ser Gly Asn Thr Val Trp Gln Ala Leu Asp Glu Ser Gln Val Gly Trp
                245                 250                 255

His Thr Ala Asn Gln Ile Gly Asn Lys Tyr Gly Tyr Gly Ile Glu Val
            260                 265                 270

Cys Gln Ser Met Gly Ala Asp Asn Ala Thr Phe Leu Lys Asn Glu Gln
        275                 280                 285

Ala Thr Phe Gln Glu Cys Ala Arg Leu Leu Lys Lys Trp Gly Leu Pro
    290                 295                 300

Ala Asn Arg Asn Thr Ile Arg Leu His Asn Glu Phe Thr Ser Thr Ser
305                 310                 315                 320

Cys Pro His Arg Ser Ser Val Leu His Thr Gly Phe Asp Pro Val Thr
                325                 330                 335

Arg Gly Leu Leu Pro Glu Asp Lys Arg Leu Gln Leu Lys Asp Tyr Phe
            340                 345                 350

Ile Lys Gln Ile Arg Ala Tyr Met Asp Gly Lys Ile Pro Val Ala Thr
        355                 360                 365

Val Ser Asn Asp Ser Ser Ala Ser Ser Asn Thr Val Lys Pro Val Ala
    370                 375                 380

Ser Ala Trp Lys Arg Asn Lys Tyr Gly Thr Tyr Tyr Met Glu Glu Ser
385                 390                 395                 400

Ala Arg Phe Thr Asn Gly Asn Gln Pro Ile Thr Val Arg Lys Val Gly
                405                 410                 415

Pro Phe Leu Ser Cys Pro Val Gly Tyr Gln Phe Gln Pro Gly Gly Tyr
            420                 425                 430

Cys Asp Tyr Thr Glu Val Met Leu Gln Asp Gly His Val Trp Val Gly
        435                 440                 445

Tyr Thr Trp Glu Gly Gln Arg Tyr Tyr Leu Pro Ile Arg Thr Trp Asn
    450                 455                 460

Gly Ser Ala Pro Pro Asn Gln Ile Leu Gly Asp Leu Trp Gly Glu Ile
465                 470                 475                 480

Ser
```

<210> SEQ ID NO 66
<211> LENGTH: 477
<212> TYPE: PRT
<213> ORGANISM: (Phi)WMY

<400> SEQUENCE: 66

Met Lys Thr Lys Ala Gln Ala Lys Ser Trp Ile Asn Ser Lys Ile Gly
1               5                   10                  15

Lys Gly Ile Asp Trp Asp Gly Met Tyr Gly Tyr Gln Cys Met Asp Glu
            20                  25                  30

Ala Val Asp Tyr Ile His His Val Thr Asp Gly Lys Val Thr Met Trp
        35                  40                  45

Gly Asn Ala Ile Asp Ala Pro Lys Asn Asn Phe Gln Gly Leu Cys Thr
    50                  55                  60

Val Tyr Thr Asn Thr Pro Glu Phe Arg Pro Ala Tyr Gly Asp Val Ile
65                  70                  75                  80

Val Trp Ser Tyr Gly Thr Phe Ala Thr Tyr Gly His Ile Ala Ile Val
                85                  90                  95

Val Asn Pro Asp Pro Tyr Gly Asp Leu Gln Tyr Ile Thr Val Leu Glu
            100                 105                 110

Gln Asn Trp Asn Gly Asn Gly Ile Tyr Lys Thr Glu Phe Ala Thr Ile
        115                 120                 125

Arg Thr His Asp Tyr Thr Gly Val Ser His Phe Ile Arg Pro Lys Phe
    130                 135                 140

Ala Asp Glu Val Lys Glu Thr Ala Lys Thr Val Asn Lys Leu Ser Val
145                 150                 155                 160

Gln Lys Lys Ile Val Thr Pro Lys Asn Ser Val Glu Arg Ile Lys Asn
                165                 170                 175

Tyr Val Lys Thr Ser Gly Tyr Ile Asn Gly Glu His Tyr Glu Leu Tyr
            180                 185                 190

Asn Arg Gly His Lys Pro Lys Gly Val Val Ile His Asn Thr Ala Gly
        195                 200                 205

Thr Ala Ser Ala Thr Gln Glu Gly Gln Arg Leu Thr Asn Met Thr Phe
    210                 215                 220

Gln Gln Leu Ala Asn Gly Val Ala His Val Tyr Ile Asp Lys Asn Thr
225                 230                 235                 240

Ile Tyr Glu Thr Leu Pro Glu Asp Arg Ile Ala Trp His Val Ala Gln
                245                 250                 255

Gln Tyr Gly Asn Thr Glu Phe Tyr Gly Ile Glu Val Cys Gly Ser Arg
            260                 265                 270

Asn Thr Asp Lys Glu Gln Phe Leu Ala Asn Glu Gln Val Ala Phe Gln
        275                 280                 285

Glu Ala Ala Arg Arg Leu Lys Ser Trp Gly Met Arg Ala Asn Arg Asn
    290                 295                 300

Thr Val Arg Leu His His Thr Phe Ser Ser Thr Glu Cys Pro Asp Met
305                 310                 315                 320

Ser Met Leu Leu His Thr Gly Tyr Ser Met Lys Asn Gly Lys Pro Thr
                325                 330                 335

Gln Asp Ile Thr Asn Lys Cys Ala Asp Tyr Phe Met Lys Gln Ile Asn
            340                 345                 350

Ala Tyr Ile Asp Gly Lys Gln Pro Thr Ser Thr Val Val Gly Ser Ser
        355                 360                 365

Ser Ser Asn Lys Leu Lys Ala Lys Asn Lys Asp Lys Ser Thr Gly Trp
    370                 375                 380

Asn Thr Asn Glu Tyr Gly Thr Leu Trp Lys Lys Glu His Ala Thr Phe
385                 390                 395                 400

Thr Cys Gly Val Arg Gln Gly Ile Val Thr Arg Thr Thr Gly Pro Phe
                405                 410                 415

```
Thr Ser Cys Pro Gln Ala Gly Val Leu Tyr Tyr Gly Gln Ser Val Asn
            420                 425                 430

Tyr Asp Thr Val Cys Lys Gln Asp Gly Tyr Val Trp Ile Ser Trp Thr
        435                 440                 445

Thr Ser Asp Gly Tyr Asp Val Trp Met Pro Ile Arg Thr Trp Asp Arg
    450                 455                 460

Ser Thr Asp Lys Val Ser Glu Ile Trp Gly Thr Ile Ser
465                 470                 475


<210> SEQ ID NO 67
<211> LENGTH: 443
<212> TYPE: PRT
<213> ORGANISM: (Phi)NCTC 11261

<400> SEQUENCE: 67

Met Ala Thr Tyr Gln Glu Tyr Lys Ser Arg Ser Asn Gly Asn Ala Tyr
1               5                   10                  15

Asp Ile Asp Gly Ser Phe Gly Ala Gln Cys Trp Asp Gly Tyr Ala Asp
            20                  25                  30

Tyr Cys Lys Tyr Leu Gly Leu Pro Tyr Ala Asn Cys Thr Asn Thr Gly
        35                  40                  45

Tyr Ala Arg Asp Ile Trp Glu Gln Arg His Glu Asn Gly Ile Leu Asn
    50                  55                  60

Tyr Phe Asp Glu Val Glu Val Met Gln Ala Gly Asp Val Ala Ile Phe
65                  70                  75                  80

Met Val Val Asp Gly Val Thr Pro Tyr Ser His Val Ala Ile Phe Asp
                85                  90                  95

Ser Asp Ala Gly Gly Gly Tyr Gly Trp Phe Leu Gly Gln Asn Gln Gly
            100                 105                 110

Gly Ala Asn Gly Ala Tyr Asn Ile Val Lys Ile Pro Tyr Ser Ala Thr
        115                 120                 125

Tyr Pro Thr Ala Phe Arg Pro Lys Val Phe Lys Asn Ala Val Thr Val
    130                 135                 140

Thr Gly Asn Ile Gly Leu Asn Lys Gly Asp Tyr Phe Ile Asp Val Ser
145                 150                 155                 160

Ala Tyr Gln Gln Ala Asp Leu Thr Thr Thr Cys Gln Gln Ala Gly Thr
                165                 170                 175

Thr Lys Thr Ile Ile Lys Val Ser Glu Ser Ile Ala Trp Leu Ser Asp
            180                 185                 190

Arg His Gln Gln Gln Ala Asn Thr Ser Asp Pro Ile Gly Tyr Tyr His
        195                 200                 205

Phe Gly Arg Phe Gly Gly Asp Ser Ala Leu Ala Gln Arg Glu Ala Asp
    210                 215                 220

Leu Phe Leu Ser Asn Leu Pro Ser Lys Lys Val Ser Tyr Leu Val Ile
225                 230                 235                 240

Asp Tyr Glu Asp Ser Ala Ser Ala Asp Lys Gln Ala Asn Thr Asn Ala
                245                 250                 255

Val Ile Ala Phe Met Asp Lys Ile Ala Ser Ala Gly Tyr Lys Pro Ile
            260                 265                 270

Tyr Tyr Ser Tyr Lys Pro Phe Thr Leu Asn Asn Ile Asp Tyr Gln Lys
        275                 280                 285

Ile Ile Ala Lys Tyr Pro Asn Ser Ile Trp Ile Ala Gly Tyr Pro Asp
    290                 295                 300

Tyr Glu Val Arg Thr Glu Pro Leu Trp Glu Phe Phe Pro Ser Met Asp
```

```
305                 310                 315                 320

Gly Val Arg Trp Trp Gln Phe Thr Ser Val Gly Val Ala Gly Gly Leu
                325                 330                 335

Asp Lys Asn Ile Val Leu Leu Ala Asp Asp Ser Ser Lys Met Asp Ile
            340                 345                 350

Pro Lys Val Asp Lys Pro Gln Glu Leu Thr Phe Tyr Gln Lys Leu Ala
        355                 360                 365

Thr Asn Thr Lys Leu Asp Asn Ser Asn Val Pro Tyr Tyr Glu Ala Thr
    370                 375                 380

Leu Ser Thr Asp Tyr Tyr Val Glu Ser Lys Pro Asn Ala Ser Ser Ala
385                 390                 395                 400

Asp Lys Glu Phe Ile Lys Ala Gly Thr Arg Val Arg Val Tyr Glu Lys
                405                 410                 415

Val Asn Gly Trp Ser Arg Ile Asn His Pro Glu Ser Ala Gln Trp Val
            420                 425                 430

Glu Asp Ser Tyr Leu Val Asn Ala Thr Asp Met
        435                 440


<210> SEQ ID NO 68
<211> LENGTH: 334
<212> TYPE: PRT
<213> ORGANISM: (Phi)FWLLm3

<400> SEQUENCE: 68

Met Val Lys Tyr Thr Val Glu Asn Lys Ile Ile Ala Gly Leu Pro Lys
1               5                   10                  15

Gly Lys Leu Lys Gly Ala Asn Phe Val Ile Ala His Glu Thr Ala Asn
            20                  25                  30

Ser Lys Ser Thr Ile Asp Asn Glu Val Ser Tyr Met Thr Arg Asn Trp
        35                  40                  45

Gln Asn Ala Phe Val Thr His Phe Val Gly Gly Gly Gly Arg Val Val
    50                  55                  60

Gln Val Ala Asn Val Asn Tyr Val Ser Trp Gly Ala Gly Gln Tyr Ala
65                  70                  75                  80

Asn Ser Tyr Ser Tyr Ala Gln Val Glu Leu Cys Arg Thr Ser Asn Ala
                85                  90                  95

Thr Thr Phe Lys Lys Asp Tyr Glu Val Tyr Cys Gln Leu Leu Val Asp
            100                 105                 110

Leu Ala Lys Lys Ala Gly Ile Pro Ile Thr Leu Asp Ser Gly Ser Lys
        115                 120                 125

Thr Ser Asp Lys Gly Ile Lys Ser His Lys Trp Val Ala Asp Lys Leu
    130                 135                 140

Gly Gly Thr Thr His Gln Asp Pro Tyr Ala Tyr Leu Ser Ser Trp Gly
145                 150                 155                 160

Ile Ser Lys Ala Gln Phe Ala Ser Asp Leu Ala Lys Val Ser Gly Gly
                165                 170                 175

Gly Asn Thr Gly Thr Ala Pro Ala Lys Pro Ser Thr Pro Ser Thr Asn
            180                 185                 190

Leu Asp Lys Leu Gly Leu Val Asp Tyr Met Asn Ala Lys Lys Met Asp
        195                 200                 205

Ser Ser Tyr Ser Asn Arg Ala Lys Leu Ala Lys Gln Tyr Gly Ile Ala
    210                 215                 220

Asn Tyr Ser Gly Thr Ala Ser Gln Asn Thr Thr Leu Leu Ser Lys Ile
225                 230                 235                 240
```

```
Lys Gly Gly Ala Pro Lys Pro Ser Thr Pro Ala Pro Lys Pro Ser Thr
                245                 250                 255

Ser Thr Ala Lys Lys Ile Tyr Phe Pro Pro Asn Lys Gly Asn Trp Ser
            260                 265                 270

Val Tyr Pro Thr Asn Lys Ala Pro Val Lys Ala Asn Ala Ile Gly Ala
        275                 280                 285

Ile Asn Pro Thr Lys Phe Gly Gly Leu Thr Tyr Thr Ile Gln Lys Asp
    290                 295                 300

Arg Gly Asn Gly Val Tyr Glu Ile Gln Thr Asp Gln Phe Gly Arg Val
305                 310                 315                 320

Gln Val Tyr Gly Ala Pro Ser Thr Gly Ala Val Ile Lys Lys
                325                 330


<210> SEQ ID NO 69
<211> LENGTH: 1278
<212> TYPE: PRT
<213> ORGANISM: (Phi)BPS13

<400> SEQUENCE: 69

Met Ala Lys Arg Glu Lys Tyr Ile Phe Asp Val Glu Ala Glu Val Gly
1               5                   10                  15

Lys Ala Ala Lys Ser Ile Lys Ser Leu Glu Ala Glu Leu Ser Lys Leu
            20                  25                  30

Gln Lys Leu Asn Lys Glu Ile Asp Ala Thr Gly Gly Asp Arg Thr Glu
        35                  40                  45

Lys Glu Met Leu Ala Thr Leu Lys Ala Ala Lys Glu Val Asn Ala Glu
    50                  55                  60

Tyr Gln Lys Met Gln Arg Ile Leu Lys Asp Leu Ser Lys Tyr Ser Gly
65                  70                  75                  80

Lys Val Ser Arg Lys Glu Phe Asn Asp Ser Lys Val Ile Asn Asn Ala
                85                  90                  95

Lys Thr Ser Val Gln Gly Gly Lys Val Thr Asp Ser Phe Gly Gln Met
            100                 105                 110

Leu Lys Asn Met Glu Arg Gln Ile Asn Ser Val Asn Lys Gln Phe Asp
        115                 120                 125

Asn His Arg Lys Ala Met Val Asp Arg Gly Gln Gln Tyr Thr Pro His
    130                 135                 140

Leu Lys Thr Asn Arg Lys Asp Ser Gln Gly Asn Ser Asn Pro Ser Met
145                 150                 155                 160

Met Gly Arg Asn Lys Ser Thr Thr Gln Asp Met Glu Lys Ala Val Asp
                165                 170                 175

Lys Phe Leu Asn Gly Gln Asn Glu Ala Thr Thr Gly Leu Asn Gln Ala
            180                 185                 190

Leu Tyr Gln Leu Lys Glu Ile Ser Lys Leu Asn Arg Arg Ser Glu Ser
        195                 200                 205

Leu Ser Arg Arg Ala Ser Ala Ser Gly Tyr Met Ser Phe Gln Gln Tyr
    210                 215                 220

Ser Asn Phe Thr Gly Asp Arg Arg Thr Val Gln Gln Thr Tyr Gly Gly
225                 230                 235                 240

Leu Lys Thr Ala Asn Arg Glu Arg Val Leu Glu Leu Ser Gly Gln Ala
                245                 250                 255

Thr Gly Ile Ser Lys Glu Leu Asp Arg Leu Asn Ser Lys Lys Gly Leu
            260                 265                 270

Thr Ala Arg Glu Gly Glu Glu Arg Lys Lys Leu Met Arg Gln Leu Glu
        275                 280                 285
```

```
Gly Ile Asp Ala Glu Leu Thr Ala Arg Lys Lys Leu Asn Ser Ser Leu
    290                 295                 300

Asp Glu Thr Thr Ser Asn Met Glu Lys Phe Asn Gln Ser Leu Val Asp
305                 310                 315                 320

Ala Gln Val Ser Val Lys Pro Glu Arg Gly Thr Met Arg Gly Met Met
                325                 330                 335

Tyr Glu Arg Ala Pro Ala Ile Ala Leu Ala Ile Gly Gly Ala Ile Thr
            340                 345                 350

Ala Thr Ile Gly Lys Leu Tyr Ser Glu Gly Gly Asn His Ser Lys Ala
        355                 360                 365

Met Arg Pro Asp Glu Met Tyr Val Gly Gln Gln Thr Gly Ala Val Gly
    370                 375                 380

Ala Asn Trp Arg Pro Asn Arg Thr Ala Thr Met Arg Ser Gly Leu Gly
385                 390                 395                 400

Asn His Leu Gly Phe Thr Gly Gln Glu Met Met Glu Phe Gln Ser Asn
                405                 410                 415

Tyr Leu Ser Ala Asn Gly Tyr His Gly Ala Glu Asp Met Lys Ala Ala
            420                 425                 430

Thr Thr Gly Gln Ala Thr Phe Ala Arg Ala Thr Gly Leu Gly Ser Asp
        435                 440                 445

Glu Val Lys Asp Phe Phe Asn Thr Ala Tyr Arg Ser Gly Gly Ile Asp
    450                 455                 460

Gly Asn Gln Thr Lys Gln Phe Gln Asn Ala Phe Leu Gly Ala Met Lys
465                 470                 475                 480

Gln Ser Gly Ala Val Gly Arg Glu Lys Asp Gln Leu Lys Ala Leu Asn
                485                 490                 495

Gly Ile Leu Ser Ser Met Ser Gln Asn Arg Thr Val Ser Asn Gln Asp
            500                 505                 510

Met Met Arg Thr Val Gly Leu Gln Ser Ala Ile Ser Ser Ser Gly Val
        515                 520                 525

Ala Ser Leu Gln Gly Thr Lys Gly Gly Ala Leu Met Glu Gln Leu Asp
    530                 535                 540

Asn Gly Ile Arg Glu Gly Phe Asn Asp Pro Gln Met Arg Val Leu Phe
545                 550                 555                 560

Gly Gln Gly Thr Lys Tyr Gln Gly Met Gly Gly Arg Ala Ala Leu Arg
                565                 570                 575

Lys Gln Met Glu Lys Gly Ile Ser Asp Pro Asp Asn Leu Asn Thr Leu
            580                 585                 590

Ile Asp Ala Ser Lys Ala Ser Ala Gly Gln Asp Pro Ala Glu Gln Ala
        595                 600                 605

Glu Val Leu Ala Thr Leu Ala Ser Lys Met Gly Val Asn Met Ser Ser
    610                 615                 620

Asp Gln Ala Arg Gly Leu Ile Asp Leu Gln Pro Ser Gly Lys Leu Thr
625                 630                 635                 640

Lys Glu Asn Ile Asp Lys Val Met Lys Glu Gly Leu Lys Glu Gly Ser
                645                 650                 655

Ile Glu Ser Ala Lys Arg Asp Lys Ala Tyr Ser Glu Ser Lys Ala Ser
            660                 665                 670

Ile Asp Asn Ser Ser Glu Ala Ala Thr Ala Lys Gln Ala Thr Glu Leu
        675                 680                 685

Asn Asp Met Gly Ser Lys Leu Arg Gln Ala Asn Ala Ala Leu Gly Gly
    690                 695                 700
```

-continued

```
Leu Pro Ala Pro Leu Tyr Thr Ala Ile Ala Ala Val Val Ala Phe Thr
705                 710                 715                 720

Ala Ala Val Ala Gly Ser Ala Leu Met Phe Lys Gly Ala Ser Trp Leu
                725                 730                 735

Lys Gly Gly Met Ala Ser Lys Tyr Gly Gly Lys Gly Gly Lys Gly Gly
            740                 745                 750

Lys Gly Gly Gly Thr Gly Gly Gly Gly Gly Ala Gly Gly Ala Ala Ala
        755                 760                 765

Thr Gly Ala Gly Ala Ala Ala Gly Ala Gly Gly Val Gly Ala Ala Ala
    770                 775                 780

Ala Gly Glu Val Gly Ala Gly Val Ala Ala Gly Gly Ala Ala Ala Gly
785                 790                 795                 800

Ala Ala Ala Gly Gly Ser Lys Leu Ala Gly Val Gly Lys Gly Phe Met
                805                 810                 815

Lys Gly Ala Gly Lys Leu Met Leu Pro Leu Gly Ile Leu Met Gly Ala
            820                 825                 830

Ser Glu Ile Met Gln Ala Pro Glu Glu Ala Lys Gly Ser Ala Ile Gly
        835                 840                 845

Ser Ala Val Gly Gly Ile Gly Gly Gly Ile Ala Gly Gly Ala Ala Thr
    850                 855                 860

Gly Ala Ile Ala Gly Ser Phe Leu Gly Pro Ile Gly Thr Ala Val Gly
865                 870                 875                 880

Gly Ile Ala Gly Gly Ile Ala Gly Gly Phe Ala Gly Ser Ser Leu Gly
                885                 890                 895

Glu Thr Ile Gly Gly Trp Phe Asp Ser Gly Pro Lys Glu Asp Ala Ser
            900                 905                 910

Ala Ala Asp Lys Ala Lys Ala Asp Ala Ser Ala Ala Ala Leu Ala Ala
        915                 920                 925

Ala Ala Gly Thr Ser Gly Ala Val Gly Ser Ser Ala Leu Gln Ser Gln
    930                 935                 940

Met Ala Gln Gly Ile Thr Gly Ala Pro Asn Met Ser Gln Val Gly Ser
945                 950                 955                 960

Met Ala Ser Ala Leu Gly Ile Ser Ser Gly Ala Met Ala Ser Ala Leu
                965                 970                 975

Gly Ile Ser Ser Gly Gln Glu Asn Gln Ile Gln Thr Met Thr Asp Lys
            980                 985                 990

Glu Asn Thr Asn Thr Lys Lys Ala  Asn Glu Ala Lys Lys  Gly Asp Asn
        995                 1000                1005

Leu Ser  Tyr Glu Arg Glu Asn  Ile Ser Met Tyr Glu  Arg Val Leu
    1010                 1015                 1020

Thr Arg  Ala Glu Gln Ile Leu  Ala Gln Ala Arg Ala  Gln Asn Gly
    1025                 1030                 1035

Ile Met  Gly Val Gly Gly Gly  Gly Thr Ala Gly Ala  Gly Gly Gly
    1040                 1045                 1050

Ile Asn  Gly Phe Thr Gly Gly  Gly Lys Leu Gln Phe  Leu Ala Ala
    1055                 1060                 1065

Gly Gln  Lys Trp Ser Ser Ser  Asn Leu Gln Gln His  Asp Leu Gly
    1070                 1075                 1080

Phe Thr  Asp Gln Asn Leu Thr  Ala Glu Asp Leu Asp  Lys Trp Ile
    1085                 1090                 1095

Asp Ser  Lys Ala Pro Gln Gly  Ser Met Met Arg Gly  Met Gly Ala
    1100                 1105                 1110

Thr Phe  Leu Lys Ala Gly Gln  Glu Tyr Gly Leu Asp  Pro Arg Tyr
```

```
    1115                1120                1125

Leu Ile  Ala His Ala Ala Glu  Glu Ser Gly Trp Gly  Thr Ser Lys
    1130                1135                1140

Ile Ala  Arg Asp Lys Gly Asn  Phe Phe Gly Ile Gly  Ala Phe Asp
    1145                1150                1155

Asp Ser  Pro Tyr Ser Ser Ala  Tyr Glu Phe Lys Asp  Gly Thr Gly
    1160                1165                1170

Ser Ala  Ala Glu Arg Gly Ile  Met Gly Gly Ala Lys  Trp Ile Ser
    1175                1180                1185

Glu Lys  Tyr Tyr Gly Lys Gly  Asn Thr Thr Leu Asp  Lys Met Lys
    1190                1195                1200

Ala Ala  Gly Tyr Ala Thr Asn  Ala Ser Trp Ala Pro  Asn Ile Ala
    1205                1210                1215

Ser Ile  Met Ala Gly Ala Pro  Thr Gly Ser Gly Ser  Gly Asn Val
    1220                1225                1230

Thr Ala  Thr Ile Asn Val Asn  Val Lys Gly Asp Glu  Lys Val Ser
    1235                1240                1245

Asp Lys  Leu Lys Asn Ser Ser  Asp Met Lys Lys Ala  Gly Lys Asp
    1250                1255                1260

Ile Gly  Ser Leu Leu Gly Phe  Tyr Ser Arg Glu Met  Thr Ile Ala
    1265                1270                1275


<210> SEQ ID NO 70
<211> LENGTH: 495
<212> TYPE: PRT
<213> ORGANISM: (Phi)GH15

<400> SEQUENCE: 70

Met Ala Lys Thr Gln Ala Glu Ile Asn Lys Arg Leu Asp Ala Tyr Ala
1               5                   10                  15

Lys Gly Thr Val Asp Ser Pro Tyr Arg Ile Lys Lys Ala Thr Ser Tyr
            20                  25                  30

Asp Pro Ser Phe Gly Val Met Glu Ala Gly Ala Ile Asp Ala Asp Gly
        35                  40                  45

Tyr Tyr His Ala Gln Cys Gln Asp Leu Ile Thr Asp Tyr Val Leu Trp
    50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Gln Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys
    130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Lys Ala Thr Leu Lys Val
            180                 185                 190

Ser Lys Asn His Ile Asn Tyr Thr Met Asp Lys Arg Gly Lys Lys Pro
        195                 200                 205
```

Glu Gly Met Val Ile His Asn Asp Ala Gly Arg Ser Ser Gly Gln Gln
    210                 215                 220

Tyr Glu Asn Ser Leu Ala Asn Ala Gly Tyr Ala Arg Tyr Ala Asn Gly
225                 230                 235                 240

Ile Ala His Tyr Tyr Gly Ser Glu Gly Tyr Val Trp Glu Ala Ile Asp
                245                 250                 255

Ala Lys Asn Gln Ile Ala Trp His Thr Gly Asp Gly Thr Gly Ala Asn
            260                 265                 270

Ser Gly Asn Phe Arg Phe Ala Gly Ile Glu Val Cys Gln Ser Met Ser
        275                 280                 285

Ala Ser Asp Ala Gln Phe Leu Lys Asn Glu Gln Ala Val Phe Gln Phe
    290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
                325                 330                 335

Met Val Leu His Thr Gly Phe Asn Pro Val Thr Gln Gly Arg Pro Ser
            340                 345                 350

Gln Ala Ile Met Asn Lys Leu Lys Asp Tyr Phe Ile Lys Gln Ile Lys
        355                 360                 365

Asn Tyr Met Asp Lys Gly Thr Ser Ser Ser Thr Val Val Lys Asp Gly
    370                 375                 380

Lys Thr Ser Ser Ala Ser Thr Pro Ala Thr Arg Pro Val Thr Gly Ser
385                 390                 395                 400

Trp Lys Lys Asn Gln Tyr Gly Thr Trp Tyr Lys Pro Glu Asn Ala Thr
                405                 410                 415

Phe Val Asn Gly Asn Gln Pro Ile Val Thr Arg Ile Gly Ser Pro Phe
            420                 425                 430

Leu Asn Ala Pro Val Gly Gly Asn Leu Pro Ala Gly Ala Thr Ile Val
        435                 440                 445

Tyr Asp Glu Val Cys Ile Gln Ala Gly His Ile Trp Ile Gly Tyr Asn
    450                 455                 460

Ala Tyr Asn Gly Asp Arg Val Tyr Cys Pro Val Arg Thr Cys Gln Gly
465                 470                 475                 480

Val Pro Pro Asn His Ile Pro Gly Val Ala Trp Gly Val Phe Lys
                485                 490                 495

<210> SEQ ID NO 71
<211> LENGTH: 264
<212> TYPE: PRT
<213> ORGANISM: (Phi)8074-B1

<400> SEQUENCE: 71

Met Lys Ile Gly Ile Asp Met Gly His Thr Leu Ser Gly Ala Asp Tyr
1               5                   10                  15

Gly Val Val Gly Leu Arg Pro Glu Ser Val Leu Thr Arg Glu Val Gly
            20                  25                  30

Thr Lys Val Ile Tyr Lys Leu Gln Lys Leu Gly His Val Val Val Asn
        35                  40                  45

Cys Thr Val Asp Lys Ala Ser Ser Val Ser Glu Ser Leu Tyr Thr Arg
    50                  55                  60

Tyr Tyr Arg Ala Asn Gln Ala Asn Val Asp Leu Phe Ile Ser Ile His
65                  70                  75                  80

Phe Asn Ala Thr Pro Gly Gly Thr Gly Thr Glu Val Tyr Thr Tyr Ala
                85                  90                  95

Gly Arg Gln Leu Gly Glu Ala Thr Arg Ile Arg Gln Glu Phe Lys Ser
100 105 110

Leu Gly Leu Arg Asp Arg Gly Thr Lys Asp Gly Ser Gly Leu Ala Val
115 120 125

Ile Arg Asn Thr Lys Ala Lys Ala Met Leu Val Glu Cys Cys Phe Cys
130 135 140

Asp Asn Pro Asn Asp Met Lys Leu Tyr Asn Ser Glu Ser Phe Ser Asn
145 150 155 160

Ala Ile Val Lys Gly Ile Thr Gly Lys Leu Pro Asn Gly Glu Ser Gly
165 170 175

Asn Asn Asn Gln Gly Gly Asn Lys Val Lys Ala Val Val Ile Tyr Asn
180 185 190

Glu Gly Ala Asp Arg Arg Gly Ala Glu Tyr Leu Ala Asp Tyr Leu Asn
195 200 205

Cys Pro Thr Ile Ser Asn Ser Arg Thr Phe Asp Tyr Ser Cys Val Glu
210 215 220

His Val Tyr Ala Val Gly Gly Lys Lys Glu Gln Tyr Thr Lys Tyr Leu
225 230 235 240

Lys Thr Leu Leu Ser Gly Ala Asn Arg Tyr Asp Thr Met Gln Gln Ile
245 250 255

Leu Asn Phe Ile Asn Gly Gly Lys
260

<210> SEQ ID NO 72
<211> LENGTH: 209
<212> TYPE: PRT
<213> ORGANISM: (Phi)SPN1S

<400> SEQUENCE: 72

Met Asp Ile Asn Gln Phe Arg Arg Ala Ser Gly Ile Asn Glu Gln Leu
1 5 10 15

Ala Ala Arg Trp Phe Pro His Ile Thr Thr Ala Met Asn Glu Phe Gly
20 25 30

Ile Thr Lys Pro Asp Asp Gln Ala Met Phe Ile Ala Gln Val Gly His
35 40 45

Glu Ser Gly Gly Phe Thr Arg Leu Gln Glu Asn Phe Asn Tyr Ser Val
50 55 60

Asn Gly Leu Ser Gly Phe Ile Arg Ala Gly Arg Ile Thr Pro Asp Gln
65 70 75 80

Ala Asn Ala Leu Gly Arg Lys Thr Tyr Glu Lys Ser Leu Pro Leu Glu
85 90 95

Arg Gln Arg Ala Ile Ala Asn Leu Val Tyr Ser Lys Arg Met Gly Asn
100 105 110

Asn Gly Pro Gly Asp Gly Trp Asn Tyr Arg Gly Arg Gly Leu Ile Gln
115 120 125

Ile Thr Gly Leu Asn Asn Tyr Arg Asp Cys Gly Asn Gly Leu Lys Val
130 135 140

Asp Leu Val Ala Gln Pro Glu Leu Leu Ala Gln Asp Glu Tyr Ala Ala
145 150 155 160

Arg Ser Ala Ala Trp Phe Phe Ser Ser Lys Gly Cys Met Lys Tyr Thr
165 170 175

Gly Asp Leu Val Arg Val Thr Gln Ile Ile Asn Gly Gly Gln Asn Gly
180 185 190

Ile Asp Asp Arg Arg Thr Arg Tyr Ala Ala Ala Arg Lys Val Leu Ala

-continued

```
        195                 200                 205

Leu


<210> SEQ ID NO 73
<211> LENGTH: 290
<212> TYPE: PRT
<213> ORGANISM: (Phi)CN77

<400> SEQUENCE: 73

Met Gly Tyr Trp Gly Tyr Pro Asn Gly Gln Ile Pro Asn Asp Lys Met
1               5                   10                  15

Ala Leu Tyr Arg Gly Cys Leu Leu Arg Ala Asp Ala Ala Ala Gln Ala
            20                  25                  30

Tyr Ala Leu Gln Asp Ala Tyr Thr Arg Ala Thr Gly Lys Pro Leu Val
        35                  40                  45

Ile Leu Glu Gly Tyr Arg Asp Leu Thr Arg Gln Lys Tyr Leu Arg Asn
    50                  55                  60

Leu Tyr Leu Ser Gly Arg Gly Asn Ile Ala Ala Val Pro Gly Leu Ser
65                  70                  75                  80

Asn His Gly Trp Gly Leu Ala Cys Asp Phe Ala Ala Pro Leu Asn Ser
                85                  90                  95

Ser Gly Ser Glu Glu His Arg Trp Met Arg Gln Asn Ala Pro Leu Phe
            100                 105                 110

Gly Phe Asp Trp Ala Arg Gly Lys Ala Asp Asn Glu Pro Trp His Trp
        115                 120                 125

Glu Tyr Gly Asn Val Pro Val Ser Arg Trp Ala Ser Leu Asp Val Thr
    130                 135                 140

Pro Ile Asp Arg Asn Asp Met Ala Asp Ile Thr Glu Gly Gln Met Gln
145                 150                 155                 160

Arg Ile Ala Val Ile Leu Leu Asp Thr Glu Ile Gln Thr Pro Leu Gly
                165                 170                 175

Pro Arg Leu Val Lys His Ala Leu Gly Asp Ala Leu Leu Leu Gly Gln
            180                 185                 190

Ala Asn Ala Asn Ser Ile Ala Glu Val Pro Asp Lys Thr Trp Asp Val
        195                 200                 205

Leu Val Asp His Pro Leu Ala Lys Asn Glu Asp Gly Thr Pro Leu Lys
    210                 215                 220

Val Arg Leu Gly Asp Val Ala Lys Tyr Glu Pro Leu Glu His Gln Asn
225                 230                 235                 240

Thr Arg Asp Ala Ile Ala Lys Leu Gly Thr Leu Gln Phe Thr Asp Lys
                245                 250                 255

Gln Leu Ala Thr Ile Gly Ala Gly Val Lys Pro Ile Asp Glu Ala Ser
            260                 265                 270

Leu Val Lys Lys Ile Val Asp Gly Val Arg Ala Leu Phe Gly Arg Ala
        275                 280                 285

Ala Ala
    290


<210> SEQ ID NO 74
<211> LENGTH: 185
<212> TYPE: PRT
<213> ORGANISM: (Phi)AB2

<400> SEQUENCE: 74

Met Ile Leu Thr Lys Asp Gly Phe Ser Ile Ile Arg Asn Glu Leu Phe
1               5                   10                  15
```

Gly Gly Lys Leu Asp Gln Thr Gln Val Asp Ala Ile Asn Phe Ile Val
20 25 30

Ala Lys Ala Thr Glu Ser Gly Leu Thr Tyr Pro Glu Ala Ala Tyr Leu
35 40 45

Leu Ala Thr Ile Tyr His Glu Thr Gly Leu Pro Ser Gly Tyr Arg Thr
50 55 60

Met Gln Pro Ile Lys Glu Ala Gly Ser Asp Ser Tyr Leu Arg Ser Lys
65 70 75 80

Lys Tyr Tyr Pro Tyr Ile Gly Tyr Gly Tyr Val Gln Leu Thr Trp Lys
85 90 95

Glu Asn Tyr Glu Arg Ile Gly Lys Leu Ile Gly Val Asp Leu Ile Lys
100 105 110

Asn Pro Glu Lys Ala Leu Glu Pro Leu Ile Ala Ile Gln Ile Ala Ile
115 120 125

Lys Gly Met Leu Asn Gly Trp Phe Thr Gly Val Gly Phe Arg Arg Lys
130 135 140

Arg Pro Val Ser Lys Tyr Asn Lys Gln Gln Tyr Val Ala Ala Arg Asn
145 150 155 160

Ile Ile Asn Gly Lys Asp Lys Ala Glu Leu Ile Ala Lys Tyr Ala Ile
165 170 175

Ile Phe Glu Arg Ala Leu Arg Ser Leu
180 185

<210> SEQ ID NO 75
<211> LENGTH: 262
<212> TYPE: PRT
<213> ORGANISM: (Phi)B4

<400> SEQUENCE: 75

Met Ala Met Ala Leu Gln Thr Leu Ile Asp Lys Ala Asn Arg Lys Leu
1 5 10 15

Asn Val Ser Gly Met Arg Lys Asp Val Ala Asp Arg Thr Arg Ala Val
20 25 30

Ile Thr Gln Met His Ala Gln Gly Ile Tyr Ile Cys Val Ala Gln Gly
35 40 45

Phe Arg Ser Phe Ala Glu Gln Asn Ala Leu Tyr Ala Gln Gly Arg Thr
50 55 60

Lys Pro Gly Ser Ile Val Thr Asn Ala Arg Gly Gly Gln Ser Asn His
65 70 75 80

Asn Tyr Gly Val Ala Val Asp Leu Cys Leu Tyr Thr Gln Asp Gly Ser
85 90 95

Asp Val Ile Trp Thr Val Glu Gly Asn Phe Arg Lys Val Ile Ala Ala
100 105 110

Met Lys Ala Gln Gly Phe Lys Trp Gly Gly Asp Trp Val Ser Phe Lys
115 120 125

Asp Tyr Pro His Phe Glu Leu Tyr Asp Val Val Gly Gly Gln Lys Pro
130 135 140

Pro Ala Asp Asn Gly Gly Ala Val Asp Asn Gly Gly Gly Ser Gly Ser
145 150 155 160

Thr Gly Gly Ser Gly Gly Gly Ser Thr Gly Gly Gly Ser Thr Gly Gly
165 170 175

Gly Tyr Asp Ser Ser Trp Phe Thr Lys Glu Thr Gly Thr Phe Val Thr
180 185 190

Asn Thr Ser Ile Lys Leu Arg Thr Ala Pro Phe Thr Ser Ala Asp Val

```
        195                 200                 205

Ile Ala Thr Leu Pro Ala Gly Ser Pro Val Asn Tyr Asn Gly Phe Gly
    210                 215                 220

Ile Glu Tyr Asp Gly Tyr Val Trp Ile Arg Gln Pro Arg Ser Asn Gly
225                 230                 235                 240

Tyr Gly Tyr Leu Ala Thr Gly Glu Ser Lys Gly Gly Lys Arg Gln Asn
                245                 250                 255

Tyr Trp Gly Thr Phe Lys
            260


<210> SEQ ID NO 76
<211> LENGTH: 274
<212> TYPE: PRT
<213> ORGANISM: (Phi)CTP1

<400> SEQUENCE: 76

Met Lys Lys Ile Ala Asp Ile Ser Asn Leu Asn Gly Asn Val Asp Val
1               5                   10                  15

Lys Leu Leu Phe Asn Leu Gly Tyr Ile Gly Ile Ile Ala Lys Ala Ser
            20                  25                  30

Glu Gly Gly Thr Phe Val Asp Lys Tyr Tyr Lys Gln Asn Tyr Thr Asn
        35                  40                  45

Thr Lys Ala Gln Gly Lys Ile Thr Gly Ala Tyr His Phe Ala Asn Phe
    50                  55                  60

Ser Thr Ile Ala Lys Ala Gln Gln Glu Ala Asn Phe Phe Leu Asn Cys
65                  70                  75                  80

Ile Ala Gly Thr Thr Pro Asp Phe Val Val Leu Asp Leu Glu Gln Gln
                85                  90                  95

Cys Thr Gly Asp Ile Thr Asp Ala Cys Leu Ala Phe Leu Asn Ile Val
            100                 105                 110

Ala Lys Lys Phe Lys Cys Val Val Tyr Cys Asn Ser Ser Phe Ile Lys
        115                 120                 125

Glu His Leu Asn Ser Lys Ile Cys Ala Tyr Pro Leu Trp Ile Ala Asn
    130                 135                 140

Tyr Gly Val Ala Thr Pro Ala Phe Thr Leu Trp Thr Lys Tyr Ala Met
145                 150                 155                 160

Trp Gln Phe Thr Glu Lys Gly Gln Val Ser Gly Ile Ser Gly Tyr Ile
                165                 170                 175

Asp Phe Ser Tyr Ile Thr Asp Glu Phe Ile Lys Tyr Ile Lys Gly Glu
            180                 185                 190

Asp Glu Val Glu Asn Leu Val Val Tyr Asn Asp Gly Ala Asp Gln Arg
        195                 200                 205

Ala Ala Glu Tyr Leu Ala Asp Arg Leu Ala Cys Pro Thr Ile Asn Asn
    210                 215                 220

Ala Arg Lys Phe Asp Tyr Ser Asn Val Lys Asn Val Tyr Ala Val Gly
225                 230                 235                 240

Gly Asn Lys Glu Gln Tyr Thr Ser Tyr Leu Thr Thr Leu Ile Ala Gly
                245                 250                 255

Ser Thr Arg Tyr Thr Thr Met Gln Ala Val Leu Asp Tyr Ile Lys Asn
            260                 265                 270

Leu Lys


<210> SEQ ID NO 77
<211> LENGTH: 628
<212> TYPE: PRT
```

<213> ORGANISM: Staphylococcus virus 187

<400> SEQUENCE: 77

```
Met Ala Leu Pro Lys Thr Gly Lys Pro Thr Ala Lys Gln Val Val Asp
1               5                   10                  15

Trp Ala Ile Asn Leu Ile Gly Ser Gly Val Asp Val Asp Gly Tyr Tyr
            20                  25                  30

Gly Arg Gln Cys Trp Asp Leu Pro Asn Tyr Ile Phe Asn Arg Tyr Trp
        35                  40                  45

Asn Phe Lys Thr Pro Gly Asn Ala Arg Asp Met Ala Trp Tyr Arg Tyr
    50                  55                  60

Pro Glu Gly Phe Lys Val Phe Arg Asn Thr Ser Asp Phe Val Pro Lys
65                  70                  75                  80

Pro Gly Asp Ile Ala Val Trp Thr Gly Gly Asn Tyr Asn Trp Asn Thr
                85                  90                  95

Trp Gly His Thr Gly Ile Val Val Gly Pro Ser Thr Lys Ser Tyr Phe
            100                 105                 110

Tyr Ser Val Asp Gln Asn Trp Asn Asn Ser Asn Ser Tyr Val Gly Ser
        115                 120                 125

Pro Ala Ala Lys Ile Lys His Ser Tyr Phe Gly Val Thr His Phe Val
    130                 135                 140

Arg Pro Ala Tyr Lys Ala Glu Pro Lys Pro Thr Pro Pro Ala Gln Asn
145                 150                 155                 160

Asn Pro Ala Pro Lys Asp Pro Glu Pro Ser Lys Lys Pro Glu Ser Asn
                165                 170                 175

Lys Pro Ile Tyr Lys Val Val Thr Lys Ile Leu Phe Thr Thr Ala His
            180                 185                 190

Ile Glu His Val Lys Ala Asn Arg Phe Val His Tyr Ile Thr Lys Ser
        195                 200                 205

Asp Asn His Asn Asn Lys Pro Asn Lys Ile Val Ile Lys Asn Thr Asn
    210                 215                 220

Thr Ala Leu Ser Thr Ile Asp Val Tyr Arg Tyr Arg Asp Glu Leu Asp
225                 230                 235                 240

Lys Asp Glu Ile Pro His Phe Phe Val Asp Arg Leu Asn Val Trp Ala
                245                 250                 255

Cys Arg Pro Ile Glu Asp Ser Ile Asn Gly Tyr His Asp Ser Val Val
            260                 265                 270

Leu Ser Ile Thr Glu Thr Arg Thr Ala Leu Ser Asp Asn Phe Lys Met
        275                 280                 285

Asn Glu Ile Glu Cys Leu Ser Leu Ala Glu Ser Ile Leu Lys Ala Asn
    290                 295                 300

Asn Lys Lys Met Ser Ala Ser Asn Ile Ile Val Asp Asn Lys Ala Trp
305                 310                 315                 320

Arg Thr Phe Lys Leu His Thr Gly Lys Asp Ser Leu Lys Ser Ser Ser
                325                 330                 335

Phe Thr Ser Lys Asp Tyr Gln Lys Ala Val Asn Glu Leu Ile Lys Leu
            340                 345                 350

Phe Asn Asp Lys Asp Lys Leu Leu Asn Asn Lys Pro Lys Asp Val Val
        355                 360                 365

Glu Arg Ile Arg Ile Arg Thr Ile Val Lys Glu Asn Thr Lys Phe Val
    370                 375                 380

Pro Ser Glu Leu Lys Pro Arg Asn Asn Ile Arg Asp Lys Gln Asp Ser
385                 390                 395                 400
```

Lys Ile Asp Arg Val Ile Asn Asn Tyr Thr Leu Lys Gln Ala Leu Asn
405 410 415

Ile Gln Tyr Lys Leu Asn Pro Lys Pro Gln Thr Ser Asn Gly Val Ser
420 425 430

Trp Tyr Asn Ala Ser Val Asn Gln Ile Lys Ser Ala Met Asp Thr Thr
435 440 445

Lys Ile Phe Asn Asn Asn Val Gln Val Tyr Gln Phe Leu Lys Leu Asn
450 455 460

Gln Tyr Gln Gly Ile Pro Val Asp Lys Leu Asn Lys Leu Leu Val Gly
465 470 475 480

Lys Gly Thr Leu Ala Asn Gln Gly His Ala Phe Ala Asp Gly Cys Lys
485 490 495

Lys Tyr Asn Ile Asn Glu Ile Tyr Leu Ile Ala His Arg Phe Leu Glu
500 505 510

Ser Ala Asn Gly Thr Ser Phe Phe Ala Ser Gly Lys Thr Gly Val Tyr
515 520 525

Asn Tyr Phe Gly Ile Gly Ala Phe Asp Asn Asn Pro Asn Asn Ala Met
530 535 540

Ala Phe Ala Arg Ser His Gly Trp Thr Ser Pro Thr Lys Ala Ile Ile
545 550 555 560

Gly Gly Ala Glu Phe Val Gly Lys Gly Tyr Phe Asn Val Gly Gln Asn
565 570 575

Thr Leu Tyr Arg Met Arg Trp Asn Pro Gln Lys Pro Gly Thr His Gln
580 585 590

Tyr Ala Thr Asp Ile Ser Trp Ala Lys Val Gln Ala Gln Met Ile Ser
595 600 605

Ala Met Tyr Lys Glu Ile Gly Leu Thr Gly Asp Tyr Phe Ile Tyr Asp
610 615 620

Gln Tyr Lys Lys
625

<210> SEQ ID NO 78
<211> LENGTH: 291
<212> TYPE: PRT
<213> ORGANISM: (Phi)P35

<400> SEQUENCE: 78

Met Ala Arg Lys Phe Thr Lys Ala Glu Leu Val Ala Lys Ala Glu Lys
1 5 10 15

Lys Val Gly Gly Leu Lys Pro Asp Val Lys Lys Ala Val Leu Ser Ala
20 25 30

Val Lys Glu Ala Tyr Asp Arg Tyr Gly Ile Gly Ile Ile Val Ser Gln
35 40 45

Gly Tyr Arg Ser Ile Ala Glu Gln Asn Gly Leu Tyr Ala Gln Gly Arg
50 55 60

Thr Lys Pro Gly Asn Ile Val Thr Asn Ala Lys Gly Gly Gln Ser Asn
65 70 75 80

His Asn Phe Gly Val Ala Val Asp Phe Ala Ile Asp Leu Ile Asp Asp
85 90 95

Gly Lys Ile Asp Ser Trp Gln Pro Ser Ala Thr Ile Val Asn Met Met
100 105 110

Lys Arg Arg Gly Phe Lys Trp Gly Gly Asp Trp Lys Ser Phe Thr Asp
115 120 125

Leu Pro His Phe Glu Ala Cys Asp Trp Tyr Arg Gly Glu Arg Lys Tyr
130 135 140

Lys Val Asp Thr Ser Glu Trp Lys Lys Lys Glu Asn Ile Asn Ile Val
145 150 155 160

Ile Lys Asp Val Gly Tyr Phe Gln Asp Lys Pro Gln Phe Leu Asn Ser
165 170 175

Lys Ser Val Arg Gln Trp Lys His Gly Thr Lys Val Lys Leu Thr Lys
180 185 190

His Asn Ser His Trp Tyr Thr Gly Val Val Lys Asp Gly Asn Lys Ser
195 200 205

Val Arg Gly Tyr Ile Tyr His Ser Met Ala Lys Val Thr Ser Lys Asn
210 215 220

Ser Asp Gly Ser Val Asn Ala Thr Ile Asn Ala His Ala Phe Cys Trp
225 230 235 240

Asp Asn Lys Lys Leu Asn Gly Gly Asp Phe Ile Asn Leu Lys Arg Gly
245 250 255

Phe Lys Gly Ile Thr His Pro Ala Ser Asp Gly Phe Tyr Pro Leu Tyr
260 265 270

Phe Ala Ser Arg Lys Lys Thr Phe Tyr Ile Pro Arg Tyr Met Phe Asp
275 280 285

Ile Lys Lys
290

<210> SEQ ID NO 79
<211> LENGTH: 342
<212> TYPE: PRT
<213> ORGANISM: (Phi)CP-7

<400> SEQUENCE: 79

Met Val Lys Lys Asn Asp Leu Phe Val Asp Val Ala Ser His Gln Gly
1 5 10 15

Tyr Asp Ile Ser Gly Ile Leu Glu Glu Ala Gly Thr Thr Asn Thr Ile
20 25 30

Ile Lys Val Ser Glu Ser Thr Ser Tyr Leu Asn Pro Cys Leu Ser Ala
35 40 45

Gln Val Ser Gln Ser Asn Pro Ile Gly Phe Tyr His Phe Ala Trp Phe
50 55 60

Gly Gly Asn Glu Glu Glu Ala Glu Ala Glu Ala Arg Tyr Phe Leu Asp
65 70 75 80

Asn Val Pro Thr Gln Val Lys Tyr Leu Val Leu Asp Tyr Glu Asp His
85 90 95

Ala Ser Ala Ser Val Gln Arg Asn Thr Thr Ala Cys Leu Arg Phe Met
100 105 110

Gln Ile Ile Ala Glu Ala Gly Tyr Thr Pro Ile Tyr Tyr Ser Tyr Lys
115 120 125

Pro Phe Thr Leu Asp Asn Val Asp Tyr Gln Gln Ile Leu Ala Gln Phe
130 135 140

Pro Asn Ser Leu Trp Ile Ala Gly Tyr Gly Leu Asn Asp Gly Thr Ala
145 150 155 160

Asn Phe Glu Tyr Phe Pro Ser Met Asp Gly Ile Arg Trp Trp Gln Tyr
165 170 175

Ser Ser Asn Pro Phe Asp Lys Asn Ile Val Leu Leu Asp Asp Glu Lys
180 185 190

Glu Asp Asn Ile Asn Asn Glu Asn Thr Leu Lys Ser Leu Thr Thr Val
195 200 205

Ala Asn Glu Val Ile Gln Gly Leu Trp Gly Asn Gly Gln Glu Arg Tyr

```
    210                 215                 220

Asp Ser Leu Ala Asn Ala Gly Tyr Asp Pro Gln Ala Val Gln Asp Lys
225                 230                 235                 240

Val Asn Glu Ile Leu Asn Ala Arg Glu Ile Ala Asp Leu Thr Thr Val
                245                 250                 255

Ala Asn Glu Val Ile Gln Gly Leu Trp Gly Asn Gly Gln Glu Arg Tyr
            260                 265                 270

Asp Ser Leu Ala Asn Ala Gly Tyr Asp Pro Gln Ala Val Gln Asp Lys
        275                 280                 285

Val Asn Glu Ile Leu Asn Ala Arg Glu Ile Ala Asp Leu Thr Thr Val
    290                 295                 300

Ala Asn Glu Val Ile Gln Gly Leu Trp Gly Asn Gly Gln Glu Arg Tyr
305                 310                 315                 320

Asp Ser Leu Ala Asn Ala Gly Tyr Asp Pro Gln Ala Val Gln Asp Lys
                325                 330                 335

Val Asn Glu Leu Leu Ser
            340


<210> SEQ ID NO 80
<211> LENGTH: 328
<212> TYPE: PRT
<213> ORGANISM: (Phi)EFAP-1

<400> SEQUENCE: 80

Met Lys Leu Lys Gly Ile Leu Leu Ser Val Val Thr Thr Phe Gly Leu
1               5                   10                  15

Leu Phe Gly Ala Thr Asn Val Gln Ala Tyr Glu Val Asn Asn Glu Phe
            20                  25                  30

Asn Leu Gln Pro Trp Glu Gly Ser Gln Gln Leu Ala Tyr Pro Asn Lys
        35                  40                  45

Ile Ile Leu His Glu Thr Ala Asn Pro Arg Ala Thr Gly Arg Asn Glu
    50                  55                  60

Ala Thr Tyr Met Lys Asn Asn Trp Phe Asn Ala His Thr Thr Ala Ile
65                  70                  75                  80

Val Gly Asp Gly Gly Ile Val Tyr Lys Val Ala Pro Glu Gly Asn Val
                85                  90                  95

Ser Trp Gly Ala Gly Asn Ala Asn Pro Tyr Ala Pro Val Gln Ile Glu
            100                 105                 110

Leu Gln His Thr Asn Asp Pro Glu Leu Phe Lys Ala Asn Tyr Lys Ala
        115                 120                 125

Tyr Val Asp Tyr Thr Arg Asp Met Gly Lys Lys Phe Gly Ile Pro Met
    130                 135                 140

Thr Leu Asp Gln Gly Gly Ser Leu Trp Glu Lys Gly Val Val Ser His
145                 150                 155                 160

Gln Trp Val Thr Asp Phe Val Trp Gly Asp His Thr Asp Pro Tyr Gly
                165                 170                 175

Tyr Leu Ala Lys Met Gly Ile Ser Lys Ala Gln Leu Ala His Asp Leu
            180                 185                 190

Ala Asn Gly Val Ser Gly Asn Thr Ala Thr Pro Thr Pro Lys Pro Asp
        195                 200                 205

Lys Pro Lys Pro Thr Gln Pro Ser Lys Pro Ser Asn Lys Lys Arg Phe
    210                 215                 220

Asn Tyr Arg Val Asp Gly Leu Glu Tyr Val Asn Gly Met Trp Gln Ile
225                 230                 235                 240
```

```
Tyr Asn Glu His Leu Gly Lys Ile Asp Phe Asn Trp Thr Glu Asn Gly
                245                 250                 255

Ile Pro Val Glu Val Val Asp Lys Val Asn Pro Ala Thr Gly Gln Pro
            260                 265                 270

Thr Lys Asp Gln Val Leu Lys Val Gly Asp Tyr Phe Asn Phe Gln Glu
        275                 280                 285

Asn Ser Thr Gly Val Val Gln Glu Gln Thr Pro Tyr Met Gly Tyr Thr
    290                 295                 300

Leu Ser His Val Gln Leu Pro Asn Glu Phe Ile Trp Leu Phe Thr Asp
305                 310                 315                 320

Ser Lys Gln Ala Leu Met Tyr Gln
                325


<210> SEQ ID NO 81
<211> LENGTH: 48
<212> TYPE: PRT
<213> ORGANISM: Homo sapiens

<400> SEQUENCE: 81

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu Glu Ser Val
            20                  25                  30

Gly Lys Gly Ala Val His Asp Val Lys Asp Val Leu Asp Ser Val Leu
        35                  40                  45


<210> SEQ ID NO 82
<211> LENGTH: 37
<212> TYPE: PRT
<213> ORGANISM: Hyalophora cecropia

<400> SEQUENCE: 82

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35


<210> SEQ ID NO 83
<211> LENGTH: 62
<212> TYPE: PRT
<213> ORGANISM: Drosophila teissieri

<400> SEQUENCE: 83

Met Lys Tyr Phe Ser Val Leu Val Val Leu Thr Leu Ile Leu Ala Ile
1               5                   10                  15

Val Asp Gln Ser Asp Ala Phe Ile Asn Leu Leu Asp Lys Val Glu Asp
            20                  25                  30

Ala Leu His Thr Gly Ala Gln Ala Gly Phe Lys Leu Ile Arg Pro Val
        35                  40                  45

Glu Arg Gly Ala Thr Pro Lys Lys Ser Glu Lys Pro Glu Lys
    50                  55                  60


<210> SEQ ID NO 84
<211> LENGTH: 66
<212> TYPE: PRT
<213> ORGANISM: Bombyx mori

<400> SEQUENCE: 84
```

```
Met Asn Ile Leu Lys Phe Phe Phe Val Phe Ile Val Ala Met Ser Leu
1               5                   10                  15

Val Ser Cys Ser Thr Ala Ala Pro Ala Lys Ile Pro Ile Lys Ala Ile
            20                  25                  30

Lys Thr Val Gly Lys Ala Val Gly Lys Gly Leu Arg Ala Ile Asn Ile
        35                  40                  45

Ala Ser Thr Ala Asn Asp Val Phe Asn Phe Leu Lys Pro Lys Lys Arg
    50                  55                  60

Lys His
65


<210> SEQ ID NO 85
<211> LENGTH: 71
<212> TYPE: PRT
<213> ORGANISM: Ceratitis capitata

<400> SEQUENCE: 85

Met Ala Asn Leu Lys Ala Val Phe Leu Ile Cys Ile Val Ala Phe Ile
1               5                   10                  15

Ala Leu Gln Cys Val Val Ala Glu Pro Ala Ala Glu Asp Ser Val Val
            20                  25                  30

Val Lys Arg Ser Ile Gly Ser Ala Leu Lys Lys Ala Leu Pro Val Ala
        35                  40                  45

Lys Lys Ile Gly Lys Ile Ala Leu Pro Ile Ala Lys Ala Ala Leu Pro
    50                  55                  60

Val Ala Ala Gly Leu Val Gly
65                  70


<210> SEQ ID NO 86
<211> LENGTH: 53
<212> TYPE: PRT
<213> ORGANISM: Apis mellifera

<400> SEQUENCE: 86

Met Lys Val Val Ile Phe Ile Phe Ala Leu Leu Ala Thr Ile Cys Ala
1               5                   10                  15

Ala Phe Ala Tyr Val Pro Leu Pro Asn Val Pro Gln Pro Gly Arg Arg
            20                  25                  30

Pro Phe Pro Thr Phe Pro Gly Gln Gly Pro Phe Asn Pro Lys Ile Lys
        35                  40                  45

Trp Pro Gln Gly Tyr
    50


<210> SEQ ID NO 87
<211> LENGTH: 283
<212> TYPE: PRT
<213> ORGANISM: Apis mellifera

<400> SEQUENCE: 87

Lys Asn Phe Ala Leu Ala Ile Leu Val Val Thr Phe Val Val Ala Val
1               5                   10                  15

Phe Gly Asn Thr Asn Leu Asp Pro Pro Thr Arg Pro Thr Arg Leu Arg
            20                  25                  30

Arg Glu Ala Lys Pro Glu Ala Glu Pro Gly Asn Asn Arg Pro Val Tyr
        35                  40                  45

Ile Pro Gln Pro Arg Pro Pro His Pro Arg Leu Arg Arg Glu Ala Glu
    50                  55                  60
```

```
Pro Glu Ala Glu Pro Gly Asn Asn Arg Pro Val Tyr Ile Pro Gln Pro
65                  70                  75                  80

Arg Pro Pro His Pro Arg Leu Arg Arg Glu Ala Glu Leu Glu Ala Glu
                85                  90                  95

Pro Gly Asn Asn Arg Pro Val Tyr Ile Ser Gln Pro Arg Pro Pro His
            100                 105                 110

Pro Arg Leu Arg Arg Glu Ala Glu Pro Glu Ala Glu Pro Gly Asn Asn
        115                 120                 125

Arg Pro Val Tyr Ile Pro Gln Pro Arg Pro Pro His Pro Arg Leu Arg
    130                 135                 140

Arg Glu Ala Glu Leu Glu Ala Glu Pro Gly Asn Asn Arg Pro Val Tyr
145                 150                 155                 160

Ile Ser Gln Pro Arg Pro Pro His Pro Arg Leu Arg Arg Glu Ala Glu
                165                 170                 175

Pro Glu Ala Glu Pro Gly Asn Asn Arg Pro Val Tyr Ile Pro Gln Pro
            180                 185                 190

Arg Pro Pro His Pro Arg Leu Arg Arg Glu Ala Glu Pro Glu Ala Glu
        195                 200                 205

Pro Gly Asn Asn Arg Pro Val Tyr Ile Pro Gln Pro Arg Pro Pro His
    210                 215                 220

Pro Arg Leu Arg Arg Glu Ala Glu Pro Glu Ala Glu Pro Gly Asn Asn
225                 230                 235                 240

Arg Pro Val Tyr Ile Pro Gln Pro Arg Pro Pro His Pro Arg Leu Arg
                245                 250                 255

Arg Glu Ala Lys Pro Glu Ala Lys Pro Gly Asn Asn Arg Pro Val Tyr
            260                 265                 270

Ile Pro Gln Pro Arg Pro Pro His Pro Arg Ile
        275                 280


<210> SEQ ID NO 88
<211> LENGTH: 228
<212> TYPE: PRT
<213> ORGANISM: Sus scrofa

<400> SEQUENCE: 88

Met Glu Thr Gln Arg Ala Ser Leu Cys Leu Gly Arg Trp Ser Leu Trp
1               5                   10                  15

Leu Leu Leu Leu Ala Leu Val Val Pro Ser Ala Ser Ala Gln Ala Leu
            20                  25                  30

Ser Tyr Arg Glu Ala Val Leu Arg Ala Val Asp Arg Leu Asn Glu Gln
        35                  40                  45

Ser Ser Glu Ala Asn Leu Tyr Arg Leu Leu Glu Leu Asp Gln Pro Pro
    50                  55                  60

Lys Ala Asp Glu Asp Pro Gly Thr Pro Lys Pro Val Ser Phe Thr Val
65                  70                  75                  80

Lys Glu Thr Val Cys Pro Arg Pro Thr Arg Arg Pro Pro Glu Leu Cys
                85                  90                  95

Asp Phe Lys Glu Asn Gly Arg Val Lys Gln Cys Val Gly Thr Val Thr
            100                 105                 110

Leu Asp Gln Ile Lys Asp Pro Leu Asp Ile Thr Cys Asn Glu Gly Val
        115                 120                 125

Arg Arg Phe Pro Trp Trp Trp Pro Phe Leu Arg Arg Pro Arg Leu Arg
    130                 135                 140

Arg Gln Ala Phe Pro Pro Pro Asn Val Pro Gly Pro Arg Phe Pro Pro
145                 150                 155                 160
```

```
Pro Asn Val Pro Gly Pro Arg Phe Pro Pro Pro Asn Phe Pro Gly Pro
                165                 170                 175

Arg Phe Pro Pro Pro Asn Phe Pro Gly Pro Arg Phe Pro Pro Pro Asn
            180                 185                 190

Phe Pro Gly Pro Pro Phe Pro Pro Pro Ile Phe Pro Gly Pro Trp Phe
        195                 200                 205

Pro Pro Pro Pro Pro Phe Arg Pro Pro Pro Phe Gly Pro Pro Arg Phe
    210                 215                 220

Pro Gly Arg Arg
225
```

<210> SEQ ID NO 89
<211> LENGTH: 144
<212> TYPE: PRT
<213> ORGANISM: Bos taurus

<400> SEQUENCE: 89

```
Met Gln Thr Gln Arg Ala Ser Leu Ser Leu Gly Arg Trp Ser Leu Trp
1               5                   10                  15

Leu Leu Leu Leu Gly Leu Val Val Pro Ser Ala Ser Ala Gln Ala Leu
            20                  25                  30

Ser Tyr Arg Glu Ala Val Leu Arg Ala Val Asp Gln Leu Asn Glu Leu
        35                  40                  45

Ser Ser Glu Ala Asn Leu Tyr Arg Leu Leu Glu Leu Asp Pro Pro Pro
    50                  55                  60

Lys Asp Asn Glu Asp Leu Gly Thr Arg Lys Pro Val Ser Phe Thr Val
65                  70                  75                  80

Lys Glu Thr Val Cys Pro Arg Thr Ile Gln Gln Pro Ala Glu Gln Cys
                85                  90                  95

Asp Phe Lys Glu Lys Gly Arg Val Lys Gln Cys Val Gly Thr Val Thr
            100                 105                 110

Leu Asp Pro Ser Asn Asp Gln Phe Asp Leu Asn Cys Asn Glu Leu Gln
        115                 120                 125

Ser Val Ile Leu Pro Trp Lys Trp Pro Trp Trp Pro Trp Arg Arg Gly
    130                 135                 140
```

<210> SEQ ID NO 90
<211> LENGTH: 149
<212> TYPE: PRT
<213> ORGANISM: Sus scrofa

<400> SEQUENCE: 90

```
Met Glu Thr Gln Arg Ala Ser Leu Cys Leu Gly Arg Trp Ser Leu Trp
1               5                   10                  15

Leu Leu Leu Leu Ala Leu Val Val Pro Ser Ala Ser Ala Gln Ala Leu
            20                  25                  30

Ser Tyr Arg Glu Ala Val Leu Arg Ala Val Asp Arg Leu Asn Glu Gln
        35                  40                  45

Ser Ser Glu Ala Asn Leu Tyr Arg Leu Leu Glu Leu Asp Gln Pro Pro
    50                  55                  60

Lys Ala Asp Glu Asp Pro Gly Thr Pro Lys Pro Val Ser Phe Thr Val
65                  70                  75                  80

Lys Glu Thr Val Cys Pro Arg Pro Thr Arg Gln Pro Pro Glu Leu Cys
                85                  90                  95

Asp Phe Lys Glu Asn Gly Arg Val Lys Gln Cys Val Gly Thr Val Thr
            100                 105                 110
```

Leu Asp Gln Ile Lys Asp Pro Leu Asp Ile Thr Cys Asn Glu Val Gln
        115                 120                 125

Gly Val Arg Gly Gly Arg Leu Cys Tyr Cys Arg Arg Arg Phe Cys Val
    130                 135                 140

Cys Val Gly Arg Gly
145

<210> SEQ ID NO 91
<211> LENGTH: 17
<212> TYPE: PRT
<213> ORGANISM: Tachypleus gigas

<400> SEQUENCE: 91

Lys Trp Cys Phe Arg Val Cys Tyr Arg Gly Ile Cys Tyr Arg Arg Cys
1               5                   10                  15

Arg

<210> SEQ ID NO 92
<211> LENGTH: 102
<212> TYPE: PRT
<213> ORGANISM: Anopheles gambiae

<400> SEQUENCE: 92

Met Lys Cys Ala Thr Ile Val Cys Thr Ile Ala Val Val Leu Ala Ala
1               5                   10                  15

Thr Leu Leu Asn Gly Ser Val Gln Ala Ala Pro Gln Glu Glu Ala Ala
            20                  25                  30

Leu Ser Gly Gly Ala Asn Leu Asn Thr Leu Leu Asp Glu Leu Pro Glu
        35                  40                  45

Glu Thr His His Ala Ala Leu Glu Asn Tyr Arg Ala Lys Arg Ala Thr
    50                  55                  60

Cys Asp Leu Ala Ser Gly Phe Gly Val Gly Ser Ser Leu Cys Ala Ala
65                  70                  75                  80

His Cys Ile Ala Arg Arg Tyr Arg Gly Gly Tyr Cys Asn Ser Lys Ala
                85                  90                  95

Val Cys Val Cys Arg Asn
            100

<210> SEQ ID NO 93
<211> LENGTH: 70
<212> TYPE: PRT
<213> ORGANISM: Drosophila melanogaster

<400> SEQUENCE: 93

Met Met Gln Ile Lys Tyr Leu Phe Ala Leu Phe Ala Val Leu Met Leu
1               5                   10                  15

Val Val Leu Gly Ala Asn Glu Ala Asp Ala Asp Cys Leu Ser Gly Arg
            20                  25                  30

Tyr Lys Gly Pro Cys Ala Val Trp Asp Asn Glu Thr Cys Arg Arg Val
        35                  40                  45

Cys Lys Glu Glu Gly Arg Ser Ser Gly His Cys Ser Pro Ser Leu Lys
    50                  55                  60

Cys Trp Cys Glu Gly Cys
65                  70

<210> SEQ ID NO 94
<211> LENGTH: 63
<212> TYPE: PRT

<213> ORGANISM: Medicago truncatula

<400> SEQUENCE: 94

```
Met Thr Lys Ile Val Val Phe Ile Tyr Val Val Ile Leu Leu Leu Thr
1               5                   10                  15

Ile Phe His Val Ser Ala Lys Lys Lys Arg Tyr Ile Glu Cys Glu Thr
            20                  25                  30

His Glu Asp Cys Ser Gln Val Phe Met Pro Pro Phe Val Met Arg Cys
        35                  40                  45

Val Ile His Glu Cys Lys Ile Phe Asn Gly Glu His Leu Arg Tyr
    50                  55                  60
```

<210> SEQ ID NO 95
<211> LENGTH: 76
<212> TYPE: PRT
<213> ORGANISM: Medicago truncatula

<400> SEQUENCE: 95

```
Met Ala Lys Ile Met Lys Phe Val Tyr Asn Met Ile Pro Phe Leu Ser
1               5                   10                  15

Ile Phe Ile Ile Thr Leu Gln Val Asn Val Val Val Cys Glu Ile Asp
            20                  25                  30

Ala Asp Cys Pro Gln Ile Cys Met Pro Pro Tyr Glu Val Arg Cys Val
        35                  40                  45

Asn His Arg Cys Gly Trp Val Asn Thr Asp Asp Ser Leu Phe Leu Thr
    50                  55                  60

Gln Glu Phe Thr Arg Ser Lys Gln Tyr Ile Ile Ser
65                  70                  75
```

<210> SEQ ID NO 96
<211> LENGTH: 76
<212> TYPE: PRT
<213> ORGANISM: Medicago truncatula

<400> SEQUENCE: 96

```
Met Tyr Lys Val Val Glu Ser Ile Phe Ile Arg Tyr Met His Arg Lys
1               5                   10                  15

Pro Asn Met Thr Lys Phe Phe Lys Phe Val Tyr Thr Met Phe Ile Leu
            20                  25                  30

Ile Ser Leu Phe Leu Val Val Thr Asn Ala Asn Ala His Asn Cys Thr
        35                  40                  45

Asp Ile Ser Asp Cys Ser Ser Asn His Cys Ser Tyr Glu Gly Val Ser
    50                  55                  60

Leu Cys Met Asn Gly Gln Cys Ile Cys Ile Tyr Glu
65                  70                  75
```

<210> SEQ ID NO 97
<211> LENGTH: 64
<212> TYPE: PRT
<213> ORGANISM: Medicago truncatula

<400> SEQUENCE: 97

```
Met Val Glu Thr Leu Arg Leu Phe Tyr Ile Met Ile Leu Phe Val Ser
1               5                   10                  15

Leu Cys Leu Val Val Val Asp Gly Glu Ser Lys Leu Glu Gln Thr Cys
            20                  25                  30

Ser Glu Asp Phe Glu Cys Tyr Ile Lys Asn Pro His Val Pro Phe Gly
        35                  40                  45
```

```
His Leu Arg Cys Phe Glu Gly Phe Cys Gln Gln Leu Asn Gly Pro Ala
    50                  55                  60


<210> SEQ ID NO 98
<211> LENGTH: 67
<212> TYPE: PRT
<213> ORGANISM: Medicago truncatula

<400> SEQUENCE: 98

Met Ala Lys Ile Val Asn Phe Val Tyr Ser Met Ile Val Phe Leu Phe
1               5                   10                  15

Leu Phe Leu Val Ala Thr Lys Ala Ala Arg Gly Tyr Leu Cys Val Thr
            20                  25                  30

Asp Ser His Cys Pro Pro His Met Cys Pro Pro Gly Met Glu Pro Arg
        35                  40                  45

Cys Val Arg Arg Met Cys Lys Cys Leu Pro Ile Gly Trp Arg Lys Tyr
    50                  55                  60

Phe Val Pro
65


<210> SEQ ID NO 99
<211> LENGTH: 96
<212> TYPE: PRT
<213> ORGANISM: Medicago truncatula

<400> SEQUENCE: 99

Met Gln Ile Gly Lys Asn Met Val Glu Thr Pro Lys Leu Asp Tyr Val
1               5                   10                  15

Ile Ile Phe Phe Phe Leu Tyr Phe Phe Phe Arg Gln Met Ile Ile Leu
            20                  25                  30

Arg Leu Asn Thr Thr Phe Arg Pro Leu Asn Phe Lys Met Leu Arg Phe
        35                  40                  45

Trp Gly Gln Asn Arg Asn Ile Met Lys His Arg Gly Gln Lys Val His
    50                  55                  60

Phe Ser Leu Ile Leu Ser Asp Cys Lys Thr Asn Lys Asp Cys Pro Lys
65                  70                  75                  80

Leu Arg Arg Ala Asn Val Arg Cys Arg Lys Ser Tyr Cys Val Pro Ile
                85                  90                  95


<210> SEQ ID NO 100
<211> LENGTH: 65
<212> TYPE: PRT
<213> ORGANISM: Medicago truncatula

<400> SEQUENCE: 100

Met Leu Arg Leu Tyr Leu Val Ser Tyr Phe Leu Leu Lys Arg Thr Leu
1               5                   10                  15

Leu Val Ser Tyr Phe Ser Tyr Phe Ser Thr Tyr Ile Ile Glu Cys Lys
            20                  25                  30

Thr Asp Asn Asp Cys Pro Ile Ser Gln Leu Lys Ile Tyr Ala Trp Lys
        35                  40                  45

Cys Val Lys Asn Gly Cys His Leu Phe Asp Val Ile Pro Met Met Tyr
    50                  55                  60

Glu
65


<210> SEQ ID NO 101
<211> LENGTH: 79
<212> TYPE: PRT
```

-continued

<213> ORGANISM: Medicago truncatula

<400> SEQUENCE: 101

Met Ala Glu Ile Leu Lys Phe Val Tyr Ile Val Ile Leu Phe Val Ser
1 5 10 15

Leu Leu Leu Ile Val Val Ala Ser Glu Arg Glu Cys Val Thr Asp Asp
20 25 30

Asp Cys Glu Lys Leu Tyr Pro Thr Asn Glu Tyr Arg Met Met Cys Asp
35 40 45

Ser Gly Tyr Cys Met Asn Leu Leu Asn Gly Lys Ile Ile Tyr Leu Leu
50 55 60

Cys Leu Lys Lys Lys Lys Phe Leu Ile Ile Ile Ser Val Leu Leu
65 70 75

<210> SEQ ID NO 102
<211> LENGTH: 95
<212> TYPE: PRT
<213> ORGANISM: Medicago truncatula

<400> SEQUENCE: 102

Met Ala Glu Ile Ile Lys Phe Val Tyr Ile Met Ile Leu Cys Val Ser
1 5 10 15

Leu Leu Leu Ile Glu Val Ala Gly Glu Glu Cys Val Thr Asp Ala Asp
20 25 30

Cys Asp Lys Leu Tyr Pro Asp Ile Arg Lys Pro Leu Met Cys Ser Ile
35 40 45

Gly Glu Cys Tyr Ser Leu Tyr Lys Gly Lys Phe Ser Leu Ser Ile Ile
50 55 60

Ser Lys Thr Ser Phe Ser Leu Met Val Tyr Asn Val Val Thr Leu Val
65 70 75 80

Ile Cys Leu Arg Leu Ala Tyr Ile Ser Leu Leu Leu Lys Phe Leu
85 90 95

<210> SEQ ID NO 103
<211> LENGTH: 100
<212> TYPE: PRT
<213> ORGANISM: Medicago truncatula

<400> SEQUENCE: 103

Met Ala Glu Ile Leu Lys Asp Phe Tyr Ala Met Asn Leu Phe Ile Phe
1 5 10 15

Leu Ile Ile Leu Pro Ala Lys Ile Arg Gly Glu Thr Leu Ser Leu Thr
20 25 30

His Pro Lys Cys His His Ile Met Leu Pro Ser Leu Phe Ile Thr Glu
35 40 45

Val Phe Gln Arg Val Thr Asp Asp Gly Cys Pro Lys Pro Val Asn His
50 55 60

Leu Arg Val Val Lys Cys Ile Glu His Ile Cys Glu Tyr Gly Tyr Asn
65 70 75 80

Tyr Arg Pro Asp Phe Ala Ser Gln Ile Pro Glu Ser Thr Lys Met Pro
85 90 95

Arg Lys Arg Glu
100

<210> SEQ ID NO 104
<211> LENGTH: 78
<212> TYPE: PRT
<213> ORGANISM: Medicago truncatula

<400> SEQUENCE: 104

Met Val Glu Ile Leu Lys Asn Phe Tyr Ala Met Asn Leu Phe Ile Phe
1               5                   10                  15

Leu Ile Ile Leu Ala Val Lys Ile Arg Gly Ala His Phe Pro Cys Val
            20                  25                  30

Thr Asp Asp Asp Cys Pro Lys Pro Val Asn Lys Leu Arg Val Ile Lys
        35                  40                  45

Cys Ile Asp His Ile Cys Gln Tyr Ala Arg Asn Leu Pro Asp Phe Ala
    50                  55                  60

Ser Glu Ile Ser Glu Ser Thr Lys Met Pro Cys Lys Gly Glu
65                  70                  75

<210> SEQ ID NO 105
<211> LENGTH: 72
<212> TYPE: PRT
<213> ORGANISM: Medicago truncatula

<400> SEQUENCE: 105

Met Phe His Ala Gln Ala Glu Asn Met Ala Lys Val Ser Asn Phe Val
1               5                   10                  15

Cys Ile Met Ile Leu Phe Leu Ala Leu Phe Phe Ile Thr Met Asn Asp
            20                  25                  30

Ala Ala Arg Phe Glu Cys Arg Glu Asp Ser His Cys Val Thr Arg Ile
        35                  40                  45

Lys Cys Val Leu Pro Arg Lys Pro Glu Cys Arg Asn Tyr Ala Cys Gly
    50                  55                  60

Cys Tyr Asp Ser Asn Lys Tyr Arg
65                  70

<210> SEQ ID NO 106
<211> LENGTH: 78
<212> TYPE: PRT
<213> ORGANISM: Medicago truncatula

<400> SEQUENCE: 106

Met Gln Met Arg Gln Asn Met Ala Thr Ile Leu Asn Phe Val Phe Val
1               5                   10                  15

Ile Ile Leu Phe Ile Ser Leu Leu Leu Val Val Thr Lys Gly Tyr Arg
            20                  25                  30

Glu Pro Phe Ser Ser Phe Thr Glu Gly Pro Thr Cys Lys Glu Asp Ile
        35                  40                  45

Asp Cys Pro Ser Ile Ser Cys Val Asn Pro Gln Val Pro Lys Cys Ile
    50                  55                  60

Met Phe Glu Cys His Cys Lys Tyr Ile Pro Thr Thr Leu Lys
65                  70                  75

<210> SEQ ID NO 107
<211> LENGTH: 71
<212> TYPE: PRT
<213> ORGANISM: Medicago truncatula

<400> SEQUENCE: 107

Met Ala Thr Ile Leu Met Tyr Val Tyr Ile Thr Ile Leu Phe Ile Ser
1               5                   10                  15

Ile Leu Thr Val Leu Thr Glu Gly Leu Tyr Glu Pro Leu Tyr Asn Phe
            20                  25                  30

Arg Arg Asp Pro Asp Cys Arg Arg Asn Ile Asp Cys Pro Ser Tyr Leu

```
        35                  40                  45

Cys Val Ala Pro Lys Val Pro Arg Cys Ile Met Phe Glu Cys His Cys
    50                  55                  60

Lys Asp Ile Pro Ser Asp His
65                  70


<210> SEQ ID NO 108
<211> LENGTH: 57
<212> TYPE: PRT
<213> ORGANISM: Medicago truncatula

<400> SEQUENCE: 108

Met Thr Thr Ser Leu Lys Phe Val Tyr Val Ala Ile Leu Phe Leu Ser
1               5                   10                  15

Leu Leu Leu Val Val Met Gly Gly Ile Arg Arg Phe Glu Cys Arg Gln
            20                  25                  30

Asp Ser Asp Cys Pro Ser Tyr Phe Cys Glu Lys Leu Thr Val Pro Lys
        35                  40                  45

Cys Phe Trp Ser Lys Cys Tyr Cys Lys
    50                  55


<210> SEQ ID NO 109
<211> LENGTH: 57
<212> TYPE: PRT
<213> ORGANISM: Medicago truncatula

<400> SEQUENCE: 109

Met Thr Thr Ser Leu Lys Phe Val Tyr Val Ala Ile Leu Phe Leu Ser
1               5                   10                  15

Leu Leu Leu Val Val Met Gly Gly Ile Arg Lys Lys Glu Cys Arg Gln
            20                  25                  30

Asp Ser Asp Cys Pro Ser Tyr Phe Cys Glu Lys Leu Thr Ile Ala Lys
        35                  40                  45

Cys Ile His Ser Thr Cys Leu Cys Lys
    50                  55


<210> SEQ ID NO 110
<211> LENGTH: 66
<212> TYPE: PRT
<213> ORGANISM: Medicago truncatula

<400> SEQUENCE: 110

Met Gln Ile Gly Lys Asn Met Val Glu Thr Pro Lys Leu Val Tyr Phe
1               5                   10                  15

Ile Ile Leu Phe Leu Ser Ile Phe Leu Cys Ile Thr Val Ser Asn Ser
            20                  25                  30

Ser Phe Ser Gln Ile Phe Asn Ser Ala Cys Lys Thr Asp Lys Asp Cys
        35                  40                  45

Pro Lys Phe Gly Arg Val Asn Val Arg Cys Arg Lys Gly Asn Cys Val
    50                  55                  60

Pro Ile
65


<210> SEQ ID NO 111
<211> LENGTH: 57
<212> TYPE: PRT
<213> ORGANISM: Medicago truncatula

<400> SEQUENCE: 111
```

```
Met Thr Ala Ile Leu Lys Lys Phe Ile Asn Ala Val Phe Leu Phe Ile
1               5                   10                  15

Val Leu Phe Leu Ala Thr Thr Asn Val Glu Asp Phe Val Gly Gly Ser
            20                  25                  30

Asn Asp Glu Cys Val Tyr Pro Asp Val Phe Gln Cys Ile Asn Asn Ile
        35                  40                  45

Cys Lys Cys Val Ser His His Arg Thr
    50                  55
```

<210> SEQ ID NO 112
<211> LENGTH: 74
<212> TYPE: PRT
<213> ORGANISM: Medicago truncatula

<400> SEQUENCE: 112

```
Met Gln Lys Arg Lys Asn Met Ala Gln Ile Ile Phe Tyr Val Tyr Ala
1               5                   10                  15

Leu Ile Ile Leu Phe Ser Pro Phe Leu Ala Ala Arg Leu Val Phe Val
            20                  25                  30

Asn Pro Glu Lys Pro Cys Val Thr Asp Ala Asp Cys Asp Arg Tyr Arg
        35                  40                  45

His Glu Ser Ala Ile Tyr Ser Asp Met Phe Cys Lys Asp Gly Tyr Cys
    50                  55                  60

Phe Ile Asp Tyr His His Asp Pro Tyr Pro
65                  70
```

<210> SEQ ID NO 113
<211> LENGTH: 76
<212> TYPE: PRT
<213> ORGANISM: Medicago truncatula

<400> SEQUENCE: 113

```
Met Gln Met Arg Lys Asn Met Ala Gln Ile Leu Phe Tyr Val Tyr Ala
1               5                   10                  15

Leu Leu Ile Leu Phe Thr Pro Phe Leu Val Ala Arg Ile Met Val Val
            20                  25                  30

Asn Pro Asn Asn Pro Cys Val Thr Asp Ala Asp Cys Gln Arg Tyr Arg
        35                  40                  45

His Lys Leu Ala Thr Arg Met Ile Cys Asn Gln Gly Phe Cys Leu Met
    50                  55                  60

Asp Phe Thr His Asp Pro Tyr Ala Pro Ser Leu Pro
65                  70                  75
```

<210> SEQ ID NO 114
<211> LENGTH: 64
<212> TYPE: PRT
<213> ORGANISM: Medicago truncatula

<400> SEQUENCE: 114

```
Met Asn His Ile Ser Lys Phe Val Tyr Ala Leu Ile Ile Phe Leu Ser
1               5                   10                  15

Ile Tyr Leu Val Val Leu Asp Gly Leu Pro Ile Ser Cys Lys Asp His
            20                  25                  30

Phe Glu Cys Arg Arg Lys Ile Asn Ile Leu Arg Cys Ile Tyr Arg Gln
        35                  40                  45

Glu Lys Pro Met Cys Ile Asn Ser Ile Cys Thr Cys Val Lys Leu Leu
    50                  55                  60
```

<210> SEQ ID NO 115
<211> LENGTH: 67
<212> TYPE: PRT
<213> ORGANISM: Medicago truncatula

<400> SEQUENCE: 115

Met Gln Arg Glu Lys Asn Met Ala Lys Ile Phe Glu Phe Val Tyr Ala
1 5 10 15

Met Ile Ile Phe Ile Leu Leu Phe Leu Val Glu Lys Asn Val Val Ala
20 25 30

Tyr Leu Lys Phe Glu Cys Lys Thr Asp Asp Asp Cys Gln Lys Ser Leu
35 40 45

Leu Lys Thr Tyr Val Trp Lys Cys Val Lys Asn Glu Cys Tyr Phe Phe
50 55 60

Ala Lys Lys
65

<210> SEQ ID NO 116
<211> LENGTH: 61
<212> TYPE: PRT
<213> ORGANISM: Medicago truncatula

<400> SEQUENCE: 116

Met Ala Gly Ile Ile Lys Phe Val His Val Leu Ile Ile Phe Leu Ser
1 5 10 15

Leu Phe His Val Val Lys Asn Asp Asp Gly Ser Phe Cys Phe Lys Asp
20 25 30

Ser Asp Cys Pro Asp Glu Met Cys Pro Ser Pro Leu Lys Glu Met Cys
35 40 45

Tyr Phe Leu Gln Cys Lys Cys Gly Val Asp Thr Ile Ala
50 55 60

<210> SEQ ID NO 117
<211> LENGTH: 59
<212> TYPE: PRT
<213> ORGANISM: Medicago truncatula

<400> SEQUENCE: 117

Met Ala Asn Thr His Lys Leu Val Ser Met Ile Leu Phe Ile Phe Leu
1 5 10 15

Phe Leu Ala Ser Asn Asn Val Glu Gly Tyr Val Asn Cys Glu Thr Asp
20 25 30

Ala Asp Cys Pro Pro Ser Thr Arg Val Lys Arg Phe Lys Cys Val Lys
35 40 45

Gly Glu Cys Arg Trp Thr Arg Met Ser Tyr Ala
50 55

<210> SEQ ID NO 118
<211> LENGTH: 63
<212> TYPE: PRT
<213> ORGANISM: Medicago truncatula

<400> SEQUENCE: 118

Met Gln Arg Arg Lys Lys Lys Ala Gln Val Val Met Phe Val His Asp
1 5 10 15

Leu Ile Ile Cys Ile Tyr Leu Phe Ile Val Ile Thr Thr Arg Lys Thr
20 25 30

Asp Ile Arg Cys Arg Phe Tyr Tyr Asp Cys Pro Arg Leu Glu Tyr His
35 40 45

Phe Cys Glu Cys Ile Glu Asp Phe Cys Ala Tyr Ile Arg Leu Asn
    50                  55                  60

<210> SEQ ID NO 119
<211> LENGTH: 57
<212> TYPE: PRT
<213> ORGANISM: Medicago truncatula

<400> SEQUENCE: 119

Met Ala Lys Val Tyr Met Phe Val Tyr Ala Leu Ile Ile Phe Val Ser
1               5                   10                  15

Pro Phe Leu Leu Ala Thr Phe Arg Thr Arg Leu Pro Cys Glu Lys Asp
            20                  25                  30

Asp Asp Cys Pro Glu Ala Phe Leu Pro Pro Val Met Lys Cys Val Asn
        35                  40                  45

Arg Phe Cys Gln Tyr Glu Ile Leu Glu
    50                  55

<210> SEQ ID NO 120
<211> LENGTH: 77
<212> TYPE: PRT
<213> ORGANISM: Medicago truncatula

<400> SEQUENCE: 120

Met Ile Lys Gln Phe Ser Val Cys Tyr Ile Gln Met Arg Arg Asn Met
1               5                   10                  15

Thr Thr Ile Leu Lys Phe Pro Tyr Ile Met Val Ile Cys Leu Leu Leu
            20                  25                  30

Leu His Val Ala Ala Tyr Glu Asp Phe Glu Lys Glu Ile Phe Asp Cys
        35                  40                  45

Lys Lys Asp Gly Asp Cys Asp His Met Cys Val Thr Pro Gly Ile Pro
    50                  55                  60

Lys Cys Thr Gly Tyr Val Cys Phe Cys Phe Glu Asn Leu
65                  70                  75

<210> SEQ ID NO 121
<211> LENGTH: 73
<212> TYPE: PRT
<213> ORGANISM: Medicago truncatula

<400> SEQUENCE: 121

Met Gln Arg Ser Arg Asn Met Thr Thr Ile Phe Lys Phe Ala Tyr Ile
1               5                   10                  15

Met Ile Ile Cys Val Phe Leu Leu Asn Ile Ala Ala Gln Glu Ile Glu
            20                  25                  30

Asn Gly Ile His Pro Cys Lys Lys Asn Glu Asp Cys Asn His Met Cys
        35                  40                  45

Val Met Pro Gly Leu Pro Trp Cys His Glu Asn Asn Leu Cys Phe Cys
    50                  55                  60

Tyr Glu Asn Ala Tyr Gly Asn Thr Arg
65                  70

<210> SEQ ID NO 122
<211> LENGTH: 85
<212> TYPE: PRT
<213> ORGANISM: Medicago truncatula

<400> SEQUENCE: 122

Met Thr Ile Ile Ile Lys Phe Val Asn Val Leu Ile Ile Phe Leu Ser
1               5                   10                  15

```
Leu Phe His Val Ala Lys Asn Asp Asp Asn Lys Leu Leu Leu Ser Phe
            20                  25                  30

Ile Glu Glu Gly Phe Leu Cys Phe Lys Asp Ser Asp Cys Pro Tyr Asn
        35                  40                  45

Met Cys Pro Ser Pro Leu Lys Glu Met Cys Tyr Phe Ile Lys Cys Val
    50                  55                  60

Cys Gly Val Tyr Gly Pro Ile Arg Glu Arg Arg Leu Tyr Gln Ser His
65                  70                  75                  80

Asn Pro Met Ile Gln
                85


<210> SEQ ID NO 123
<211> LENGTH: 69
<212> TYPE: PRT
<213> ORGANISM: Medicago truncatula

<400> SEQUENCE: 123

Met Arg Lys Asn Met Thr Lys Ile Leu Met Ile Gly Tyr Ala Leu Met
1               5                   10                  15

Ile Phe Ile Phe Leu Ser Ile Ala Val Ser Ile Thr Gly Asn Leu Ala
            20                  25                  30

Arg Ala Ser Arg Lys Lys Pro Val Asp Val Ile Pro Cys Ile Tyr Asp
        35                  40                  45

His Asp Cys Pro Arg Lys Leu Tyr Phe Leu Glu Arg Cys Val Gly Arg
    50                  55                  60

Val Cys Lys Tyr Leu
65


<210> SEQ ID NO 124
<211> LENGTH: 58
<212> TYPE: PRT
<213> ORGANISM: Medicago truncatula

<400> SEQUENCE: 124

Met Ala His Lys Leu Val Tyr Ala Ile Thr Leu Phe Ile Phe Leu Phe
1               5                   10                  15

Leu Ile Ala Asn Asn Ile Glu Asp Asp Ile Phe Cys Ile Thr Asp Asn
            20                  25                  30

Asp Cys Pro Pro Asn Thr Leu Val Gln Arg Tyr Arg Cys Ile Asn Gly
        35                  40                  45

Lys Cys Asn Leu Ser Phe Val Ser Tyr Gly
    50                  55


<210> SEQ ID NO 125
<211> LENGTH: 61
<212> TYPE: PRT
<213> ORGANISM: Medicago truncatula

<400> SEQUENCE: 125

Met Asp Glu Thr Leu Lys Phe Val Tyr Ile Leu Ile Leu Phe Val Ser
1               5                   10                  15

Leu Cys Leu Val Val Ala Asp Gly Val Lys Asn Ile Asn Arg Glu Cys
            20                  25                  30

Thr Gln Thr Ser Asp Cys Tyr Lys Lys Tyr Pro Phe Ile Pro Trp Gly
        35                  40                  45

Lys Val Arg Cys Val Lys Gly Arg Cys Arg Leu Asp Met
    50                  55                  60
```

<210> SEQ ID NO 126
<211> LENGTH: 62
<212> TYPE: PRT
<213> ORGANISM: Medicago truncatula

<400> SEQUENCE: 126

```
Met Ala Lys Ile Ile Lys Phe Val Tyr Val Leu Ala Ile Phe Phe Ser
1               5                   10                  15

Leu Phe Leu Val Ala Lys Asn Val Asn Gly Trp Thr Cys Val Glu Asp
            20                  25                  30

Ser Asp Cys Pro Ala Asn Ile Cys Gln Pro Pro Met Gln Arg Met Cys
        35                  40                  45

Phe Tyr Gly Glu Cys Ala Cys Val Arg Ser Lys Phe Cys Thr
    50                  55                  60
```

<210> SEQ ID NO 127
<211> LENGTH: 61
<212> TYPE: PRT
<213> ORGANISM: Medicago truncatula

<400> SEQUENCE: 127

```
Met Val Lys Ile Ile Lys Phe Val Tyr Phe Met Thr Leu Phe Leu Ser
1               5                   10                  15

Met Leu Leu Val Thr Thr Lys Glu Asp Gly Ser Val Glu Cys Ile Ala
            20                  25                  30

Asn Ile Asp Cys Pro Gln Ile Phe Met Leu Pro Phe Val Met Arg Cys
        35                  40                  45

Ile Asn Phe Arg Cys Gln Ile Val Asn Ser Glu Asp Thr
    50                  55                  60
```

<210> SEQ ID NO 128
<211> LENGTH: 67
<212> TYPE: PRT
<213> ORGANISM: Medicago truncatula

<400> SEQUENCE: 128

```
Met Asp Glu Ile Leu Lys Phe Val Tyr Thr Leu Ile Ile Phe Phe Ser
1               5                   10                  15

Leu Phe Phe Ala Ala Asn Asn Val Asp Ala Asn Ile Met Asn Cys Gln
            20                  25                  30

Ser Thr Phe Asp Cys Pro Arg Asp Met Cys Ser His Ile Arg Asp Val
        35                  40                  45

Ile Cys Ile Phe Lys Lys Cys Lys Cys Ala Gly Gly Arg Tyr Met Pro
    50                  55                  60

Gln Val Pro
65
```

<210> SEQ ID NO 129
<211> LENGTH: 62
<212> TYPE: PRT
<213> ORGANISM: Medicago truncatula

<400> SEQUENCE: 129

```
Met Gln Arg Arg Lys Asn Met Ala Asn Asn His Met Leu Ile Tyr Ala
1               5                   10                  15

Met Ile Ile Cys Leu Phe Pro Tyr Leu Val Val Thr Phe Lys Thr Ala
            20                  25                  30

Ile Thr Cys Asp Cys Asn Glu Asp Cys Leu Asn Phe Phe Thr Pro Leu
        35                  40                  45
```

Asp Asn Leu Lys Cys Ile Asp Asn Val Cys Glu Val Phe Met
    50                  55                  60

<210> SEQ ID NO 130
<211> LENGTH: 65
<212> TYPE: PRT
<213> ORGANISM: Medicago truncatula

<400> SEQUENCE: 130

Met Val Asn Ile Leu Lys Phe Ile Tyr Val Ile Ile Phe Phe Ile Leu
1               5                   10                  15

Met Phe Phe Val Leu Ile Asp Val Asp Gly His Val Leu Val Glu Cys
            20                  25                  30

Ile Glu Asn Arg Asp Cys Glu Lys Gly Met Cys Lys Phe Pro Phe Ile
        35                  40                  45

Val Arg Cys Leu Met Asp Gln Cys Lys Cys Val Arg Ile His Asn Leu
    50                  55                  60

Ile
65

<210> SEQ ID NO 131
<211> LENGTH: 74
<212> TYPE: PRT
<213> ORGANISM: Medicago truncatula

<400> SEQUENCE: 131

Met Ile Ile Gln Phe Ser Ile Tyr Tyr Met Gln Arg Arg Lys Leu Asn
1               5                   10                  15

Met Val Glu Ile Leu Lys Phe Ser His Ala Leu Ile Ile Phe Leu Phe
            20                  25                  30

Leu Ser Ala Leu Val Thr Asn Ala Asn Ile Phe Phe Cys Ser Thr Asp
        35                  40                  45

Glu Asp Cys Thr Trp Asn Leu Cys Arg Gln Pro Trp Val Gln Lys Cys
    50                  55                  60

Arg Leu His Met Cys Ser Cys Glu Lys Asn
65                  70

<210> SEQ ID NO 132
<211> LENGTH: 58
<212> TYPE: PRT
<213> ORGANISM: Medicago truncatula

<400> SEQUENCE: 132

Met Asp Glu Val Phe Lys Phe Val Tyr Val Met Ile Ile Phe Pro Phe
1               5                   10                  15

Leu Ile Leu Asp Val Ala Thr Asn Ala Glu Lys Ile Arg Arg Cys Phe
            20                  25                  30

Asn Asp Ala His Cys Pro Pro Asp Met Cys Thr Leu Gly Val Ile Pro
        35                  40                  45

Lys Cys Ser Arg Phe Thr Ile Cys Ile Cys
    50                  55

<210> SEQ ID NO 133
<211> LENGTH: 64
<212> TYPE: PRT
<213> ORGANISM: Medicago truncatula

<400> SEQUENCE: 133

Met His Arg Lys Pro Asn Met Thr Lys Phe Phe Lys Phe Val Tyr Thr

```
1               5                   10                  15

Met Phe Ile Leu Ile Ser Leu Phe Leu Val Val Thr Asn Ala Asn Ala
            20                  25                  30

Asn Asn Cys Thr Asp Thr Ser Asp Cys Ser Ser Asn His Cys Ser Tyr
        35                  40                  45

Glu Gly Val Ser Leu Cys Met Asn Gly Gln Cys Ile Cys Ile Tyr Glu
    50                  55                  60


<210> SEQ ID NO 134
<211> LENGTH: 69
<212> TYPE: PRT
<213> ORGANISM: Medicago truncatula

<400> SEQUENCE: 134

Met Gln Met Lys Lys Met Ala Thr Ile Leu Lys Phe Val Tyr Leu Ile
1               5                   10                  15

Ile Leu Leu Ile Tyr Pro Leu Leu Val Val Thr Glu Glu Ser His Tyr
            20                  25                  30

Met Lys Phe Ser Ile Cys Lys Asp Asp Thr Asp Cys Pro Thr Leu Phe
        35                  40                  45

Cys Val Leu Pro Asn Val Pro Lys Cys Ile Gly Ser Lys Cys His Cys
    50                  55                  60

Lys Leu Met Val Asn
65


<210> SEQ ID NO 135
<211> LENGTH: 64
<212> TYPE: PRT
<213> ORGANISM: Medicago truncatula

<400> SEQUENCE: 135

Met Val Glu Thr Leu Arg Leu Phe Tyr Ile Met Ile Leu Phe Val Ser
1               5                   10                  15

Leu Tyr Leu Val Val Val Asp Gly Val Ser Lys Leu Ala Gln Ser Cys
            20                  25                  30

Ser Glu Asp Phe Glu Cys Tyr Ile Lys Asn Pro His Ala Pro Phe Gly
        35                  40                  45

Gln Leu Arg Cys Phe Glu Gly Tyr Cys Gln Arg Leu Asp Lys Pro Thr
    50                  55                  60


<210> SEQ ID NO 136
<211> LENGTH: 63
<212> TYPE: PRT
<213> ORGANISM: Medicago truncatula

<400> SEQUENCE: 136

Met Thr Thr Phe Leu Lys Val Ala Tyr Ile Met Ile Ile Cys Val Phe
1               5                   10                  15

Val Leu His Leu Ala Ala Gln Val Asp Ser Gln Lys Arg Leu His Gly
            20                  25                  30

Cys Lys Glu Asp Arg Asp Cys Asp Asn Ile Cys Ser Val His Ala Val
        35                  40                  45

Thr Lys Cys Ile Gly Asn Met Cys Arg Cys Leu Ala Asn Val Lys
    50                  55                  60


<210> SEQ ID NO 137
<211> LENGTH: 61
<212> TYPE: PRT
<213> ORGANISM: Medicago truncatula
```

<400> SEQUENCE: 137

Met Arg Ile Asn Arg Thr Pro Ala Ile Phe Lys Phe Val Tyr Thr Ile
1               5                   10                  15

Ile Ile Tyr Leu Phe Leu Leu Arg Val Val Ala Lys Asp Leu Pro Phe
            20                  25                  30

Asn Ile Cys Glu Lys Asp Glu Asp Cys Leu Glu Phe Cys Ala His Asp
        35                  40                  45

Lys Val Ala Lys Cys Met Leu Asn Ile Cys Phe Cys Phe
    50                  55                  60

<210> SEQ ID NO 138
<211> LENGTH: 54
<212> TYPE: PRT
<213> ORGANISM: Medicago truncatula

<400> SEQUENCE: 138

Met Ala Glu Ile Leu Lys Ile Leu Tyr Val Phe Ile Ile Phe Leu Ser
1               5                   10                  15

Leu Ile Leu Ala Val Ile Ser Gln His Pro Phe Thr Pro Cys Glu Thr
            20                  25                  30

Asn Ala Asp Cys Lys Cys Arg Asn His Lys Arg Pro Asp Cys Leu Trp
        35                  40                  45

His Lys Cys Tyr Cys Tyr
    50

<210> SEQ ID NO 139
<211> LENGTH: 65
<212> TYPE: PRT
<213> ORGANISM: Medicago truncatula

<400> SEQUENCE: 139

Met Arg Lys Ser Met Ala Thr Ile Leu Lys Phe Val Tyr Val Ile Met
1               5                   10                  15

Leu Phe Ile Tyr Ser Leu Phe Val Ile Glu Ser Phe Gly His Arg Phe
            20                  25                  30

Leu Ile Tyr Asn Asn Cys Lys Asn Asp Thr Glu Cys Pro Asn Asp Cys
        35                  40                  45

Gly Pro His Glu Gln Ala Lys Cys Ile Leu Tyr Ala Cys Tyr Cys Val
    50                  55                  60

Glu
65

<210> SEQ ID NO 140
<211> LENGTH: 58
<212> TYPE: PRT
<213> ORGANISM: Medicago truncatula

<400> SEQUENCE: 140

Met Asn Thr Ile Leu Lys Phe Ile Phe Val Val Phe Leu Phe Leu Ser
1               5                   10                  15

Ile Phe Leu Ser Ala Gly Asn Ser Lys Ser Tyr Gly Pro Cys Thr Thr
            20                  25                  30

Leu Gln Asp Cys Glu Thr His Asn Trp Phe Glu Val Cys Ser Cys Ile
        35                  40                  45

Asp Phe Glu Cys Lys Cys Trp Ser Leu Leu
    50                  55

<210> SEQ ID NO 141
<211> LENGTH: 64
<212> TYPE: PRT
<213> ORGANISM: Medicago truncatula

<400> SEQUENCE: 141

```
Met Ala Glu Ile Ile Lys Phe Val Tyr Ile Met Ile Leu Cys Val Ser
1               5                   10                  15

Leu Leu Leu Ile Ala Glu Ala Ser Gly Lys Glu Cys Val Thr Asp Ala
            20                  25                  30

Asp Cys Glu Asn Leu Tyr Pro Gly Asn Lys Lys Pro Met Phe Cys Asn
        35                  40                  45

Asn Thr Gly Tyr Cys Met Ser Leu Tyr Lys Glu Pro Ser Arg Tyr Met
    50                  55                  60
```

<210> SEQ ID NO 142
<211> LENGTH: 64
<212> TYPE: PRT
<213> ORGANISM: Medicago truncatula

<400> SEQUENCE: 142

```
Met Ala Lys Ile Ile Lys Phe Val Tyr Ile Met Ile Leu Cys Val Ser
1               5                   10                  15

Leu Leu Leu Ile Val Glu Ala Gly Gly Lys Glu Cys Val Thr Asp Val
            20                  25                  30

Asp Cys Glu Lys Ile Tyr Pro Gly Asn Lys Lys Pro Leu Ile Cys Ser
        35                  40                  45

Thr Gly Tyr Cys Tyr Ser Leu Tyr Glu Glu Pro Pro Arg Tyr His Lys
    50                  55                  60
```

<210> SEQ ID NO 143
<211> LENGTH: 64
<212> TYPE: PRT
<213> ORGANISM: Medicago truncatula

<400> SEQUENCE: 143

```
Met Ala Lys Val Thr Lys Phe Gly Tyr Ile Ile Ile His Phe Leu Ser
1               5                   10                  15

Leu Phe Phe Leu Ala Met Asn Val Ala Gly Gly Arg Glu Cys His Ala
            20                  25                  30

Asn Ser His Cys Val Gly Lys Ile Thr Cys Val Leu Pro Gln Lys Pro
        35                  40                  45

Glu Cys Trp Asn Tyr Ala Cys Val Cys Tyr Asp Ser Asn Lys Tyr Arg
    50                  55                  60
```

<210> SEQ ID NO 144
<211> LENGTH: 55
<212> TYPE: PRT
<213> ORGANISM: Medicago truncatula

<400> SEQUENCE: 144

```
Met Ala Lys Ile Phe Asn Tyr Val Tyr Ala Leu Ile Met Phe Leu Ser
1               5                   10                  15

Leu Phe Leu Met Gly Thr Ser Gly Met Lys Asn Gly Cys Lys His Thr
            20                  25                  30

Gly His Cys Pro Arg Lys Met Cys Gly Ala Lys Thr Thr Lys Cys Arg
        35                  40                  45

Asn Asn Lys Cys Gln Cys Val
    50                  55
```

<210> SEQ ID NO 145
<211> LENGTH: 69
<212> TYPE: PRT
<213> ORGANISM: Medicago truncatula

<400> SEQUENCE: 145

```
Met Thr Glu Ile Leu Lys Phe Val Cys Val Met Ile Ile Phe Ile Ser
1               5                   10                  15

Ser Phe Ile Val Ser Lys Ser Leu Asn Gly Gly Gly Lys Asp Lys Cys
            20                  25                  30

Phe Arg Asp Ser Asp Cys Pro Lys His Met Cys Pro Ser Ser Leu Val
        35                  40                  45

Ala Lys Cys Ile Asn Arg Leu Cys Arg Cys Arg Arg Pro Glu Leu Gln
    50                  55                  60

Val Gln Leu Asn Pro
65
```

<210> SEQ ID NO 146
<211> LENGTH: 69
<212> TYPE: PRT
<213> ORGANISM: Medicago truncatula

<400> SEQUENCE: 146

```
Met Ala His Ile Ile Met Phe Val Tyr Ala Leu Ile Tyr Ala Leu Ile
1               5                   10                  15

Ile Phe Ser Ser Leu Phe Val Arg Asp Gly Ile Pro Cys Leu Ser Asp
            20                  25                  30

Asp Glu Cys Pro Glu Met Ser His Tyr Ser Phe Lys Cys Asn Asn Lys
        35                  40                  45

Ile Cys Glu Tyr Asp Leu Gly Glu Met Ser Asp Asp Asp Tyr Tyr Leu
    50                  55                  60

Glu Met Ser Arg Glu
65
```

<210> SEQ ID NO 147
<211> LENGTH: 77
<212> TYPE: PRT
<213> ORGANISM: Medicago truncatula

<400> SEQUENCE: 147

```
Met Tyr Arg Glu Lys Asn Met Ala Lys Thr Leu Lys Phe Val Tyr Val
1               5                   10                  15

Ile Val Leu Phe Leu Ser Leu Phe Leu Ala Ala Lys Asn Ile Asp Gly
            20                  25                  30

Arg Val Ser Tyr Asn Ser Phe Ile Ala Leu Pro Val Cys Gln Thr Ala
        35                  40                  45

Ala Asp Cys Pro Glu Gly Thr Arg Gly Arg Thr Tyr Lys Cys Ile Asn
    50                  55                  60

Asn Lys Cys Arg Tyr Pro Lys Leu Leu Lys Pro Ile Gln
65                  70                  75
```

<210> SEQ ID NO 148
<211> LENGTH: 56
<212> TYPE: PRT
<213> ORGANISM: Medicago truncatula

<400> SEQUENCE: 148

```
Met Ala His Ile Phe Asn Tyr Val Tyr Ala Leu Leu Val Phe Leu Ser
1               5                   10                  15
```

```
Leu Phe Leu Met Val Thr Asn Gly Ile His Ile Gly Cys Asp Lys Asp
            20                  25                  30

Arg Asp Cys Pro Lys Gln Met Cys His Leu Asn Gln Thr Pro Lys Cys
        35                  40                  45

Leu Lys Asn Ile Cys Lys Cys Val
    50                  55


<210> SEQ ID NO 149
<211> LENGTH: 77
<212> TYPE: PRT
<213> ORGANISM: Medicago truncatula

<400> SEQUENCE: 149

Met Ala Glu Ile Leu Lys Cys Phe Tyr Thr Met Asn Leu Phe Ile Phe
1               5                   10                  15

Leu Ile Ile Leu Pro Ala Lys Ile Arg Glu His Ile Gln Cys Val Ile
            20                  25                  30

Asp Asp Asp Cys Pro Lys Ser Leu Asn Lys Leu Leu Ile Ile Lys Cys
        35                  40                  45

Ile Asn His Val Cys Gln Tyr Val Gly Asn Leu Pro Asp Phe Ala Ser
    50                  55                  60

Gln Ile Pro Lys Ser Thr Lys Met Pro Tyr Lys Gly Glu
65                  70                  75


<210> SEQ ID NO 150
<211> LENGTH: 70
<212> TYPE: PRT
<213> ORGANISM: Medicago truncatula

<400> SEQUENCE: 150

Met Ala Tyr Ile Ser Arg Ile Phe Tyr Val Leu Ile Ile Phe Leu Ser
1               5                   10                  15

Leu Phe Phe Val Val Ile Asn Gly Val Lys Ser Leu Leu Leu Ile Lys
            20                  25                  30

Val Arg Ser Phe Ile Pro Cys Gln Arg Ser Asp Asp Cys Pro Arg Asn
        35                  40                  45

Leu Cys Val Asp Gln Ile Ile Pro Thr Cys Val Trp Ala Lys Cys Lys
    50                  55                  60

Cys Lys Asn Tyr Asn Asp
65                  70


<210> SEQ ID NO 151
<211> LENGTH: 64
<212> TYPE: PRT
<213> ORGANISM: Medicago truncatula

<400> SEQUENCE: 151

Met Ala Asn Val Thr Lys Phe Val Tyr Ile Ala Ile Tyr Phe Leu Ser
1               5                   10                  15

Leu Phe Phe Ile Ala Lys Asn Asp Ala Thr Ala Thr Phe Cys His Asp
            20                  25                  30

Asp Ser His Cys Val Thr Lys Ile Lys Cys Val Leu Pro Arg Thr Pro
        35                  40                  45

Gln Cys Arg Asn Glu Ala Cys Gly Cys Tyr His Ser Asn Lys Phe Arg
    50                  55                  60


<210> SEQ ID NO 152
<211> LENGTH: 62
```

```
<212> TYPE: PRT
<213> ORGANISM: Medicago truncatula

<400> SEQUENCE: 152

Met Gly Glu Ile Met Lys Phe Val Tyr Val Met Ile Ile Tyr Leu Phe
1               5                   10                  15

Met Phe Asn Val Ala Thr Gly Ser Glu Phe Ile Phe Thr Lys Lys Leu
            20                  25                  30

Thr Ser Cys Asp Ser Ser Lys Asp Cys Arg Ser Phe Leu Cys Tyr Ser
        35                  40                  45

Pro Lys Phe Pro Val Cys Lys Arg Gly Ile Cys Glu Cys Ile
    50                  55                  60


<210> SEQ ID NO 153
<211> LENGTH: 61
<212> TYPE: PRT
<213> ORGANISM: Medicago truncatula

<400> SEQUENCE: 153

Met Gly Glu Met Phe Lys Phe Ile Tyr Thr Phe Ile Leu Phe Val His
1               5                   10                  15

Leu Phe Leu Val Val Ile Phe Glu Asp Ile Gly His Ile Lys Tyr Cys
            20                  25                  30

Gly Ile Val Asp Asp Cys Tyr Lys Ser Lys Lys Pro Leu Phe Lys Ile
        35                  40                  45

Trp Lys Cys Val Glu Asn Val Cys Val Leu Trp Tyr Lys
    50                  55                  60


<210> SEQ ID NO 154
<211> LENGTH: 63
<212> TYPE: PRT
<213> ORGANISM: Medicago truncatula

<400> SEQUENCE: 154

Met Ala Arg Thr Leu Lys Phe Val Tyr Ser Met Ile Leu Phe Leu Ser
1               5                   10                  15

Leu Phe Leu Val Ala Asn Gly Leu Lys Ile Phe Cys Ile Asp Val Ala
            20                  25                  30

Asp Cys Pro Lys Asp Leu Tyr Pro Leu Leu Tyr Lys Cys Ile Tyr Asn
        35                  40                  45

Lys Cys Ile Val Phe Thr Arg Ile Pro Phe Pro Phe Asp Trp Ile
    50                  55                  60


<210> SEQ ID NO 155
<211> LENGTH: 66
<212> TYPE: PRT
<213> ORGANISM: Medicago truncatula

<400> SEQUENCE: 155

Met Ala Asn Ile Thr Lys Phe Val Tyr Ile Ala Ile Leu Phe Leu Ser
1               5                   10                  15

Leu Phe Phe Ile Gly Met Asn Asp Ala Ala Ile Leu Glu Cys Arg Glu
            20                  25                  30

Asp Ser His Cys Val Thr Lys Ile Lys Cys Val Leu Pro Arg Lys Pro
        35                  40                  45

Glu Cys Arg Asn Asn Ala Cys Thr Cys Tyr Lys Gly Gly Phe Ser Phe
    50                  55                  60

His His
65
```

<210> SEQ ID NO 156
<211> LENGTH: 68
<212> TYPE: PRT
<213> ORGANISM: Medicago truncatula

<400> SEQUENCE: 156

```
Met Gln Arg Val Lys Lys Met Ser Glu Thr Leu Lys Phe Val Tyr Val
1               5                   10                  15

Leu Ile Leu Phe Ile Ser Ile Phe His Val Val Ile Val Cys Asp Ser
            20                  25                  30

Ile Tyr Phe Pro Val Ser Arg Pro Cys Ile Thr Asp Lys Asp Cys Pro
        35                  40                  45

Asn Met Lys His Tyr Lys Ala Lys Cys Arg Lys Gly Phe Cys Ile Ser
    50                  55                  60

Ser Arg Val Arg
65
```

<210> SEQ ID NO 157
<211> LENGTH: 72
<212> TYPE: PRT
<213> ORGANISM: Medicago truncatula

<400> SEQUENCE: 157

```
Met Gln Ile Arg Lys Ile Met Ser Gly Val Leu Lys Phe Val Tyr Ala
1               5                   10                  15

Ile Ile Leu Phe Leu Phe Leu Phe Leu Val Ala Arg Glu Val Gly Gly
            20                  25                  30

Leu Glu Thr Ile Glu Cys Glu Thr Asp Gly Asp Cys Pro Arg Ser Met
        35                  40                  45

Ile Lys Met Trp Asn Lys Asn Tyr Arg His Lys Cys Ile Asp Gly Lys
    50                  55                  60

Cys Glu Trp Ile Lys Lys Leu Pro
65                  70
```

<210> SEQ ID NO 158
<211> LENGTH: 54
<212> TYPE: PRT
<213> ORGANISM: Medicago truncatula

<400> SEQUENCE: 158

```
Met Phe Val Tyr Asp Leu Ile Leu Phe Ile Ser Leu Ile Leu Val Val
1               5                   10                  15

Thr Gly Ile Asn Ala Glu Ala Asp Thr Ser Cys His Ser Phe Asp Asp
            20                  25                  30

Cys Pro Trp Val Ala His His Tyr Arg Glu Cys Ile Glu Gly Leu Cys
        35                  40                  45

Ala Tyr Arg Ile Leu Tyr
    50
```

<210> SEQ ID NO 159
<211> LENGTH: 69
<212> TYPE: PRT
<213> ORGANISM: Medicago truncatula

<400> SEQUENCE: 159

```
Met Gln Arg Arg Lys Lys Ser Met Ala Lys Met Leu Lys Phe Phe Phe
1               5                   10                  15

Ala Ile Ile Leu Leu Leu Ser Leu Phe Leu Val Ala Thr Glu Val Gly
```

```
            20                  25                  30

Gly Ala Tyr Ile Glu Cys Glu Val Asp Asp Asp Cys Pro Lys Pro Met
        35                  40                  45

Lys Asn Ser His Pro Asp Thr Tyr Tyr Lys Cys Val Lys His Arg Cys
    50                  55                  60

Gln Trp Ala Trp Lys
65


<210> SEQ ID NO 160
<211> LENGTH: 140
<212> TYPE: PRT
<213> ORGANISM: Medicago truncatula

<400> SEQUENCE: 160

Met Phe Val Tyr Thr Leu Ile Ile Phe Leu Phe Pro Ser His Val Ile
1               5                   10                  15

Thr Asn Lys Ile Ala Ile Tyr Cys Val Ser Asp Asp Asp Cys Leu Lys
            20                  25                  30

Thr Phe Thr Pro Leu Asp Leu Lys Cys Val Asp Asn Val Cys Glu Phe
        35                  40                  45

Asn Leu Arg Cys Lys Gly Lys Cys Gly Glu Arg Asp Glu Lys Phe Val
    50                  55                  60

Phe Leu Lys Ala Leu Lys Lys Met Asp Gln Lys Leu Val Leu Glu Glu
65                  70                  75                  80

Gln Gly Asn Ala Arg Glu Val Lys Ile Pro Lys Lys Leu Leu Phe Asp
                85                  90                  95

Arg Ile Gln Val Pro Thr Pro Ala Thr Lys Asp Gln Val Glu Glu Asp
            100                 105                 110

Asp Tyr Asp Asp Asp Asp Glu Glu Glu Glu Glu Glu Glu Asp Asp Val
        115                 120                 125

Asp Met Trp Phe His Leu Pro Asp Val Val Cys His
    130                 135                 140


<210> SEQ ID NO 161
<211> LENGTH: 60
<212> TYPE: PRT
<213> ORGANISM: Medicago truncatula

<400> SEQUENCE: 161

Met Ala Lys Phe Ser Met Phe Val Tyr Ala Leu Ile Asn Phe Leu Ser
1               5                   10                  15

Leu Phe Leu Val Glu Thr Ala Ile Thr Asn Ile Arg Cys Val Ser Asp
            20                  25                  30

Asp Asp Cys Pro Lys Val Ile Lys Pro Leu Val Met Lys Cys Ile Gly
        35                  40                  45

Asn Tyr Cys Tyr Phe Phe Met Ile Tyr Glu Gly Pro
    50                  55                  60


<210> SEQ ID NO 162
<211> LENGTH: 58
<212> TYPE: PRT
<213> ORGANISM: Medicago truncatula

<400> SEQUENCE: 162

Met Ala His Lys Phe Val Tyr Ala Ile Ile Leu Phe Ile Phe Leu Phe
1               5                   10                  15

Leu Val Ala Lys Asn Val Lys Gly Tyr Val Val Cys Arg Thr Val Asp
            20                  25                  30
```

```
Asp Cys Pro Pro Asp Thr Arg Asp Leu Arg Tyr Arg Cys Leu Asn Gly
        35                  40                  45

Lys Cys Lys Ser Tyr Arg Leu Ser Tyr Gly
    50                  55


<210> SEQ ID NO 163
<211> LENGTH: 61
<212> TYPE: PRT
<213> ORGANISM: Medicago truncatula

<400> SEQUENCE: 163

Met Gln Arg Lys Lys Asn Met Gly Gln Ile Leu Ile Phe Val Phe Ala
1               5                   10                  15

Leu Ile Asn Phe Leu Ser Pro Ile Leu Val Glu Met Thr Thr Thr Thr
            20                  25                  30

Ile Pro Cys Thr Phe Ile Asp Asp Cys Pro Lys Met Pro Leu Val Val
        35                  40                  45

Lys Cys Ile Asp Asn Phe Cys Asn Tyr Phe Glu Ile Lys
    50                  55                  60


<210> SEQ ID NO 164
<211> LENGTH: 57
<212> TYPE: PRT
<213> ORGANISM: Medicago truncatula

<400> SEQUENCE: 164

Met Ala Gln Thr Leu Met Leu Val Tyr Ala Leu Ile Ile Phe Thr Ser
1               5                   10                  15

Leu Phe Leu Val Val Ile Ser Arg Gln Thr Asp Ile Pro Cys Lys Ser
            20                  25                  30

Asp Asp Ala Cys Pro Arg Val Ser Ser His His Ile Glu Cys Val Lys
        35                  40                  45

Gly Phe Cys Thr Tyr Trp Lys Leu Asp
    50                  55


<210> SEQ ID NO 165
<211> LENGTH: 77
<212> TYPE: PRT
<213> ORGANISM: Medicago truncatula

<400> SEQUENCE: 165

Met Leu Arg Arg Lys Asn Thr Val Gln Ile Leu Met Phe Val Ser Ala
1               5                   10                  15

Leu Leu Ile Tyr Ile Phe Leu Phe Leu Val Ile Thr Ser Ser Ala Asn
            20                  25                  30

Ile Pro Cys Asn Ser Asp Ser Asp Cys Pro Trp Lys Ile Tyr Tyr Thr
        35                  40                  45

Tyr Arg Cys Asn Asp Gly Phe Cys Val Tyr Lys Ser Ile Asp Pro Ser
    50                  55                  60

Thr Ile Pro Gln Tyr Met Thr Asp Leu Ile Phe Pro Arg
65                  70                  75


<210> SEQ ID NO 166
<211> LENGTH: 59
<212> TYPE: PRT
<213> ORGANISM: Medicago truncatula

<400> SEQUENCE: 166

Met Ala Val Ile Leu Lys Phe Val Tyr Ile Met Ile Ile Phe Leu Phe
```

```
1               5                   10                  15

Leu Leu Tyr Val Val Asn Gly Thr Arg Cys Asn Arg Asp Glu Asp Cys
            20                  25                  30

Pro Phe Ile Cys Thr Gly Pro Gln Ile Pro Lys Cys Val Ser His Ile
        35                  40                  45

Cys Phe Cys Leu Ser Ser Gly Lys Glu Ala Tyr
    50                  55
```

<210> SEQ ID NO 167
<211> LENGTH: 62
<212> TYPE: PRT
<213> ORGANISM: Medicago truncatula

<400> SEQUENCE: 167

```
Met Asp Ala Ile Leu Lys Phe Ile Tyr Ala Met Phe Leu Phe Leu Phe
1               5                   10                  15

Leu Phe Val Thr Thr Arg Asn Val Glu Ala Leu Phe Glu Cys Asn Arg
            20                  25                  30

Asp Phe Val Cys Gly Asn Asp Asp Glu Cys Val Tyr Pro Tyr Ala Val
        35                  40                  45

Gln Cys Ile His Arg Tyr Cys Lys Cys Leu Lys Ser Arg Asn
    50                  55                  60
```

<210> SEQ ID NO 168
<211> LENGTH: 67
<212> TYPE: PRT
<213> ORGANISM: Medicago truncatula

<400> SEQUENCE: 168

```
Met Gln Ile Gly Arg Lys Lys Met Gly Glu Thr Pro Lys Leu Val Tyr
1               5                   10                  15

Val Ile Ile Leu Phe Leu Ser Ile Phe Leu Cys Thr Asn Ser Ser Phe
            20                  25                  30

Ser Gln Met Ile Asn Phe Arg Gly Cys Lys Arg Asp Lys Asp Cys Pro
        35                  40                  45

Gln Phe Arg Gly Val Asn Ile Arg Cys Arg Ser Gly Phe Cys Thr Pro
    50                  55                  60

Ile Asp Ser
65
```

<210> SEQ ID NO 169
<211> LENGTH: 76
<212> TYPE: PRT
<213> ORGANISM: Medicago truncatula

<400> SEQUENCE: 169

```
Met Gln Met Arg Lys Asn Met Ala Gln Ile Leu Phe Tyr Val Tyr Ala
1               5                   10                  15

Leu Leu Ile Leu Phe Ser Pro Phe Leu Val Ala Arg Ile Met Val Val
            20                  25                  30

Asn Pro Asn Asn Pro Cys Val Thr Asp Ala Asp Cys Gln Arg Tyr Arg
        35                  40                  45

His Lys Leu Ala Thr Arg Met Val Cys Asn Ile Gly Phe Cys Leu Met
    50                  55                  60

Asp Phe Thr His Asp Pro Tyr Ala Pro Ser Leu Pro
65                  70                  75
```

<210> SEQ ID NO 170

<211> LENGTH: 77
<212> TYPE: PRT
<213> ORGANISM: Medicago truncatula

<400> SEQUENCE: 170

Met Tyr Val Tyr Tyr Ile Gln Met Gly Lys Asn Met Ala Gln Arg Phe
1 5 10 15

Met Phe Ile Tyr Ala Leu Ile Ile Phe Leu Ser Gln Phe Phe Val Val
20 25 30

Ile Asn Thr Ser Asp Ile Pro Asn Asn Ser Asn Arg Asn Ser Pro Lys
35 40 45

Glu Asp Val Phe Cys Asn Ser Asn Asp Asp Cys Pro Thr Ile Leu Tyr
50 55 60

Tyr Val Ser Lys Cys Val Tyr Asn Phe Cys Glu Tyr Trp
65 70 75

<210> SEQ ID NO 171
<211> LENGTH: 67
<212> TYPE: PRT
<213> ORGANISM: Medicago truncatula

<400> SEQUENCE: 171

Met Ala Lys Ile Val Asn Phe Val Tyr Ser Met Ile Ile Phe Val Ser
1 5 10 15

Leu Phe Leu Val Ala Thr Lys Gly Gly Ser Lys Pro Phe Leu Thr Arg
20 25 30

Pro Tyr Pro Cys Asn Thr Gly Ser Asp Cys Pro Gln Asn Met Cys Pro
35 40 45

Pro Gly Tyr Lys Pro Gly Cys Glu Asp Gly Tyr Cys Asn His Cys Tyr
50 55 60

Lys Arg Trp
65

<210> SEQ ID NO 172
<211> LENGTH: 62
<212> TYPE: PRT
<213> ORGANISM: Medicago truncatula

<400> SEQUENCE: 172

Met Val Arg Thr Leu Lys Phe Val Tyr Val Ile Ile Leu Ile Leu Ser
1 5 10 15

Leu Phe Leu Val Ala Lys Gly Gly Gly Lys Lys Ile Tyr Cys Glu Asn
20 25 30

Ala Ala Ser Cys Pro Arg Leu Met Tyr Pro Leu Val Tyr Lys Cys Leu
35 40 45

Asp Asn Lys Cys Val Lys Phe Met Met Lys Ser Arg Phe Val
50 55 60

<210> SEQ ID NO 173
<211> LENGTH: 62
<212> TYPE: PRT
<213> ORGANISM: Medicago truncatula

<400> SEQUENCE: 173

Met Ala Arg Thr Leu Lys Phe Val Tyr Ala Val Ile Leu Phe Leu Ser
1 5 10 15

Leu Phe Leu Val Ala Lys Gly Asp Asp Val Lys Ile Lys Cys Val Val
20 25 30

Ala Ala Asn Cys Pro Asp Leu Met Tyr Pro Leu Val Tyr Lys Cys Leu

```
        35                  40                  45

Asn Gly Ile Cys Val Gln Phe Thr Leu Thr Phe Pro Phe Val
    50                  55                  60
```

```
<210> SEQ ID NO 174
<211> LENGTH: 65
<212> TYPE: PRT
<213> ORGANISM: Medicago truncatula

<400> SEQUENCE: 174

Met Ser Asn Thr Leu Met Phe Val Ile Thr Phe Ile Val Leu Val Thr
1               5                   10                  15

Leu Phe Leu Gly Pro Lys Asn Val Tyr Ala Phe Gln Pro Cys Val Thr
            20                  25                  30

Thr Ala Asp Cys Met Lys Thr Leu Lys Thr Asp Glu Asn Ile Trp Tyr
        35                  40                  45

Glu Cys Ile Asn Asp Phe Cys Ile Pro Phe Pro Ile Pro Lys Gly Arg
    50                  55                  60

Lys
65
```

```
<210> SEQ ID NO 175
<211> LENGTH: 76
<212> TYPE: PRT
<213> ORGANISM: Medicago truncatula

<400> SEQUENCE: 175

Met Lys Arg Val Val Asn Met Ala Lys Ile Val Lys Tyr Val Tyr Val
1               5                   10                  15

Ile Ile Ile Phe Leu Ser Leu Phe Leu Val Ala Thr Lys Ile Glu Gly
            20                  25                  30

Tyr Tyr Tyr Lys Cys Phe Lys Asp Ser Asp Cys Val Lys Leu Leu Cys
        35                  40                  45

Arg Ile Pro Leu Arg Pro Lys Cys Met Tyr Arg His Ile Cys Lys Cys
    50                  55                  60

Lys Val Val Leu Thr Gln Asn Asn Tyr Val Leu Thr
65                  70                  75
```

```
<210> SEQ ID NO 176
<211> LENGTH: 66
<212> TYPE: PRT
<213> ORGANISM: Medicago truncatula

<400> SEQUENCE: 176

Met Lys Arg Gly Lys Asn Met Ser Lys Ile Leu Lys Phe Ile Tyr Ala
1               5                   10                  15

Thr Leu Val Leu Tyr Leu Phe Leu Val Val Thr Lys Ala Ser Asp Asp
            20                  25                  30

Glu Cys Lys Ile Asp Gly Asp Cys Pro Ile Ser Trp Gln Lys Phe His
        35                  40                  45

Thr Tyr Lys Cys Ile Asn Gln Lys Cys Lys Trp Val Leu Arg Phe His
    50                  55                  60

Glu Tyr
65
```

```
<210> SEQ ID NO 177
<211> LENGTH: 64
<212> TYPE: PRT
<213> ORGANISM: Medicago truncatula
```

<400> SEQUENCE: 177

Met Ala Lys Thr Leu Asn Phe Met Phe Ala Leu Ile Leu Phe Ile Ser
1 5 10 15

Leu Phe Leu Val Ser Lys Asn Val Ala Ile Asp Ile Phe Val Cys Gln
20 25 30

Thr Asp Ala Asp Cys Pro Lys Ser Glu Leu Ser Met Tyr Thr Trp Lys
35 40 45

Cys Ile Asp Asn Glu Cys Asn Leu Phe Lys Val Met Gln Gln Met Val
50 55 60

<210> SEQ ID NO 178
<211> LENGTH: 59
<212> TYPE: PRT
<213> ORGANISM: Medicago truncatula

<400> SEQUENCE: 178

Met Ala Asn Thr His Lys Leu Val Ser Met Ile Leu Phe Ile Phe Leu
1 5 10 15

Phe Leu Val Ala Asn Asn Val Glu Gly Tyr Val Asn Cys Glu Thr Asp
20 25 30

Ala Asp Cys Pro Pro Ser Thr Arg Val Lys Arg Phe Lys Cys Val Lys
35 40 45

Gly Glu Cys Arg Trp Thr Arg Met Ser Tyr Ala
50 55

<210> SEQ ID NO 179
<211> LENGTH: 59
<212> TYPE: PRT
<213> ORGANISM: Medicago truncatula

<400> SEQUENCE: 179

Met Ala His Phe Leu Met Phe Val Tyr Ala Leu Ile Thr Cys Leu Ser
1 5 10 15

Leu Phe Leu Val Glu Met Gly His Leu Ser Ile His Cys Val Ser Val
20 25 30

Asp Asp Cys Pro Lys Val Glu Lys Pro Ile Thr Met Lys Cys Ile Asn
35 40 45

Asn Tyr Cys Lys Tyr Phe Val Asp His Lys Leu
50 55

<210> SEQ ID NO 180
<211> LENGTH: 66
<212> TYPE: PRT
<213> ORGANISM: Medicago truncatula

<400> SEQUENCE: 180

Met Asn Gln Ile Pro Met Phe Gly Tyr Thr Leu Ile Ile Phe Phe Ser
1 5 10 15

Leu Phe Pro Val Ile Thr Asn Gly Asp Arg Ile Pro Cys Val Thr Asn
20 25 30

Gly Asp Cys Pro Val Met Arg Leu Pro Leu Tyr Met Arg Cys Ile Thr
35 40 45

Tyr Ser Cys Glu Leu Phe Phe Asp Gly Pro Asn Leu Cys Ala Val Glu
50 55 60

Arg Ile
65

<210> SEQ ID NO 181
<211> LENGTH: 61
<212> TYPE: PRT
<213> ORGANISM: Medicago truncatula

<400> SEQUENCE: 181

Met Arg Lys Asp Met Ala Arg Ile Ser Leu Phe Val Tyr Ala Leu Ile
1               5                   10                  15

Ile Phe Phe Ser Leu Phe Phe Val Leu Thr Asn Gly Glu Leu Glu Ile
            20                  25                  30

Arg Cys Val Ser Asp Ala Asp Cys Pro Leu Phe Pro Leu Pro Leu His
        35                  40                  45

Asn Arg Cys Ile Asp Asp Val Cys His Leu Phe Thr Ser
    50                  55                  60

<210> SEQ ID NO 182
<211> LENGTH: 60
<212> TYPE: PRT
<213> ORGANISM: Medicago truncatula

<400> SEQUENCE: 182

Met Ala Gln Ile Leu Met Phe Val Tyr Phe Leu Ile Ile Phe Leu Ser
1               5                   10                  15

Leu Phe Leu Val Glu Ser Ile Lys Ile Phe Thr Glu His Arg Cys Arg
            20                  25                  30

Thr Asp Ala Asp Cys Pro Ala Arg Glu Leu Pro Glu Tyr Leu Lys Cys
        35                  40                  45

Gln Gly Gly Met Cys Arg Leu Leu Ile Lys Lys Asp
    50                  55                  60

<210> SEQ ID NO 183
<211> LENGTH: 56
<212> TYPE: PRT
<213> ORGANISM: Medicago truncatula

<400> SEQUENCE: 183

Met Ala Arg Val Ile Ser Leu Phe Tyr Ala Leu Ile Ile Phe Leu Phe
1               5                   10                  15

Leu Phe Leu Val Ala Thr Asn Gly Asp Leu Ser Pro Cys Leu Arg Ser
            20                  25                  30

Gly Asp Cys Ser Lys Asp Glu Cys Pro Ser His Leu Val Pro Lys Cys
        35                  40                  45

Ile Gly Leu Thr Cys Tyr Cys Ile
    50                  55

<210> SEQ ID NO 184
<211> LENGTH: 62
<212> TYPE: PRT
<213> ORGANISM: Medicago truncatula

<400> SEQUENCE: 184

Met Gln Arg Arg Lys Asn Met Ala Gln Ile Leu Leu Phe Ala Tyr Val
1               5                   10                  15

Phe Ile Ile Ser Ile Ser Leu Phe Leu Val Val Thr Asn Gly Val Lys
            20                  25                  30

Ile Pro Cys Val Lys Asp Thr Asp Cys Pro Thr Leu Pro Cys Pro Leu
        35                  40                  45

Tyr Ser Lys Cys Val Asp Gly Phe Cys Lys Met Leu Ser Ile
    50                  55                  60

<210> SEQ ID NO 185
<211> LENGTH: 66
<212> TYPE: PRT
<213> ORGANISM: Medicago truncatula

<400> SEQUENCE: 185

Met Asn His Ile Ser Lys Phe Val Tyr Ala Leu Ile Ile Phe Leu Ser
1 5 10 15

Val Tyr Leu Val Val Leu Asp Gly Arg Pro Val Ser Cys Lys Asp His
20 25 30

Tyr Asp Cys Arg Arg Lys Val Lys Ile Val Gly Cys Ile Phe Pro Gln
35 40 45

Glu Lys Pro Met Cys Ile Asn Ser Met Cys Thr Cys Ile Arg Glu Ile
50 55 60

Val Pro
65

<210> SEQ ID NO 186
<211> LENGTH: 86
<212> TYPE: PRT
<213> ORGANISM: Medicago truncatula

<400> SEQUENCE: 186

Met Lys Ser Gln Asn His Ala Lys Phe Ile Ser Phe Tyr Lys Asn Asp
1 5 10 15

Leu Phe Lys Ile Phe Gln Asn Asn Asp Ser His Phe Lys Val Phe Phe
20 25 30

Ala Leu Ile Ile Phe Leu Tyr Thr Tyr Leu His Val Thr Asn Gly Val
35 40 45

Phe Val Ser Cys Asn Ser His Ile His Cys Arg Val Asn Asn His Lys
50 55 60

Ile Gly Cys Asn Ile Pro Glu Gln Tyr Leu Leu Cys Val Asn Leu Phe
65 70 75 80

Cys Leu Trp Leu Asp Tyr
85

<210> SEQ ID NO 187
<211> LENGTH: 62
<212> TYPE: PRT
<213> ORGANISM: Medicago truncatula

<400> SEQUENCE: 187

Met Thr Tyr Ile Ser Lys Val Val Tyr Ala Leu Ile Ile Phe Leu Ser
1 5 10 15

Ile Tyr Val Gly Val Asn Asp Cys Met Leu Val Thr Cys Glu Asp His
20 25 30

Phe Asp Cys Arg Gln Asn Val Gln Gln Val Gly Cys Ser Phe Arg Glu
35 40 45

Ile Pro Gln Cys Ile Asn Ser Ile Cys Lys Cys Met Lys Gly
50 55 60

<210> SEQ ID NO 188
<211> LENGTH: 63
<212> TYPE: PRT
<213> ORGANISM: Medicago truncatula

<400> SEQUENCE: 188

Met Thr His Ile Ser Lys Phe Val Phe Ala Leu Ile Ile Phe Leu Ser
1 5 10 15

```
Ile Tyr Val Gly Val Asn Asp Cys Lys Arg Ile Pro Cys Lys Asp Asn
            20                  25                  30

Asn Asp Cys Asn Asn Asn Trp Gln Leu Leu Ala Cys Arg Phe Glu Arg
        35                  40                  45

Glu Val Pro Arg Cys Ile Asn Ser Ile Cys Lys Cys Met Pro Met
    50                  55                  60


<210> SEQ ID NO 189
<211> LENGTH: 60
<212> TYPE: PRT
<213> ORGANISM: Medicago truncatula

<400> SEQUENCE: 189

Met Val Gln Thr Pro Lys Leu Val Tyr Val Ile Val Leu Leu Leu Ser
1               5                   10                  15

Ile Phe Leu Gly Met Thr Ile Cys Asn Ser Ser Phe Ser His Phe Phe
            20                  25                  30

Glu Gly Ala Cys Lys Ser Asp Lys Asp Cys Pro Lys Leu His Arg Ser
        35                  40                  45

Asn Val Arg Cys Arg Lys Gly Gln Cys Val Gln Ile
    50                  55                  60


<210> SEQ ID NO 190
<211> LENGTH: 77
<212> TYPE: PRT
<213> ORGANISM: Medicago truncatula

<400> SEQUENCE: 190

Met Thr Lys Ile Leu Met Leu Phe Tyr Ala Met Ile Val Phe His Ser
1               5                   10                  15

Ile Phe Leu Val Ala Ser Tyr Thr Asp Glu Cys Ser Thr Asp Ala Asp
            20                  25                  30

Cys Glu Tyr Ile Leu Cys Leu Phe Pro Ile Ile Lys Arg Cys Ile His
        35                  40                  45

Asn His Cys Lys Cys Val Pro Met Gly Ser Ile Glu Pro Met Ser Thr
    50                  55                  60

Ile Pro Asn Gly Val His Lys Phe His Ile Ile Asn Asn
65                  70                  75


<210> SEQ ID NO 191
<211> LENGTH: 64
<212> TYPE: PRT
<213> ORGANISM: Medicago truncatula

<400> SEQUENCE: 191

Met Ala Lys Thr Leu Asn Phe Val Cys Ala Met Ile Leu Phe Ile Ser
1               5                   10                  15

Leu Phe Leu Val Ser Lys Asn Val Ala Leu Tyr Ile Ile Glu Cys Lys
            20                  25                  30

Thr Asp Ala Asp Cys Pro Ile Ser Lys Leu Asn Met Tyr Asn Trp Arg
        35                  40                  45

Cys Ile Lys Ser Ser Cys His Leu Tyr Lys Val Ile Gln Phe Met Val
    50                  55                  60


<210> SEQ ID NO 192
<211> LENGTH: 72
<212> TYPE: PRT
<213> ORGANISM: Medicago truncatula
```

<400> SEQUENCE: 192

Met Gln Lys Glu Lys Asn Met Ala Lys Thr Phe Glu Phe Val Tyr Ala
1               5                   10                  15

Met Ile Ile Phe Ile Leu Leu Phe Leu Val Glu Asn Asn Phe Ala Ala
            20                  25                  30

Tyr Ile Ile Glu Cys Gln Thr Asp Asp Asp Cys Pro Lys Ser Gln Leu
        35                  40                  45

Glu Met Phe Ala Trp Lys Cys Val Lys Asn Gly Cys His Leu Phe Gly
    50                  55                  60

Met Tyr Glu Asp Asp Asp Asp Pro
65                  70

<210> SEQ ID NO 193
<211> LENGTH: 57
<212> TYPE: PRT
<213> ORGANISM: Medicago truncatula

<400> SEQUENCE: 193

Met Ala Ala Thr Arg Lys Phe Ile Tyr Val Leu Ser His Phe Leu Phe
1               5                   10                  15

Leu Phe Leu Val Thr Lys Ile Thr Asp Ala Arg Val Cys Lys Ser Asp
            20                  25                  30

Lys Asp Cys Lys Asp Ile Ile Ile Tyr Arg Tyr Ile Leu Lys Cys Arg
        35                  40                  45

Asn Gly Glu Cys Val Lys Ile Lys Ile
    50                  55

<210> SEQ ID NO 194
<211> LENGTH: 75
<212> TYPE: PRT
<213> ORGANISM: Medicago truncatula

<400> SEQUENCE: 194

Met Gln Arg Leu Asp Asn Met Ala Lys Asn Val Lys Phe Ile Tyr Val
1               5                   10                  15

Ile Ile Leu Leu Leu Phe Ile Phe Leu Val Ile Ile Val Cys Asp Ser
            20                  25                  30

Ala Phe Val Pro Asn Ser Gly Pro Cys Thr Thr Asp Lys Asp Cys Lys
        35                  40                  45

Gln Val Lys Gly Tyr Ile Ala Arg Cys Arg Lys Gly Tyr Cys Met Gln
    50                  55                  60

Ser Val Lys Arg Thr Trp Ser Ser Tyr Ser Arg
65                  70                  75

<210> SEQ ID NO 195
<211> LENGTH: 102
<212> TYPE: PRT
<213> ORGANISM: Medicago truncatula

<400> SEQUENCE: 195

Met Lys Phe Ile Tyr Ile Met Ile Leu Phe Leu Ser Leu Phe Leu Val
1               5                   10                  15

Gln Phe Leu Thr Cys Lys Gly Leu Thr Val Pro Cys Glu Asn Pro Thr
            20                  25                  30

Thr Cys Pro Glu Asp Phe Cys Thr Pro Pro Met Ile Thr Arg Cys Ile
        35                  40                  45

Asn Phe Ile Cys Leu Cys Asp Gly Pro Glu Tyr Ala Glu Pro Glu Tyr
    50                  55                  60

Asp Gly Pro Glu Pro Glu Tyr Asp His Lys Gly Asp Phe Leu Ser Val
65 70 75 80

Lys Pro Lys Ile Ile Asn Glu Asn Met Met Met Arg Glu Arg His Met
85 90 95

Met Lys Glu Ile Glu Val
100

<210> SEQ ID NO 196
<211> LENGTH: 59
<212> TYPE: PRT
<213> ORGANISM: Medicago truncatula

<400> SEQUENCE: 196

Met Ala Gln Phe Leu Met Phe Ile Tyr Val Leu Ile Ile Phe Leu Tyr
1 5 10 15

Leu Phe Tyr Val Glu Ala Ala Met Phe Glu Leu Thr Lys Ser Thr Ile
20 25 30

Arg Cys Val Thr Asp Ala Asp Cys Pro Asn Val Val Lys Pro Leu Lys
35 40 45

Pro Lys Cys Val Asp Gly Phe Cys Glu Tyr Thr
50 55

<210> SEQ ID NO 197
<211> LENGTH: 70
<212> TYPE: PRT
<213> ORGANISM: Medicago truncatula

<400> SEQUENCE: 197

Met Lys Met Arg Ile His Met Ala Gln Ile Ile Met Phe Phe Tyr Ala
1 5 10 15

Leu Ile Ile Phe Leu Ser Pro Phe Leu Val Asp Arg Arg Ser Phe Pro
20 25 30

Ser Ser Phe Val Ser Pro Lys Ser Tyr Thr Ser Glu Ile Pro Cys Lys
35 40 45

Ala Thr Arg Asp Cys Pro Tyr Glu Leu Tyr Tyr Glu Thr Lys Cys Val
50 55 60

Asp Ser Leu Cys Thr Tyr
65 70

<210> SEQ ID NO 198
<211> LENGTH: 41
<212> TYPE: PRT
<213> ORGANISM: Medicago truncatula

<400> SEQUENCE: 198

Thr Arg Met Leu Thr Ile Pro Cys Thr Ser Asp Asp Asn Cys Pro Lys
1 5 10 15

Val Ile Ser Pro Cys His Thr Lys Cys Phe Asp Gly Phe Cys Gly Trp
20 25 30

Tyr Ile Glu Gly Ser Tyr Glu Gly Pro
35 40

<210> SEQ ID NO 199
<211> LENGTH: 69
<212> TYPE: PRT
<213> ORGANISM: Medicago truncatula

<400> SEQUENCE: 199

Met Ala Gln Phe Leu Leu Phe Val Tyr Ser Leu Ile Ile Phe Leu Ser

```
1               5                   10                  15

Leu Phe Phe Gly Glu Ala Ala Phe Glu Arg Thr Glu Thr Arg Met Leu
            20                  25                  30

Thr Ile Pro Cys Thr Ser Asp Asp Asn Cys Pro Lys Val Ile Ser Pro
        35                  40                  45

Cys His Thr Lys Cys Phe Asp Gly Phe Cys Gly Trp Tyr Ile Glu Gly
    50                  55                  60

Ser Tyr Glu Gly Pro
65


<210> SEQ ID NO 200
<211> LENGTH: 78
<212> TYPE: PRT
<213> ORGANISM: Buchnera aphidicola

<400> SEQUENCE: 200

Met Lys Leu Leu His Gly Phe Leu Ile Ile Met Leu Thr Met His Leu
1               5                   10                  15

Ser Ile Gln Tyr Ala Tyr Gly Gly Pro Phe Leu Thr Lys Tyr Leu Cys
            20                  25                  30

Asp Arg Val Cys His Lys Leu Cys Gly Asp Glu Phe Val Cys Ser Cys
        35                  40                  45

Ile Gln Tyr Lys Ser Leu Lys Gly Leu Trp Phe Pro His Cys Pro Thr
    50                  55                  60

Gly Lys Ala Ser Val Val Leu His Asn Phe Leu Thr Ser Pro
65                  70                  75


<210> SEQ ID NO 201
<211> LENGTH: 77
<212> TYPE: PRT
<213> ORGANISM: Buchnera aphidicola

<400> SEQUENCE: 201

Met Lys Leu Leu Tyr Gly Phe Leu Ile Ile Met Leu Thr Ile His Leu
1               5                   10                  15

Ser Val Gln Tyr Phe Glu Ser Pro Phe Glu Thr Lys Tyr Asn Cys Asp
            20                  25                  30

Thr His Cys Asn Lys Leu Cys Gly Lys Ile Asp His Cys Ser Cys Ile
        35                  40                  45

Gln Tyr His Ser Met Glu Gly Leu Trp Phe Pro His Cys Arg Thr Gly
    50                  55                  60

Ser Ala Ala Gln Met Leu His Asp Phe Leu Ser Asn Pro
65                  70                  75


<210> SEQ ID NO 202
<211> LENGTH: 86
<212> TYPE: PRT
<213> ORGANISM: Buchnera aphidicola

<400> SEQUENCE: 202

Met Ser Val Arg Lys Asn Val Leu Pro Thr Met Phe Val Val Leu Leu
1               5                   10                  15

Ile Met Ser Pro Val Thr Pro Thr Ser Val Phe Ile Ser Ala Val Cys
            20                  25                  30

Tyr Ser Gly Cys Gly Ser Leu Ala Leu Val Cys Phe Val Ser Asn Gly
        35                  40                  45

Ile Thr Asn Gly Leu Asp Tyr Phe Lys Ser Ser Ala Pro Leu Ser Thr
    50                  55                  60
```

```
Ser Glu Thr Ser Cys Gly Glu Ala Phe Asp Thr Cys Thr Asp His Cys
65                  70                  75                  80

Leu Ala Asn Phe Lys Phe
                85


<210> SEQ ID NO 203
<211> LENGTH: 69
<212> TYPE: PRT
<213> ORGANISM: Buchnera aphidicola

<400> SEQUENCE: 203

Met Arg Leu Leu Tyr Gly Phe Leu Ile Ile Met Leu Thr Ile Tyr Leu
1               5                   10                  15

Ser Val Gln Asp Phe Asp Pro Thr Glu Phe Lys Gly Pro Phe Pro Thr
            20                  25                  30

Ile Glu Ile Cys Ser Lys Tyr Cys Ala Val Val Cys Asn Tyr Thr Ser
        35                  40                  45

Arg Pro Cys Tyr Cys Val Glu Ala Ala Lys Glu Arg Asp Gln Trp Phe
    50                  55                  60

Pro Tyr Cys Tyr Asp
65


<210> SEQ ID NO 204
<211> LENGTH: 77
<212> TYPE: PRT
<213> ORGANISM: Buchnera aphidicola

<400> SEQUENCE: 204

Met Arg Leu Leu Tyr Gly Phe Leu Ile Ile Met Leu Thr Ile His Leu
1               5                   10                  15

Ser Val Gln Asp Ile Asp Pro Asn Thr Leu Arg Gly Pro Tyr Pro Thr
            20                  25                  30

Lys Glu Ile Cys Ser Lys Tyr Cys Glu Tyr Asn Val Val Cys Gly Ala
        35                  40                  45

Ser Leu Pro Cys Ile Cys Val Gln Asp Ala Arg Gln Leu Asp His Trp
    50                  55                  60

Phe Ala Cys Cys Tyr Asp Gly Gly Pro Glu Met Leu Met
65                  70                  75


<210> SEQ ID NO 205
<211> LENGTH: 108
<212> TYPE: PRT
<213> ORGANISM: Buchnera aphidicola

<400> SEQUENCE: 205

Met Lys Leu Phe Val Val Val Val Leu Val Ala Val Gly Ile Met Phe
1               5                   10                  15

Val Phe Ala Ser Asp Thr Ala Ala Ala Pro Thr Asp Tyr Glu Asp Thr
            20                  25                  30

Asn Asp Met Ile Ser Leu Ser Ser Leu Val Gly Asp Asn Ser Pro Tyr
        35                  40                  45

Val Arg Val Ser Ser Ala Asp Ser Gly Gly Ser Ser Lys Thr Ser Ser
    50                  55                  60

Lys Asn Pro Ile Leu Gly Leu Leu Lys Ser Val Ile Lys Leu Leu Thr
65                  70                  75                  80

Lys Ile Phe Gly Thr Tyr Ser Asp Ala Ala Pro Ala Met Pro Pro Ile
                85                  90                  95
```

Pro Pro Ala Leu Arg Lys Asn Arg Gly Met Leu Ala
            100                 105

<210> SEQ ID NO 206
<211> LENGTH: 178
<212> TYPE: PRT
<213> ORGANISM: Buchnera aphidicola

<400> SEQUENCE: 206

Met Val Ala Cys Lys Val Ile Leu Ala Val Ala Val Val Phe Val Ala
1               5                   10                  15

Ala Val Gln Gly Arg Pro Gly Gly Glu Pro Glu Trp Ala Ala Pro Ile
            20                  25                  30

Phe Ala Glu Leu Lys Ser Val Ser Asp Asn Ile Thr Asn Leu Val Gly
        35                  40                  45

Leu Asp Asn Ala Gly Glu Tyr Ala Thr Ala Ala Lys Asn Asn Leu Asn
    50                  55                  60

Ala Phe Ala Glu Ser Leu Lys Thr Glu Ala Ala Val Phe Ser Lys Ser
65                  70                  75                  80

Phe Glu Gly Lys Ala Ser Ala Ser Asp Val Phe Lys Glu Ser Thr Lys
                85                  90                  95

Asn Phe Gln Ala Val Val Asp Thr Tyr Ile Lys Asn Leu Pro Lys Asp
            100                 105                 110

Leu Thr Leu Lys Asp Phe Thr Glu Lys Ser Glu Gln Ala Leu Lys Tyr
        115                 120                 125

Met Val Glu His Gly Thr Glu Ile Thr Lys Lys Ala Gln Gly Asn Thr
    130                 135                 140

Glu Thr Glu Lys Glu Ile Lys Glu Phe Phe Lys Lys Gln Ile Glu Asn
145                 150                 155                 160

Leu Ile Gly Gln Gly Lys Ala Leu Gln Ala Lys Ile Ala Glu Ala Lys
                165                 170                 175

Lys Ala

<210> SEQ ID NO 207
<211> LENGTH: 311
<212> TYPE: PRT
<213> ORGANISM: Buchnera aphidicola

<400> SEQUENCE: 207

Met Lys Thr Ser Ser Ser Lys Val Phe Ala Ser Cys Val Ala Ile Val
1               5                   10                  15

Cys Leu Ala Ser Val Ala Asn Ala Leu Pro Val Gln Lys Ser Val Ala
            20                  25                  30

Ala Thr Thr Glu Asn Pro Ile Val Glu Lys His Gly Cys Arg Ala His
        35                  40                  45

Lys Asn Leu Val Arg Gln Asn Val Val Asp Leu Lys Thr Tyr Asp Ser
    50                  55                  60

Met Leu Ile Thr Asn Glu Val Val Gln Lys Gln Ser Asn Glu Val Gln
65                  70                  75                  80

Ser Ser Glu Gln Ser Asn Glu Gly Gln Asn Ser Glu Gln Ser Asn Glu
                85                  90                  95

Gly Gln Asn Ser Glu Gln Ser Asn Glu Val Gln Ser Ser Glu His Ser
            100                 105                 110

Asn Glu Gly Gln Asn Ser Lys Gln Ser Asn Glu Gly Gln Asn Ser Glu
        115                 120                 125

Gln Ser Asn Glu Val Gln Ser Ser Glu His Ser Asn Glu Gly Gln Asn

```
    130                 135                 140

Ser Glu Gln Ser Asn Glu Val Gln Ser Ser Glu His Ser Asn Glu Gly
145                 150                 155                 160

Gln Asn Ser Lys Gln Ser Asn Glu Gly Gln Asn Ser Lys Gln Ser Asn
                165                 170                 175

Glu Val Gln Ser Ser Glu His Trp Asn Glu Gly Gln Asn Ser Lys Gln
            180                 185                 190

Ser Asn Glu Asp Gln Asn Ser Glu Gln Ser Asn Glu Gly Gln Asn Ser
        195                 200                 205

Lys Gln Ser Asn Glu Gly Gln Asn Ser Lys Gln Ser Asn Glu Asp Gln
    210                 215                 220

Asn Ser Glu Gln Ser Asn Glu Gly Gln Asn Ser Lys Gln Ser Asn Glu
225                 230                 235                 240

Val Gln Ser Ser Glu Gln Ser Asn Glu Gly Gln Asn Ser Lys Gln Ser
                245                 250                 255

Asn Glu Gly Gln Ser Ser Glu Gln Ser Asn Glu Gly Gln Asn Ser Lys
            260                 265                 270

Gln Ser Asn Glu Val Gln Ser Pro Glu Glu His Tyr Asp Leu Pro Asp
        275                 280                 285

Pro Glu Ser Ser Tyr Glu Ser Glu Glu Thr Lys Gly Ser His Glu Ser
    290                 295                 300

Gly Asp Asp Ser Glu His Arg
305                 310


<210> SEQ ID NO 208
<211> LENGTH: 431
<212> TYPE: PRT
<213> ORGANISM: Buchnera aphidicola

<400> SEQUENCE: 208

Met Lys Thr Ile Ile Leu Gly Leu Cys Leu Phe Gly Ala Leu Phe Trp
1               5                   10                  15

Ser Thr Gln Ser Met Pro Val Gly Glu Val Ala Pro Ala Val Pro Ala
            20                  25                  30

Val Pro Ser Glu Ala Val Pro Gln Lys Gln Val Glu Ala Lys Pro Glu
        35                  40                  45

Thr Asn Ala Ala Ser Pro Val Ser Asp Ala Lys Pro Glu Ser Asp Ser
    50                  55                  60

Lys Pro Val Asp Ala Glu Val Lys Pro Thr Val Ser Glu Val Lys Ala
65                  70                  75                  80

Glu Ser Glu Gln Lys Pro Ser Gly Glu Pro Lys Pro Glu Ser Asp Ala
                85                  90                  95

Lys Pro Val Val Ala Ser Glu Ser Lys Pro Glu Ser Asp Pro Lys Pro
            100                 105                 110

Ala Ala Val Val Glu Ser Lys Pro Glu Asn Asp Ala Val Ala Pro Glu
        115                 120                 125

Thr Asn Asn Asp Ala Lys Pro Glu Asn Ala Ala Ala Pro Val Ser Glu
    130                 135                 140

Asn Lys Pro Ala Thr Asp Ala Lys Ala Glu Thr Glu Leu Ile Ala Gln
145                 150                 155                 160

Ala Lys Pro Glu Ser Lys Pro Ala Ser Asp Leu Lys Ala Glu Pro Glu
                165                 170                 175

Ala Ala Lys Pro Asn Ser Glu Val Pro Val Ala Leu Pro Leu Asn Pro
            180                 185                 190
```

```
Thr Glu Thr Lys Ala Thr Gln Gln Ser Val Glu Thr Asn Gln Val Glu
        195                 200                 205

Gln Ala Ala Pro Ala Ala Ala Gln Ala Asp Pro Ala Ala Ala Pro Ala
    210                 215                 220

Ala Asp Pro Ala Pro Ala Pro Ala Ala Ala Pro Val Ala Ala Glu Glu
225                 230                 235                 240

Ala Lys Leu Ser Glu Ser Ala Pro Ser Thr Glu Asn Lys Ala Ala Glu
                245                 250                 255

Glu Pro Ser Lys Pro Ala Glu Gln Gln Ser Ala Lys Pro Val Glu Asp
            260                 265                 270

Ala Val Pro Ala Ala Ser Glu Ile Ser Glu Thr Lys Val Ser Pro Ala
        275                 280                 285

Val Pro Ala Val Pro Glu Val Pro Ala Ser Pro Ser Ala Pro Ala Val
    290                 295                 300

Ala Asp Pro Val Ser Ala Pro Glu Ala Glu Lys Asn Ala Glu Pro Ala
305                 310                 315                 320

Lys Ala Ala Asn Ser Ala Glu Pro Ala Val Gln Ser Glu Ala Lys Pro
                325                 330                 335

Ala Glu Asp Ile Gln Lys Ser Gly Ala Val Val Ser Ala Glu Asn Pro
            340                 345                 350

Lys Pro Val Glu Glu Gln Lys Pro Ala Glu Val Ala Lys Pro Ala Glu
        355                 360                 365

Gln Ser Lys Ser Glu Ala Pro Ala Glu Ala Pro Lys Pro Thr Glu Gln
    370                 375                 380

Ser Ala Ala Glu Glu Pro Lys Lys Pro Glu Ser Ala Asn Asp Glu Lys
385                 390                 395                 400

Lys Glu Gln His Ser Val Asn Lys Arg Asp Ala Thr Lys Glu Lys Lys
                405                 410                 415

Pro Thr Asp Ser Ile Met Lys Lys Gln Lys Gln Lys Lys Ala Asn
            420                 425                 430


<210> SEQ ID NO 209
<211> LENGTH: 160
<212> TYPE: PRT
<213> ORGANISM: Buchnera aphidicola

<400> SEQUENCE: 209

Met Asn Gly Lys Ile Val Leu Cys Phe Ala Val Val Phe Ile Gly Gln
1               5                   10                  15

Ala Met Ser Ala Ala Thr Gly Thr Thr Pro Glu Val Glu Asp Ile Lys
            20                  25                  30

Lys Val Ala Glu Gln Met Ser Gln Thr Phe Met Ser Val Ala Asn His
        35                  40                  45

Leu Val Gly Ile Thr Pro Asn Ser Ala Asp Ala Gln Lys Ser Ile Glu
    50                  55                  60

Lys Ile Arg Thr Ile Met Asn Lys Gly Phe Thr Asp Met Glu Thr Glu
65                  70                  75                  80

Ala Asn Lys Met Lys Asp Ile Val Arg Lys Asn Ala Asp Pro Lys Leu
                85                  90                  95

Val Glu Lys Tyr Asp Glu Leu Glu Lys Glu Leu Lys Lys His Leu Ser
            100                 105                 110

Thr Ala Lys Asp Met Phe Glu Asp Lys Val Val Lys Pro Ile Gly Glu
        115                 120                 125

Lys Val Glu Leu Lys Lys Ile Thr Glu Asn Val Ile Lys Thr Thr Lys
    130                 135                 140
```

Asp Met Glu Ala Thr Met Asn Lys Ala Ile Asp Gly Phe Lys Lys Gln
145 150 155 160

<210> SEQ ID NO 210
<211> LENGTH: 415
<212> TYPE: PRT
<213> ORGANISM: Buchnera aphidicola

<400> SEQUENCE: 210

Met His Leu Phe Leu Ala Leu Gly Leu Phe Ile Val Cys Gly Met Val
1 5 10 15

Asp Ala Thr Phe Tyr Asn Pro Arg Ser Gln Thr Phe Asn Gln Leu Met
20 25 30

Glu Arg Arg Gln Arg Ser Ile Pro Ile Pro Tyr Ser Tyr Gly Tyr His
35 40 45

Tyr Asn Pro Ile Glu Pro Ser Ile Asn Val Leu Asp Ser Leu Ser Glu
50 55 60

Gly Leu Asp Ser Arg Ile Asn Thr Phe Lys Pro Ile Tyr Gln Asn Val
65 70 75 80

Lys Met Ser Thr Gln Asp Val Asn Ser Val Pro Arg Thr Gln Tyr Gln
85 90 95

Pro Lys Asn Ser Leu Tyr Asp Ser Glu Tyr Ile Ser Ala Lys Asp Ile
100 105 110

Pro Ser Leu Phe Pro Glu Glu Asp Ser Tyr Asp Tyr Lys Tyr Leu Gly
115 120 125

Ser Pro Leu Asn Lys Tyr Leu Thr Arg Pro Ser Thr Gln Glu Ser Gly
130 135 140

Ile Ala Ile Asn Leu Val Ala Ile Lys Glu Thr Ser Val Phe Asp Tyr
145 150 155 160

Gly Phe Pro Thr Tyr Lys Ser Pro Tyr Ser Ser Asp Ser Val Trp Asn
165 170 175

Phe Gly Ser Lys Ile Pro Asn Thr Val Phe Glu Asp Pro Gln Ser Val
180 185 190

Glu Ser Asp Pro Asn Thr Phe Lys Val Ser Ser Pro Thr Ile Lys Ile
195 200 205

Val Lys Leu Leu Pro Glu Thr Pro Glu Gln Glu Ser Ile Ile Thr Thr
210 215 220

Thr Lys Asn Tyr Glu Leu Asn Tyr Lys Thr Thr Gln Glu Thr Pro Thr
225 230 235 240

Glu Ala Glu Leu Tyr Pro Ile Thr Ser Glu Glu Phe Gln Thr Glu Asp
245 250 255

Glu Trp His Pro Met Val Pro Lys Glu Asn Thr Thr Lys Asp Glu Ser
260 265 270

Ser Phe Ile Thr Thr Glu Glu Pro Leu Thr Glu Asp Lys Ser Asn Ser
275 280 285

Ile Thr Ile Glu Lys Thr Gln Thr Glu Asp Glu Ser Asn Ser Ile Glu
290 295 300

Phe Asn Ser Ile Arg Thr Glu Glu Lys Ser Asn Ser Ile Thr Thr Glu
305 310 315 320

Glu Asn Gln Lys Glu Asp Asp Glu Ser Met Ser Thr Thr Ser Gln Glu
325 330 335

Thr Thr Thr Ala Phe Asn Leu Asn Asp Thr Phe Asp Thr Asn Arg Tyr
340 345 350

Ser Ser Ser His Glu Ser Leu Met Leu Arg Ile Arg Glu Leu Met Lys

```
        355                 360                 365

Asn Ile Ala Asp Gln Gln Asn Lys Ser Gln Phe Arg Thr Val Asp Asn
    370                 375                 380

Ile Pro Ala Lys Ser Gln Ser Asn Leu Ser Ser Asp Glu Ser Thr Asn
385                 390                 395                 400

Gln Gln Phe Glu Pro Gln Leu Val Asn Gly Ala Asp Thr Tyr Lys
                405                 410                 415


<210> SEQ ID NO 211
<211> LENGTH: 126
<212> TYPE: PRT
<213> ORGANISM: Sitophilus zeamais

<400> SEQUENCE: 211

Met Thr Arg Thr Met Leu Phe Leu Ala Cys Val Ala Ala Leu Tyr Val
1               5                   10                  15

Cys Ile Ser Ala Thr Ala Gly Lys Pro Glu Glu Phe Ala Lys Leu Ser
            20                  25                  30

Asp Glu Ala Pro Ser Asn Asp Gln Ala Met Tyr Glu Ser Ile Gln Arg
        35                  40                  45

Tyr Arg Arg Phe Val Asp Gly Asn Arg Tyr Asn Gly Gly Gln Gln Gln
    50                  55                  60

Gln Gln Gln Pro Lys Gln Trp Glu Val Arg Pro Asp Leu Ser Arg Asp
65                  70                  75                  80

Gln Arg Gly Asn Thr Lys Ala Gln Val Glu Ile Asn Lys Lys Gly Asp
                85                  90                  95

Asn His Asp Ile Asn Ala Gly Trp Gly Lys Asn Ile Asn Gly Pro Asp
            100                 105                 110

Ser His Lys Asp Thr Trp His Val Gly Gly Ser Val Arg Trp
        115                 120                 125


<210> SEQ ID NO 212
<211> LENGTH: 220
<212> TYPE: PRT
<213> ORGANISM: Acyrthosiphon pisum

<400> SEQUENCE: 212

Met Lys Glu Thr Thr Val Val Trp Ala Lys Leu Phe Leu Ile Leu Ile
1               5                   10                  15

Ile Leu Ala Lys Pro Leu Gly Leu Lys Ala Val Asn Glu Cys Lys Arg
            20                  25                  30

Leu Gly Asn Asn Ser Cys Arg Ser His Gly Glu Cys Cys Ser Gly Phe
        35                  40                  45

Cys Phe Ile Glu Pro Gly Trp Ala Leu Gly Val Cys Lys Arg Leu Gly
    50                  55                  60

Thr Pro Lys Lys Ser Asp Asp Ser Asn Asn Gly Lys Asn Ile Glu Lys
65                  70                  75                  80

Asn Asn Gly Val His Glu Arg Ile Asp Asp Val Phe Glu Arg Gly Val
                85                  90                  95

Cys Ser Tyr Tyr Lys Gly Pro Ser Ile Thr Ala Asn Gly Asp Val Phe
            100                 105                 110

Asp Glu Asn Glu Met Thr Ala Ala His Arg Thr Leu Pro Phe Asn Thr
        115                 120                 125

Met Val Lys Val Glu Gly Met Gly Thr Ser Val Val Val Lys Ile Asn
    130                 135                 140

Asp Arg Lys Thr Ala Ala Asp Gly Lys Val Met Leu Leu Ser Arg Ala
```

-continued

```
145                 150                 155                 160

Ala Ala Glu Ser Leu Asn Ile Asp Glu Asn Thr Gly Pro Val Gln Cys
                165                 170                 175

Gln Leu Lys Phe Val Leu Asp Gly Ser Gly Cys Thr Pro Asp Tyr Gly
            180                 185                 190

Asp Thr Cys Val Leu His His Glu Cys Cys Ser Gln Asn Cys Phe Arg
        195                 200                 205

Glu Met Phe Ser Asp Lys Gly Phe Cys Leu Pro Lys
    210                 215                 220


<210> SEQ ID NO 213
<211> LENGTH: 16
<212> TYPE: PRT
<213> ORGANISM: Artificial Sequence
<220> FEATURE:
<223> OTHER INFORMATION: Penetratin

<400> SEQUENCE: 213

Arg Gln Ile Lys Ile Trp Phe Gln Asn Arg Arg Met Lys Trp Lys Lys
1               5                   10                  15


<210> SEQ ID NO 214
<211> LENGTH: 13
<212> TYPE: PRT
<213> ORGANISM: Human immunodeficiency virus type 1

<400> SEQUENCE: 214

Gly Arg Lys Lys Arg Arg Gln Arg Arg Arg Pro Pro Gln
1               5                   10


<210> SEQ ID NO 215
<211> LENGTH: 18
<212> TYPE: PRT
<213> ORGANISM: Artificial Sequence
<220> FEATURE:
<223> OTHER INFORMATION: pVEC

<400> SEQUENCE: 215

Leu Leu Ile Ile Leu Arg Arg Arg Ile Arg Lys Gln Ala His Ala His
1               5                   10                  15

Ser Lys


<210> SEQ ID NO 216
<211> LENGTH: 27
<212> TYPE: PRT
<213> ORGANISM: Artificial Sequence
<220> FEATURE:
<223> OTHER INFORMATION: Transportan

<400> SEQUENCE: 216

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25


<210> SEQ ID NO 217
<211> LENGTH: 27
<212> TYPE: PRT
<213> ORGANISM: Artificial Sequence
<220> FEATURE:
<223> OTHER INFORMATION: MPG

<400> SEQUENCE: 217
```

-continued

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 218
<211> LENGTH: 21
<212> TYPE: PRT
<213> ORGANISM: Artificial Sequence
<220> FEATURE:
<223> OTHER INFORMATION: Pep-1

<400> SEQUENCE: 218

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 219
<211> LENGTH: 18
<212> TYPE: PRT
<213> ORGANISM: Artificial Sequence
<220> FEATURE:
<223> OTHER INFORMATION: MAP

<400> SEQUENCE: 219

Lys Leu Ala Leu Lys Leu Ala Leu Lys Ala Leu Lys Ala Ala Leu Lys
1               5                   10                  15

Leu Ala

<210> SEQ ID NO 220
<211> LENGTH: 9
<212> TYPE: PRT
<213> ORGANISM: Artificial Sequence
<220> FEATURE:
<223> OTHER INFORMATION: R6W3

<400> SEQUENCE: 220

Arg Arg Trp Trp Arg Arg Trp Arg Arg
1               5

<210> SEQ ID NO 221
<211> LENGTH: 25
<212> TYPE: DNA
<213> ORGANISM: Artificial Sequence
<220> FEATURE:
<223> OTHER INFORMATION: Asaia forward primer

<400> SEQUENCE: 221
gtgccgatct ctaaaagccg tctca                                            25

<210> SEQ ID NO 222
<211> LENGTH: 20
<212> TYPE: DNA
<213> ORGANISM: Artificial Sequence
<220> FEATURE:
<223> OTHER INFORMATION: Asaia reverse primer

<400> SEQUENCE: 222
ttcgctcacc ggcttcgggt                                                  20

<210> SEQ ID NO 223
<211> LENGTH: 19
<212> TYPE: DNA
<213> ORGANISM: Artificial Sequence
<220> FEATURE:
<223> OTHER INFORMATION: S7 forward primer

<400> SEQUENCE: 223
gtgcgcgagt tggagaaga 19

<210> SEQ ID NO 224
<211> LENGTH: 19
<212> TYPE: DNA
<213> ORGANISM: Artificial Sequence
<220> FEATURE:
<223> OTHER INFORMATION: S7 reverse primer

<400> SEQUENCE: 224
atcggtttgg gcagaatgc 19

<210> SEQ ID NO 225
<211> LENGTH: 20
<212> TYPE: DNA
<213> ORGANISM: Artificial Sequence
<220> FEATURE:
<223> OTHER INFORMATION: Wolbachia forward primer

<400> SEQUENCE: 225
tcagccacac tggaactgag 20

<210> SEQ ID NO 226
<211> LENGTH: 20
<212> TYPE: DNA
<213> ORGANISM: Artificial Sequence
<220> FEATURE:
<223> OTHER INFORMATION: Wolbachia reverse primer

<400> SEQUENCE: 226
taacgctagc cctctccgta 20

<210> SEQ ID NO 227
<211> LENGTH: 20
<212> TYPE: DNA
<213> ORGANISM: Artificial Sequence
<220> FEATURE:
<223> OTHER INFORMATION: S7 forward primer

<400> SEQUENCE: 227
aaggtcgaca ccttcacgtc 20

<210> SEQ ID NO 228
<211> LENGTH: 20
<212> TYPE: DNA
<213> ORGANISM: Artificial Sequence
<220> FEATURE:
<223> OTHER INFORMATION: S7 reverse primer

<400> SEQUENCE: 228
ccgtttggtg agggtcttta 20

<210> SEQ ID NO 229
<211> LENGTH: 19
<212> TYPE: DNA
<213> ORGANISM: Artificial Sequence
<220> FEATURE:
<223> OTHER INFORMATION: Rickettsia forward primer

<400> SEQUENCE: 229
tacgccactc cctgtgtca 19

<210> SEQ ID NO 230
<211> LENGTH: 24
<212> TYPE: DNA
<213> ORGANISM: Artificial Sequence
<220> FEATURE:
<223> OTHER INFORMATION: Rickettsia reverse primer

<400> SEQUENCE: 230
gatgtaacgg tattacacca acag 24

<210> SEQ ID NO 231
<211> LENGTH: 20
<212> TYPE: DNA
<213> ORGANISM: Artificial Sequence
<220> FEATURE:
<223> OTHER INFORMATION: Bacillus forward primer

<400> SEQUENCE: 231
gaggtagacg aagcgacctg 20

<210> SEQ ID NO 232
<211> LENGTH: 20
<212> TYPE: DNA
<213> ORGANISM: Artificial Sequence
<220> FEATURE:
<223> OTHER INFORMATION: Bacillus reverse primer

<400> SEQUENCE: 232
ttccctcacg gtactggttc 20

<210> SEQ ID NO 233
<211> LENGTH: 17
<212> TYPE: DNA
<213> ORGANISM: Artificial Sequence
<220> FEATURE:
<223> OTHER INFORMATION: Buchnera forward primer

<400> SEQUENCE: 233
gtcggctcat cacatcc 17

<210> SEQ ID NO 234
<211> LENGTH: 20
<212> TYPE: DNA
<213> ORGANISM: Artificial Sequence
<220> FEATURE:
<223> OTHER INFORMATION: Buchnera reverse primer

<400> SEQUENCE: 234
ttccgtctgt attatctcct 20

<210> SEQ ID NO 235
<211> LENGTH: 390
<212> TYPE: DNA
<213> ORGANISM: Sitophilus zeamais

<400> SEQUENCE: 235
catatgatga cccgcaccat gctgtttctg gcgtgcgtgg cggcgctgta tgtgtgcatt 60
agcgcgaccg cgggcaaacc ggaagaattt gcgaaactga gcgatgaagc gccgagcaac 120
gatcaggcga tgtatgaaag cattcagcgc tatcgccgct ttgtggatgg caaccgctat 180
aacggcggcc agcagcagca gcagcagccg aaacagtggg aagtgcgccc ggatctgagc 240
cgcgatcagc gcggcaacac caaagcgcag gtggaaatta acaaaaaagg cgataaccat 300
gatattaacg cgggctgggg caaaaacatt aacggcccgg atagccataa agatacctgg 360
catgtgggcg gcagcgtgcg ctggctcgag 390

<210> SEQ ID NO 236
<211> LENGTH: 34
<212> TYPE: DNA
<213> ORGANISM: Artificial Sequence
<220> FEATURE:
<223> OTHER INFORMATION: ColA forward primer

<400> SEQUENCE: 236
gtatctattc ccgtctacga acatatggaa ttcc 34

<210> SEQ ID NO 237
<211> LENGTH: 29
<212> TYPE: DNA
<213> ORGANISM: Artificial Sequence
<220> FEATURE:
<223> OTHER INFORMATION: ColA reverse primer

<400> SEQUENCE: 237
ccgctcgagc catctgacac ttcctccaa 29

<210> SEQ ID NO 238
<211> LENGTH: 21
<212> TYPE: DNA
<213> ORGANISM: Artificial Sequence
<220> FEATURE:
<223> OTHER INFORMATION: Buch_groES_18F forward primer

<400> SEQUENCE: 238
catgatcgtg tgcttgttaa g 21

<210> SEQ ID NO 239
<211> LENGTH: 21
<212> TYPE: DNA
<213> ORGANISM: Artificial Sequence
<220> FEATURE:
<223> OTHER INFORMATION: Buch_groES_98R reverse primer

<400> SEQUENCE: 239
ctgttcctcg agtcgatttc c 21

<210> SEQ ID NO 240
<211> LENGTH: 21
<212> TYPE: DNA
<213> ORGANISM: Artificial Sequence
<220> FEATURE:
<223> OTHER INFORMATION: ApEF1a 107F forward primer

<400> SEQUENCE: 240
ctgattgtgc cgtgcttatt g 21

<210> SEQ ID NO 241
<211> LENGTH: 21
<212> TYPE: DNA
<213> ORGANISM: Artificial Sequence
<220> FEATURE:
<223> OTHER INFORMATION: ApEF1a 246R reverse primer

<400> SEQUENCE: 241
tatggtggtt cagtagagtc c 21

<210> SEQ ID NO 242
<211> LENGTH: 20
<212> TYPE: DNA

<213> ORGANISM: Artificial Sequence
<220> FEATURE:
<223> OTHER INFORMATION: Sod_F forward primer

<400> SEQUENCE: 242
atagctgtcc agacgcttcg 20

<210> SEQ ID NO 243
<211> LENGTH: 20
<212> TYPE: DNA
<213> ORGANISM: Artificial Sequence
<220> FEATURE:
<223> OTHER INFORMATION: Sod_R reverse primer

<400> SEQUENCE: 243
atgtcgtcga ggcgattacc 20

<210> SEQ ID NO 244
<211> LENGTH: 20
<212> TYPE: DNA
<213> ORGANISM: Artificial Sequence
<220> FEATURE:
<223> OTHER INFORMATION: SACT144_FOR forward primer

<400> SEQUENCE: 244
ggtgttggcg tacaagtcct 20

<210> SEQ ID NO 245
<211> LENGTH: 20
<212> TYPE: DNA
<213> ORGANISM: Artificial Sequence
<220> FEATURE:
<223> OTHER INFORMATION: SACT314_REV reverse primer

<400> SEQUENCE: 245
gaattgcctg atggacaggt 20

<210> SEQ ID NO 246
<211> LENGTH: 24
<212> TYPE: PRT
<213> ORGANISM: Artificial Sequence
<220> FEATURE:
<223> OTHER INFORMATION: Uy192 + cell penetrating peptide

<400> SEQUENCE: 246

Tyr Gly Arg Lys Lys Arg Arg Gln Arg Arg Arg Phe Leu Ser Thr Ile
1 5 10 15

Trp Asn Gly Ile Lys Gly Leu Leu
20

<210> SEQ ID NO 247
<211> LENGTH: 11
<212> TYPE: PRT
<213> ORGANISM: Artificial Sequence
<220> FEATURE:
<223> OTHER INFORMATION: synthetic construct

<400> SEQUENCE: 247

Tyr Gly Arg Lys Lys Arg Arg Gln Arg Arg Arg
1 5 10